US007407965B2

(12) United States Patent
Chen et al.

(10) Patent No.: US 7,407,965 B2
(45) Date of Patent: Aug. 5, 2008

(54) PHOSPHONATE ANALOGS FOR TREATING METABOLIC DISEASES

(75) Inventors: James M. Chen, San Ramon, CA (US); Xiaowu Chen, San Mateo, CA (US); Aesop Cho, Mountain View, CA (US); Lee S. Chong, Newark, CA (US); Maria Fardis, San Carlos, CA (US); Thorsten Kirschberg, Belmont, CA (US); Steven Krawczyk, San Carlos, CA (US); Hyung-Jung Pyun, Freemont, CA (US); William J. Watkins, Sunnyvale, CA (US)

(73) Assignee: Gilead Sciences, Inc., Foster City, CA (US)

( * ) Notice: Subject to any disclaimer, the term of this patent is extended or adjusted under 35 U.S.C. 154(b) by 377 days.

(21) Appl. No.: 10/832,817

(22) Filed: Apr. 26, 2004

(65) Prior Publication Data

US 2005/0227947 A1 Oct. 13, 2005

Related U.S. Application Data

(60) Provisional application No. 60/465,536, filed on Apr. 25, 2003, provisional application No. 60/465,763, filed on Apr. 25, 2003, provisional application No. 60/465,339, filed on Apr. 25, 2003, provisional application No. 60/465,292, filed on Apr. 25, 2003, provisional application No. 60/465,399, filed on Apr. 25, 2003, provisional application No. 60/465,355, filed on Apr. 25, 2003, provisional application No. 60/465,751, filed on Apr. 25, 2003, provisional application No. 60/465,317, filed on Apr. 25, 2003, provisional application No. 60/465,689, filed on Apr. 25, 2003, provisional application No. 60/465,475, filed on Apr. 25, 2003, provisional application No. 60/465,325, filed on Apr. 25, 2003, provisional application No. 60/465,286, filed on Apr. 25, 2003, provisional application No. 60/495,753, filed on Aug. 15, 2003, provisional application No. 60/495,681, filed on Aug. 15, 2003, provisional application No. 60/495,534, filed on Aug. 15, 2003, provisional application No. 60/495,347, filed on Aug. 15, 2003, provisional application No. 60/495,762, filed on Aug. 15, 2003, provisional application No. 60/495,526, filed on Aug. 15, 2003, provisional application No. 60/495,361, filed on Aug. 15, 2003, provisional application No. 60/495,354, filed on Aug. 15, 2003, provisional application No. 60/495,683, filed on Aug. 15, 2003, provisional application No. 60/495,489, filed on Aug. 15, 2003, provisional application No. 60/495,669, filed on Aug. 15, 2003, provisional application No. 60/495,531, filed on Aug. 15, 2003, provisional application No. 60/513,954, filed on Oct. 24, 2003, provisional application No. 60/513,966, filed on Oct. 24, 2003, provisional application No. 60/514,465, filed on Oct. 24, 2003, provisional application No. 60/514,303, filed on Oct. 24, 2003, provisional application No. 60/514,104, filed on Oct. 24, 2003, provisional application No. 60/532,273, filed on Dec. 22, 2003, provisional application No. 60/532,184, filed on Dec. 22, 2003, provisional application No. 60/532,183, filed on Dec. 22, 2003, provisional application No. 60/532,274, filed on Dec. 22, 2003, provisional application No. 60/532,683, filed on Dec. 23, 2003, provisional application No. 60/532,682, filed on Dec. 23, 2003, provisional application No. 60/532,587, filed on Dec. 23, 2003, provisional application No. 60/532,415, filed on Dec. 23, 2003, provisional application No. 60/536,179, filed on Jan. 12, 2004.

(51) Int. Cl.
*A61K 31/505* (2006.01)
*C07F 9/02* (2006.01)

(52) U.S. Cl. ...................................... 514/275; 544/243

(58) Field of Classification Search ................ 514/275; 544/243

See application file for complete search history.

(56) References Cited

U.S. PATENT DOCUMENTS

| | | | | |
|---|---|---|---|---|
| 5,260,440 | A * | 11/1993 | Hirai et al. | 544/332 |
| 5,413,996 | A | 5/1995 | Bodor | |
| 5,493,030 | A | 2/1996 | Morgans et al. | |
| 5,585,397 | A | 12/1996 | Tung et al. | |
| 5,633,279 | A | 5/1997 | Morgans et al. | |
| 5,654,286 | A | 8/1997 | Hostetler | |

(Continued)

FOREIGN PATENT DOCUMENTS

EP 0 267 050 5/1988

(Continued)

OTHER PUBLICATIONS

Abdel-Meguid, Sherin S. et al., Inhibition of Human Immunodeficiency Virus-1 Protease by a $C_2$-Symmetric Phosphinate. Synthesis and Crystallographic Analysis, *Biochemistry*, 1993, 1543-1572, vol. 32, No. 31.

(Continued)

*Primary Examiner*—Rei-Tsang Shiao
(74) *Attorney, Agent, or Firm*—Viksnins Harris & Padys PLLP

(57) ABSTRACT

The invention is related to phosphorus substituted compounds with activity for treating metabolic diseases and/or disorders, e.g., diabetes and hypercholesterolemia, compositions containing such compounds, and therapeutic methods that include the administration of such compounds, as well as to processes and intermediates useful for preparing such compounds.

12 Claims, No Drawings

U.S. PATENT DOCUMENTS

| | | | | |
|---|---|---|---|---|
| 5,670,497 | A | 9/1997 | Bold et al. | |
| 5,747,498 | A | 5/1998 | Schnur et al. | |
| 5,750,343 | A | 5/1998 | Maag et al. | |
| 5,750,493 | A | 5/1998 | Schinazi et al. | |
| 5,811,422 | A | 9/1998 | Lam et al. | |
| 5,874,577 | A | 2/1999 | Chen et al. | |
| 5,914,332 | A | 6/1999 | Chen et al. | |
| 6,072,053 | A | 6/2000 | Vince et al. | |
| 6,174,888 | B1 | 1/2001 | McQuire et al. | |
| 6,312,662 | B1 | 11/2001 | Robinson et al. | |
| 6,319,946 | B1 | 11/2001 | Hale et al. | |
| 6,395,763 | B1 | 5/2002 | Stamos et al. | |
| 6,608,027 | B1 | 8/2003 | Tsantrizos et al. | |
| 6,767,900 | B2 | 7/2004 | Ubasawa et al. | |
| 6,858,618 | B2 * | 2/2005 | Raza et al. | 514/275 |
| 2001/0031773 | A1 | 10/2001 | Camden | |
| 2002/0119443 | A1 | 8/2002 | Becker et al. | |
| 2003/0109498 | A1 | 6/2003 | Yuasa et al. | |
| 2004/0121316 | A1 | 6/2004 | Birkus et al. | |
| 2004/0167096 | A1 | 8/2004 | Cheng et al. | |

FOREIGN PATENT DOCUMENTS

| | | | |
|---|---|---|---|
| EP | 0 441 192 | | 1/1991 |
| EP | 0 465 297 | | 1/1992 |
| EP | 0 531 597 | | 3/1993 |
| EP | 0 632 048 | | 1/1995 |
| EP | 0 786 455 | | 7/1997 |
| EP | 0 852 233 | | 7/1998 |
| EP | 0 919 562 | | 6/1999 |
| EP | 1 295 879 | | 3/2003 |
| WO | WO 88/06158 | | 8/1988 |
| WO | WO91/19721 | | 12/1991 |
| WO | WO 92/00988 | | 1/1992 |
| WO | WO 92/18520 | | 10/1992 |
| WO | WO 93/12123 | | 6/1993 |
| WO | WO 93/24510 | | 12/1993 |
| WO | WO 96/14314 | | 5/1996 |
| WO | WO 96/40156 | | 12/1996 |
| WO | WO 97/01558 | | 1/1997 |
| WO | WO 98/04569 | | 2/1998 |
| WO | WO 98/11906 | | 3/1998 |
| WO | WO 98/15563 | | 4/1998 |
| WO | WO 99/33815 | | 7/1999 |
| WO | WO 99/62921 | | 12/1999 |
| WO | WO 00/04033 | | 1/2000 |
| WO | WO 00/52015 | A2 | 9/2000 |
| WO | WO 00/52015 | A3 | 2/2001 |
| WO | WO 01/13957 | | 3/2001 |
| WO | WO 01/17982 | | 3/2001 |
| WO | WO 01/19320 | | 3/2001 |
| WO | WO 01/39724 | A2 | 6/2001 |
| WO | WO 01/46204 | | 6/2001 |
| WO | WO 01/64693 | | 9/2001 |
| WO | WO 01/39724 | A3 | 10/2001 |
| WO | WO 01/96329 | | 12/2001 |
| WO | WO 01/96354 | | 12/2001 |
| WO | WO 02/03997 | | 1/2002 |
| WO | WO 02/06292 | | 1/2002 |
| WO | WO 02/08241 | | 1/2002 |
| WO | WO 02/14344 | | 2/2002 |
| WO | WO 02/48165 | A2 | 6/2002 |
| WO | WO 02/057425 | | 7/2002 |
| WO | WO 02/100415 | | 12/2002 |
| WO | WO 02/103008 | A2 | 12/2002 |
| WO | WO 02/103008 | A3 | 12/2002 |
| WO | WO 03/028737 | | 4/2003 |
| WO | WO 02/48165 | A3 | 5/2003 |
| WO | WO 03/050129 | | 6/2003 |
| WO | WO 03/059255 | | 7/2003 |
| WO | WO 03/064383 | | 8/2003 |
| WO | WO 03/066005 | | 8/2003 |
| WO | WO 03/080078 | | 10/2003 |
| WO | WO 03/090690 | | 11/2003 |
| WO | WO 2004/096234 | | 11/2004 |
| WO | WO 2004/096818 | A2 | 11/2004 |
| WO | WO 2004/096818 | A3 | 11/2004 |
| WO | WO 2005/011709 | | 2/2005 |
| WO | WO 2005/011709 | A1 | 2/2005 |

OTHER PUBLICATIONS

De Clercq, Erik, New Developments in Anti-HIV Chemotherapy, *Current Medicinal Chemistry*, 2001, 1543-1572, vol. 8, No. 13, Bentham Science Publishers Ltd.

Dvorakova, Hana et al., Synthesis of 2'-Aminomethyl Derivatives of N-(2-(Phosphonomethoxy)ethyl) Nucleotide Analogues as Potential Antiviral Agents, *J. Med. Chem.*, 1996, 3263-3268. vol. 38, No. 17.

Menendez-Arias, Luis et al. Targeting HIV: antiretroviral therapy and development of drug resistance, *TRENDS in Pharmacological Sciences*, 2002, 381-388, vol. 23, No. 8, Elsevier Science Ltd.

Vielhaber, Bernd, Bericht vom 3rd International Workshop on Salvage Therapy for HIV-Infection, *Deutsche Aids-Hilfe e. V. Fax Report zu HIV und AIDS*, 2000, 12-14.

Allen, Lee F. et al., CI-1040 (PDI84352), a Targeted Signal Transduction Inhibitor of MEK (MAPKK), *Seminars in Oncology*, Oct. 2003, pp. 105-116, vol. 30, No. 5, Elsevier Inc.

Bantia, Shanta et al., Purine nucleoside phosphorylase inhibitor BCX-1777 (Immucillin-H)—a novel potent and orally active immunosuppressive agent, *International Immunopharmacology*, 2001, pp. 1199-1210, Elsevier Science B.V.

Beauchamp, Lilia M., et al., Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase, *Journal of Medicinal Chemistry*, 1996, pp. 949-956, American Chemical Society.

Bohani D. W. et al., A-420983: a potent, orally active inhibitor of lck with efficacy in a model of transplant rejection, *Bioorganic & Medicinal Chemistry Letters*, 2004, vol. 14.

Bzowska, Agnieszka et al., Purine nucleoside phosphorylases: properties, functions, and clinical aspects, *Pharmacology & Therapeutics*, 2000, pp. 349-425, vol. 88, Elsevier Science Inc.

Chapman, H. et al., Practical Synthesis, Separation, and Stereochemical Assignment of the PMPA Pro-Drug GS-7340, Nucleosides, Nucleotides & Nucleic Acids, 2001, pp. 621-628, vol. 20, Nos. 4-7, Marcel Dekker, Inc.

Clark, Jeremy L. et al., Mycophenolic Acid Analogues as Potential Agents Against West Nile Virus Infection.

Conklyn, Maryrose et al., The JAK3 inhibitor CP-690550 selectively reduces NK and CD8+ cell numbers in cynomolgus monkey blood following chronic oral dosing, *Journal of Leukocyte Biology*, Dec. 2004, pp. 1-8, vol. 76, The Society for Leukocyte Biology.

De Clereq, E., Highlights in the Development of New Antiviral Agents, *Mini Reviews in Medicinal Chemistry*, 2002, 163-175, vol. 2, No. 2., Bentham Science Publishers, Ltd.

Evans, Gary B., Exploring Structure—Activity Relationships of Transition State Analogues of Human Purine Nucleoside Phosphorylase, *J. Med. Chem.*, 2003, 3412-3423, vol. 46, No. 15, American Chemical Society.

Gumina, Giuseppe et al., Advances in antiviral agents for hepatitis B virus, *Antiviral Chemistry & Chemotherapy*, 2001, 93-112, vol. 12, Suppl. 1, International Medical Press.

Gobec, S. et al., Phosphonate inhibitors of antiget 85C, a crucial enzyme involved in the biosynthesis of the mycobacterium tuberculosis cell wall, *Bioorganic and Medicinal Chemistry Letters*, 2004, vol. 14.

Hegedus, Louis S. et al., Synthesis of 4'-Methyl and 4'-cyano Carbocyclic 2',3'-Didehydro Nucleoside Analogues via 1,4-Addition to Substituted Cyclopentenones, *J. Org. Chem.*, 2004, 8492-8495, vol. 69, No. 24, American Chemical Society.

Herczegh P., et al., Osteoadsorptive bisphosphonate derivatives of fluoroquinolone antibacterials, *J. Med. Chem.*, 2002, vol. 45.

Hirabayashi, Hideki et al., Bone-Specific Drug Delivery Systems, *Clinical Pharacokinetics*, 2003, 1319-1330, vol. 42, No. 15.

Holy A. et al., Synthesis, *Cllect. Czech. Chem. Commun.*, 1989, vol. 54, pp. 2190-2210.
Jain, Jugnu et al., Characterization of Pharmacological Efficacy of VX-148, a New, Potent Immunosuppressive Inosine 5'-Monophosphate Dehydrogenase Inhibitor, *Journal of Pharmacology and Experimental Therapeutics*, 2002, 1272-1277, vol. 302, No. 3, The American Society for Pharmacology and Experimental Therapeutics.
Karpenko, Inna L. et al., Synthesis and Antitherpetic Activity of Acyclovir Phosphonates, *Nucleosides, Nucleotides & Nucleic Acids*, 2003, 319-328, vol. 22, No. 3, Marcel Dekker, Inc.
Kato, Keisuke et al., Stereoselective synthesis of 4'-.alpha.-alkyclcarbovir derivatives based on an asymmetric synthesis or chemo-enzymatic procedure, *Chemical & Pharmaceutical Bulletin*, 1999, 1256-1264, vol. 49, No. 9, Pharmaceutical Society of Japan.
Kato, Keisuke et al., Enantio- and diastereoselective syntheis of 4'-α-substituted carbocyclic nucleosides, Tetrahedron: *Asymmetry*, 1998, 911-914, vol. 9, Elsevier Science Ltd.
Kilpatrick, J. Michael, Intravenous and oral pharmacokinetic study of BCX-1777, a novel purine nucleoside phosphorylase transition-state inhibitor, In vivo effects on blood 2'-deoxyguanosine in primates, *International Immunopharmacology*, 2003, 541-548, vol. 3, Elsevier Science B.V.
Kim, Choung Un et al., Regiospecific and Highly Stereoselective Electrophilic Addition to Furanoid Glycals: Synthesis of Phosphonate Nucleotide Analogues with Potent Activity against HIV, J. Org. Chem., 1991, 2642-2647, vol. 56, No. 8, American Chemical Society.
Kinsky, Stephen C. et al., Inhibition of cell proliferation by putative metabolites and non-degradable analogs of methotrexate-.gama.-dimyristoylphosphatidylethanolamine, *Biochimica et Biphysica Acta*, 19878, 211-218, vol. 917, No. 2., Elsevier Science Publishers B. V.
Kinsky, Stephen C. et al., Effect of liposomes sentitized with methotrexate-γ-dimyristoylphosphatidylethanolamine on cells that are resistant to methotrexate, *Biochimica et Biophysica Acta*, 1986, 129-135, vol. 885, Elsevier Science Publishers B.V.
Kinsky, Stephen C. et al., Circumvention of the methotrexate transport system by methotrexate-phosphatidylethanolamine derivatives effect of fatty acid chain length, *Biochmica et Biophysica Acta*, 1987, 96-103, vol. 921, Elsevier Science Publishers B.V.
Ko, Ok Hyun et al., Efficient synthesis of novel carbocyclic nucleosides via sequential Claisen rearrangement and ring-closing metathesis, *Tetrahedron Letters*, 2002, 6399-6402, vol. 43, Elsevier Science Ltd.
Reed, Leff et al., Antidiabetic PPARγ Ligands: An update on Compounds in development, *Curr. Med. Chem.—Imun., Endoc. & Metab. Agents*, 2002, 33-47, vol. 2, No. 1, Bentham Science Publishers Ltd.
Lewandowicz, Andrzej et al., Achieving the Ultimate Physiological Goal in Transition State Analogue Inhibitors for Purine Nucleoside Phosphorylase, *The Journal of Biological Chemistry*, 2003, 31465-31468, vol. 278, No. 34, The American Society for Biochemistry and Molecular Biology, Inc.
Pankiewicz, Krzysztof W., Novel Mycophenolic Adenine Bis(phosphonate) Analogues As Potential Differentiation Agents against Human Leukemia, *J. Med. Chem.*, 2002 703-712, vol. 45, No. 3, American Chemical Society.
Ono-Nita, Suzane Kioko et al., Novel Nucleoside Analogue MCC-478 (LY582563) Is Effective against Wild-Type or Lamivudine-Resistant Hepatitis B Virus, *Antimicrobial Agents and Chemotherapy*, 2002, 2602-2605, vol. 46, No. 8, American Society for Microbiology.
Parang, Keykavous et al., Novel Approaches for Designing 5'-O-Ester Prodrugs of 3'-Azido-2', 3'-dideoxythymidine (AZT), *Current Medicinal Chemistry*, 2000, 995-1039, vol. 7, No. 10, Bentham Science Publishers Ltd.
Prashad, Mahavir et al., An Efficient and Large-Scale Enantioselective Synthesis of PNP405: A Purine Nucleoside Phosphorylase Inhibitor, *J. Org. Chem.*, 2002, 6612-6617, vol. 67, No. 19, American Chemical Society.
Ray, Adrian S. et al., Role of Purine Nucleoside Phosphorylase in Interactions between 2', 3'-Dideoxyinosine and Allopurinal, Ganciclovir, or Tenofovir, Antimicrobial Agents and Chemotherapy, 2004, 1089-1095, vol. 48, No. 4, American Society for Microbiology.
Roberts, Stanley M., Development of the route to the new anti-AIDS drug abacavir: A highlight of academic/industry laison, *IDrugs*, 1998, 896-899, vol. 1, No. 8, Current Drugs Ltd.
Rosowsky, Andre et al., Methotrexate Analogues—27, *Biochemical Pharmacology*, 1986, 3327-3333, vol. 35, No. 19, Pergamon Journals Ltd.
Rosowsky, Andre et al., Methotrexate Analogues, 32, Chain Extension, α-Carboxyl Replacement by Sulfonate and Phosphonate: Effect on Enzyme Binding and Cell-Growth Inhibition, *J. Med. Chem.*, 1988, 1326-1331, vol. 31, No. 7, American Chemical Society.
Schultz, C., Prodrugs of biologically active phosphate esters, *Bioorganic & Medicinal Chemistry*, 2003, 885-898, vol. 11, Elsevier Science Ltd., GB.
Sekiya, Kouichi et al., 2-Amino-6-arylthio-9-[2-(phosphonomethoxy) ethyl) purine Bis (2,2,2-trifluoroethyl) Esters as Novel HBV-Specific Antiviral Reagents, Journal of Medicinal Chemistry, 2002, 3138-3142, vol. 45, No. 14, American Chemical Society.
Shi, Wuxian et al., *Plasmodium falciparum* Purine Nucleoside Phosphorylase, The Journal of Biological Chemistry, 2004, 18103-18106, vol. 279, No. 18, The American Society of Biochemistry and Molecular Biology, Inc.
Sintchak, Michael D. et al., The structure of inosine 5'-monophosphate dehydrogenase and the design of novel inhibitors, Immunopharmachology, 2000, 163-184, vol. 47, Elsevier.
Srinivas, Ranga V. et al., Metabolism and In Vitro Antiretroviral Activities of Bis(Pivaloyloxymethyl) Prodrugs of Acyclic Nucleoside Phosphonates, Antimicrobial Agents and Chemotherapy, 1993, 2247-2250, vol. 37, No. 10, American Society for Microbiology.
Sturtz, Georges et al., Su rune nouvelle approche de pharmacomodulation du methotrexate: synthese d'analogues gem-diphosphoniques d'amethopterine et de la N-10 deaza amethopterine, Medicinal Chemistry, C. R. Acad. Sci. Paris, 1990, vol. 10, No. 2, 739-742, Academie des Sciences.
Sturtz, Georges et al., Analogues phosphonoglutamiques d'amethopterine (methotrexate), Eur. J. Med. Chem—Chim. Ther., 1984, 267-273, vol. 19, No. 3.
Sturtz, G. et al., Synthesis of gem-bisphosphonic methotrexate conjugates and their biological response towards Walker's osteosarcoma, *Eur. J. Med. Chem.*, 1993, 899-903, vol. 28, Elsevier.
Sturtz, G. et al., A study of the delivery-targeting concept applied to antineoplasic drugs active on human osteosarcoma, I. Synthesis and biological activity in nude mice carrying human osteosarcoma xenografts of gem-bisphosphonic methotrexate analogues, Eur J. Med. Chem., 1992, 825-833, vol. 27, No. 8, Elsevier.
Waegell W. et al. A420983, a novel, small molecule inhibitor of LCK prevents allograft rejection, Transplantation Proceedings, 2002, 1411-1417, vol. 34.
Wroblewski, Andrzej et al., Synthesis of (1R,2S)- and (1S,2S)-3-(4-carbamoyl-1,2,3-triazol-1-yl)-1,2-dihydroxypropylphosphonates, Tetrahedron: Asymmetry, 2004, 1457-1464, vol. 15, Elsevier.
Hostetler, CAS:127:185859 (1997).
Morgans et al., CAS:124:86709 (1995).
Sturtz et al., CAS:101:143560 (1984).

* cited by examiner

PHOSPHONATE ANALOGS FOR TREATING METABOLIC DISEASES

PRIORITY OF INVENTION

This application claims the benefit of priority under 35 U.S.C. § 119(e) to U.S. Provisional Patent Application Ser. Nos. 60/465,536, 60/465,763, 60/465,339, 60/465,292, 60/465,399, 60/465,355, 60/465,751, 60/465,317, 60/465, 689, 60/465,475, 60/465,325, and 60/465,286, all filed Apr. 25, 2003; to U.S. Provisional Patent Application Ser. Nos. 60/495,753, 60/495,681, 60/495,534, 60/495,347, 60/495, 762, 60/495,526, 60/495,361, 60/495,354, 60/495,683, 60/495,489, 60/495,669, and 60/495,531, all filed Aug. 15, 2003; to U.S. Provisional Patent Application Ser. Nos. 60/513,954, 60/513,966, 60/514,465, 60/514,303, and 60/514,104, all filed Oct. 24, 2003; to U.S. Provisional Patent Application Ser. Nos. 60/532,273, 60/532,184, 60/532,183 and 60/532,274, all filed Dec. 22, 2003; to U.S. Provisional Patent Application Ser. Nos. 60/532,683, 60/532,682, 60/532,587 and 60/532,415, all filed Dec. 23, 2003; and to U.S. Provisional Patent Application Ser. No. 60/536,179, filed Jan. 12, 2004. The entirety of all Provisional Applications listed above are incorporated herein by reference.

FIELD OF THE INVENTION

The invention relates generally to compounds with activity for treating metabolic diseases and/or disorders, e.g., diabetes and hypercholesterolemia.

BACKGROUND OF THE INVENTION

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., glucocorticoids and other anti-inflammatory drugs) that can be administered. By comparison, although oral administration of drugs is generally recognized as a convenient and economical method of administration, oral administration can result in either (a) uptake of the drug through the cellular and tissue barriers, e.g., blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Statins lower plasma cholesterol level by decreasing hepatic cholesterol biosynthesis and by upregulating low-density lipoprotein (LDL) receptors on hepatocytes. Their side effects, such as gastrointestinal discomfort, headache, rash and elevations in serum transaminase activity (a sign of hepatotoxicity) have been the principal problems preventing their usage.

Pitavastatin (U.S. Pat. No. 5,856,336), Rosuvastatin (Crestor) (U.S. Pat. No. RE37,314 and U.S. Pat. No. 5,260,440), Pravastatin (U.S. Pat. No. 4,346,227), Fluvastatin (U.S. Pat. Nos. 5,354,772 and 4,739,073), Lovastatin and Sivastatin (mevalonate analogs; U.S. Pat. Nos. 4,231,938and 4,444, 784), Cerivastatin (a substituted pyridine; U.S. Pat. No. 5,006,530) are members of the statin class of HMG-CoA reductase inhibitors used as oral treatments for hypercholesterolemia and dyslipidemia. They are structural analogs of the half-reduced intermediate of HMG-CoA and, as such, inhibit the formation of mevalonate.

Compounds such as Pitavastatin and its opened chain form are useful for inhibiting chloesterol biosynthesis and lowering blood cholesterol levels and, as such, are useful in the treatment of atherosclerosis hypercholesterolemia and hyper lipoproteinemia as described in U.S. Pat. No. 5,856,336.

Certain triaryl ethylenes are useful in the treatment of hypercholesterolemia and osteoporosis by acting as selective estrogen receptor modulators. One such derivative, Ospemifene, is described in WO01/36360.

Certain 2,6-dialkylated phenols and their derivatives are useful in the treatment of atherosclerosis and hyperlipedemia through the reduction in the expression of VCAM-1. One such derivative, AGI-1067, is described in U.S. Pat. No. 6,147,250.

Certain trans-6-[2-(3- or 4-carboxamido-substituted pyrrol-1-yl)alkyl]-4-hydroxypyran-2-ones and the corresponding ring-opened acids derived therefrom are potent inhibitors of the enzyme 3-hydroxy-3-methylglutaryl-coenzyme A reductase (HMG CoA reductase) and are thus useful hypolipidemic or hypocholesterolemic agents (U.S. Pat. No. 4,681,893). Atorvastatin, a member of the statin class of HMG-CoA reductase inhibitors, is used as an oral treatment for hypercholesterolemia and dyslipidemia. It is a structural analog of the half-reduced intermediate of HMG-CoA and, as such, inhibits the formation of mevalonate.

Compound ML-236B (U.S. Pat. No. 3,983,140) has been isolated and purified from the metabolic products of microorganisms of the genus *Penicillium*, especially *Penicillium citrinum*. It has been shown to inhibit the biosynthesis of cholesterol by enzymes or cultured cells separated from experimental animals by competing with the rate-limiting enzyme active in the biosynthesis of cholesterol, namely 3-hydroxy-3-methylglutaryl-coenzyme A reductase and, as a result, significantly reduces serum cholesterol levels of animals (*Journal of Antibiotics*, 29:1346 (1976)). A number of compounds structurally related to ML-236B also inhibit the biosynthesis of cholesterol. A series of new compounds, which may be prepared by the enzymatic hydroxylation of ML-236B or of derivatives thereof, possess an ability to inhibit the biosynthesis of cholesterol which is at least comparable with, and in some instances substantially exceeds, that of ML-236B itself, are described in U.S. Pat. No. 4,346, 227.

Humans as well as other animal organisms need insulin, a pancreatic hormone, in order to utilize glucose. Insulin stimulates the movement of the glucose from the blood into tissue cells, especially muscular cells, and expedites the synthesis of fats as well as of proteins in practically all organs. In diabetics, the pancreas does not produce this hormone in sufficient quantity, resulting in glucose levels in the blood elevating, which causes the known symptoms of diabetes mellitus.

Specific sulfonylureas, which may be administered orally, possess a blood sugar reducing effect, especially in those cases were diabetes occurs during old age (see U.S. Pat. No. 4,146,613). Compounds such as Troglitazone and Rosiglitazone can be useful for blood-glucose lowering activity and are therefore of potential use in the treatment and/or prophylaxis of hyperglycaemia and are of particular use in the treatment of Type II diabetes. These compounds are also useful for the treatment and/or prophylaxis of other diseases including hyperlipidaemia, hypertension, and cardiovascular disease, especially atherosclerosis. In addition these compounds are considered to be useful for treating certain eating disorders, in particular the regulation of appetite and food intake in subjects suffering from disorders associated with under-eating, such as anorexia nervosa, and disorders associated with over-eating, such as obesity and anorexia bulimia. (U.S. Pat. No. 6,288,095)

MK-767 (U.S. Pat. No. 6,030,990) is a useful therapeutic agent for the treatment of type-II diabetes. Type-II diabetes is a metabolic disorder characterized by hyperglycemia as well as insulin resistance and/or impaired insulin secretion. MK-767 is a peroxisome proliferator-activated receptor (PPAR) alpha and gamma agonist. There are three isoforms of PPARs, α, β, and γ. Although they have similar insulin-like effects, these isoforms act via different mechanisms in different target tissues (Calkin, A. C. et al., *Current Opinions in Investigational Drugs*, 2003, 4, 4, 444). Experimental data have suggested that drugs combining both PPARα and PPARγ activation may exert a more potent hypotriglyceridemic effect than either compound alone.

Rosiglitazone (U.S. Pat. No. 5,002,953) is a useful therapeutic agent for the treatment of Type II diabetes. Rosiglitazone maleate is an oral antidiabetic agent, which acts primarily by increasing insulin sensitivity. Rosiglitazone improves glycemic control while reducing circulating insulin levels. A number of side effects are associated with rosiglitazone.

Pioglitazone (U.S. Pat. Nos. 5,356,913 and 4,687,777) is a useful therapeutic agent for the treatment of Type II diabetes. Mechanistically, pioglitazone hydrochloride decreases insulin resistance in the periphery and in the liver, resulting in increased insulin-dependent glucose disposal and decreased hepatic glucose output. Pioglitazone hydrochloride, like other thiazolidinediones, can cause fluid retention when used alone or in combination with other antidiabetic agents, including insulin.

R-483 (WO 02/080913) is a useful therapeutic agent for the treatment of Type II diabetes. R-483 is a potent agonist for the peroxisome proliferator-activated receptor-gamma (PPAR-γ).

Tesaglitazar (WO 0140171 and U.S. Pat. No. 6,531,622) is a useful therapeutic agent for the treatment of Type II diabetes. Tesaglitazar is a potent agonist for the peroxisome proliferator-activated receptor-gamma and alpha (PPAR-γ and PPAR-α). Activation of PPAR-γ nuclear hormone receptors improves insulin sensitivity. PPAR-α activation decreases serum triglycerides and increases serum HDL-cholestrol. Hypertriglyceridemia and low serum HDL-cholestrol are characteristic of both diabeticdyslipidemia and insulin resistance syndrome. A potent activator of both PPAR-α and PPAR-γ therefore, could possibly replace two classes of drugs used commonly for Type II diabetes, namely selective PPAR-γ activator such as rosiglitazone and pioglitazone and PPAR-α-activating compounds of the fibrate group, such as bezafibrate and fenofibrate.

Thus, there is a need for therapeutic agents for treating metabolic disorders having improved pharmacological properties, e.g., drugs having improved activity for treating hypercholesterolemia, dyslipidemia, hyperlipoproteinemia, osteoporosis, atherosclerosis, hyperlipedemia, hypolipidemic, hypocholesterolemic, hyperglycaemia, type II diabetes, hypertension, cardiovascular disease, atherosclerosis, eating disorders, anorexia nervosa, obesity and/or anorexia bulimia, and pharmacokinetic properties, including improved oral bioavailability, greater potency and extended effective half-life in vivo. New compounds should have fewer side effects, less complicated dosing schedules, and be orally active. In particular, there is a need for a less onerous dosage regimen, such as one pill, once per day.

Assay methods capable of determining the presence or absence of metabolic disease are of practical utility in the search for treatment as well as for diagnosing the presence of metabolic diseases.

SUMMARY OF THE INVENTION

Intracellular targeting may be achieved by methods and compositions that allow accumulation or retention of biologically active agents inside cells. The present invention provides novel analogs of compounds useful to treat metabolic disorders such as hypercholesterolemia, dyslipidemia, hyperlipoproteinemia, osteoporosis, atherosclerosis, hyperlipedemia, hypolipidemic, hypocholesterolemic, hyperglycaemia, type II diabetes, hypertension, cardiovascular disease, atherosclerosis, eating disorders, anorexia nervosa, obesity and/or anorexia bulimia. Such novel analogs possess all the utilities of the parent compounds and optionally provide cellular accumulation as set forth below. In addition, the present invention provides compositions and methods for treating metabolic disorders or therapeutic activity against metabolic disorders.

The present invention relates generally to the accumulation or retention of therapeutic compounds inside cells. The invention is more particularly related to attaining high concentrations of phosphonate-containing molecules in target cells. Such effective targeting may be applicable to a variety of therapeutic formulations and procedures. Compositions of the invention include compounds for treating metabolic disorders having at least one phosphonate group.

In one embodiment the invention provides a conjugate comprising a compound having activity against a metabolic disease; or a pharmaceutically acceptable salt or solvate thereof.

In another embodiment the invention provides a conjugate, or a pharmaceutically acceptable salt or solvate thereof, that is a compound of any one of formulae 500-523:

500
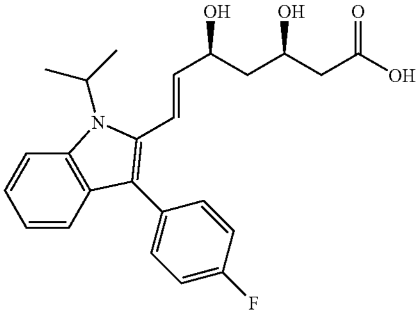
501
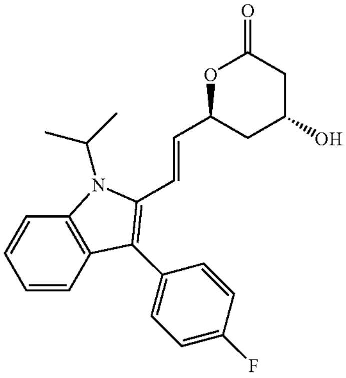
502
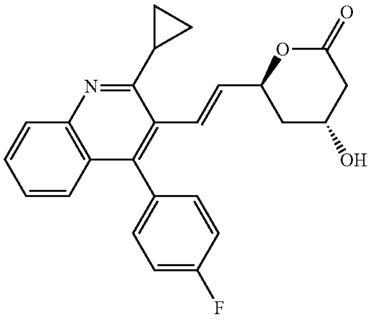
503
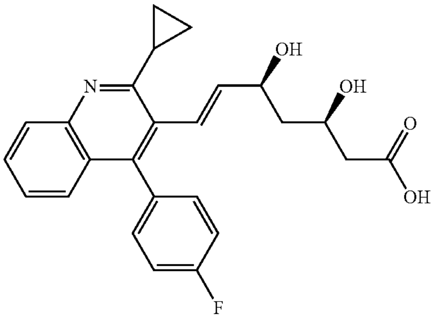
-continued
504
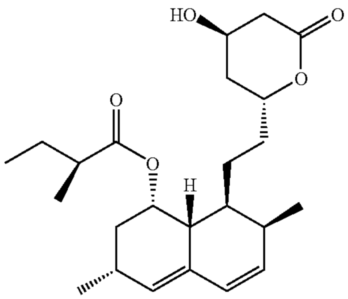
505
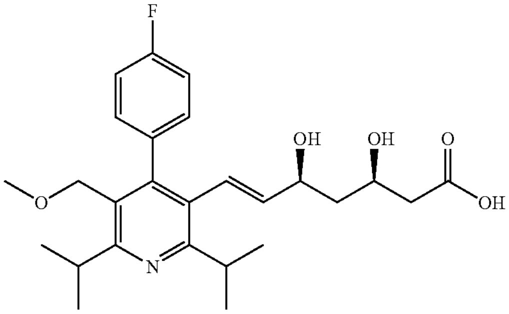
506
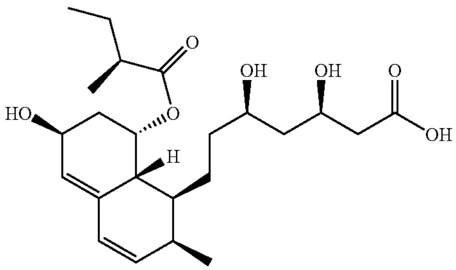
507
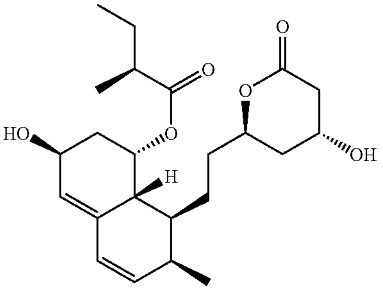

-continued
508
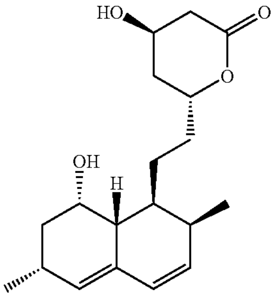
509
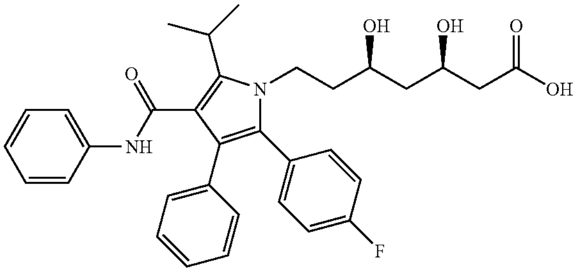
510
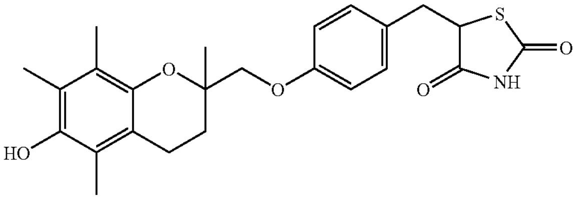
511
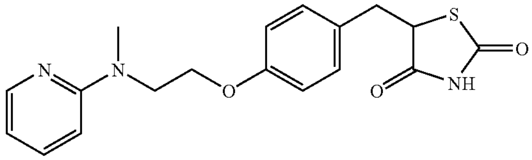
512
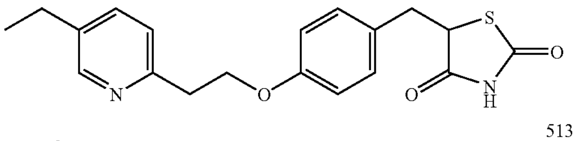
513
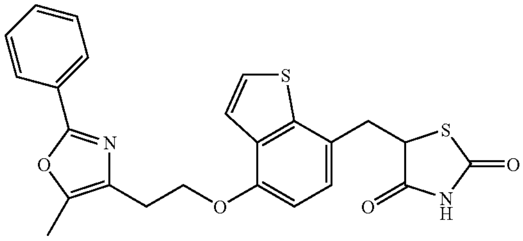
514
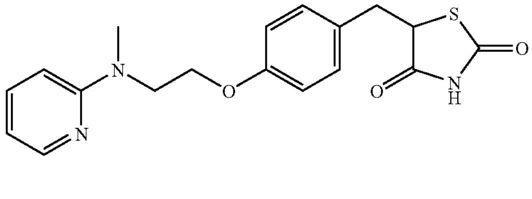
-continued
515
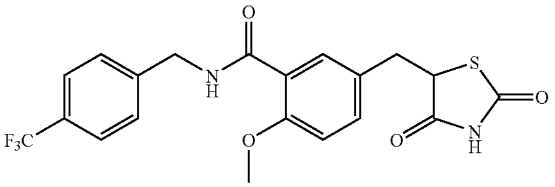
516
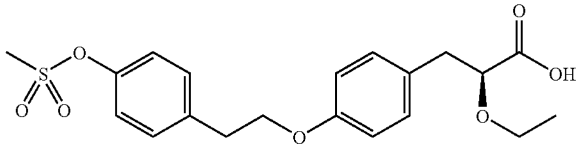
517
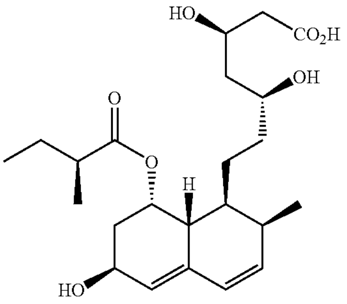
518
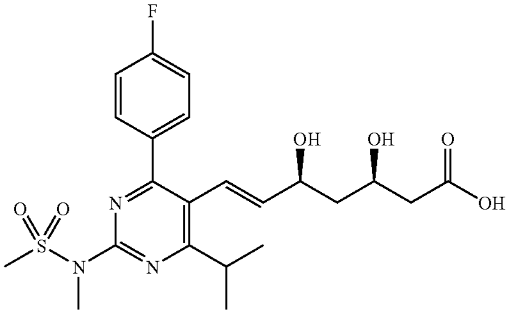
519
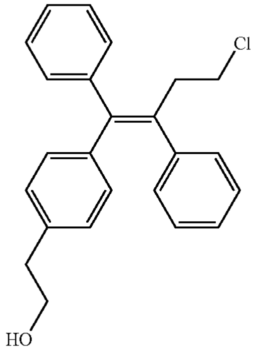
520
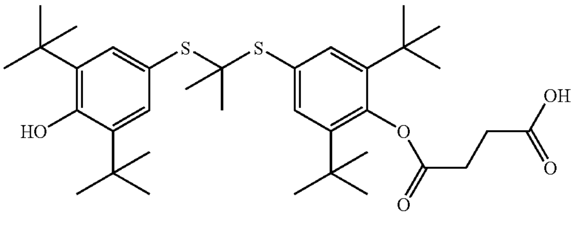

-continued

521

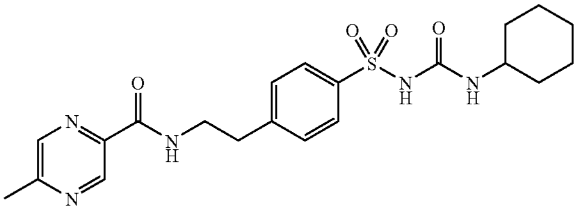

522

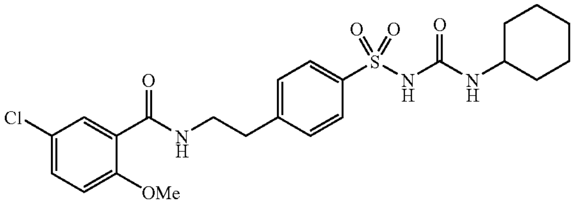

523

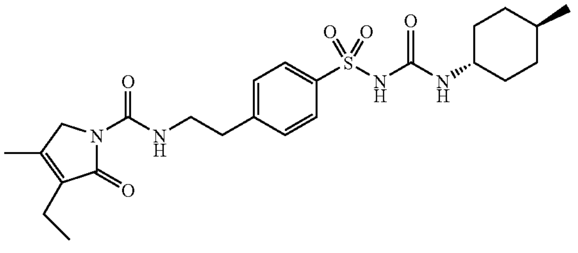

substituted with one or more groups $A^0$;

wherein:

$A^0$ is $A^1$, $A^2$ or $W^3$ with the proviso that the conjugate includes at least one $A^1$;

$A^1$ is:

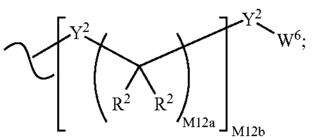

$A^2$ is:

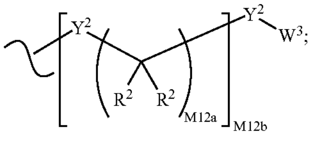

$A^3$ is:

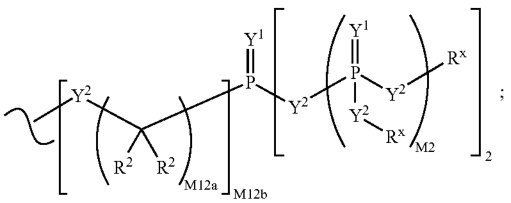

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$; and when $Y^2$ joins two phosphorous atoms $Y^2$ can also be $C(R^2)(R^2)$;

$R^x$ is independently H, $R^1$, $R^2$, $W^3$, a protecting group, or the formula:

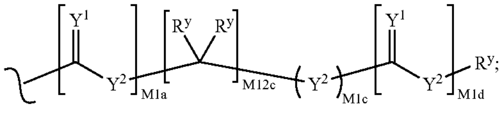

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $—C(Y^1)R^5$, $—C(Y^1)W^5$, $—SO_{M2}R^5$, $—SO_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another embodiment, the invention also provides a conjugate, or a pharmaceutically acceptable salt or solvate thereof, which has the formula:

$$[DRUG]-(A^0)_{nn}$$

wherein:

DRUG is a compound of any one of formulae 500-523; nn is 1, 2, or 3;

$A^0$ is $A^1$, $A^2$ or $W^3$ with the proviso that the conjugate includes at least one $A^1$;

$A^1$ is:

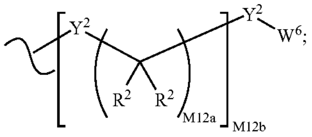

-continued $A^2$ is:

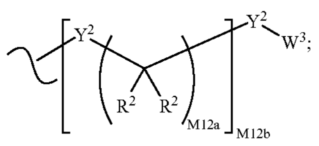

$A^3$ is:

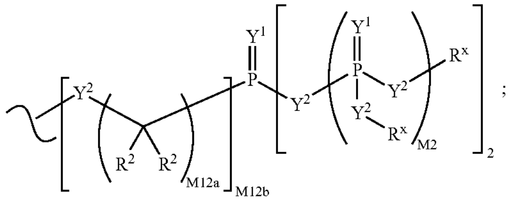

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$; and when $Y^2$ joins two phosphorous atoms $Y^2$ can also be $C(R^2)(R^2)$;

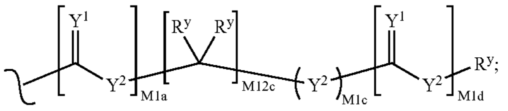

wherein:

$R^1$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)Rx$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $—C(Y^1)R^5$, $—C(Y^1)W^5$, $—SO_{M2}R^5$, or $—SO_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another embodiment, the invention also provides a conjugate which has any one of formulae 1-51:

1

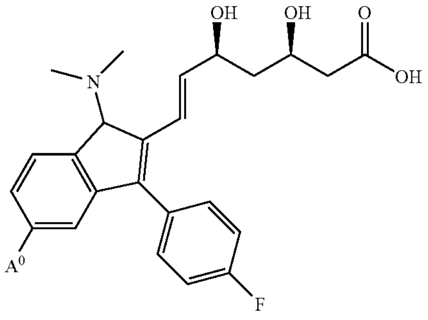

2

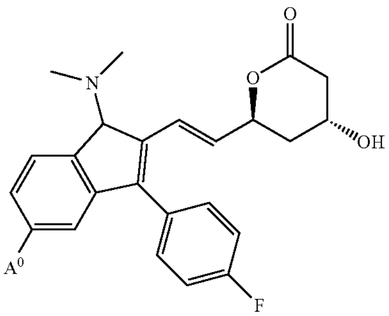

3

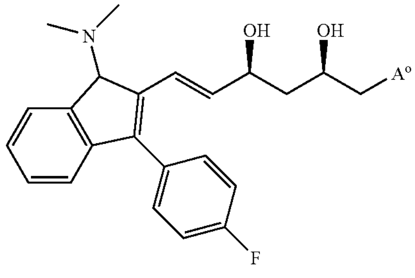

4

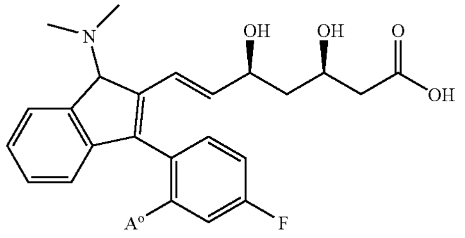

-continued
5
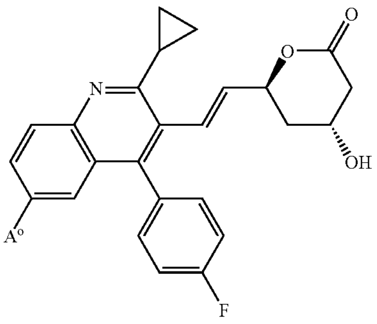
6
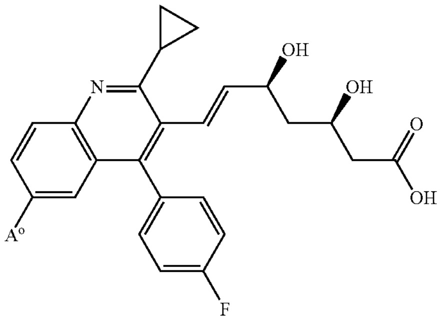
7
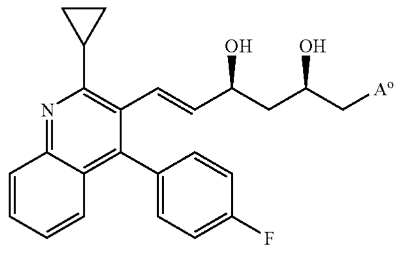
8
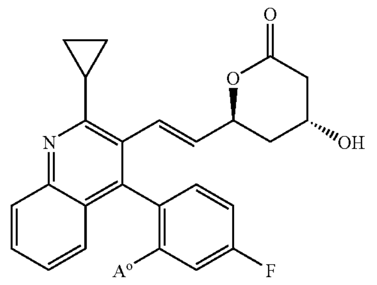
-continued
9
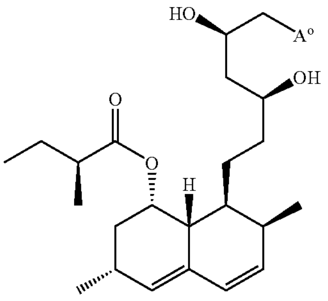
10
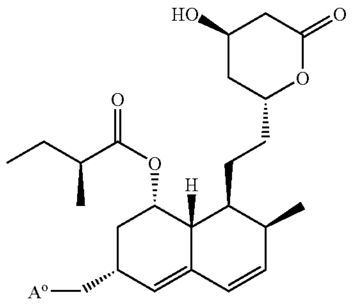
11
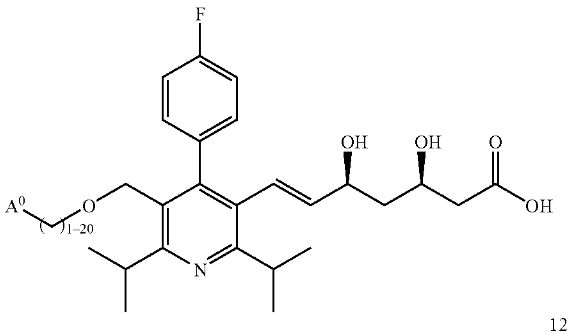
12
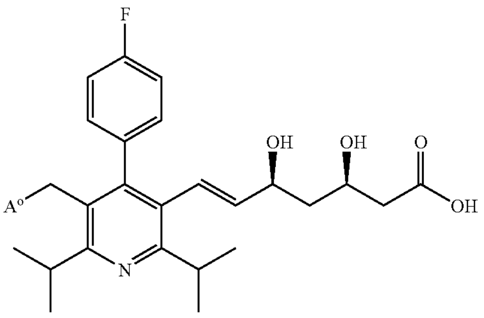
13
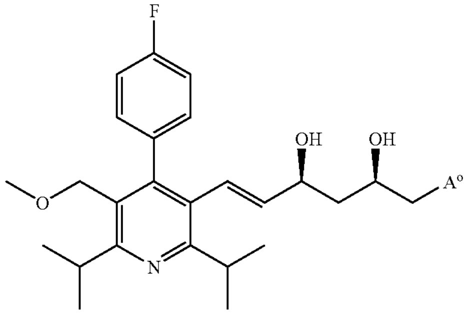

-continued
14
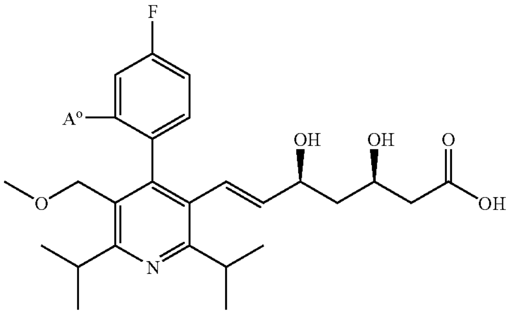
15
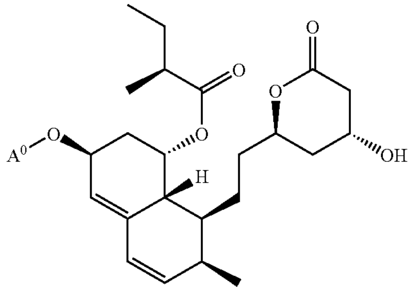
16
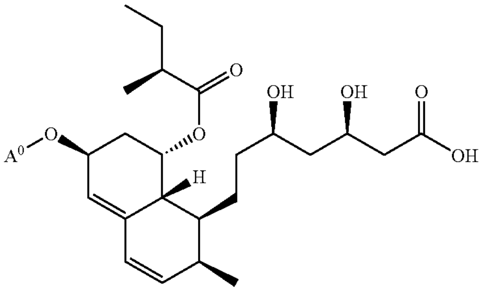
17
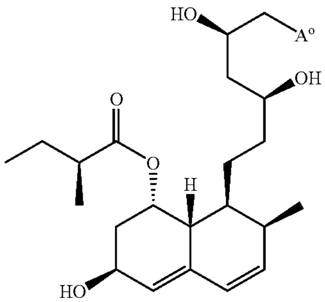
18
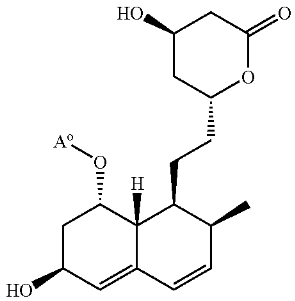
-continued
19
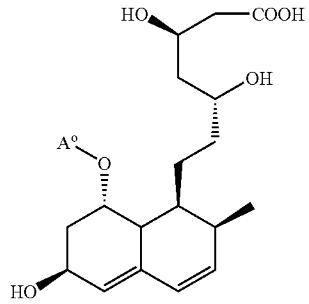
20
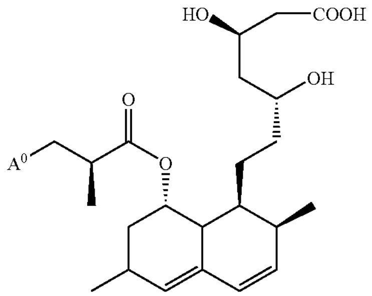
21
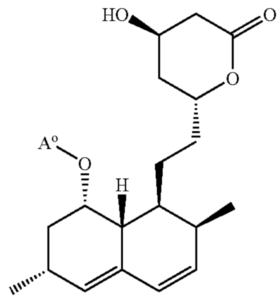
22
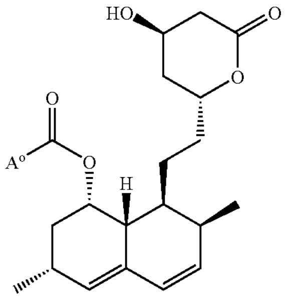
23
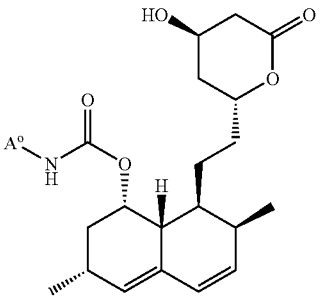

-continued
24
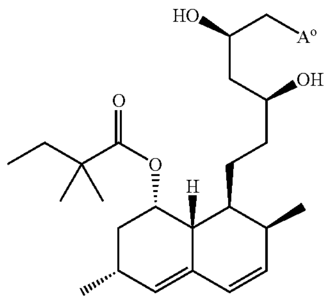
25
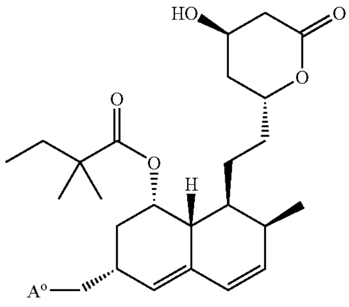
26
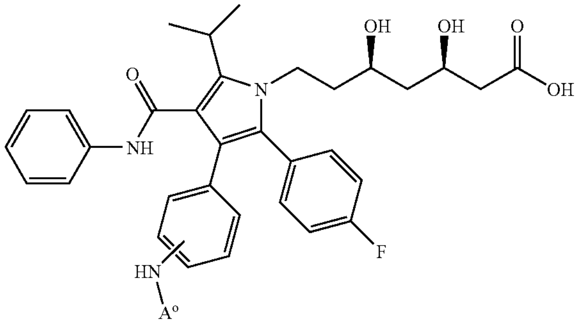
27
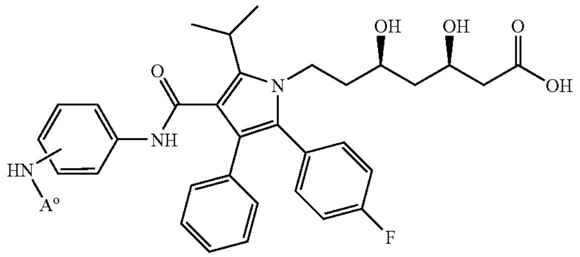
28
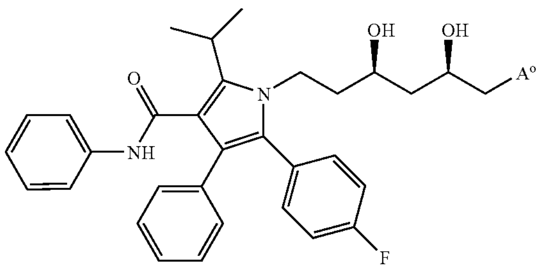
-continued
29
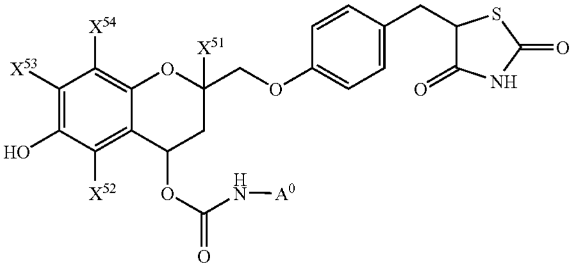
30
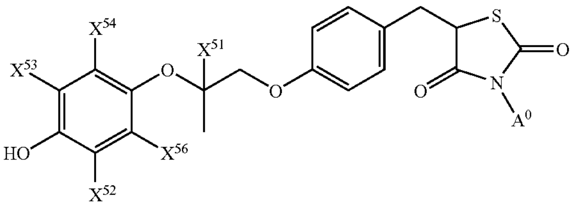
31
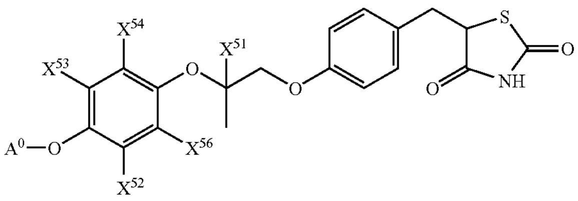
32
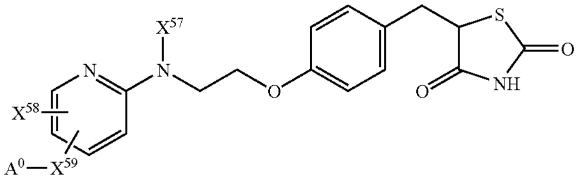
33
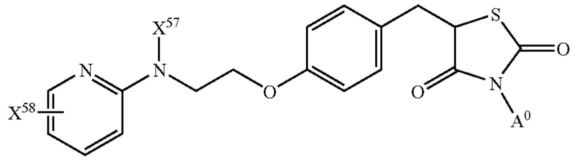
34
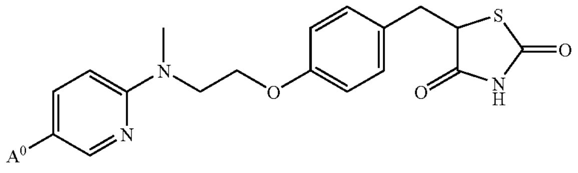

-continued
35
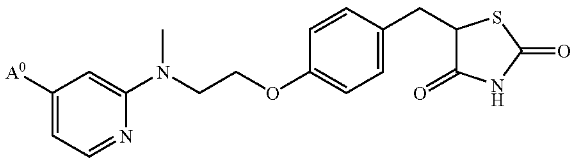
36
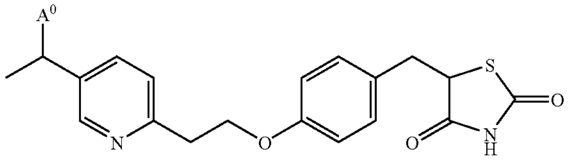
37
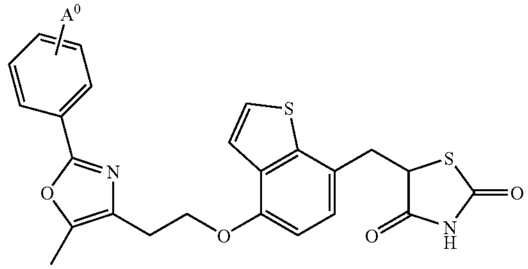
38
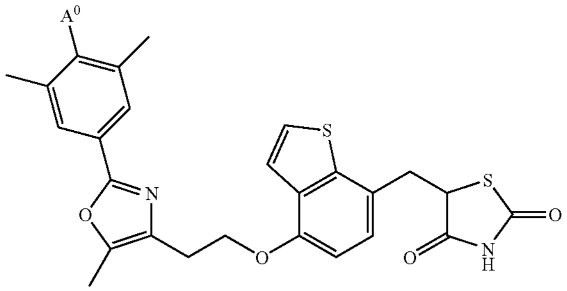
39
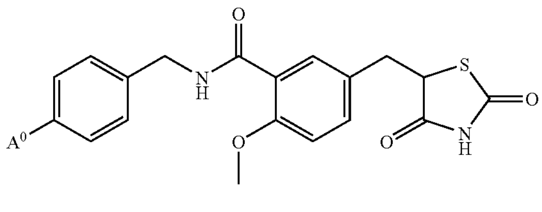
40
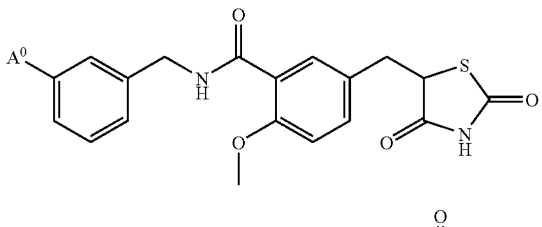
41
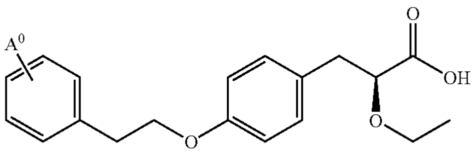
-continued
42
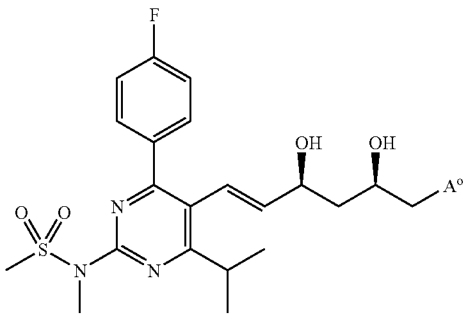
43
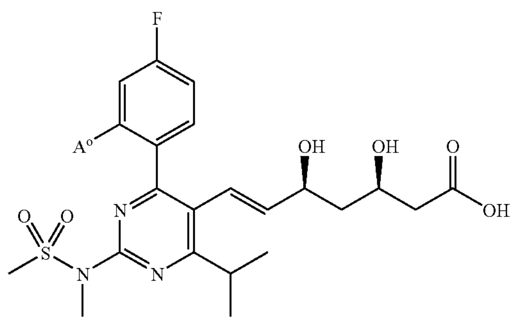
44
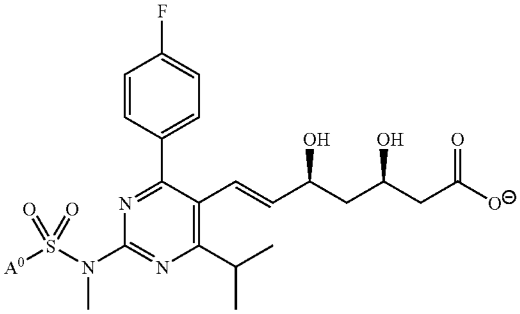
45
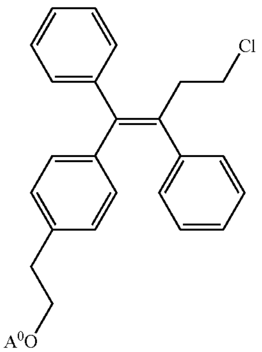
46
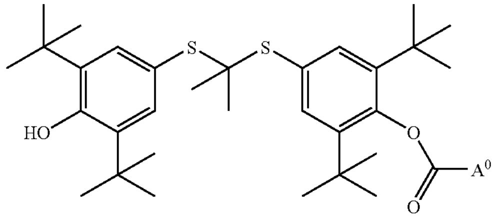

-continued

47

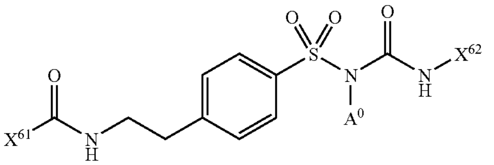

48

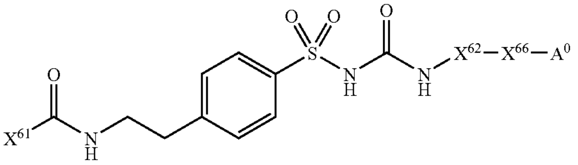

49

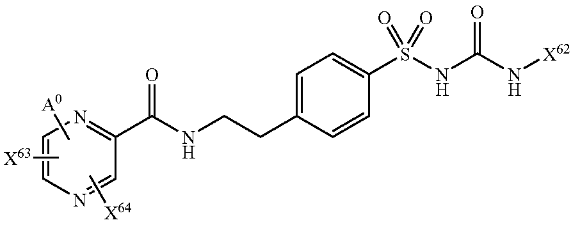

50

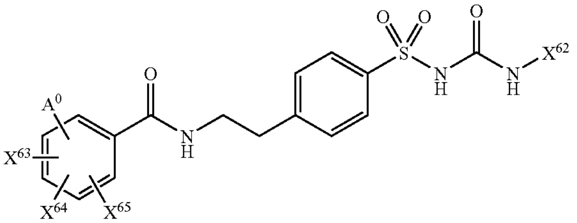

51

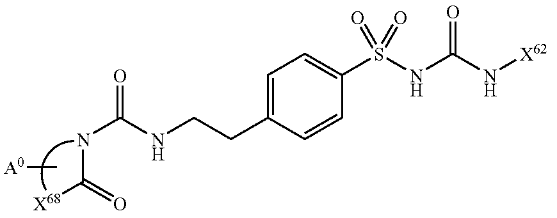

wherein:

$A^0$ is $A^1$;

$A^1$ is:

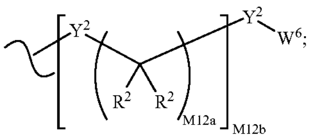

$A^3$ is:

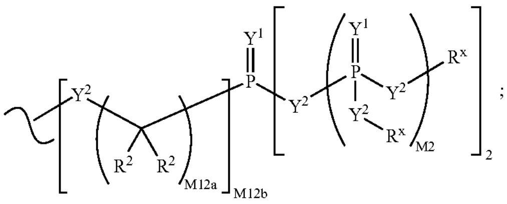

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms $Y^2$ can also be $C(R^2)(R^2)$;

$R^x$ is independently H, $R^2$, $W^3$, a protecting group, or the formula:

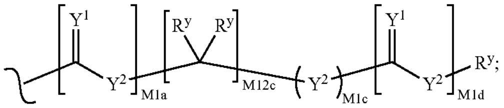

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 A3 groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{51}$ and $X^{52}$ are the same or different and each represents hydrogen or $C_1$-$C_5$ alkyl;

$X^{53}$ and $X^{54}$ are the same or different and each represents hydrogen, a $C_1$-$C_5$ alkyl group or a $C_1$-$C_5$ alkoxy group, or $X^{53}$ and $X^{54}$ together represent a $C_1$-$C_4$ alkylenedioxy group;

$X^{56}$ represents a -$CH_2$ —, >CO or >CH—O $X^{55}$ group;

$X^{55}$ represents hydrogen; $C_1$-$C_6$ aliphatic acyl; ($C_5$-$C_7$ cycloalkane)carbonyl; benzoyl, benzoyl substituted with one to three substituents selected from the group of $C_1$-$C_4$ alkyl, $C_1$-$C_4$ alkoxy, hydroxy, halogen, nitro, amino and di($C_1$-$C_4$ alkyl)amino; naphthoyl; 4-7 membered heterocyclic acyl wherein heterocyclic moiety has O, S or N hetero atoms; phenyl($C_2$-$C_3$)aliphatic acyl; cinnamoyl; ($C_1$-$C_6$ alkoxy)carbonyl; or benzoyloxycarbonyl;

$X^{57}$ represents a hydrogen atom, an alkyl group, an acyl group, an aralkyl group, wherein the aryl moiety may be substituted or unsubstituted, or a substituted or unsubstituted aryl group;

$X^{58}$ represents hydrogen or 1 to 4 optional substituents selected from the group consisting of alkyl, alkoxy, aryl and halogen or $X^{58}$ represents two substituents on adjacent carbon atoms, which substituents together with the carbon atoms to which they are attached form a substituted or unsubstituted aryl group;

$X^{59}$ represents O, $NX^{60}$, $CH_2O$, $CH_2NX^{60}$;

$X^{60}$ represents H or lower alkyl with one or two carbons;

$X^{61}$ is selected from 5 or 6 membered aromatic ring with zero, one, or two heteroatoms with substituents. The substituents of the aromatic ring can be hydrogen, halogen, alkyl and alkoxy of one to six carbon atoms, hydroxy, amino, acetylamino and phenyl, wherein the alkyl, alkoxy and phenyl radicals may be substituted by at least one member selected from the group consisting of halogen, lower alkyl and lower alkoxy;

$X^{62}$ is selected from the group consisting of lower alkyl of one to four carbon atoms, lower alkenyl of one to four carbon atoms, cycloaliphatic and substituted cycloaliphatic, preferably cycloalkyl and substituted cycloalkyl wherein the cyclic ring contains five to eight carbon atoms preferably five to six carbon atoms, and may be substituted by lower alkyl or lower alkoxy;

$X^{63}$, $X^{64}$, and $X^{65}$ are independently selected from the group consisting of hydrogen, halogen, alkyl and alkoxy of one to six carbon atoms, hydroxy, amino, acetylamino and phenyl, wherein the alkyl, alkoxy and phenyl radicals may be substituted by at least one member selected from the group consisting of halogen, lower alkyl and lower alkoxy;

$X^{66}$ is selected from the group consisting of O, N $X^{67}$, $CH_2O$, $CH_2N$ $X^{67}$;

$X^{67}$ is selected from H or lower alkyl with one or two carbons; and $X^{68}$ is selected from alkylene or alkenylene having from 3 to 6 carbon atoms, optionally substituted by up to 3 alkyl groups each having from 1 to 4 carbon atoms, or a phenyl radical; or cycloalkylenealkyl having up to 3 carbon atoms in the alkyl moiety and from 5 to 7 ring carbon atoms, optionally substituted by up to 3 methyl groups.

The invention also provides a pharmaceutical composition comprising an effective amount of a compound of the invention, or a pharmaceutically acceptable salt or solvate thereof, in combination with a pharmaceutically acceptable diluent or carrier.

This invention pertains to a method of increasing cellular accumulation and retention of drug compounds, thus improving their therapeutic and diagnostic value.

The invention also provides a method of treating metabolic disorders comprising administering to a mammal afflicted with a metabolic disorder, an amount of a compound of the invention, or a pharmaceutically acceptable salt or solvate thereof, effective to treat a metabolic disorder, e.g., to inhibit cholesterol synthesis.

The invention also provides a compound of the invention or a pharmaceutically acceptable salt or solvate thereof, for use in medical therapy (preferably for use in treating a metabolic disorder), as well as the use of a compound of the invention for the manufacture of a medicament useful for the treatment of a metabolic disorder.

The invention also provides processes and novel intermediates disclosed herein which are useful for preparing compounds of the invention. Some of the compounds of the invention are useful to prepare other compounds of the invention.

In another aspect of the invention, a metabolic disease is inhibited by a method comprising the step of treating a sample suspected of having a metabolic disease with a compound or composition of the invention.

DETAILED DESCRIPTION OF THE INVENTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When tradenames are used herein, applicants intend to independently include the tradename product and the active pharmaceutical ingredient(s) of the tradename product.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteristics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteristics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the-compound retains a phosphorous having such characteristics.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters $—CH_2OC(=O)R^9$ and acyloxymethyl carbonates $—CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) $—CH_2OC(=O)C(CH_3)_3$. An exemplary acyloxymethyl carbonate prodrug moiety is pivaloyloxymethylcarbonate (POC) $—CH_2OC(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.* 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids.

Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—$CH{=}CH_2$), allyl (—$CH_2CH{=}CH_2$), cyclopentenyl (—$C_5H_7$), and 5-hexenyl (—$CH_2$ $CH_2CH_2CH_2CH{=}CH_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—$C{\equiv}CH$) and propargyl (—$CH_2C{\equiv}CH$).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—$CH{=}CH$—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—$C{\equiv}C$—), propargyl (—$CH_2C{\equiv}C$—), and 4-pentynyl (—$CH_2CH_2CH_2C{\equiv}CH$—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O, —OR, —SR, —$S^-$, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)NRR —$S(=O)_2O^-$, —$S(=O)_2OH$, —$S(=O)_2R$, —$OS(=O)_2OR$, —$S(=O)_2NR$, —S(=O)R, —$OP(=O)O_2RR$, —$P(=O)O_2RR$ —$P(=O)(O^-)_2$, —$P(=O)(OH)_2$, —C(=O)R, —C(=O)X, —C(S)R, —C(O)OR, —$C(O)O^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modem Heterocyclic Chemistry* (W. A. Benjamin, New York, 1968), particularly Chapters 1, 3, 4, 6, 7, and 9; *The Chemistry of Heterocyclic Compounds. A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

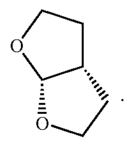

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" refers to a chemical moiety comprising a covalent bond or a chain or group of atoms that covalently attaches a phosphonate group to a drug. Linkers include portions of substituents $A^1$ and $A^3$, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisormers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) are claims of "ether- or ester-forming groups." Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary phosphonate ester-forming group is the phenyl carbocycle in substructure $A_3$ having the formula:

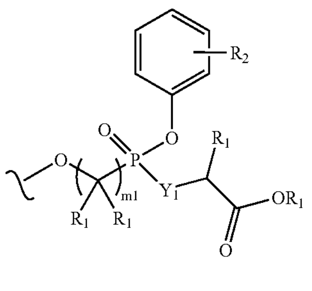

wherein $R_1$ may be H or $C_1$-$C_{12}$ alkyl; m1 is 1, 2, 3, 4, 5, 6, 7 or 8, and the phenyl carbocycle is substituted with 0 to 3 $R_2$ groups. Where $Y_1$ is O, a lactate ester is formed, and where $Y_1$ is $N(R_2)$, $N(OR_2)$ or $N(N(R_2)_2$, a phosphonamidate ester results.

In its ester-forming role, a protecting group typically is bound to any acidic group such as, by way of example and not limitation, a —$CO_2H$ or —C(S)OH group, thereby resulting in —$CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R^1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-,3- and 4-acetylphenyl, 1,8-dihydroxynaphthyl (—$C_{10}H_6$—OH) and aryloxy ethyl [$C_6$-$C_9$ aryl (including phenoxy ethyl)], 2,2'-dihydroxybiphenyl, 2-, 3- and 4-N, N-dialkylaminophenol, —$C_6H_4CH_2$—$N(CH_3)_2$, trimethoxybenzyl, triethoxybenzyl, 2-alkyl pyridinyl ($C_{1-4}$ alkyl);

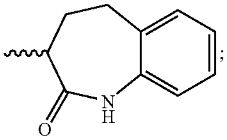 ; 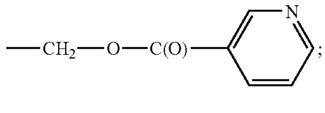 ;

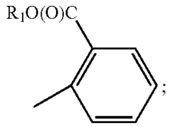 ; $C_4$-$C_8$ esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including —$CH_2$—$CH_2$—O—$CH_3$ (methoxy ethyl)]; alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, $-(CH_2)_2CH_3$, $-(CH_2)_3CH_3$, $-(CH_2)_4CH_3$, $-(CH_2)_5CH_3$, $-CH_2CH_2F$, $-CH_2CH_2Cl$, $-CH_2CF_3$, and $-CH_2CCl_3$);

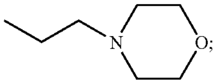

—N-2-propylmorpholino, 2,3-dihydro-6-hydroxyindene, sesamol, catechol monoester, $-CH_2-C(O)-N(R^1)_2$, $-CH_2-S(O)(R^1)$, $-CH_2-S(O)_2(R^1)$, $-CH_2-CH(OC(O)CH_2R^1)-CH_2(OC(O)CH_2R^1)$, cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671);

cyclic carbonates such as (5-$R_d$-2-oxo-1,3-dioxolen-4-yl) methyl esters (Sakamoto et al., *Chem. Pharm. Bull.* (1984) 32(6)2241-2248) where $R_d$ is $R_1$, $R_4$ or aryl; and

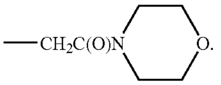

The hydroxyl groups of the compounds of this invention optionally are substituted with one of groups III, IV or V disclosed in WO 94/21604, or with isopropyl.

Table A lists examples of protecting group ester moieties that for example can be bonded via oxygen to —C(O)O— and $-P(O)(O-)_2$ groups. Several amidates also are shown, which are bound directly to —C(O)— or $-P(O)_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| 1. | $-CH_2-C(O)-N(R_1)_2$* |
| 2. | $-CH_2-S(O)(R_1)$ |
| 3. | $-CH_2-S(O)_2(R_1)$ |
| 4. | $-CH_2-O-C(O)-CH_2-C_6H_5$ |
| 5. | 3-cholesteryl |
| 6. | 3-pyridyl |
| 7. | N-ethylmorpholino |
| 8. | $-CH_2-O-C(O)-C_6H_5$ |
| 9. | $-CH_2-O-C(O)-CH_2CH_3$ |
| 10. | $-CH_2-O-C(O)-C(CH_3)_3$ |
| 11. | $-CH_2-CCl_3$ |
| 12. | $-C_6H_5$ |
| 13. | $-NH-CH_2-C(O)O-CH_2CH_3$ |
| 14. | $-N(CH_3)-CH_2-C(O)O-CH_2CH_3$ |
| 15. | $-NHR_1$ |
| 16. | $-CH_2-O-C(O)-C_{10}H_{15}$ |
| 17. | $-CH_2-O-C(O)-CH(CH_3)_2$ |
| 18. | $-CH_2-C\#H(OC(O)CH_2R_1)-CH_2-$ $-(OC(O)CH_2R_1)$* |
| 19. | 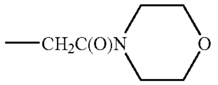 |
| 20. | 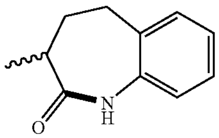 |
| 21. | 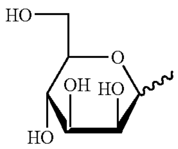 |
| 22. | 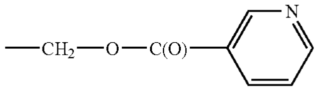 |
| 23. | 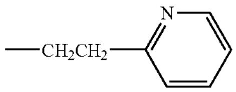 |
| 24. | 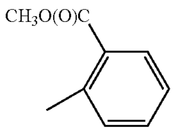 |
| 25. | 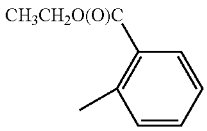 |
| 26. | 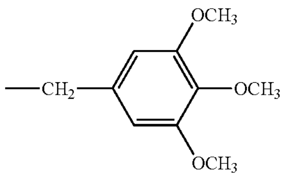 |

#—chiral center is (R), (S) or racemate.

Other esters that are suitable for use herein are described in EP 632048.

Protecting groups also includes "double ester" forming profunctionalities such as $-CH_2OC(O)OCH_3$,

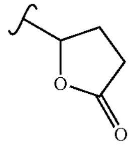

$—CH_2SCOCH_3$, $—CH_2OCON(CH_3)_2$, or alkyl- or aryl-acyloxyalkyl groups of the structure $—CH(R^1$ or $W^5)O((CO)R^{37})$ or $—CH(R^1$ or $W^5)((CO)OR^{38})$ (linked to oxygen of the acidic group) wherein $R^{37}$ and $R^{38}$ are alkyl, aryl, or alkylaryl groups (see U.S. Pat. No. 4,968,788). Frequently $R^{37}$ and $R^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including $—CH(CH_2CH_2OCH_3)OC(O)C(CH_3)_3$,

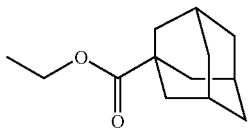 ;

$CH_2OC(O)C_{10}H_{15}$, $—CH_2OC(O)C(CH_3)_3$, $—CH(CH_2OCH_3)OC(O)C(CH_3)_3$, $—CH(CH(CH_3)_2)OC(O)C(CH_3)_3$, $—CH_2OC(O)CH_2CH(CH_3)_2$, $—CH_2OC(O)C_6H_{11}$, $—CH_2OC(O)C_6H_5$, $—CH_2OC(O)C_{10}H_{15}$, $—CH_2OC(O)CH_2CH_3$, $—CH_2OC(O)CH(CH_3)_2$, $—CH_2OC(O)C(CH_3)_3$ and $—CH_2OC(O)CH_2C_6H_5$.

In some claims the protected acidic group is an ester of the acidic group and is the residue of a hydroxyl-containing functionality. In other claims, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under $R^{31}$ or $R^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl;

p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylnethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate,p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-lodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

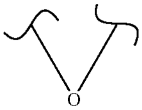

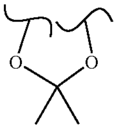

TABLE B-continued

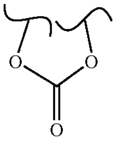

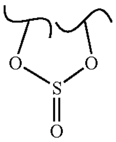

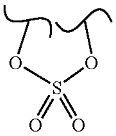

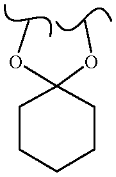

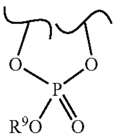

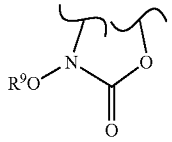

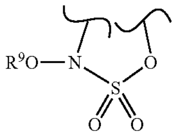

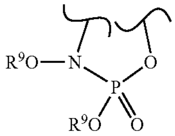

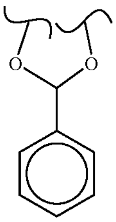

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-lodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N,N'-dimethylaminomethylene, N,-isopropylidene, N-p-nitrobenzylidene, N-salicylidene, N-5-chlorosalicylidene, N-(5-chloro-2-hydroxyphenyl)phenylnethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)$R^1$ or —N=C$R^1$N($R^1$)$_2$. Another protecting group, also useful as a prodrug for amino or —NH($R^5$), is:

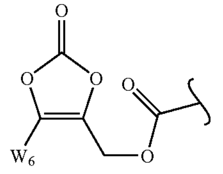

See for example Alexander, J. et al. (1996) *J. Med. Chem.* 39:480-486.

Amino Acid and Polypeptide Protecting Group and Conjugates

An amino acid or polypeptide protecting group of a compound of the invention has the structure $R^{15}NHCH(R^{16})C(O)$—, where $R^{15}$ is H, an amino acid or polypeptide residue, or $R^5$, and $R^{16}$ is defined below.

$R^{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R^{10}$ also is taken together with the amino acid $\alpha_{10}N$ to form a proline residue ($R^{10}$=—$(CH_2)_3$—). However, $R^{10}$ is generally the side group of a naturally-occurring amino acid such as H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—$C(NH_2)$—$NH_2$. $R_{10}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —$NHSO_2R$, NHC(O)R, —$N(R)_2$, $NH_2$ or —NH(R)(H), whereby for example a carboxylic acid is reacted, i.e. coupled, with the amine to form an amide, as in $C(O)NR_2$. A phosphonic acid may be reacted with the amine to form a phosphonamidate, as in —P(O)(OR)($NR_2$).

In general, amino acids have the structure $R^{17}C(O)CH(R^{16})NH$—, where $R^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono-or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at $R^3$ of substituents $A^1$, $A^2$ or $A^3$ in a compound of the invention. These conjugates are produced by forming an amide bond between a carboxyl group of the amino acid (or C-terminal amino acid of a polypeptide for example). Similarly, conjugates are formed between $R^3$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g., by $R^1$, esterified with $R^5$ or amidated. Similarly, the amino side chains $R^{16}$ optionally will be blocked with $R^1$ or substituted with $R^5$.

Such ester or amide bonds with side chain amino or carboxyl groups, like the esters or amides with the parental molecule, optionally are hydrolyzable in vivo or in vitro under acidic (pH <3) or basic (pH >10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g., a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In claims where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, Fl, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$- pro-$X^5$- (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

SPECIFIC EMBODIMENTS OF THE INVENTION

Specific values described for radicals, substituents, and ranges, as well as specific embodiments of the invention described herein, are for illustration only; they do not exclude other defined values or other values within defined ranges.

In one specific embodiment of the invention, the conjugate is a compound that is substituted with one or more phosphonate groups either directly or indirectly through a linker; and that is optionally substituted with one or more groups $A^0$; or a pharmaceutically acceptable salt thereof, wherein:

$A^0$ is $A^1$, $A^2$ or $W^3$;

$A^1$ is:

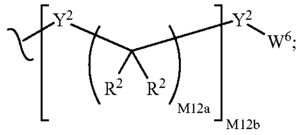

$A^2$ is:

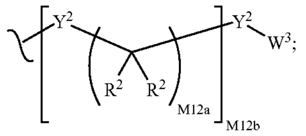

-continued $A^3$ is:

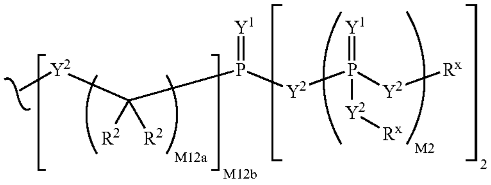

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$ $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $R^1$, $W^3$, a protecting group, or the formula:

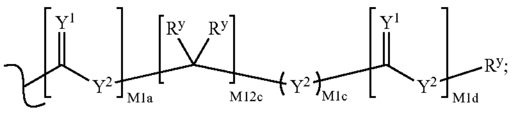

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12 a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment of the invention Al is of the formula:

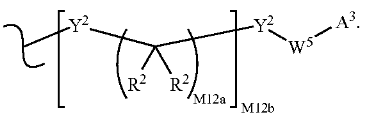

In another specific embodiment of the invention $A^1$ is of the formula:

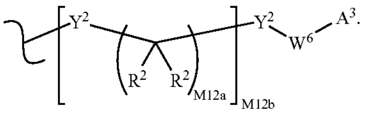

In another specific embodiment of the invention $A^1$ is of the formula:

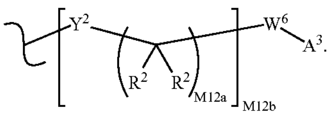

In another specific embodiment of the invention $A^1$ is of the formula:

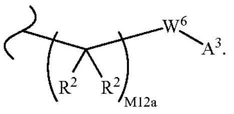

In another specific embodiment of the invention $A^1$ is of the formula:

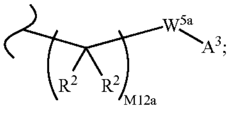

and $W^{5a}$ is a carbocycle or a heterocycle where $W^{5a}$ is independently substituted with 0 or 1 $R^2$ groups. A specific velue for M12a is 1.

In another specific embodiment of the invention $A^1$ is of the formula:

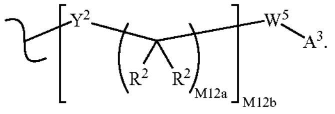

In another specific embodiment of the invention $A^1$ is of the formula:

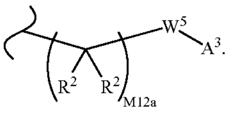

In another specific embodiment of the invention $A^1$ is of the formula:

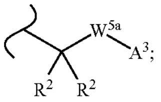

wherein $W^{5a}$ is a carbocycle independently substituted with 0 or 1 $R^2$ groups.

In another specific embodiment of the invention $A^1$ is of the formula:

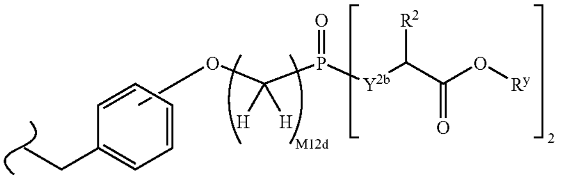

wherein $Y^{2b}$ is O or $N(R^2)$; and M12d is 1, 2, 3, 4, 5, 6, 7 or 8.

In another specific embodiment of the invention $A^1$ is of the formula:

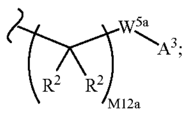

wherein $W^{5a}$ is a carbocycle independently substituted with 0 or 1 $R^2$ groups.

In another specific embodiment of the invention $A^1$ is of the formula:

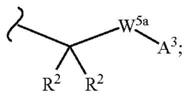

wherein $W^{5a}$ is a carbocycle or heterocycle where $W^{5a}$ is independently substituted with 0 or 1 $R^2$ groups.

In another specific embodiment of the invention $A^1$ is of the formula:

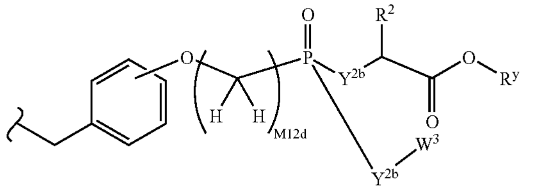

wherein $Y^{2b}$ is O or $N(R^2)$; and M12d is 1, 2, 3, 4, 5, 6, 7 or 8.

In a specific embodiment of the invention $A^2$ is of the formula:

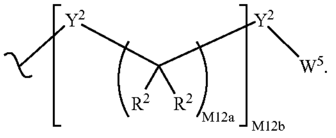

In another specific embodiment of the invention $A^2$ is of the formula:

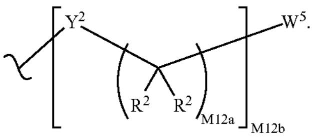

In another specific embodiment of the invention M12b is 1.

In another specific embodiment of the invention e M12b is 0, $Y^2$ is a bond and $W^5$ is a carbocycle or heterocycle where $W^5$ is optionally and independently substituted with 1, 2, or 3 $R^2$ groups.

In another specific embodiment of the invention $A^2$ is of the formula:

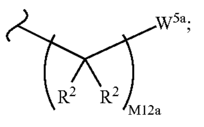

wherein $W^5$, is a carbocycle or heterocycle where $W^{5a}$ is optionally and independently substituted with 1, 2, or 3 $R^2$ groups.

In another specific embodiment of the invention M12a is 1.

In another specific embodiment of the invention $A^2$ is selected from phenyl, substituted phenyl, benzyl, substituted benzyl, pyridyl and substituted pyridyl.

In another specific embodiment of the invention $A^2$ is of the formula:

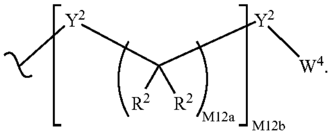

In another specific embodiment of the invention $A^2$ is of the formula:

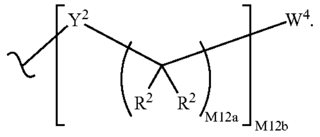

In another specific embodiment of the invention M12b is 1.

In a specific embodiment of the invention $A^3$ is of the formula:

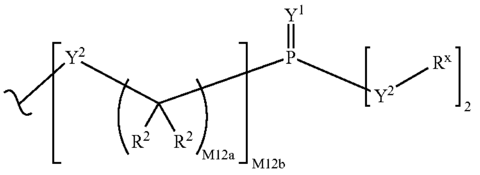

In another specific embodiment of the invention $A^3$ is of the formula:

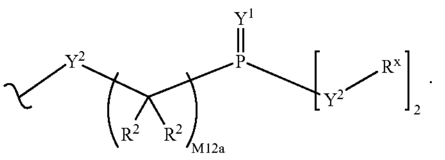

In another specific embodiment of the invention $A^3$ is of the formula:

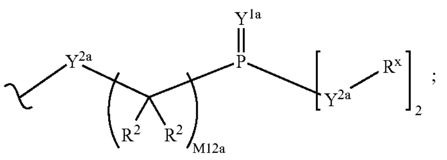

wherein $Y^{1a}$ is O or S; and $Y^{2a}$ is O, $N(R^x)$ or S.

In another specific embodiment of the invention $A^3$ is of the formula:

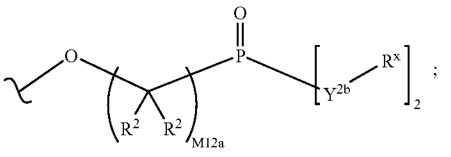

wherein $Y^{2b}$ is O or $N(R^x)$.

In another specific embodiment of the invention $A^3$ is of the formula:

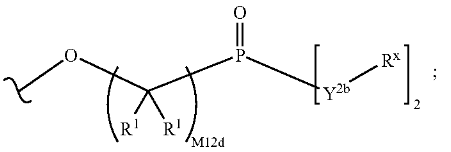

wherein $Y^{2b}$ is O or $N(R^x)$; and M12d is 1, 2, 3, 4, 5, 6, 7 or 8.

In another specific embodiment of the invention $A^3$ is of the formula:

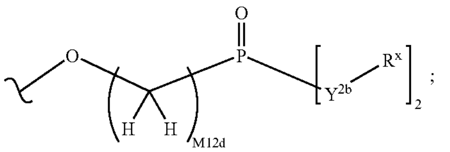

wherein $Y^{2b}$ is O or $N(R^x)$; and M12d is 1, 2, 3, 4, 5, 6, 7 or 8.

In another specific embodiment of the invention M12d is 1.

In another specific embodiment of the invention $A^3$ is of the formula:

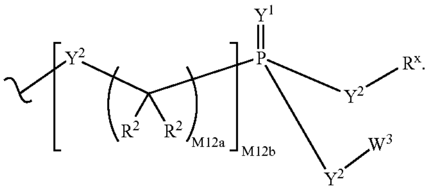

In another specific embodiment of the invention $A^3$ is of the formula:

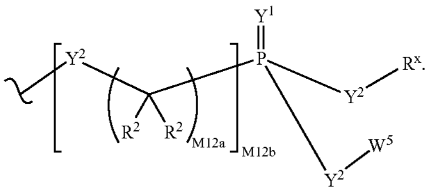

In another specific embodiment of the invention $W^5$ is a carbocycle.

In another specific embodiment of the invention $A^3$ is of the formula:

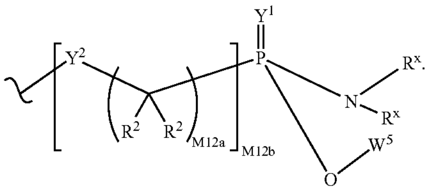

In another specific embodiment of the invention $W^5$ is phenyl.

In another specific embodiment of the invention $A^3$ is of the formula:

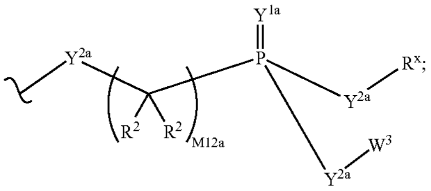

wherein $Y^{1a}$ is O or S; and $Y^{2a}$ is O, $N(R^x)$ or S.

In another specific embodiment of the invention $A^3$ is of the formula:

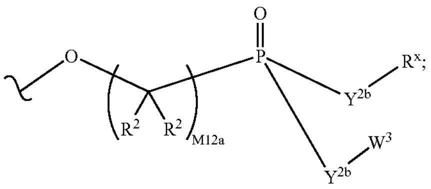

wherein $Y^{2b}$ is O or $N(R^x)$.

In another specific embodiment of the invention $A^3$ is of the formula:

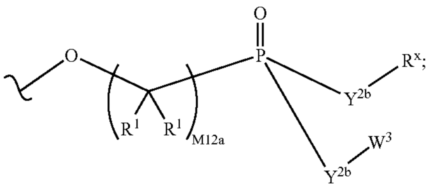

wherein $Y^{2b}$ is O or $N(R^x)$; and M12d is 1, 2, 3, 4, 5, 6, 7 or 8.

In another specific embodiment of the invention $R^1$ is H.

In another specific embodiment of the invention $A^3$ is of the formula:

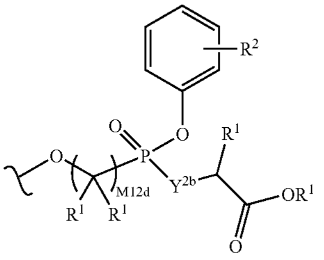

wherein the phenyl carbocycle is substituted with 0, 1, 2, or 3 $R^2$ groups.

In another specific embodiment of the invention $A^3$ is of the formula:

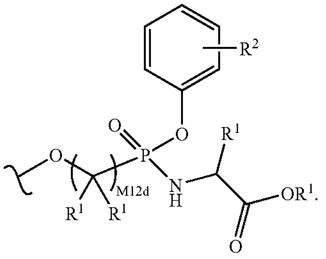

In another specific embodiment of the invention $A^3$ is of the formula:

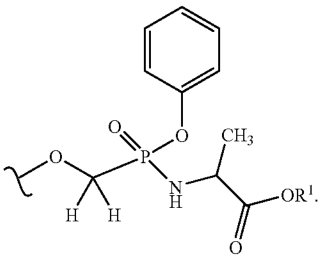

In another specific embodiment of the invention $A^3$ is of the formula:

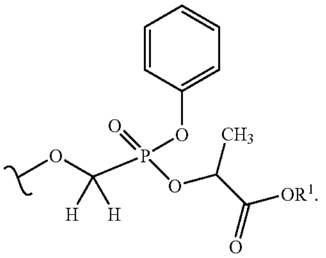

In another specific embodiment of the invention $A^3$ is of the formula:

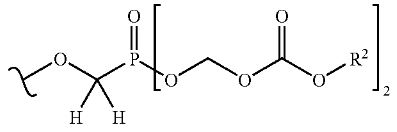

.

In another specific embodiment of the invention $A^3$ is of the formula:

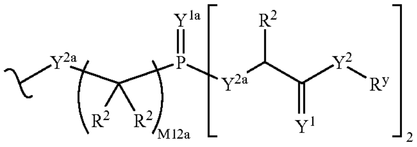

;

wherein $Y^{1a}$ is O or S; and $Y^{2a}$ is O, $N(R^2)$ or S.

In another specific embodiment of the invention $A^3$ is of the formula:

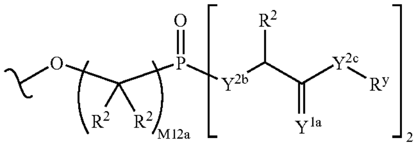

;

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

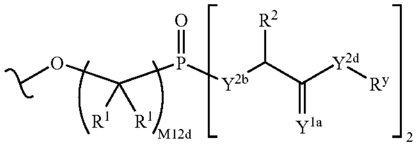

wheren $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

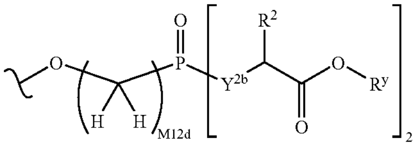

;

wherein $Y^{2b}$ is O or $N(R^2)$; and M12d is 1, 2, 3, 4, 5, 6, 7 or 8.

In another specific embodiment of the invention $A^3$ is of the formula:

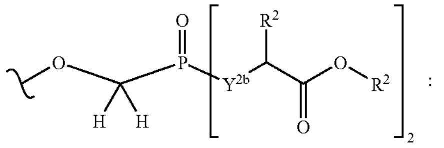

wherein $Y^{2b}$ is O or $N(R^2)$.

In another specific embodiment of the invention $A^3$ is of the formula:

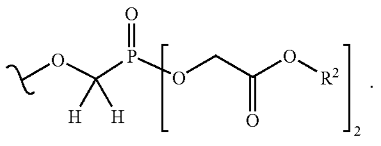

In another specific embodiment of the invention $A^3$ is of the formula:

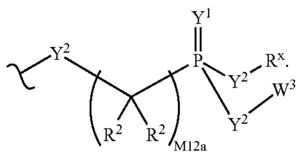

In another specific embodiment of the invention $A^3$ is of the formula:

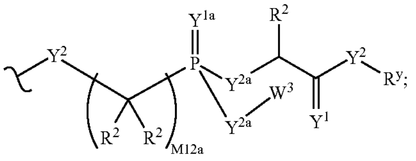

wherein $Y^{1a}$ is O or S; and $Y^{2a}$ is O, $N(R^2)$ or S.

In another specific embodiment of the invention $A^3$ is of the formula:

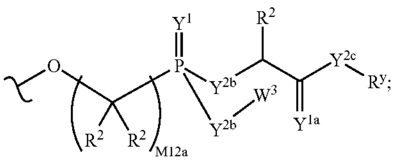

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

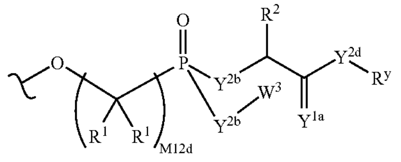

wherein $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

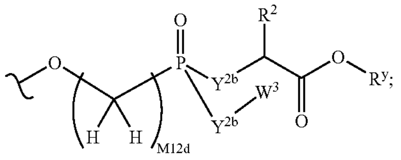

wherein $Y^{2b}$ is O or $N(R^2)$; and M12d is 1, 2, 3, 4, 5, 6, 7 or 8.

In another specific embodiment of the invention $A^3$ is of the formula:

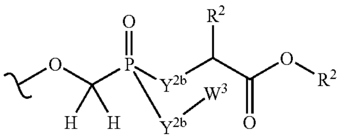

wherein $Y^{2b}$ is O or $N(R^2)$.

In another specific embodiment of the invention $A^3$ is of the formula:

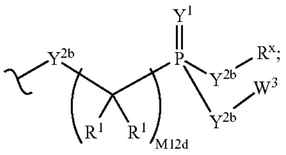

wherein: $Y^{2b}$ is O or $N(R^x)$; and M12d is 1, 2, 3, 4, 5, 6, 7 or 8.

In another specific embodiment of the invention $A^3$ is of the formula:

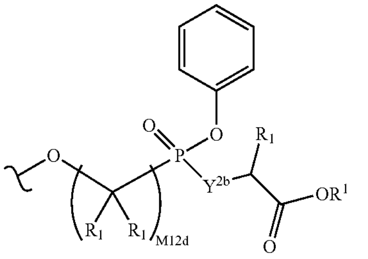

wherein the phenyl carbocycle is substituted with 0, 1, 2, or 3 $R^2$ groups.

In another specific embodiment of the invention $A^3$ is of the formula:

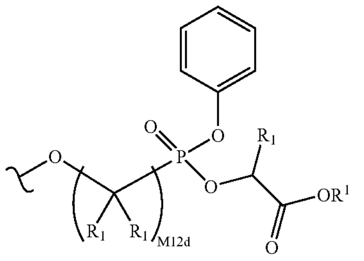

wherein the phenyl carbocycle is substituted with 0, 1, 2, or 3 $R^2$ groups.

In another specific embodiment of the invention $A^3$ is of the formula:

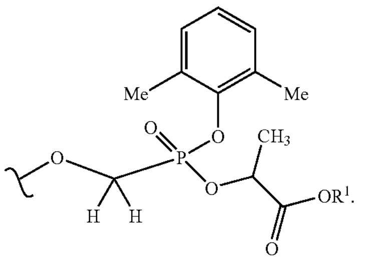

In a specific embodiment of the invention $A^0$ is of the formula:

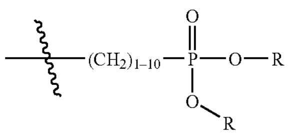

wherein each R is independently ($C_1$-$C_6$)alkyl.

In a specific embodiment of the invention $R^x$ is independently H, $R^1$, $W^3$, a protecting group, or the formula:

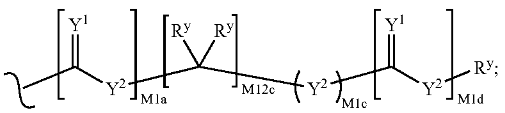

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups.

In a specific embodiment of the invention $R^x$ is of the formula:

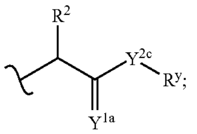

wherein $Y^{1a}$ is O or S; and $Y^{2c}$ is O, N($R^y$) or S.

In a specific embodiment of the invention $R^x$ is of the formula:

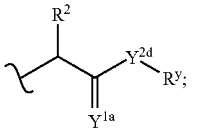

wherein $Y^{1a}$ is O or S; and $Y^{2d}$ is O or N($R^y$).

In a specific embodiment of the invention $R^x$ is of the formula:

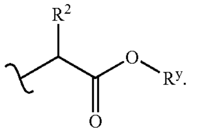

In a specific embodiment of the invention $R^y$ is hydrogen or alkyl of 1 to 10 carbons.

In a specific embodiment of the invention $R^x$ is of the formula:

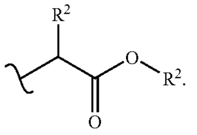

In a specific embodiment of the invention $R^x$ is of the formula:

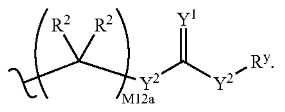

In a specific embodiment of the invention $R^x$ is of the formula:

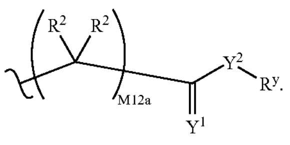

In a specific embodiment of the invention $Y^1$ is O or S.

In a specific embodiment of the invention $Y^2$ is O, N($R^y$) or S.

In one specific embodiment of the invention $R^x$ is a group of the formula:

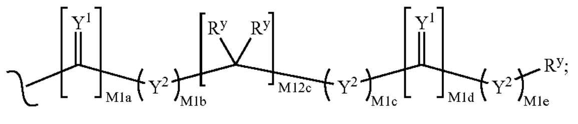

wherein:

m1a, m1b, m1c, m1d and m1e are independently 0 or 1;

m12c is 0, 1, 2, 3, 4, 5, 6, 7, 8, 9, 10, 11 or 12;

$R^y$ is H, $W^3$, $R^2$ or a protecting group;

provided that:

if m1a, m12c, and m1d are 0, then m1b, m1c and m1e are 0;

if m1a and m12c are 0 and m1d is not 0, then m1b and m1c are 0;

if m1a and m1d are 0 and m12c is not 0, then m1b and at least one of m1c and m1e are 0;

if m1a is 0 and m12c and m1d are not 0, then m1b is 0;

if m12c and mid are 0 and m1a is not 0, then at least two of m1b, m1c and m1e are 0;

if m12c is 0 and m1a and m1d are not 0, then at least one of m1b and m1c are 0; and if m1d is 0 and m1a and m12c are not 0, then at least one of m1c and m1e are 0.

In another specific embodiment, the invention provides a compound of the formula:

$[DRUG]\text{-}(A^0)_{nn}$ or a pharmaceutically acceptable salt thereof wherein, DRUG is a compound of any one of formulae 500-523:

nn is 1, 2, or 3;

$A^0$ is $A^1$, $A^2$ or $W^3$ with the proviso that the compound includes at least one $A^1$;

$A^1$ is:

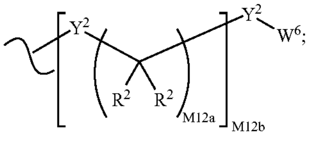

$A^2$ is:

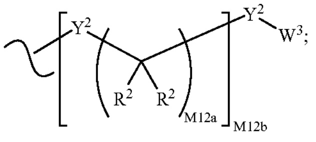

$A^3$ is:

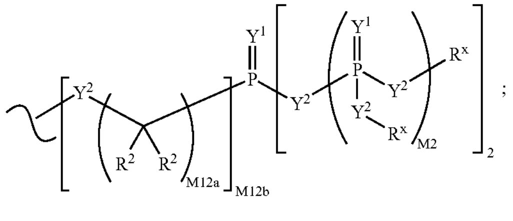

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, N(RX), $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $R^1$, $W^3$, a protecting group, or the formula:

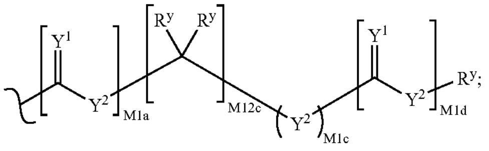

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^3$a is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment, the invention provides a compound of the formula 1-51:

or a pharmaceutically acceptable salt thereof wherein:

$A^0$ is $A^1$;

$A^1$ is:

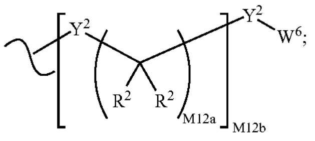

-continued $A^3$ is:

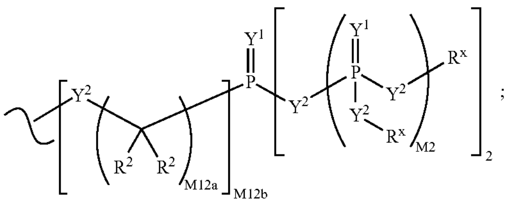

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $W^3$, a protecting group, or the formula:

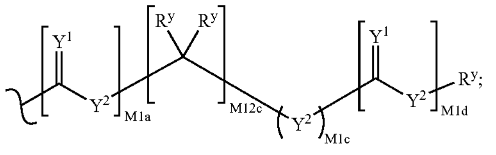

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

The invention also provides a compound of any one of formulae 1-51 wherein:

$A^0$ is $A^1$;

$A^1$ is:

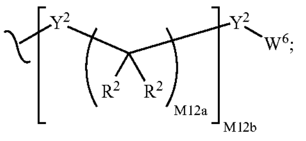

$A^3$ is:

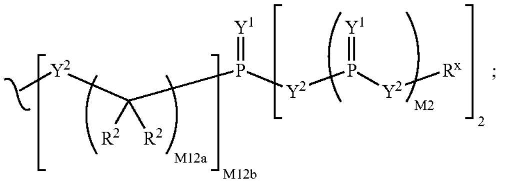

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $W^3$, a protecting group, or the formula:

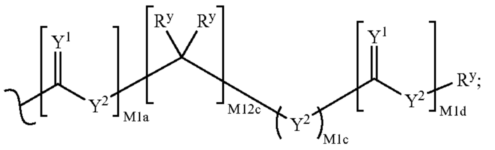

$R^y$ is independently H, $W^3$, R or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 A groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment, the invention provides a compound of the formula:

$$[DRUG]\text{-}[L\text{-}P(=Y^1)—Y^2—R^x]_{nn}$$

or a pharmaceutically acceptable salt thereof wherein,

DRUG is a compound of any one of 500-523;

$Y^1$ is independently O, S, $N(R^x)$, $N(O)(R^x)$, $N(OR^x)$, $N(O)(OR^x)$, or $N(N(R^x)(R^y))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $W^3$, a protecting group, or the formula:

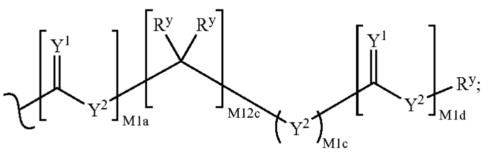

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

nn is 1, 2, or 3; and

L is a linking group.

In another specific embodiment, the invention provides a compound of which is a compound of the formula:

$$[DRUG]\text{-}(A^0)_{nn}$$

or a pharmaceutically acceptable salt thereof wherein,

DRUG is a compound of any one of formulae 500-523;

nn is 1, 2, or 3;

$A^0$ is $A^1$, $A^2$, or $W^3$ with the proviso that the compound includes at least one $A^1$;

$A^1$ is:

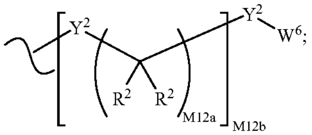

$A^2$ is:

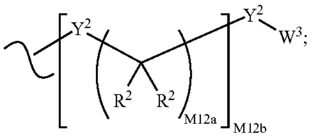

$A^3$ is:

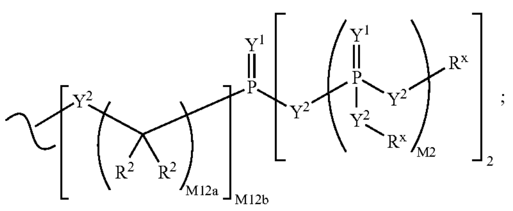

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$;

$R^x$ is independently H, $W^3$, a protecting group, or the formula:

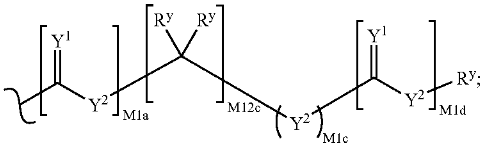

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then R is $R^{3c}$ or $R^{3d}$;

$R^{3a}$ is F, Cl, Br, I, —CN, $N_3$ or $—NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $—C(Y^1)R^5$, $—C(Y^1)W^5$, $—SO_2R^5$, or $—SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In compounds of the invention $W^5$ carbocycles and $W^5$ heterocycles may be independently substituted with 0 to 3 $R^2$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

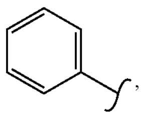, 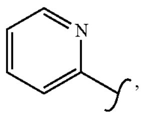, 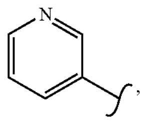,

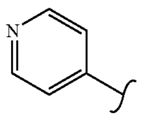, 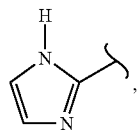, 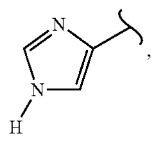,

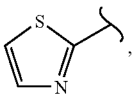, 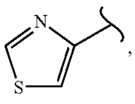, and 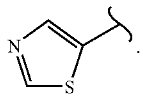.

$W^5$ carbocycles and heterocycles may be independently substituted with 0 to 3 $R^2$ groups, as defined above. For example, substituted $W^5$ carbocycles include:

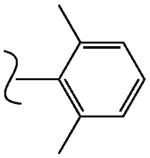 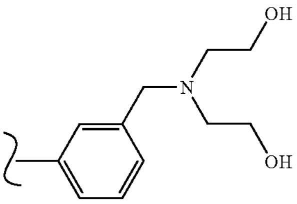

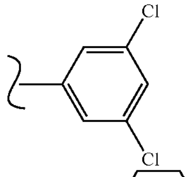 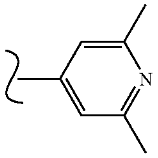

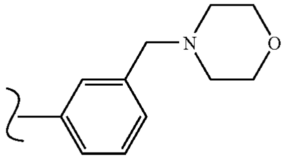 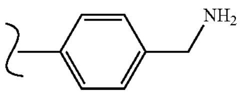

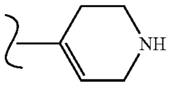 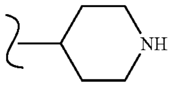 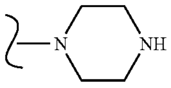

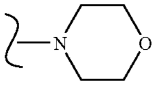 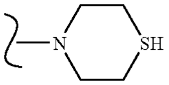 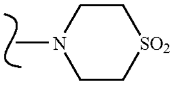

Examples of substituted phenyl carbocycles include:

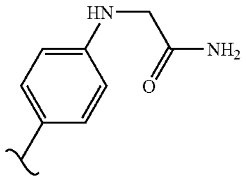 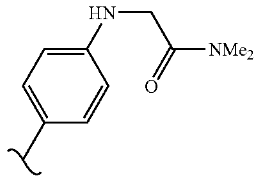

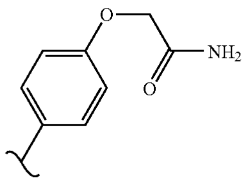 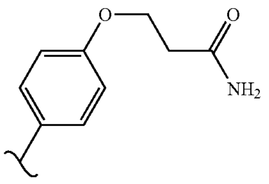

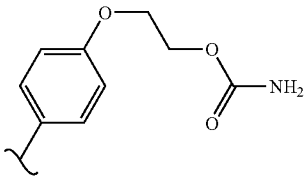

-continued

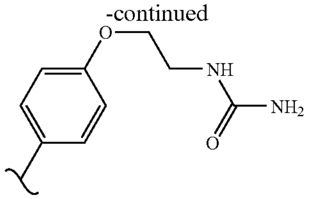

Linking Groups and Linkers

The invention provides conjugates that comprise a compound having activity against one or more metabolic diseases that is linked to one or more phosphonate groups either directly (e.g. through a covalent bond) or through a linking group (i.e. a linker). The nature of the linker is not critical provided it does not interfere with the ability of the phosphonate containing compound to function as a therapeutic agent. The phosphonate or the linker can be linked to the compound (e.g. a compound of 500-523) at any synthetically feasible position on the compound by removing a hydrogen or any portion of the compound to provide an open valence for attachment of the phosphonate or the linker.

In one embodiment of the invention the linking group or linker (which can be designated "L") can include all or a portions of the group $A^0$, $A^1$, $A^2$, or $W^3$ described herein.

In another embodiment of the invention the linking group or linker has a molecular weight of from about 20 daltons to about 400 daltons.

In another embodiment of the invention the linking group or linker has a length of about 5 angstroms to about 300 angstroms. 5 In another embodiment of the invention the linking group or linker separates the DRUG and a $P(=Y^1)$ residue by about 5 angstroms to about 200 angstroms, inclusive, in length.

In another embodiment of the invention the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, hydroxy, oxo (=O), carboxy, aryl, aryloxy, heteroaryl, and heteroaryloxy.

In another embodiment of the invention the linking group or linker is of the formula W-A wherein A is $(C_1$-$C_{24})$alkyl, $(C_2$-$C_{24})$alkenyl, $(C_2$-$C_{24})$alkynyl, $(C_3$-$C_8)$cycloalkyl, $(C_6$-$C_{10})$aryl or a combination thereof, wherein W is —N(R)C(=O)—, —C(=O)N(R)—, —OC(=O)—, —C(=O)O—, —O—, —S—, —S(O)—, $—S(O)_2—$, —N(R)—, —C(=O)—, or a direct bond; wherein each R is independently H or $(C_1$-$C_6)$alkyl.

In another embodiment of the invention the linking group or linker is a divalent radical formed from a peptide.

In another embodiment of the invention the linking group or linker is a divalent radical formed from an amino acid.

In another embodiment of the invention the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment of the invention the linking group or linker is of the formula $W—(CH_2)_n$ wherein, n is between about 1 and about 10; and W is —N(R)C(=O)—, —C(=O)N(R)—, —OC(=O)—, —C(=O)O—, —O—, —S—, —S(O)—, $—S(O)_2—$, —C(=O)—, —N(R)—, or a direct bond; wherein each R is independently H or $(C_1$-$C_6)$alkyl.

In another embodiment of the invention the linking group or linker is methylene, ethylene, or propylene.

In another embodiment of the invention the linking group or linker is attached to the phosphonate group through a carbon atom of the linker.

Intracellular Targeting

The phosphonate group of the compounds of the invention may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in a compound of the invention thus affords an unstable intermediate which releases a negatively charged "locked in" intermediate.

After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect are achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

From the foregoing, it will be apparent that many different drugs can be derivatized in accord with the present invention. Numerous such drugs are specifically mentioned herein. However, it should be understood that the discussion of drug families and their specific members for derivatization according to this invention is not intended to be exhaustive, but merely illustrative.

Compounds for Treating Metabolic Diseases

The compounds of the invention include those that are useful in treating metabolic diseases. Metabolic diseases include, but are not limited to, hypercholesterolemia, dyslipidemia, hyperlipoproteinemia, osteoporosis, atherosclerosis, hyperlipedemia, hypolipidemic, hypocholesterolemic, hyperglycaemia, type II diabetes, hypertension, cardiovascular disease, atherosclerosis, eating disorders, anorexia nervosa, obesity and/or anorexia bulimia. In some embodiments, the compounds are useful for treating diabetes, e.g, type II diabetes, and/or high cholesterol and those conditions caused by and/or associated with high cholesterol. The compounds of the inventions bear one or more (e.g. 1, 2, 3, or 4) phosphonate groups, which may be a prodrug moiety.

The term compounds of the invention include those compounds that are useful for treating at least one metabolic disease. In particular, the compounds include Fluvastatin, pitavastatin, ospemifene, AGI-1067, lovastatin, cerivastatin, pravastatin, simvastatin, atorvastatin, sulfonylurea, troglitazone, rosiglitazone, pioglitazone, R-483, MK-767, tesaglitazar, and rosuvastatin.

Typically, compounds of the invention have a molecular weight of from about 400 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a logD (polarity) less than about 5. In one embodiment the invention provides compounds having a logD less than about 4; in another one embodiment the invention provides compounds having a logD less than about 3; in another one embodiment the invention provides compounds having a logD greater than about −5; in another one embodiment the invention provides compounds having a logD greater than about −3; and in another one embodiment the invention provides compounds having a logD greater than about 0 and less than about 3.

Selected substituents within the compounds of the invention are present to a recursive degree. In this context, "recursive substituent" means that a substituent may recite another instance of itself. Because of the recursive nature of such substituents, theoretically, a large number may be present in any given claim. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain claims. Typically, each of these may independently occur 20, 19, 18, 17, 16, 15, 14, 13, 12, 11, 10, 9, 8, 7, 6, 5, 4, 3, 2, 1, or 0, times in a given claim. More typically, each of these may independently occur 12 or fewer times in a given claim. More typically yet, $W^3$ will occur 0 to 8 times, $R^y$ will occur 0 to 6 times and $R^3$ will occur 0 to 10 times in a given claim. Even more typically, $W^3$ will occur 0 to 6 times, $R^y$ will occur 0 to 4 times and $R^3$ will occur 0 to 8 times in a given claim.

Recursive substituents are an intended aspect of the invention. One of ordinary skill in the art of medicinal chemistry understands the versatility of such substituents. To the degree that recursive substituents are present in an claim of the invention, the total number will be determined as set forth above.

Whenever a compound described herein is substituted with more than one of the same designated group, e.g., "$R^1$" or "$R^{6a}$", then it will be understood that the groups may be the same or different, i.e., each group is independently selected. Wavy lines indicate the site of covalent bond attachments to the adjoining groups, moieties, or atoms.

The phosphonate group may be a phosphonate prodrug moiety. The prodrug moiety may be sensitive to hydrolysis, such as, but not limited to, a pivaloyloxymethyl carbonate (POC) or POM group. Alternatively, the prodrug moiety may be sensitive to enzymatic potentiated cleavage, such as a lactate ester or a phosphonamidate-ester group.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

In one embodiment of the invention, the compound is not an anti-inflammatory compound; in another embodiment of the invention the compound is not an anti-infective; in another embodiment of the invention the compound is not a compound that is active against immune-mediated conditions; in another embodiment of the invention the compound is not a compound that is not an antimetabolite; in another embodiment of the invention the compound is not an antiviral agent; in another embodiment of the invention the compound is not a nucleoside; in another embodiment of the invention the compound is not a IMPDH inhibitor; in another embodiment of the invention the compound is not a kinase inhibitor; in another embodiment of the invention the compound is not a PNP inhibitor; in another embodiment of the invention the compound is a substituted compound of formula 519; in another embodiment of the invention the compound is not a substituted compound of formula 510; in another embodiment of the invention the compound is not a compound of any one of formulae 29-31; in another embodiment of the invention the compound is not a compound of formula 45.

Cellular Accumulation

In one embodiment, the invention provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this claim may further comprise a phosphonate or phosphonate prodrug. More typically, the phosphonate or phosphonate prodrug can have the structure $A^3$ as described herein.

Typically, compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment of the invention the intracellular half-life of a metabolite of the compound in human PBMCs is improved when compared to an analog of the compound not having the phosphonate or phosphonate prodrug. In such claims, the metabolite may be generated intracellularly, e.g.

generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the iinvention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Treating Metabolic Diseases

Another aspect of the invention relates to methods of treating a metabolic disease comprising the step of treating a sample suspected of exhibiting a phenotype of the disease with a composition of the invention.

Compositions of the invention may be used to treat metabolic diseases, as intermediates for such compounds or have other utilities as described below. The compositions will bind to locations on the surface or in a cavity of a target, e.g., an enzyme, having a unique geometry. Compositions binding may bind with varying degrees of reversibility. Those compounds binding substantially irreversibly are ideal candidates for use in this method of the invention. Once labeled, the substantially irreversibly binding compositions are useful as probes for the detection of target involved in and/or associated with the metabolic disease. Accordingly, the invention relates to methods of detecting such binding in a sample comprising the steps of: treating a sample with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity after application of the composition can be observed by any method including direct and indirect methods of detecting activity, e.g., enzymatic activity. Quantitative, qualitative, and semiquantitative methods of determining such activity are all contemplated. Typically one of the screening methods described above are applied, however, any other method such as observation of the physiological properties of a living organism are also applicable.

Many organisms suffer from metabolic diseases such as diabetes. The compounds of this invention are useful in the treatment or prophylaxis of such conditions in animals or in man.

However, in screening compounds it should be kept in mind that the results of enzyme assays may not correlate with cell culture assays. Thus, a cell based assay should be the primary screening tool.

Screens for Useful Compounds and Compositions

Compositions of the invention are screened for activity by any of the conventional techniques for evaluating enzyme activity. Within the context of the invention, typically compositions are first screened in vitro and compositions showing appropriate activity are then screened for activity in vivo.

Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, the examples describe suitable in vitro assays. For example, biological activity of compounds of the invention can be assessed by HMG-CoA reductase inhibition (*J. Biol. Chem*., 269: 6810 (1994)). Representative compounds of the invention were found to have biological activity when measured by this assay.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl pahnitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of metabolic diseases as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no effective activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry Third Edition*, (John Wiley & Sons, New York, 1985), *Comprehensive Organic Synthesis. Selectivity Strategy & Efficiency in Modern Organic Chemistry. In 9 Volumes*, Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

Schemes and Examples

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr*., 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem*. 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), aracemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr*. 513:375-378). Enriched or purified enantiomers can be distinguished by methods used to distinguish other chiral molecules with asymmetric carbon atoms, such as optical rotation and circular dichroism.

EXAMPLES GENERAL SECTION

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. For example, the interconversion of various phosphonate compounds of the invention is illustrated below.

Interconversions of the Phosphonates R-LINK-P(O)($OR^1$)$_2$, R-LINK-P(O)($OR^1$)(OH) AND R-LINK-P(O)(OH)$_2$.

The following schemes 32-38 described the preparation of phosphonate esters of the general structure R-link-P(O)($OR^1$)$_2$, in which the groups $R^1$ may be the same or different. The $R^1$ groups attached to a phosphonate ester, or to precursors thereto, may be changed using established chemical transformations. The interconversion reactions of phosphonates are illustrated in Scheme S32. The group R in Scheme 32 represents the substructure, i.e. the drug "scaffold, to which the substituent link-P(O)($OR^1$)$_2$ is attached, either in the compounds of the invention, or in precursors thereto. At the point in the synthetic route of conducting a phosphonate interconversion, certain functional groups in R may be protected. The methods employed for a given phosphonate transformation depend on the nature of the substituent $R^1$, and of the substrate to which the phosphonate group is attached. The preparation and hydrolysis of phosphonate esters is described in *Organic Phosphorus Compounds*, G. M. Kosolapoff, L. Maeir, eds, Wiley, 1976, p. 9ff.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem*. 35:1650). Chlorophosphonates are made by oxidation of the corresponding chlorophospholanes (Anderson, et al, (1984) *J. Org. Chem*. 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I*, 1577). Chlorophosphonate species may also be generated in situ from corresponding cyclic phosphites (Silverburg, et al., (1996) *Tetrahedron lett*., 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron lett*., 29:5763-66).

Phosphonate prodrugs of the present invention may also be prepared from the free acid by Mitsunobu reactions (Mitsunobu, (1981) *Synthesis*, 1; Campbell, (1992) *J. Org. Chem.* 57:6331), and other acid coupling reagents including, but not limited to, carbodiimides (Alexander, et al, (1994) *Collect. Czech. Chem. Commun.* 59:1853; Casara et al, (1992) *Bioorg. Med. Chem. Lett.* 2:145; Ohashi et al, (1988) *Tetrahedron lett.*, 29:1189), and benzotriazolyloxytris-(dimethylamino) phosphonium salts (Campagne et al (1993) *Tetrahedron lett.* 34:6743).

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis et al (1987) *J. Am. Chem. Soc.* 109:2831; Lu et al (1987) *Synthesis* 726). In another method, aryl phosphonate esters are prepared from aryl phosphates under anionic rearrangement conditions (Melvin (1981) *Tetrahedron lett.* 22:3375; Casteel et al (1991) *Syntheses*, 691). N-Alkoxy aryl salts with alkali met al derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The conversion of a phosphonate diester S32.1 into the corresponding phosphonate monoester S32.2 (Scheme 32, Reaction 1) is accomplished by a number of methods. For example, the ester S32.1 in which $R^1$ is an aralkyl group such as benzyl, is converted into the monoester compound S32.2 by reaction with a tertiary organic base such as diazabicyclooctane (DABCO) or quinuclidine, as described in *J. Org. Chem.* (1995) 60:2946. The reaction is performed in an inert hydrocarbon solvent such as toluene or xylene, at about 110° C. The conversion of the diester S32.1 in which $R^1$ is an aryl group such as phenyl, or an alkenyl group such as allyl, into the monoester S32.2 is effected by treatment of the ester S32.1 with a base such as aqueous sodium hydroxide in acetonitrile or lithium hydroxide in aqueous tetrahydrofuran. Phosphonate diesters S32.1 in which one of the groups $R^1$ is aralkyl, such as benzyl, and the other is alkyl, is converted into the monoesters S32.2 in which $R^1$ is alkyl by hydrogenation, for example using a palladium on carbon catalyst. Phosphonate diesters in which both of the groups $R^1$ are alkenyl, such as allyl, is converted into the monoester S32.2 in which $R^1$ is alkenyl, by treatment with chlorotris(triphenylphosphine) rhodium (Wilkinson's catalyst) in aqueous ethanol at reflux, optionally in the presence of diazabicyclooctane, for example by using the procedure described in *J. Org. Chem.* (1973) 38:3224, for the cleavage of allyl carboxylates.

The conversion of a phosphonate diester S32.1 or a phosphonate monoester S32.2 into the corresponding phosphonic acid S32.3 (Scheme 32, Reactions 2 and 3) can be effected by reaction of the diester or the monoester with trimethylsilyl bromide, as described in *J. Chem. Soc., Chem. Comm.*, (1979) 739. The reaction is conducted in an inert solvent such as, for example, dichloromethane, optionally in the presence of a silylating agent such as bis(trimethylsilyl)trifluoroacetamide, at ambient temperature. A phosphonate monoester S32.2 in which $R^1$ is aralkyl such as benzyl, is converted into the corresponding phosphonic acid S32.3 by hydrogenation over a palladium catalyst, or by treatment with hydrogen chloride in an ethereal solvent such as dioxane. A phosphonate monoester S32.2 in which $R^1$ is alkenyl such as, for example, allyl, is converted into the phosphonic acid S32.3 by reaction with Wilkinson's catalyst in an aqueous organic solvent, for example in 15% aqueous acetonitrile, or in aqueous ethanol, for example using the procedure described in *Helv. Chim. Acta.* (1985) 68:618. Palladium catalyzed hydrogenolysis of phosphonate esters S32.1 in which $R^1$ is benzyl is described in *J. Org. Chem.* (1959) 24:434. Platinum-catalyzed hydrogenolysis of phosphonate esters S32.1 in which $R^1$ is phenyl is described in *J. Am. Chem. Soc.* (1956) 78:2336.

The conversion of a phosphonate mono ester S32.2 into a phosphonate diester S32.1 (Scheme 32, Reaction 4) in which the newly introduced $R^1$ group is alkyl, aralkyl, haloalkyl such as chloroethyl, or aralkyl is effected by a number of reactions in which the substrate S32.2 is reacted with a hydroxy compound $R^1OH$, in the presence of a coupling agent. Typically, the second phosphonate ester group is different than the first introduced phosphonate ester group, i.e. $R^1$ is followed by the introduction of $R^2$ where each of $R^1$ and $R^2$ is alkyl, aralkyl, haloalkyl such as chloroethyl, or aralkyl (Scheme 32, Reaction 4a) whereby S32.2 is converted to S32.1a. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester S32.2 to the diester S32.1 is effected by the use of the Mitsunobu reaction, as described above. The substrate is reacted with the hydroxy compound $R^1OH$, in the presence of diethyl azodicarboxylate and a triarylphosphine such as triphenyl phosphine. Alternatively, the phosphonate monoester S32.2 is transformed into the phosphonate diester S32.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester S32.2 is transformed into the chloro analog $RP(O)(OR^1)Cl$ by reaction with thionyl chloride or oxalyl chloride and the like, as described in *Organic Phosphorus Compounds*, G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester S32.1.

A phosphonic acid R-link-$P(O)(OH)_2$ is transformed into a phosphonate monoester $RP(O)(OR^1)(OH)$ (Scheme 32, Reaction 5) by means of the methods described above of for the preparation of the phosphonate diester R-link-$P(O)(OR_1)_2$ S32.1, except that only one molar proportion of the component $R^1OH$ or $R^1Br$ is employed. Dialkyl phosphonates may be prepared according to the methods of: Quast et al (1974) *Synthesis* 490; Stowell et al (1990) *Tetrahedron Lett.* 3261; U.S. Pat. No. 5,663,159.

A phosphonic acid R-link-P(O)(OH)$_2$ S32.3 is transformed into a phosphonate diester R-link-P(O)(OR$^1$)$_2$ S32.1 (Scheme 32, Reaction 6) by a coupling reaction with the hydroxy compound R$^1$OH, in the presence of a coupling agent such as Aldrithiol-2 (Aldrich) and triphenylphosphine. The reaction is conducted in a basic solvent such as pyridine. Alternatively, phosphonic acids S32.3 are transformed into phosphonic esters S32.1 in which R$^1$ is aryl, by means of a coupling reaction employing, for example, dicyclohexylcarbodiimide in pyridine at ca 70° C. Alternatively, phosphonic acids S32.3 are transformed into phosphonic esters S32.1 in which R$^1$ is alkenyl, by means of an alkylation reaction. The phosphonic acid is reacted with the alkenyl bromide R$^1$Br in a polar organic solvent such as acetonitrile solution at reflux temperature, the presence of a base such as cesium carbonate, to afford the phosphonic ester S32.1.

Scheme 32

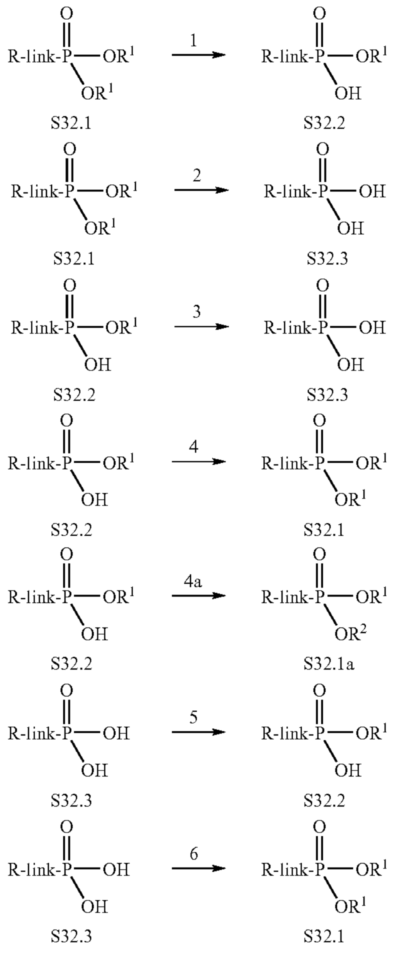

S32.1 → S32.2; S32.1 → S32.3; S32.2 → S32.3; S32.2 → S32.1; S32.2 → S32.1a; S32.3 → S32.2; S32.3 → S32.1

Preparation of Phosphonate Carbamates

Phosphonate esters may contain a carbamate linkage. The preparation of carbamates is described in *Comprehensive Organic Functional Group Transformations*, A. R. Katritzky, ed., Pergamon, 1995, Vol. 6, p. 416ff, and in *Organic Functional Group Preparations*, by S. R. Sandler and W. Karo, Academic Press, 1986, p. 260ff. The carbamoyl group may be formed by reaction of a hydroxy group according to the methods known in the art, including the teachings of Ellis, US 2002/0103378 A1 and Hajima, U.S. Pat. No. 6,018,049.

Scheme 33 illustrates various methods by which the carbamate linkage is synthesized. As shown in Scheme 33, in the general reaction generating carbamates, an alcohol S33.1, is converted into the activated derivative S33.2 in which Lv is a leaving group such as halo, imidazolyl, benztriazolyl and the like, as described herein. The activated derivative S33.2 is then reacted with an amine S33.3, to afford the carbamate product S33.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroformyl derivative of the alcohol S33.5. In this procedure, the alcohol S33.5 is reacted with phosgene, in an inert solvent such as toluene, at about 0° C., as described in *Org. Syn. Coll. Vol.* 3, 167, 1965, or with an equivalent reagent such as trichloromethoxy chloroformate, as described in *Org. Syn. Coll. Vol.* 6, 715, 1988, to afford the chloroformate S33.6. The latter compound is then reacted with the amine component S33.3, in the presence of an organic or inorganic base, to afford the carbamate S33.7. For example, the chloroformyl compound S33.6 is reacted with the amine S33.3 in a water-miscible solvent such as tetrahydrofuran, in the presence of aqueous sodium hydroxide, as described in *Org. Syn. Coll. Vol.* 3, 167, 1965, to yield the carbamate S33.7. Alternatively, the reaction is performed in dichloromethane in the presence of an organic base such as diisopropylethylamine or dimethylaminopyridine.

Scheme 33, Example 2 depicts the reaction of the chloroformate compound S33.6 with imidazole to produce the imidazolide S33.8. The imidazolide product is then reacted with the amine S33.3 to yield the carbamate S33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in *J. Med. Chem.*, 1989, 32, 357.

Scheme 33 Example 3, depicts the reaction of the chloroformate S33.6 with an activated hydroxyl compound R"OH, to yield the mixed carbonate ester S33.10. The reaction is conducted in an inert organic solvent such as ether or dichloromethane, in the presence of a base such as dicyclohexylamine or triethylamine. The hydroxyl component R"OH is selected from the group of compounds S33.19-S33.24 shown in Scheme 33, and similar compounds. For example, if the component R"OH is hydroxybenztriazole S33.19, N-hydroxysuccinimide S33.20, or pentachlorophenol, S33.21, the mixed carbonate S33.10 is obtained by the reaction of the chloroformate with the hydroxyl compound in an ethereal solvent in the presence of dicyclohexylamine, as described in *Can. J. Chem.*, 1982, 60, 976. A similar reaction in which the component R"OH is pentafluorophenol S33.22 or 2-hydroxypyridine S33.23 is performed in an ethereal solvent in the presence of triethylamine, as described in *Syn.*, 1986, 303, and *Chem. Ber.* 118, 468, 1985.

Scheme 33 Example 4 illustrates the preparation of carbamates in which an alkyloxycarbonylimidazole S33.8 is employed. In this procedure, an alcohol S33.5 is reacted with an equimolar amount of carbonyl diimidazole S33.11 to prepare the intermediate S33.8. The reaction is conducted in an aprotic organic solvent such as dichloromethane or tetrahydrofuran. The acyloxyimidazole S33.8 is then reacted with an equimolar amount of the amine R'NH$_2$ to afford the carbamate S33.7. The reaction is performed in an aprotic organic solvent such as dichloromethane, as described in *Tet. Lett.*, 42, 2001, 5227, to afford the carbamate S33.7.

Scheme 33, Example 5 illustrates the preparation of carbamates by means of an intermediate alkoxycarbonylbenztriazole S33.13. In this procedure, an alcohol ROH is reacted at ambient temperature with an equimolar amount of benztriazole carbonyl chloride S33.12, to afford the alkoxycarbonyl product S33.13. The reaction is performed in an organic solvent such as benzene or toluene, in the presence of a tertiary organic amine such as triethylaamine, as described in *Synthesis.*, 1977, 704. The product is then reacted with the amine $R'NH_2$ to afford the carbamate S33.7. The reaction is conducted in toluene or ethanol, at from ambient temperature to about 80° C. as described in *Synthesis.*, 1977, 704.

Scheme 33, Example 6 illustrates the preparation of carbamates in which a carbonate $(R''O)_2CO$, S33.14, is reacted with an alcohol S33.5 to afford the intermediate alkyloxycarbonyl intermediate S33.15. The latter reagent is then reacted with the amine $R'NH_2$ to afford the carbamate S33.7. The procedure in which the reagent S33.15 is derived from hydroxybenztriazole S33.19 is described in *Synthesis*, 1993, 908; the procedure in which the reagent S33.15 is derived from N-hydroxysuccinimide S33.20 is described in *Tet. Lett.*, 1992, 2781; the procedure in which the reagent S33.15 is derived from 2-hydroxypyridine S33.23 is described in *Tet. Lett.*, 1991, 4251; the procedure in which the reagent S33.15 is derived from 4-nitrophenol S33.24 is described in *Synthesis*. 1993, 103. The reaction between equimolar amounts of the alcohol ROH and the carbonate S33.14 is conducted in an inert organic solvent at ambient temperature.

Scheme 33, Example 7 illustrates the preparation of carbamates from alkoxycarbonyl azides S33.16. In this procedure, an alkyl chloroformate S33.6 is reacted with an azide, for example sodium azide, to afford the alkoxycarbonyl azide S33.16. The latter compound is then reacted with an equimolar amount of the amine $R'NH_2$ to afford the carbamate S33.7. The reaction is conducted at ambient temperature in a polar aprotic solvent such as dimethylsulfoxide, for example as described in *Synthesis.*, 1982, 404.

Scheme 33, Example 8 illustrates the preparation of carbamates by means of the reaction between an alcohol ROH and the chloroformyl derivative of an amine S33.17. In this procedure, which is described in *Synthetic Organic Chemistry*, R. B. Wagner, H. D. Zook, Wiley, 1953, p. 647, the reactants are combined at ambient temperature in an aprotic solvent such as acetonitrile, in the presence of a base such as triethylamine, to afford the carbamate S33.7.

Scheme 33, Example 9 illustrates the preparation of carbamates by means of the reaction between an alcohol ROH and an isocyanate S33.18. In this procedure, which is described in *Synthetic Organic Chemistry*, R. B. Wagner, H. D. Zook, Wiley, 1953, p. 645, the reactants are combined at ambient temperature in an aprotic solvent such as ether or dichloromethane and the like, to afford the carbamate S33.7.

Scheme 33, Example 10 illustrates the preparation of carbamates by means of the reaction between an alcohol ROH and an amine $R'NH_2$. In this procedure, which is described in *Chem. Lett.* 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate S33.7.

Scheme 33. Preparation of carbamates.

General reaction

ROH S33.1 → ROCOLv S33.2 —($R'NH_2$ S33.3)→ ROCONHR' S33.4

EXAMPLES (1):

ROH S33.5 → ROCOCl S33.6 —($R'NH_2$ S33.3)→ ROCONHR' S33.7

(2)

ROH S33.5

ROCOCl S33.6

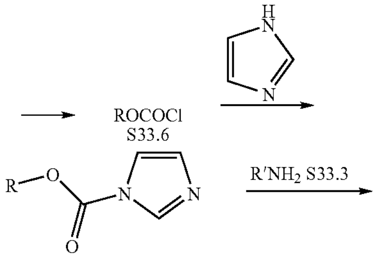

ROCONHR' S33.7

S33.8

(3)

ROH S33.5 → ROCOCl S33.6 —(R"OH S33.9)→ ROCOOR" S33.10 —($R'NH_2$ S33.3)→ ROCONHR' S33.7

(4)

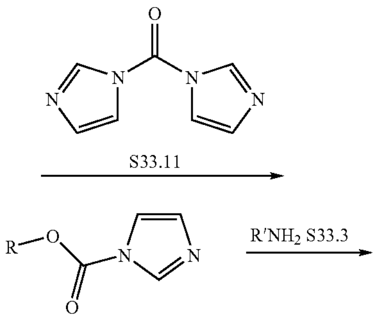

S33.11

ROH S33.5

ROCONHR' S33.7

S33.8

(5)

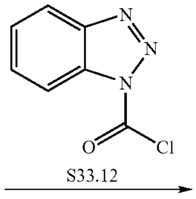

S33.12

ROH S33.5

-continued

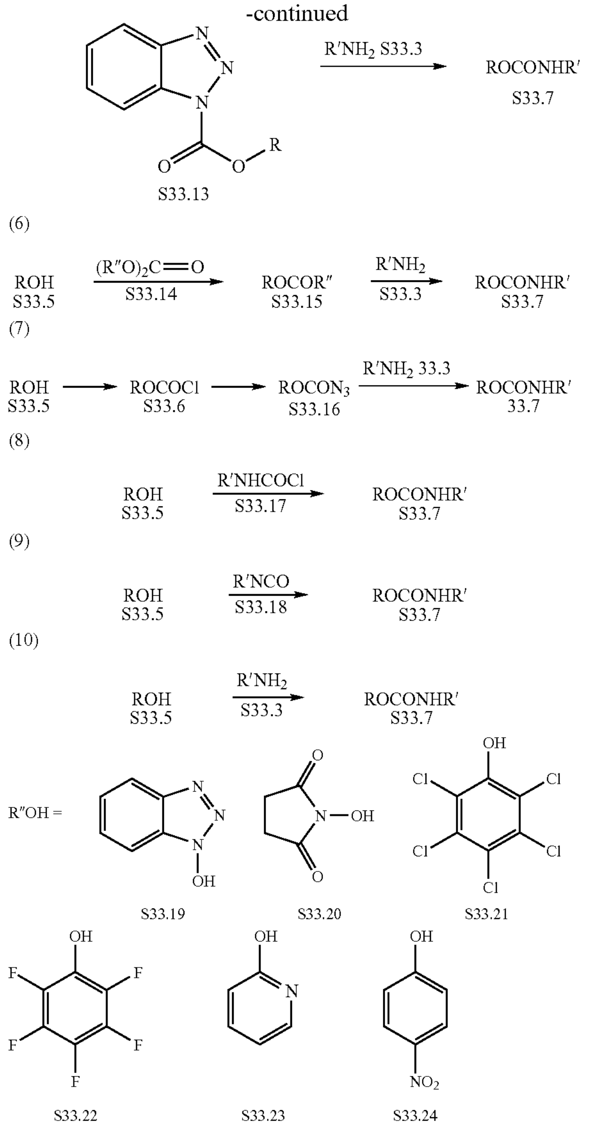

Preparation of Carboalkoxy-Substituted Phosphonate Bisamidates, Monoamidates, Diesters and Monoesters A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in *J. Gen. Chem. USSR*, 1983, 53, 480, *Zh. Obschei Khim.*, 1958, 28, 1063, or *J. Org. Chem.*, 1994, 59, 6144, or by reaction with oxalyl chloride, as described in *J. Am. Chem. Soc.*, 1994, 116, 3251, or *J. Org. Chem.*, 1994, 59, 6144, or by reaction with phosphorus pentachloride, as described in *J. Org. Chem.*, 2001, 66, 329, or in *J. Med. Chem.*, 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in *J. Chem. Soc., Chem. Comm.* (1991) 312, or *Nucleosides & Nucleotides* (2000) 19:1885. Activated sulfonyloxy derivatives are obtained by the reaction of phosphonic acids with trichloromethylsulfonyl chloride or with triisopropylbenzenesulfonyl chloride, as described in *Tet. Lett.* (1996) 7857, or *Bioorg. Med. Chem. Lett.* (1998) 8:663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in *J. Chem. Soc., Chem. Comm.* (1991) 312 or *Coll. Czech. Chem. Comm.* (1987) 52:2792. The use of ethyl dimethylaminopropyl carbodiimide for activation and coupling of phosphonic acids is described in *Tet. Lett.*, (2001) 42:8841, or *Nucleosides & Nucleotides* (2000) 19:1885.

A number of additional coupling reagents have been described for the preparation of amidates and esters from phosphonic acids. The agents include Aldrithiol-2, and PYBOP and BOP, as described in *J. Org. Chem.*, 1995, 60, 5214, and *J. Med. Chem.* (1997) 40:3842, mesitylene-2-sulfonyl-3-nitro-1,2,4-triazole (MSNT), as described in *J. Med. Chem.* (1996) 39:4958, diphenylphosphoryl azide, as described in *J. Org. Chem.* (1984) 49:1158, 1-(2,4,6-triisopropylbenzenesulfonyl-3-nitro-1,2,4-triazole (TPSNT) as described in *Bioorg. Med. Chem. Lett.* (1998) 8:1013, bromotris(dimethylamino)phosphonium hexafluorophosphate (BroP), as described in *Tet. Lett.*, (1996) 37:3997, 2-chloro-5,5-dimethyl-2-oxo-1,3,2-dioxaphosphinane, as described in *Nucleosides Nucleotides* 1995, 14, 871, and diphenyl chlorophosphate, as described in *J. Med. Chem.*, 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in *Org. Lett.*, 2001, 3, 643, or *J. Med. Chem.*, 1997, 40, 3842.

Phosphonic esters are also obtained by the reaction between phosphonic acids and halo compounds, in the presence of a suitable base. The method is described, for example, in *Anal. Chem.*, 1987, 59, 1056, or *J. Chem. Soc. Perkin Trans., I*, 1993, 19, 2303, or *J. Med. Chem.*, 1995, 38, 1372, or *Tet. Lett.*, 2002, 43, 1161.

Schemes 34-37 illustrate the conversion of phosphonate esters and phosphonic acids into carboalkoxy-substituted phosphonbisamidates (Scheme 34), phosphonamidates (Scheme 35), phosphonate monoesters (Scheme 36) and phosphonate diesters, (Scheme 37). Scheme 38 illustrates synthesis of gem-dialkyl amino phosphonate reagents.

Scheme 34 illustrates various methods for the conversion of phosphonate diesters S34.1 into phosphonbisamidates S34.5. The diester S34.1, prepared as described previously, is hydrolyzed, either to the monoester S34.2 or to the phosphonic acid S34.6. The methods employed for these transformations are described above. The monoester S34.2 is converted into the monoamidate S34.3 by reaction with an aminoester S34.9, in which the group $R^2$ is H or alkyl; the group $R^{4b}$ is a divalent alkylene moiety such as, for example, $CHCH_3$, $CHCH_2CH_3$, $CH(CH(CH_3)_2)$, $CH(CH_2Ph)$, and the like, or a side chain group present in natural or modified aminoacids; and the group $R^{5b}$ is $C_1$-$C_{12}$ alkyl, such as methyl, ethyl, propyl, isopropyl, or isobutyl; $C_6$-$C_{20}$ aryl, such as phenyl or substituted phenyl; or $C_6$-$C_{20}$ arylalkyl, such as benzyl or benzyhydryl. The reactants are combined in the presence of a coupling agent such as a carbodiimide, for example dicyclohexyl carbodiimide, as described in *J. Am. Chem. Soc.*, (1957) 79:3575, optionally in the presence of an activating agent such as hydroxybenztriazole, to yield the amidate product S34.3. The amidate-forming reaction is also effected in the presence of coupling agents such as BOP, as described in *J. Org. Chem.* (1995) 60:5214, Aldrithiol, PYBOP and similar coupling agents used for the preparation of amides and esters. Alternatively, the reactants S34.2 and S34.9 are transformed into the monoamidate S34.3 by means of a Mitsunobu reaction. The preparation of amidates by means of the Mitsunobu reaction is described in *J. Med. Chem.* (1995) 38:2742. Equimolar amounts of the reactants are combined in an inert solvent such as tetrahydrofuran in the presence of a triaryl phosphine and a dialkyl azodicarboxylate. The thus-obtained monoamidate ester S34.3 is then transformed into amidate phosphonic acid S34.4. The conditions used for the hydrolysis reaction depend on the nature of the $R^1$ group, as described previously. The phosphonic acid amidate S34.4 is then reacted with an aminoester S34.9, as described above, to yield the bisamidate product S34.5, in which the amino substituents are the same or different. Alternatively, the phosphonic acid S34.6 may be treated with two different amino ester reagents simulataneously, i.e. S34.9 where $R^2$, $R^{4b}$ or $R^{5b}$ are different. The resulting mixture of bisamidate products S34.5 may then be separable, e.g. by chromatography.

An example of this procedure is shown in Scheme 34, Example 1. In this procedure, a dibenzyl phosphonate S34.14 is reacted with diazabicyclooctane (DABCO) in toluene at reflux, as described in *J. Org. Chem.*, 1995, 60, 2946, to afford the monobenzyl phosphonate S34.15. The product is then reacted with equimolar amounts of ethyl alaninate S34.16 and dicyclohexyl carbodiimide in pyridine, to yield the amidate product S34.17. The benzyl group is then removed, for example by hydrogenolysis over a palladium catalyst, to give the monoacid product S34.18 which may be unstable according to J. Med. Chem. (1997) 40(23):3842. This compound S34.18 is then reacted in a Mitsunobu reaction with ethyl leucinate S34.19, triphenyl phosphine and diethylazodicarboxylate, as described in *J. Med. Chem.*, 1995, 38, 2742, to produce the bisamidate product S34.20.

Using the above procedures, but employing in place of ethyl leucinate S34.19 or ethyl alaninate S34.16, different aminoesters S34.9, the corresponding products S34.5 are obtained.

Alternatively, the phosphonic acid S34.6 is converted into the bisamidate S34.5 by use of the coupling reactions described above. The reaction is performed in one step, in which case the nitrogen-related substituents present in the product S34.5 are the same, or in two steps, in which case the nitrogen-related substituents can be different.

Scheme 34

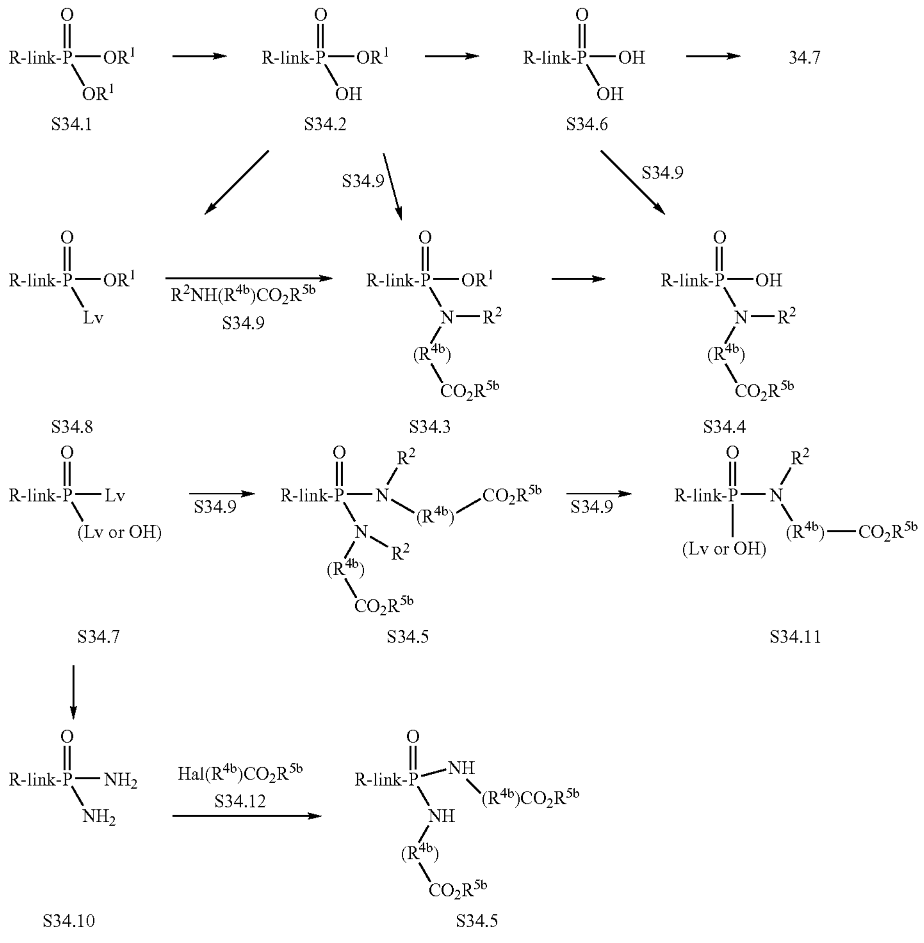

S34.1 S34.2 S34.6 S34.8 S34.3 S34.4 S34.7 S34.5 S34.11 S34.10 S34.5

An example of the method is shown in Scheme 34, Example 2. In this procedure, a phosphonic acid S34.6 is reacted in pyridine solution with excess ethyl phenylalaninate S34.21 and dicyclohexylcarbodiimide, for example as described in *J. Chem. Soc., Chem. Comm.*, 1991, 1063, to give the bisamidate product S34.22.

Using the above procedures, but employing, in place of ethyl phenylalaninate, different aminoesters S34.9, the corresponding products S34.5 are obtained.

As a further alternative, the phosphonic acid S34.6 is converted into the mono or bis-activated derivative S34.7, in which Lv is a leaving group such as chloro, imidazolyl, triisopropylbenzenesulfonyloxy etc. The conversion of phosphonic acids into chlorides S34.7 (Lv=Cl) is effected by reaction with thionyl chloride or oxalyl chloride and the like, as described in *Organic Phosphorus Compounds*, G. M. Kosolapoff, L. Maeir, eds, Wiley, 1976, p. 17. The conversion of phosphonic acids into monoimidazolides S34.7 (Lv=imidazolyl) is described in *J. Med. Chem.*, 2002, 45, 1284 and in *J. Chem. Soc. Chem. Comm.*, 1991, 312. Alternatively, the phosphonic acid is activated by reaction with triisopropylbenzenesulfonyl chloride, as described in *Nucleosides and Nucleotides*, 2000, 10, 1885. The activated product is then reacted with the aminoester S34.9, in the presence of a base, to give the bisamidate S34.5. The reaction is performed in one step, in which case the nitrogen substituents present in the product S34.5 are the same, or in two steps, via the intermediate S34.11, in which case the nitrogen substituents can be different.

Examples of these methods are shown in Scheme 34, Examples 3 and 5. In the procedure illustrated in Scheme 34, Example 3, a phosphonic acid S34.6 is reacted with ten molar equivalents of thionyl chloride, as described in *Zh. Obschei Khim.*, 1958, 28, 1063, to give the dichloro compound S34.23. The product is then reacted at reflux temperature in a polar aprotic solvent such as acetonitrile, and in the presence of a base such as triethylamine, with butyl serinate S34.24 to afford the bisamidate product S34.25.

Using the above procedures, but employing, in place of butyl serinate S34.24, different aminoesters S34.9, the corresponding products S34.5 are obtained.

In the procedure illustrated in Scheme 34, Example 5, the phosphonic acid S34.6 is reacted, as described in *J. Chem. Soc. Chem. Comm.*, 1991, 312, with carbonyl diimidazole to give the imidazolide S34.32. The product is then reacted in acetonitrile solution at ambient temperature, with one molar equivalent of ethyl alaninate S34.33 to yield the monodisplacement product S34.34. The latter compound is then reacted with carbonyl diimidazole to produce the activated intermediate S34.35, and the product is then reacted, under the same conditions, with ethyl N-methylalaninate S34.33a to give the bisamidate product S34.36.

Using the above procedures, but employing, in place of ethyl alaninate S34.33 or ethyl N-methylalaninate S34.33a, different aminoesters S34.9, the corresponding products S34.5 are obtained.

The intermediate monoamidate S34.3 is also prepared from the monoester S34.2 by first converting the monoester into the activated derivative S34.8 in which Lv is a leaving group such as halo, imidazolyl etc, using the procedures described above. The product S34.8 is then reacted with an aminoester S34.9 in the presence of a base such as pyridine, to give an intermediate monoamidate product S34.3. The latter compound is then converted, by removal of the $R^1$ group and coupling of the product with the aminoester S34.9, as described above, into the bisamidate S34.5.

An example of this procedure, in which the phosphonic acid is activated by conversion to the chloro derivative S34.26, is shown in Scheme 34, Example 4. In this procedure, the phosphonic monobenzyl ester S34.15 is reacted, in dichloromethane, with thionyl chloride, as described in *Tet. Letters*., 1994, 35, 4097, to afford the phosphoryl chloride S34.26. The product is then reacted in acetonitrile solution at ambient temperature with one molar equivalent of ethyl 3-amino-2-methylpropionate S34.27 to yield the monoamidate product S34.28. The latter compound is hydrogenated in ethylacetate over a 5% palladium on carbon catalyst to produce the monoacid product S34.29. The product is subjected to a Mitsunobu coupling procedure, with equimolar amounts of butyl alaninate S34.30, triphenyl phosphine, diethylazodicarboxylate and triethylamine in tetrahydrofuran, to give the bisamidate product S34.31.

Using the above procedures, but employing, in place of ethyl 3-amino-2-methylpropionate S34.27 or butyl alaninate S34.30, different aminoesters S34.9, the corresponding products S34.5 are obtained.

The activated phosphonic acid derivative S34.7 is also converted into the bisamidate S34.5 via the diamino compound S34.10. The conversion of activated phosphonic acid derivatives such as phosphoryl chlorides into the corresponding amino analogs S34.10, by reaction with ammonia, is described in *Organic Phosphorus Compounds*, G. M. Kosolapoff, L. Maeir, eds, Wiley, 1976. The bisamino compound S34.10 is then reacted at elevated temperature with a haloester S34.12 (Hal=halogen, i.e. F, Cl, Br, I), in a polar organic solvent such as dimethylformamide, in the presence of a base such as 4,4-dimethylaminopyridine (DMAP) or potassium carbonate, to yield the bisamidate S34.5. Alternatively, S34.6 may be treated with two different amino ester reagents simulataneously, i.e. S34.12 where $R^{4b}$ or $R^{5b}$ are different. The resulting mixture of bisamidate products S34.5 may then be separable, e.g. by chromatography.

An example of this procedure is shown in Scheme 34, Example 6. In this method, a dichlorophosphonate S34.23 is reacted with ammonia to afford the diamide S34.37. The reaction is performed in aqueous, aqueous alcoholic or alcoholic solution, at reflux temperature. The resulting diamino compound is then reacted with two molar equivalents of ethyl 2-bromo-3-methylbutyrate S34.38, in a polar organic solvent such as N-methylpyrrolidinone at ca. 150° C., in the presence of a base such as potassium carbonate, and optionally in the presence of a catalytic amount of potassium iodide, to afford the bisamidate product S34.39.

Using the above procedures, but employing, in place of ethyl 2-bromo-3-methylbutyrate S34.38, different haloesters S34.12 the corresponding products S34.5 are obtained.

The procedures shown in Scheme 34 are also applicable to the preparation of bisamidates in which the aminoester moiety incorporates different functional groups. Scheme 34, Example 7 illustrates the preparation of bisamidates derived from tyrosine. In this procedure, the monoimidazolide S34.32 is reacted with propyl tyrosinate S34.40, as described in Example 5, to yield the monoamidate S34.41. The product is reacted with carbonyl diimidazole to give the imidazolide S34.42, and this material is reacted with a further molar equivalent of propyl tyrosinate to produce the bisamidate product S34.43.

Using the above procedures, but employing, in place of propyl tyrosinate S34.40, different aminoesters S34.9, the corresponding products S34.5 are obtained. The aminoesters employed in the two stages of the above procedure can be the same or different, so that bisamidates with the same or different amino substituents are prepared.

Scheme 35 illustrates methods for the preparation of phosphonate monoamidates.

In one procedure, a phosphonate monoester S34.1 is converted, as described in Scheme 34, into the activated derivative S34.8. This compound is then reacted, as described above, with an aminoester S34.9, in the presence of a base, to afford the monoamidate product S35.1.

The procedure is illustrated in Scheme 35, Example 1. In this method, a monophenyl phosphonate S35.7 is reacted with, for example, thionyl chloride, as described in *J. Gen. Chem.* USSR., 1983, 32, 367, to give the chloro product S35.8. The product is then reacted, as described in Scheme 34, with ethyl alaninate, to yield the amidate S35.10.

Using the above procedures, but employing, in place of ethyl alaninate S35.9, different aminoesters S34.9, the corresponding products S35.1 are obtained.

Alternatively, the phosphonate monoester S34.1 is coupled, as described in Scheme 34, with an aminoester S34.9 to produce the amidate S35.1. If necessary, the $R^1$ substituent is then altered, by initial cleavage to afford the phosphonic acid S35.2. The procedures for this transformation depend on the nature of the $R^1$ group, and are described above. The phosphonic acid is then transformed into the ester amidate product S35.3, by reaction with the hydroxy compound $R^3OH$, in which the group $R^3$ is aryl, heterocycle, alkyl, cycloalkyl, haloalkyl etc, using the same coupling procedures (carbodiimide, Aldrithiol-2, PYBOP, Mitsunobu reaction etc) described in Scheme 34 for the coupling of amines and phosphonic acids.

Scheme 34 Example 1

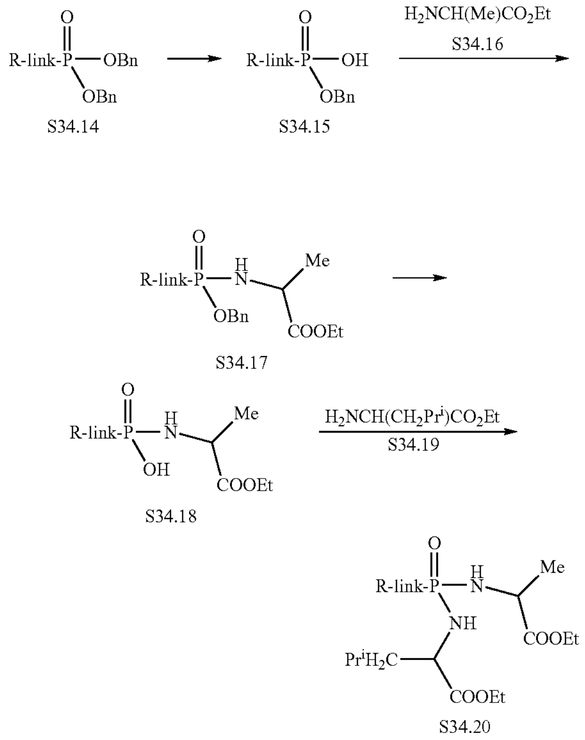

S34.14 S34.15 S34.17 S34.18 S34.20

-continued

Scheme 34 Example 2

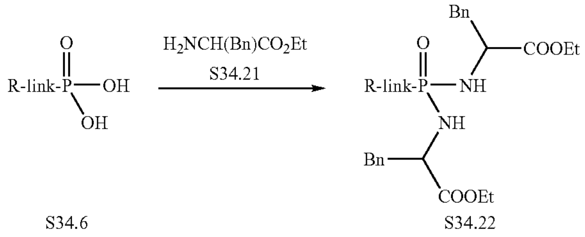

S34.6 S34.22

Scheme 34 Example 3

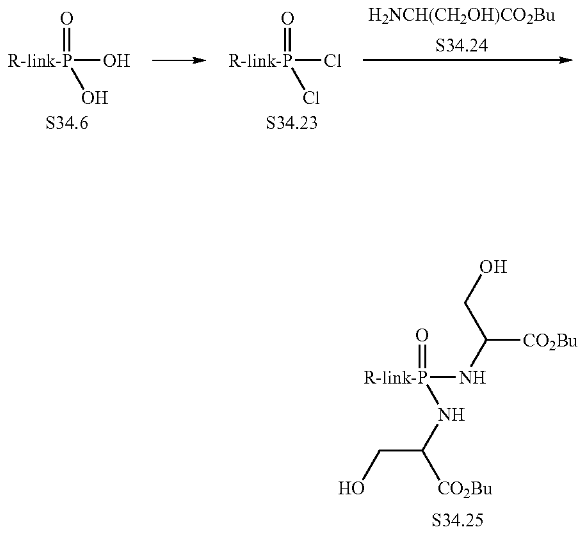

S34.6 S34.23 S34.25

Scheme 34 Example 4

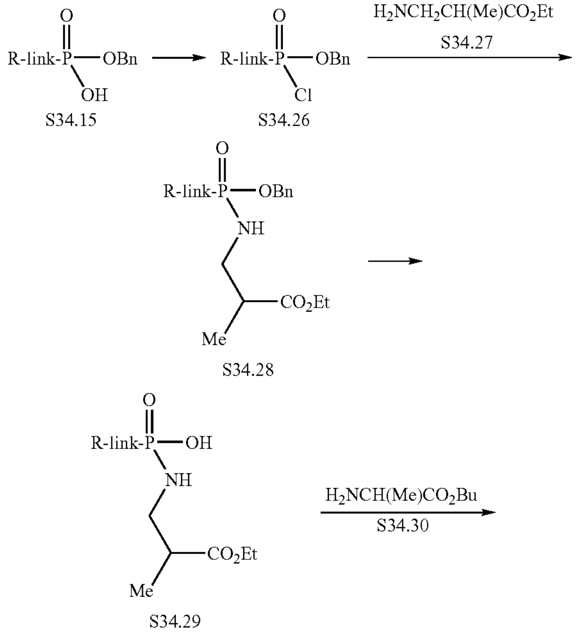

S34.15 S34.26 S34.28 S34.29

-continued

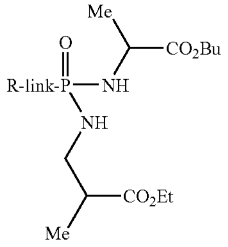

S34.31

Scheme 34 Example 5

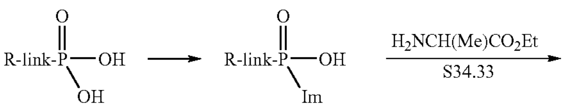

S34.6 S34.32

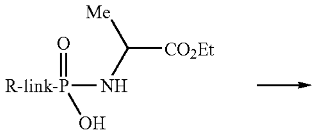

S34.34

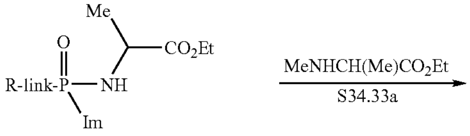

S34.35

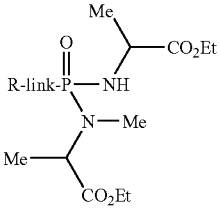

S34.36

Scheme 34 Example 6

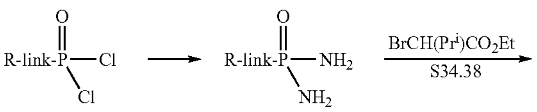

S34.23 S34.37

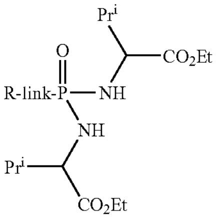

S34.39

-continued

Scheme 34 Example 7

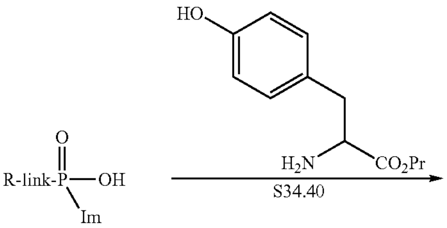

S34.32

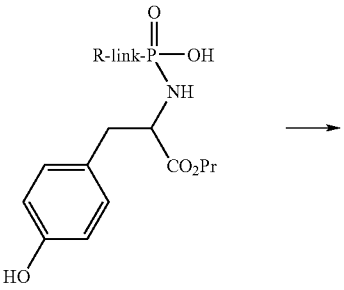

S34.41

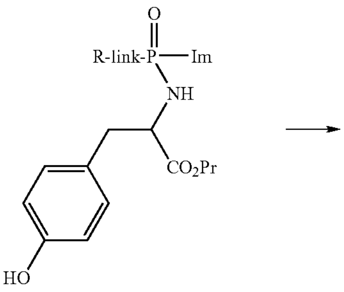

S34.42

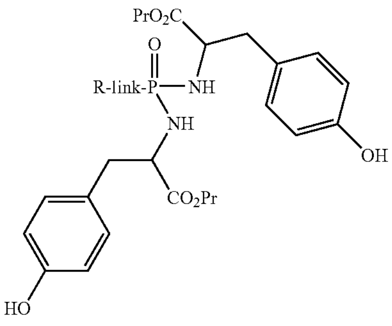

S34.43

Examples of this method are shown in Scheme 35, Examples and 2 and 3. In the sequence shown in Example 2, a monobenzyl phosphonate S35.11 is transformed by reaction with ethyl alaninate, using one of the methods described above, into the monoamidate S35.12. The benzyl group is then removed by catalytic hydrogenation in ethylacetate solution over a 5% palladium on carbon catalyst, to afford the phosphonic acid amidate S35.13. The product is then reacted in dichloromethane solution at ambient temperature with equimolar amounts of 1-(dimethylaminopropyl)-3-ethylcarbodiimide and trifluoroethanol S35.14, for example as described in *tet. Lett.*, 2001, 42, 8841, to yield the amidate ester S35.15.

In the sequence shown in Scheme 35, Example 3, the monoamidate S35.13 is coupled, in tetrahydrofuran solution at ambient temperature, with equimolar amounts of dicyclohexyl carbodiimide and 4-hydroxy-N-methylpiperidine S35.16, to produce the amidate ester product S35.17.

Using the above procedures, but employing, in place of the ethyl alaninate product S35.12 different monoacids S35.2, and in place of trifluoroethanol S35.14 or 4-hydroxy-N-methylpiperidine S35.16, different hydroxy compounds $R^3OH$, the corresponding products S35.3 are obtained.

Alternatively, the activated phosphonate ester S34.8 is reacted with ammonia to yield the amidate S35.4. The product is then reacted, as described in Scheme 34, with a haloester S35.5, in the presence of a base, to produce the amidate product S35.6. If appropriate, the nature of the $R^1$ group is changed, using the procedures described above, to give the product S35.3. The method is illustrated in Scheme 35, Example 4. In this sequence, the monophenyl phosphoryl chloride S35.18 is reacted, as described in Scheme 34, with ammonia, to yield the amino product S35.19. This material is then reacted in N-methylpyrrolidinone solution at 170° with butyl 2-bromo-3-phenylpropionate S35.20 and potassium carbonate, to afford the amidate product S35.21.

Using these procedures, but employing, in place of butyl 2-bromo-3-phenylpropionate S35.20, different haloesters S35.5, the corresponding products S35.6 are obtained.

The monoamidate products S35.3 are also prepared from the doubly activated phosphonate derivatives S34.7. In this procedure, examples of which are described in *Synlett.*, 1998, 1, 73, the intermediate S34.7 is reacted with a limited amount of the aminoester S34.9 to give the mono-displacement product S34.11. The latter compound is then reacted with the hydroxy compound $R^3OH$ in a polar organic solvent such as dimethylformamide, in the presence of a base such as diisopropylethylamine, to yield the monoamidate ester S35.3.

The method is illustrated in Scheme 35, Example 5. In this method, the phosphoryl dichloride S35.22 is reacted in dichloromethane solution with one molar equivalent of ethyl N-methyl tyrosinate S35.23 and dimethylaminopyridine, to generate the monoamidate S35.24. The product is then reacted with phenol S35.25 in dimethylformamide containing potassium carbonate, to yield the ester amidate product S35.26.

Using these procedures, but employing, in place of ethyl N-methyl tyrosinate S35.23 or phenol S35.25, the aminoesters 34.9 and/or the hydroxy compounds $R^3OH$, the corresponding products S35.3 are obtained.

Scheme 35

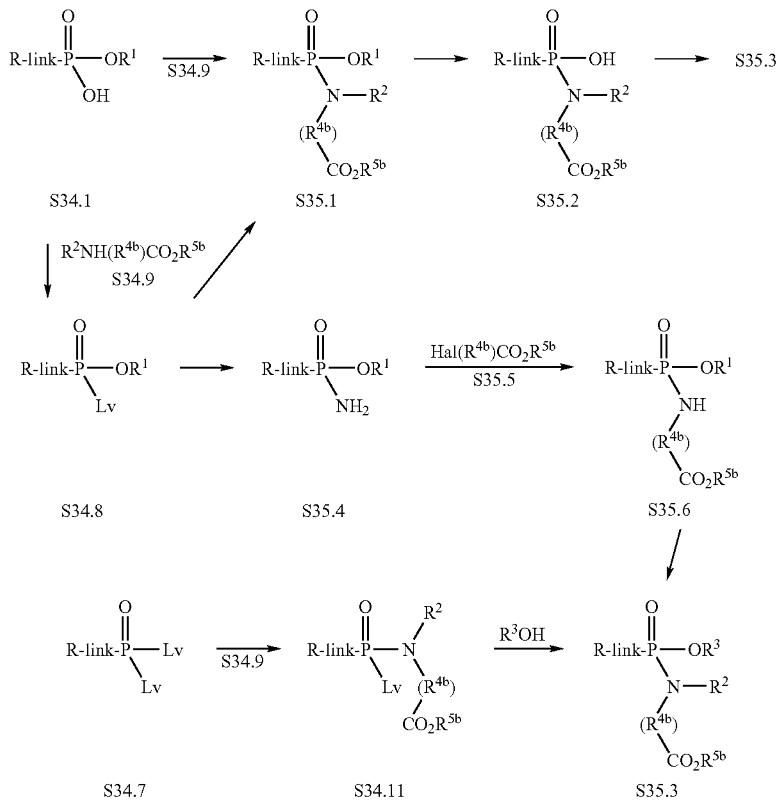

S34.1 S35.1 S35.2 S35.3

S34.8 S35.4 S35.6

S34.7 S34.11 S35.3

-continued
Scheme 35 Example 1
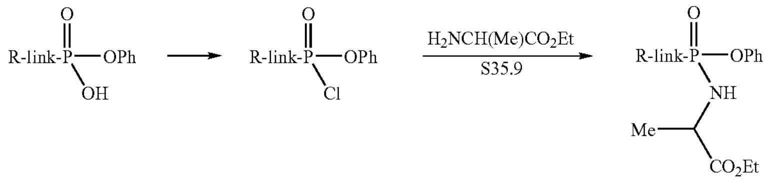
S35.7 S35.8 S35.10
Scheme 35 Example 2
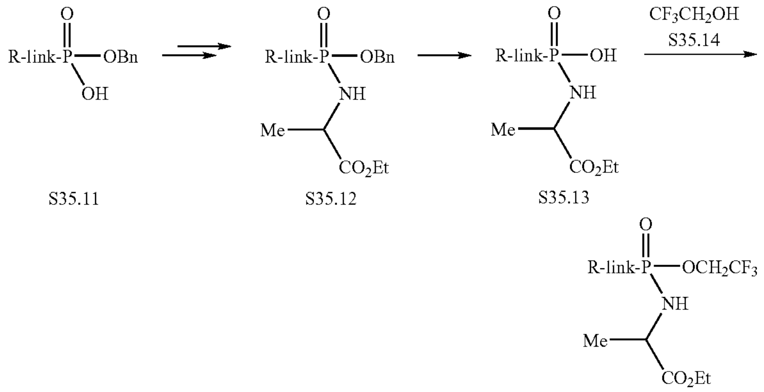
S35.11 S35.12 S35.13
S35.15
Scheme 35 Example 3
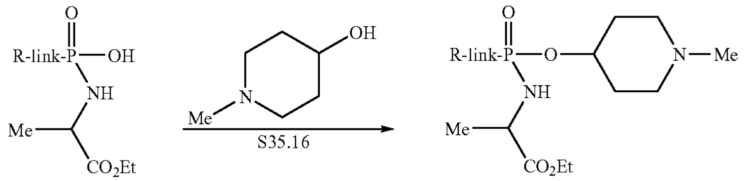
S35.13 S35.17
Scheme 35 Example 4
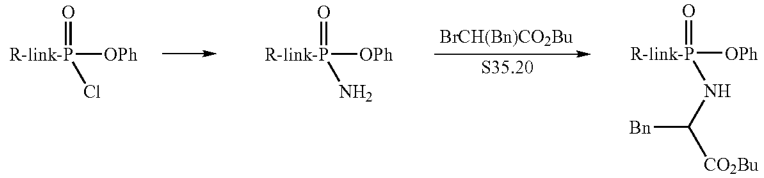
S35.18 S35.19 S35.21
Scheme 35 Example 5
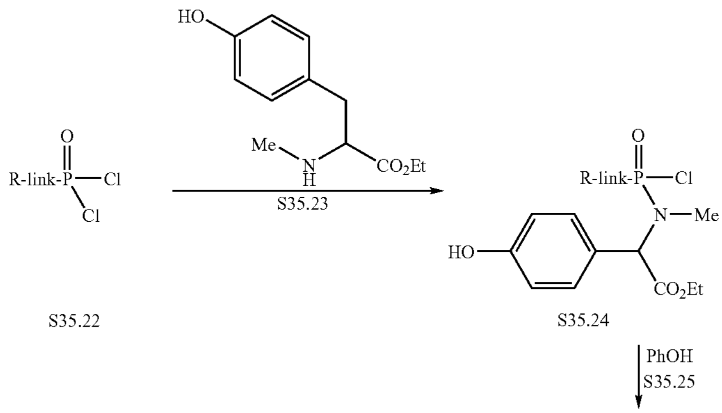
S35.22 S35.24

-continued

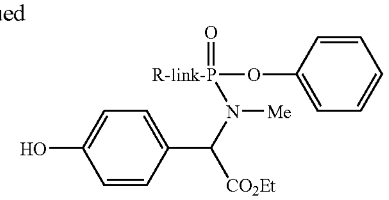

S35.26

Scheme 36 illustrates methods for the preparation of carboalkoxy-substituted phosphonate diesters in which one of the ester groups incorporates a carboalkoxy substituent.

In one procedure, a phosphonate monoester S34.1, prepared as described above, is coupled, using one of the methods described above, with a hydroxyester S36.1, in which the groups $R^{4b}$ and $R^{5b}$ are as described in Scheme 34. For example, equimolar amounts of the reactants are coupled in the presence of a carbodiimide such as dicyclohexyl carbodiimide, as described in *Aust. J. Chem.*, 1963, 609, optionally in the presence of dimethylaminopyridine, as described in *Tet.*, 1999, 55, 12997. The reaction is conducted in an inert solvent at ambient temperature.

The procedure is illustrated in Scheme 36, Example 1. In this method, a monophenyl phosphonate S36.9 is coupled, in dichloromethane solution in the presence of dicyclohexyl carbodiimide, with ethyl 3-hydroxy-2-methylpropionate S36.10 to yield the phosphonate mixed diester S36.11.

Using this procedure, but employing, in place of ethyl 3-hydroxy-2-methylpropionate S36.10, different hydroxyesters S33.1, the corresponding products S33.2 are obtained.

The conversion of a phosphonate monoester S34.1 into a mixed diester S36.2 is also accomplished by means of a Mitsunobu coupling reaction with the hydroxyester S36.1, as described in *Org. Lett.*, 2001, 643. In this method, the reactants 34.1 and S36.1 are combined in a polar solvent such as tetrahydrofuran, in the presence of a triarylphosphine and a dialkyl azodicarboxylate, to give the mixed diester S36.2. The $R^1$ substituent is varied by cleavage, using the methods described previously, to afford the monoacid product S36.3. The product is then coupled, for example using methods described above, with the hydroxy compound $R^3OH$, to give the diester product S36.4.

The procedure is illustrated in Scheme 36, Example 2. In this method, a monoallyl phosphonate S36.12 is coupled in tetrahydrofuran solution, in the presence of triphenylphosphine and diethylazodicarboxylate, with ethyl lactate S36.13 to give the mixed diester S36.14. The product is reacted with tris(triphenylphosphine) rhodium chloride (Wilkinson catalyst) in acetonitrile, as described previously, to remove the allyl group and produce the monoacid product S36.15. The latter compound is then coupled, in pyridine solution at ambient temperature, in the presence of dicyclohexyl carbodiimide, with one molar equivalent of 3-hydroxypyridine S36.16 to yield the mixed diester S36.17.

Using the above procedures, but employing, in place of the ethyl lactate S36.13 or 3-hydroxypyridine, a different hydroxyester S36.1 and/or a different hydroxy compound $R^3OH$, the corresponding products S36.4 are obtained.

The mixed diesters S36.2 are also obtained from the monoesters S34.1 via the intermediacy of the activated monoesters S36.5. In this procedure, the monoester S34.1 is converted into the activated compound S36.5 by reaction with, for example, phosphorus pentachloride, as described in *J. Org. Chem.*, 2001, 66, 329, or with thionyl chloride or oxalyl chloride (Lv =Cl), or with triisopropylbenzenesulfonyl chloride in pyridine, as described in *Nucleosides and Nucleotides*, 2000, 19, 1885, or with carbonyl diimidazole, as described in *J. Med. Chem.*, 2002, 45, 1284. The resultant activated monoester is then reacted with the hydroxyester S36.1, as described above, to yield the mixed diester S36.2.

The procedure is illustrated in Scheme 36, Example 3. In this sequence, a monophenyl phosphonate S36.9 is reacted, in acetonitrile solution at 70° C., with ten equivalents of thionyl chloride, so as to produce the phosphoryl chloride S36.19. The product is then reacted with ethyl 4-carbamoyl-2-hydroxybutyrate S36.20 in dichloromethane containing triethylamine, to give the mixed diester S36.21.

Using the above procedures, but employing, in place of ethyl 4-carbamoyl-2-hydroxybutyrate S36.20, different hydroxyesters S36.1, the corresponding products S36.2 are obtained.

The mixed phosphonate diesters are also obtained by an alternative route for incorporation of the $R^3O$ group into intermediates S36.3 in which the hydroxyester moiety is already incorporated. In this procedure, the monoacid intermediate S36.3 is converted into the activated derivative S36.6 in which Lv is a leaving group such as chloro, imidazole, and the like, as previously described. The activated intermediate is then reacted with the hydroxy compound $R^3OH$, in the presence of a base, to yield the mixed diester product S36.4.

The method is illustrated in Scheme 36, Example 4. In this sequence, the phosphonate monoacid S36.22 is reacted with trichloromethanesulfonyl chloride in tetrahydrofuran containing collidine, as described in *J. Med. Chem.*, 1995, 38, 4648, to produce the trichloromethanesulfonyloxy product S36.23. This compound is reacted with 3-(morpholinomethyl)phenol S36.24 in dichloromethane containing triethylamine, to yield the mixed diester product S36.25.

Using the above procedures, but employing, in place of with 3-(morpholinomethyl)phenol S36.24, different alcohols $R^3OH$, the corresponding products S36.4 are obtained.

The phosphonate esters S36.4 are also obtained by means of alkylation reactions performed on the monoesters S34.1. The reaction between the monoacid S34.1 and the haloester S36.7 is performed in a polar solvent in the presence of a base such as diisopropylethylamine, as described in *Anal Chem.*, 1987, 59, 1056, or triethylamine, as described in *J. Med. Chem.*, 1995, 38, 1372, or in a non-polar solvent such as benzene, in the presence of 18-crown-6, as described in *Syn. Comm.*, 1995, 25, 3565.

The method is illustrated in Scheme 36, Example 5. In this procedure, the monoacid S36.26 is reacted with ethyl 2-bromo-3-phenylpropionate S36.27 and diisopropylethylamine in dimethylformamide at 80° C. to afford the mixed diester product S36.28.

Using the above procedure, but employing, in place of ethyl 2-bromo-3-phenylpropionate S36.27, different haloesters S36.7, the corresponding products S36.4 are obtained.
Scheme 36
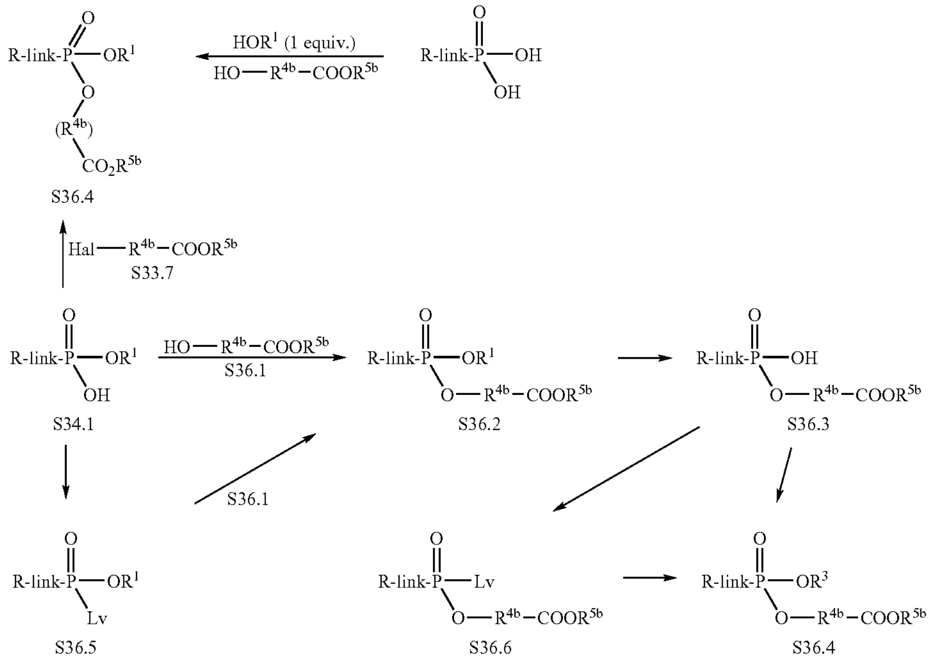
Scheme 36 Example 1
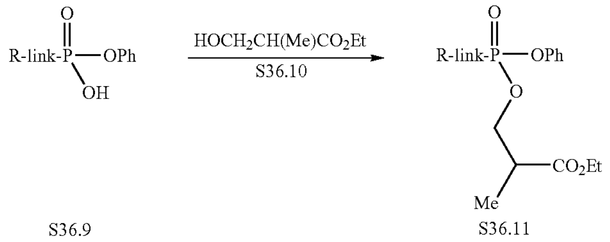
Scheme 36 Example 2
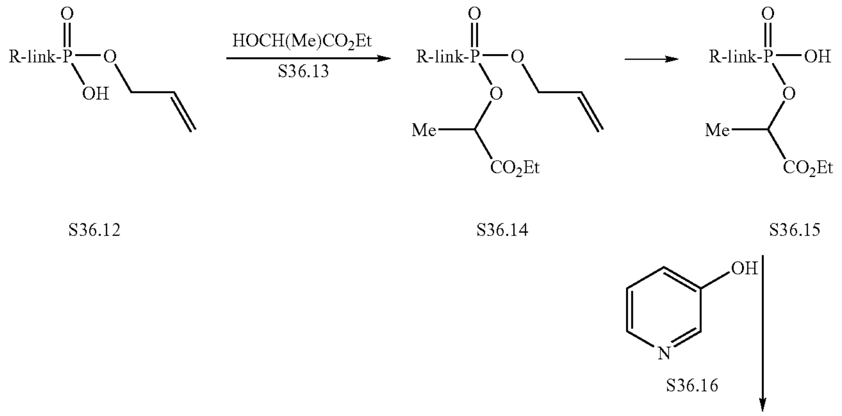

-continued

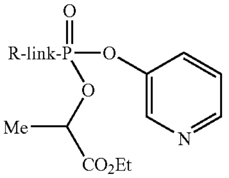

S36.17

Scheme 36 Example 3

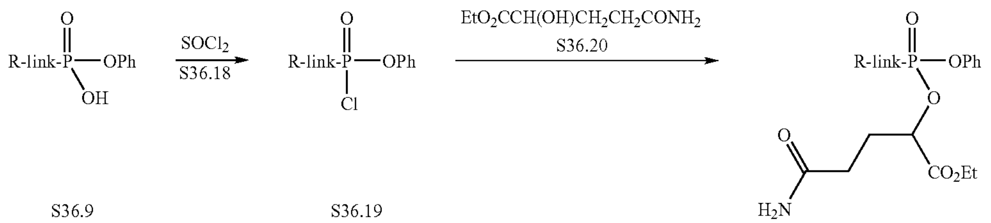

S36.9 S36.19 S36.21

Scheme 36 Example 4

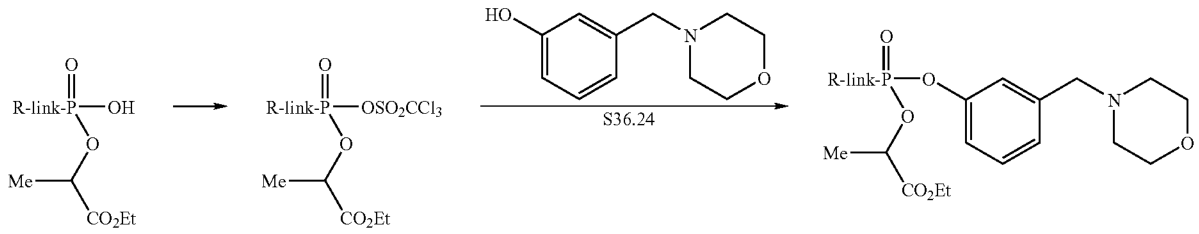

S36.22 S36.23 S36.25

Scheme 36 Example 5

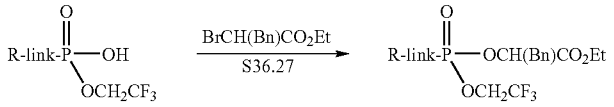

S36.26 S36.28

Scheme 37 illustrates methods for the preparation of phosphonate diesters in which both the ester substituents incorporate carboalkoxy groups.

The compounds are prepared directly or indirectly from the phosphonic acids S34.6. In one alternative, the phosphonic acid is coupled with the hydroxyester S37.2, using the conditions described previously in Schemes 34-36, such as coupling reactions using dicyclohexyl carbodiimide or similar reagents, or under the conditions of the Mitsunobu reaction, to afford the diester product S37.3 in which the ester substituents are identical.

This method is illustrated in Scheme 37, Example 1. In this procedure, the phosphonic acid S34.6 is reacted with three molar equivalents of butyl lactate S37.5 in the presence of Aldrithiol-2 and triphenyl phosphine in pyridine at ca. 70° C., to afford the diester S37.6.

Using the above procedure, but employing, in place of butyl lactate S37.5, different hydroxyesters S37.2, the corresponding products S37.3 are obtained.

Alternatively, the diesters S37.3 are obtained by alkylation of the phosphonic acid S34.6 with a haloester S37.1. The alkylation reaction is performed as described in Scheme 36 for the preparation of the esters S36.4.

This method is illustrated in Scheme 37, Example 2. In this procedure, the phosphonic acid S34.6 is reacted with excess ethyl 3-bromo-2-methylpropionate S37.7 and diisopropylethylamine in dimethylformamide at ca. 80° C., as described in *Anal. Chem.*, 1987, 59, 1056, to produce the diester S37.8.

Using the above procedure, but employing, in place of ethyl 3-bromo-2-methylpropionate S37.7, different haloesters S37.1, the corresponding products S37.3 are obtained.

The diesters S37.3 are also obtained by displacement reactions of activated derivatives S34.7 of the phosphonic acid with the hydroxyesters S37.2. The displacement reaction is performed in a polar solvent in the presence of a suitable base, as described in Scheme 36. The displacement reaction is performed in the presence of an excess of the hydroxyester, to afford the diester product S37.3 in which the ester substituents are identical, or sequentially with limited amounts of different hydroxyesters, to prepare diesters S37.3 in which the ester substituents are different.

The methods are illustrated in Scheme 37, Examples 3 and 4. As shown in Example 3, the phosphoryl dichloride S35.22 is reacted with three molar equivalents of ethyl 3-hydroxy-2-(hydroxymethyl)propionate S37.9 in tetrahydrofuran containing potassium carbonate, to obtain the diester product S37.10.

Using the above procedure, but employing, in place of ethyl 3-hydroxy-2-(hydroxymethyl)propionate S37.9, different hydroxyesters S37.2, the corresponding products S37.3 are obtained.

Scheme 37, Example 4 depicts the displacement reaction between equimolar amounts of the phosphoryl dichloride S35.22 and ethyl 2-methyl-3-hydroxypriopionate S37.11, to yield the monoester product S37.12. The reaction is conducted in acetonitrile at 70° in the presence of diisopropylethylamine. The product S37.12 is then reacted, under the same conditions, with one molar equivalent of ethyl lactate S37.13, to give the diester product S37.14.

Using the above procedures, but employing, in place of ethyl 2-methyl-3-hydroxypropionate S37.11 and ethyl lactate S37.13, sequential reactions with different hydroxyesters S37.2, the corresponding products S37.3 are obtained.

Scheme 37

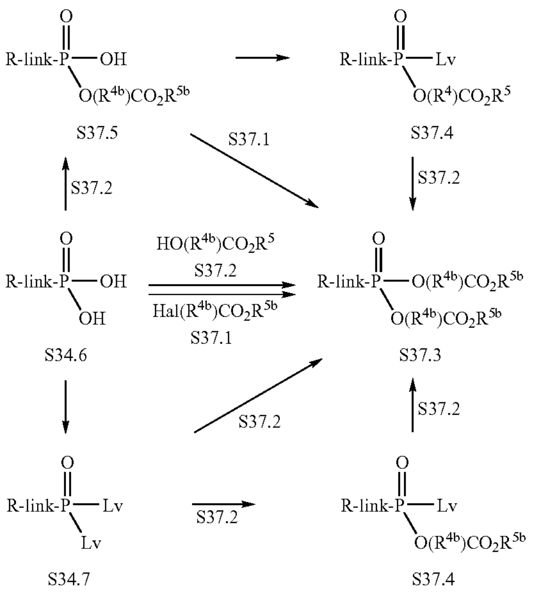

Scheme 37 Example 1

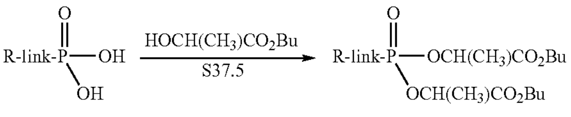

S34.6 S37.6

Scheme 37 Example 2

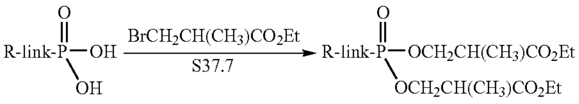

S34.6 S37.8

Scheme 37 Example 3

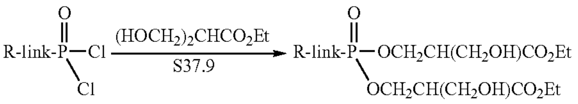

S35.22 S37.10

-continued

Scheme 37 Example 4

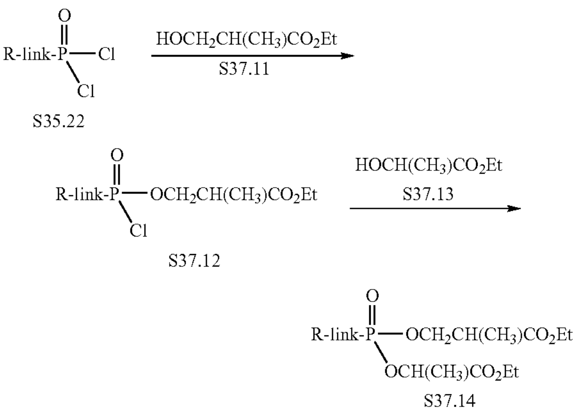

2,2-Dimethyl-2-aminoethylphosphonic acid intermediates can be prepared by the route in Scheme 5. Condensation of 2-methyl-2-propanesulfinamide with acetone give sulfinyl imine S38.11 (*J. Org. Chem.* 1999, 64, 12). Addition of dimethyl methylphosphonate lithium to S38.11 afford S38.12. Acidic methanolysis of S38.12 provide amine S38.13. Protection of amine with Cbz group and removal of methyl groups yield phosphonic acid S38.14, which can be converted to desired S38.15 (Scheme 38a) using methods reported earlier on. An alternative synthesis of compound S38.14 is also shown in Scheme 38b. Commercially available 2-amino-2-methyl-1-propanol is converted to aziridines S38.16 according to literature methods (*J. Org. Chem.* 1992, 57, 5813; *Syn. Lett.* 1997, 8, 893). Aziridine opening with phosphite give S38.17 (*Tetrahedron Lett.* 1980, 21, 1623). Reprotection) of S38.17 affords S38.14.

Scheme 38a

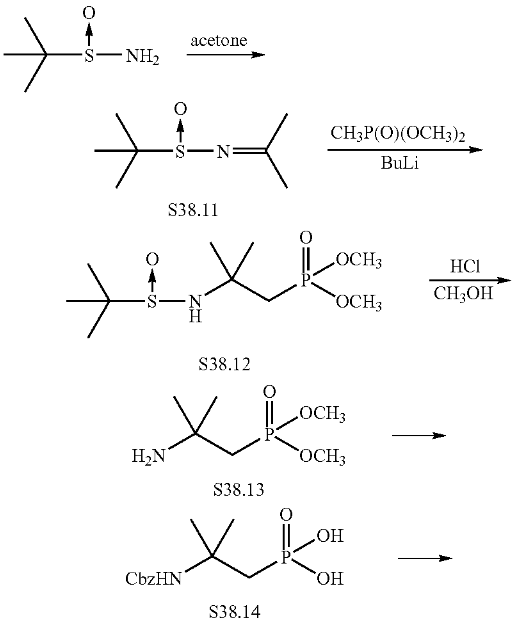

-continued

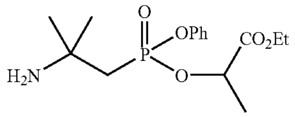

S38.15

Scheme 38b

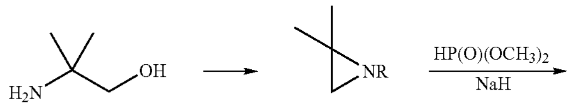

S38.16

R = Cbz, R'SO2

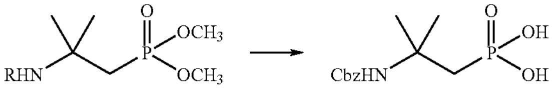

S38.17

S38.14

The invention will now be illustrated by the following non-limiting Examples.

Example 1

Preparation of Representative Compounds of the Invention

Representative compounds of the invention can be prepared as described herein.

1.1

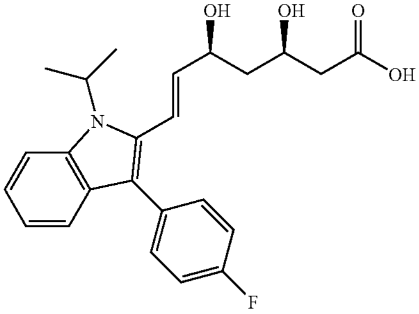

-continued 1.2

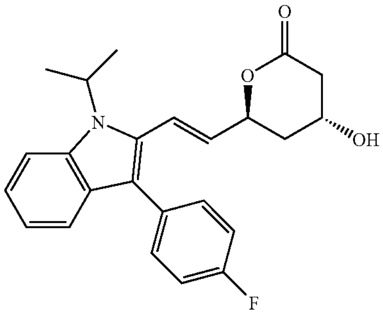

1.3

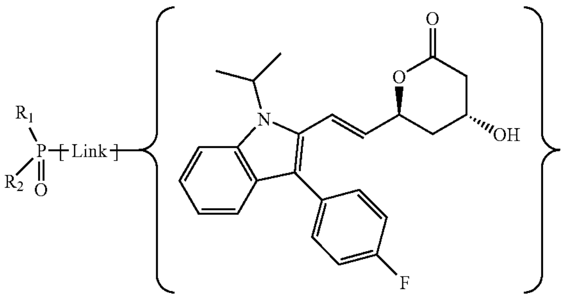

$R_1$ = O—aryl, O—heteroaryl, alpha or beta amino acid ester
$R_2$ = lactate ester or alpha or beta amino acid ester 1.4

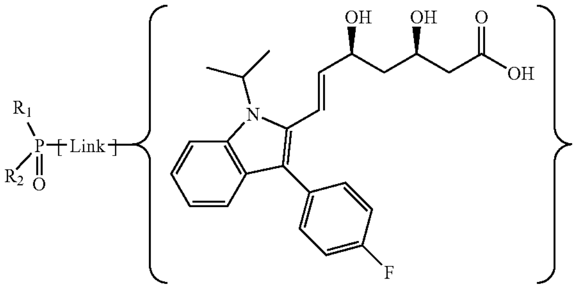

[Link] = uninterupted chain of atoms excluding hydrogen optionaly including cycles connecting a sustitutable position on Atorvastatin with the described phosphorous atom -continued
1.5
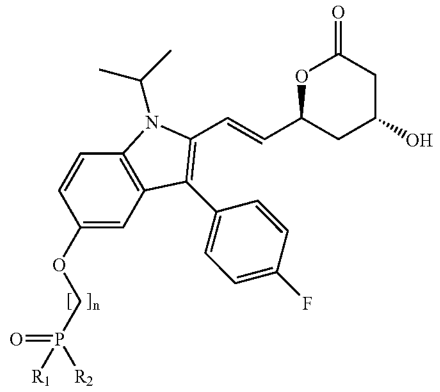
n = 1 to 20
1.6
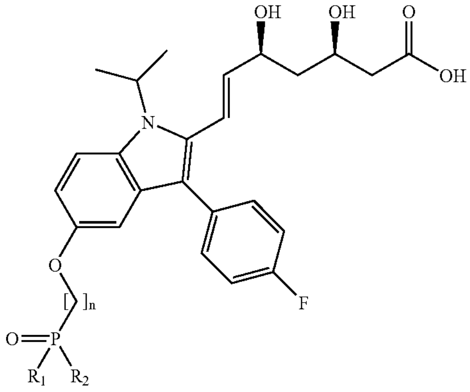
n = 1 to 20
Specific compounds of the invention can be prepared as follows:
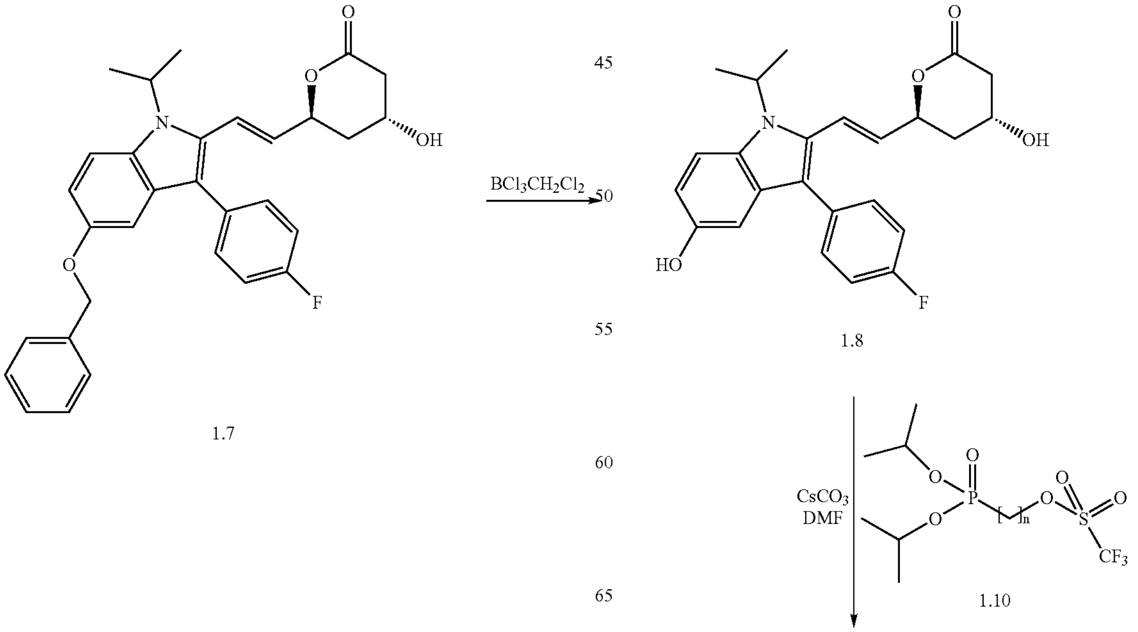

-continued

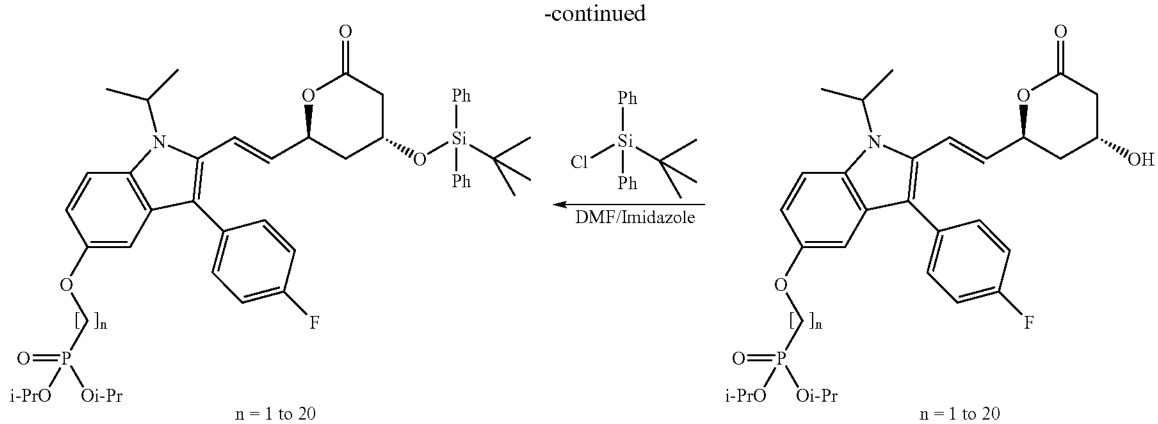

n = 1 to 20

1.12 n = 1 to 20

1.11

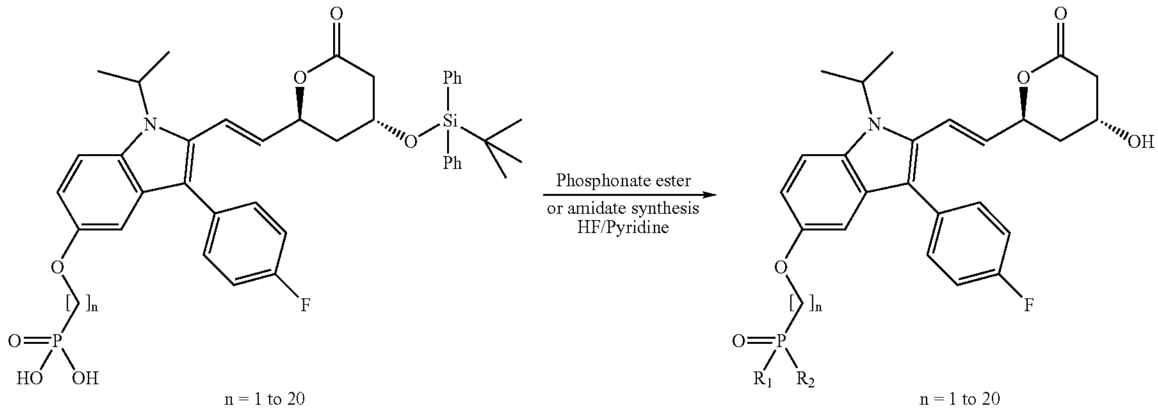

n = 1 to 20

1.13 n = 1 to 20

1.14

$R_1$ = O—aryl, O—heteroaryl, alpha or beta amino acid ester
$R_2$ = lactate ester or alpha or beta amino acid ester A method of synthesis of compound 1.7 is described in U.S. Pat. No. 4,739,073 (column 77, Example 122A in Table II). This material is treated with boron trichloride in dichloromethane to afford the phenol 1.8. Phenol 1.8 is then alkylated with a dialkyl ester of a phosphonoalkyltriflate, such as the diiospropyl ester of general structure 1.10, which can be prepared as follows:

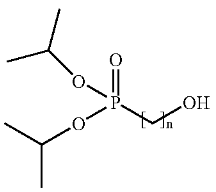

1.9

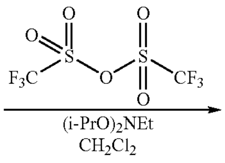

-continued

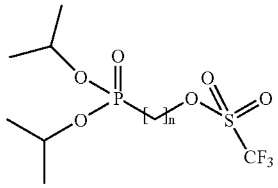

1.10

The product 1.11 is then treated with tertbutyldiphenylsilyl chloride to afford compound 1.12, which is then treated with trimethylsilylbromide in acetonitrile containing collidine to afford the free phosphonate 1.13. Compound 1.13 is then converted to the desired prodrug by the methods of phosphonate ester and amidate synthesis outlined below. The silyl group is then removed with hydrogen fluoride in pyridine to afford the compound of general structure 1.14.
Example 2
Preparation of Representative Compounds of the Invention
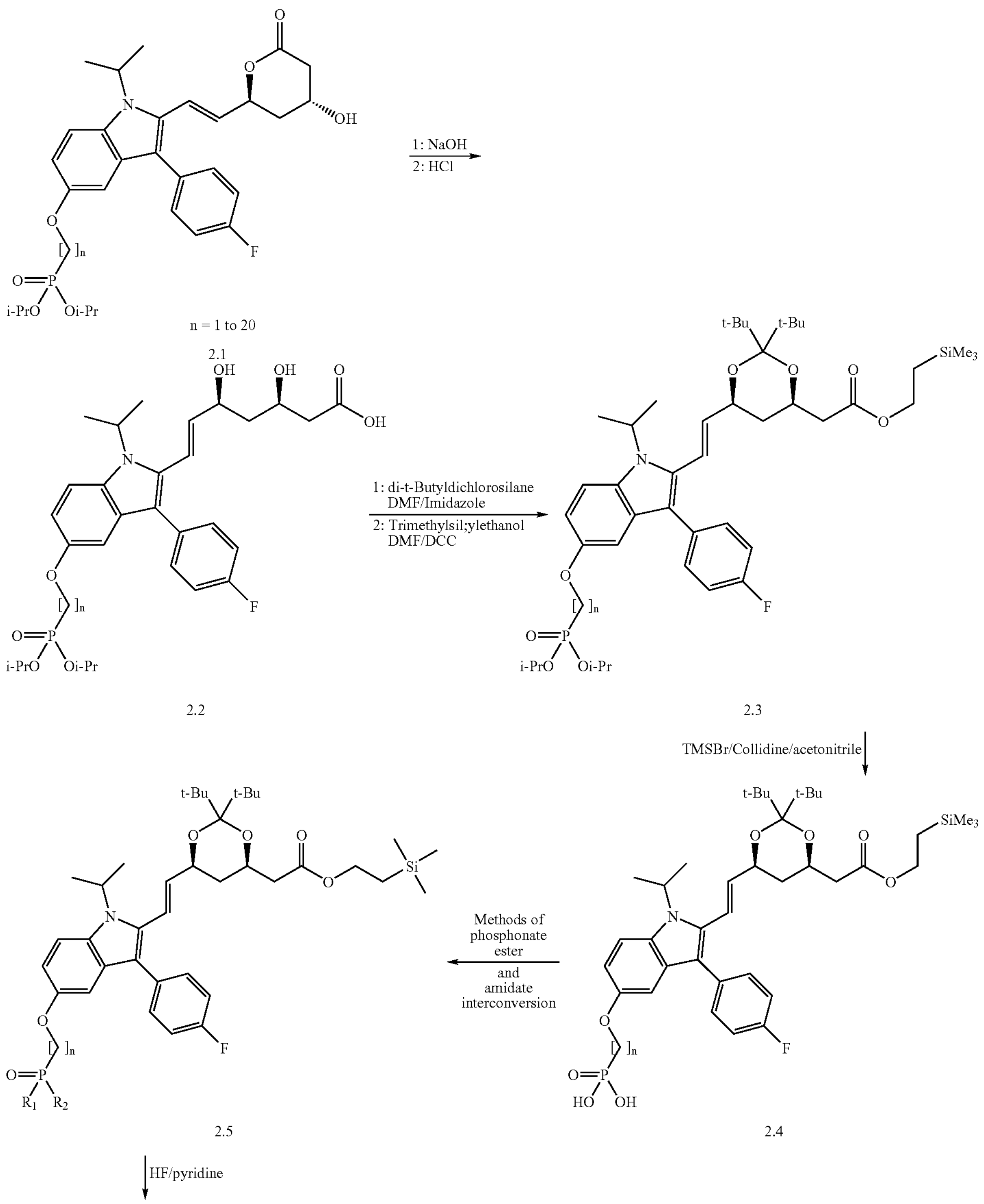
n = 1 to 20
2.1
2.2
2.3
2.4
2.5

-continued

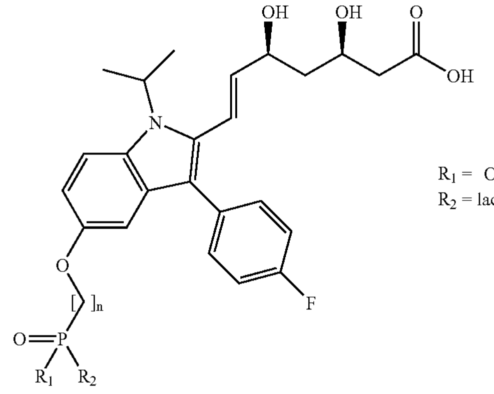

$R_1$ = O—aryl, O—heteroaryl, alpha or beta amino acid ester
$R_2$ = lactate ester or alpha or beta amino acid ester 2.6

The synthesis of the hydrolysed beta carboxylic acid forms of fluvastatin lactone is illustrated above. Compound 2.1 is hydrolyzed to compound 2.2 using aqueous sodium hydroxide. The free hydroxyl groups are protected as the cyclic silyl ether by treatment with ditertbutyldichlorosilane in DMF containing imidazole. The carboxylic acid is then protected at the trimethylsilylethyl ester by treatment with trimethylsilylethanol and dicyclohexylcarbodiimide in DMF to afford compound 2.3. Compound 2.3 is then treated with trimethylsilyl bromide in acetonitrile containing collidine to afford the compound of the general structure 2.4. The phosphonic acid 2.4 is then converted to the desired prodrug form by the methods of phosphonic acid ester and amidate formation outlined below, and the protecting groups are removed with hydrogen fluoride in pyridine to afford the prodrug of the general structure 2.6.

Specific compounds of the invention are prepared as follows:

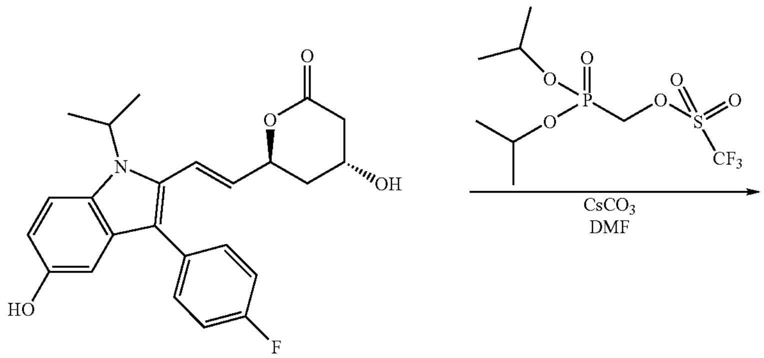

2.7

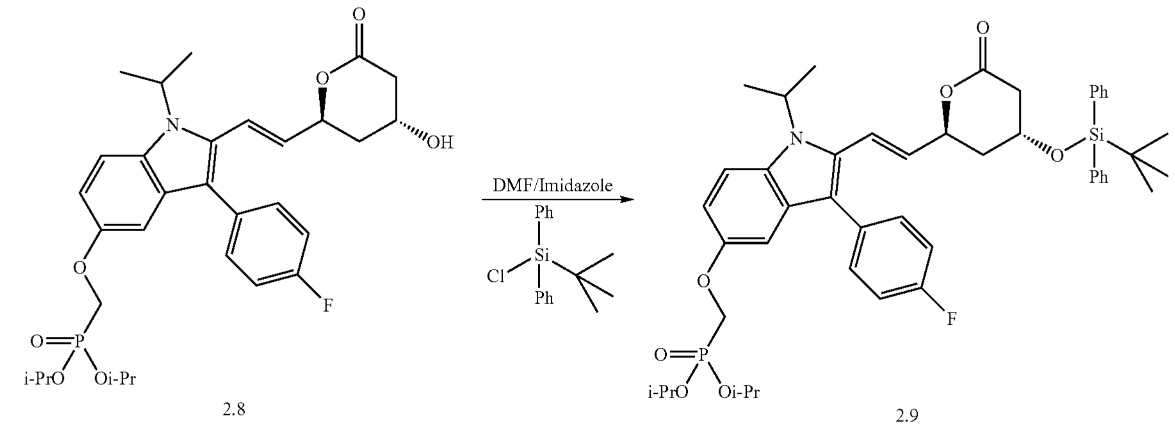

2.8

2.9

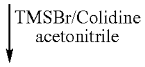

-continued

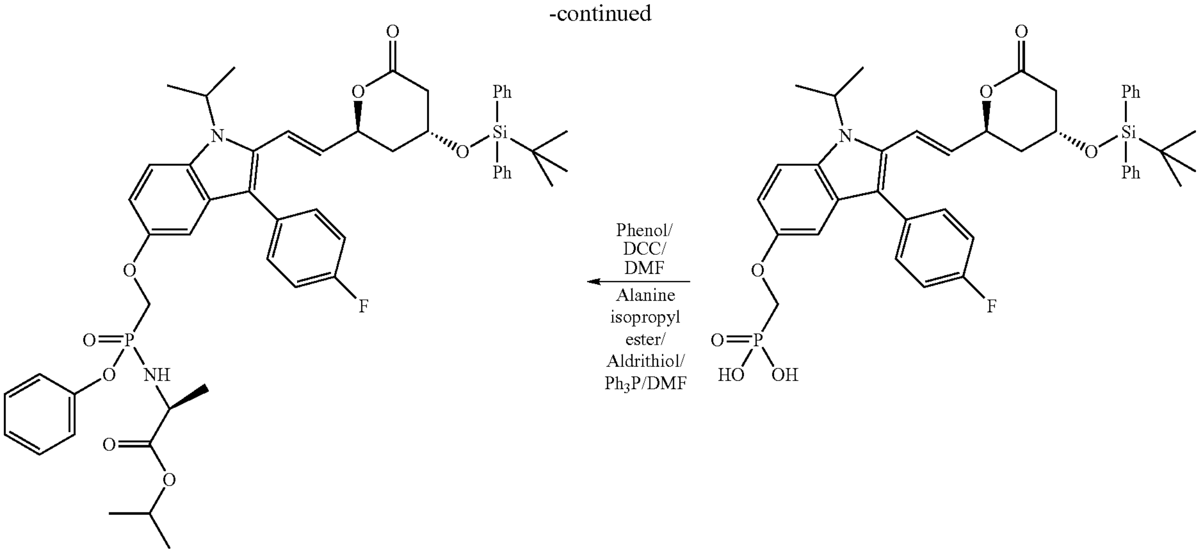

2.11 2.10

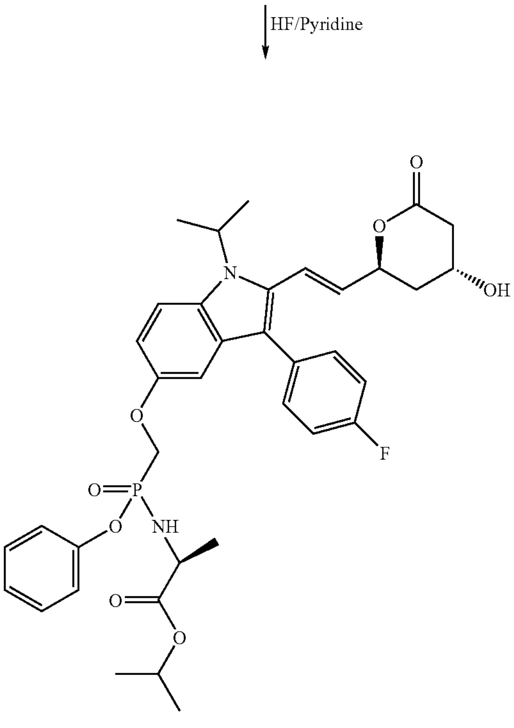

2.12

The synthesis of 2.12, which is a member of the class of compounds more generally described by 1.14, is described. Compound 2.7 is prepared according to Example 1, and the free phenolic hydroxyl group is then selectively alkylated with diisopropyl trifluoromethylsulfonyloxymethylphophonate in a solvent such as DMF using cesium carbonate, magnesium tert-butoxide or any other suitable base to yield the phosphonyl ether 2.8. The free hydroxyl group of 2.8 is then protected by treatment with tertbutyldiphenylsilyl chloride in DMF containing imidazole to yield the protected phosphonate diester 2.9. The alkyl protecting groups of the phosphonate moiety are then removed with trimethylsilylbromide in acetonitrile containing a base such as collidine to yield 2.10. The free phosphonate 2.10 is converted into the monophenol derivative with dicyclohexylcarbodiimide in DMF, and then condensed with the isopropyl ester of alanine, under the action of triphenyl phosphine and aldrithiol to yield compound 2.11. The silyl protecting group of 2.11 is removed with buffered fluoride source such as hydrogen fluoride in pyridine, yielding the prodrug of the lactone of structure 2.12.

An additional specific compound of the invention may be prepared as follows:

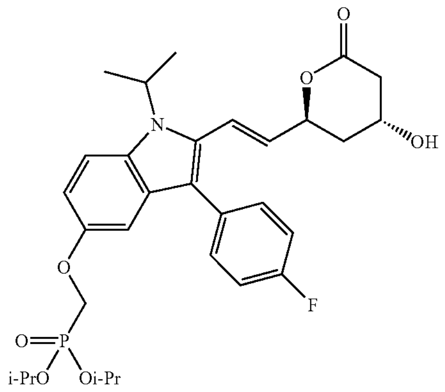
2.8
1: NaOH
2: HCl
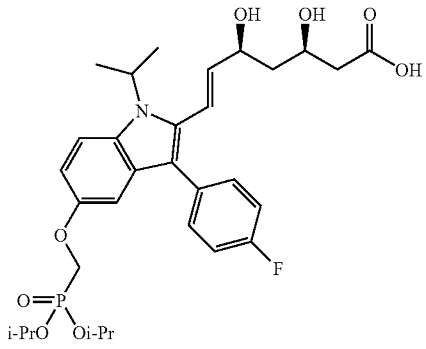
2.13
1: di-t-Butyldichlorosilane
DMF/Imidazole
2: Trimethylsil;ylethanol
DMF/DCC
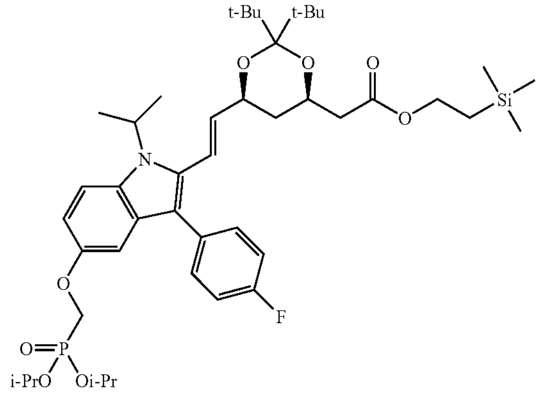
2.14
TMSBr/Collidine/acetonitrile
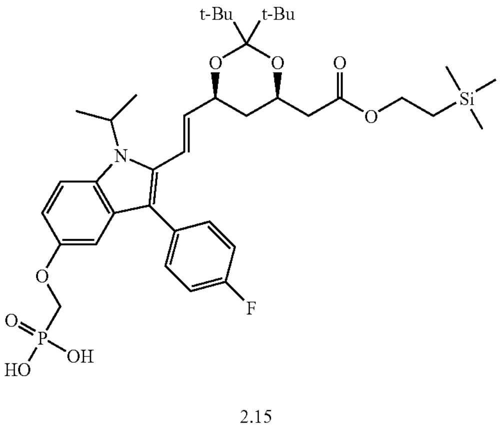
2.15
Phenol/
DCC/DMF
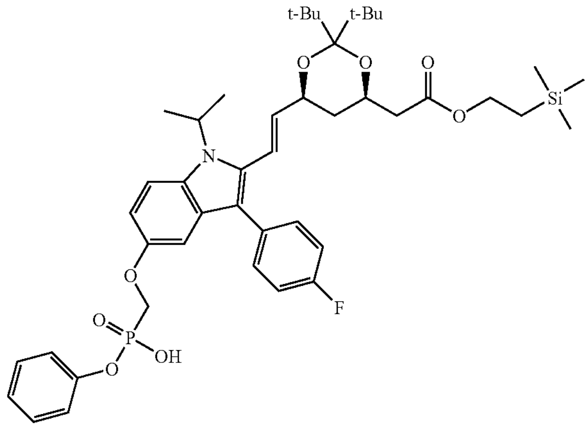
2.16
Alanine isopropyl
ester/aldrithiol/tripenylphosphine
DMF -continued

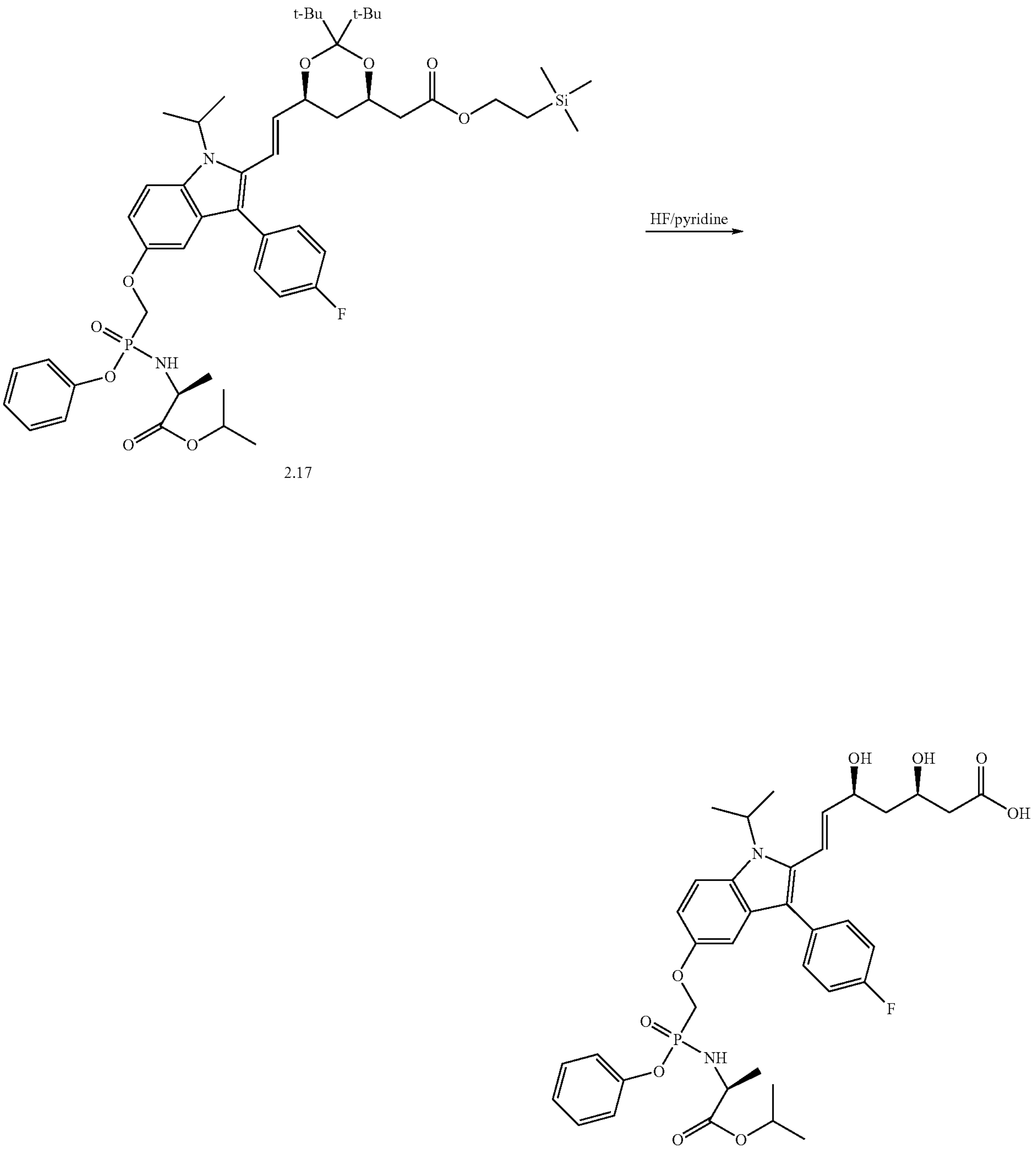

2.17

2.18

The synthesis of 2.18, a member of the class of compounds more generally described by structure 2.6 is shown above. Compound 2.8, prepared as described above, is hydrolyzed to compound 2.13 using aqueous sodium hydroxide. The free hydroxyl groups are protected as the cyclic silyl ether by treatment with ditertbutyldichlorosilane in DMF containing imidazole. The carboxylic acid is then protected at the trimethylsilylethyl ester by treatment with trimethylsilylethanol and dicyclohexylcarbodiimide in DMF to afford compound 2.14. Compound 2.14 is then treated with trimethylsilyl bromide in acetonitrile containing collidine to afford the compound of the general structure 2.15. The free phosphonate 2.15 is converted into the monophenol derivative 2.16 with dicyclohexylcarbodiimide in DMF, and then condensed with the isopropyl ester of alanine, under the action of triphenyl phosphine and aldrithiol to yield compound 2.17. The silyl protecting group of 2.17 is removed with buffered fluoride source such as hydrogen fluoride in pyridine, yielding the prodrug 2.18.

Example 3

Preparation of Representative Compounds of the Invention

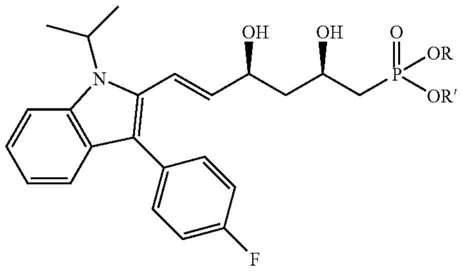

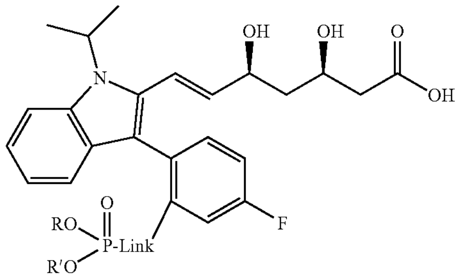

link is 0-8 atoms;
2-6 is preferred

In general, representative compounds of the invention can be made as follows:

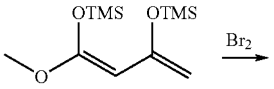

3.1

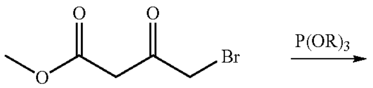

3.2

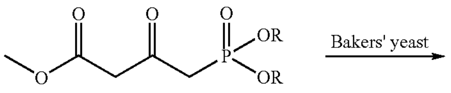

3.3

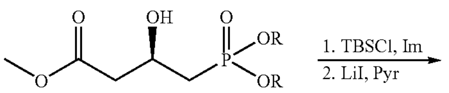

3.4

-continued

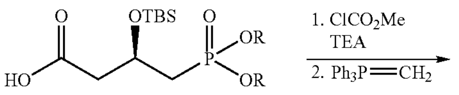

3.5

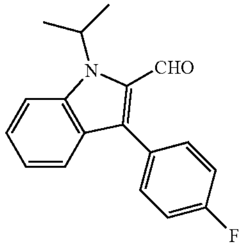

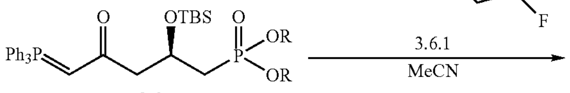

3.6

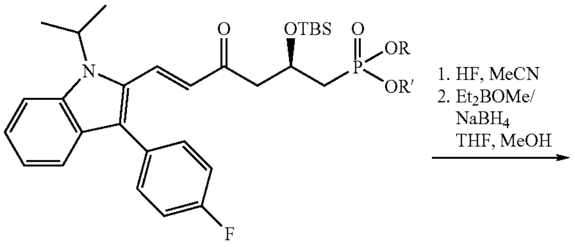

3.7

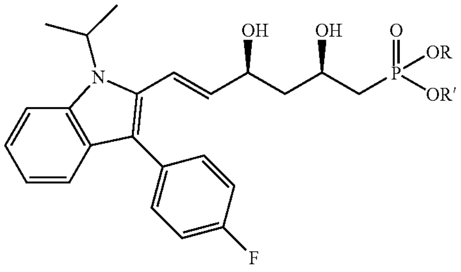

3.8

Specific compounds of the invention can be prepared as follows:

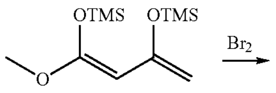

3.1

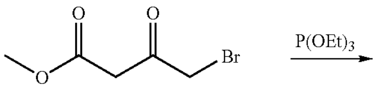

3.2

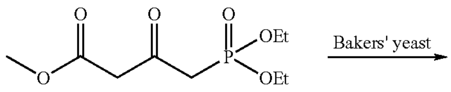

3.9

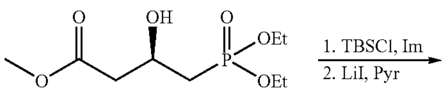

3.10

-continued

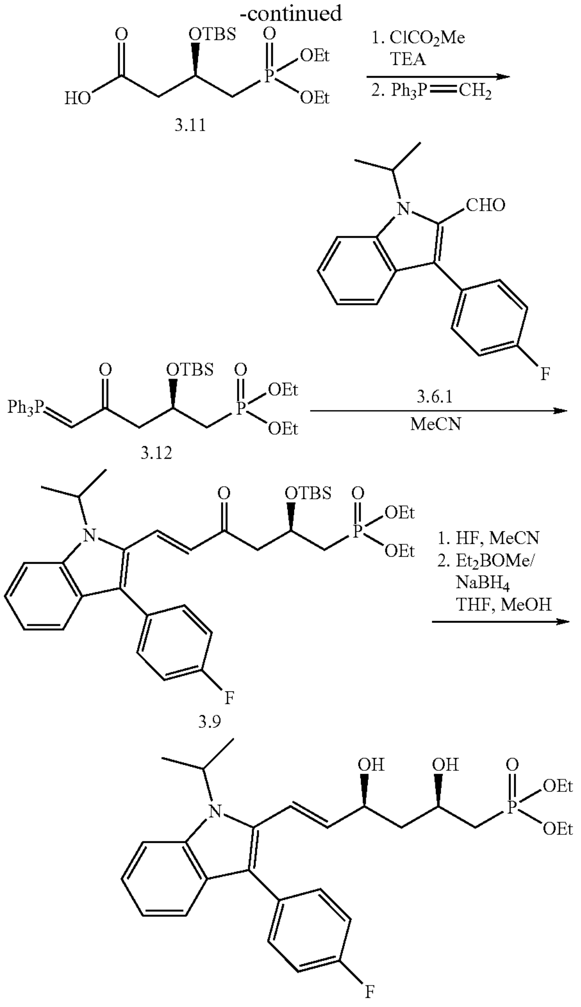

3.11

3.12

3.9

3.10

A generic phosphonate bis-ester can be prepared as demonstrated above and the substituents at phosphorus can be manipulated according to transformations shown herein. The synthesis begins with formation of silyl enol ether of methyl acetoacetate (available from Aldrich) using TMSCl and LDA as described in Jullien et al., *tetrahedron Lett.*, 23(47):4943 (1982) to form compound 3.1. Bromination under the conditions reported by Chan et al., *J. Chem. Soc. Chem. Commun.*, 578 (1979) yields 4-bromo-3-oxo-butyric acid methyl ester 3.2. Arbuzov reaction of the bromide 3.2 with triethylphosphite as reported by Yuan et al:, *Heteroatom Chemistry*, 13(2): 153 (2002) provides diethyl phosphonate 3.3. Addition of ester 3.3 to bakers' yeast in water yields 4-(diethoxyphosphoryl)-3-R-hydroxybutanoic acid methyl ester 3.4 as described by Yuan, E. et al. Silylation of the newly generated secondary alcohol using TBSCl and imidazole followed by selective removal of the methyl ester protecting group as described in Greene, T., "Protective Groups in Organic Synthesis, Wiley-Interscience (1999) provides compound 3.5. Carboxylic acid 3.5 is treated with methyl chloroformate and triethylamine to give a mixed anhydride which is then converted to compound 3.6 by reacting with methylidenetriphenylphosphorane according to the method described in Konoike et al., *J. Org. Chem.*, 59:7849 (1994). A Wittig reaction between compound 3.6 and aldehyde 3.6.1 (prepared as described in WO 84/12131) provides the olefin analog 3.7. Removal of the TBS protecting group with HF in MeCN followed by stereoselective chelation-controlled reduction with $Et_2BOMe$ and sodium borohydride in THF: MeOH gives the desired phosphonate 3.8.

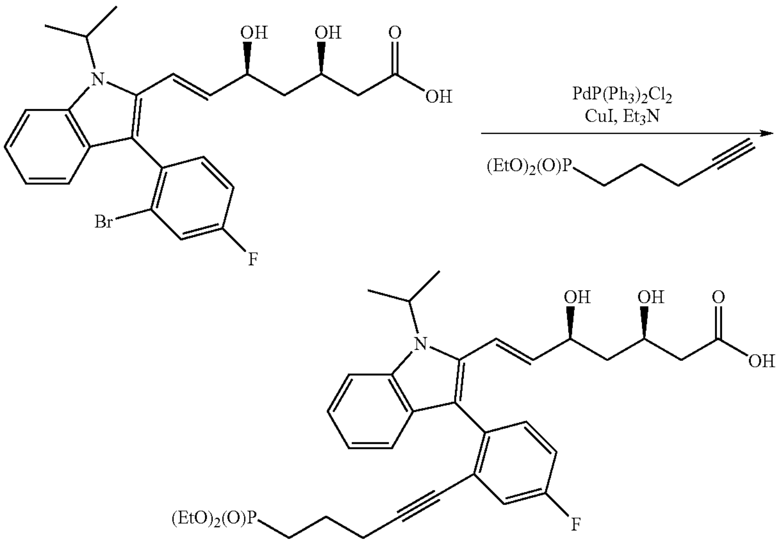

An example of the synthesis of a representative compound of the invention is depicted above. A Sonagashira coupling (see Stang, P. J. and Diederich, F., *Metal Catalyzed Cross Coupling Reactions*, Wiley-VCH, Weinheim, (1988)) is used to attach the phosphonate moiety. The requisite acetylene is made by heating 5-chloro-1-pentyne with triethylphosphite in a solvent such as toluene (or other Arbuzov reaction conditions: see Engel, R., "Synthesis of Carbon-phosphorus Bonds," CRC press, (1988)), and the aryl bromide by the analogous route as for fluvastatin itself.

Example 4

Preparation of Representative Compounds of the Invention

Pitavastatin 4.1

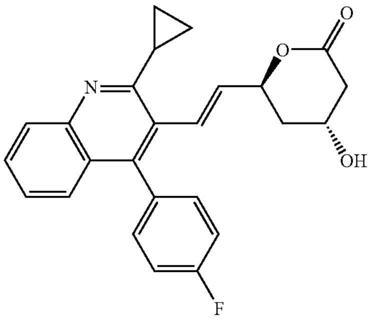

4.2

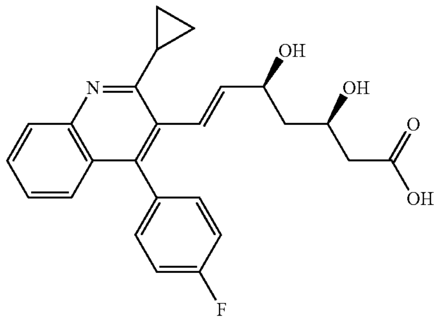

4.3

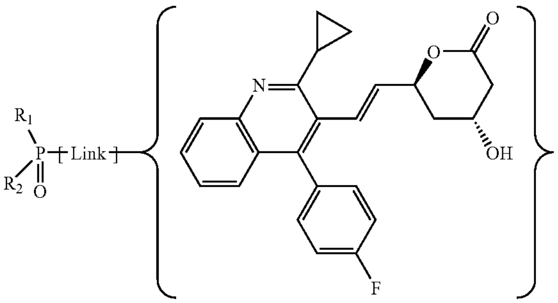

$R_1$ = O—aryl, O—heteroaryl, alpha or beta amino acid ester
$R_2$ = lactate ester or alpha or beta amino acid ester -continued 4.4

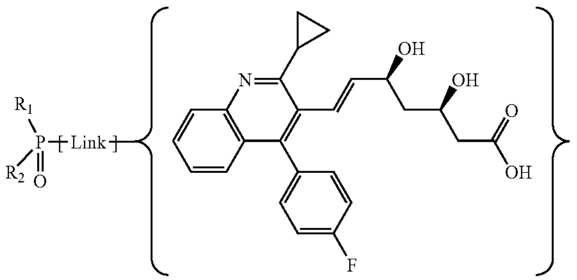

[Link] = uninterupted chain of atoms excluding hydrogen optionaly including cycles connecting a sustitutable position on Atorvastatin with the described phosphorous atom 4.5

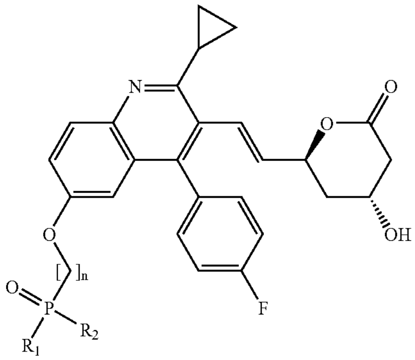

n = 1 to 20

4.6

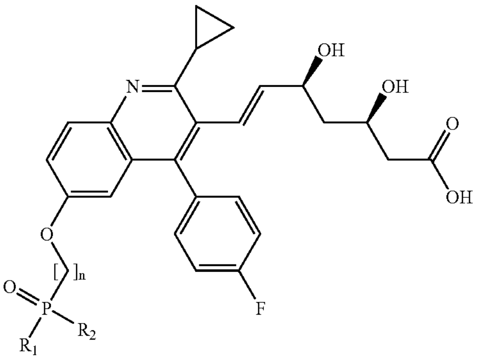

n = 1 to 20

Compounds such as Pitavastatin, 4.1, and its opened chain form, 4.2, are useful for inhibiting chloesterol biosynthesis and lowering blood cholesterol levels. As such, they are useful in the treatment of atherosclerosis hypercholesterolemia and hyper lipoproteinemia as described in U.S. Pat. No. 5,856,336 (Column 1, line 40).

The present invention provides novel analogs of Pitavastatin, 4.1, and its opened chain form, 4.2. Such novel analogs, e.g., general structures 4.3 and 4.4, above, possess all the utilities of Pitavastatin and its opened chain form, and optionally provide cellular accumulation.

Representative compounds of the invention can be prepared as described herein.

Specific compounds of the invention can be prepared as follows:
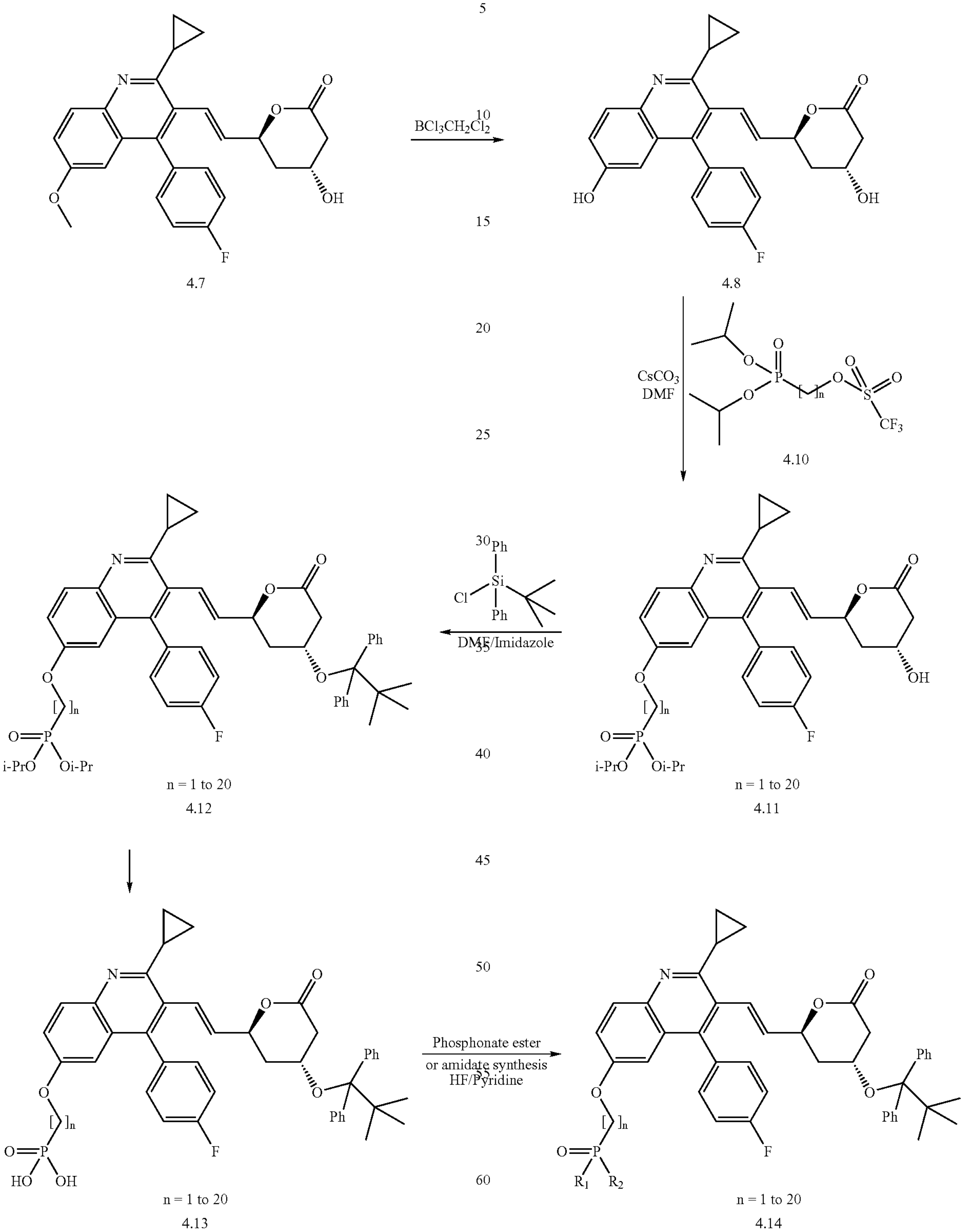
4.7, 4.8, 4.10, 4.11, 4.12, 4.13, 4.14
$R_1$ = O—aryl, O—heteroaryl, alpha or beta amino acid ester
$R_2$ = lactate ester or alpha or beta amino acid ester A method of synthesis of compound 4.7 is described in U.S. Pat. No. 5,856,336 (column 11, in Table I). This material is treated with boron trichioride in dichloromethane to afford the phenol 4.8. Phenol 4.8 is then alkylated with a dialkyl ester of a phosphonoalkyltriflate, such as the diiospropyl ester of general structure 4.10, which can be prepared as follows:

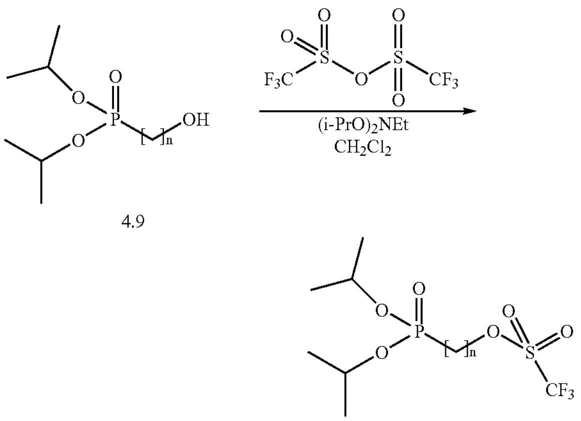

4.9

4.10

The product 4.11 is then treated with tertbutyldiphenylsilyl chloride to afford compound 4.12, which is then treated with trimethylsilylbromide in acetonitrile containing collidine to afford the free phosphonate 4.13.

Compound 4.13 is then converted to the desired prodrug by the methods of phosphonate ester and amidate synthesis outlined below. Then, the silyl group is removed with hydrogen fluoride in pyridine to afford the compound of general structure 4.14.

Example 5

Preparation of Representative Compounds of the Invention

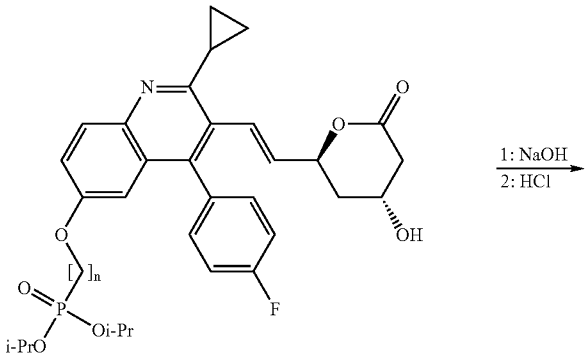

n = 1–20

5.1

-continued
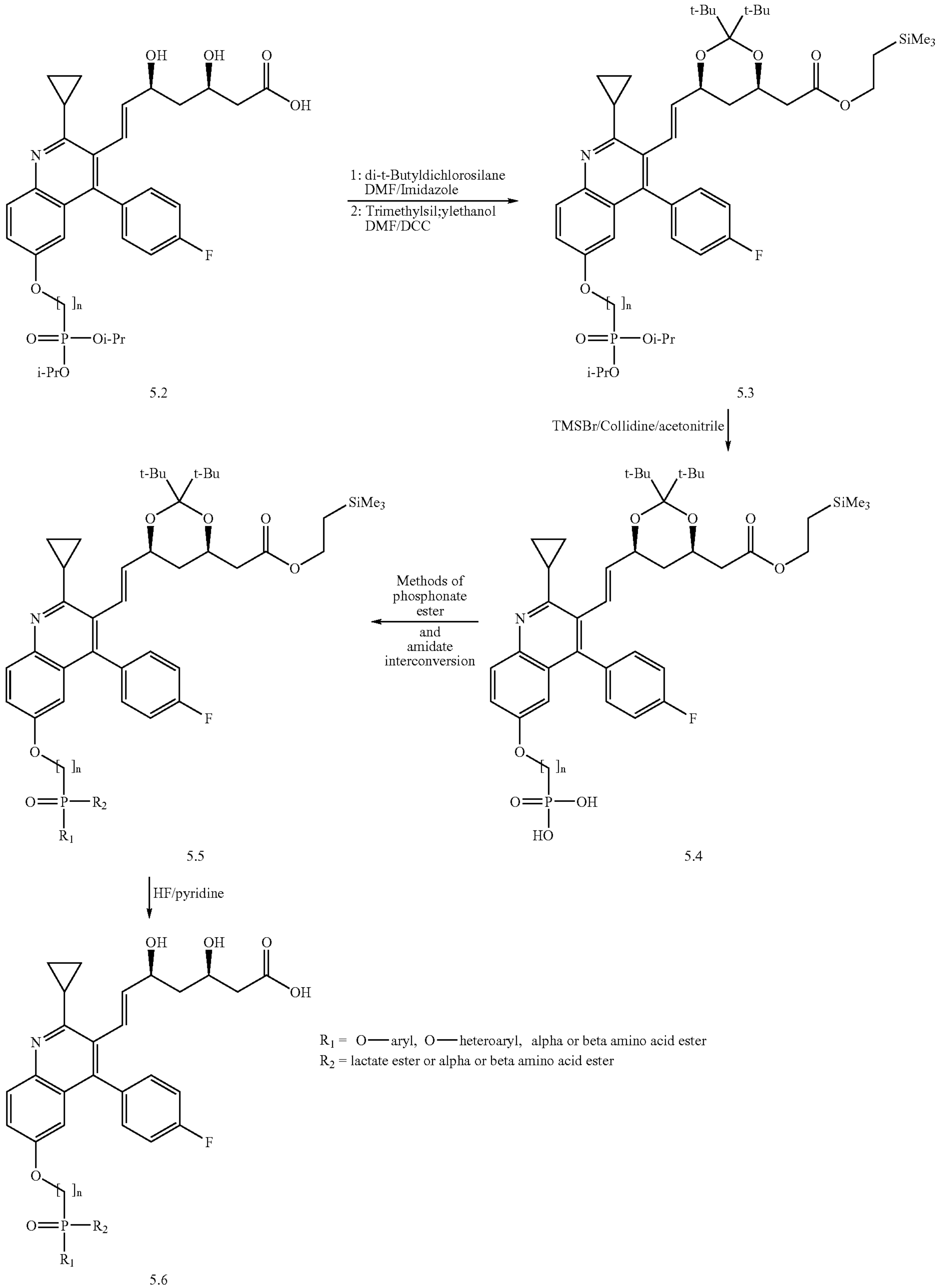
5.2 5.3 5.4 5.5 5.6
$R_1$ = O—aryl, O—heteroaryl, alpha or beta amino acid ester
$R_2$ = lactate ester or alpha or beta amino acid ester The synthesis of the hydrolysed beta carboxylic acid forms of fluvastatin lactone is shown above.

Compound 5.1 is hydrolyzed to compound 5.2 using aqueous sodium hydroxide. The free hydroxyl groups are protected as the cyclic silyl ether by treatment with ditertbutyldichlorosilane in DMF containing imidazole. The carboxylic acid is then protected at the trimethylsilylethyl ester by treatment with trimethylsilylethanol and dicyclohexylcarbodiimide in DMF to afford compound 5.3. Compound 5.3 is then treated with trimethylsilyl bromide in acetonitrile containing collidine to afford the compound of the general structure 5.4.

The phosphonic acid 5.4 is then converted to the desired prodrug form by the methods of phosphonic acid ester and amidate formation outlined below, and the protecting groups are removed with hydrogen fluoride in pyridine to afford the prodrug of the general structure 5.6.

Specific compounds of the invention can be prepared as follows:

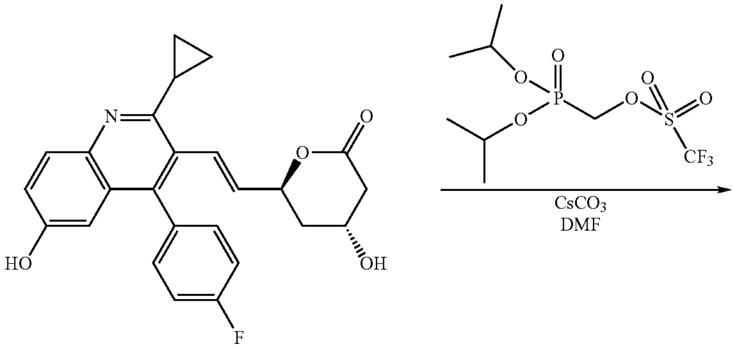

5.8

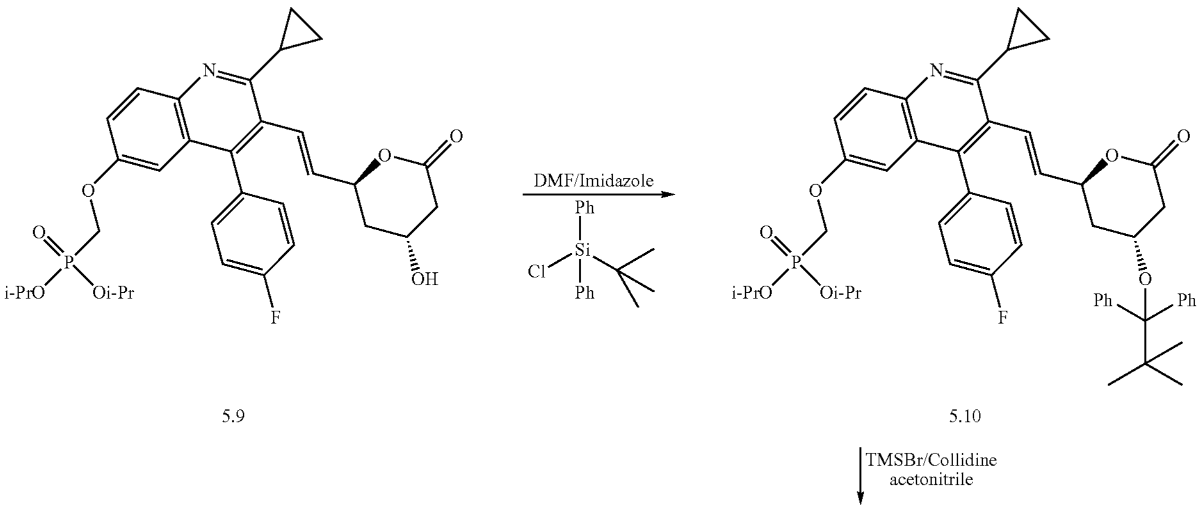

5.9

5.10

-continued

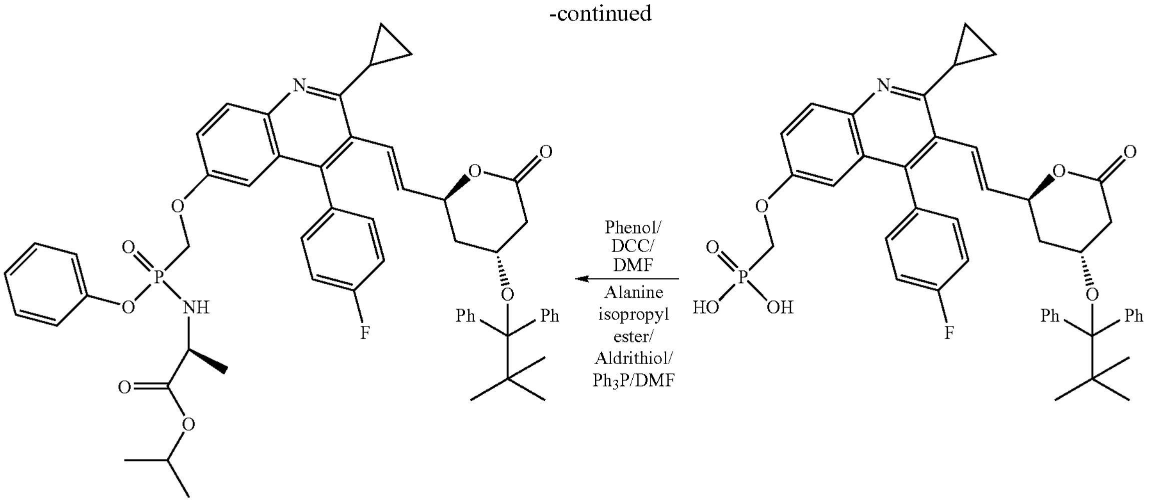

5.12 5.11

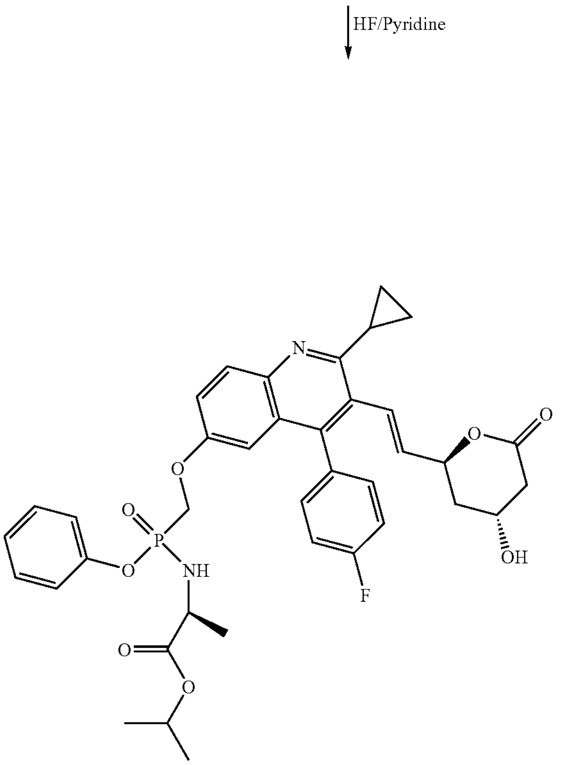

5.13

The synthesis of compound 5.13 is illustrated above. Compound 5.8 is prepared according to Example 4, and the free phenolic hydroxyl group is then selectively alkylated with diisopropyl trifluoromethylsulfonyloxymethylphophonate in a solvent such as DMF using cesium carbonate, magnesium tert-butoxide or any other suitable base to yield the phosphonyl ether 5.9. The free hydroxyl group of 5.9 is then protected by treatment with tertbutyldiphenylsilyl chloride in DMF conataing imidazole to yield the protected phosphonate diester 5.10. The alkyl protecting groups of the phosphonate moiety are then removed with trimethylsilylbromide in acetonitrile containing a base such as collidine to yield 5.1 1. The free phosphonate 5.11 is converted into the monophenol derivative with dicyclohexylcarbodiimide in DMF, and then condensed with the isopropyl ester of alanine, under the action of triphenyl phosphine and aldrithiol to yield compound 5.12. The silyl protecting group of 5.12 is removed with buffered fluoride source such as hydrogen fluoride in pyridine, yielding the prodrug of the lactone of structure 5.13.

Example 6

Preparation of Representative Compounds of the Invention

Specific compounds of the invention can be prepared as follows:

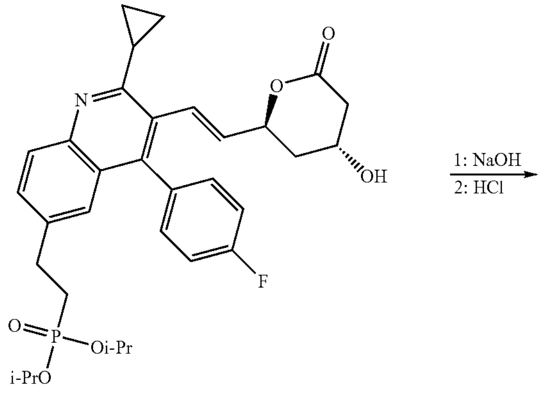
6.1
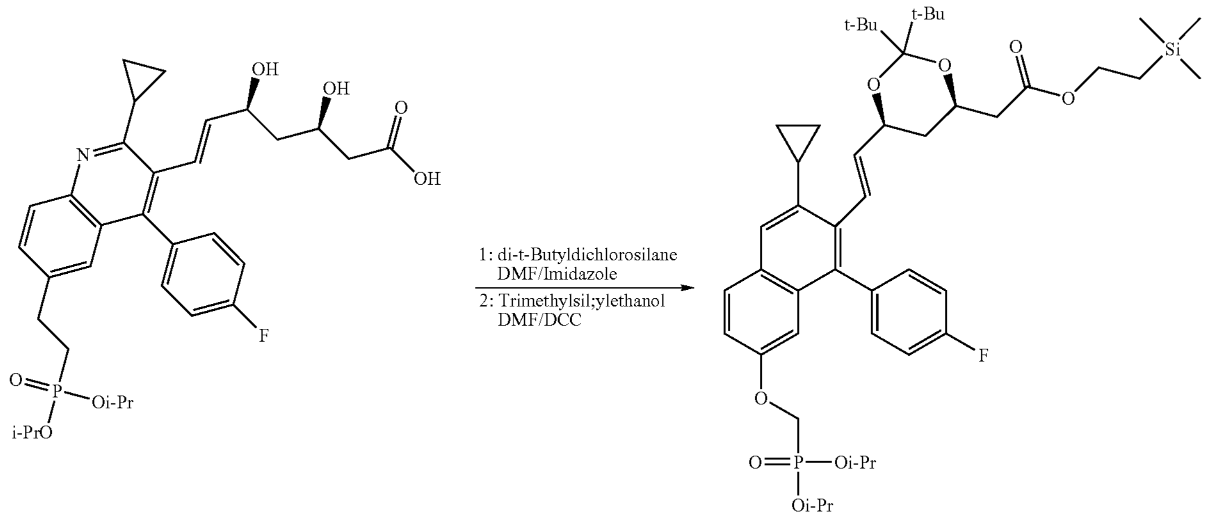
6.2 6.3
TMSBr/Collidine/acetonitrile

-continued

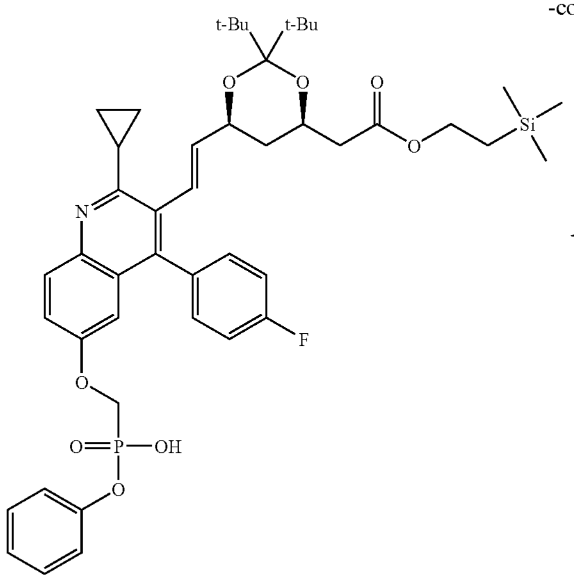

Phenol/
DCC/DMF

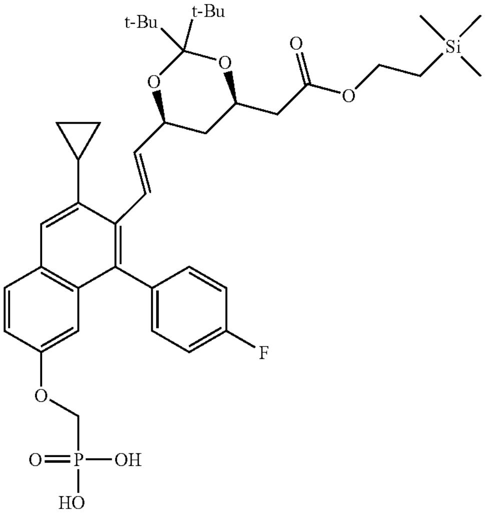

6.5

6.4

Alanine isopropyl
ester/aldrithiol/tripenylphosphine
DMF

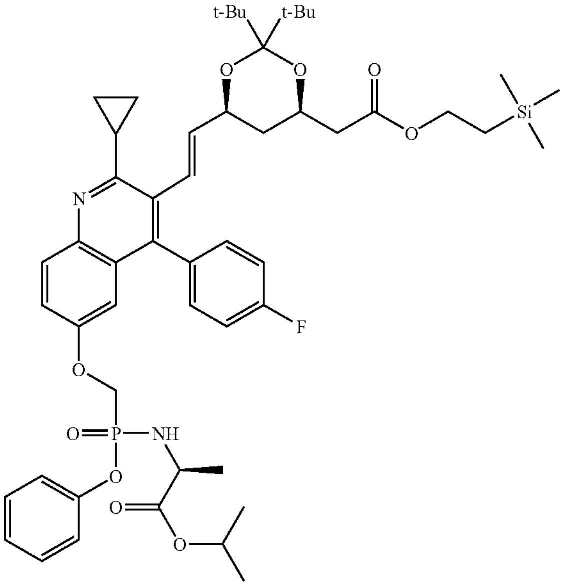

HF/pyridine

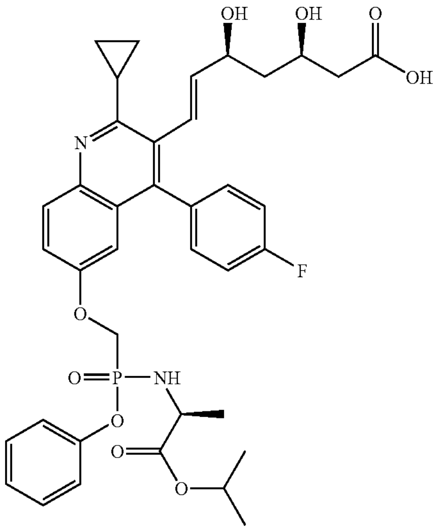

6.6

6.7

The synthesis of 6.7, a member of the class of compounds more generally described in Example 4 (compound 4.6), is depicted above. Compound 6.1 is prepared as described herein. Compound 6.1 is hydrolyzed to compound 6.2 using aqueous sodium hydroxide and the free hydroxyl groups are protected as the cyclic silyl ether by treatment with ditertbutyldichlorosilane in DMF containing imidazole. The carboxylic acid is then protected at the trimethylsilylethyl ester by treatment with trimethylsilylethanol and dicyclohexylcarbodiimide in DMF to afford compound 6.3. Compound 6.3 is then treated with trimethylsilyl bromide in acetonitrile containing collidine to afford the compound of the general structure 6.4. The free phosphonate 6.4 is converted into the monophenol derivative 6.5 with dicyclohexylcarbodiimide in DMF, and then condensed with the isopropyl ester of alanine, under the action of triphenyl phosphine and aldrithiol to yield compound 6.6. The silyl protecting group of 6.6 is removed with buffered fluoride source such as hydrogen fluoride in pyridine, yielding the prodrug 6.7.

Example 7

Preparation of Representative Compounds of the Invention

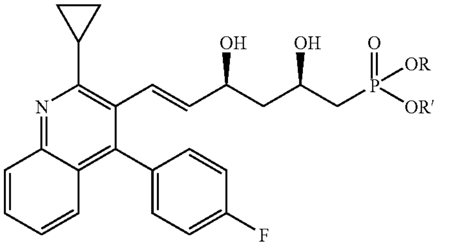

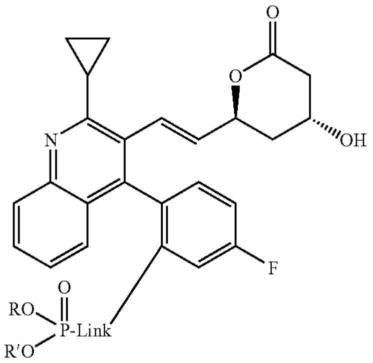

link is 0–8 atoms;
2–6 is preferred

Representative compounds can be made according to the following:

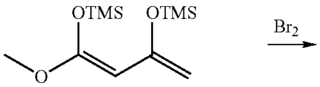

7.1

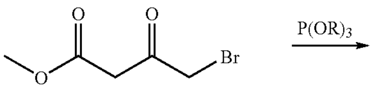

7.2

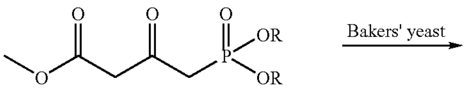

7.3

-continued

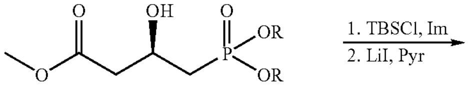

7.4

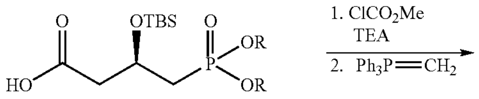

7.5

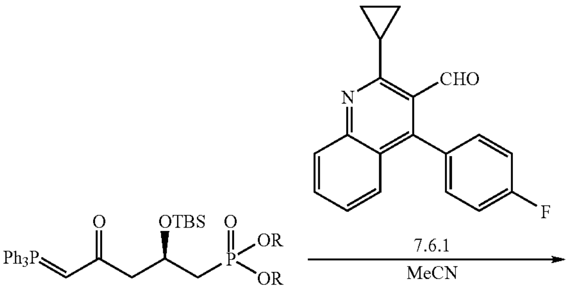

7.6

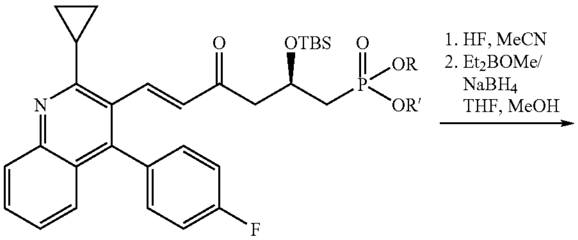

7.7

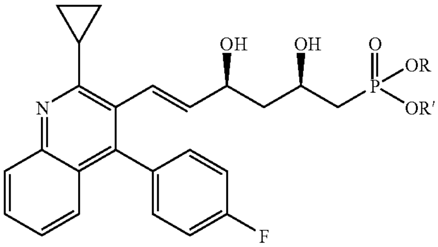

7.8

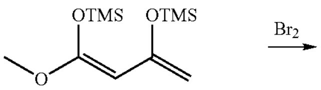

7.1

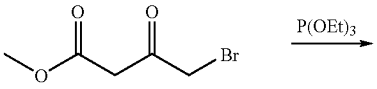

7.2

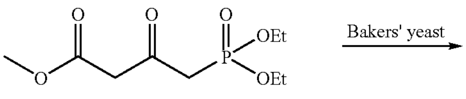

7.9

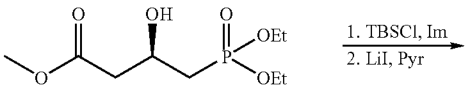

7.10

-continued

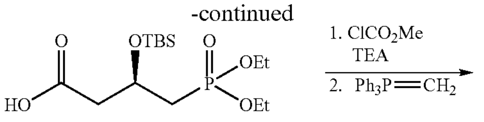

7.11

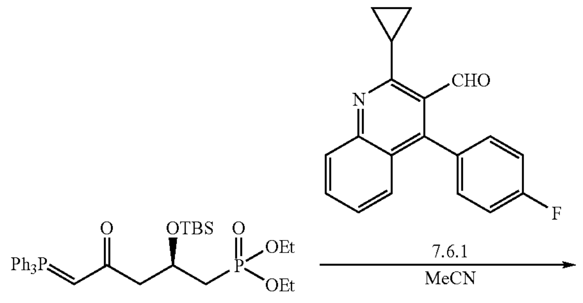

7.12

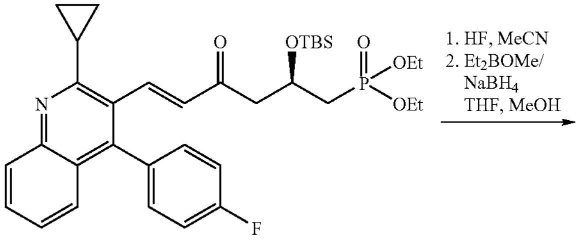

7.16

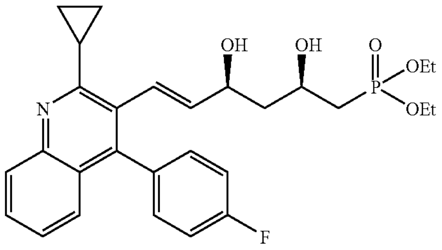

7.17

The preparation of analog 7.8, e.g., 7.17, is shown above. A generic phosphonate bis-ester can be prepared as demonstrated above and the substituents at phosphorus can be manipulated according to transformations.

A specific compound of the invention, 7.17, is also shown above. The synthesis begins with formation of silyl enol ether of methylacetoacetate (available from Aldrich) using TMSCl and LDA as described in Jullien et al., *Tetrahedron Lett.*, 23(47):4943 (1982) to form compound 7.1. Bromination under the conditions reported by Chan et al., *J. Chem. Soc. Chem. Commun.*, 578 (1979) yields 4-bromo-3-oxo-butyric acid methyl ester 7.2. Arbuzov reaction of the bromide 7.2 with triethylphosphite as reported by Yuan et al., *Heteroatom Chemistry*, 13(2):153 (2002) provides diethyl phosphonate 7.3, e.g., 7.9. Addition of ester 7.3 to bakers' yeast in water yields 4-(diethoxyphosphoryl)-3-R-hydroxybutanoic acid methyl ester 7.4 as described by Yuan et al. Silylation of the newly generated secondary alcohol using TBSCl and imidazole followed by selective removal of the methyl ester protecting group as described in Greene, T., "Protective Groups in Organic Synthesis," Wiley-Interscience (1999) provides compound 7.5. Carboxylic acid 7.5 is treated with methyl chlorocarbonate and triethylamine to give a mixed anhydride which is then converted to compound 7.6 by reacting with methylidenetriphenylphosphorane according to the method described in Konoike et al., *J. Org. Chem.*, 59:7849 (1994). A Wittig reaction between compound 7.6 and aldehyde 7.6.1 (prepared according to D. R. Sliskovic et al., *J. Med. Chem.*, 34:367 (1991)) provides the olefin analog 7.7. Removal of the TBS protecting group with HF in MeCN followed by stereoselective chelation-controlled reduction with $Et_2BOMe$ and sodium borohydride in THF:MeOH gives the desired phosphonate 7.8.

An example of the synthesis of a compound of the invention is depicted below.

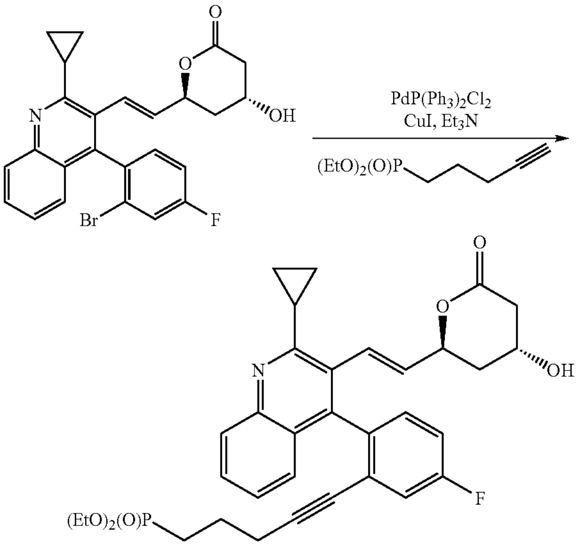

A Sonagashira coupling (see Stang, P. J. and Diederich, F., "Metal Catalyzed Cross Coupling Reactions," Wiley-VCH, Weinheim (1988)) is used to attach the phosphonate moiety. The requisite acetylene is made by heating 5-chloro-1-pentyne with triethylphosphite in a solvent such as toluene (or other Arbuzov reaction conditions: see Engel, R., "Synthesis of Carbon-phosphorus Bonds," CRC press (1988)), and the aryl bromide by the same route as described for other pitavastatin analogs (Sliskovic et al., *J. Med. Chem.*, 34:367 (1991)), starting from 2-bromo-4-fluoro-2'-aminobenzophenone.

Example 8

Preparation of Representative Compounds of the Invention

The synthesis of representative compounds of the invention is described below.

The preparation of intermediate 8.9 is described in U.S. Pat. No. 4,444,784 and the references within.

The side chain containing the phosphonate moiety, carboxylic acid 8.8, can be prepared from alpha methyl gamma butyrolactone. First, the racemic lactone is resolved using a chiral preparative HPLC column, and the S isomer is hydrolized with lithium hydroxide in aqueous tetrahydrofuran. The resulting acid is converted to its tert butyl ester with isobutene and sulfuric acid. Then, the ester is alkylated with diisopropylphosphonomethylbromide in dimethylformamide using sodium hydride as the base to afford compound 8.7. Compound 8.7 is then deprotected with trifluoroaceic acid to afford the synthon 8.8.

The coupling between intermediate 8.9 and carboxylic acid 8.8 is effected through the action of dicyclohexylcarbodiimide in DMF to afford the phosphonate containing protected lovastatin analog 8.10. The isopropyl groups are removed with trimethylsilylbromide in acetonitrile containing collidine to afford the free phosphonic acid 8.11. Phosphonate 8.11 can then be converted into a variety of phophonic ester as described by the general structure 8.15 by the methods of phosphonate interconversion described below. In this example, 8.11 is treated with dicyclohexycarbodiimide and phenol to afford the monoester 8.12, which is further condensed with alanine isopropyl ester using aldrithiol and triphenylphosphine to afford 8.13. Finally, intermediate 8.13 is deprotected with hydrogen fluoride in pyridine to afford the desired compound 8.14

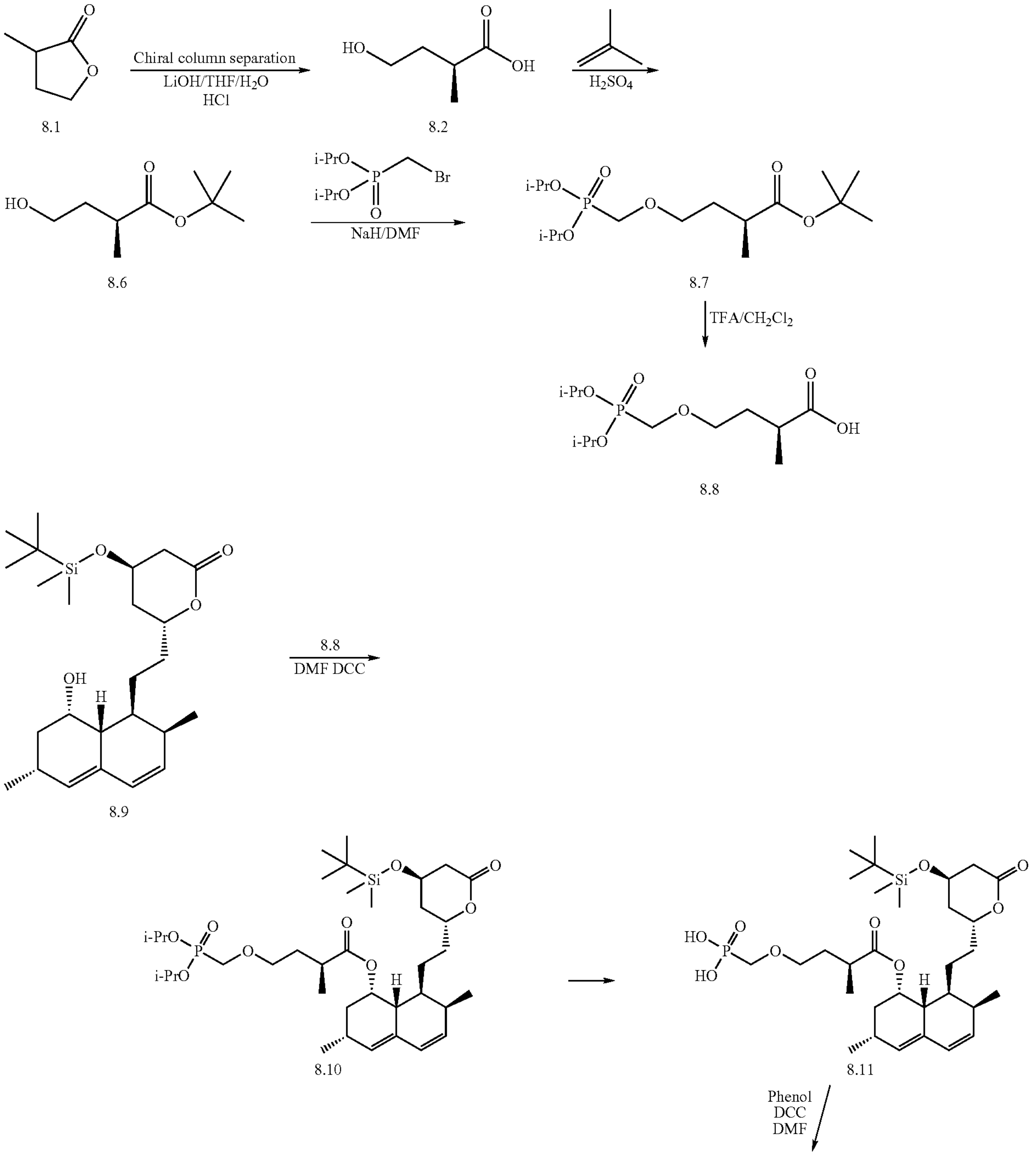

8.1 8.2 8.6 8.7 8.8 8.9 8.10 8.11

-continued
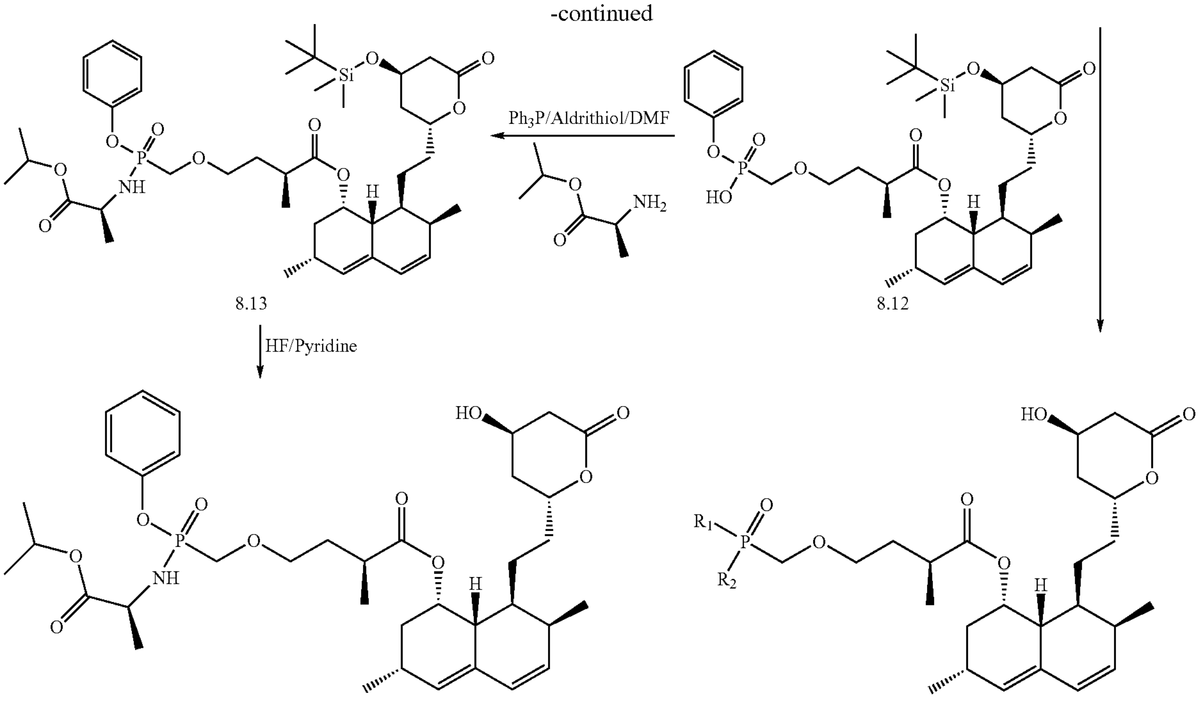
8.13 8.12
8.14 8.15
Example 9
Preparation of Representative Compounds of the Invention
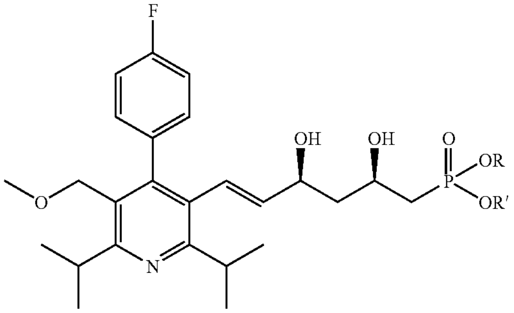
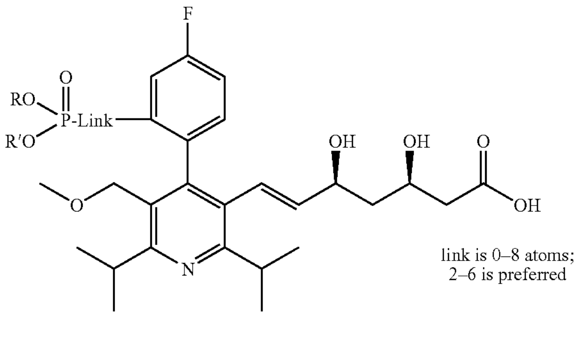
link is 0–8 atoms; 2–6 is preferred
Representative compounds of the invention, e.g., as shown above, can be made according to the following:
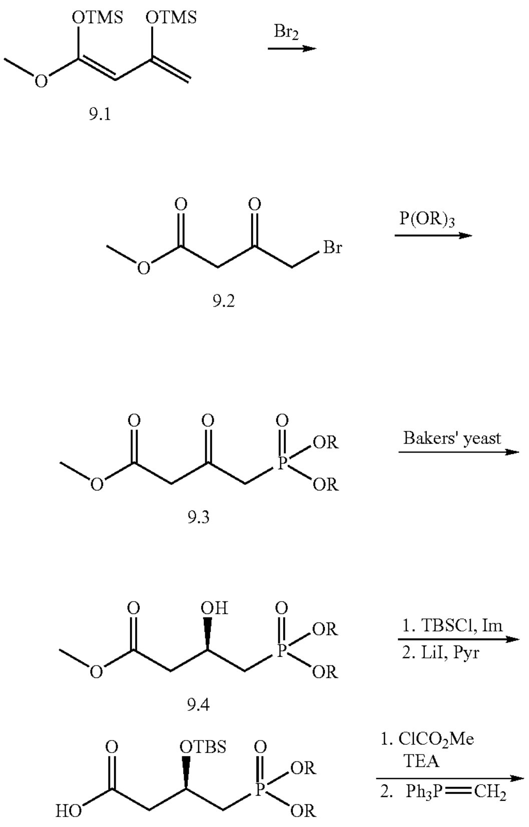
9.1
9.2
9.3
9.4
9.5

-continued

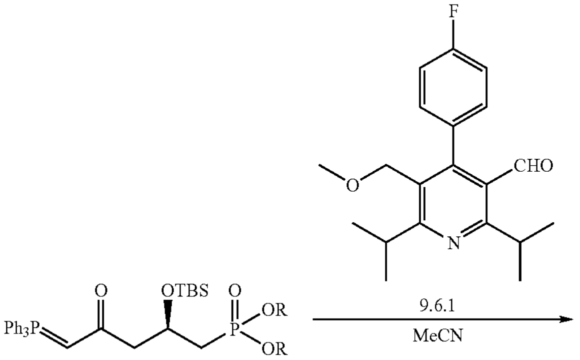

9.6

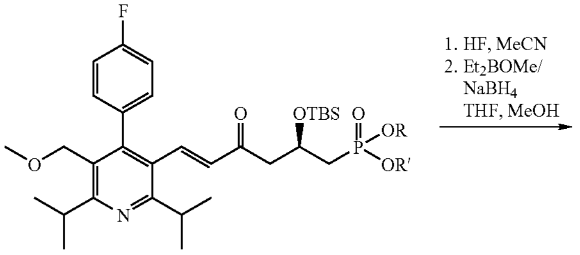

9.7

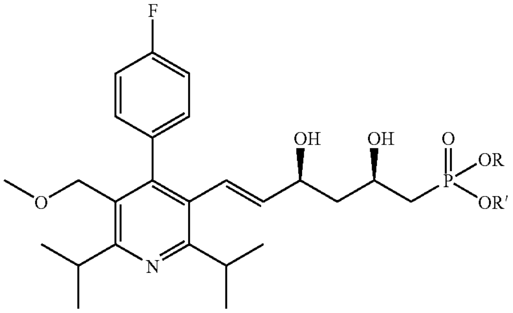

9.8

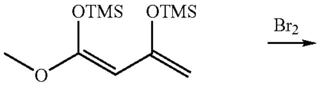

9.1

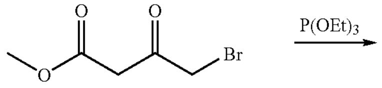

9.2

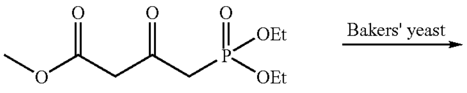

9.9

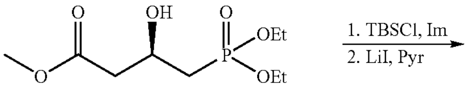

9.10

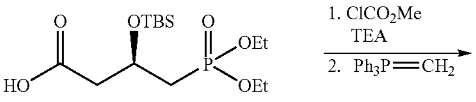

9.11

-continued

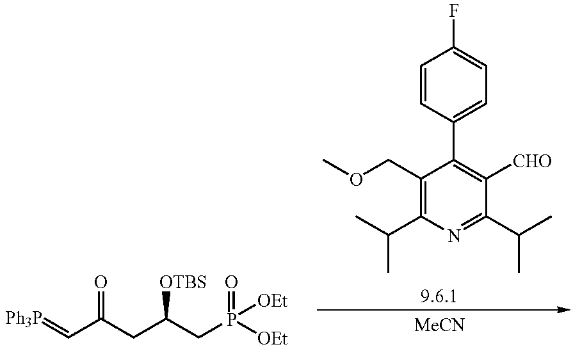

9.12

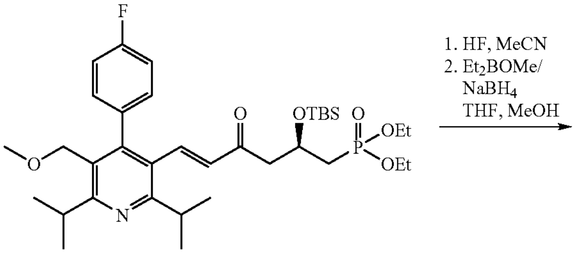

9.13

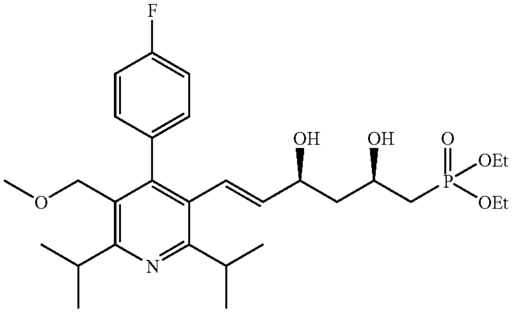

9.14

Preparation of analog 9.8, e.g., 9.14, is shown above. A generic phosphonate bis-ester can be prepared as demonstrated above and the substituents at phosphorus can be manipulated according to transformations. A specific example for compound 9.8 is shown.

The synthesis begins with formation of silyl enol ether of methylacetoacetate (available from Aldrich) using TMSCl and LDA as described in Jullien et al., *Terahedron Lett.*, 23(47):4943 (1982) to form compound 9.1. Bromination under the conditions reported by Chan et al., *J. Chem. Soc. Chem. Commun.*, 578 (1979) yields 4-bromo-3-oxo-butyric acid methyl ester 9.2. Arbuzov reaction of the bromide 9.2 with triethylphosphite as reported by Yuan et al., *Heteroatom Chemistry*, 13(2):153 (2002) provides diethyl phosphonate 9.9. Addition of ester 9.9 to bakers' yeast in water yields 4-(diethoxyphosphoryl)-3-R-hydroxybutanoic acid methyl ester 9.10 as described by Yuan, E. et al. Silylation of the newly generated secondary alcohol using TBSCl and imidazole followed by selective removal of the methyl ester protecting group as described in Greene, T., "Protective Groups in Organic Synthesis," Wiley-Interscience (1999) provides compound 9.11. Carboxylic acid 9.11 is treated with methyl chlorocarbonate and triethylamine to give a mixed anhydride which is then converted to compound 9.12 by reacting with methylidenetriphenylphosphorane according to the method described in Konoike et al., *J. Org. Chem.*, 59:7849 (1994). A Wittig reaction between compound 9.6 and aldehyde 9.6.1 (prepared according to U.S. Pat. No. 5,006,530) provides the olefin analog 9.13. Removal of the TBS protecting group with HF in MeCN followed by stereoselective chelation-controlled reduction with $Et_2BOMe$ and sodium borohydride in THF: MeOH gives the desired phosphonate 9.11.

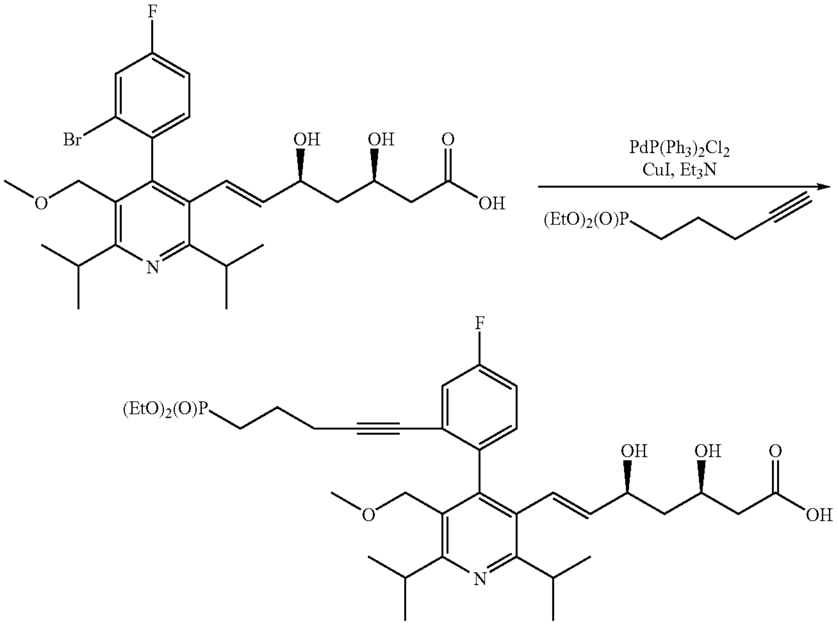

An example of the synthesis of an analog of a compound of the invention is depicted above. A Sonagashira coupling (see Stang, P. J. and Diederich, F., "Metal Catalyzed Cross Coupling Reactions," Wiley-VCH, Weinheim, (1988)) is used to attach the phosphonate moiety. The requisite acetylene is made by heating 5-chloro-1-pentyne with triethylphosphite in a solvent such as toluene (or other Arbuzov reaction conditions see Engel, R., "Synthesis of Carbon-phosphorus Bonds, CRC press, (1988)), and the aryl bromide by the analogous route as for cerivastatin itself (U.S. Pat. No. 5,006,530).

Example 10

Preparation of Representative Compounds of the Invention

Representative compounds of the invention can be prepared as follows:

The linkage between the phosphonate moiety and Cerivastatin can be formed by alkylating the free hydroxyl group of intermediate 10.1, whose synthesis is described in U.S. Pat. No. 5,006,530, (column 65, line 5).

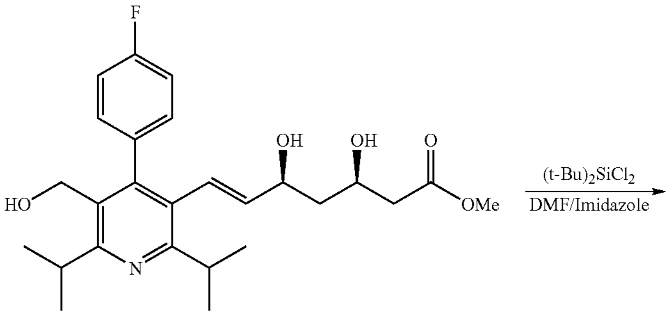

10.1

-continued

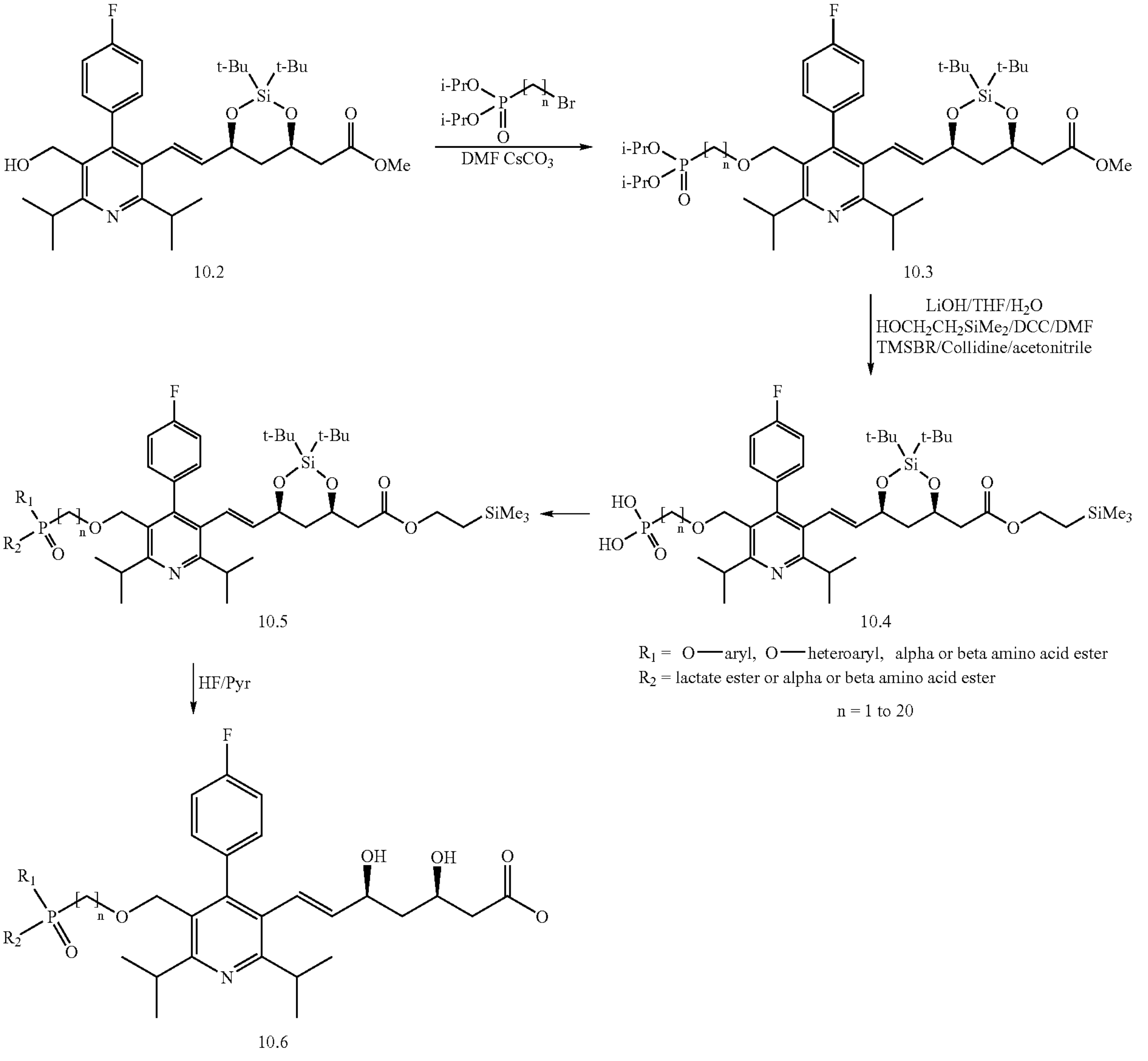

Compound 10.1 is reacted with ditetbutyldichlorosilane in pyridine to afford the protected intermediate 10.2. The free hydroxyl group of compound 10.2 is alkylated with an alkyl protected phosphonoalkylhalide such as diisopropylphoshonomethylbromide to afford the conjugate 10.3. The methyl ester of compound 10.3 is exchanged for the trimethylsilylethylester by hydrolysis with lithium hydroxide, followed by coupling with trimethylsilylethanol with dicyclohexycarbodiimide in DMF, followed by the removal of the phosphonate protecting groups with trimethylsilylbromide and collidine in acetonitrile to yield compound 10.4.

Compound 10.4 is then transformed into the desired prodrug form by the methods of phosphonic acid transformation described below, and the silyl protecting groups are removed with a fluoride source such as hydrogen fluoride in pyridine to yield the desired prodrug of the general structure 10.6.

Specific compounds of the invention, conforming to the description rendered by the general structure 10.6, can be synthesized as follows:

Compound 10.7 is alkylated with the commercially available diisopropyl phosphonomethylbromide in DMF with cesium carbonate as base. The resulting phosphonate 10.8 is treated with lithium hydroxide. The resulting carboxylic acid is coupled to trimethylsilylethanol to yield the trimethylsilylethylester. Removal of the isopropyl esters with trimethylsilylbromide in collidine and DMF affords the phosphonic acid 10.9, which is then coupled with phenol with dicyclohexylcarbodiimide in DMF to afford compound 10.10. Compound 10.10 is then coupled with the isopropyl ester of alanine using triphenylphosphine and aldrithiol in DMF to afford compound 10.11. The silyl protecting groups of 10.11 are then removed with a hydrogen fluoride in pyridine to afford the desired prodrug 10.12.

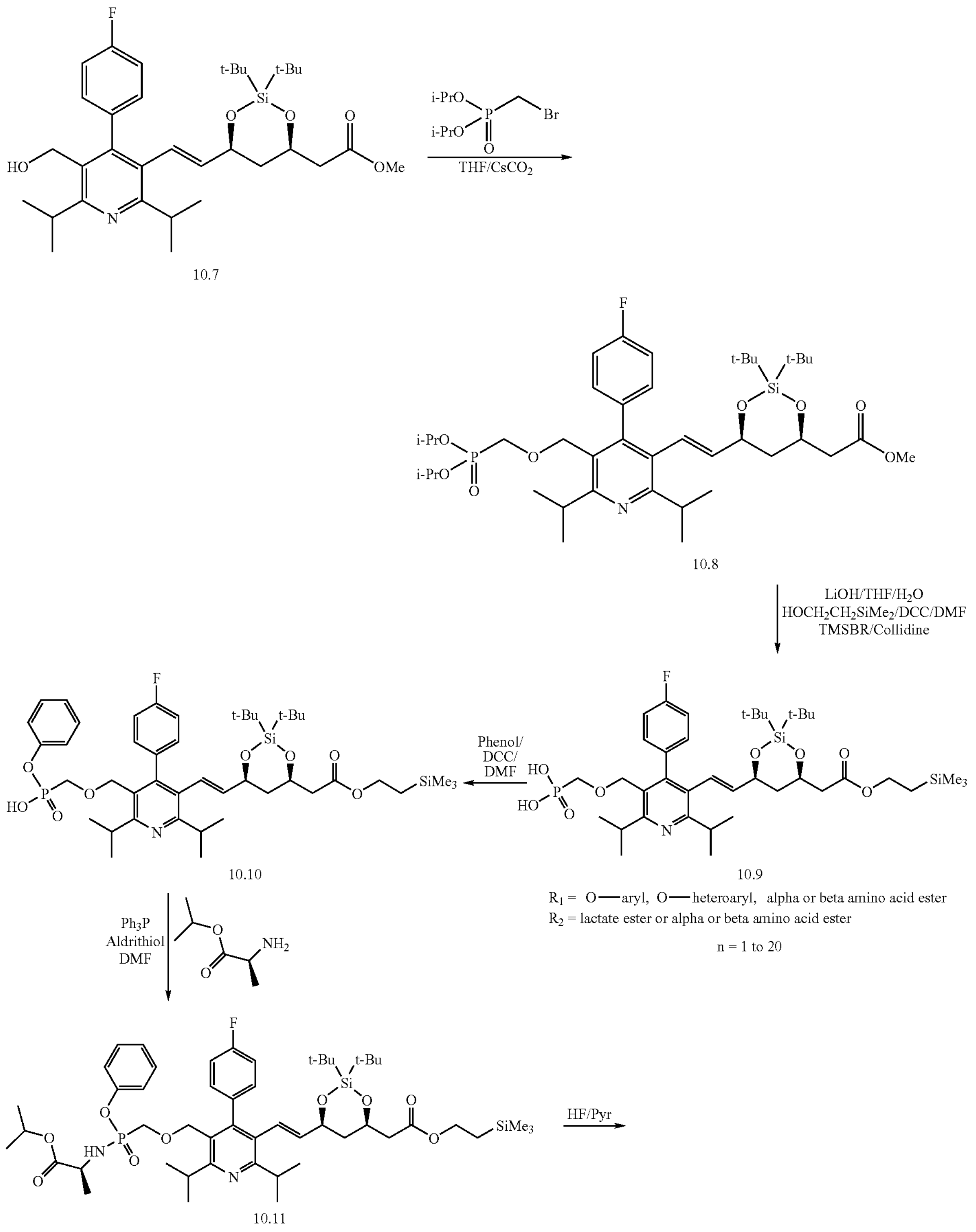
$R_1$ = O—aryl, O—heteroaryl, alpha or beta amino acid ester
$R_2$ = lactate ester or alpha or beta amino acid ester
n = 1 to 20

-continued
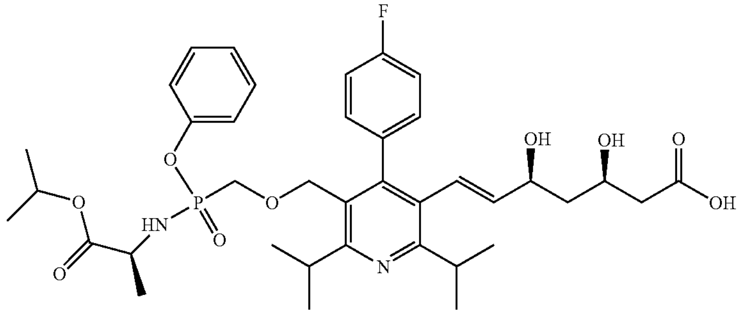
10.12
Example 11
Preparation of Representative Compounds of the Invention
Representative compounds of the invention can be synthesized as follows:
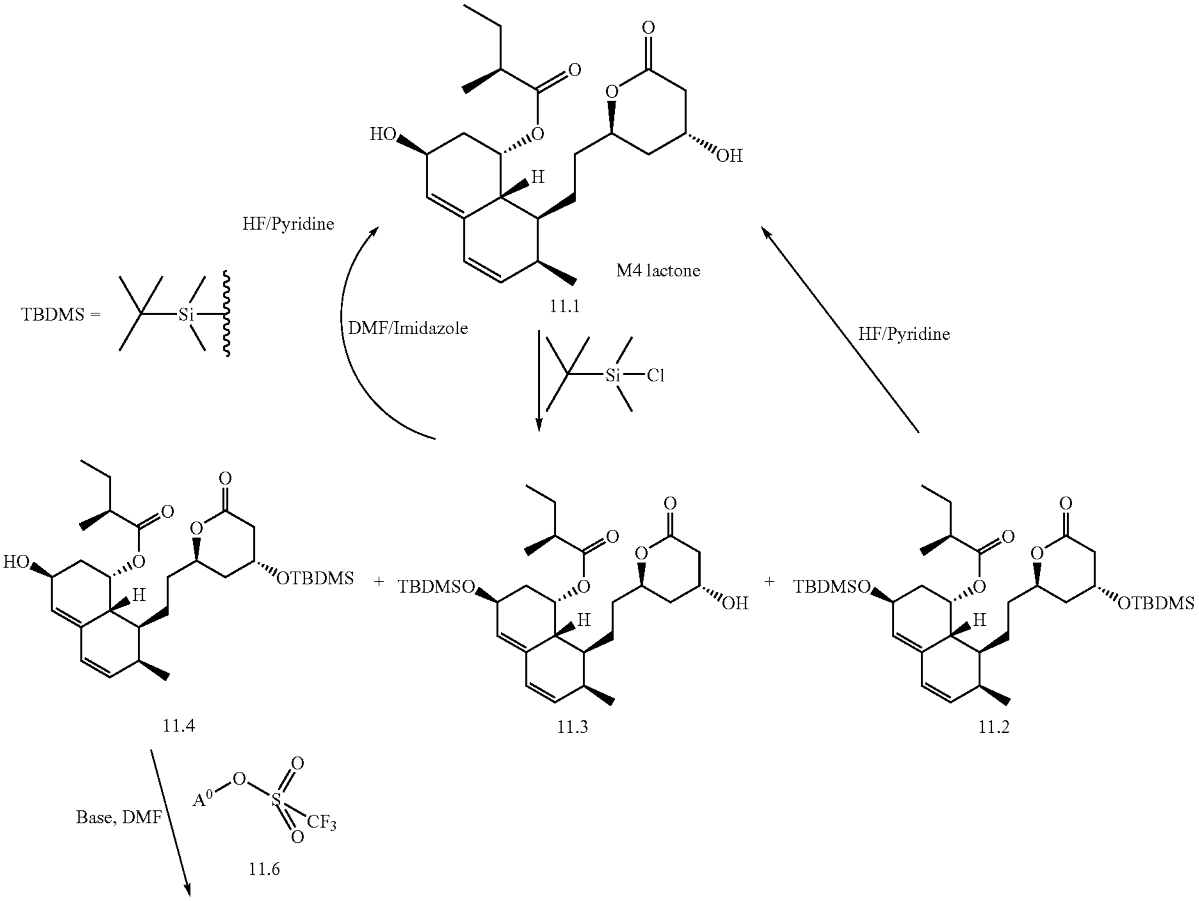
TBDMS =
M4 lactone
11.1
11.4 + 11.3 + 11.2
11.6

-continued

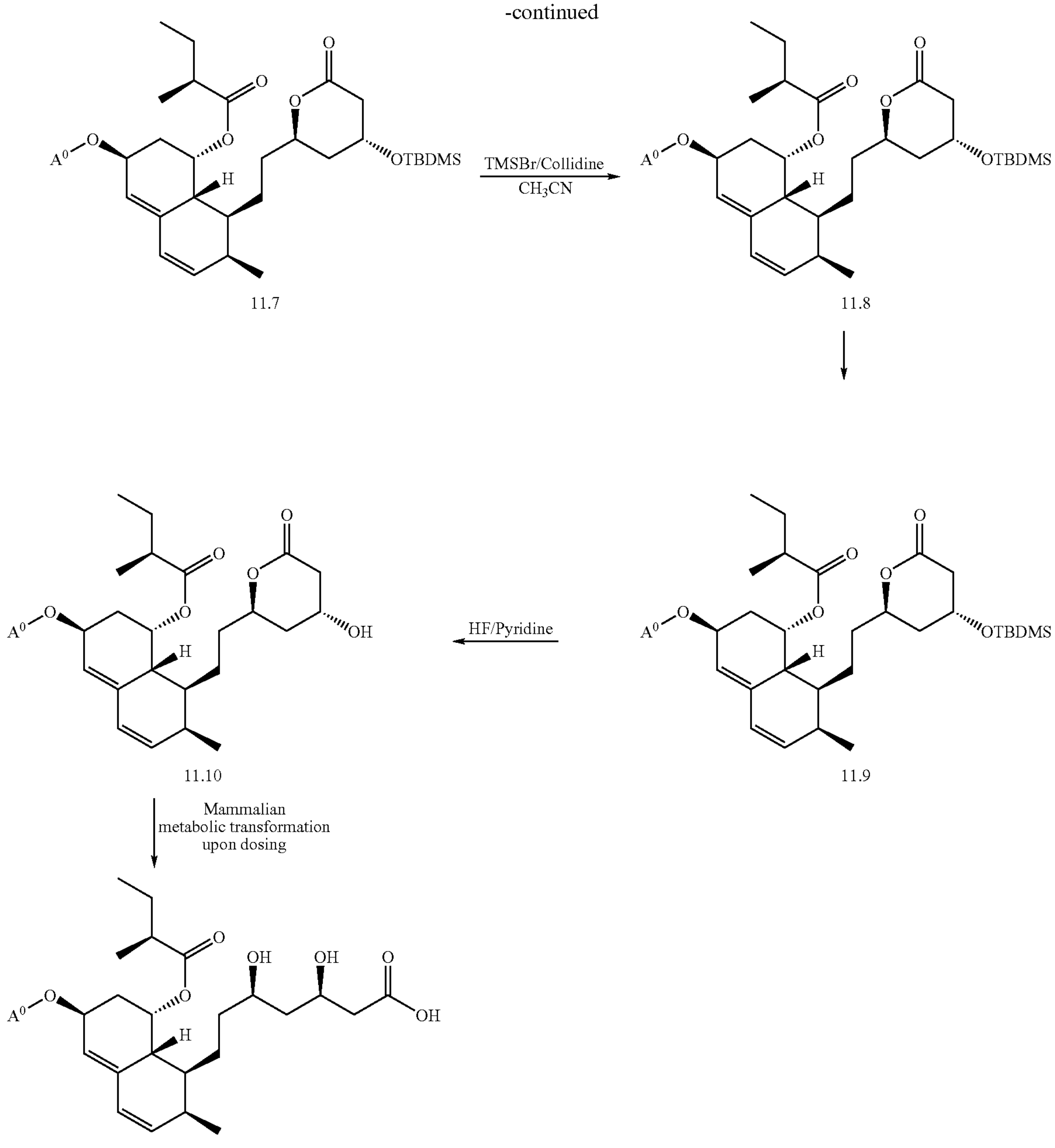

11.7

11.8

11.9

11.10

11.11

The preparation of compound 11.1, also known as M-4 lactone, is described in U.S. Pat. No. 4,346,227. (See column 10, line 30.) Compound 11.1, is treated with one equivalent of a silyl based protecting group, such as tert-butyldimethylsilyl in a solvent such as DMF with imidazole serving as base, to yield a mixture of unsilylated, mono-silylated and bis-silylated derivatives 11.1, 11.2,11.3, and 11.4.

The desired compound 11.4 is separated by chromatography, such as silica gel chromatography or reverse phase chromatography. The free hydroxyl group is then alkylated with a dialkyl protected trifluoromethylsulfonylalkylphosphonate of general structure 11.6 (the synthesis of which is described below) in a solvent such as DMF using cesium carbonate, magnesium tert-butoxide or any other suitable base to yield the phosphonyl ether of general structure 11.7. The alkyl protecting groups of the phosphonate moiety are then removed with trimethylsilylbromide in acetonitrile containing a base such as collidine. The free phosphonate is then converted into the desired prodrug of general structure 11.9 by the methods of phosphonic acid interconversions described herein. The silyl protecting group of 11.9 is removed with buffered fluoride source such as hydrogen fluoride in pyridine, yielding the prodrug of the lactone of general structure 11.10.

Upon oral administration of this prodrug, normal mammalian metabolic processes are able to hydrolyse lactones such as 11.10 to the corresponding dihydroxycarboxylic acid, as exemplified by Example 19 of U.S. Pat. No. 4,346,227 (column 15, line 55).

Synthesis of 11.6 is described as follows:
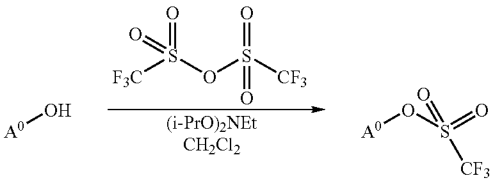
11.5 11.6
The synthesis specific compounds of the invention, in particular, prodrugs 11.17 and 11.18, is described as follows:
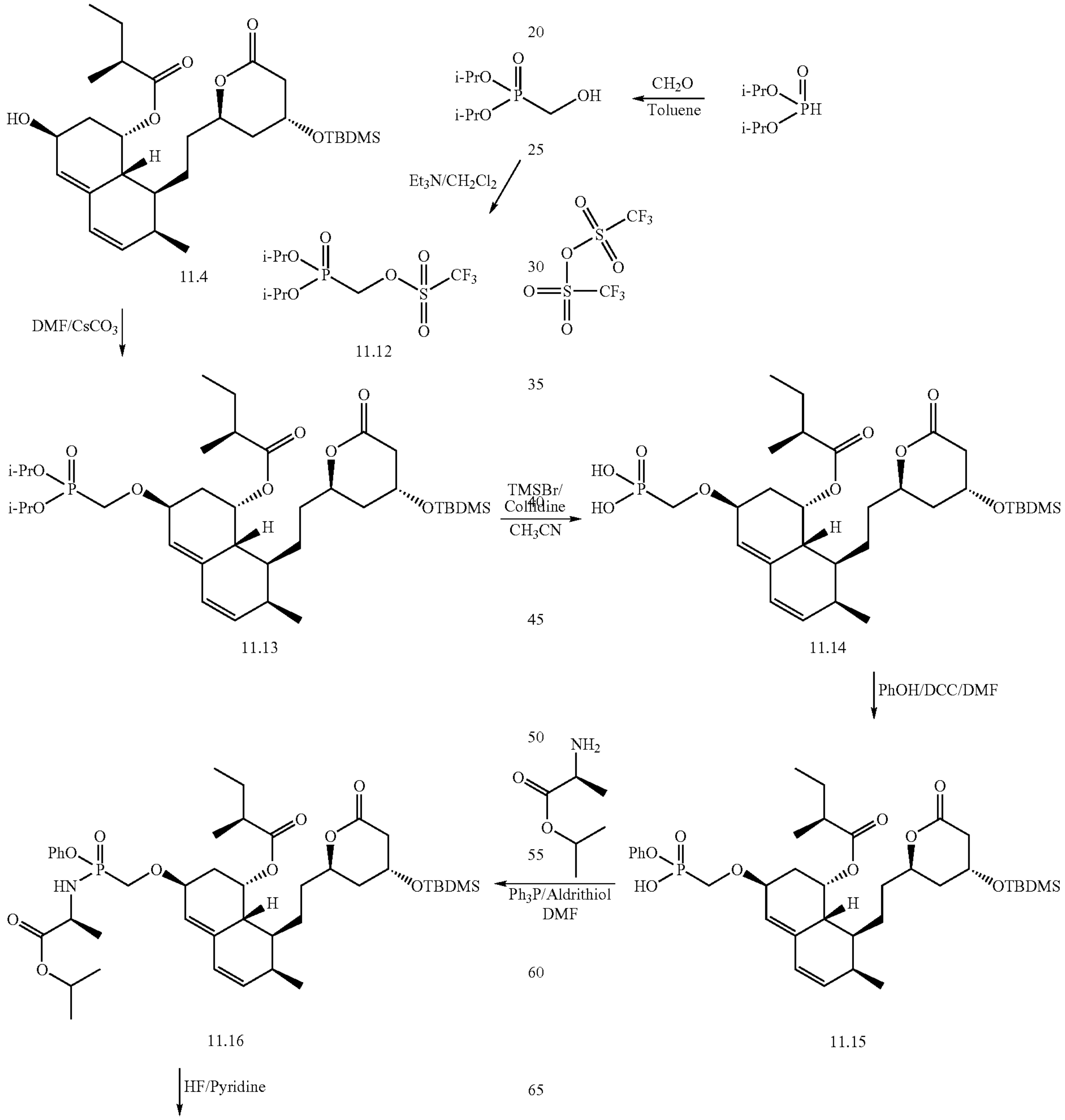
11.4 11.12 11.13 11.14 11.15 11.16

-continued

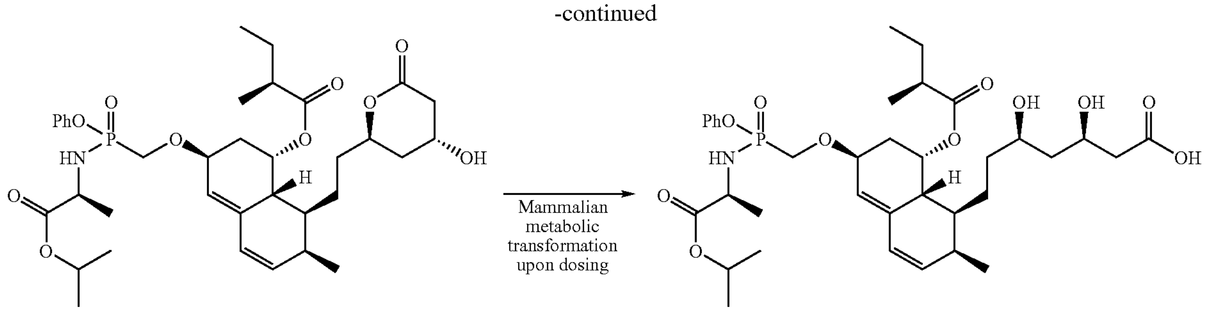

11.17 11.18

Compound 11.4 is prepared as discussed above. The free hydroxyl group is then alkylated with diisopropyl trifluoromethylsulfonyloxymethylphophonate 11.12, in a solvent such as DMF using cesium carbonate, magnesium tert-butoxide or any other suitable base to yield the phosphonyl ether 11.13. The alkyl protecting groups of the phosphonate moiety are then removed with trimethylsilylbromide in acetonitrile containing a base such as collidine to yield 11.14 and the free phosphonate is converted into the monophenol derivative 11.15 with dicyclohexylcarbodiimide in DMF. Compound 11.15 is then condensed with the isopropyl ester of alanine under the action of triphenyl phosphine and aldrithiol to yield 11.16. The silyl protecting group of 11.16 is removed with buffered fluoride source such as hydrogen fluoride in pyridine, yielding the prodrug of the lactone of structure 11.17. Upon oral administration of this prodrug, normal mammalian metabolic processes are able to convert it to the corresponding dihydroxycarboxylic acid of structure 11.18.

Example 12

Preparation of Representative Compounds of the Invention

Representative compounds can be made according to the general route outlined below.

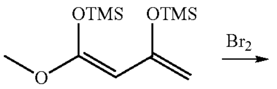

12.1

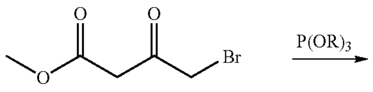

12.2

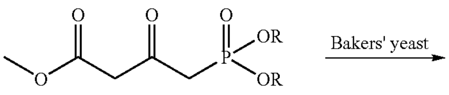

12.3

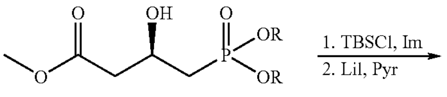

12.4

-continued

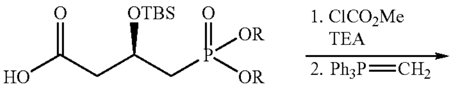

12.5

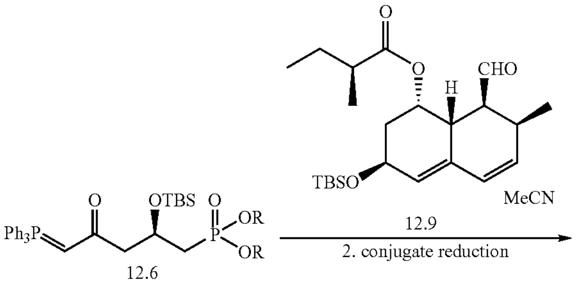

12.6

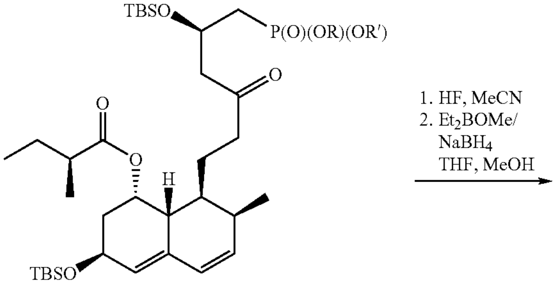

12.7

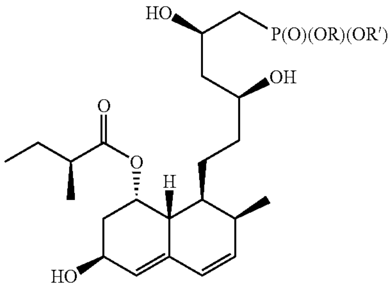

12.8

The preparation of analog 12.8 is described above. A phosphonate bis-ester can be prepared as shown. The substituents at phosphorus can be manipulated according to transformations described herein.

An example of the synthesis of specific compounds of the invention is shown below.

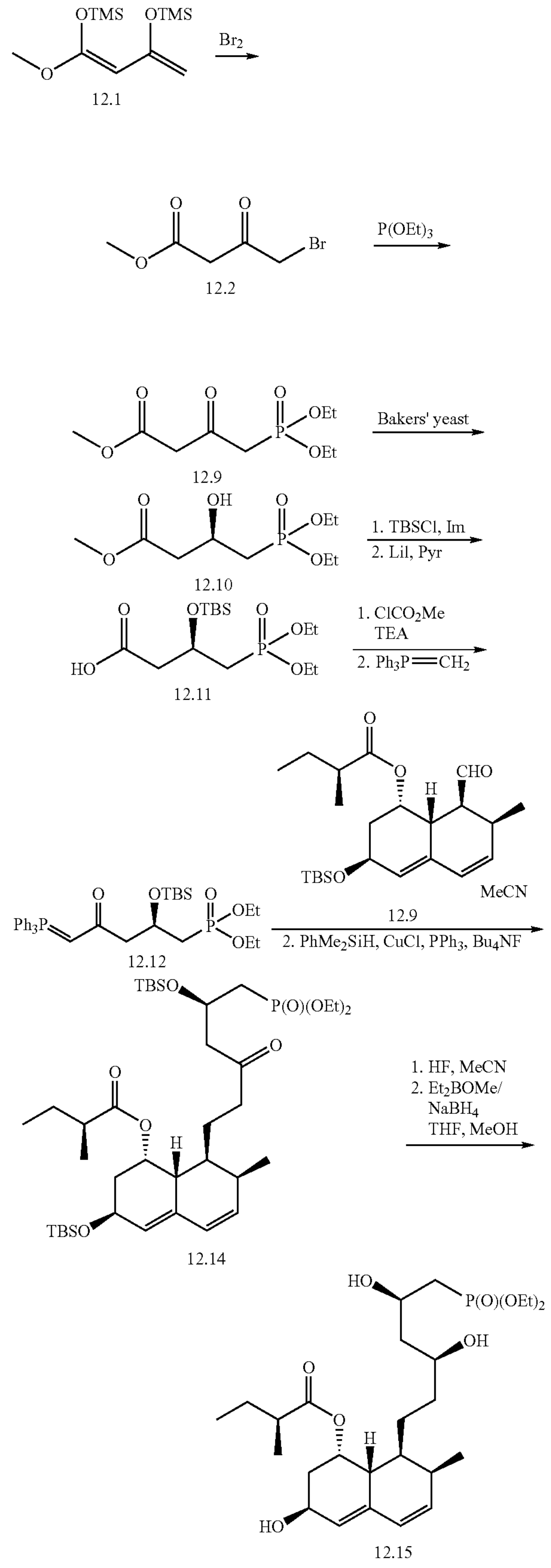

12.1

12.2

12.9

12.10

12.11

12.12

12.9

12.14

12.15

The synthesis begins with the formation of silylenol ether of methyl acetoacetate (available from Aldrich) using TMSCl and LDA as described in Jullien et al., *Tetrahedron Lett.*, 23:47, 4943 (1982) to form compound 12.1. Bromination under the conditions reported by Chan et al., *J. Chem. Soc. Chem. Commun.*, 578 (1979) yields 4-bromo-3-oxo-butyric acid methyl ester 12.2. Arbuzov reaction of the bromide 12.2 with triethyl phosphite as reported by Yuan et al., *Heteroatom Chemistry*, 13:2, 153 (2002) provides diethyl phosphonate 12.9. Addition of ester 12.9 to bakers' yeast in water yields 4-(diethoxyphosphoryl)-3-R-hydroxybutanoic acid methyl ester 12.10 as described by Yuan et al.

Silylation of the newly generated secondary alcohol using TBSCl and imidazole followed by selective removal of the methyl ester protecting group as described in Greene, T., "Protective Groups in Organic Synthesis," Wiley-Interscience (1999) provides compound 12.11. Carboxylic acid 12.11 is treated with methyl chloroformate and triethylamine to give a mixed anhydride that is then converted to compound 12.12 by reacting with methylidenetriphenylphosphorane according to the method described in Konoike et al., *J. Org. Chem.*, 59:7849 (1994).

A Wittig reaction between compound 12.12 and aldehyde 12.13 (prepared according to Watanabe et al., *Bioorg. & Med. Chem.*, 5:437 (1997)) provides the olefin analog 12.14. Removal of the TBS protecting group with HF in MeCN followed by stereoselective chelation-controlled reduction with $Et_2BOMe$ and sodium borohydride in THF: MeOH gives the desired phosphonate 12.15.

A representative compound of the invention may be synthesized as illustrated below:

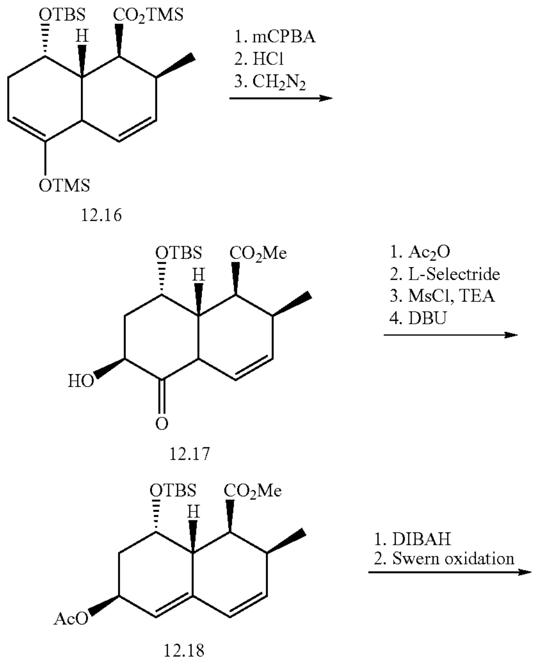

12.16

12.17

12.18

-continued

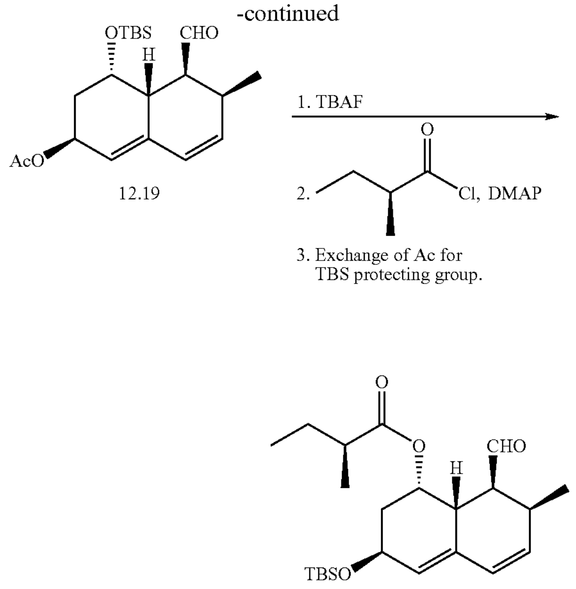

12.19

12.20

Preparation of the desired aldehyde 12.20 is shown. The starting material 12.16 is prepared as reported in Danishefsky. et al., *J. Am. Chem. Soc.*, 111:2599 (1989). The silylenolether 12.16 can be reacted with m-chloroperbenzoic acid in hexanes, followed by acidic workup and esterification with diazomethane to provide compound 12.17. Protection of the secondary alcohol as the acetate followed by reduction of the ketone and generation of the mesylate allows for elimination to provide diene 12.18. Reduction of the methylester using DIBAH followed by Swem oxidation of the primary alcohol to aldehyde creates compound 12.19. Installation of a variety of esters are possible after removal of the TBS group according to the procedure of Hoffman, et al., *J. Med. Chem.*, 29:849 (1986). After protecting group manipulations, the isobutyryl group is installed using isobutyryl chloride in pyridine containing DMAP to provide compound 12.20.

Representative compounds of the invention can be made according to the general route outlined below:

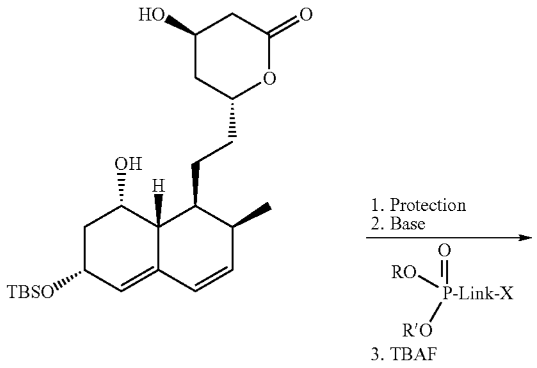

-continued

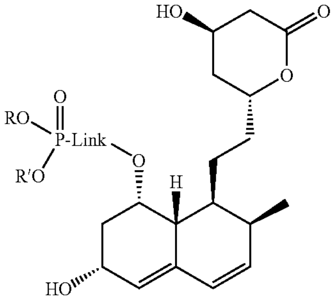

12.21

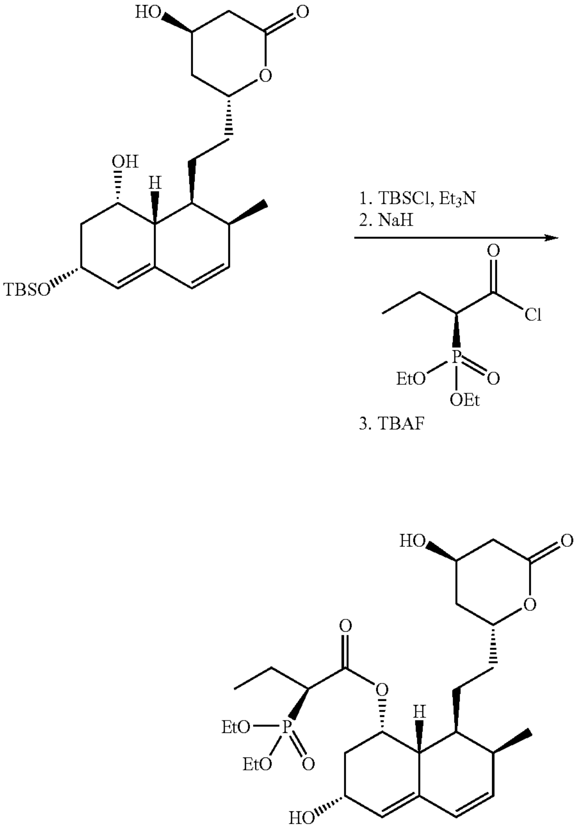

12.22

Formation of pro-drug 12.21, e.g., 12.22, is shown. Formation of an appropriate acylating reagent, (1-chlorocarbonyl-propyl)-phosphonic acid diethyl ester, can be achieved from the benzyl protected carboxylic acid (Salvino et al., *J. Org. Chem.*, 64(6):1823 1999)) after removal of the benzyl group and formation of the acid chloride using standard reactions. Acylation of the hindered axial alcohol can be achieved after protection of the other free secondary alcohol in the substrate, using this reagent in pyridine containing DMAP according to the procedure of Hoffman et al., *J. Med. Chem.*, 29:849 (1986). Removal of the TBS protecting groups is achieved using TBAF to provide pro-drug 12.21, such as 12.22.

Example 13
Preparation of Representative Compounds of the Invention
A synthetic scheme for the preparation of compounds of the invention is as follows:
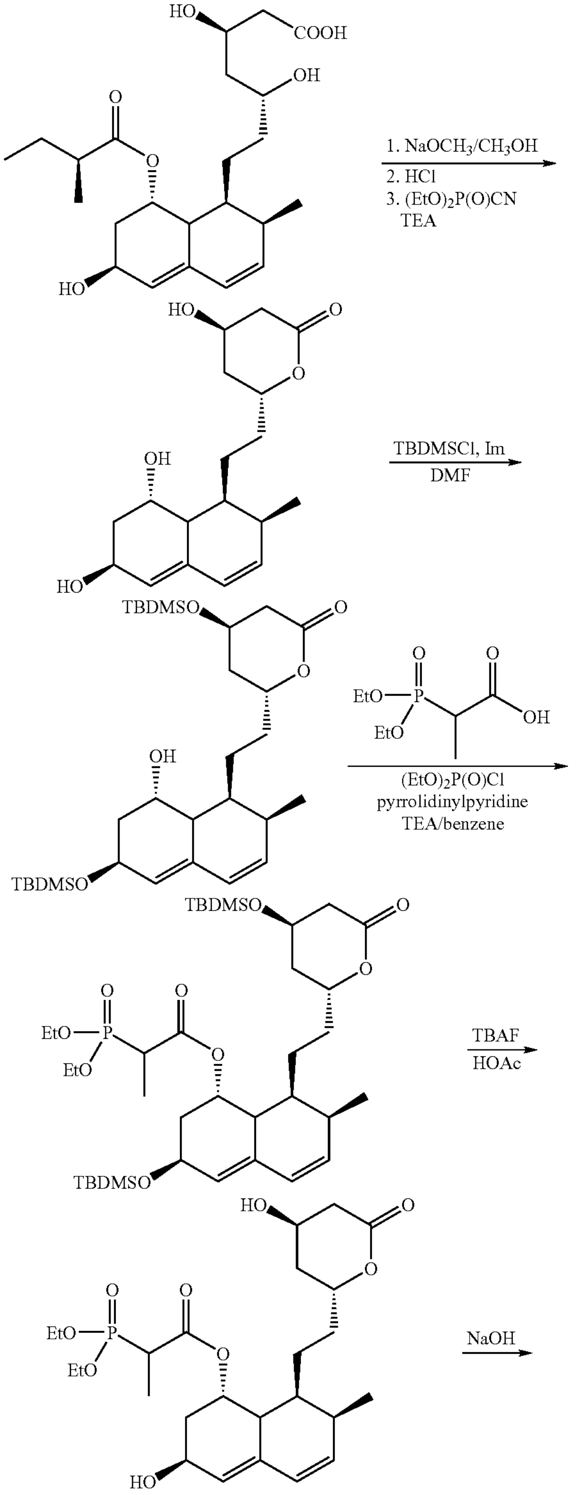
-continued
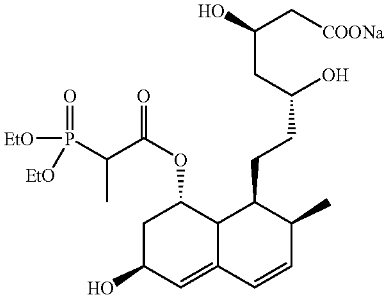
Target I
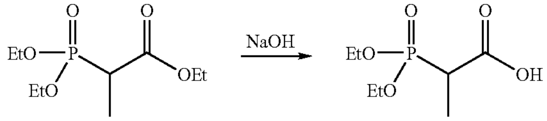
The de-acylation and re-acylation of pravastatin is disclosed in EP 0609058 A2.
In addition, representative compounds of the invention may be prepared as follows:
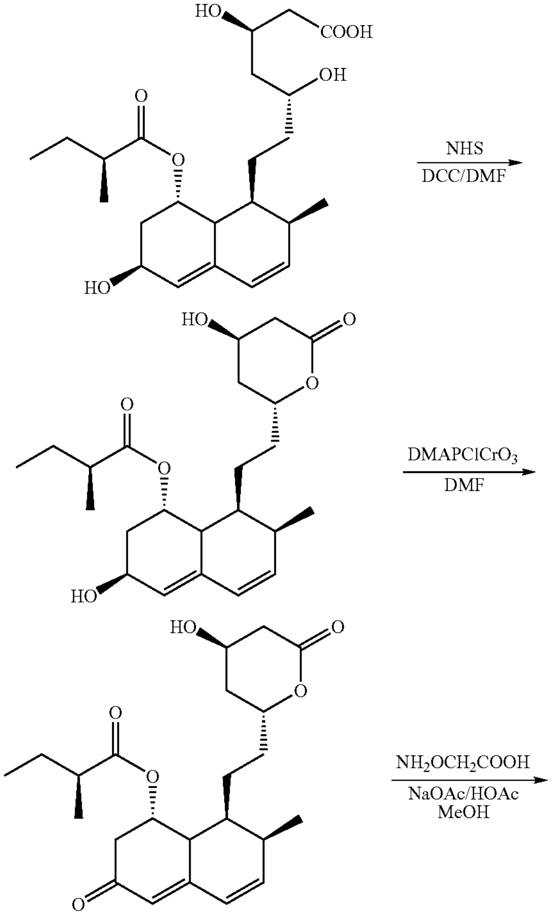

-continued

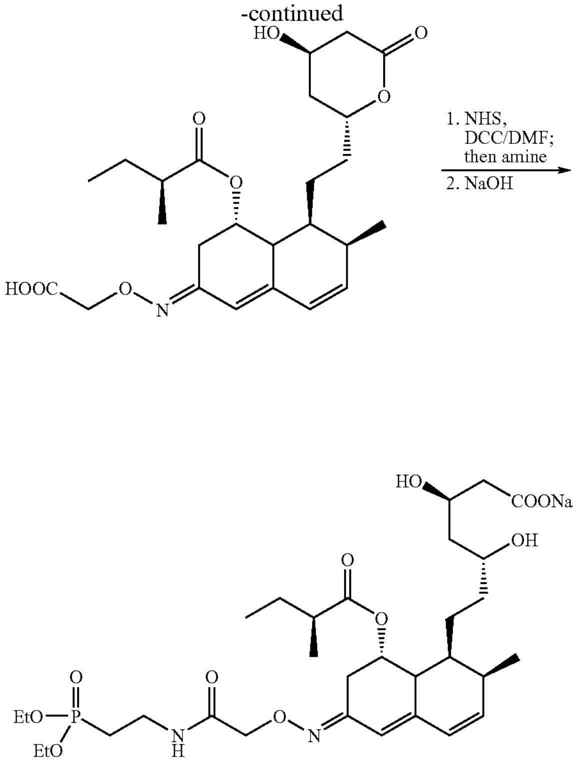

Targets II

The oxime formation is disclosed in *Bioorg. Med. Chem.*, 3:1479 (1995).

Example 14

Preparation of Representative Components of the Invention

The preparation of representative compounds of the invention is described as follows:

Intermediate 14.1 is described in U.S. Pat. No. 4,444,784 and references within. Intermediates for the synthesis of compounds containing the ether linkage between the phosphonate and Simvastatin moiety can be constructed as follows:

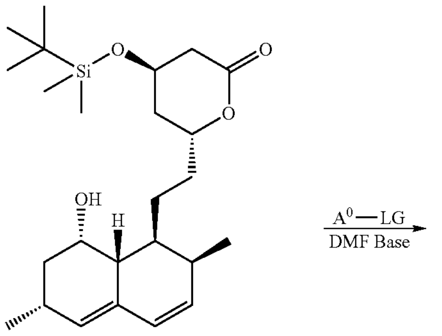

14.1

-continued

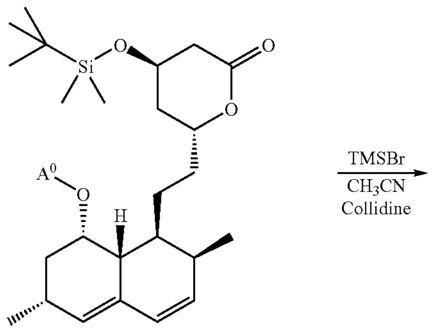

14.2

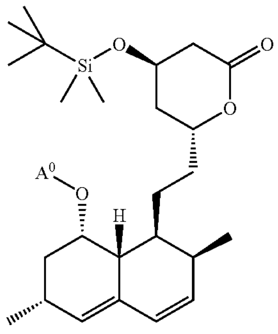

14.3

LG = Leaving Group

Intermediate 14.1 is treated with an protected alkylphosphonate bearing a leaving group and a base to afford the phosphonomethyl Simvastatin conjugate 14.2. 14.2 is then dealkylated with trimethylsilyl bromide to afford the protected phosphonic acid 14.3, which is then converted to the desired prodrug using the methods of interconversion of phosphonates and their prodrugs as described herein, and removal of the silyl protecting group with a fluoride source.

An example of the synthesis of specific compounds of the invention is illustrated below:

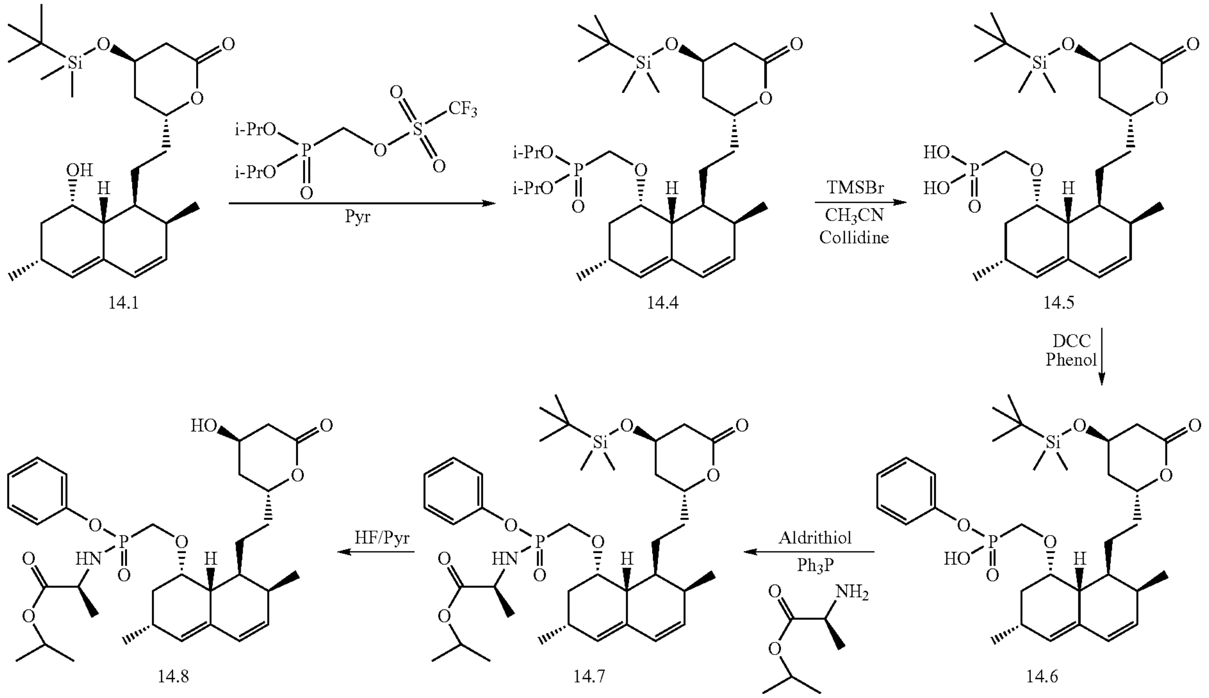

14.1 14.4 14.5 14.6 14.7 14.8

The intermediate 14.1 is treated with diisopropylphosphonomethyl triflate in pyridine to afford the conjugate 14.4. Although in this example triflate is the leaving group and the phosphonate is protected as the diisopropyl ester, any other suitable leaving groups can be used, such as tosyl, mesyl, benzenesulfonyl, bromo, iodo, chloro, and so forth. The phosphonate moiety can be protected with any suitable group including, but not limited to, methyl, ethyl, phenyl, substituted phenyl benzyl, substituted benzyl, cyanoethyl, nitrophenethyl and so forth, as long as the conditions for deprotection are compatible with the stability of the conjugate and the deprotected conjugate. Furthermore, the conjugate 14.4 is deprotected. In this example, it is deprotected with trimethylsilyl bromide in a suitable solvent such as acetonitrile, dichloromethane, dimethylformamide, or any other solvent compatible with the reactivity of the deprotection agent containing a base such as pyridine, collidine, or lutidine, or any other suitable organic or inorganic base to afford the phosphonate 14.5.

Phosphonate 14.5 can then be converted to the desired prodrug by the methods described herein. In this example, 14.5 is treated with dicyclohexycarbodiimide and phenol to afford the monoester 14.6, which is further condensed with alanine isopropyl ester using aldrithiol and triphenylphosphine to afford 14.7. Finally, intermediate 14.7 is deprotected with hydrogen fluoride in pyridine to afford the desired compound 14.8.

The synthesis of compounds of the invention containing an ester is shown below:

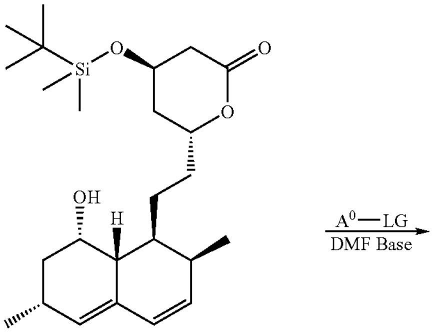

14.1

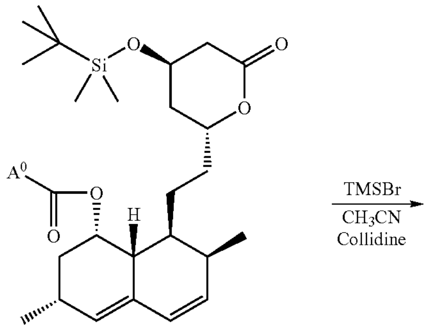

14.9

-continued

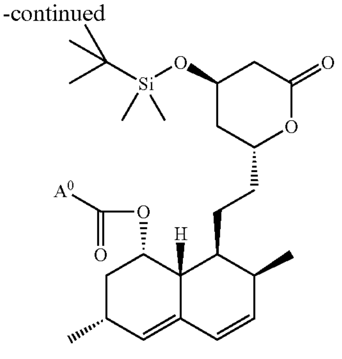

14.10

LG = Leaving Group, e.g., halogen, pentafluorophenol

Intermediate 14.1 is treated with a protected alkylphosphonocarboxylic acid bearing a leaving group such as halogen, pentafluorophenol, or any other such group normally used to activate a carboxylic acid for coupling to an alcohol and a base to afford the phosphonomethyl Simvastatin conjugate 14.9. Compound 14.9 is then dealkylated with trimethylsilyl bromide to afford the protected phosphonic acid 14.10, which is then converted to the desired prodrug using the methods of interconversion of phosphonates and their prodrugs as described herein, and removal of the silyl protecting group with a fluoride source.

Specific compounds of the invention can also be prepared as follows:

The intermediate 14.1 is treated with the protected phosphonoacetyl chloride, prepared form the commercially available diethylphosphonoacetic acid by the action of thionyl chloride, in pyridine to afford the conjugate 14.11. The conjugate 14.11 is deprotected, in this example with trimethylsilyl bromide in a suitable solvent such as acetonitrile, dichloromethane, dimethylformamide, or any other solvent compatible with the reactivity of the deprotection agent containing a base such as pyridine, collidine, lutidine or any other suitable organic or inorganic base to afford the phosphonate 14.12.

Phosphonate 14.12 can then be converted to the desired prodrug by the following methods. 14.12 is treated with dicyclohexycarbodiimide and phenol to afford the monoester 14.13, which is further condensed with alanine isopropyl ester using aldrithiol and triphenyiphosphine to afford intermediate 14.14. Finally, intermediate 14.14 is deprotected with hydrogen fluoride in pyridine to afford the desired compound 14.15.

A representative compound of the invention containing a carbamate linkage can be prepared as follows:

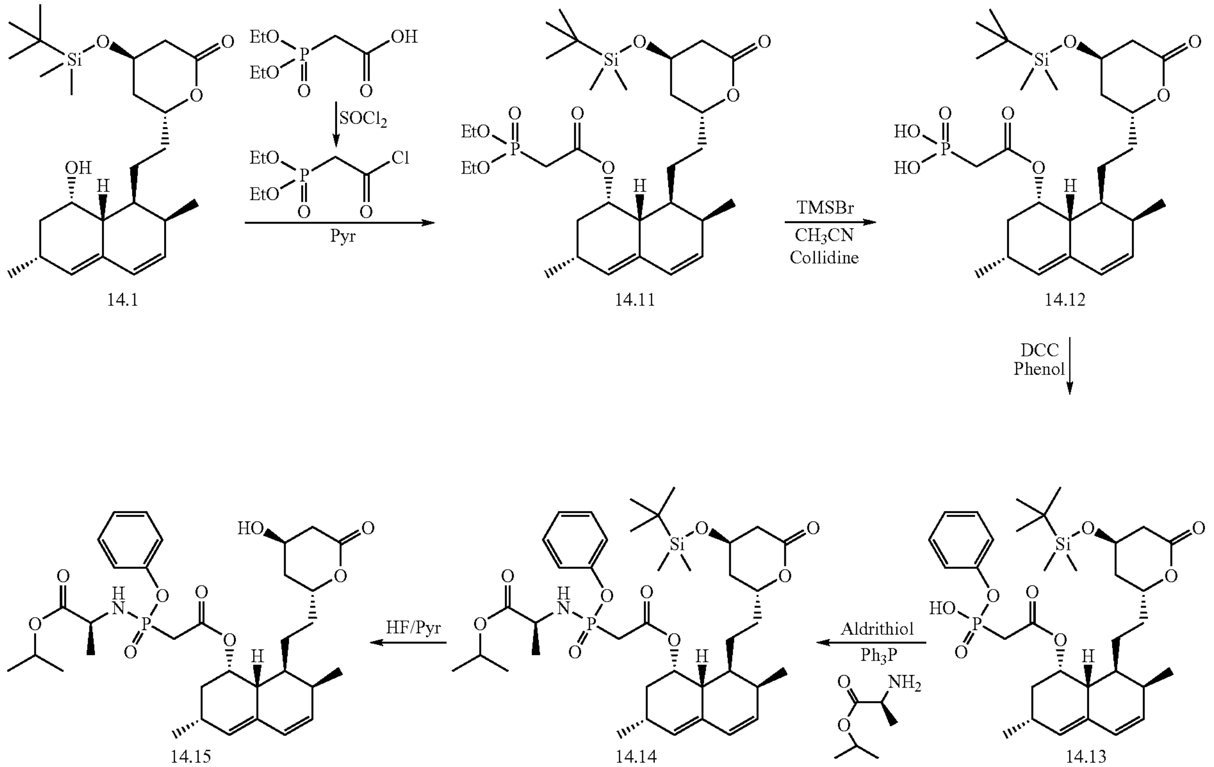

14.1 14.11 14.12 14.13 14.14 14.15

-continued

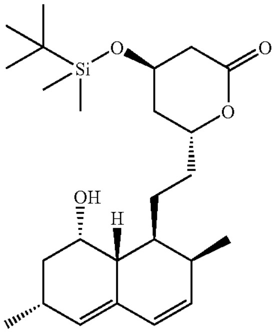

14.6

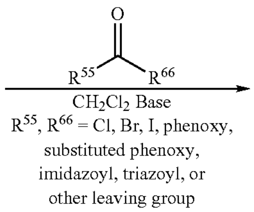

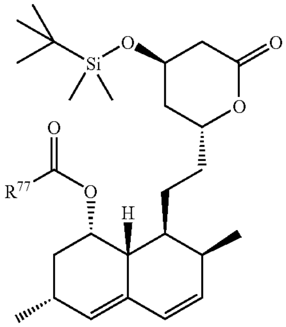

14.16

$R^{77}$ = Cl, Br, I, phenoxy, substituted phenoxy

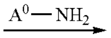

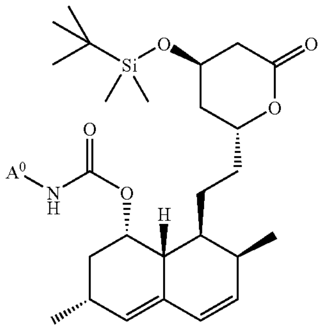

14.17

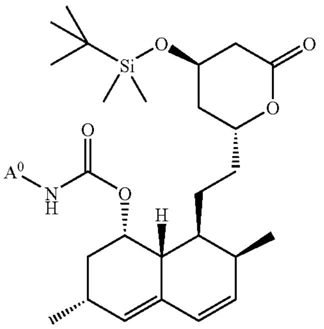

14.18

Intermediate 14.6 is treated with phosgene or a carbonate derivative bearing two active leaving groups to afford the activated intermediate 14.16. This intermediate is treated with a protected phosphonoalkyl amine and a base to afford the phosphonoalkylcarbamoyl ester of Simvastatin 14.17. 14.17 is then dealkylated with trimethylsilyl bromide to afford the protected phosphonic acid 14.18. 14.18 is then converted to the desired prodrug using the methods of interconversion of phosphonates and their prodrugs as described herein, and removal of the silyl protecting group with a fluoride source.

Another example of the synthesis of specific compounds of the invention is presented below:

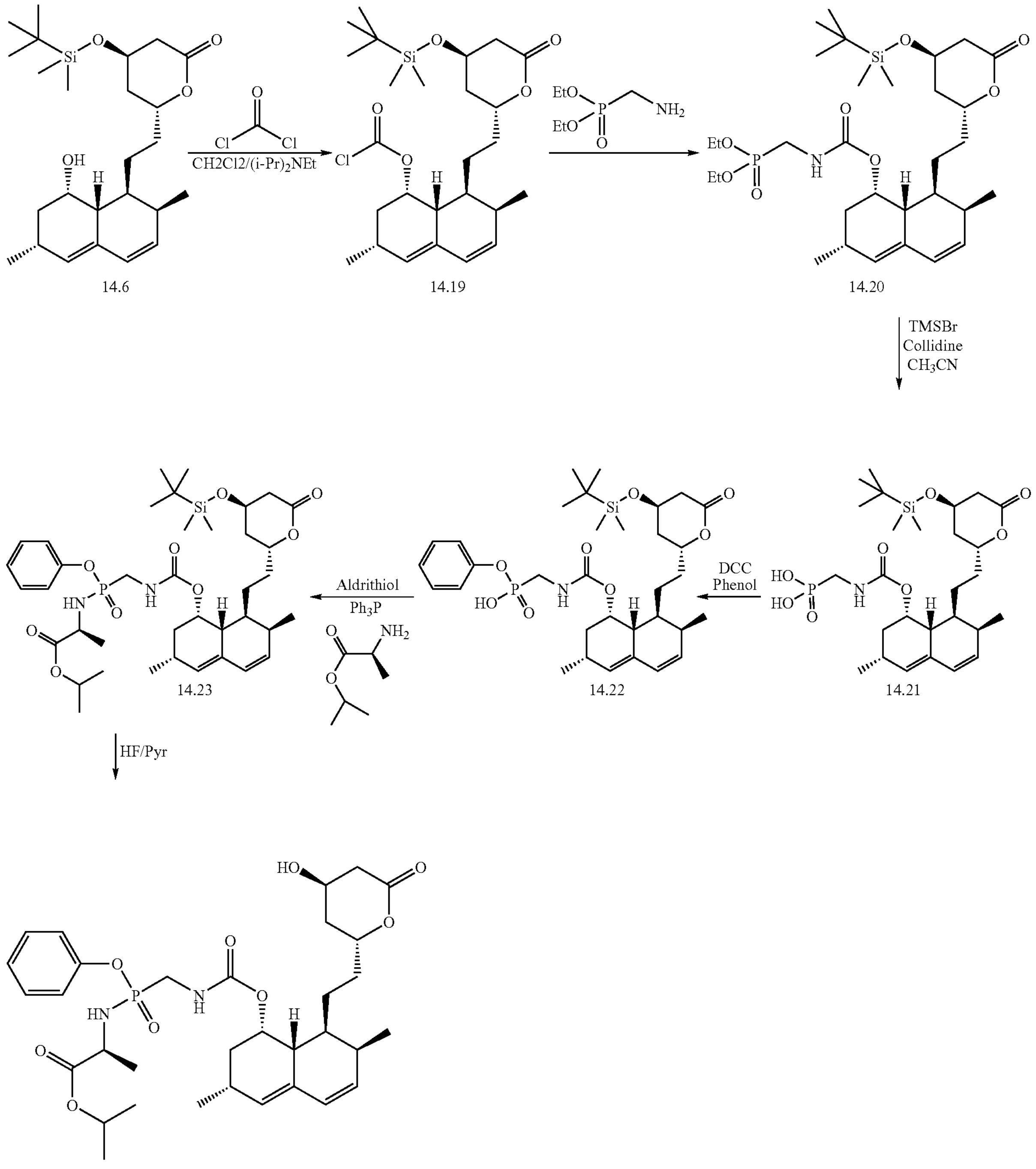

14.24

The intermediate 14.6 is treated with phosgene in dichloromethane containing diisoproylethylamine to afford the chloroformate 14.19. The intermediate 14.19 is reacted with the commercially available diethylphosphonomethylamine yielding the protected conjugate 14.20. The phosphonate moiety is then deprotected, in this example, with trimethylsilyl bromide in a suitable solvent such as acetonitrile, dichloromethane, dimethylformamide, or any other solvent compatible with the reactivity of the deprotection agent containing a base such as pyridine, collidine, or lutidine or any other suitable organic or inorganic base to afford the phosphonic acid 14.21.

Phosphonic acid 14.21 can then be converted to the desired prodrug by the methods described herein. In this example, 14.21 is treated with dicyclohexycarbodiimide and phenol to afford the monoester 14.22, which is further condensed with alanine isopropyl ester using aldrithiol and triphenylphosphine to afford intermediate 14.23. Finally, intermediate 14.23 is deprotected with hydrogen fluoride in pyridine to afford the desired compound 14.24.
Example 15
Preparation of Representative Compounds of the Invention
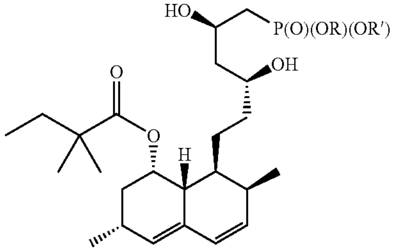
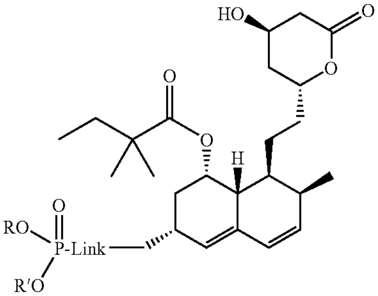
Representative compounds of the invention such as those illustrated above can be made according to the following:
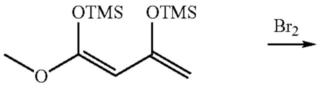
15.1
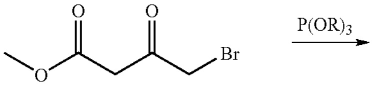
15.2
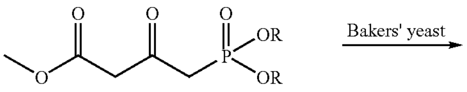
15.3
-continued
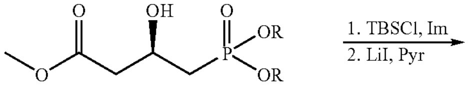
15.4
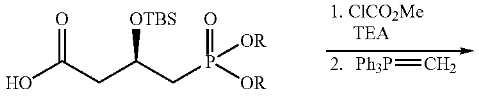
15.5
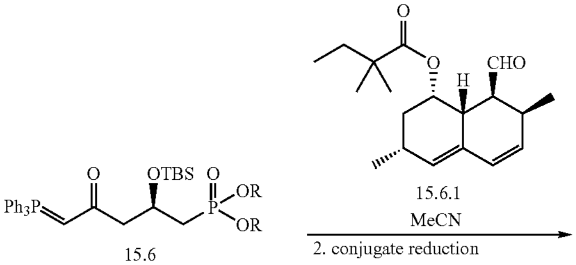
15.6.1
15.6
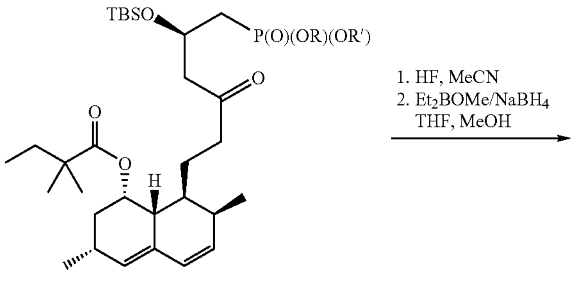
15.7
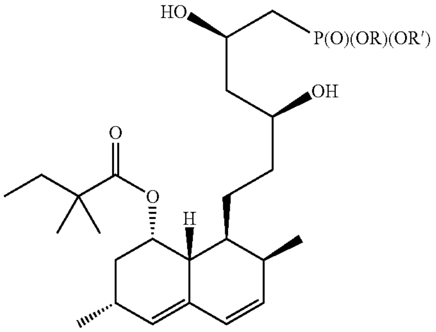
15.8
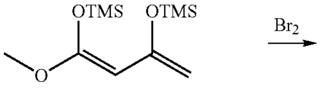
15.1
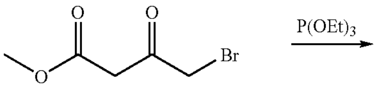
15.2
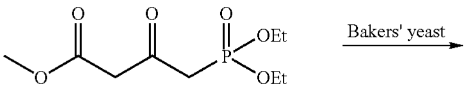
15.9
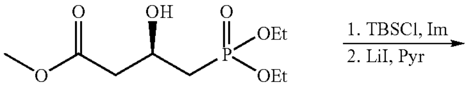
15.10

-continued

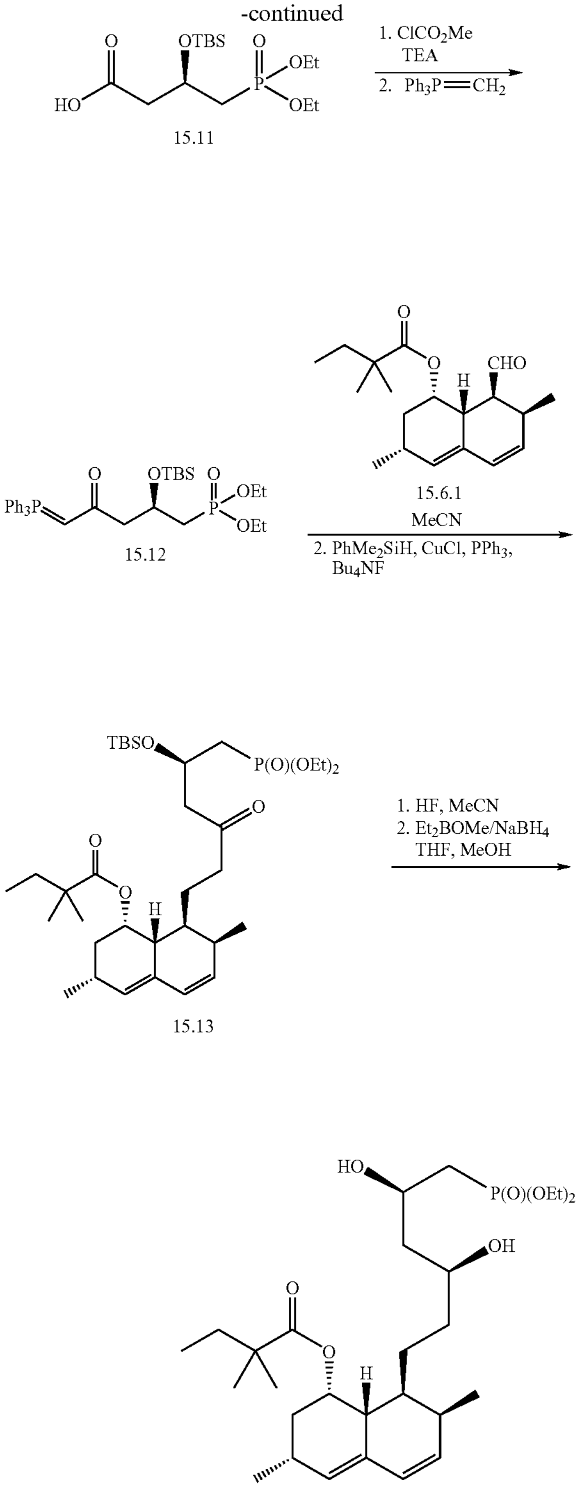

15.11

15.12

15.13

15.14

The preparation of analog 15.8 is shown above. A phosphonate bis-ester can be prepared as demonstrated above and the substituents at phosphorus can be manipulated according to transformations. The synthesis of a specific example for compound 15.8, i.e., 15.14, is also shown.

The synthesis begins with formation of silyl enol ether of methyl acetoacetate (available from Aldrich) using TMSCl and LDA as described in Jullien et al., *Tetrahedron Lett.*, 23(47):4943 (1982) to form compound 15.1. Bromination under the conditions reported by Chan et al., *J. Chem. Soc. Chem. Commun.*, 578 (1979) yields 4-bromo-3-oxo-butyric acid methyl ester 15.2. Arbuzov reaction of the bromide 15.2 with triethylphosphite as reported by Yuan et al., *Heteroatom Chemistry*, 13(2): 153 (2002) provides diethyl phosphonate 15.3. Addition of ester 15.3 to bakers' yeast in water yields 4-(diethoxyphosphoryl)-3-R-hydroxybutanoic acid methyl ester 15.4 as described by Yuan et al. Silylation of the newly-generated secondary alcohol using TBSCl and imidazole followed by selective removal of the methyl ester protecting group as described in Greene, T., "Protective Groups in Organic Synthesis," Wiley-Interscience (1999) provides compound 15.5. Carboxylic acid 15.5 is treated with methyl chloroformate and triethylamine to give a mixed anhydride which is then converted to compound 15.6 by reacting with methylidenetriphenylphosphorane according to the method described in Konoike et al., *J. Org. Chem.*, 59:7849 (1994). A Wittig reaction between compound 15.6 and aldehyde 15.6.1 (prepared according to WO 9,302,089 and U.S. Pat. No. 4,950,775) provides the olefin analog 15.7. Removal of the TBS protecting group with HF in MeCN followed by stereoselective chelation-controlled reduction with $Et_2BOMe$ and sodium borohydride in THF: MeOH gives the desired phosphonate 15.8.

Representative compounds such as 15.17 can be made according to the following:

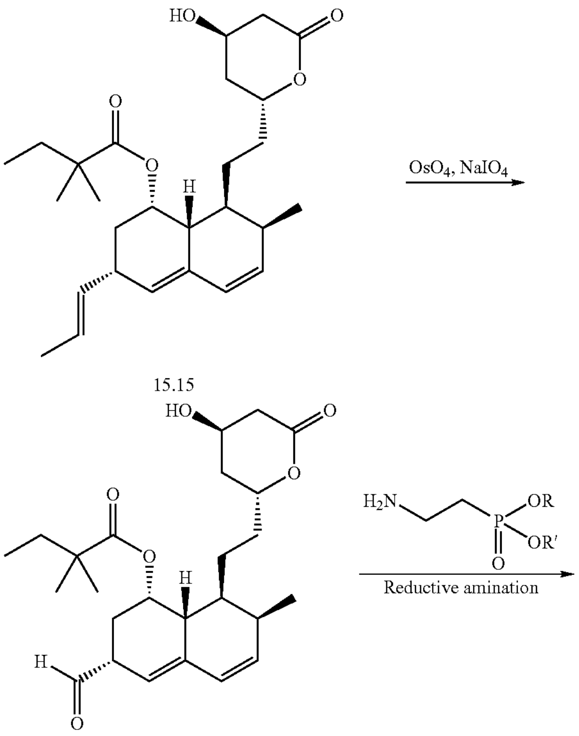

15.15

15.16

-continued

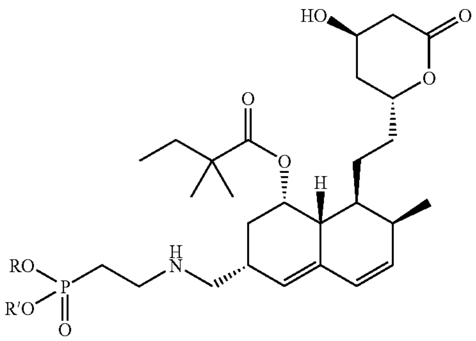

15.17

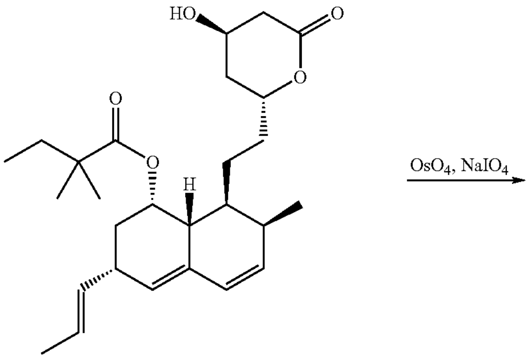

15.1

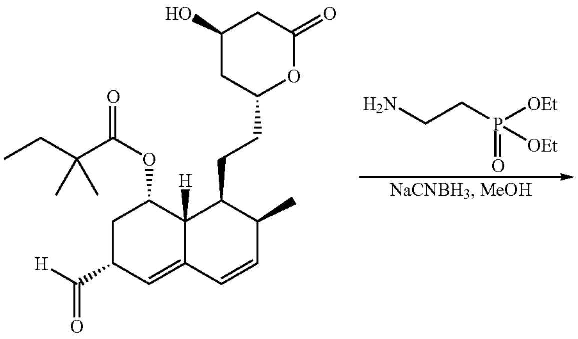

15.16

-continued

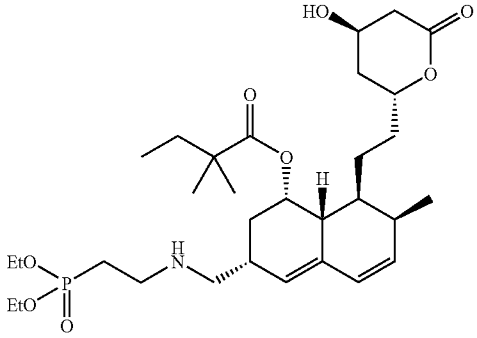

15.18

Installation of the prodrug moiety on the methyl substitution of the decalin system to provide pro-drug 15.17 is shown above. Starting material 15.15, described in WO 93/02089, undergoes dihydroxylation followed by cleavage of the diol to provide aldehyde 15.16. A one-step reductive amination reaction using mild reducing agents such as sodium cyanoborohydride or sodium triacetoxyborohydride in alcoholic solution yields the desired pro-drug 15.17, e.g., 15.18.

Example 16

Preparation of Representative Compounds of the Invention

Representative compounds of the invention can be synthesized as described herein.

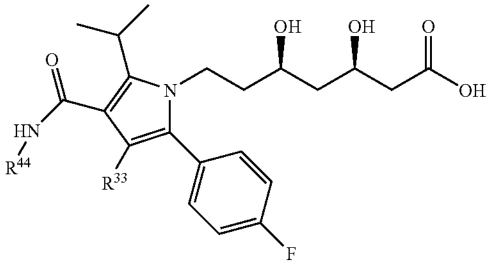

The linkage between the phosphonate moiety and Atorvastatin can be formed by substituting the phenyl ring at $R^{44}$ or the phenyl ring at $R^{33}$ with an amino group as described herein below and then conjugating the amino group with a protected phosphonoalkylaldehyde of the general structure 16.23, by reductive alkylation. The substitution can be ortho, meta or para to the point of attachment of the phenyl ring.

For compounds of the invention substituted at the $R^{44}$ position, a method of synthesis is as follows:

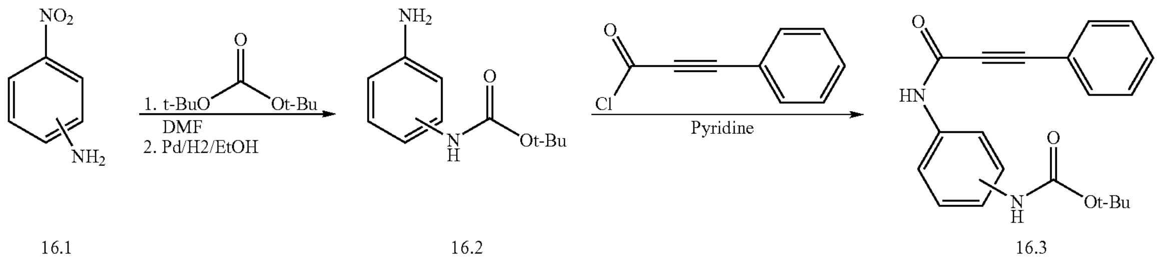
16.1 16.2 16.3
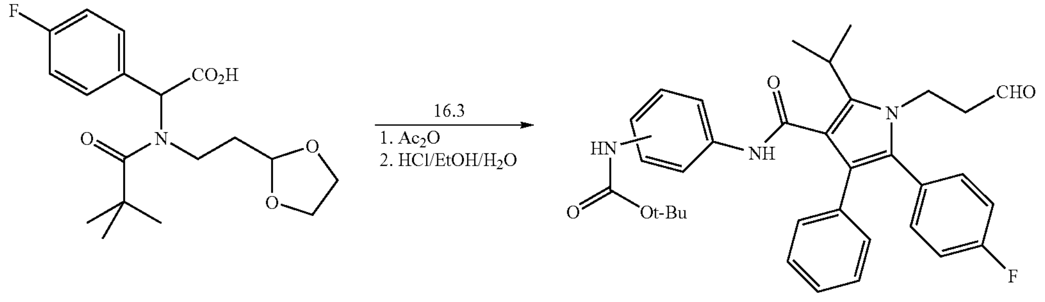
16.4 16.4
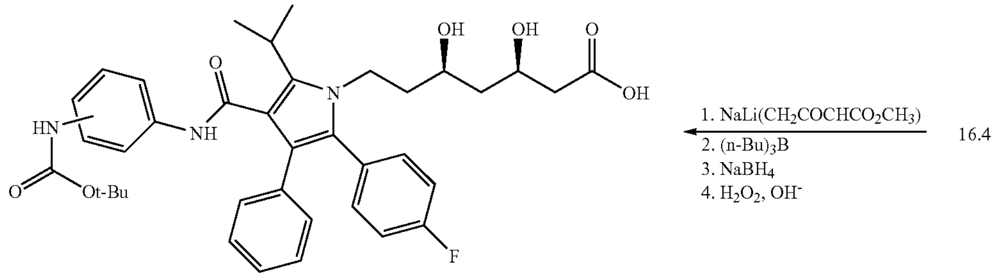
16.5
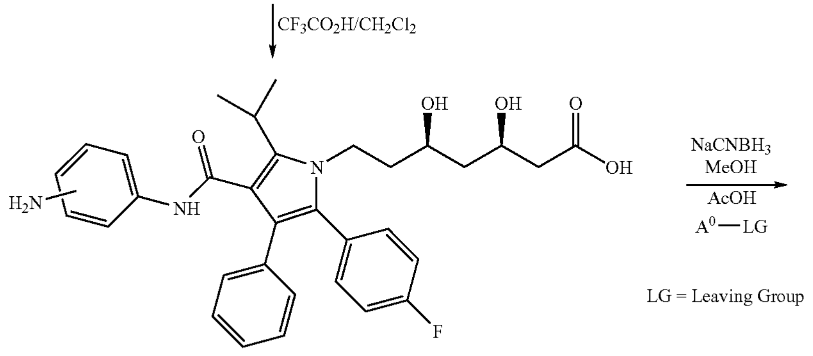
16.6
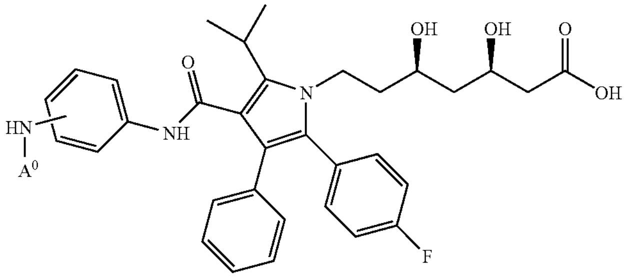
16.7

The synthesis of intermediate 16.4 is described in U.S. Pat. No. 4,681,893 (column 4, line 50). Compound 16.4 is reacted according to the procedure disclosed in U.S. Pat. No. 4,681, 893 with an acetylenecarboxamide of the general structure 16.3, derived from ortho, para or meta nitro-aniline 16.1 by protection of the amino group as the t-butylcarbamate to yield, followed by the reduction of the nitro group by hydrogenation with hydrogen and a catalyst such as palladium on carbon in a suitable solvent such as ethanol, methanol or ethyl acetate, compound 16.2.

The acylation of the newly formed amino group with the acyl chloride of phenylpropynoic acid yields the pyrrole 16.4, after mild aqueous hydrolysis of the acetal moiety. The derivative 16.4 is then condensed with the dianion of ethyl acetylacetate followed by reduction of the carbonyl moiety and hydrolysis of the acid ester to yield the pyrrole of general structure 16.5. The resulting beta hydroxy carboxylic acid 16.5 is then treated with an acid such as trifluoroacetic acid in an appropriate anhydrous aprotic solvent to deprotect the masked aniline function to yield compound 16.6. A compound of general structure 16.6 is then treated with an aldehyde of general structure 16.23 (the synthesis of which is described below), and the reductive alkylation is effected with the addition of a reducing agent such as sodium cyanoborohydride, or by catalytic hydrogenation with a catalyst such as palladium on charcoal in a solvent such as ethanol, methanol, ethyl acetate, or DMF to afford the desired compound.

Specific compounds of the invention can be prepared as follows:

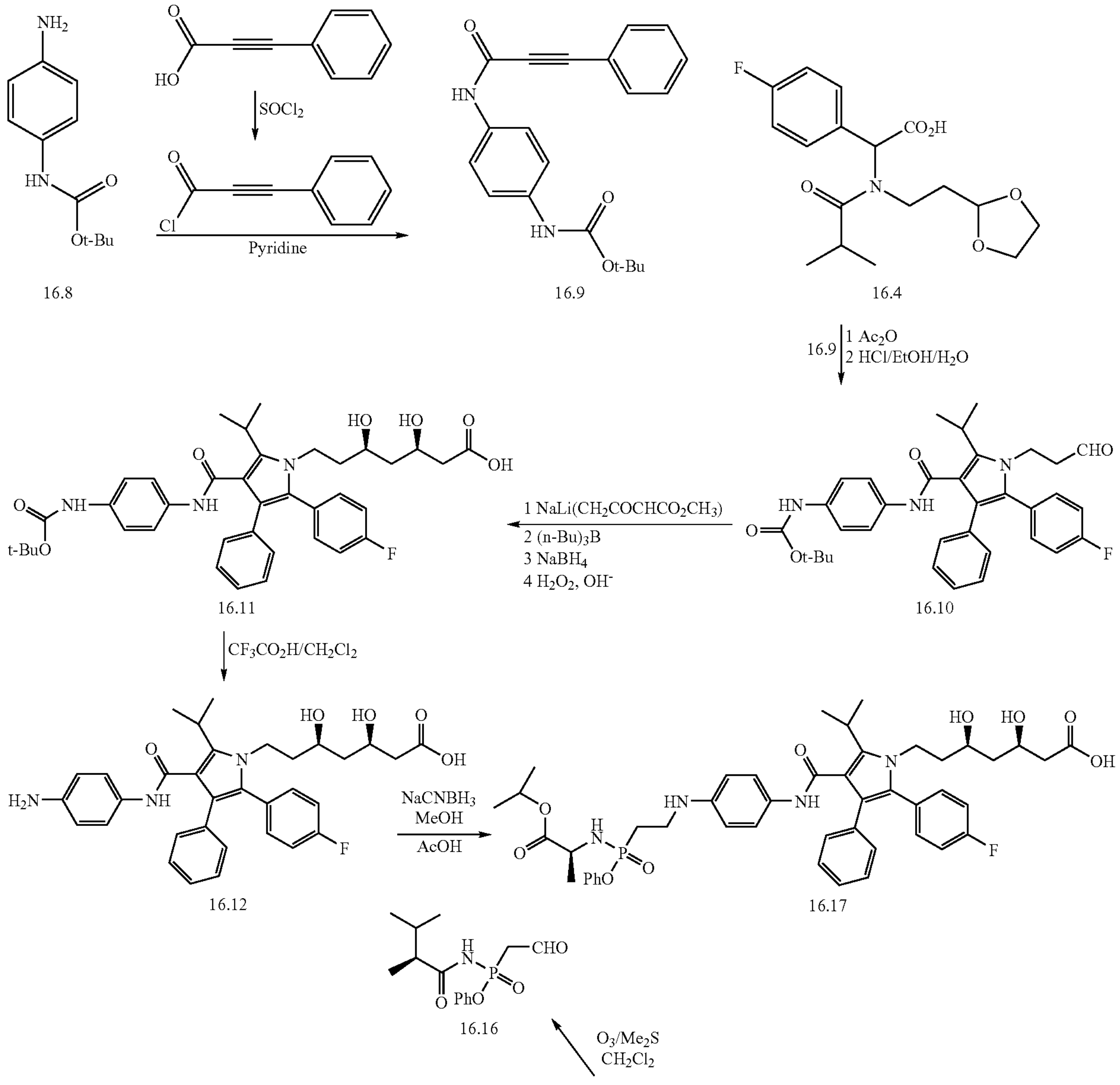

16.8

16.9

16.4

16.11

16.10

16.12

16.17

16.16

-continued

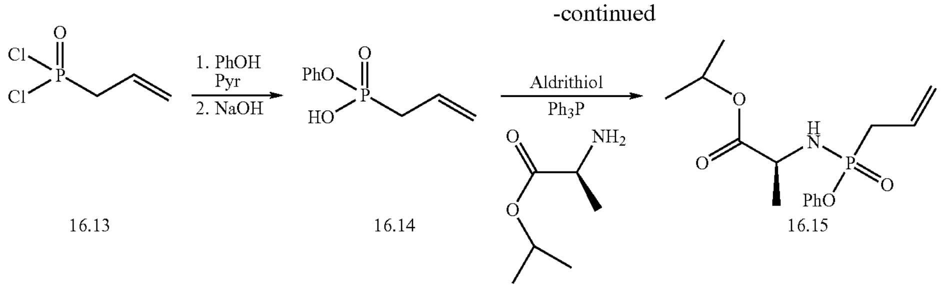

16.13 16.14 16.15

The commercially available tert-butoxycarbonyl protected p-phenylenediamine 16.8 is treated with the acid chloride prepared from phenylpropynoic acid by the action of thionyl chloride. The resulting phenyl carboxamido acetylene 16.9 is reacted with the amino acid 16.4 in the presence of acetic anhydride. The acetal of the resulting intermediate pyrrole is hydrolyzed with 80% aqueous acetic acid to yield 16.10. Condensation of 16.10 with the dianion of ethyl acetylacetate followed by reduction of the carbonyl moiety and hydrolysis of the acid ester yields the pyrrole 16.11. The protecting group of 16.11 is removed with trifluoroacetic acid in dichloromethane to afford the unmasked aniline 16.12, which is subsequently reductively alkylated with the protected phosphonoacetaldehyde 16.16 to afford the desired Atorvastatin phosphonate conjugate 16.17. The phosphonoacetaldehyde 16.16 can be obtained from the commercially available phosphonodichloridate 16.13 by reaction with an excess of phenol and a suitable base, hydrolysis to the monophenol 16.14, coupling with the isopropyl ester of alanine, followed by ozonolysis and reductive workup.

For the compounds substituted at the $R^{33}$ position, the method of synthesis is outlined as follows:

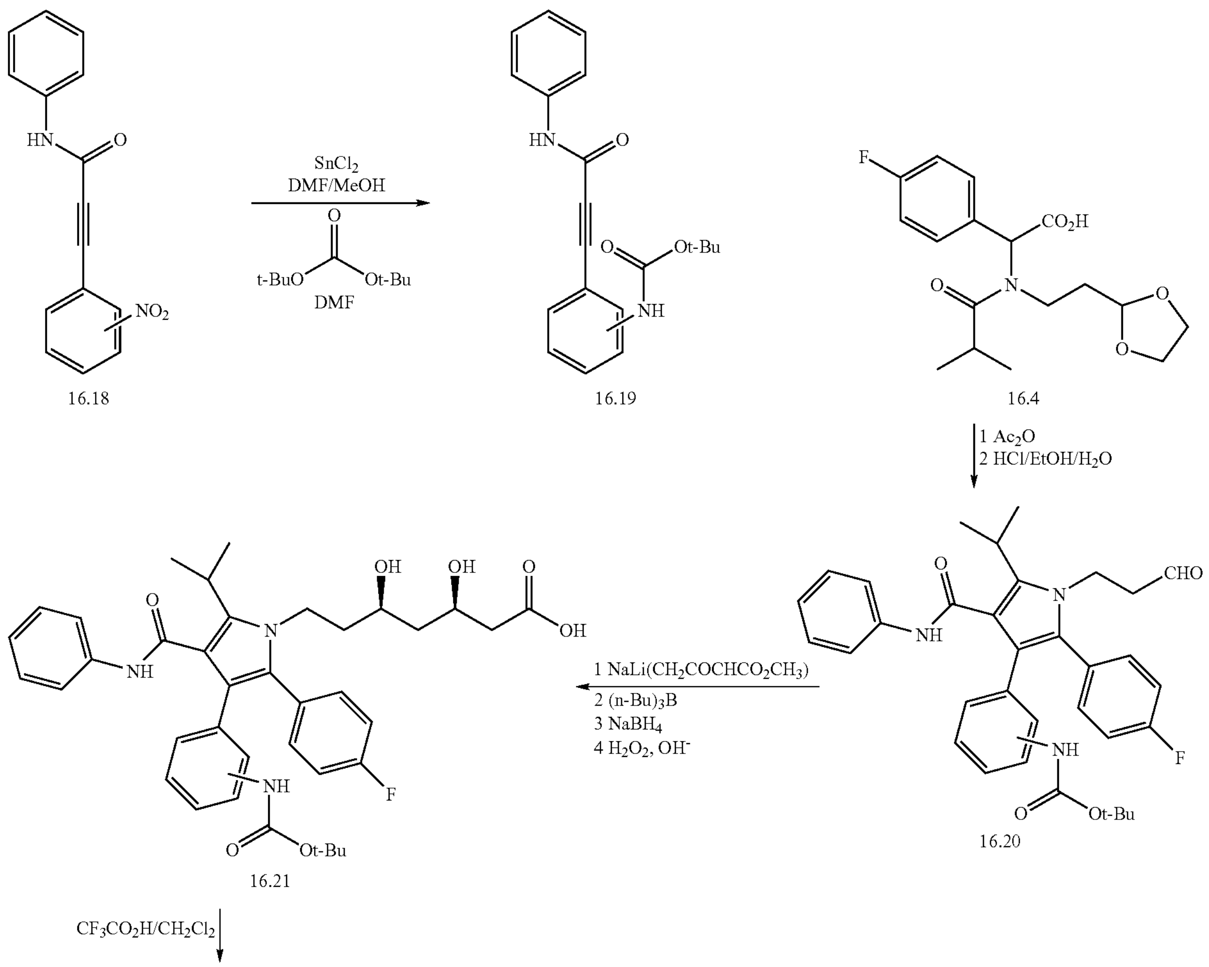

16.18 16.19 16.4 16.20 16.21

-continued

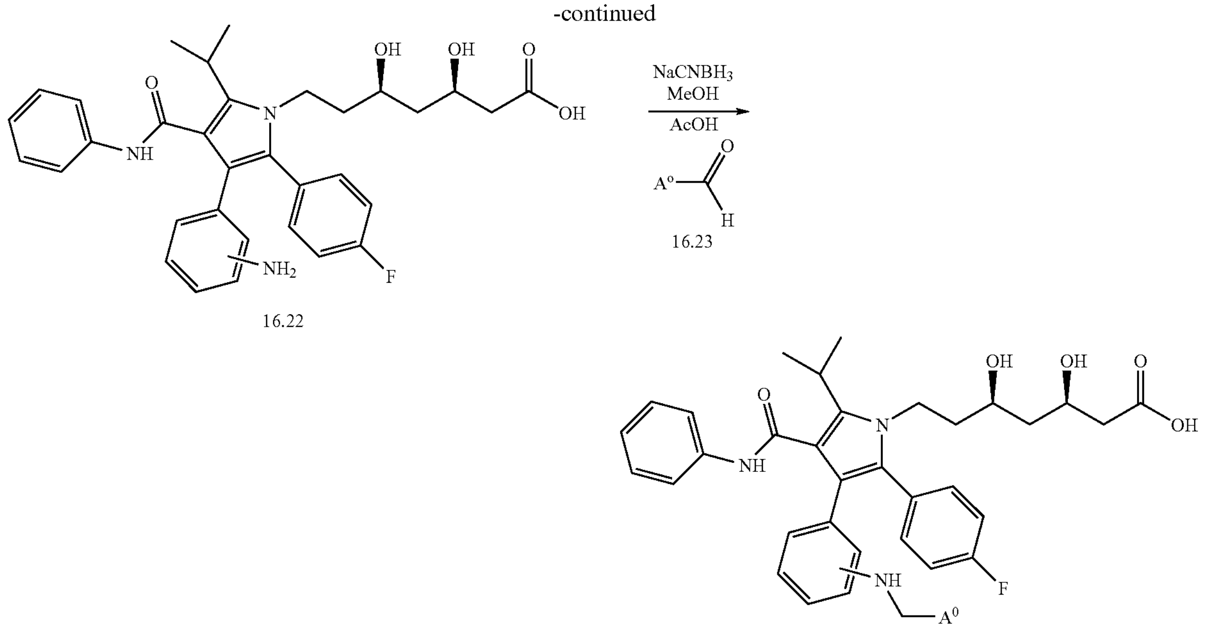

16.22

16.23

16.24

The synthesis of intermediate 16.4 is described in U.S. Pat. No. 4,681,893 (column 4, line 50). Compound 16.4 is reacted according to the procedure disclosed in U.S. Pat. No. 4,681,893 with an acetylenecarboxamide of the general structure 16.19, which can be obtained by the reduction of the nitro group of an ortho, meta or para nitrophenylpropynoic acid phenylamide of general structure 16.18 with a reagent such as stannous chloride in a solvent such as methanol or DMF, followed by protection of the amine moiety with di-t-butylcarbonate in DMF, to yield compound 16.20 after mild aqueous hydrolysis of the acetal moiety. Condensation of 16.20 with the dianion of ethyl acetylacetate followed by reduction of the carbonyl moiety and hydrolysis of the acid ester yields the pyrrole 16.21, which is then treated with an acid such as trifluoroacetic acid in an appropriate anhydrous aprotic solvent to deprotect the masked aniline function to yield compound 16.22. The compound 16.22 is then treated with an aldehyde of general structure 16.23. The reductive alkylation is effected with the addition of a reducing agent such as sodium cyanoborohydride, or by catalytic hydrogenation with a catalyst such as palladium on charcoal in a solvent such as ethanol, methanol, ethyl acetate, or DMF to afford the desired compound of general structure 16.24.

In addition, the synthesis of specific compounds of the invention is described below.

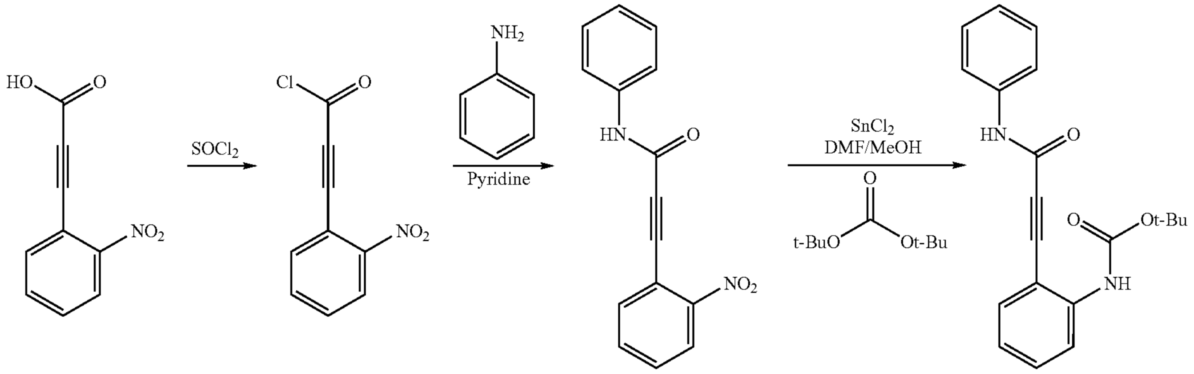

16.25 16.26 16.27 16.28

-continued

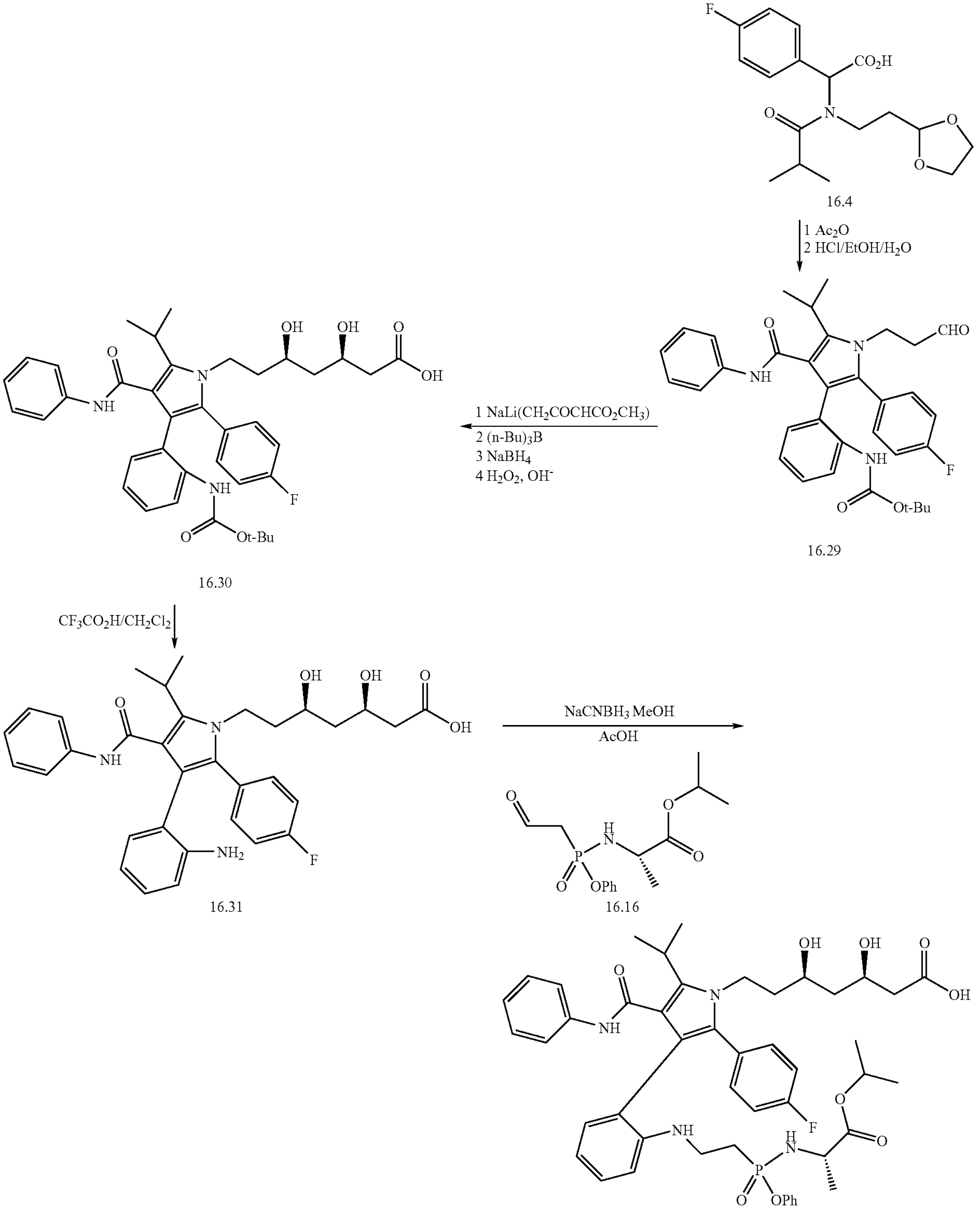

16.4

16.29

16.30

16.31

16.16

16.32

The commercially available phenylpropynoic acid 16.25 is converted to its acid chloride by the action of thionyl chloride. The resulting acyl chloride 16.26 is reacted with aniline to afford the carboxamide 16.27. The nitro group of 16.27 is reduced to furnish an intermediate aniline that is then protected through the action of di-t-butylcarbonate in a solvent such as DMF. The resulting acetylene 16.28 is then reacted with amino acid 16.4 in the presence of acetic anhydride, followed by the hydrolysis of the acetal function with aqueous acetic acid to yield the aldehyde 16.29. Condensation of 16.29 with the dianion of ethyl acetylacetate followed by reduction of the keto moiety and hydrolysis of the acid ester yields the pyrrole 16.30. The t-butoxycarbonyl group of 16.30 is removed with trifluoroacetic acid in a solvent such as dichloromethane and the resulting aniline 16.31 with the phosphonoaldehyde 16.16 to yield the Atorvastatin phosphonate conjugate 16.32.

Example 17

Preparation of Representative Compounds of the Invention

Representative compounds of the invention such as shown above, can be made according to the following method.

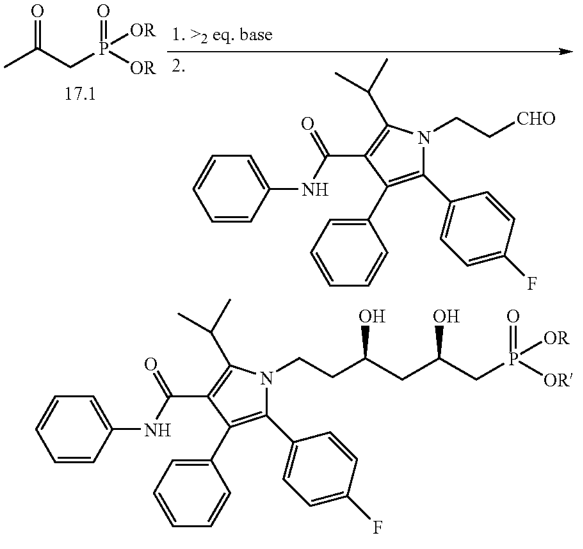

17.1

17.2

-continued

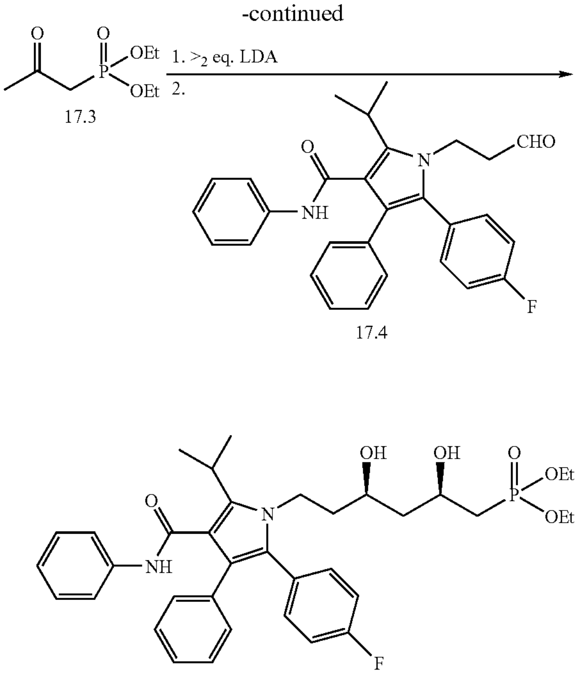

17.3

17.4

17.5

Preparation of analog 17.1 is shown above. A generic phosphonate bis-ester can be prepared as demonstrated above and the substituents at phosphorus can be manipulated according to transformations shown herein. The synthesis of specific compound of the invention 17.5 is also shown. The dianion of (2-oxo-propyl)-phosphonic acid diethyl ester is generated by treatment with over two equivalents of lithium diisopropylamide at low temperature, and the 17.4 (prepared according to Roth et al., *J. Med. Chem.*, 34:357 (1991)) is added. The isomer with the desired stereochemistry is isolated by chromatography.

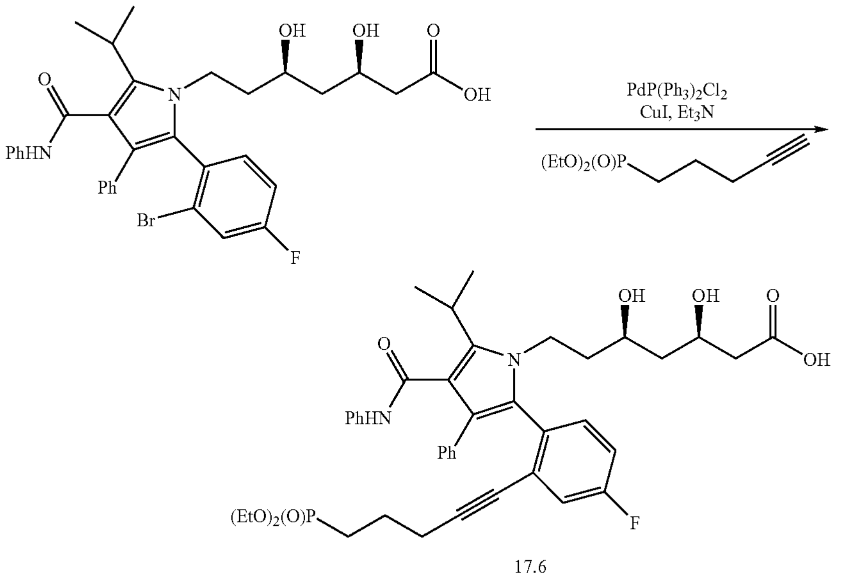

17.6

An example of the synthesis of an additional compound of the invention, 17.6, is depicted above. A Sonagashira coupling (see Stang, P. J. and Diederich, F., "Metal Catalyzed Cross Coupling Reactions," Wiley-VCH, Weinheim (1988)) is used to attach the phosphonate moiety. The requisite acetylene is made by heating 5-chloro-1-pentyne with triethylphosphite in a solvent such as toluene (or other Arbuzov reaction conditions; see Engel, R., "Synthesis of Carbon-phosphorus Bonds," CRC press (1988)), and the aryl bromide by the same route as described for other atorvastatin analogs (Roth et al., *J. Med. Chem.*, 34:357 (1991)), starting from 2-bromo-4-fluorobenzaldehyde.

Example 18

Preparation of Representative Compounds of the Invention

Representative compounds of the invention can be prepared as discussed below.

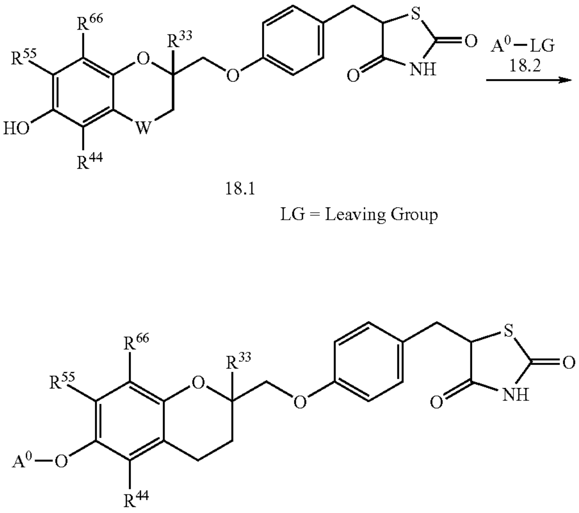

18.1

LG = Leaving Group 18.3

Specific compounds of the invention can be prepared as follows:

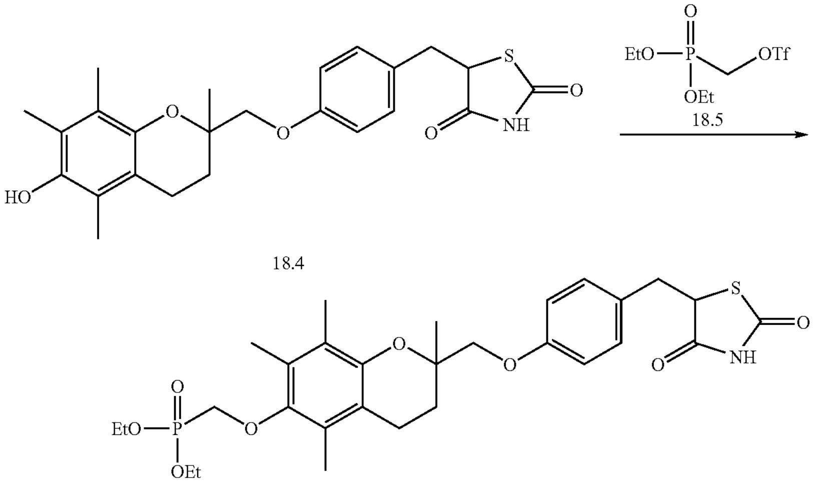

18.4

18.6

The phosphorus containing thiazolidinedione derivative 18.3 is synthesized from parent compounds by alkylation. The parent compound 18.1 is obtained by the procedure as described in U.S. Pat. No. 4,572,912. The attachment of the phosphonate linkage to the phenolic OH of 18.1 to give compounds of formula 18.3 is shown. Compound 18.1 is dissolved in a suitable aprotic solvent such as, DMF and is then treated with the phosphonate reagent ($A^0$) bearing a leaving group, for example, bromine, mesyl, tosyl, or trifluoromethanesulfonyl, in the presence of a suitable organic or inorganic base.

A solution of 18.4 in DMF is treated with cesium carbonate and one equivalent of (trifluoromethanesulfonyloxy)methylphosphonic acid diethyl ester 18.5, to give troglitazone-phosphonate 18.6. The linkage is a methylene group as shown. Using the above procedure but employing a different 18.1 and phosphonate reagents 18.2, the corresponding products 18.3 bearing different substituents and linking groups can be obtained.

The preparation of phosphorus containing thiazolidinedione derivative of another type is shown below.

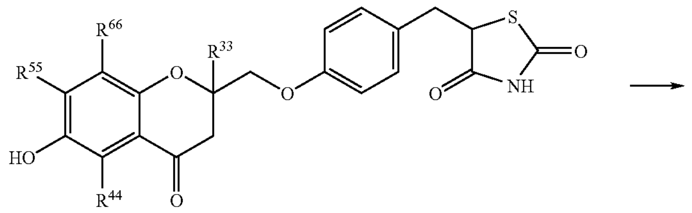

18.7

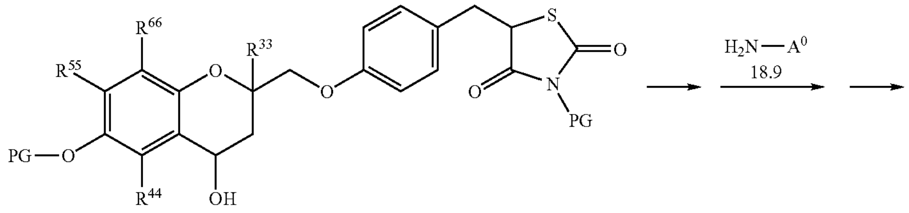

18.8

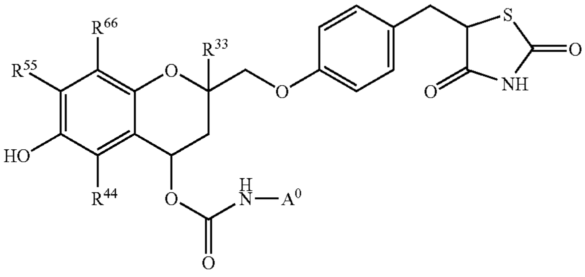

18.10

The parent compound 18.7 is obtained by the procedure as described in U.S. Pat. No. 4,572,912. The phenolic OH and thiazolidinedione unit are protected with suitable protecting group, for example SEM group, and the hydroxyl group at C4 position of chroman alcohol analogs is generated by reduction of the carbonyl group, using suitable reducing agent, for example sodium borohydride. The alcohol 18.8 is then treated with suitable chloroformate ester, for example, phenyl chloroformate or p-nitrophenyl chloroformate, or carbonate, such as bis(p-nitrophenyl)carbonate, to generate an active carbonate. The resulting active carbonate is reacted with phosphonate reagents bearing amino group 18.9, and subsequent deprotection of protecting groups produces the phosphonates 18.10.

Another specific compound of the invention can be prepared as follows. A solution of 18.11 in THF is treated with diisopropylethylamine and two equivalent of 2-(trimethylsilyl)ethoxymethyl chloride to protect the phenolic OH and thiazolidinedione unit. A solution of the protected product in methanol is then reduced using sodium borohydride to obtain the alcohol 18.12. The alcohol 18.12 is treated with phenyl chloroformate to provide phenyl carbonate, which is reacted with 2-aminoethylphosphonate diethyl ester 18.13, to obtain the protected phosphonate derivative. The protected phosphonate derivative is deprotected by tetrabutylammonium fluoride in THF to result 18.14. Using the above procedure, but employing a different 18.7 and phosphonate reagents 18.9, the corresponding products 18.10 bearing different substituents and linking groups can be obtained.

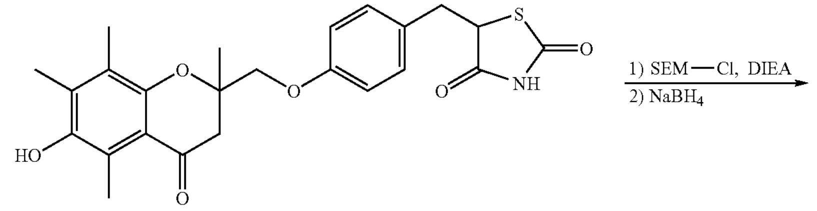

18.11

-continued

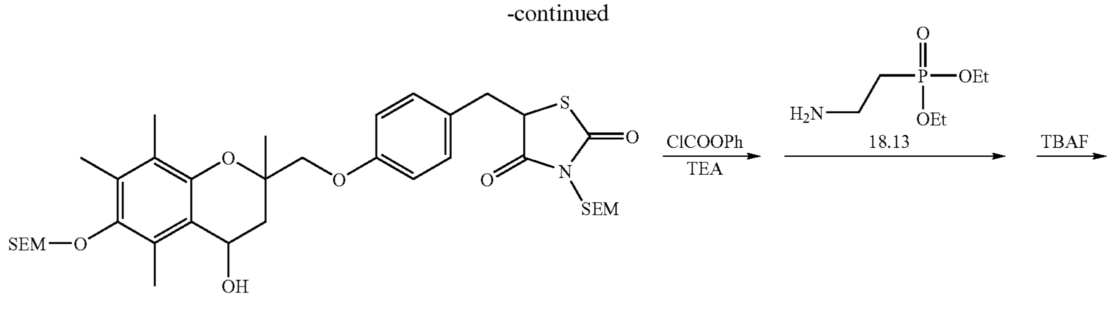

18.12

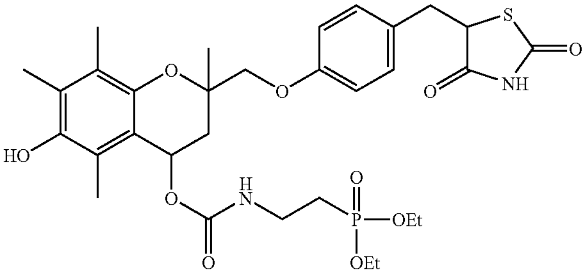

18.14

The preparation of phosphorus containing a thiazolidinedione derivative of type 18.10 is illustrated below. Thiazolidinedione with phosphorus containing moiety 18.16 is generated by the alkylation of thiazolidinedione 18.15 in a suitable aprotic solvent such as DMF 18.15 is then treated with the phosphonate reagent 18.2 bearing a leaving group, for example, bromine, mesyl, tosyl, or trifluoromethanesulfonyl, in the presence of a suitable organic or inorganic base. Compound 18.16 is then reacted with benzaldehyde 18.17 with protected phenol at the para position.

The protecting group $R^{88}$ can be any protecting group for phenolic OH, for example, alkoxyalkyl groups, such as the methoxymethyl group; aralkyl groups, such as the benzyl group; the 2-tetrahydropyranyl group; and acyl groups, such as the acetyl or benzoyl groups, preferably benzyl group. The reaction is carried out in an aprotic solvent, such as toluene, at an elevated temperature, such as the reflux temperature of the solvent, and in one embodiment in the presence of a suitable catalyst, such as piperidinium acetate or benzoate. The water produced in the reaction can be removed from the reaction mixture, for example, by means of a Dean and Stark apparatus.

The reduction of 18.18 to 18.19 is accomplished by catalytic reduction with suitable catalysts, such as palladium on carbon catalysts, e.g., a 10% palladium on charcoal catalyst. (U.S. Pat. No. 6,288,095) The coupling of 18.19 with chroman alcohol homolog 18.20, which is obtained by the procedure described in *J. American Oil Chemical Society*. 51:200 (1974) or in U.S. Pat. No. 4,572,912 yields 18.10. The alcoholic functional groups are suitably protected as described in U.S. Pat. No. 4,572,912 using Mitsunobu condition.

A.

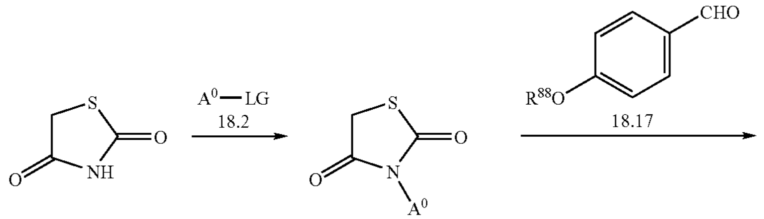

18.15 18.16

-continued

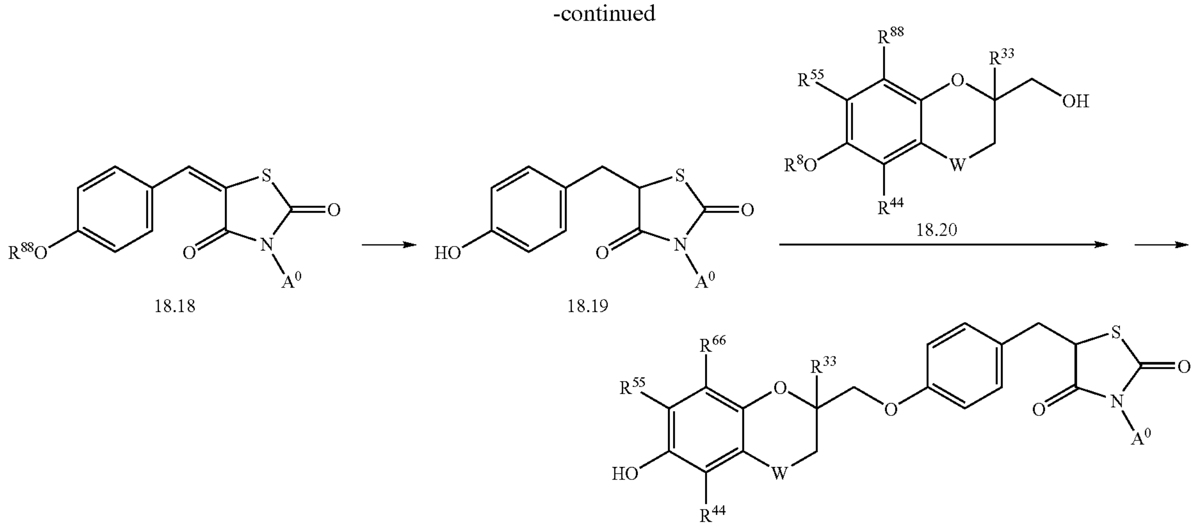

18.18 18.19 18.20 18.10

LG = Leaving Group

For example, specific compounds of the invention can be prepared as follows:

A solution of 18.15 in DMF is treated with sodium hydride and one equivalent of (trifluoromethanesulfonyloxy)methylphosphonic acid diethyl ester 18.5 to give thiazolidinedione-phosphonate 18.21 in which the linkage is a methylene group as shown. The thiazolidinedione-phosphonate 18.21 is then reacted with the benzaldehyde 18.22 bearing benzyloxy substituent in toluene in reflux condition in the presence of catalytic piperidinium acetate with Dean-Stark apparatus, which results in 18.23. The reduction of 18.23 in dioxane by catalytic hydrogenation in the presence of 10% palladium on charcoal provides 18.24. The reaction between 18.24 and chroman alcohol analogs 18.25 in the presence of diethyl azodicarboxylate and triphenylphosphine followed by deprotection of SEM group by TBAF provides 18.26. Using the above procedure, but employing different chroman alcohol analogs and phosphonate reagents 18.5 the corresponding products 18.26 bearing different substituents and linking groups can be obtained.

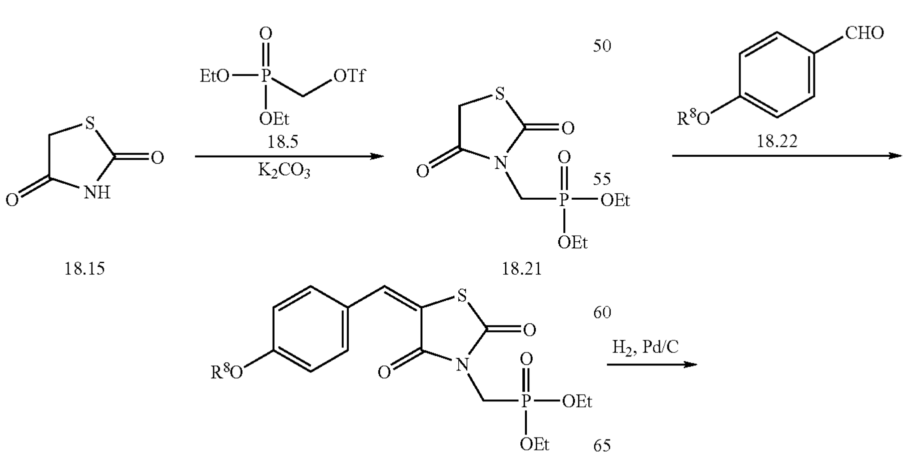

18.15 18.21 18.23

-continued

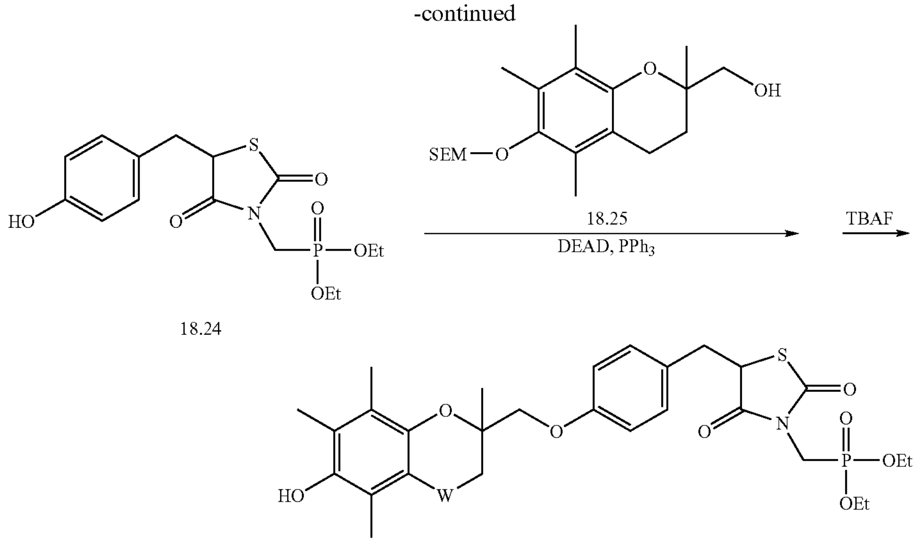

18.24

18.26

Example 19

Preparation of Representative Compounds of the Invention

Synthesis of representative compounds of the invention can be conducted as described herein.

The phosphonate ester of type 19.5 is synthesized by the coupling between the aldehyde 19.3, which is obtained as described in U.S. Pat. No. 6,288,095, and thiazolidinedione 19.2 bearing phosphonate group ($A^0$). A solution of thiazolidinedione 19.1 in a suitable aprotic solvent, for example DMF, is treated with the phosphonate reagent ($A^0$) bearing a leaving group, for example, bromine, mesyl, tosyl, or trifluoromethanesulfonyl, in the presence of a suitable organic or inorganic base.

The reaction between 19.2 and the aldehyde 19.3 is carried out in an aprotic solvent, such as toluene, at an elevated temperature, such as the reflux temperature of the solvent, and in one embodiment in the presence of a suitable catalyst, e.g., piperidinium acetate or benzoate. In one embodiment, the water produced in the reaction can be removed from the reaction mixture, for example, by means of a Dean and Stark apparatus.

The reduction of 19.4 to 19.5 is accomplished by either catalytic reduction with suitable catalysts, such as palladium on carbon catalysts, e.g., a 10% palladium on charcoal catalyst, or the use of a metal/solvent reducing system, such as magnesium in methanol (U.S. Pat. No. 6,288,095).

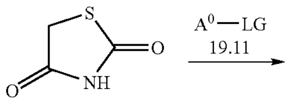

19.1

-continued

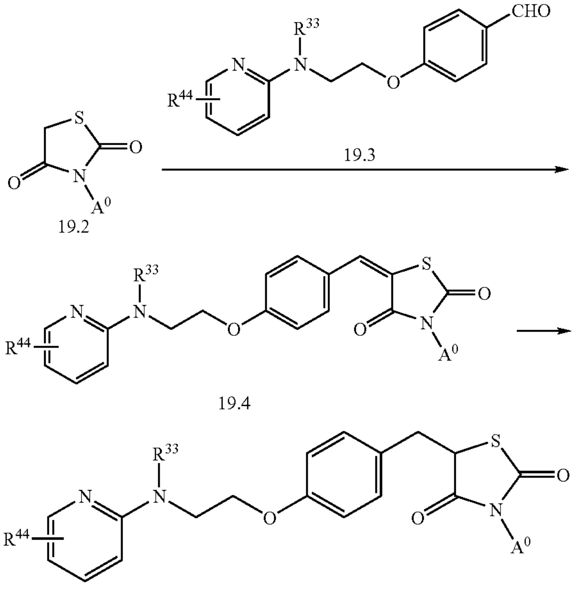

19.2

19.4

19.5

LG = Leaving Group

For example, specific compounds of the invention can be prepared by treating a solution of 19.1 in DMF with sodium hydride and one equivalent of (trifluoromethanesulfonyloxy) methylphosphonic acid diethyl ester to give thiazolidinedione-phosphonate 19.7 in which the linkage is a methylene group. The thiazolidinedione-phosphonate 19.7 is then reacted with the aldehyde 19.8 in toluene, in reflux conditions, in the presence of catalytic piperidinium acetate with Dean-Stark apparatus 19.9 results. The reduction of 19.9 in dioxane by catalytic hydrogenation in the presence of 10% palladium on charcoal provides 19.10.

Using this procedure, but employing different aldehyde 19.3 and phosphonate reagents, the corresponding products 19.5 bearing different substituents and linking groups can be obtained.

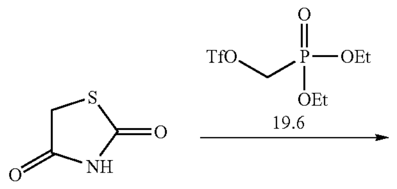

19.1

19.6

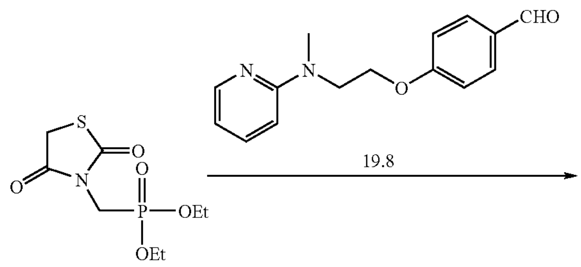

19.7

19.8

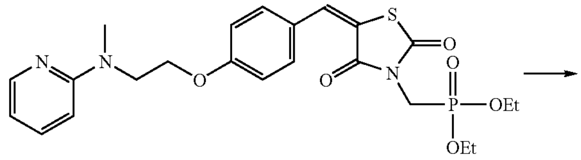

19.9

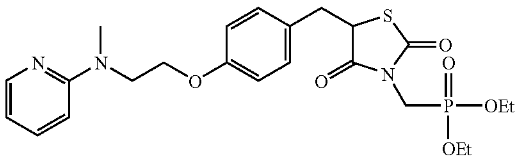

19.10

Example 20

Preparation of Representative Compounds of the Invention

Representative compounds of the invention can be prepared as follows:

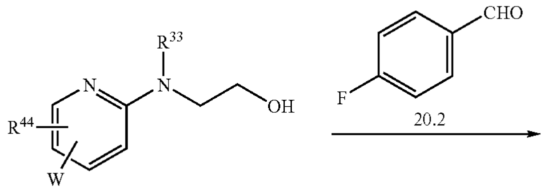

20.1

20.2

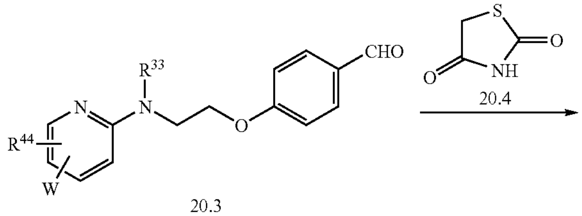

20.3

20.4

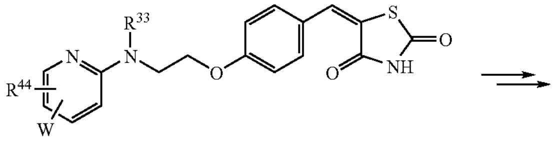

20.5

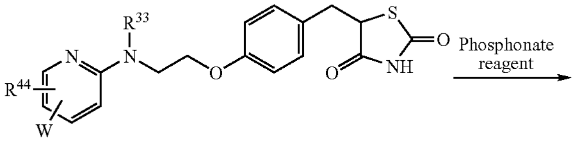

20.6

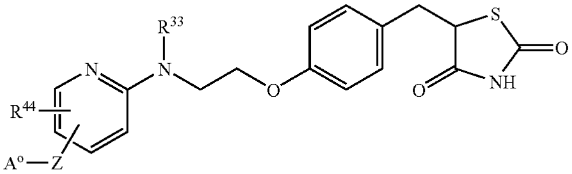

20.7

The preparation of phosphonate and phosphonamidate conjugates of thiazolidinedione derivatives of type 20.7 is shown above. These types of compounds are obtained by the reactions described in U.S. Pat. No. 6,288,095 using 20.1 bearing a suitable substituent, for example nitro and cyano groups, which can be converted to the functional group to introduce a phosphorus containing moiety. The substituent of 20.5 or 20.6 is converted to adequate functional group, such as an amino or aldehyde group, either during the reduction of benzylidene thiazolidinedione or by a separate step. The attachment of phosphonate moieties is accomplished by suitable reduction conditions. The phosphonate group bearing moiety is attached by reductive amination using a suitable reducing agent, such as sodium cyanoborohydride, in suitable solvents, such as dichloroethane or methanol, under acidic condition using an acid, such as acetic acid.

For example, the synthesis of specific compounds of the invention is described below.

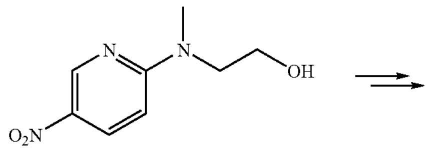

20.8

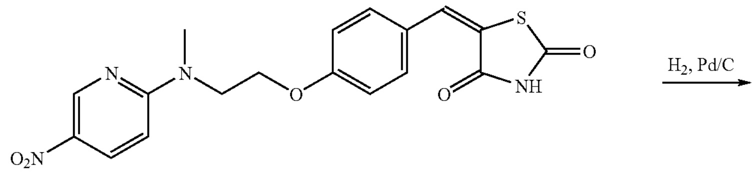

20.9

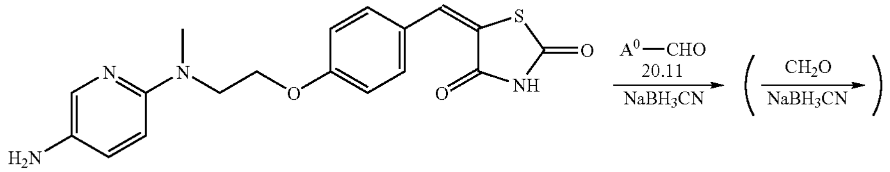

20.10

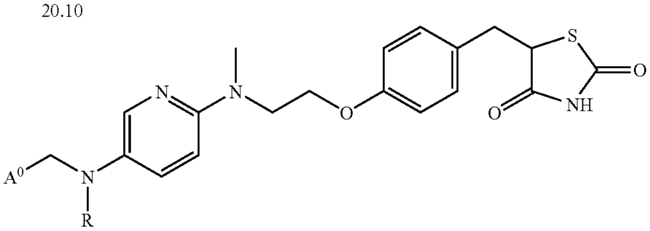

(R = H, Me)
20.12

The nitropyridine derivative 20.8 is converted to 20.9 according to a series of the reactions described in U.S. Pat. No. 6,288,095. The reduction of the nitro group of 20.9 occurs during reduction of the benzylidenethiazolidinedione under catalytic hydrogenation conditions with a 10% palladium on charcoal catalyst. A phosphonate moiety is then introduced to the amino group of 20.10 by reductive amination in dichloroethane using 2-oxoethylphosphonic acid diethyl ester 20.11 and sodium cyanoborohydride and acetic acid. The resulting secondary amine 20.12 (R═H) may be converted to the corresponding tertiary amine 20.12 (R═Me) by reductive amination using formaldehyde and sodium cyanoborohydride.

Another example for the synthesis of specific compounds of the invention is shown below.

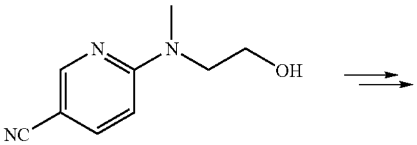

20.13

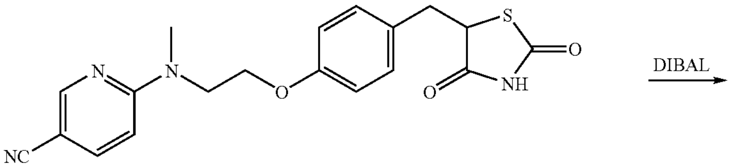

20.14

-continued

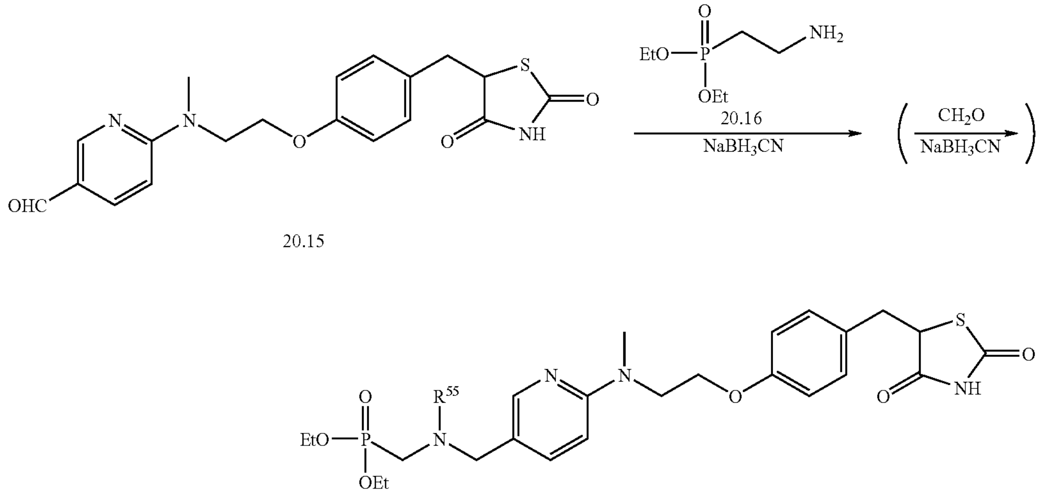

20.15

(R = H, Me)
20.17

The pyridine 20.13 bearing a cyano group is converted to 20.14 according to a series of the reactions described in U.S. Pat. No. 6,288,095. The reduction of the cyano group of 20.14 to the corresponding aldehyde 20.15 is accomplished by DIBAL. Phosphonate moiety is then introduced to the aldehyde group of 20.15 by reductive amination procedure using 2-aminoethylphosphonic acid diethyl ester 20.16 and sodium cyanoborohydride and acetic acid. The resulting secondary amine 20.17 (R═H) may be converted to the corresponding tertiary amine 20.17 (R═Me) by reductive amination using formaldehyde and sodium cyanoborohydride.

The synthesis of a specific compound of the invention, a conjugate of 20.7 with carbamate linker, is shown below. The aldehyde bearing 20.16 is further reduced with sodium borohydride, and the corresponding alcohol 20.18 is treated with phenyl chloroformate providing the phenyl carbonate 20.19. Treatment of 20.19 with phosphonate reagents 20.16 bearing amino group generates 20.21.

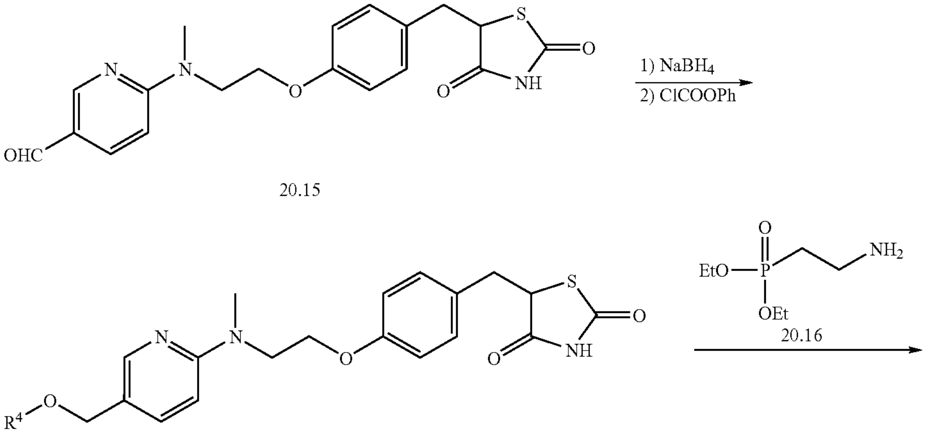

20.15

20.18: $R^4 = H$
20.19: $R^4 = COOPh$

-continued
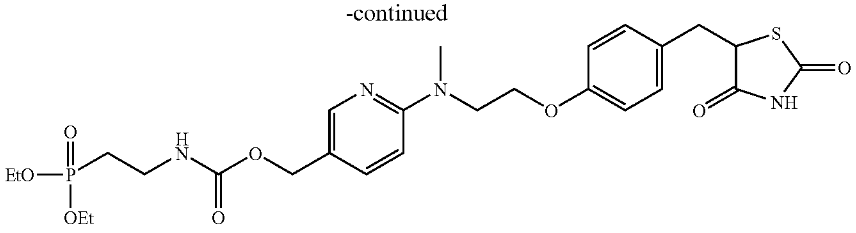
20.21
Example 21
Preparation of Representative Compounds of the Invention
Representative compounds of the invention can be prepared as described below.
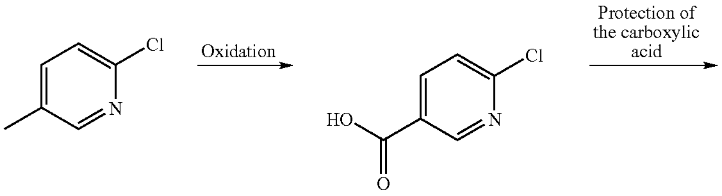
21.1
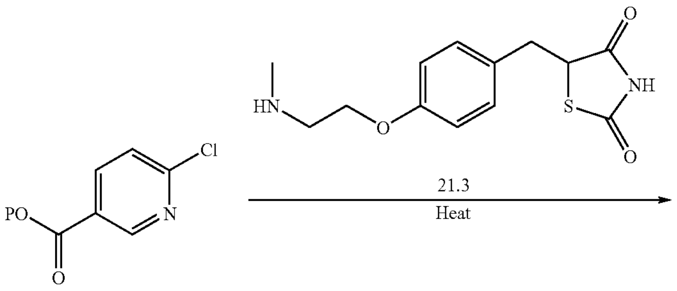
21.2
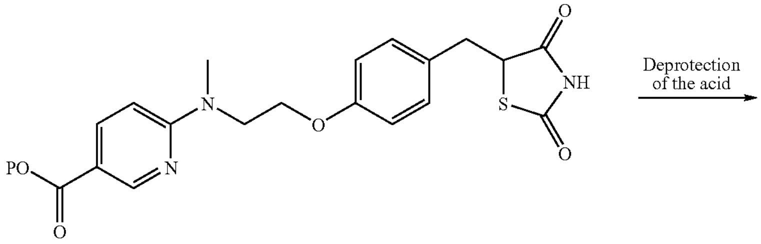
21.4
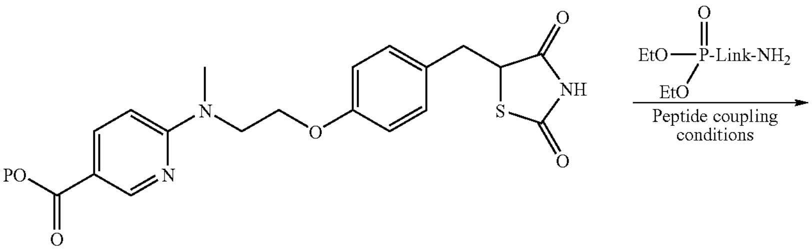
21.5

-continued

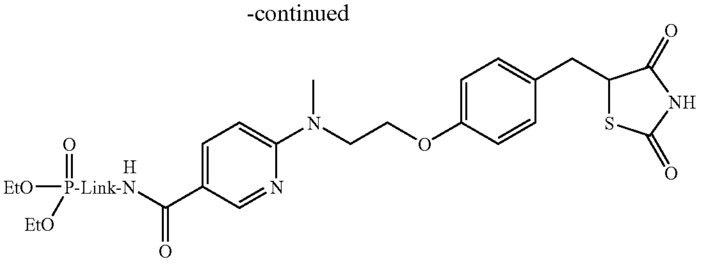

21.6

The synthesis of representative compounds of the invention can be achieved via a variety of routes. For example, the protected core of rosiglitazone can be assembled first, followed by addition of the pro-drug group.

The preparation of a specific example, compound 21.6, in which X is C═O, is shown above. Oxidation of the benzylic position of 2-chloro-5-methylpyridine according to the procedure of Collie, *J. Chem. Soc.*, 71:653 (1897) provides compound 21.1. Protection of the carboxylic acid followed by reaction with compound 21.3 prepared as described in Cantello et al., *J. Med. Chem.*, 37:3977 (1994) gives compound 21.4. Deprotection of the ester followed by coupling of the acid 21.5 to an amine carrying the phosphonate moiety provides compound 21.6.

Detailed synthesis of specific compounds of the invention is shown below.

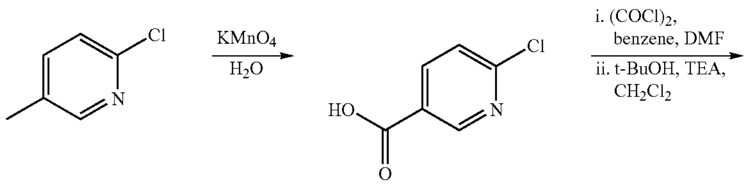

21.1

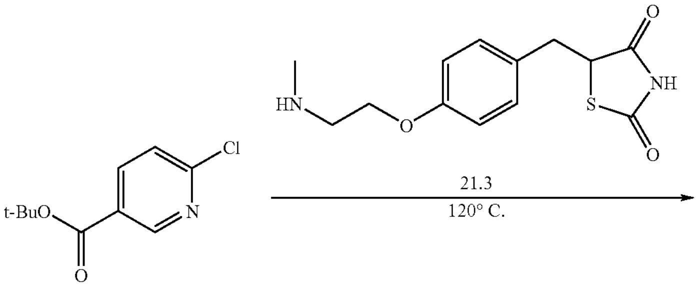

21.2

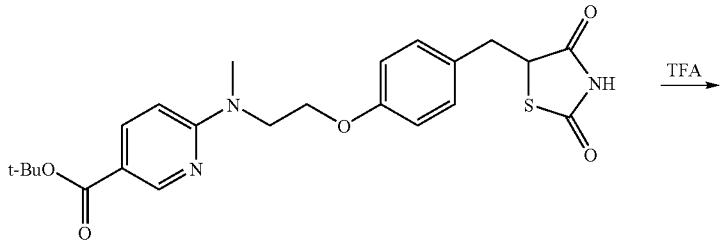

21.4

-continued

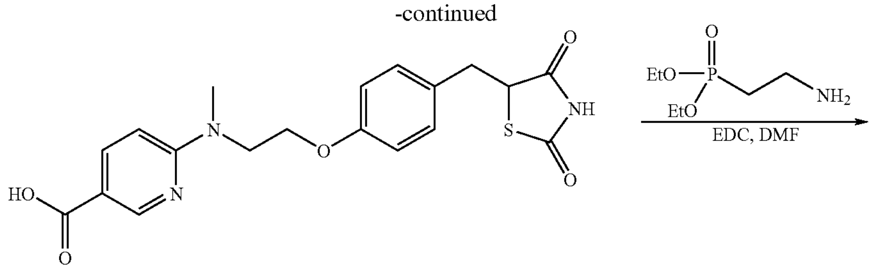

21.5

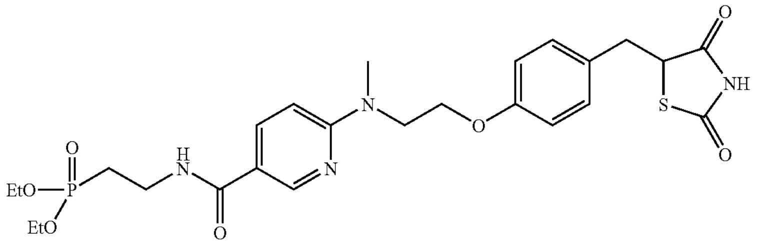

21.7

The starting material, 2-chloro-5-methylpyridine (commercially available), can be oxidized at the benzylic position using potassium permanganate to provide compound 21.1 (Collie, *J. Chem. Soc.*, 71:653 (1897)). Carboxylic acid 21.1 is blocked with a bulky protecting group such as t-butyl to form 21.2. The 2-chloro-pyridine moiety undergoes an addition-elimination reaction with amine 21.3 (described in Cantello et al.) to give compound 21.4. Removal of the ester protecting group using trifluoroacetic acid (TFA) (Greene, "Protective Groups in Organic Synthesis," Wiley-Interscience, (1999)) provides the precursor for attachment of the pro-drug. Standard peptide coupling conditions provide compound 21.7.

Example 22

Preparation of Representative Compounds of the Invention

Synthesis of a representative compound of the invention is shown below.

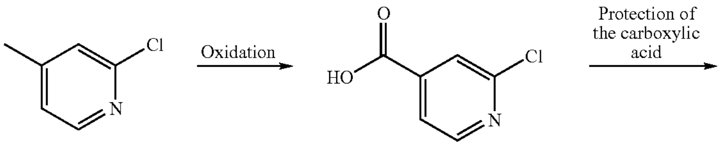

22.1

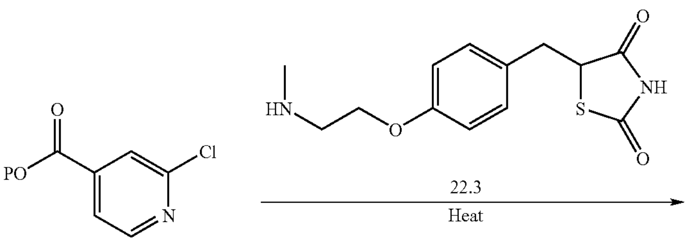

22.2

-continued
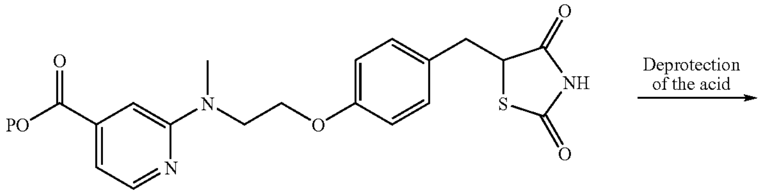
22.4
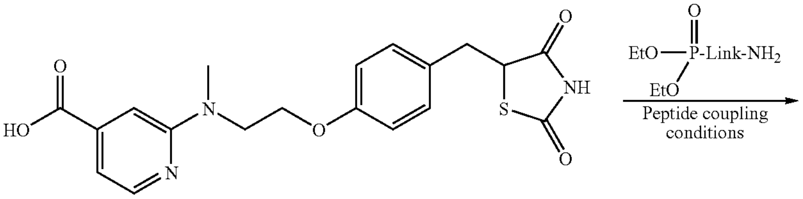
22.5
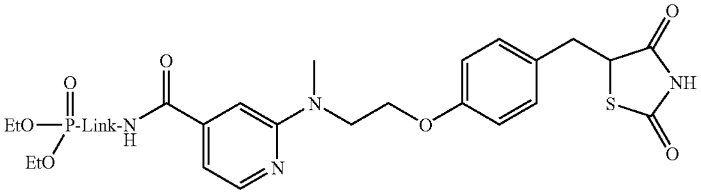
22.6
The above route is similar to that illustrated in Example 20. An example of the preparation of specific compounds of the invention is described below.
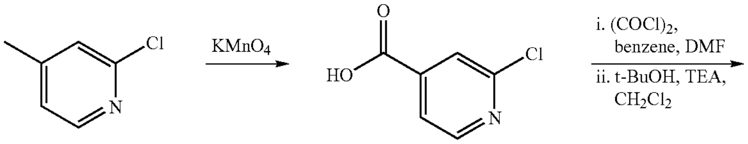
22.1
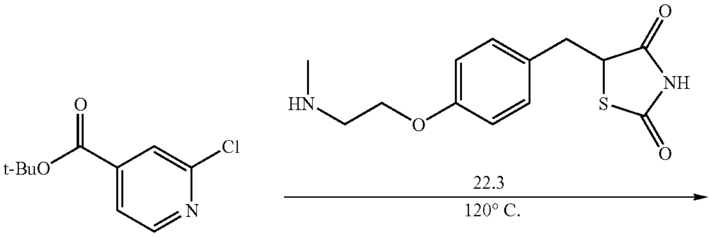
22.2
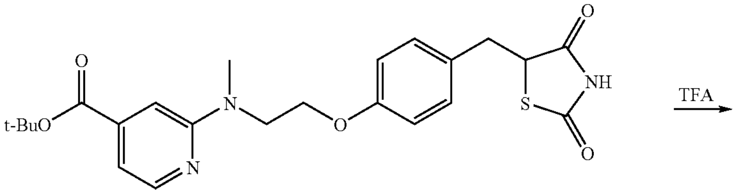
22.4

-continued

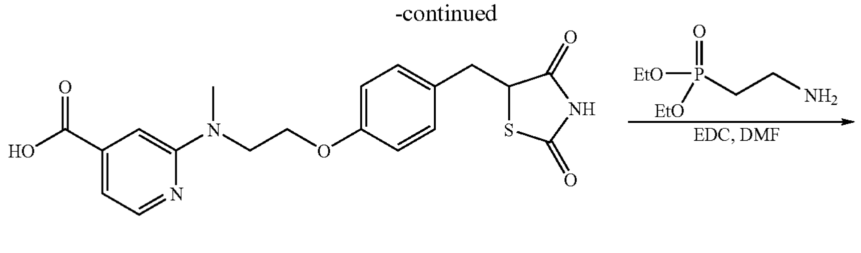

22.5

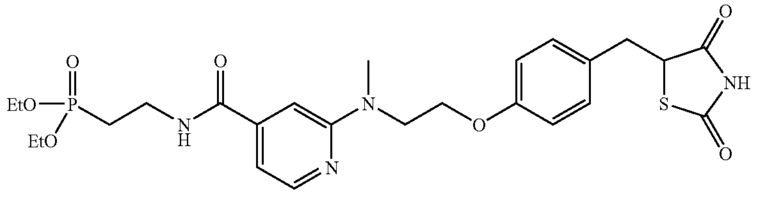

22.7

The starting material, 2-chloro-4-methylpyridine (commercially available), can be oxidized at the benzylic position using potassium permanganate to provide compound 22.1 (Collie, *J. Chem. Soc.*, 71:653 (1897)). Carboxylic acid 22.1 is blocked with a bulky protecting group, such as t-butyl, to form 22.2. The 2-chloro-pyridine moiety undergoes an addition-elimination reaction with amine 22.3 (described in Cantello et al., *J. Med. Chem.*, 37:3977 (1994)). Removal of the ester protecting group using TFA (Greene, T., "Protective Groups in Organic Synthesis," Wiley-Interscience, (1999)) provides the precursor for attachment of the pro-drug 22.7. Standard peptide coupling conditions provide compound 22.5.

A variety of linking groups can be utilized on the pyridinium ring. For example, the use of 6-chloro-pyridine-3-carbaldehyde allows for attachment of the phosphonate containing group via reductive amination. In this case, the attachment point would be a carbon (X═C).

Example 23

Preparation of Representative Compounds of the Invention

Representative compounds of the invention can be made according to the general route outlined below:

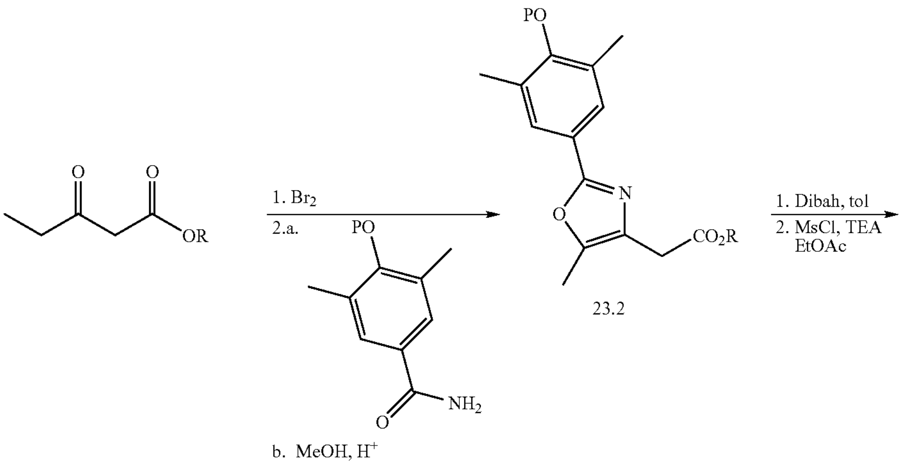

23.2

-continued

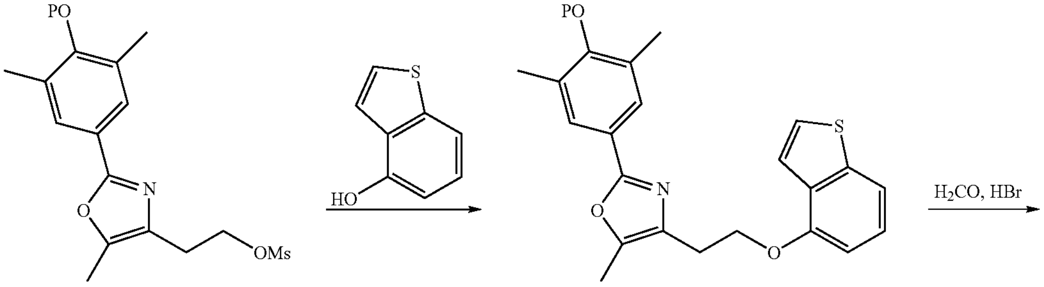

23.3 23.4

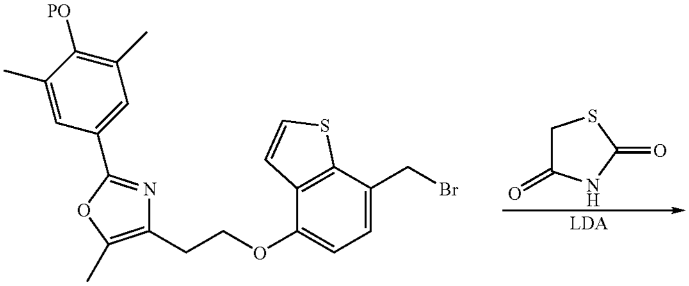

23.5

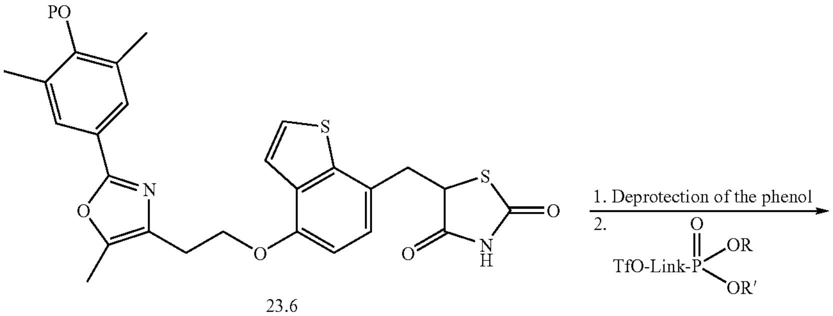

23.6

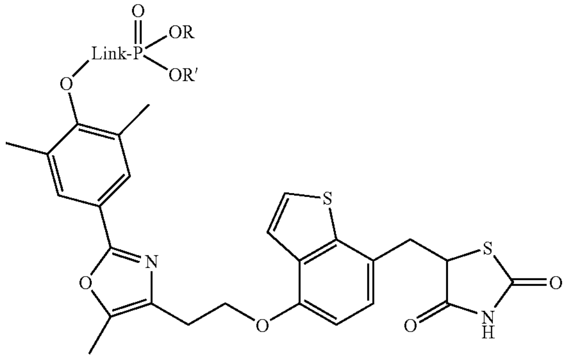

23.1

The preparation of compound 23.1, which is one example of the attachment of the pro-drug at the 4-phenoxy moiety of R-483, is shown above. In addition, a number of salts of the final pro-drug can be prepared. Specifically, a sodium salt may be prepared by addition of NaOH at the last step (see WO 01/79202).

Compound 23.1 is prepared by bromination of a β-keto ester at the γ-position. Condensation with 4-allyloxy-3,5-dimethyl-benzamide (prepared according to U.S. Pat. No. 2,912,453; *Chem. Abstracts*, 4500 (1960)) provides compound 23.2. Reduction of the ester followed by conversion of the alcohol to mesylate provides compound 23.3. Displacement of the mesylate by benzo[b]thiophen-4-ol gives compound 23.4. Reaction of compound 23.4 with formaldehyde and HBr provides for the convenient addition of 2,4-thiazolidinedione anion to form compound 23.6. Removal of the protecting group, followed by treatment of the liberated phenol in a solvent such as tetrahydrofuran or dimethylformamide with a base such as sodium hydride with addition of diethyl phosphonomethyltriflate (prepared according to *Tetrahedron Lett.*, 27:1477 (1986)) yields the desired phosphonate diester.

The synthesis of specific compounds of the invention is shown below.

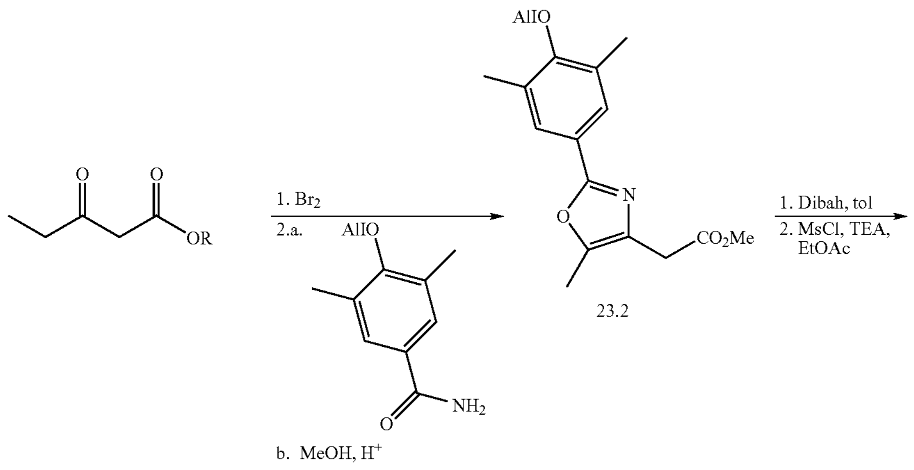
23.2
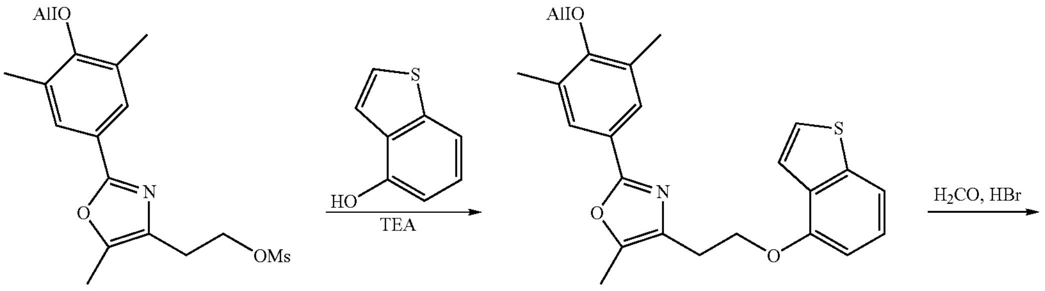
23.3
23.4
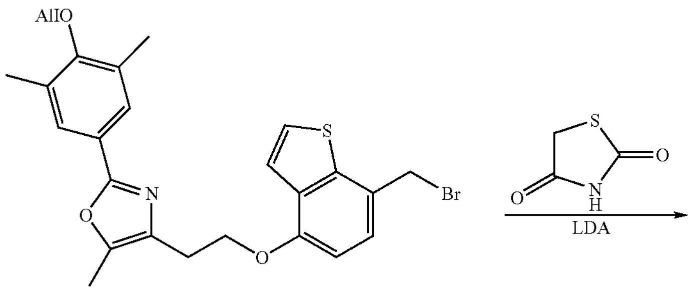
23.5
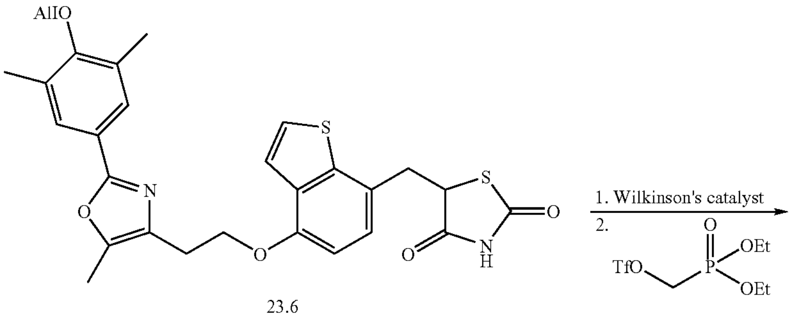
23.6

-continued

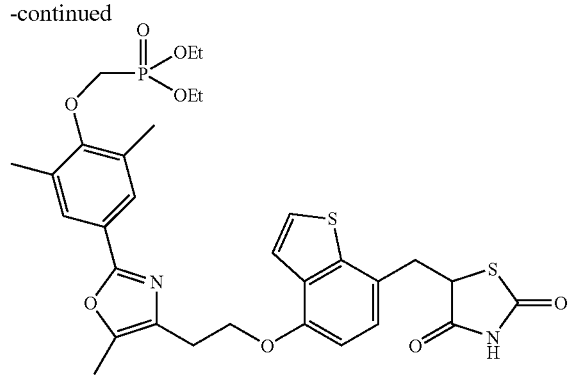

23.7

The protecting group used for 4-hydroxy-3,5-dimethylbenzamide is the allyl group (U.S. Pat. No. 2,912,453; see also Chem. Abstracts, 4500 (1960)). The synthesis is followed as described above. Removal of the allyl group can be achieved using Wilkinson's catalyst to provide the phenol (Greene, "Protective Groups in Organic Synthesis," Wiley-Interscience, (1999)). Alkylation of the phenol using diethyl phosphonomethyltriflate (prepared according to *Tetrahedron Lett.*, 27:1477 (1986)) yields the desired phosphonate diester 23.7.

Example 24

Preparation of Representative Compounds of the Invention

Representative compounds of the invention can be made according to the general route outlined below.

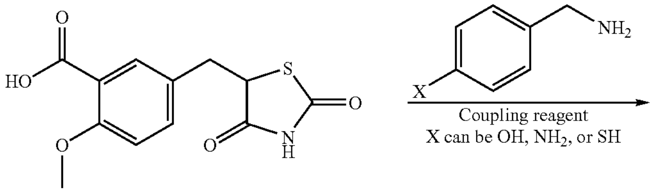

24.1

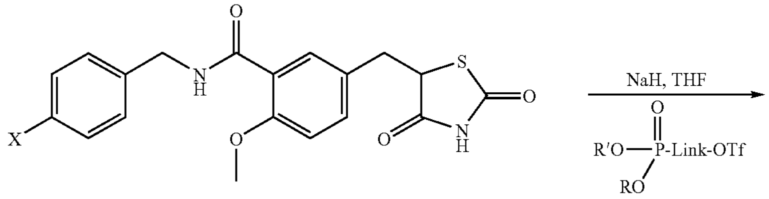

24.2

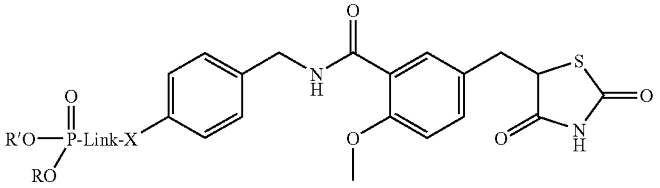

24.3

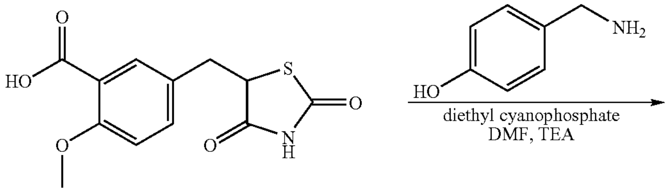

24.1

-continued

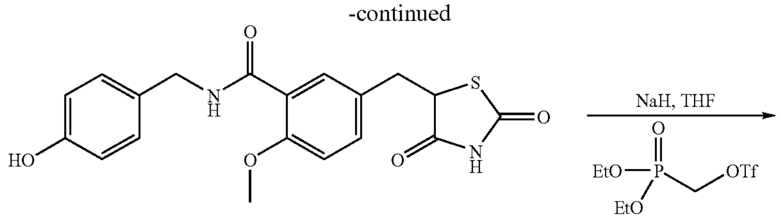

24.4

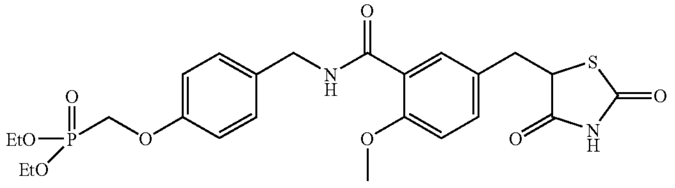

24.5

Compound 24.1, 5-(2,4-dioxo-thiazolidin-5-ylmethyl)-2-methoxy-benzoic acid, can be prepared according to U.S. Pat. No. 6,030,990. Acid 24.1 can be coupled to a variety of benzyl amines utilizing well-known coupling conditions, such as 1-ethyl-3-(3'-dimethylaminopropyl) carbodiimide or diethyl cyanophosphate in an organic solvent such as dimethyl sulfoxide or N,N-dimethylformamide to produce amide 24.4. The handle on compound 24.4 can be utilized for attachment of the pro-drug.

4-(aminomethyl)phenol from Apin Chemicals can be used as the coupling partner to the acid 24.1 to provide phenol 24.4. Compound 24.4 can be treated in a solvent such as tetrahydrofuran or dimethylformamide with a base such as sodium hydride. When bubbling ceases, diethyl phosphonomethyltriflate (prepared according to *Tetrahedron Lett.*, 27:1477 (1986)) is added, yielding the desired phosphonate diester 24.5.

The synthesis of compound 24.6 is shown below.

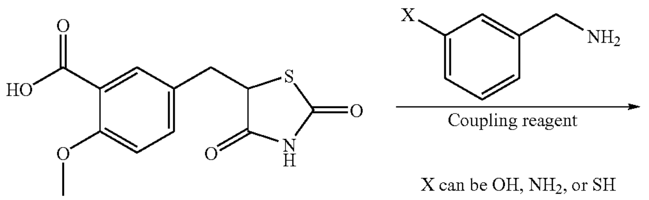

24.1

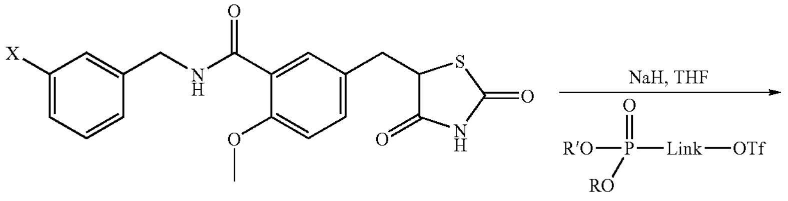

24.6

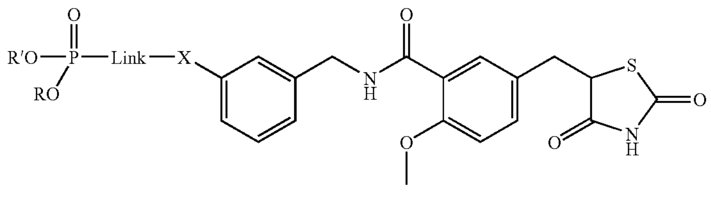

24.7

-continued

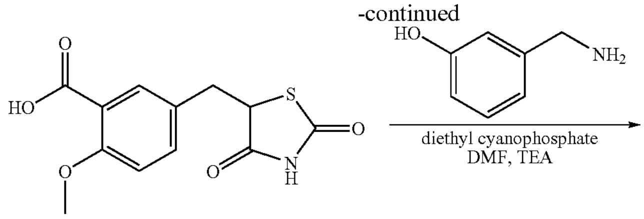

24.1

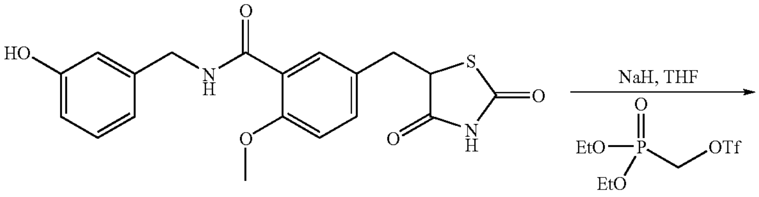

24.8

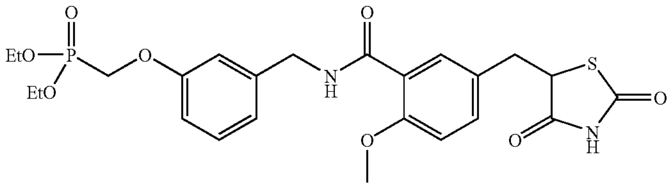

24.9

Preparation of 24.1 can be achieved according U.S. Pat. No. 6,030,990. Coupling of 3-(aminomethyl)phenol from Apin Chemicals to the acid 24.1 using common coupling reagents provides phenol 24.6. Treatment of 24.6 in a solvent such as tetrahydrofuran or dimethylformamide with a base such as sodium hydride followed by addition of diethyl phosphonomethyltriflate (prepared according to *Tetrahedron Lett.*, 27:1477 (1986)) after cessation of bubbling, yields the desired phosphonate 24.7, e.g., 24.9.

Example 25

Preparation of Representative Compounds of the Invention

Compounds of the invention can be made according to the general route outlined below.

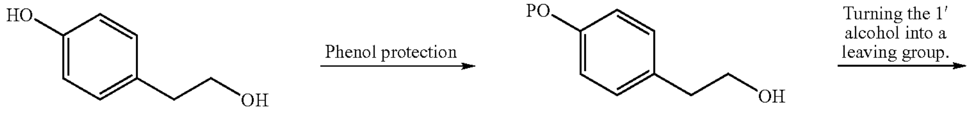

25.1

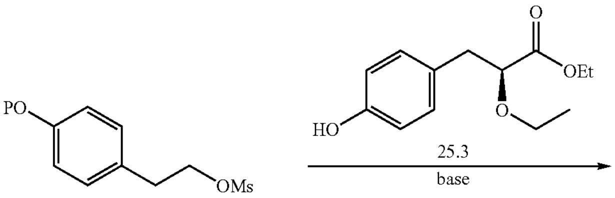

25.2

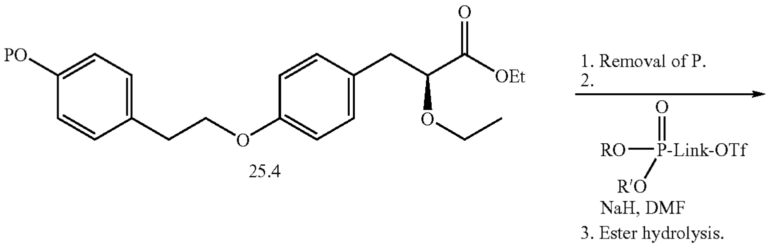

25.4

-continued

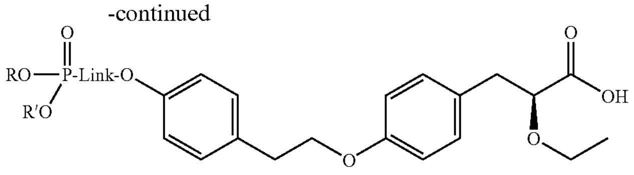

25.5

2-(4-Hydroxyphenyl)ethanol is first protected on the phenolic hydroxyl group to provide compound 25.1. The primary alcohol is then turned into a good leaving group and is displaced using compound 25.1 (as disclosed in U.S. Pat. No. 6,531,622). The phenol of the fully-protected compound 25.4 is deprotected and alkylated, and the ester is saponified to provide compound 25.5.

The detailed synthesis of a representative compound of the invention is shown below.

group with a source of fluoride ion such as tetrabutylammonium fluoride, liberates the phenol, which can then react with diethyl phosphonomethyltriflate (prepared according to *Tetrahedron Lett.*, 27:1477 (1986)) in a solvent such as DMF using a base such as sodium hydride. Finally, the carboxylate ester is selectively hydrolyzed by treatment with lithium hydroxide to provide pro-drug 25.6.

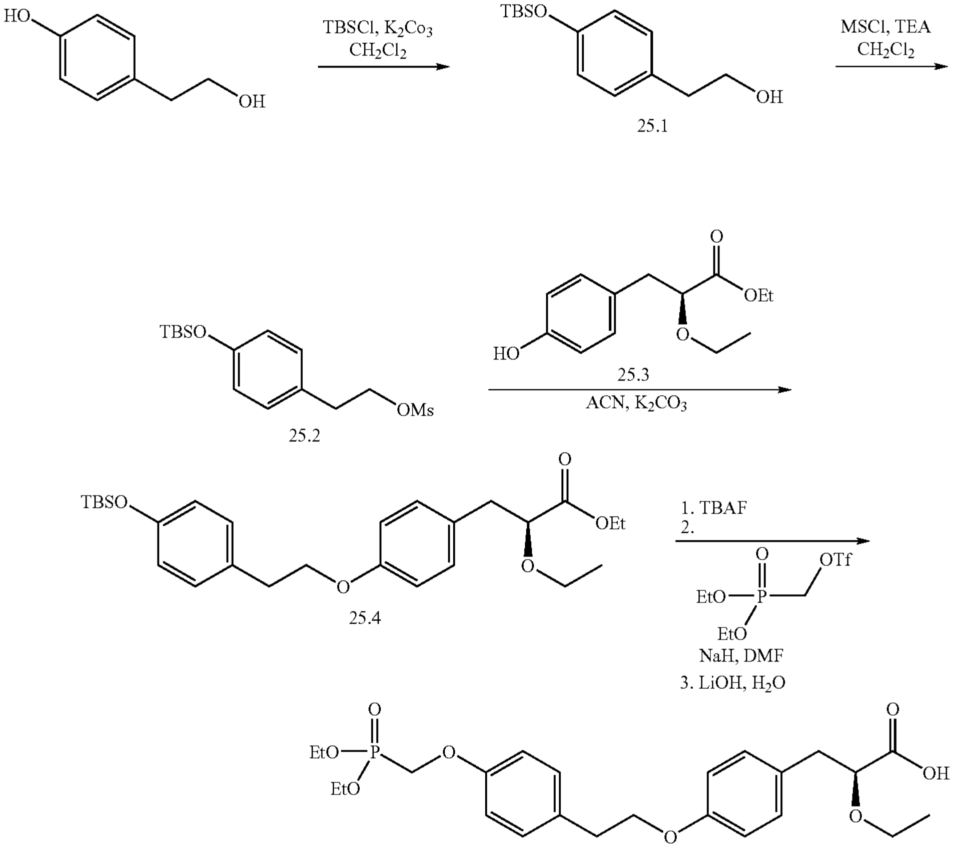

25.6

2-(4-Hydroxyphenyl)ethanol is first protected on the phenolic OH group with a tert-butyldimethyl silyl group to provide compound 25.1. Turning the primary alcohol into a suitable leaving group is achieved using mesyl chloride in dichloromethane and a teriary amine such as triethylamine as a base. Displacement of the mesylate is achieved using ethyl (S)-2-ethoxy-3-(4-hydroxyphenyl)propanoate 25.3 as described in U.S. Pat. No. 6,531,622. Removal of the silyl

Example 26

Preparation of Representative Compounds of the Invention

Representative compounds of the invention can be prepared as follows:

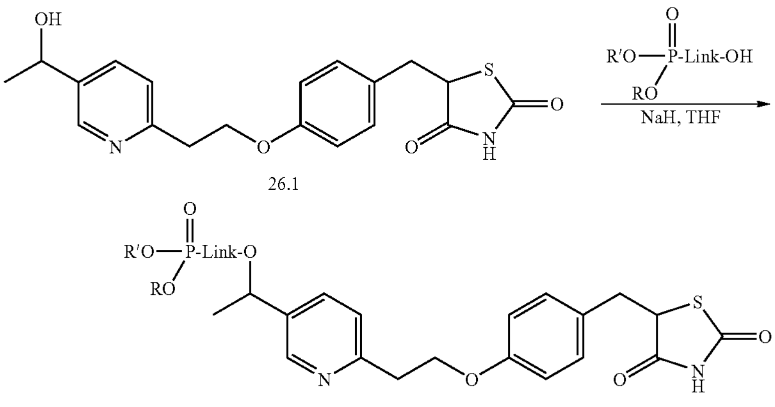

26.1

26.2

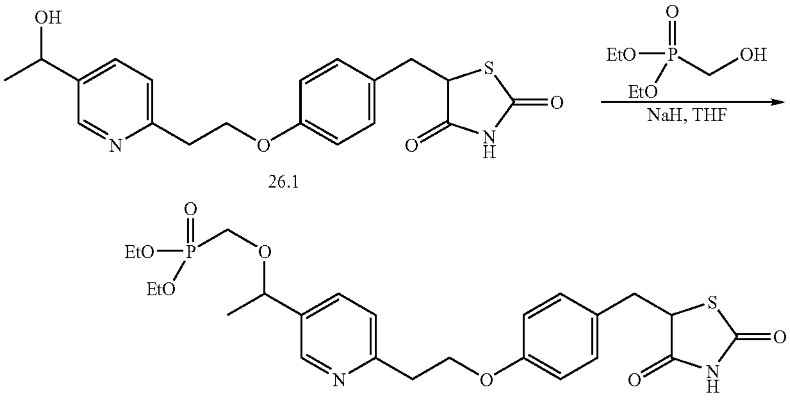

26.1

26.3

The 5-(4-{2-[5-(1-Hydroxy-ethyl)-pyridin-2-yl]-ethoxy}-benzyl)-thiazolidine-2,4-dione can be prepared according to the procedure reported in Tanis et al., *J. Med. Chem.*, 39:5053 (1996). Compound 26.1 can be treated in a solvent such as tetrahydrofuran or dimethylformnamide with a base such as sodium hydride. When bubbling ceases, diethyl phosphonomethyltriflate (prepared according to *Tetrahedron Lett.*, 27:1477 (1986)) is added, yielding the desired phosphonate diester 26.2, e.g., 26.3.

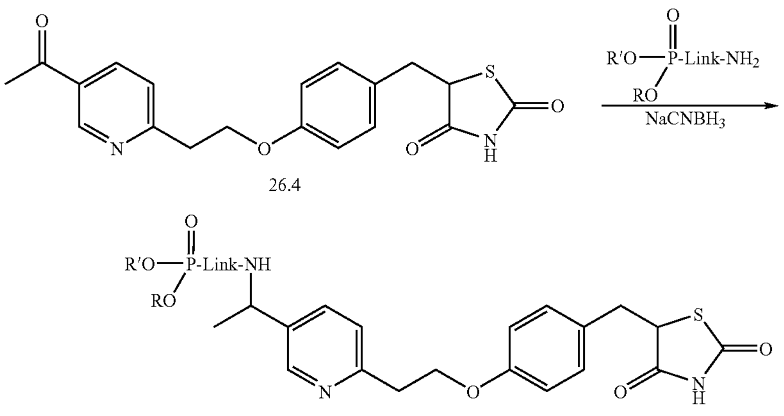

26.4

26.5

-continued

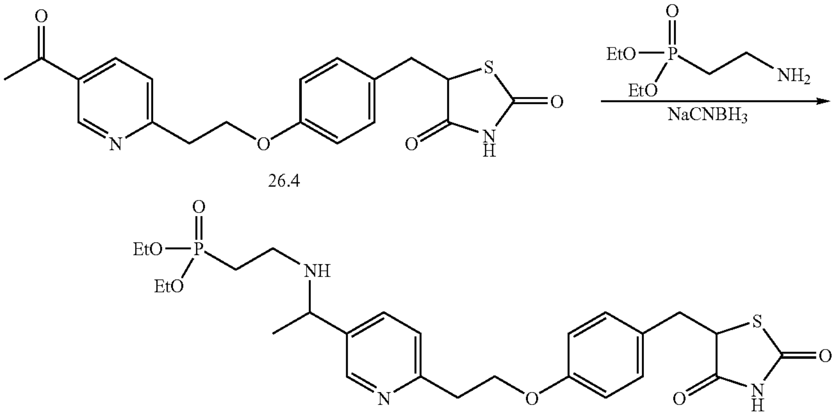

26.4

26.6

Synthesis of another representative compound of the invention is shown above. Preparation of 26.4 can be achieved according to Tanis et al., *J. Med. Chem.*, 39:5053 (1996). Reductive amination of compound 26.4 using an amino phosphonate under sodium cyano borohydride or sodium triacetoxy borohydride in solvents such as methanol or THF yields product 26.5, e.g., 26.6, in a few hours. A number of amino diethyl phosphonates are available from Fluka.

Example 27

Preparation of Representative Compounds of the Invention

Representative compounds of the invention can be made according to the general route outlined below:

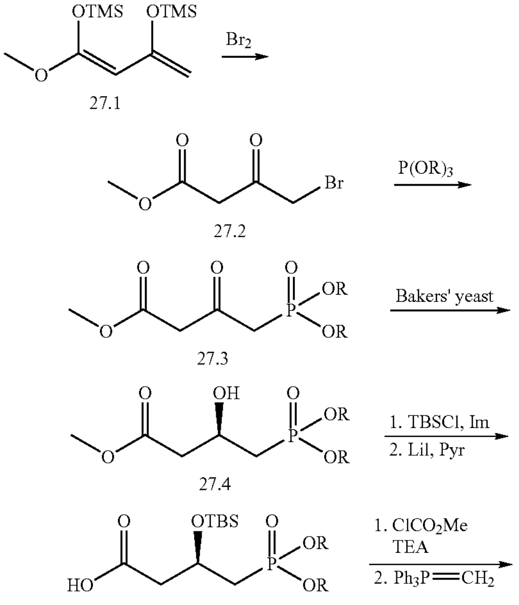

27.1

27.2

27.3

27.4

27.5

-continued

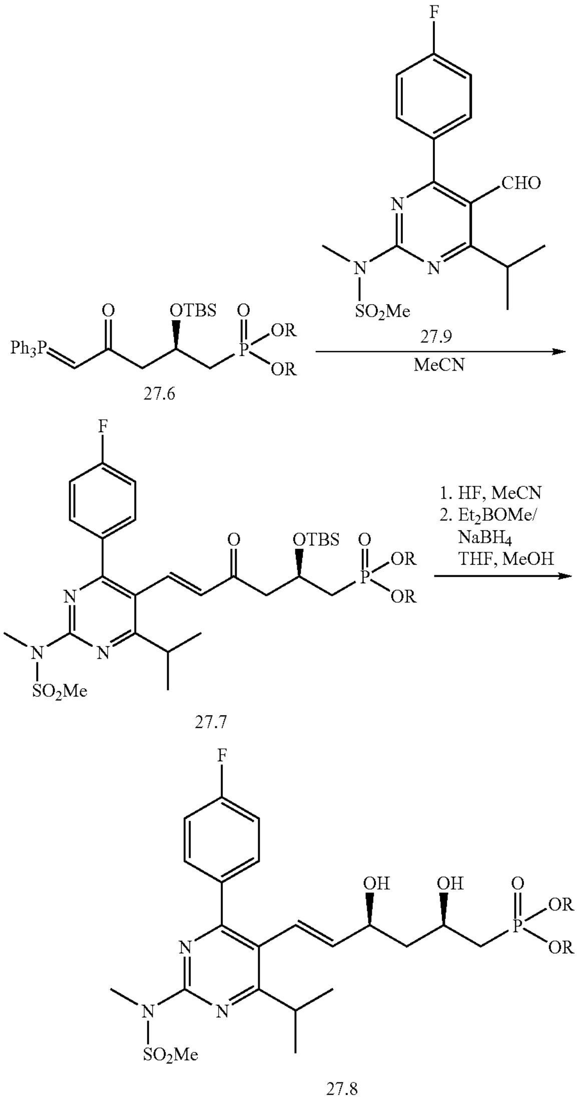

27.6

27.9

27.7

27.8

The preparation of analog 27.8 is described herein. A generic phosphonate bis-ester can be prepared as demonstrated above. The substituents at phosphorus can be manipulated according to transformations described herein.

An example of the synthesis of specific compounds of the invention is shown below:

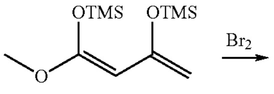

27.1

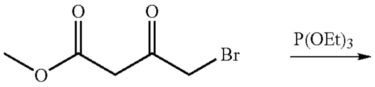

27.2

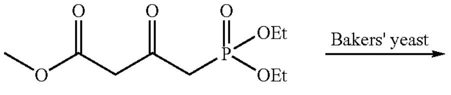

27.3

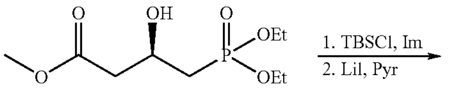

27.4

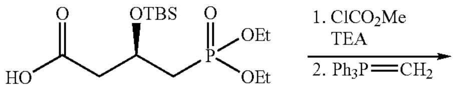

27.5

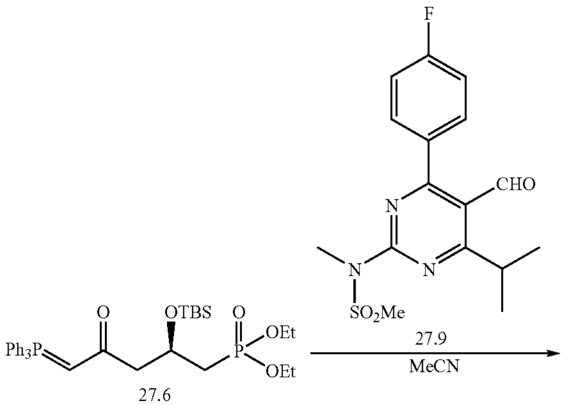

27.9

27.6

-continued

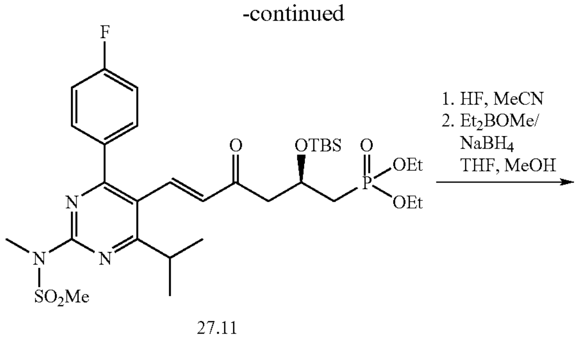

27.11

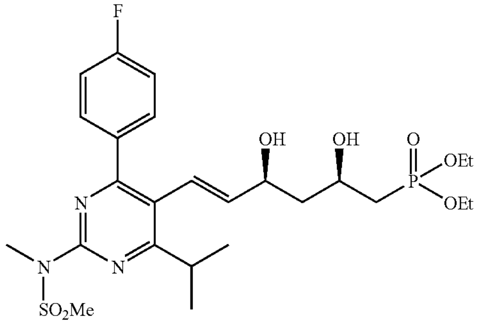

27.12

The synthesis begins with the formation of silyl enol ether of methylacetoacetate (available from Aldrich) using TMSCl and LDA as described in Jullien et al., *Tetrahedron Lett.*, 23(47):4943 (1982) to form compound 27.1. Bromination under the conditions reported by Chan et al., *J. Chem. Soc. Chem. Commun.*, 578 (1979) yields 4-bromo-3-oxo-butyric acid methyl ester 27.2. Arbuzov reaction of the bromide 27.2 with triethylphosphite as reported by Yuan et al., *Heteroatom Chemistry*, 13(2): 153 (2002) provides diethyl phosphonate 27.3. Addition of ester 27.3 to bakers' yeast in water yields 4-(diethoxyphosphoryl)-3-R-hydroxybutanoic acid methyl ester 27.4 as described by Yuan et al.

Silylation of the newly generated secondary alcohol using TBSCl and imidazole followed by selective removal of the methyl ester protecting group as described in Greene, T., "Protective Groups in Organic Synthesis," Wiley-Interscience (1999) provides compound 27.5. Carboxylic acid 27.5 is treated with methyl chlorocarbonate and triethylamine to give a mixed anhydride that is then converted to compound 27.6 by reacting with methylidenetriphenylphosphorane according to the method described in Konoike et al., *J. Org. Chem.*, 59:7849 (1994).

A Wittig reaction between compound 27.6 and aldehyde 27.9 (prepared according to Watanabe et al., *Bioorg. & Med. Chem.*, 5:437 (1997)) provides the olefin analog 27.11. Removal of the TBS protecting group with HF in MeCN followed by stereoselective chelation-controlled reduction with $Et_2BOMe$ and sodium borohydride in THF: MeOH gives the desired phosphonate 27.12.

Example 28

Preparation of Representative Compounds of the Invention

The general route outlined below can be used to prepare representative compounds of the invention.

-continued
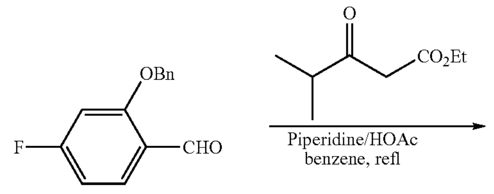
28.1
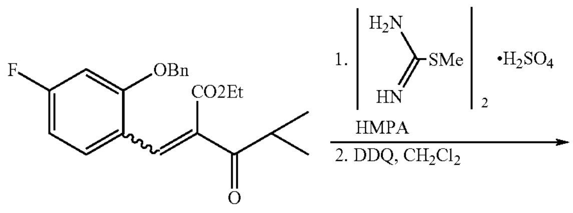
28.2
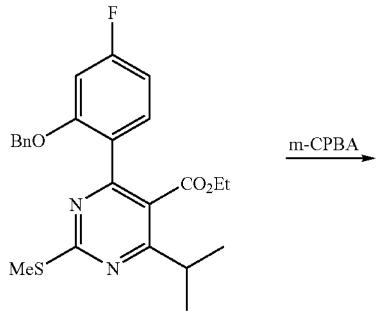
28.3
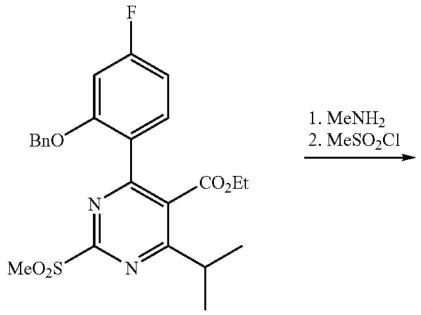
28.4
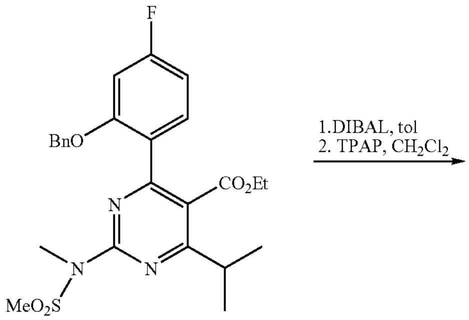
28.5
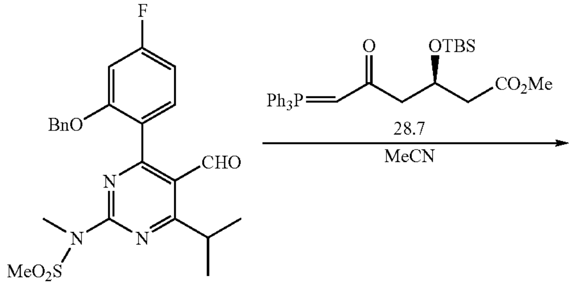
28.6
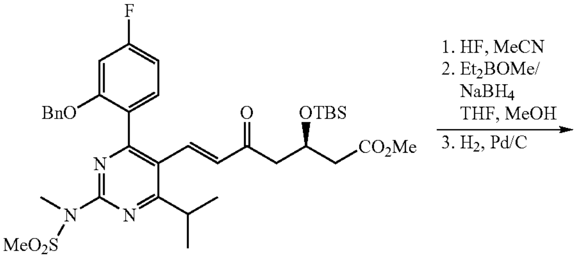
28.8
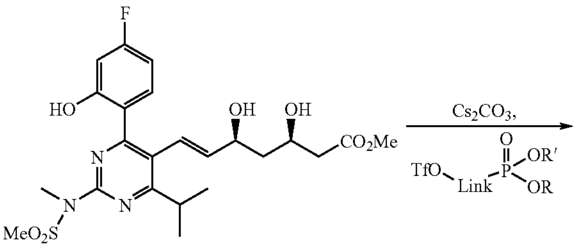
28.9
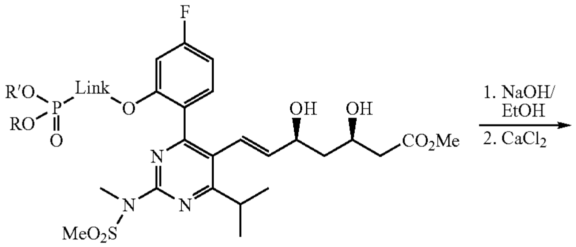
28.10
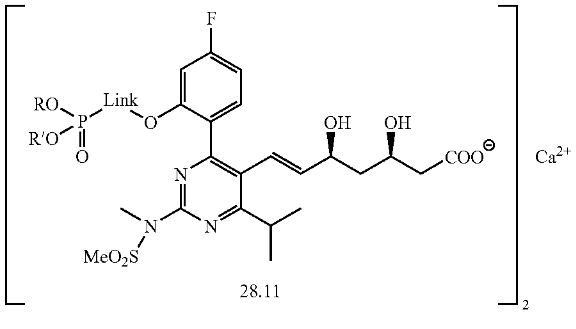
28.11

Pro-drugs such as 28.11 can be prepared as demonstrated above (see also Watanabe et al., *Bioorg. & Med. Chem.*, 5(2):437 (1997)).

More specifically, preparation of a diethyl phosphonomethyl pro-drug 28.13 is as follows:

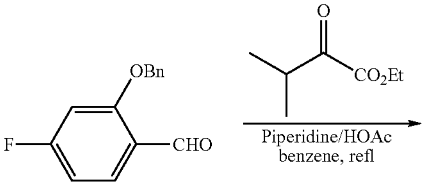

28.1

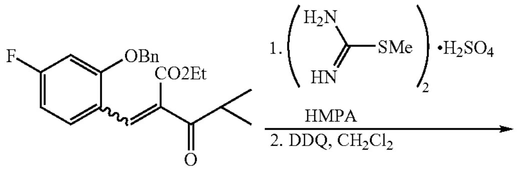

28.2

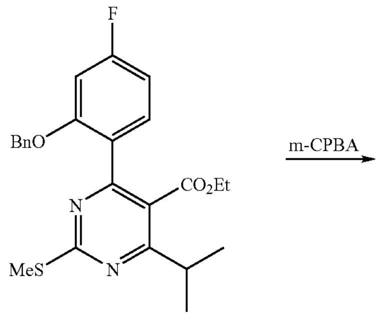

28.3

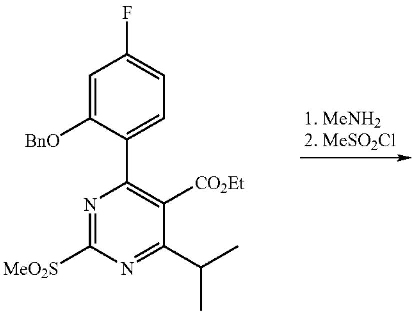

28.4

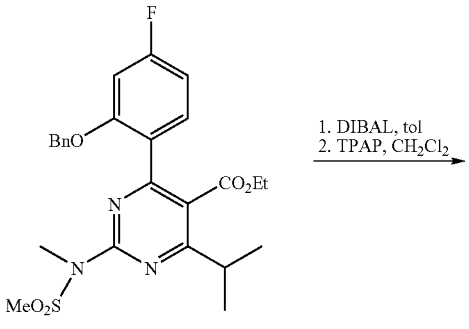

28.5

-continued

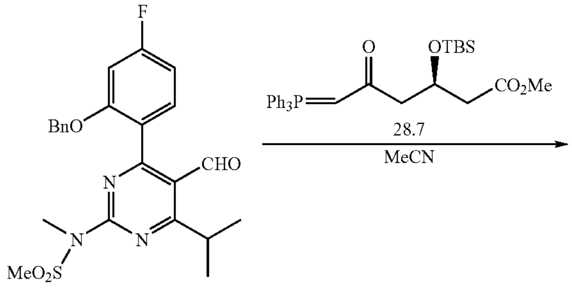

28.6

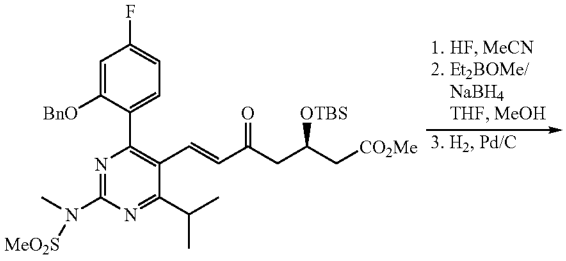

28.8

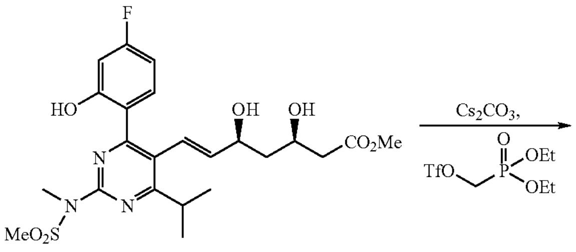

28.9

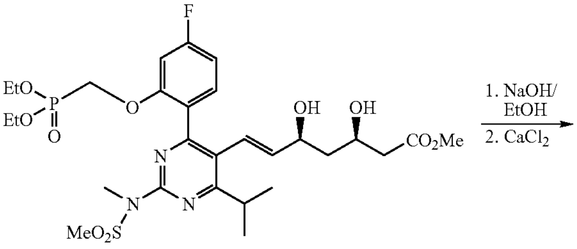

28.12

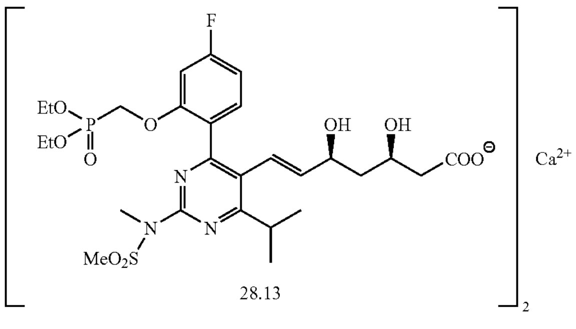

28.13

Protection of the phenolic group of 4-fluoro-2-hydroxybenzaldehyde (available from Apollo chemicals) according to methods described in described in Greene, “Protective Groups in Organic Synthesis,” Wiley-Interscience (1999) provides compound 28.1. Knoevenagel reaction of compound 28.1 with ethyl isobutyrylacetate provides the unsaturated ketoester. Cyclocondensation of 28.2 with S-methylisothiourea hydrogen sulfate followed by dehydrogenation with DDQ affords the pyrimidine ring in 28.3. The thioether is oxidized with m-chloroperbenzoic acid to give sulfonylpyrimidine 28.4. Displacement of the sulfone with $MeNH_2$ in MeOH followed by treatment with methanesulfonyl chloride gives the N-methanesulfonyl amino derivative 28.5.

Reduction of the ester in 28.5 with DIBAL-H followed by TPAP oxidation afforded the corresponding aldehyde 28.6. The desired side chain is attached by Wittig reaction of aldehyde 28.6 with the optically active ylide 28.7 (prepared according to Konoike et al., *J. Org. Chem.*, 59:7849 (1994)). Deprotection of 28.8 with HF in MeCN and stereoselective chelation-controlled reduction with $Et_2BOMe$ and $NaBH_4$ in THF:MeOH followed by removal of the benzyl protecting group gives compound 28.9.

If the hydrogenation conditions necessary for removal of the benzyl group reduce the trans olefin, an exchange of the phenol protecting group can be done on 28.6. The benzyl protecting group may be exchanged for an acid labile group such as TMSE or DPM which can be removed simultaneously with the TBS removal step. Ultimately, the benzyl protecting group may be removed on compound 28.6 and the phenol may be carried forward without protection.

Attachment of the phosphonate pro-drug is achieved by suspending 28.9 in an anhydrous solvent and addition of a base such as cesium carbonate, followed by addition of diethyl phosphonomethyltriflate (prepared according to *Tetrahedron Lett.*, 27:1477 (1986)), yielding the desired compound 28.12. Removal of the methyl ester protecting group generates the free carboxylic acid, from which a variety of salts such as that shown may be prepared.

Example 29

Preparation of Representative Compounds of the Invention

The general route outlined below can be used to prepare representative compounds of the invention.

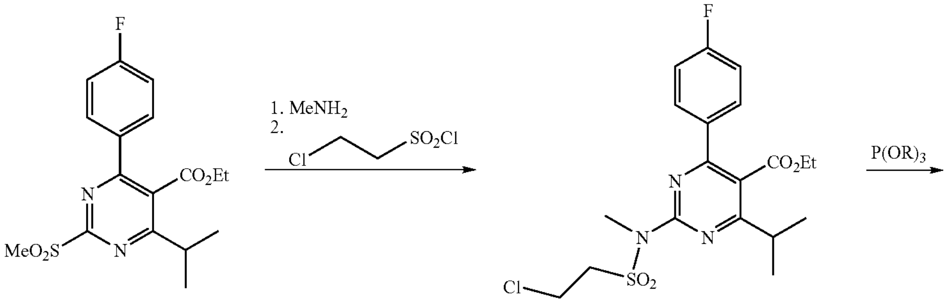

29.1 29.2

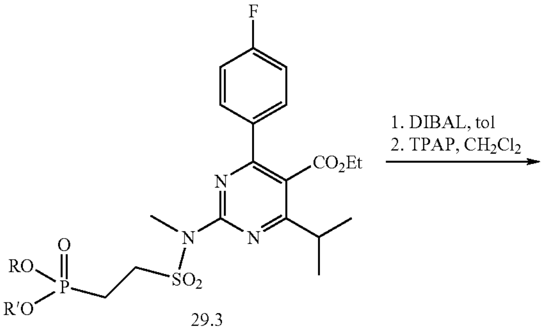

29.3

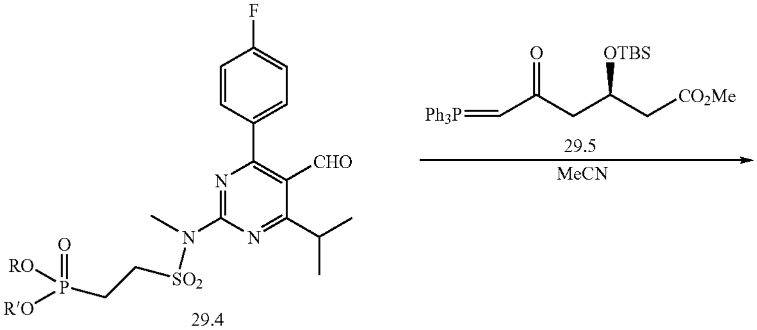

29.5

29.4

-continued

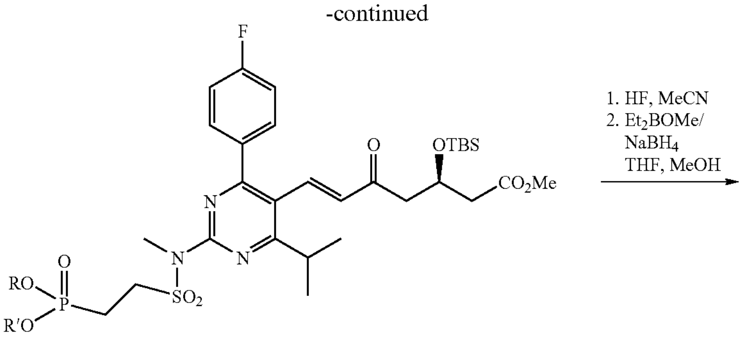

29.6

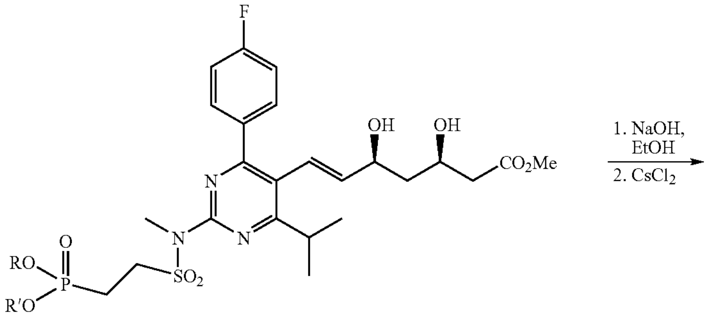

29.7

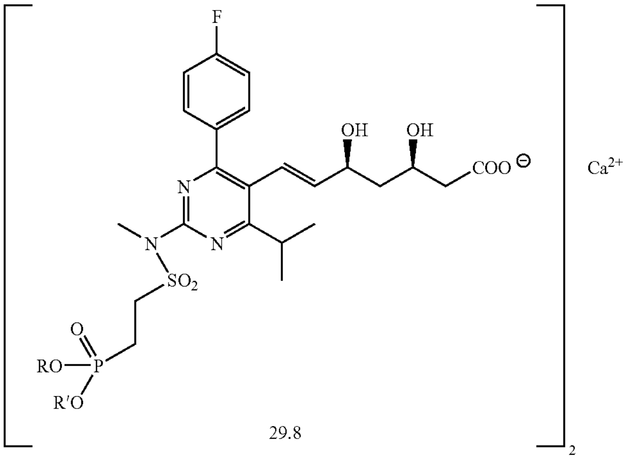

29.8

Synthesis of pro-drugs described herein follows the literature (Watanabe et al., *Bioorg. & Med. Chem.*, 5(2):437 (1997)). The starting materials, compound 29.1, is treated with methylamine followed by 2-chloroethane sulfonyl chloride (available from Aldrich) to provide compound 29.2. Addition of the phosphonate moiety via an Arbuzov reaction yields the pro-drug 29.3.

Subsequent reduction of the ester group with DIBAL-H followed by TPAP oxidation gives the corresponding aldehyde. Formation of the heptanoate 29.6 using the optically active 29.5, as discussed previously, via a Wittig reaction yields the desired product 29.6. Removal of the TBS protecting group using HF in MeCN, and the stereoselective chelation-controlled reduction with $Et_2BOMe$ and $NaBH_4$ provides compound 29.7. Release of the methyl ester protecting group under basic conditions provides the free carboxylic acid, from which a variety of salts such as shown may be prepared.

Specific compounds of the invention may be prepared as follows:

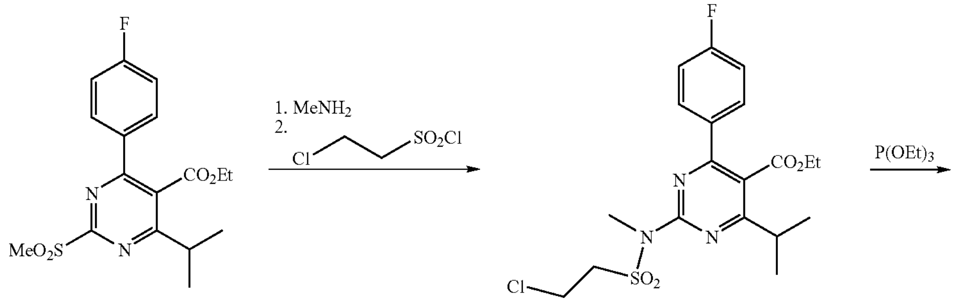
29.1 29.2
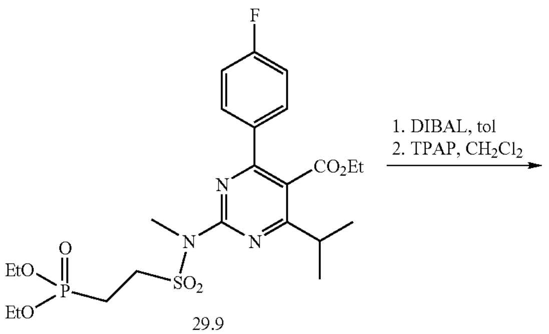
29.9
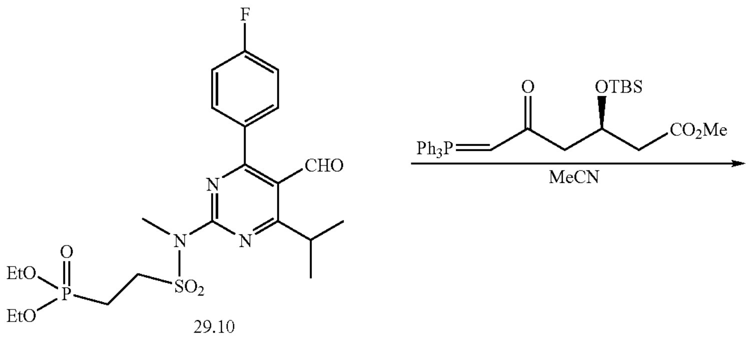
29.10
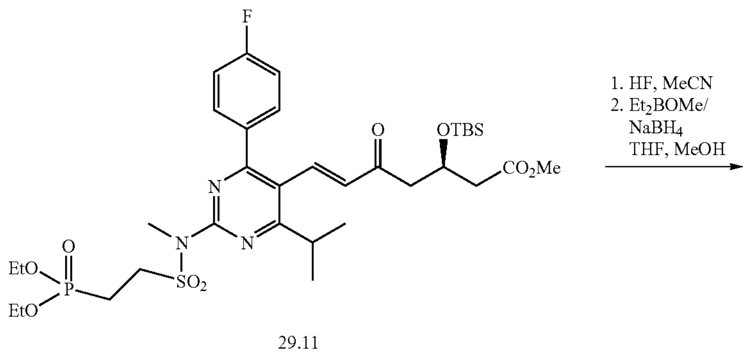
29.11

-continued

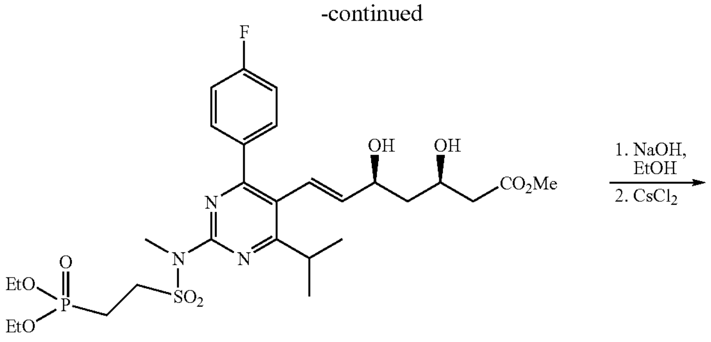

29.12

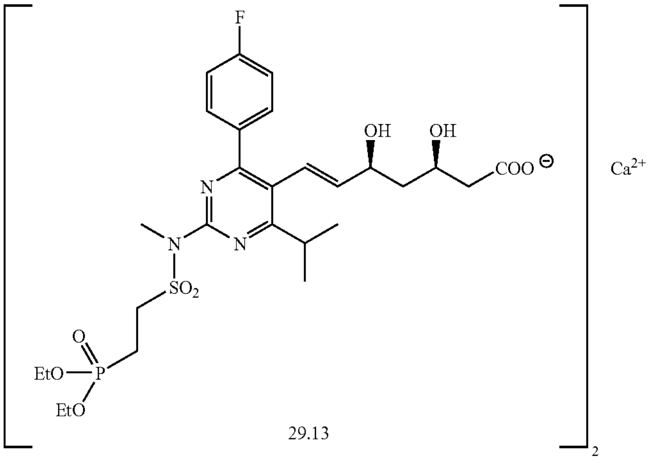

29.13

Example 30

Preparation of Representative Compounds of the Invention

Representative compounds of the invention can be prepared according to the following methods.

Synthesis of Compound 30.5

To a solution of 2-(diethylphosphono)butyric acid (183 mg, 0.87 mmol) in benzene (5 mL), triethylamine (0.20 mL, 1.45 mmol) and diethyl chlorophosphate were added, followed by 4-pyrrolidinopyridine (162 mg, 1.1 mmol). The resulting mixture was stirred for 30 minutes when 25.4 (200 mg, 0.36 mmol) was added. After 18 hours the reaction mixture was partitioned between ethyl acetate and 1N HCl. After separating the layers, the organic extract was washed with water, saturated aqueous sodium bicarbonate, and saturated brine, and then dried over anhydrous sodium sulfate. The solvent was removed to produce an oil that was purified by silica gel chromatography, eluting with ethyl acetate/hexanes (gradient 1/3 to 1/1), giving 247 mg of compound 30.5 as a white foam.

MS m/z (M+H)+743.42;

1H NMR (300 MHz, CDC13) δ 0.072-0.094 (m, 12H), 0.87-0.89 (m, 21H), 1.27-1.46 (m, 12H), 1.61-1.88 (m, 5H), 2.32-2.59 (m, 5H), 2.96-3.10 (M, 1H), 4.05-4.18 (m, 4H), 4.25-4.30 (m, 1H), 4.47-4.68 (m, 2H), 5.40-5.43 (m, 1H), 5.45-5.48 (m, 1H), 5.84 (dd, 1H, J=5.9, 9.3 Hz), 5.96 (d, 1H, J=9.7 Hz).

Synthesis of Compound 30.7

To a solution of 30.5 (240 mg, 0.32 mmol) in tetrahydrofuran cooled to 0° C., acetic acid (0.31 mL, 5.39 mmol) was added followed by tetraethylammonium fluoride dihydrate (598 mg, 3.23 mmol). After stirring 18 hours at room temperature, the solvents were removed under reduced pressure and the residue was partitioned between dichloromethane and saturated aqueous sodium bicarbonate. After separating the layers, the organic extract was washed with saturated aqueous sodium bicarbonate and saturated brine, and then dried over anhydrous sodium sulfate. The solvent was removed to produce an oil that was purified by silica gel chromatography, eluting with chloroform/methanol (gradient 98/2 to 95/5), to give the compound 30.7 as a white foam (44 mg). MS m/z (M+H)+515.18

1H NMR (300MHz, CDC13) δ 0.90 (d, 3H, J=7.0 Hz), 1.26-1.47 (m,9H), 1.52-1.60 (m, 5H, 1H, D20 exchangeable), 1.71-1.99 (m, 4H), 2.31-2.45 (m, 2H), 2.52-2.65 (m,2H), 2.70-2.81 (m, 1H), 2.90-3.13 (m, 1H), 3.60-3.64 (m, 0.5H, D20 exchangeable), 3.99-4.32 (m, 5.5H, 0.5H, D20 exchangeable), 4.38-4.56 (m, 1H), 4.60-4.77 (m, 1H), 5.47-5.55 (m, 1H), 5.56(bs, 1H), 5.85-5.93 (m, 1H), 5.96-6.01 (m, 1H).

Synthesis of Compound 30.8

To a solution of lactone 25.7 (41 mg, 79.7 μmol) in dioxane (1 ml) and deionized water (0.5 ml), 0.1N NaOH (0.77 ml, 77 μmol) was added. After 30 minutes at room temperature, the sample was lyophilized overnight, giving 69 mg of a white powder that was shown by HPLC to be a 63/34 mixture of 30.8/30.7.

MS m/z (M+H)+515 (30.7), 533 (open lactone), 555 (30.8)

31 P NMR (121.7 MHz, CDC13/external H3PO4): δ 26.3-28.7 (m)

HPLC (Sphereclone 5μ, H20: MeCN, 20 min liner gradient from 10-90%

MeCN, 1.0mL/min)—30.8 ret. time 5.17,63%; 30.7 ret. time 11.96,33.7%.

Example 31

Preparation of Representative Compounds of the Invention

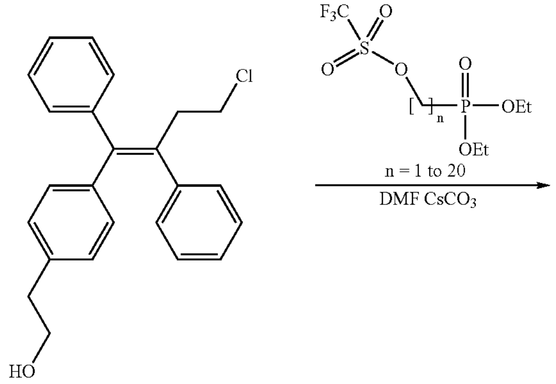

Ospemifene 31.1

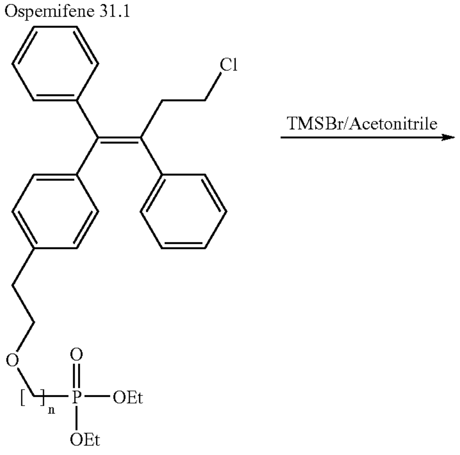

n = 1 to 20

31.2

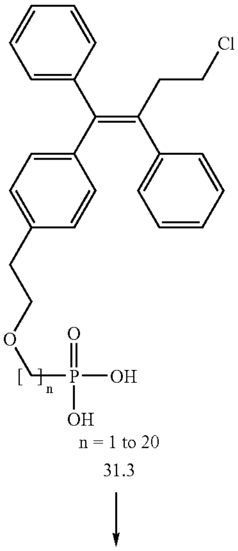

n = 1 to 20

31.3

-continued $R_1$ = O—aryl, O—heteroaryl, alpha or beta amino acid ester $R_2$ = lactate ester or alpha or beta amino acid ester

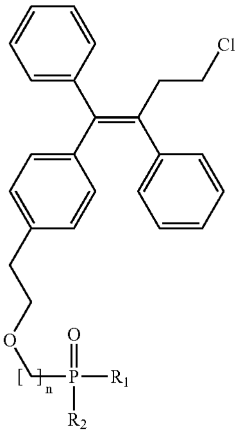

n = 1 to 20

31.4

The synthesis of Ospemifene, 31.1 is described in WO01/36360. Compound 31.1 is treated with a dialkylphosphonoalkyltrifluromethylsulphonate in a solvent such as pyridine or a non basic solvent such as dichloromethane containing a base such as triethylamine to furnish the ether of 31.2. The alkyl groups are removed from the phosphonate moiety with trimethylsilylbromide in a solvent such as DMF or acetonitrile to furnish compound 31.3, which then can be converted to the desired prodrug 31.4 using the methods of phosphonate ester and amidate formation described below.

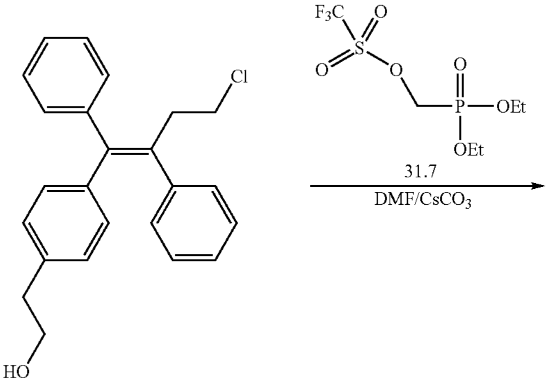

Ospemifene 31.1

-continued

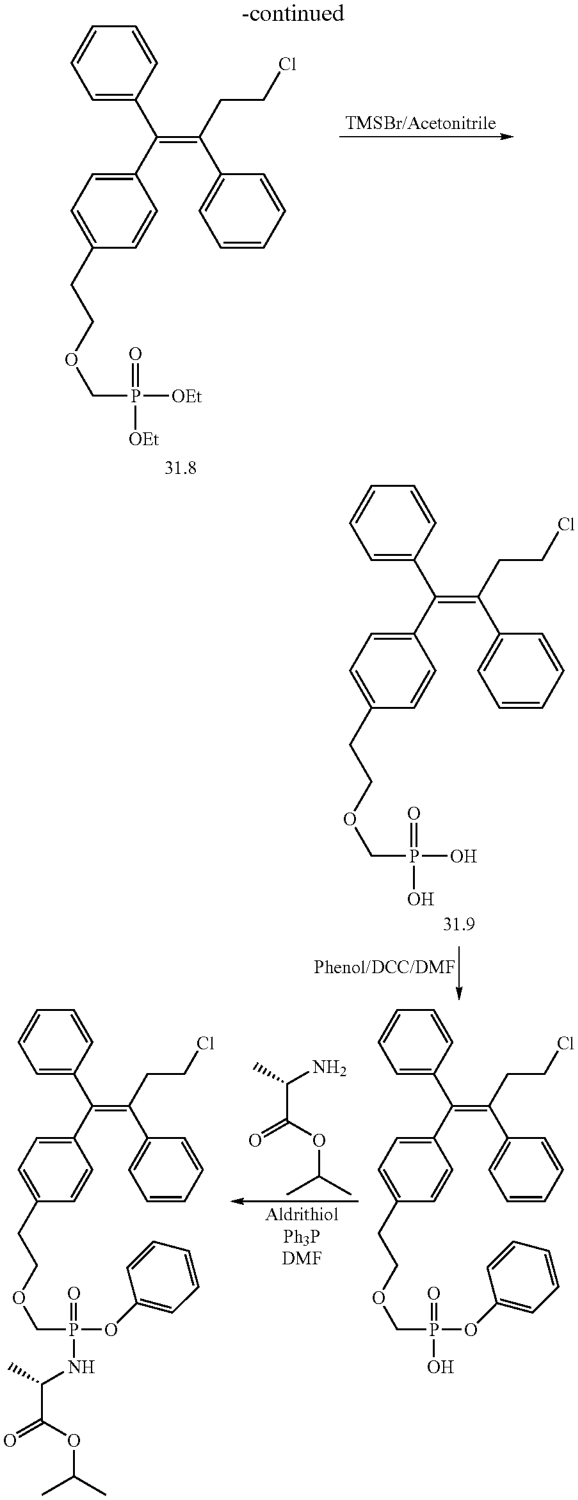

31.8

31.9

31.11 31.10

This example describes the synthesis of a compound 3 1.1 1, a particular member of the general class of compounds described by the structure 31.4. Compound 31.1 is treated with diethylphosphonomethyltrifluorosulphonate, 31.7, in pyridine to yield the ether 31.8. Compound 31.8 is treated with trimethylsilylbromide in acetonitrile to yield the free phophonic acid 31.9. Compound 31.9 is then treated with dicyclohexylcarbodiimide and phenol in DMF to yield the monophenol ester 31.10, which is then condensed with the isopropylester of alanine using aldrithiol and triphenylphosphine in DMF to yield the desired prodrug 31.11

Example 32

Preparation of Representative Compounds of the Invention

AGI-1067

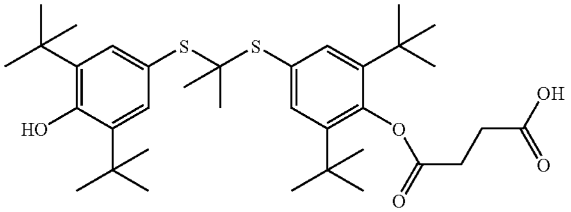

32.2

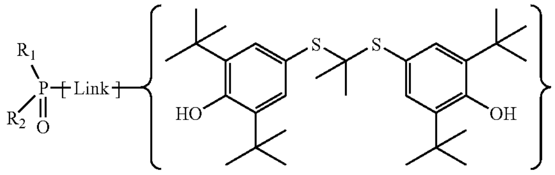

$R_1$ = O—aryl, O—heteroaryl, alpha or beta amino acid ester
$R_2$ = lactate ester or alpha or beta amino acid ester

[Link] = uninterupted chain of atoms excluding hydrogen optionaly including cycles connecting a substitutable position on Atorvastatin with the described phosphorous atom 32.3

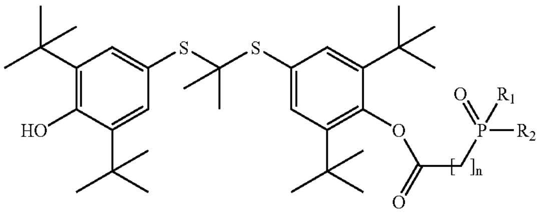

n = 1 to 20

32.4

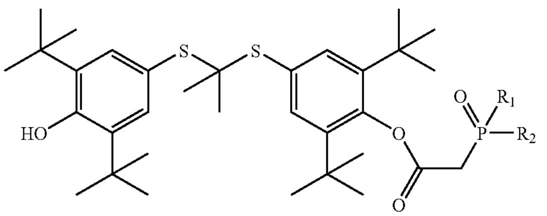

The synthesis of compound 32.5 is described in U.S. Pat. No. 3,576,883. Compound 32.5 is treated with one equivalent of an acyl chloride of a dialkylphosphonoalkylcarboxylic acid in a solvent such as pyridine or a non basic solvent such as dichloromethane containing a base such as triethylamine to furnish the monoester of 32.5, compound 32.6. The alkyl groups are removed from the phosphonate moiety with trimethylsilylbromide in a solvent such as DMF or acetonitrile to furnish compound 32.7, which then can be converted to the desired prodrug 32.3 using the methods of phosphonate ester and amidate formation described below.

This example describes the synthesis of a compound 32.14, a particular member of the general class of compounds described by the structure 32.3. Compound 32.5 is treated with diethylphosphonomethylchloroformate, 32.10, in pyridine to yield the monoester 32.11. Compound 32.11 is treated with trimethylsilylbromide in acetonitrile to yield the free phophonic acid 32.12.

Compound 32.12 is then treated with dicyclohexylcarbodiimide and phenol in DMF to yield the monophenol ester 32.13, which is then condensed with the isopropylester of alanine using aldrithiol and triphenylphosphine in DMF to yield the desired prodrug 32.14.

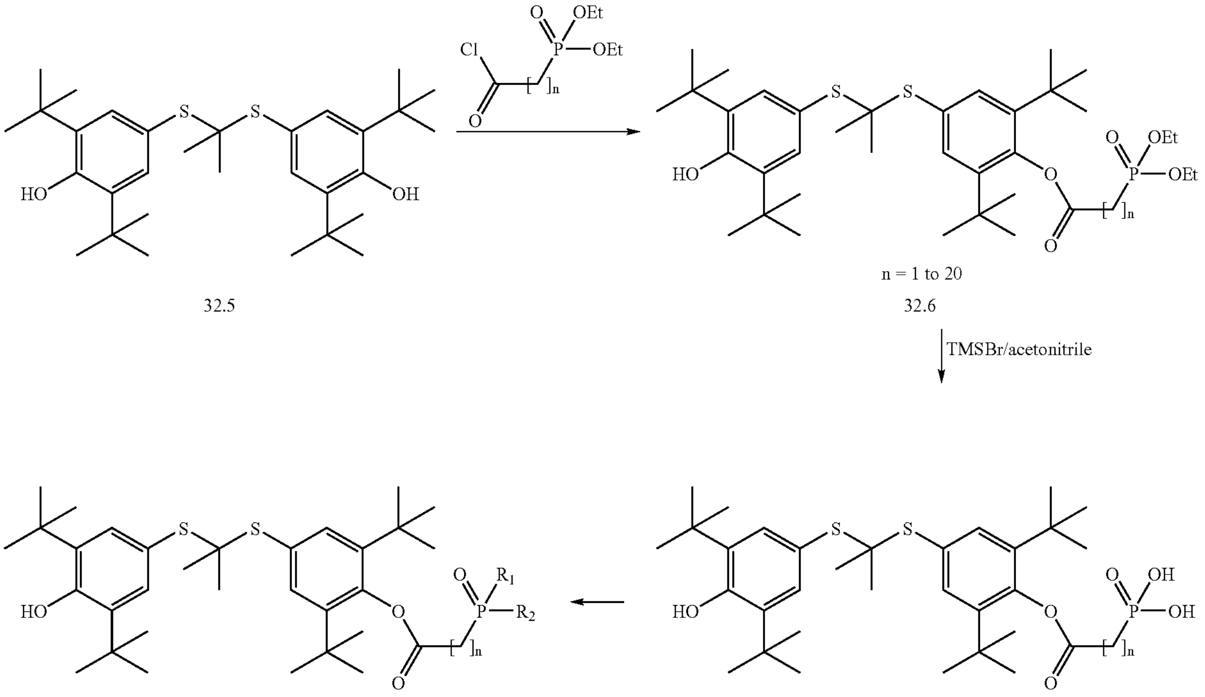

32.5 n = 1 to 20

32.6 n = 1 to 20

32.3 n = 1 to 20

32.7

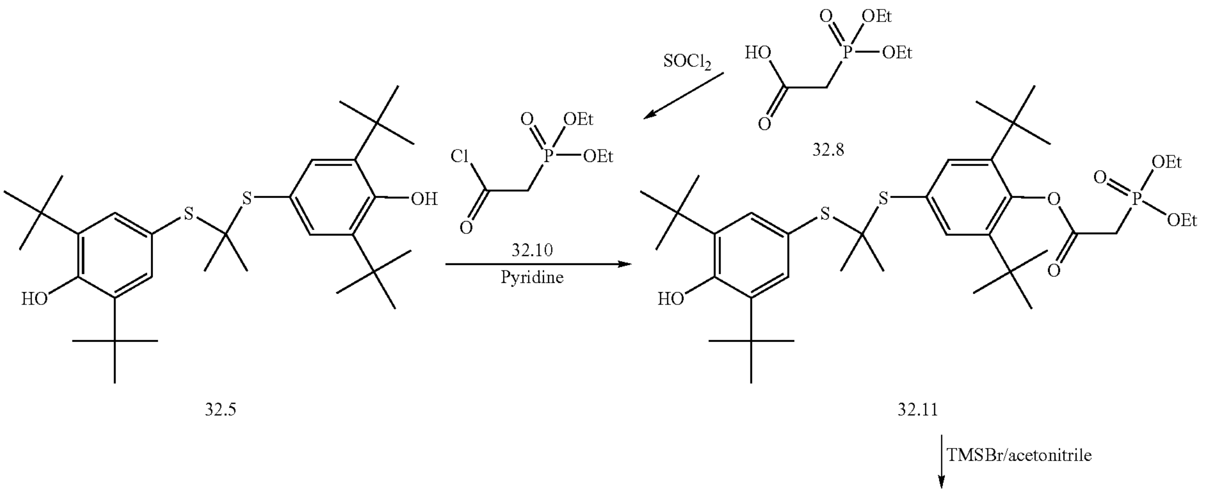

32.8

32.5

32.11

-continued

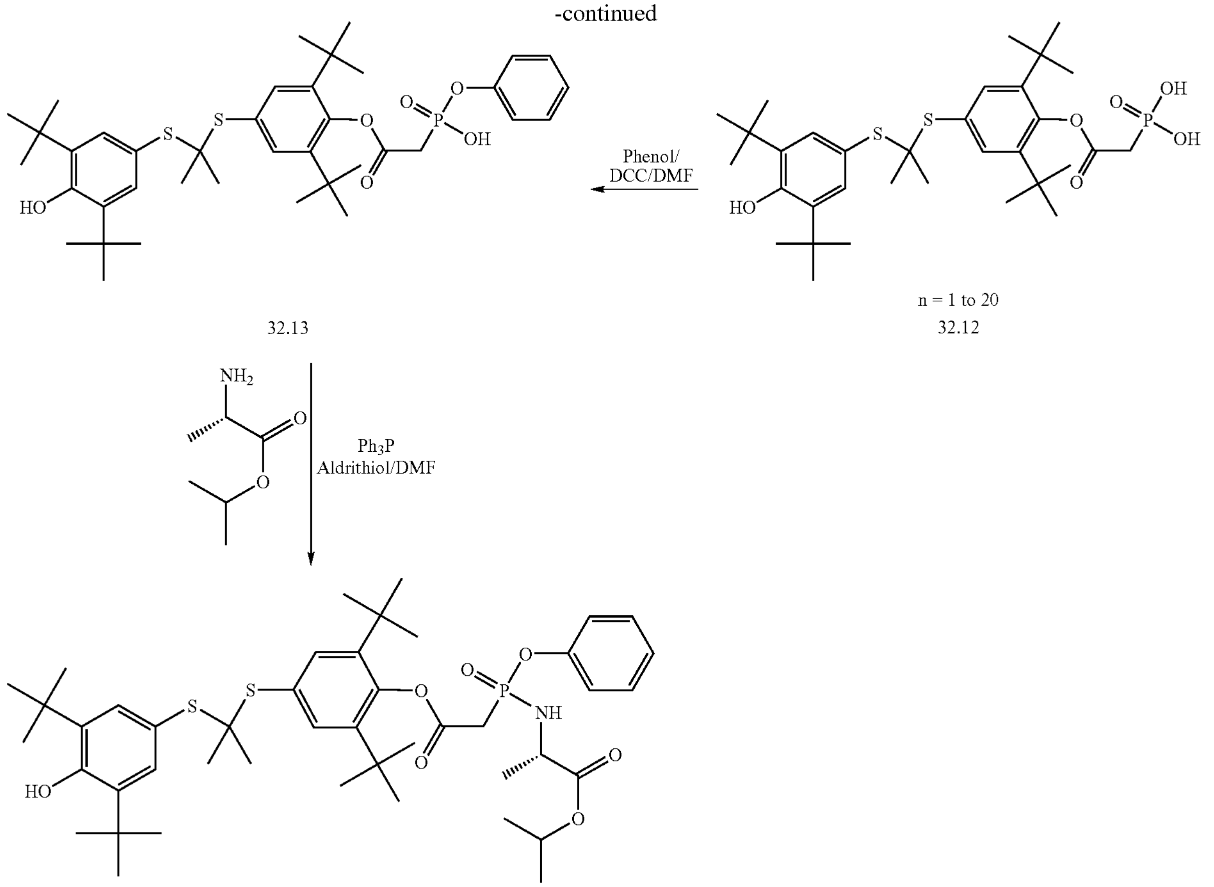

32.13 n = 1 to 20
32.12

32.14

The phosphonate esters of type 32.4 are synthesized from the sulfonylurea derivatives by alkylation and converted to the final conjugates. Sulfonylurea derivatives are either commercially available or obtained by the known procedure, for example, as described in U.S. Pat. No. 3,454,635, U.S. Pat. No. 3,669,966, and U.S. Pat. No. 4,379,785.

The attachment of the phosphonate linkage to the nitrogen of sulfamido group is shown to give compounds of the invention. Sulfonylurea derivative 32.9 is dissolved in a suitable aprotic solvent, for example, DMF, with the phosphonate reagent ($A^0$), bearing a leaving group, for example, bromine, mesyl, tosyl, or trifluoromethanesulfonyl, in the presence of a suitable organic or inorganic base. For example, a solution of 32.1 in DMF is treated with sodium hydride and one equivalent of (trifluoromethanesulfonyloxy)methylphosphonic acid diethyl ester 32.11 to give the analog 32.12 in which the linkage is a methylene group. Using the above procedure but employing different sulfonylurea derivatives 32.9 in place of 32.1 and phosphonate reagents 32.10 in place of 32.11 the corresponding products 32.4 bearing different substituents and linking groups can be obtained.

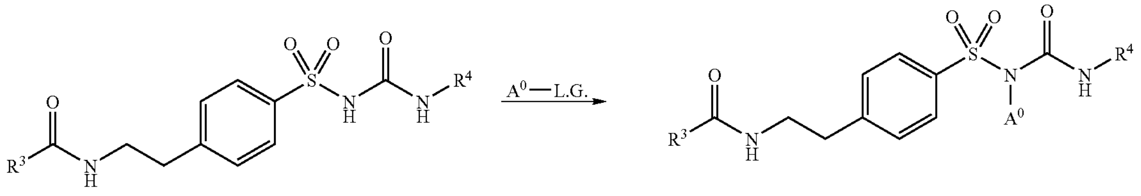

32.9 L.G. = Leaving Group 32.4

-continued

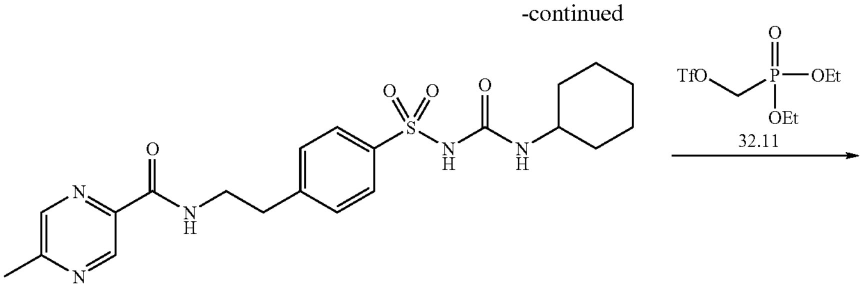

32.1

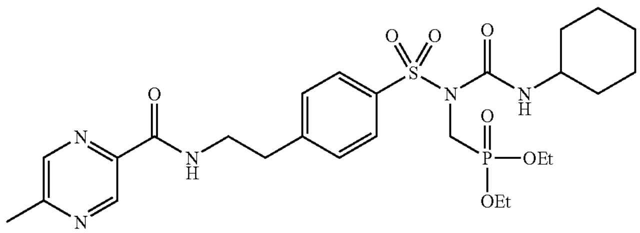

32.12

Some phosphonates of type 32.5, where Z is oxygen or sulfur, can be prepared. The sunfonamide 32.13 is reacted with isocyanate 32.14 bearing a suitable phosphorus containing substituent, ($A^0$). The isocyanate reagent 32.14 is obtained by Curtius rearrangement reaction from the corresponding carboxylic acid, as explained in *Organic Reactions*, 1946, 3, 337-449. Attachment of the phosphorus containing moiety to the Z group, such as hydroxyl or thiol group, is accomplished byalkylation procedure in a suitable aprotic solvent, for example, DMF, with the phosphonate reagent 32.10, bearing a leaving group, for example, bromine, mesyl, tosyl, or trifluoromethanesulfonyl, in the presence of a suitable organic or inorganic base.

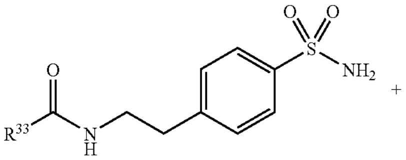

32.13

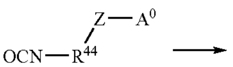

32.14

-continued

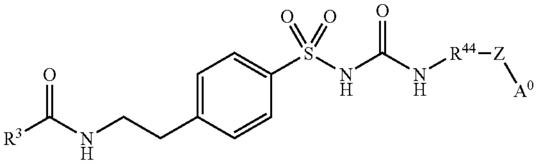

32.5: Z = O, S

For example, a solution of 32.15 in DMF is treated with 2 equivalent of sodium hydride and one equivalent of (trifluoromethanesulfonyloxy)methylphosphonic acid diethyl ester 32.11 to provide 32.16 in which the linkage is a methylene group. The carboxylic acid of 32.16 is treated with oxalyl chloride, followed by the reaction with sodium azide and pyrolysis to give the isocyanate 32.17. The sulfonylurea derivative 32.19 is obtained by the reaction of isocyanate 32.17 with the sulfonamide 32.18, which is obtained by the procedure of U.S. Patent 3,669,966. Using the above procedure but employing different sulfonamide 32.13, $R^4$ bearing hydroxy or thiol group, and phosphonate reagents 32.10 the corresponding products 32.5, where Z is oxygen or sulfur, bearing different $R^3$, $R^4$ and linking groups can be obtained.

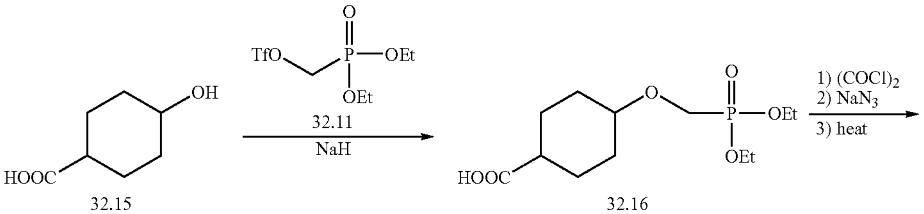

32.15

32.16

-continued

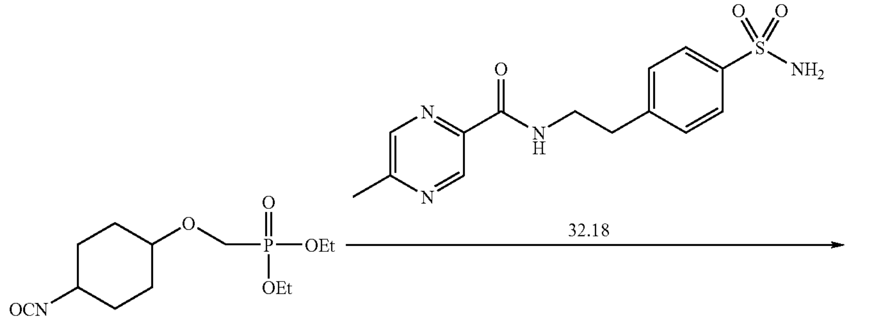

32.17

32.18

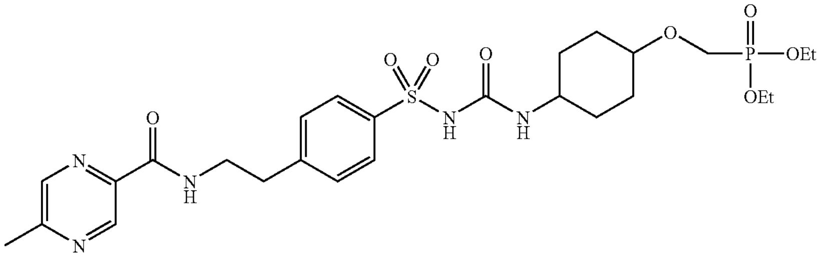

32.19

The preparation of sulfonylurea derivatives bearing phosphorus containing moiety of type 32.5, where Z is carbamate linker, is shown. These types of compounds are obtained by the coupling of sunfonamide 32.13 using isocyanate 32.20 bearing a suitably protected alcohol, such as benzyl group. The isocyanate reagent 32.20 is obtained by aforementioned rearrangements from the corresponding carboxylic acid. After the protective group of 32.21 is removed by a suitable method, the alcohol group is treated with suitable chloroformate ester, for example phenyl chloroformate or p-nitrophenyl chloroformate, or carbonate, such as bis(p-nitrophenyl) carbonate to generate an active carbonate. The resulting active carbonate is reacted with phosphonate reagents bearing amino group to produce the phosphonates of type 32.5, where Z is carbamate linker.

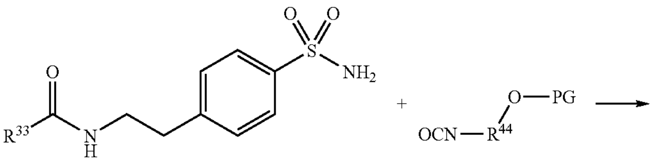

32.13

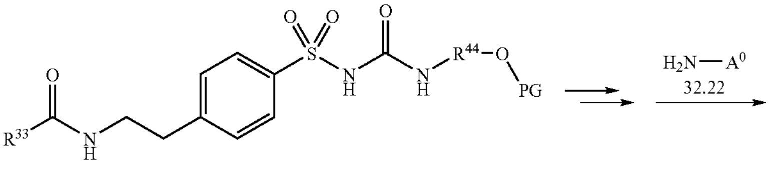

32.12

32.22

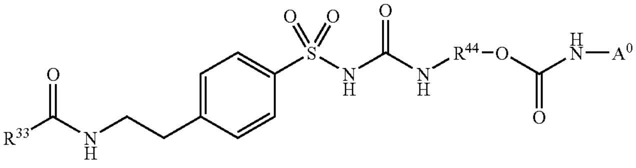

32.5: Z = OCONH

For example, the carboxylic acid of 32.23 is converted to the isocyanate 32.24 by Curtius rearrangement of the acyl azide, which is produced from the carboxylic acid 32.23 through acyl chloride and acyl azide. The isocyanate 32.24 is treated with the anion of sulfonamide 32.18, which is generated with sodium hydroxide as described. The benzyl protecting group of 32.25 is removed by catalytic hydrogenation using 10% Palladium on charcoal as a catalyst, and the resulting alcohol is treated with phenyl chloroformate to provide phenyl carbonate, which is reacted with 2-aminoethylphosphonate diethyl ester 32.26, to obtain sulfonylurea derivative 32.27. Using the above procedure but employing different sulfonamide 32.13, isocyanate 32.20 and phosphonate reagents 32.22 the corresponding products 32.5, where Z is carbamate, bearing different $R^3$, $R^4$ and linking groups can be obtained.

resulting secondary amine 32.5 ($R^{99}$=H) may be converted to the corresponding tertiary amine 32.5 ($R^{99}$=alkyl) by reductive amination.

For example, a solution of 32.31 in THF is treated with oxalyl chloride followed by sodium azide and the resulting acyl azide is converted to the isocyanate 32.32 by heating. A solution of the sulfonamide 32.18, which is obtained as described in U.S. Pat. No. 3,669,966, in DMF is treated with one equivalent of sodium hydride followed by the isocyanate 32.32 to generate 32.33. The Boc protecting group is removed by treatment with trifluoroacetic acid and the resulting amine is treated with one equivalent of 2-oxoethylphosphonate

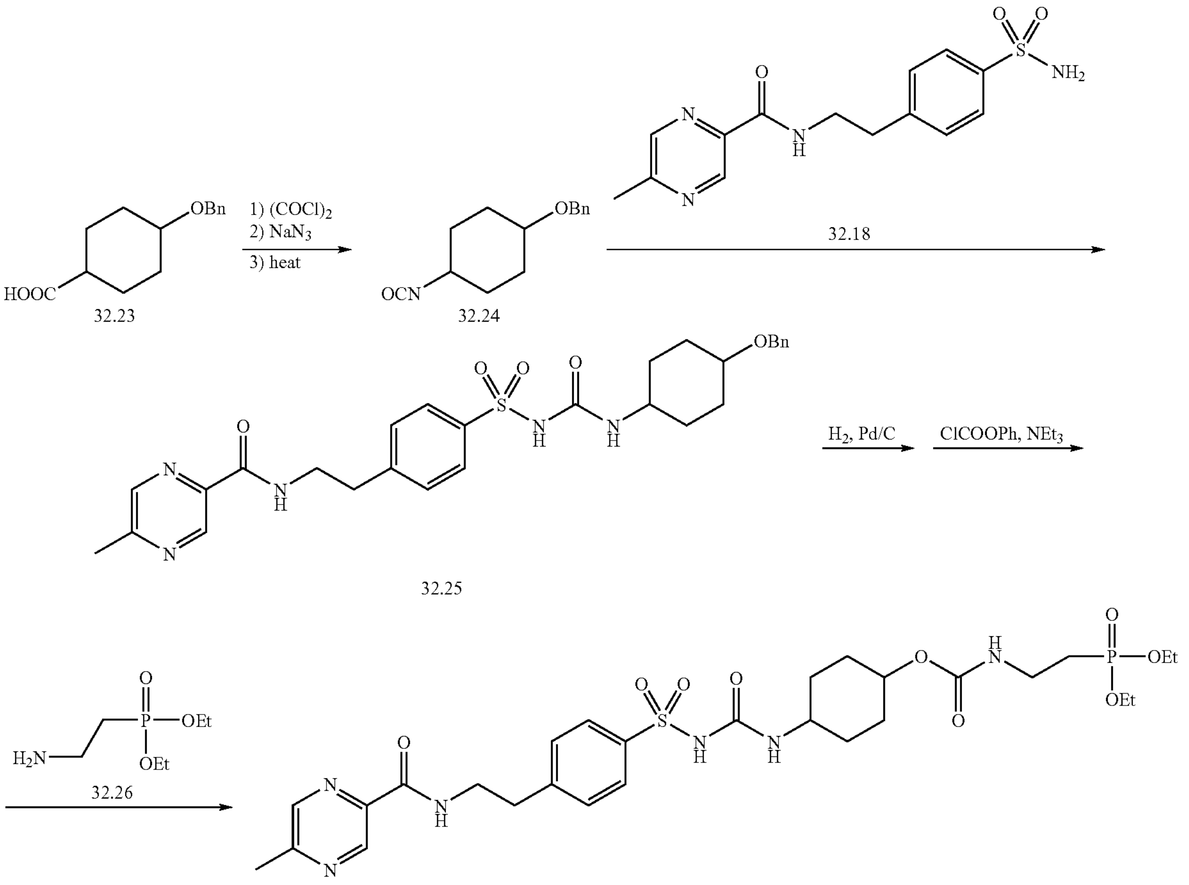

32.23 32.24 32.25 32.27

Phosphonates of type 32.5, where Z is nitrogen, are prepared. These types of compounds are obtained by the coupling of sunfonamide 32.13 using isocyanate 32.28 bearing $R^{44}$ with a suitably protected amine substituent. The phosphonate group bearing moiety is attached by reductive amination using a suitable phosphonate reagent 32.30 bearing aldehyde group with reducing agent, such as sodium cyanoborohydride, in suitable solvents, such as dichloroethane or methanol, in the presence of an acid, such as acetic acid. The diethyl ester 32.34 with sodium cyanoborohydride and acetic acid in dichloroethane to obtain 32.35 in which the linkage is an ethylene group and $R^{99}$ is hydrogen as shown in Example 2.3. The resulting secondary amine 32.35 ($R^{99}$=H) is converted to the corresponding tertiary amine 32.35 ($R^{99}$=Me) by reductive amination with formaldehyde using sodium cyanoborohydride and acetic acid. Using the above procedure but employing different sulfonylamide 32.13, isocyanate 32.28, and phosphonate reagents 32.30 the corresponding products 32.5, where Z is NH or $NR^{99}$, bearing different $R^{33}$, $R^{44}$, $R^{99}$, and linking groups can be obtained.

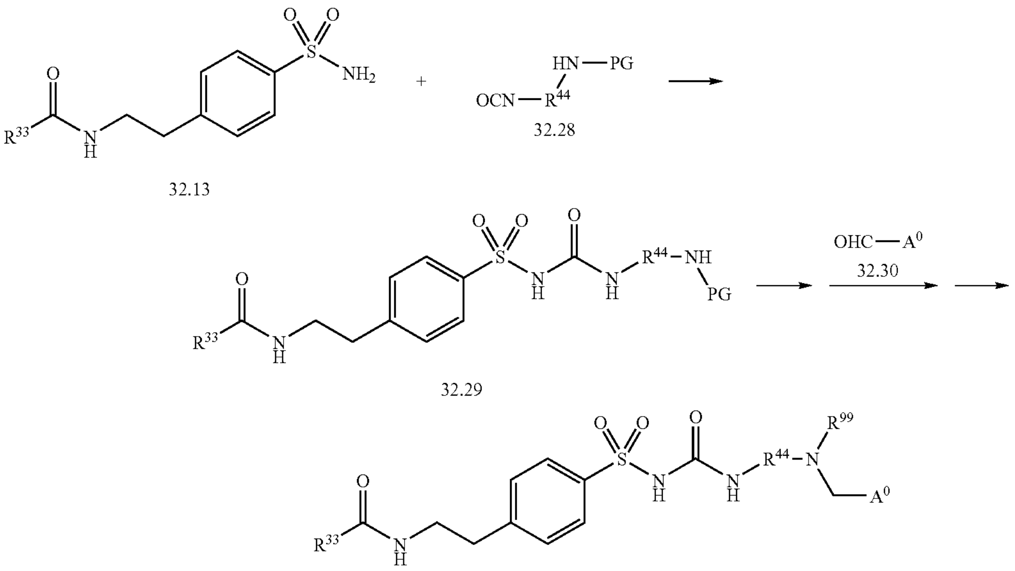

32.13

32.28

32.29

32.5: Z = NH, $NR^7$

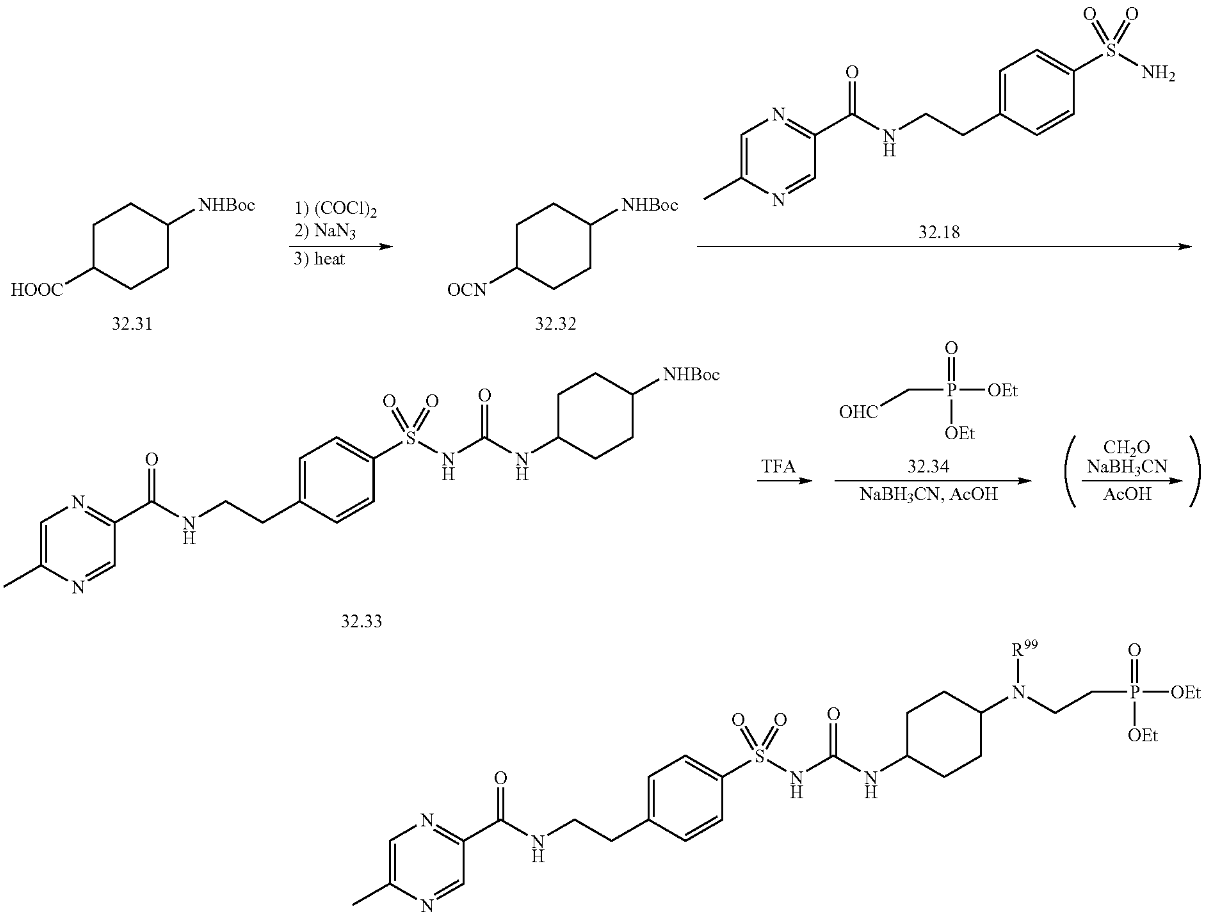

32.31

32.32

32.33

32.35 ($R^{99}$ = H or Me)

Phosphonate analogs of type 32.6 are synthesized. These types of compounds are obtained by the coupling, as described in U.S. Pat. No. 3,669,966, of substituted pyrazine carboxylic acid 32.36 bearing amino, hydroxyl, or other substituents, which can convert to appropriate functional group for the attachment of phosphonate moiety, for example carboxylic ester, with sulfonylurea moiety 32.37. Substituted pyrazine carboxylic acids are commercially available or may be prepared by the method described in Ber. 1907, 40, 4850 or in Ber. 1966, 99, 364. Phosphonate moiety is introduced to a substituent on the pyrazine ring, if necessary after conversion of the substituent to a suitable functional group bearing substituent, either by alkylation, reductive amination, or reaction with active carbonate intermediate as described previously.

For example, pyrazine-2,5-dicarboxylic acid mono ester 32.39, which is generated by partial hydrolysis, is treated with sulfonylurea 32.40 in the presence of EDC and HOBt to form the amide 32.41. The carboxylic ester of 32.41 is then reduced with $LiBH_4$ in methanol and the resulting alcohol was treated with phenyl chloroformate to generate the active carbonate. Treatment of the active carbonate with 2-aminoethyl phosphonate diethyl ester 32.26 generates the phosphonate analog 32.42 in which the linker is carbamate group. The ester may be treated with DIBAL to generate aldehyde functional group and subsequent reductive amination produces analog 32.43. Using the above procedures but employing different pyrazine carboxylic acid 32.36, sulfonulurea 32.37, and phosphonate reagents, the corresponding products 32.6 bearing different linking groups can be obtained.

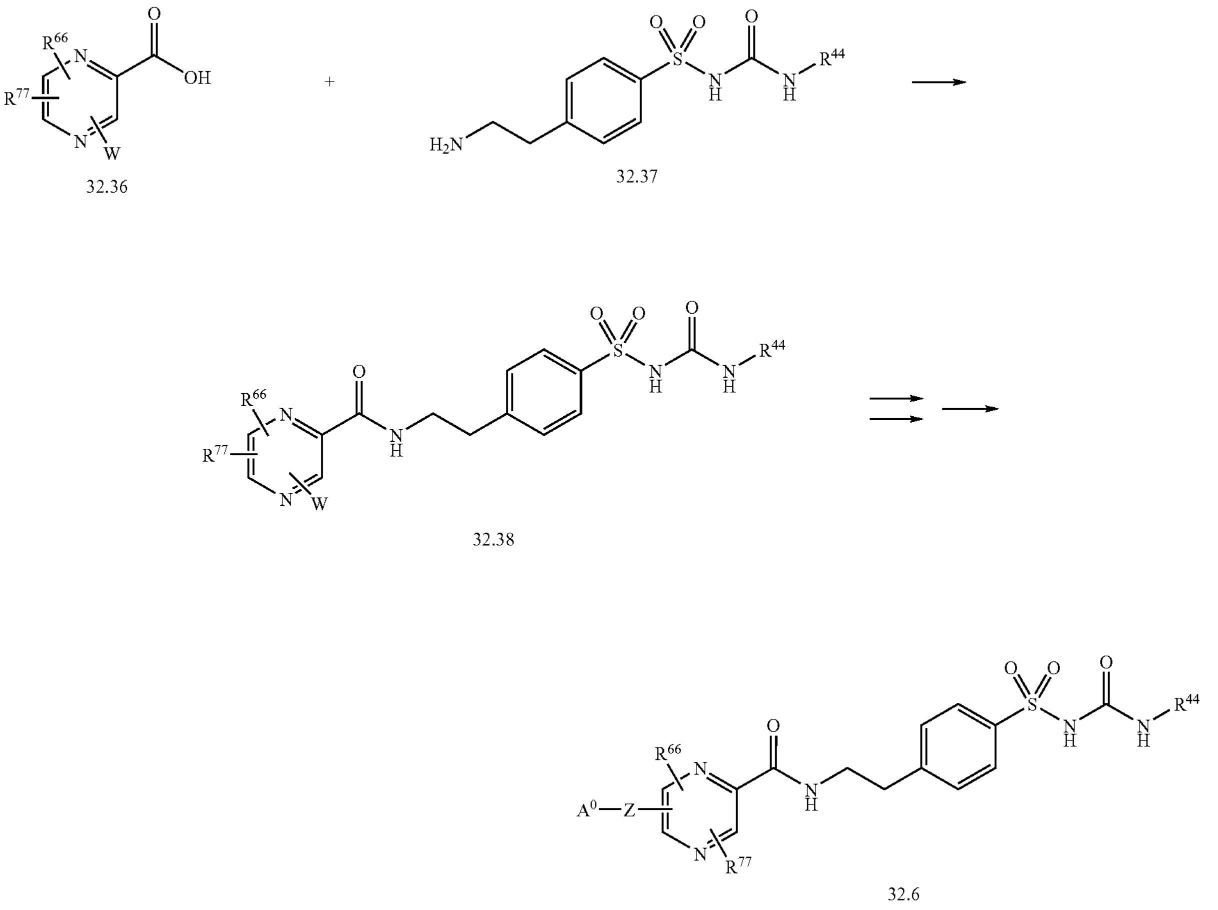

32.36 32.37

32.38

32.6

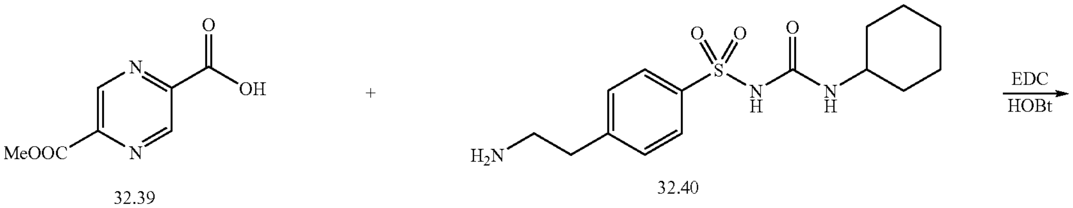

32.39 32.40

-continued

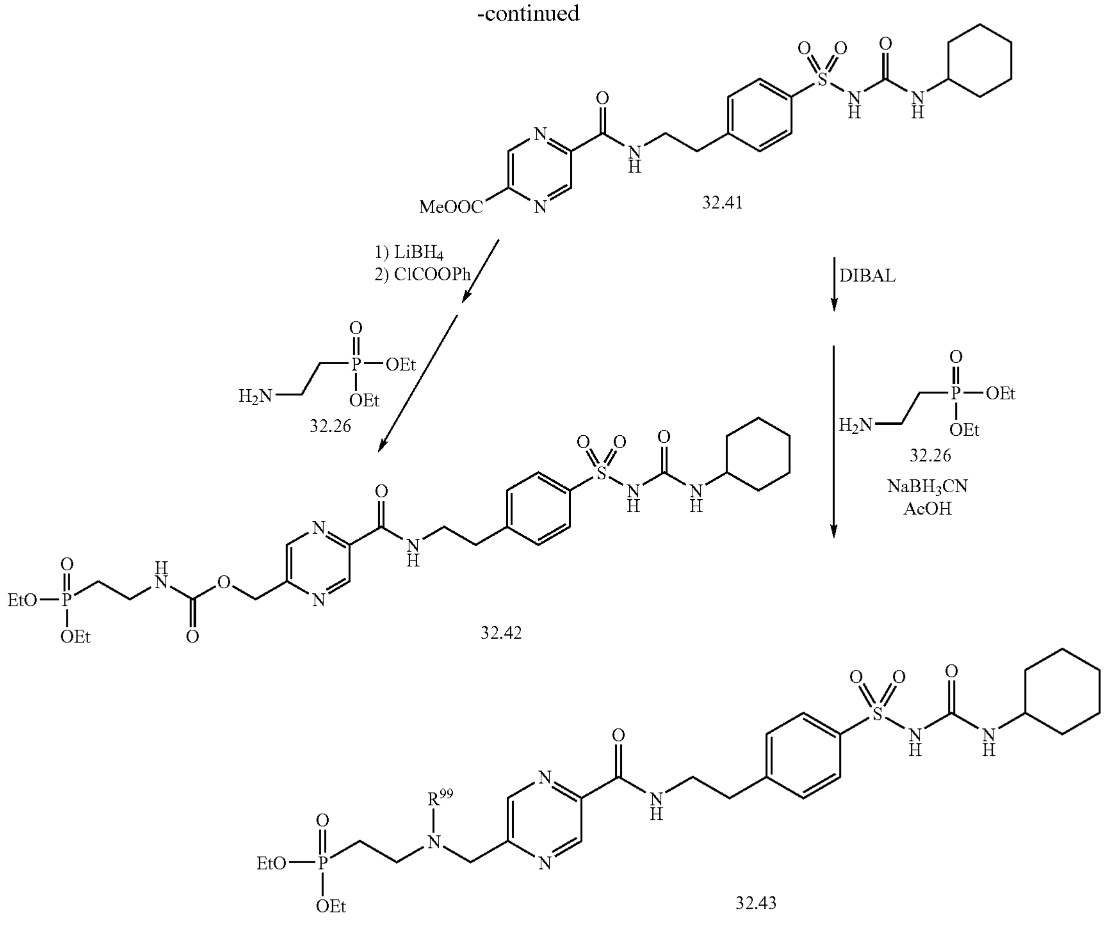

32.41

32.26

32.42

32.26

32.43

Phosphonate analogs of type 32.7 are prepared. This type of compound is obtained by the coupling, as described in U.S. Pat. No. 3,669,966, of substituted benzoic acid 32.44 bearing amino, hydroxyl, or other substituents, which can convert to appropriate functional group for the attachment of phosphonate moiety with sulfonylurea moiety 32.37. Phosphonate moiety is introduced to a substituent on the aromatic ring, if necessary after conversion of the substituent to a suitable functional group bearing substituent, either by alkylation, reductive amination, or reaction with active carbonate intermediate as described previously. Alternatively, the phosphorus containing moiety is attached to a substituent of benzoic acid analogs 32.44 and the resulting 32.45 is coupled with sulfonylurea moiety.

For example, a solution of 3-chloro-2-hydroxybenzoic acid 32.39 in DMF is treated with cesium carbonate and one equivalent of (trifluoromethanesulfonyloxy)methylphosphonic acid diethyl ester to give the analog 32.12 in which the linkage is a methylene group as shown in Example 3.2. Using the above procedure but employing benzoic acid 32.44, sulfonulurea 32.37, and phosphonate reagents 32.10, 32.22, or 32.30, the corresponding products 32.6 bearing different $R^{44}$, $R^{66}$, $R^{77}$, $R^{88}$, and linking groups can be obtained.

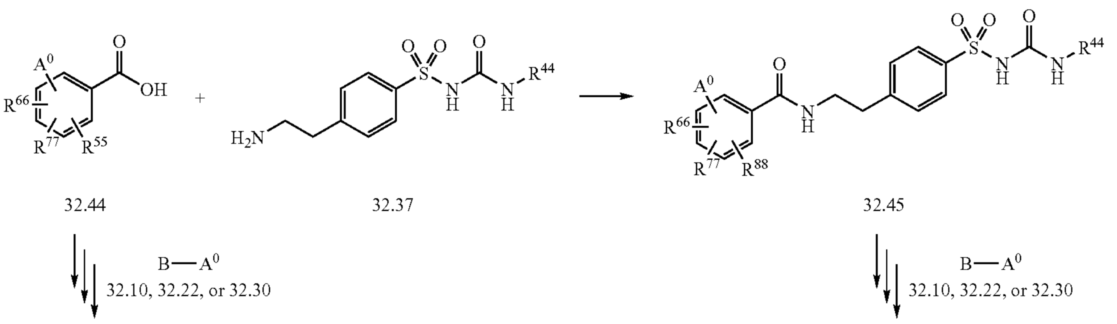

32.44

32.37

32.45

-continued

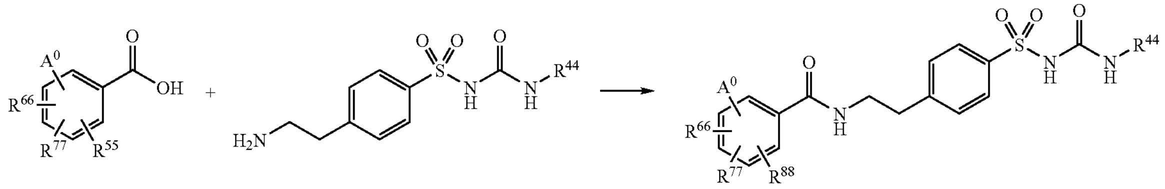

32.46 32.37 32.7

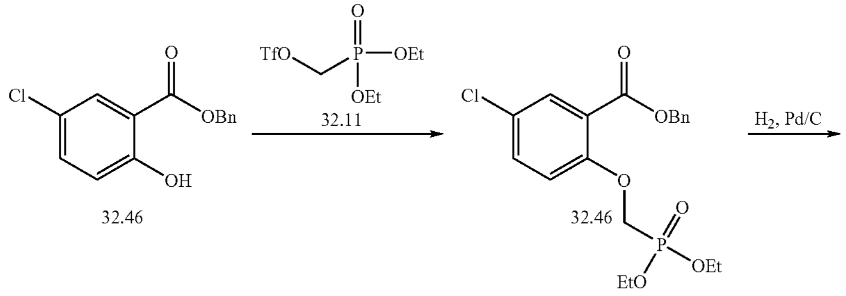

32.46 32.47

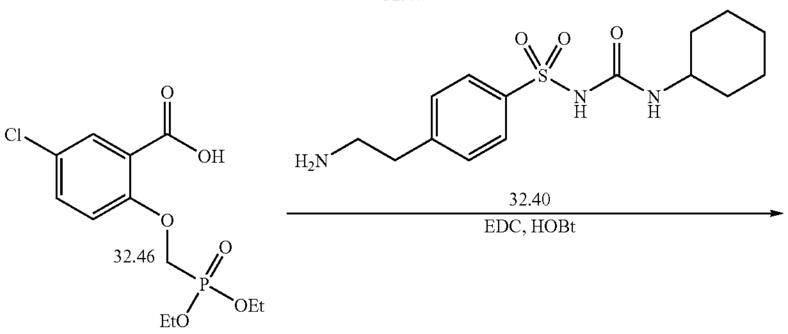

32.48

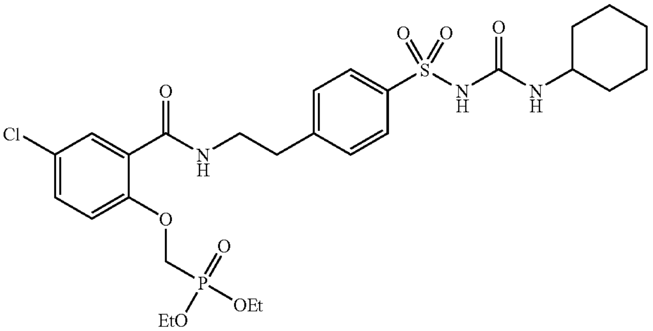

32.49

The synthesis of phosphonate analogs of type 32.8 is shown. This type of compounds are obtained by the coupling, as described in U.S. Pat. No. 4,379,785, of substituted 32.50 bearing amino, hydroxyl, or other substituents, which can convert to appropriate functional group for the attachment of phosphorus containing moiety with isocyanate 32.51 bearing sulfonylurea moiety. Alternatively, the phosphorus containing moiety is attached to a substituent of 32.50 and the resulting 32.53 is coupled with the isocyanate bearing sulfonylurea moiety 32.51. Phosphonate moiety is introduced to a substituent on 32.50 or 32.53, if necessary after conversion of the substituent to a suitable functional group bearing substituent, either by alkylation, reductive amination, or reaction with active carbonate intermediate as described previously.

For example, 32.54, which is available by the procedure in *Tetrahedron Lett*. 2000, 40, 2825, is protected using Boc group and then the silyl protecting group is removed by tetrabutylammonium fluoride, which results 32.55. The phosphorus containing moiety is introduced by alkylation using one equivalent of (trifluoromethanesulfonyloxy)methylphosphonic acid diethyl ester 32.11 with sodium hydride, and the Boc protecting group is removed using trifluoroacetic acid. The reaction of 32.56 with 32.57 in elevated temperature produces 32.58 in which the linkage is a methylene group. Using the above procedure but employing 32.50, 32.51, and phosphonate reagents 32.10, 32.22, or 32.30, the corresponding products 32.6 bearing different heterocycles and linking groups can be obtained.

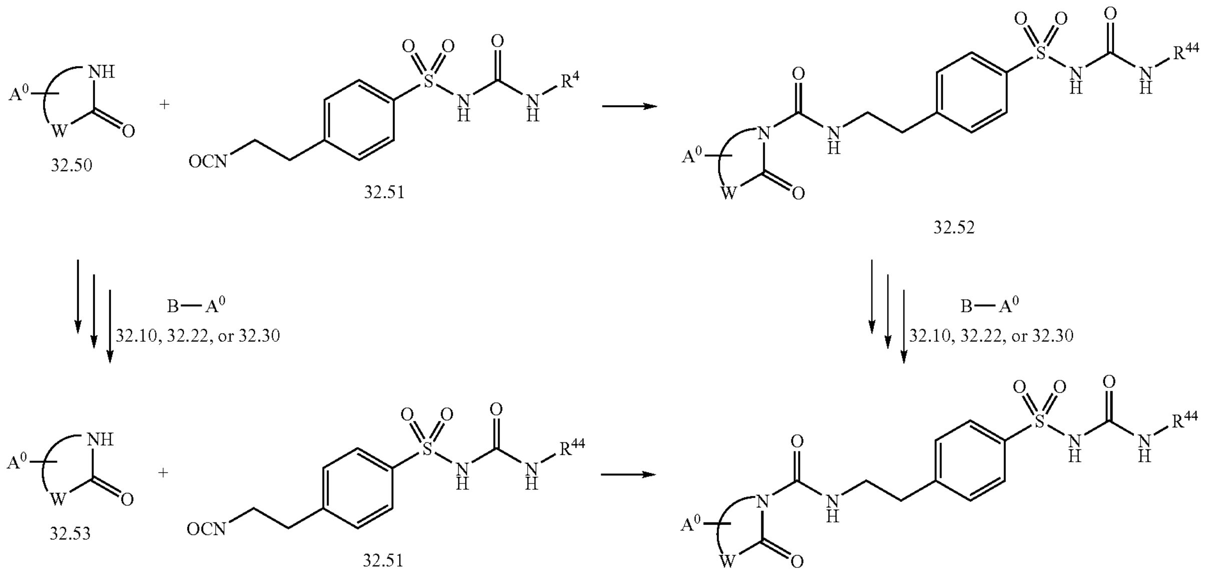

32.50 32.51 32.52 32.53 32.51 32.8

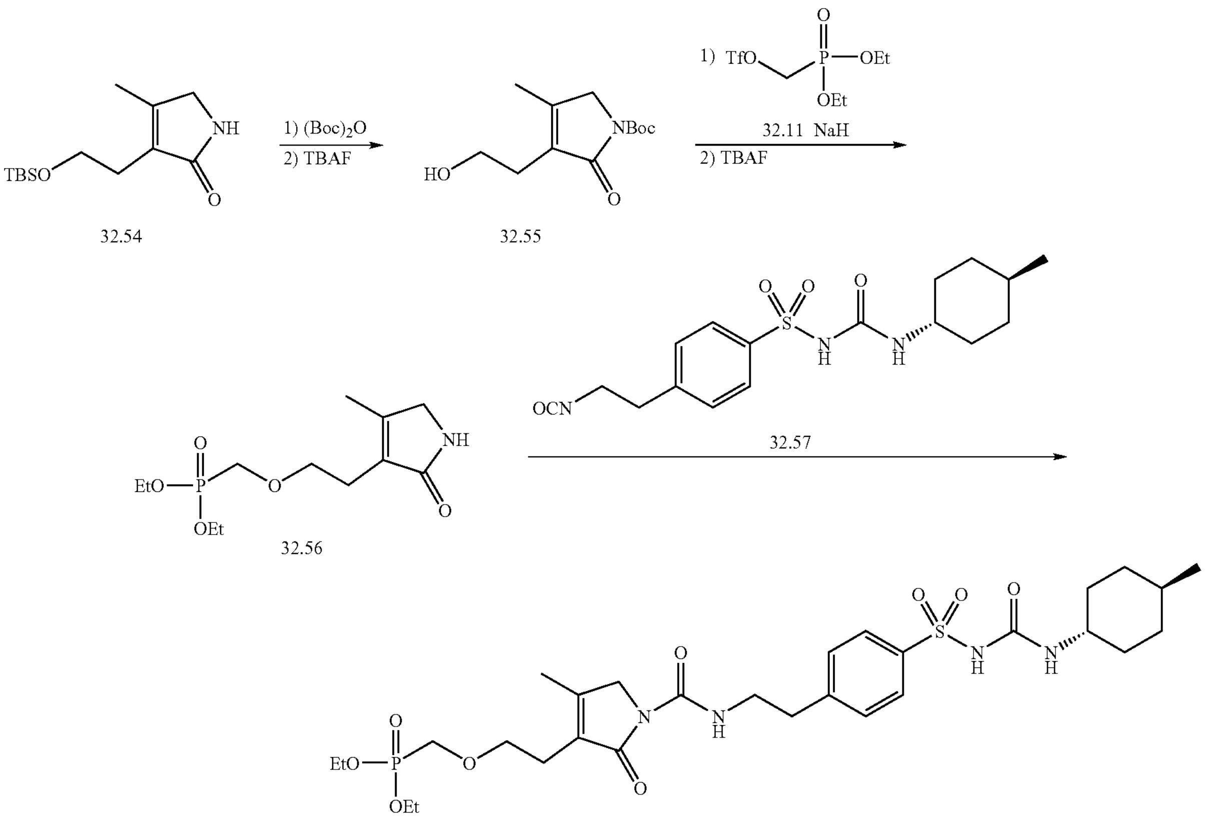

32.54 32.55 32.56 32.57 32.58

Example 33

Preparation of Representative Compounds of the Invention

The phosphonate esters of type 33.4 are synthesized from the sulfonylurea derivatives by alkylation and converted to the final conjugates. Sulfonylurea derivatives are either commercially available or obtained by the known procedure, for example, as described in U.S. Pat. No. 3,454,635, U.S. Pat. No. 3,669,966, and U.S. Pat. No. 4,379,785.

Attachment of the phosphonate linkage to the nitrogen of sulfamido group to gives compounds of formula 33.4. Sulfonylurea derivative 33.9 is dissolved in a suitable aprotic solvent, for example, DMF, with the phosphonate reagent ($A^0$), bearing a leaving group, for example, bromine, mesyl, tosyl, or trifluoromethanesulfonyl, in the presence of a suitable organic or inorganic base. For example, a solution of 33.1 in DMF is treated with sodium hydride and one equivalent of (trifluoromethanesulfonyloxy)methylphosphonic acid diethyl ester 33.11 to give the analog 33.12 in which the linkage is a methylene group. Using the above procedure but employing different sulfonylurea derivatives 33.9 in place of 33.1 and phosphonate reagents 33.10 in place of 33.11 the corresponding products 33.4 bearing different substituents and linking groups can be obtained.

-continued

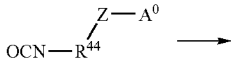

33.14

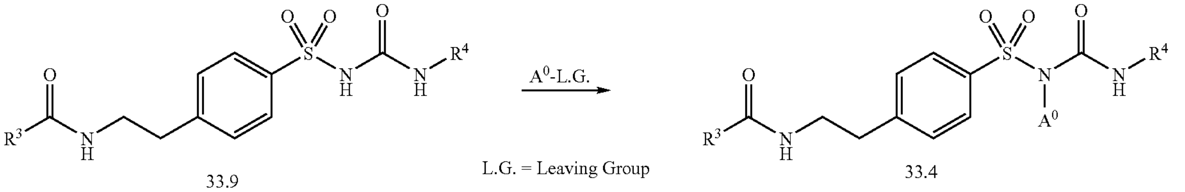

33.9

L.G. = Leaving Group 33.4

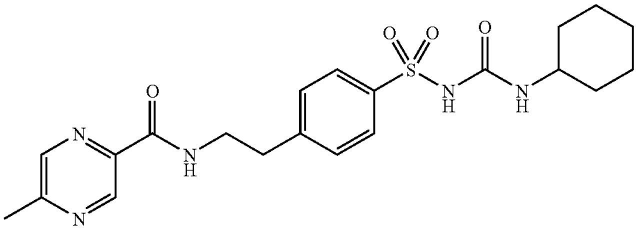

33.1

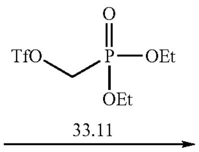

33.11

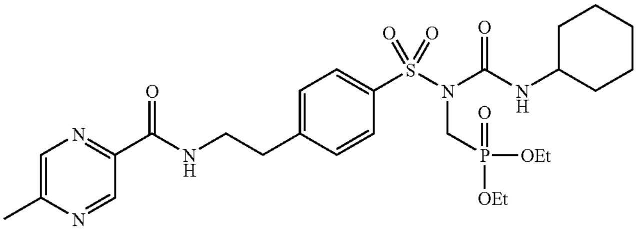

33.12

Some phosphonates of type 33.5, where Z is oxygen or sulfur, can be prepared. The sunfonamide 33.13 is reacted with isocyanate 33.14 bearing a suitable phosphorus containing substituent, ($A^0$). The isocyanate reagent 33.14 is obtained by Curtius rearrangement reaction from the corresponding carboxylic acid, as explained in *Organic Reactions*, 1946, 3, 337-449. Attachment of the phosphorus containing moiety to the Z group, such as hydroxyl or thiol group, is accomplished by alkylation procedure in a suitable aprotic solvent, for example, DMF, with the phosphonate reagent 33.10, bearing a leaving group, for example, bromine, mesyl, tosyl, or trifluoromethanesulfonyl, in the presence of a suitable organic or inorganic base.

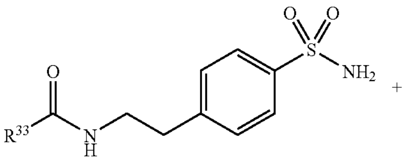

33.13

-continued

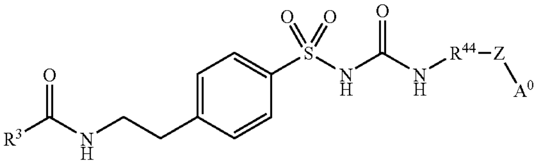

33.5
Z = O, S

For example, a solution of 33.15 in DMF is treated with 2 equivalent of sodium hydride and one equivalent of (trifluoromethanesulfonyloxy)methylphosphonic acid diethyl ester 33.11 to provide 33.16 in which the linkage is a methylene group as shown in Example 2.1. The carboxylic acid of 33.16 is treated with oxalyl chloride, followed by the reaction with sodium azide and pyrolysis to give the isocyanate 33.17. The sulfonylurea derivative 33.19 is obtained by the reaction of isocyanate 33.17 with the sulfonamide 33.18, which is obtained by the procedure of U.S. Pat. No. 3,669,966. Using the above procedure but employing different sulfonamide 33.13, $R^4$ bearing hydroxy or thiol group, and phosphonate reagents 33.10 the corresponding products 5, where Z is oxygen or sulfur, bearing different $R^3$, $R^4$ and linking groups can be obtained.

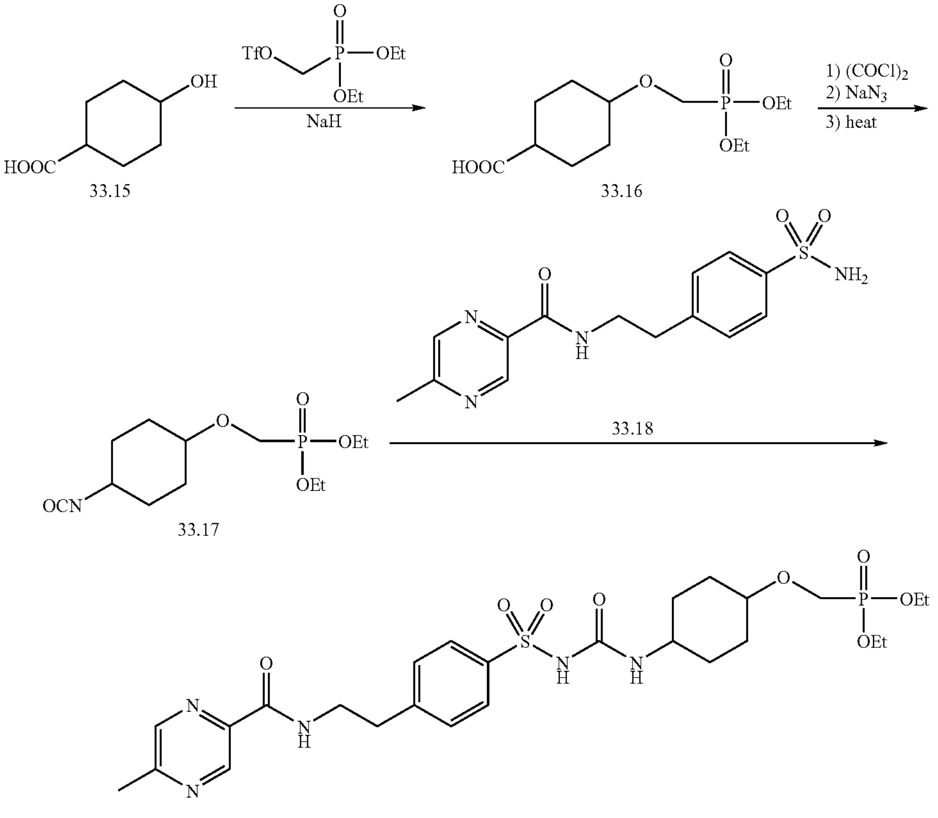

33.15 33.16 33.17 33.19

The preparation of sulfonylurea derivatives bearing phosphorus containing moiety of type 33.5 is shown, where Z is carbamate linker. This type of compounds are obtained by the coupling of sunfonamide 33.13 using isocyanate 33.20 bearing a suitably protected alcohol, such as benzyl group. The isocyanate reagent 33.20 is obtained by aforementioned rearrangements from the corresponding carboxylic acid. After the protective group of 33.21 is removed by a suitable method, the alcohol group is treated with suitable chloroformate ester, for example phenyl chloroformate or p-nitrophenyl chloroformate, or carbonate, such as bis(p-nitrophenyl)carbonate to generate an active carbonate. The resulting active carbonate is reacted with phosphonate reagents bearing amino group to produce the phosphonates of type 33.5, where Z is carbamate linker.

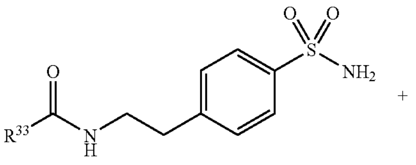

33.13

-continued

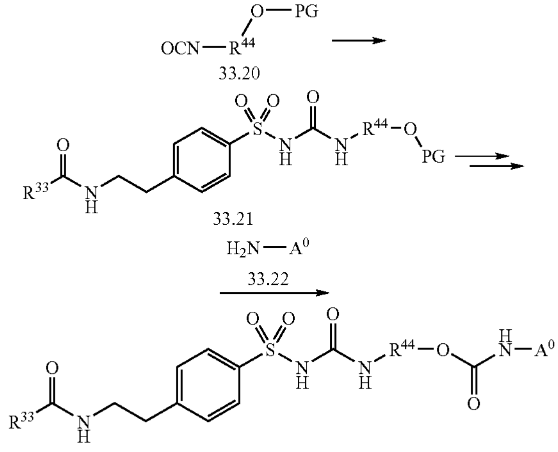

33.20 33.21 33.5: Z = OCONH

For example, the carboxylic acid of 33.23 is converted to the isocyanate 33.24 by Curtius rearrangement of the acyl azide, which is produced from the carboxylic acid 33.23 through acyl chloride and acyl azide. The isocyanate 33.24 is treated with the anion of sulfonamide 33.18, which is generated with sodium hydroxide. The benzyl protecting group of 33.25 is removed by catalytic hydrogenation using 10% Palladium on charcoal as a catalyst, and the resulting alcohol is treated with phenyl chloroformate to provide phenyl carbonate, which is reacted with 2-aminoethylphosphonate diethyl ester 33.26, to obtain sulfonylurea derivative 33.27. Using the above procedure but employing different sulfonamide 33.13, isocyanate 33.20 and phosphonate reagents 33.22 the corresponding products 33.5, where Z is carbamate, bearing different $R^3$, $R^4$ and linking groups can be obtained.

For example, a solution of 33.31 in THF is treated with oxalyl chloride followed by sodium azide and the resulting acyl azide is converted to the isocyanate 33.32 by heating. A solution of the sulfonamide 33.18, which is obtained as described in U.S. Pat. No. 3,669,966, in DMF is treated with one equivalent of sodium hydride followed by the isocyanate 33.32 to generate 33.33. The Boc protecting group is removed by treatment with trifluoroacetic acid and the resulting amine is treated with one equivalent of 2-oxoethylphosphonate

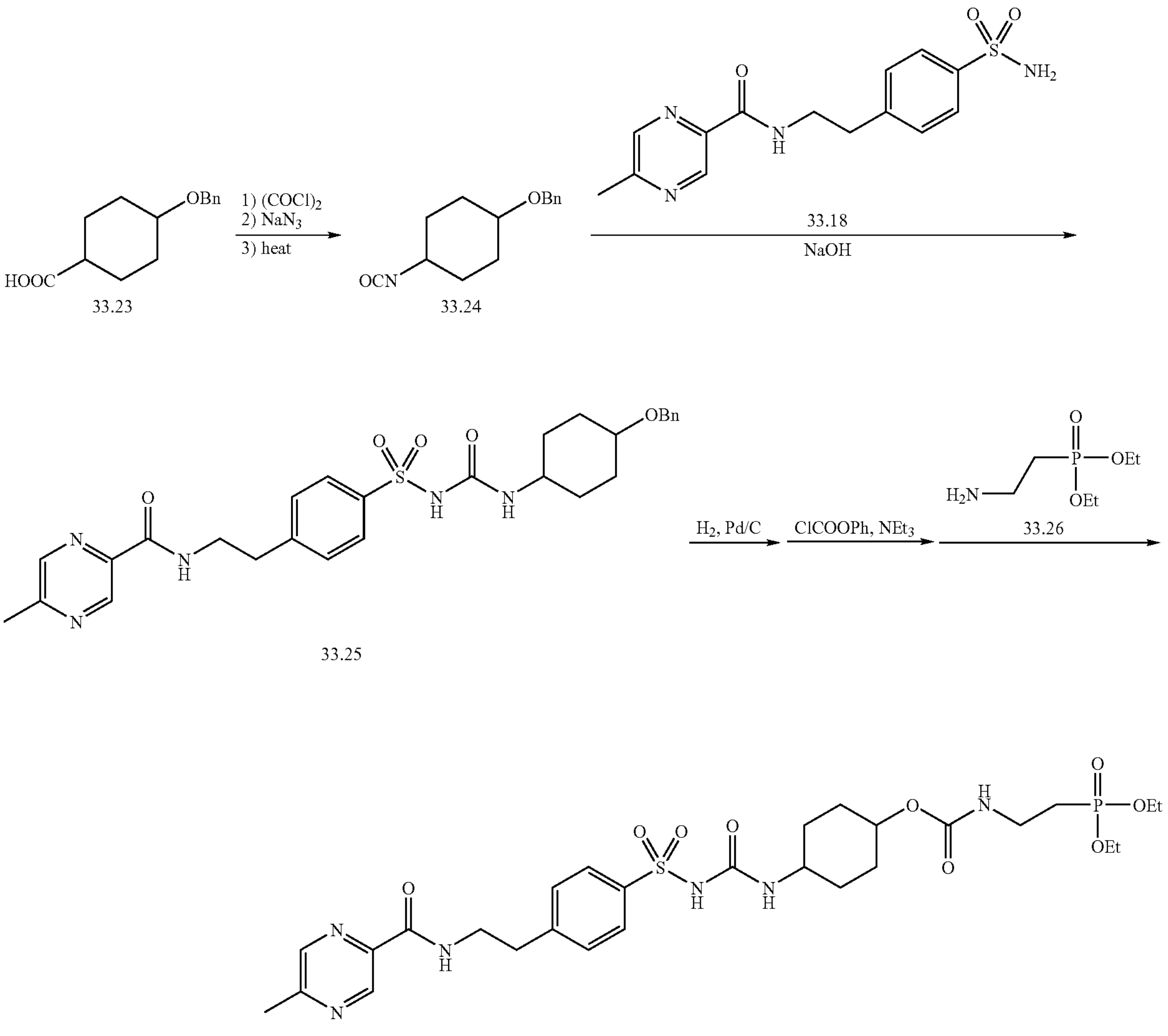

33.23 33.24 33.18 33.25 33.26 33.27

Phosphonates of type 33.5, where Z is nitrogen, are prepared by the procedure shown. These types of compounds are obtained by the coupling of sunfonamide 33.13 using isocyanate 33.28 bearing $R^{44}$ with a suitably protected amine substituent. The phosphonate group bearing moiety is attached by reductive amination using a suitable phosphonate reagent 33.30 bearing aldehyde group with reducing agent, such as sodium cyanoborohydride, in suitable solvents, such as dichloroethane or methanol, in the presence of an acid, such as acetic acid. The resulting secondary amine 33.5 ($R^{99}$=H) may be converted to the corresponding tertiary amine 33.5 ($R^{99}$=alkyl) by reductive amination.

diethyl ester 33.34 with sodium cyanoborohydride and acetic acid in dichloroethane to obtain 33.35 in which the linkage is an ethylene group and $R^{99}$ is hydrogen. The resulting secondary amine 33.35 ($R^{99}$=H) is converted to the corresponding tertiary amine 33.35 ($R^{99}$=Me) by reductive amination with formaldehyde using sodium cyanoborohydride and acetic acid. Using the above procedure but employing different sulfonylamide 33.13, isocyanate 33.28, and phosphonate reagents 33.30 the corresponding products, where Z is NH or $NR^{99}$, bearing different $R^{33}$, $R^{44}$, $R^{99}$, and linking groups can be obtained.

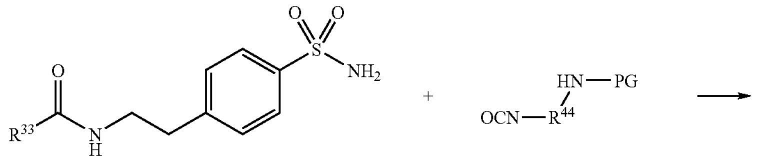
33.13 33.28
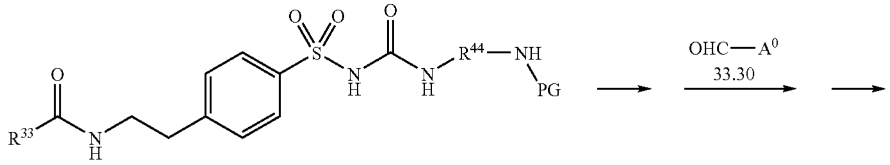
33.29
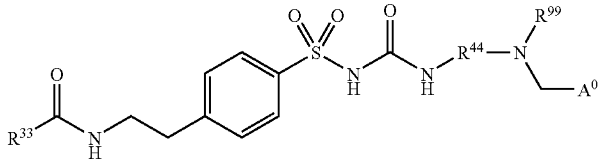
33.5: Z = NH, $NR^7$
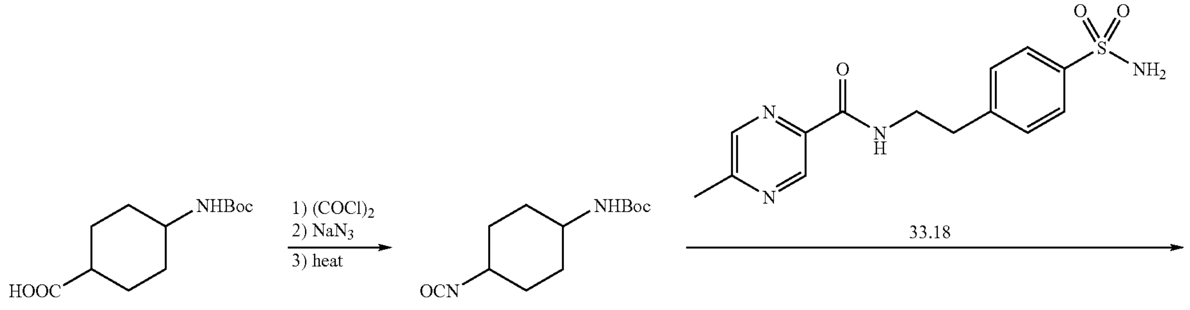
33.31 33.32
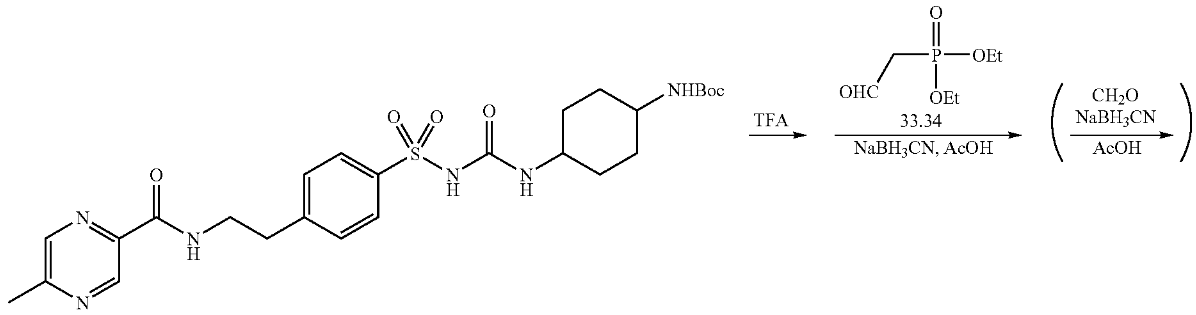
33.33
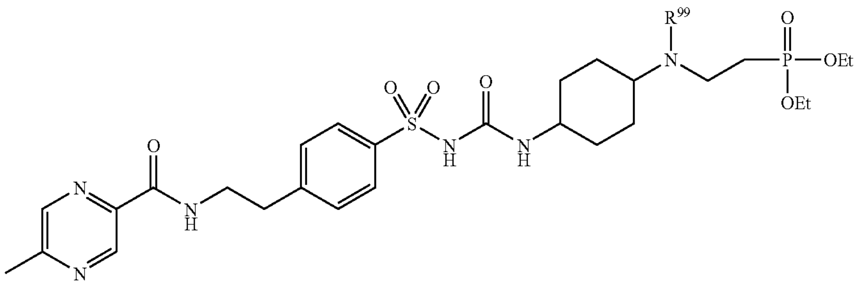
33.35 ($R^{99}$ = H or Me)

Phosphonate analogs of type 33.6 are synthesized according to the procedure shown. This type of compounds are obtained by the coupling, as described in U.S. Pat. No. 3,669,966, of substituted pyrazine carboxylic acid 33.36 bearing amino, hydroxyl, or other substituents, which can convert to appropriate functional group for the attachment of phosphonate moiety, for example carboxylic ester, with sulfonylurea moiety 33.37. Substituted pyrazine carboxylic acids are commercially available or may be prepared by the method described in Ber. 1907, 40, 4850 or in Ber. 1966, 99, 364. Phosphonate moiety is introduced to a substituent on the pyrazine ring, if necessary after conversion of the substituent to a suitable functional group bearing substituent, either by alkylation, reductive amination, or reaction with active carbonate intermediate as described previously.

For example, pyrazine-2,5-dicarboxylic acid mono ester 33.39, which is generated by partial hydrolysis, is treated with sulfonylurea 33.40 in the presence of EDC and HOBt to form the amide 33.41. The carboxylic ester of 33.41 is then reduced with $LiBH_4$ in methanol and the resulting alcohol was treated with phenyl chloroformate to generate the active carbonate. Treatment of the active carbonate with 2-aminoethyl phosphonate diethyl ester 33.26 generates the phosphonate analog 33.42 in which the linker is carbamate group. The ester may be treated with DIBAL to generate aldehyde functional group and subsequent reductive amination produces analog 33.43. Using the above procedures but employing different pyrazine carboxylic acid 33.36, sulfonulurea 33.37, and phosphonate reagents, the corresponding products 33.6 bearing different linking groups can be obtained.

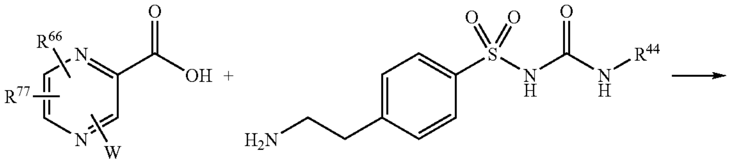

33.36 33.37

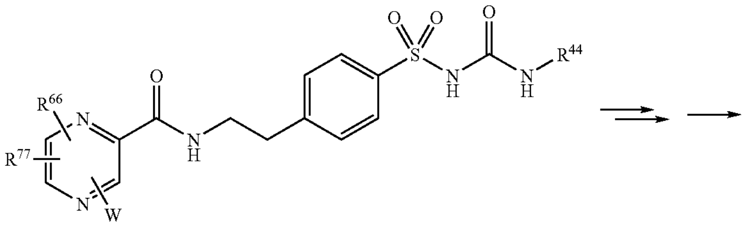

33.38

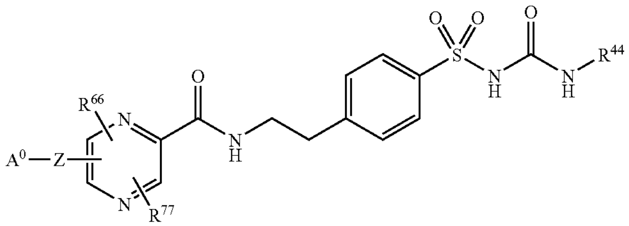

33.6

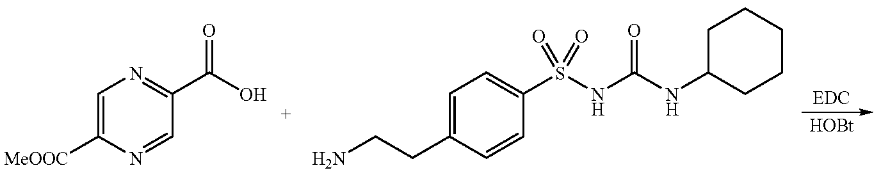

33.38 33.40

-continued

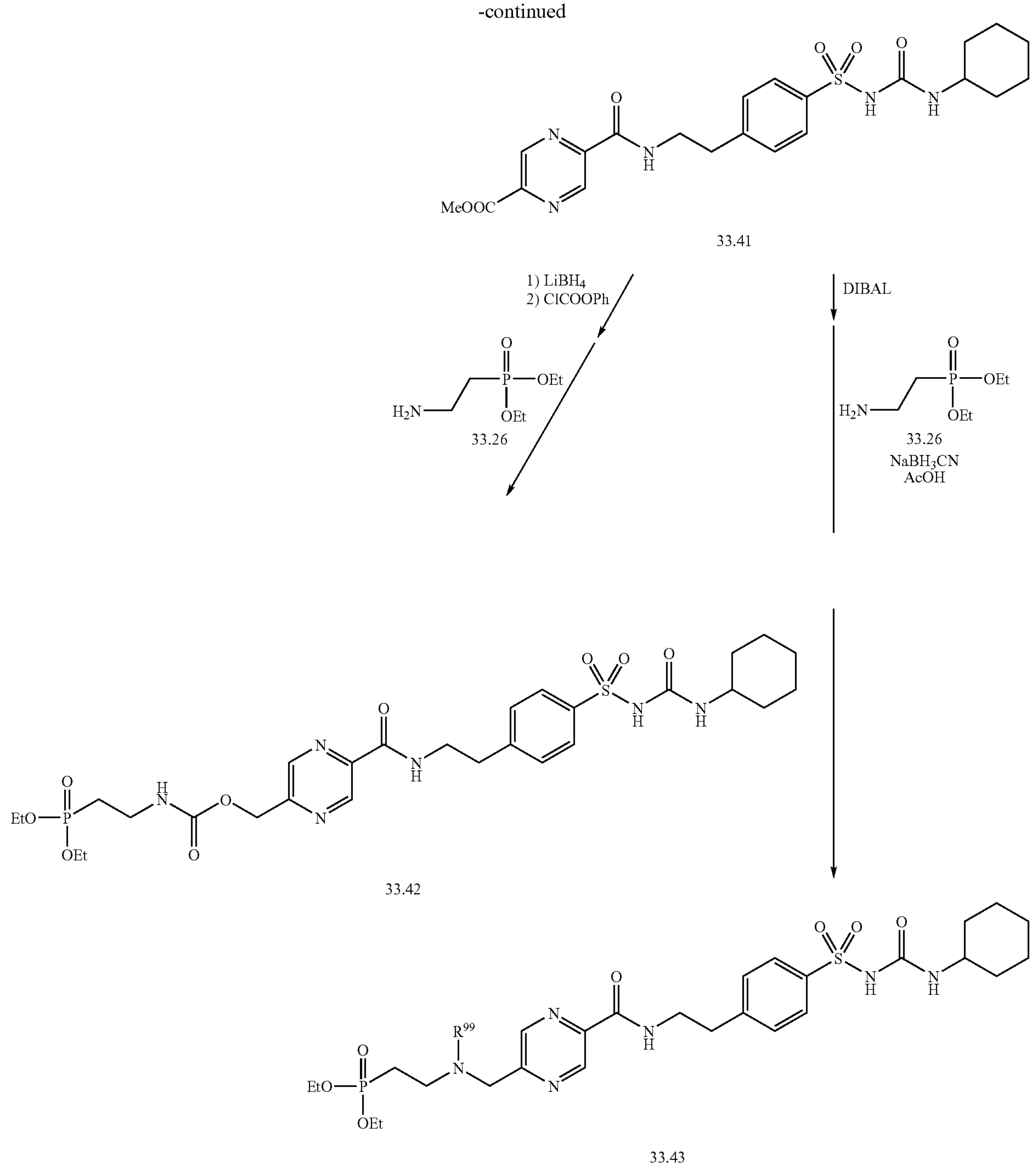

33.41

33.42

33.43

The synthesis of phosphonate analogs of type 33.7 is shown. This type of compound is obtained by the coupling, as described in U.S. Pat. No. 3,669,966, of substituted benzoic acid 33.44 bearing amino, hydroxyl, or other substituents, which can convert to appropriate functional group for the attachment of phosphonate moiety with sulfonylurea moiety 33.37. Phosphonate moiety is introduced to a substituent on the aromatic ring, if necessary after conversion of the substituent to a suitable functional group bearing substituent, either by alkylation, reductive amination, or reaction with active carbonate intermediate as described previously. Alternatively, the phosphorus containing moiety is attached to a substituent of benzoic acid analogs 33.44 and the resulting 33.45 is coupled with sulfonylurea moiety 33.37.

For example, a solution of 3-chloro-2-hydroxybenzoic acid 33.39 in DMF is treated with cesium carbonate and one equivalent of (trifluoromethanesulfonyloxy)methylphosphonic acid diethyl ester to give the analog 33.12 in which the linkage is a methylene group. Using the above procedure but employing benzoic acid 33.44, sulfonulurea 33.37, and phosphonate reagents 33.10, 33.22, or 33.30, the corresponding products 33.6 bearing different $R^{44}$, $R^{66}$, $R^{77}$, $R^{88}$, and linking groups can be obtained.

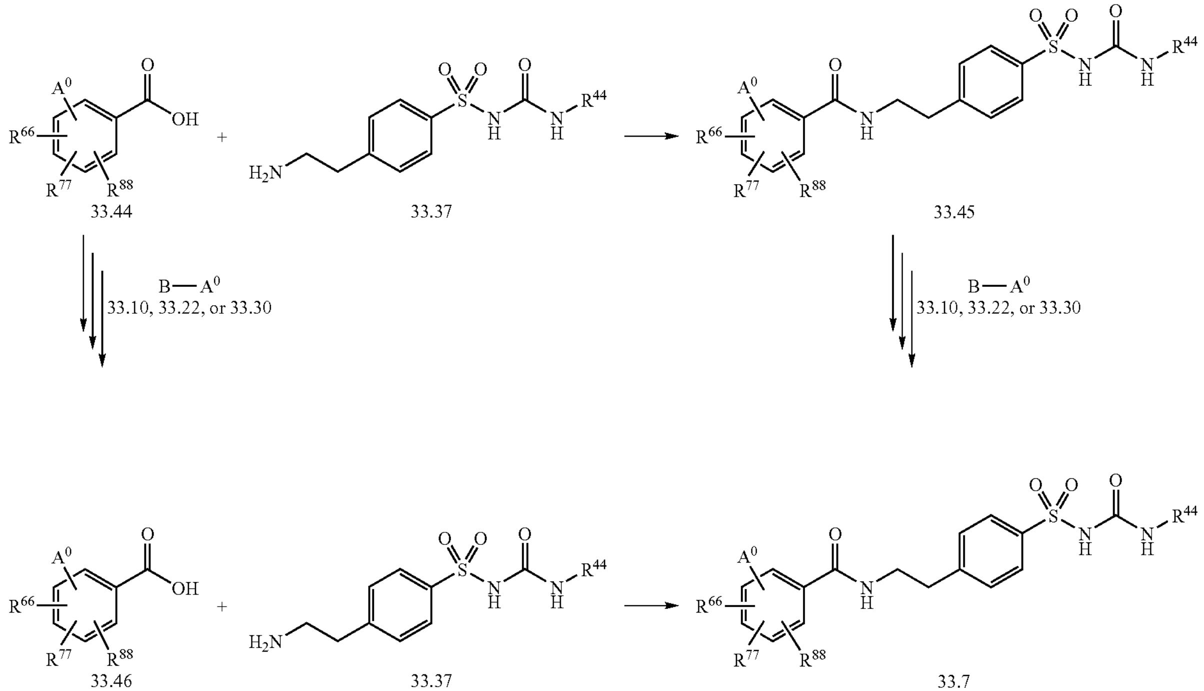
33.44 33.37 33.45
33.46 33.37 33.7
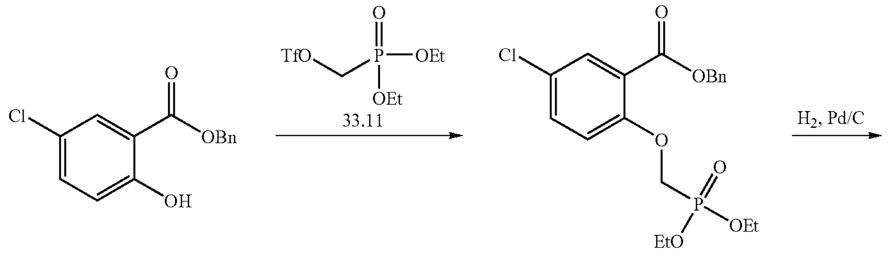
33.46 33.47
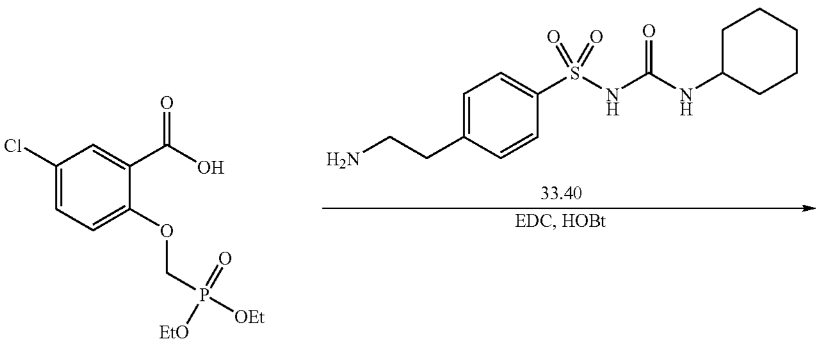
33.48

-continued

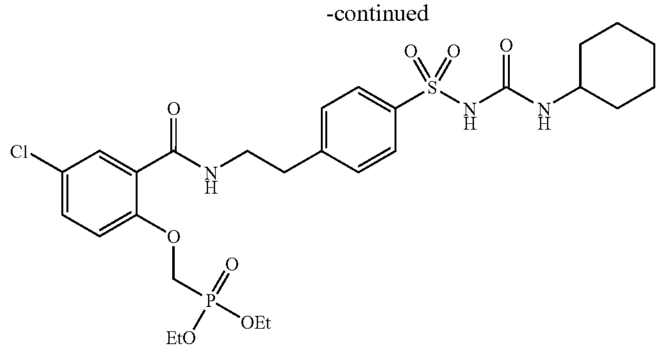

33.49

The synthesis of phosphonate analogs of type 33.8 is shown. This type of compounds are obtained by the coupling, as described in U.S. Pat. No. 4,379,785, of substituted 33.50 bearing amino, hydroxyl, or other substituents, which can convert to appropriate functional group for the attachment of phosphorus containing moiety with isocyanate 33.51 bearing sulfonylurea moiety. Alternatively, the phosphorus containing moiety is attached to a substituent of 33.50 and the resulting 33.53 is coupled with the isocyanate bearing sulfonylurea moiety 33.51. Phosphonate moiety is introduced to a substituent on 33.50 or 33.53, if necessary after conversion of the substituent to a suitable functional group bearing substituent, either by alkylation, reductive amination, or reaction with active carbonate intermediate as described previously.

For example, 33.54, which is available by the procedure in *Tetrahedron Lett.* 2000, 40, 2825, is protected using Boc group and then the silyl protecting group is removed by tetrabutylammonium fluoride, which results 33.55. The phosphorus containing moiety is introduced by alkylation using one equivalent of (trifluoromethanesulfonyloxy)methylphosphonic acid diethyl ester 33.11 with sodium hydride, and the Boc protecting group is removed using trifluoroacetic acid. The reaction of 33.56 with 33.57 in elevated temperature produces 33. 58 in which the linkage is a methylene group. Using the above procedure but employing 33.50, 33.51, and phosphonate reagents 33.10, 33.22, or 33.30, the corresponding products 33.6 bearing different heterocycles and linking groups can be obtained.

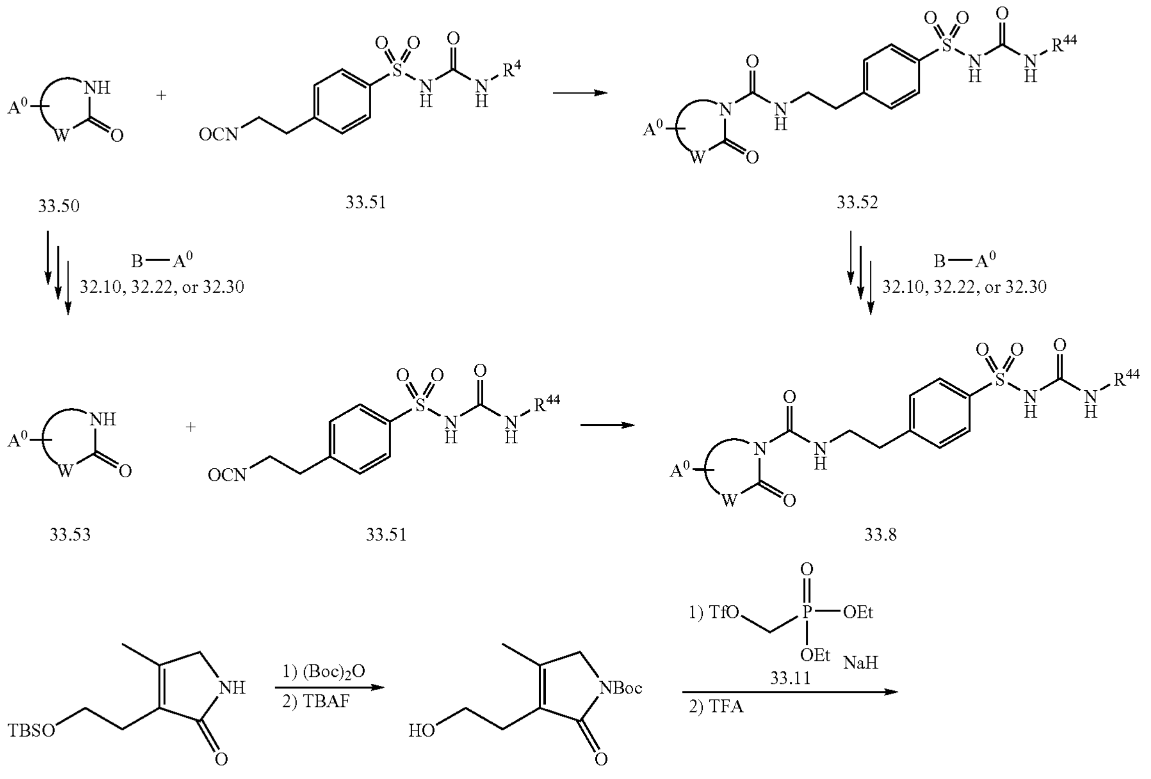

33.50 33.51 33.52

33.53 33.51 33.8

33.54 33.55

-continued

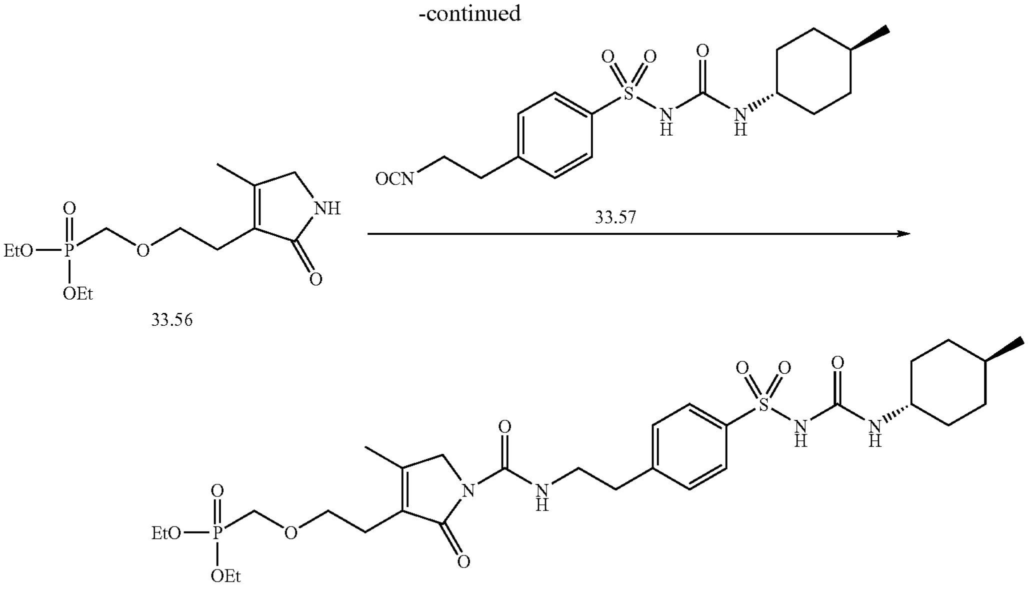
33.56

33.57

33.58

Example 34

By way of example and not limitation, embodiments of the invention are named below in tabular format (Table 100). These embodiments are of the general formula "MBF":

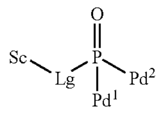
MBF

Each embodiment of MBF is depicted as a substituted nucleus (Sc). Sc is described in formula 1-51 herein, wherein $A^0$ is the point of covalent attachment of Sc to Lg, as well as in Tables 1.1 to 1.5 below. For those embodiments described in Table 100, Sc is a nucleus designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug ($Pd^1$ and $Pd^2$) substituents, again by letter or number designation, respectively. Accordingly, a compound of the formula MBF includes compounds having Sc groups based on formula 1-51 herein as well as compounds according to Table 100 below. In all cases, compounds of the formula MBF have groups Lg, $Pd^1$ and $Pd^2$ set forth in the Tables below.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups ($Pd^1$ and $Pd^2$) from Table 20.1-20.36. In graphical tabular form, each embodiment of Table 100 appears as a name having the syntax:

$Sc.Lg.Pd^1.Pd^2$

Each Sc group is shown having a tilda ("~"). The tilda is the point of covalent attachment of Sc to Lg. $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the tilda symbol ("~"). Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1

| | |
|---|---|
| 1 | 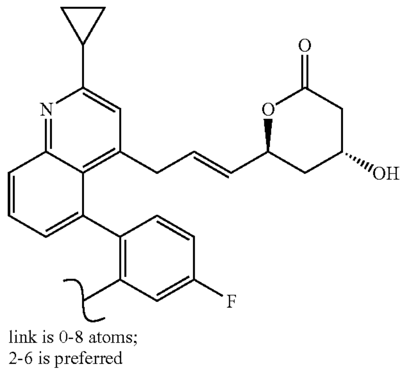 link is 0-8 atoms; 2-6 is preferred |

TABLE 1.1-continued
2
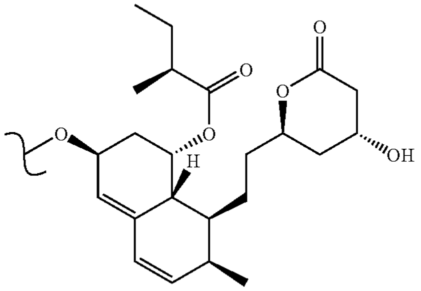
3
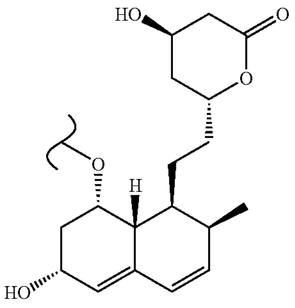
4
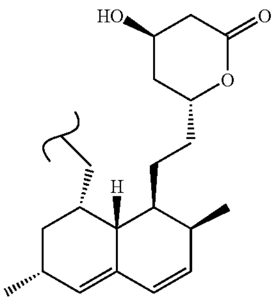
TABLE 1.2
5
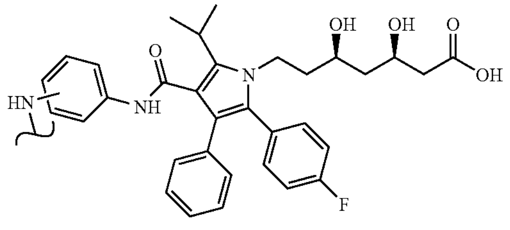
6
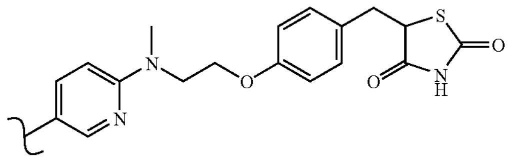
TABLE 1.2-continued
TABLE 1.3
7
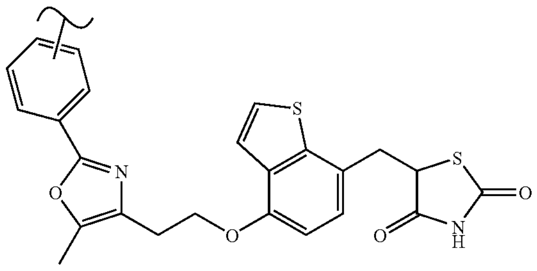
8
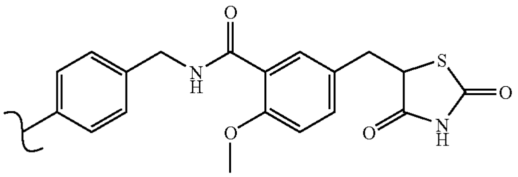
9
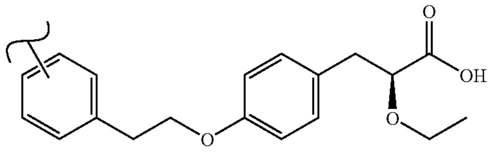
10
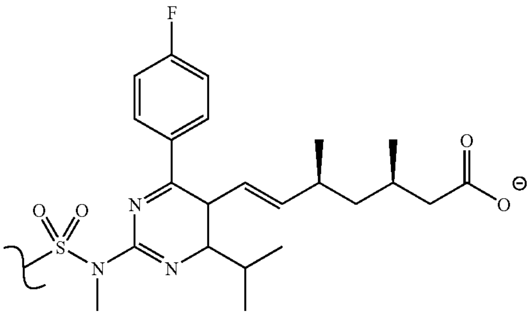
TABLE 1.4
11
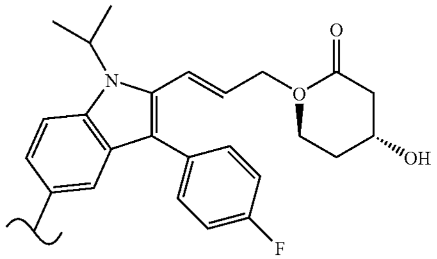

TABLE 1.4-continued
| | |
|---|---|
| 12 | 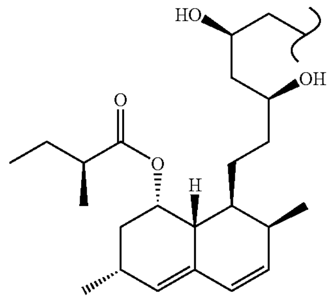 |
TABLE 1.5
| | |
|---|---|
| 13 | 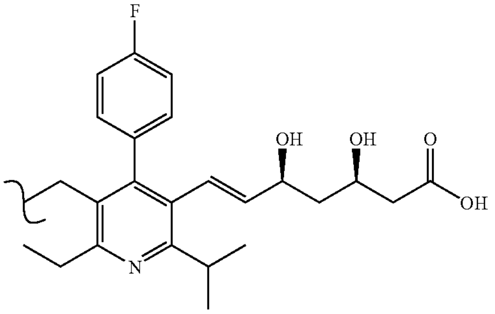 |
| 14 | 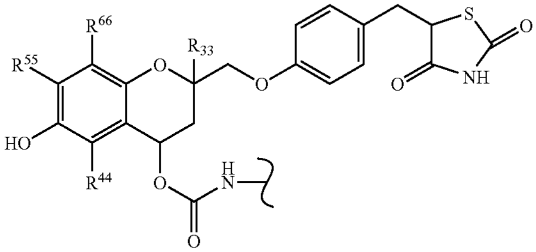 |
TABLE 10.1
| | |
|---|---|
| A | 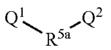 |
| B | 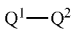 |
| C | 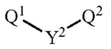 |
| D | 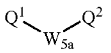 |
| E | 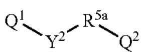 |
| F | 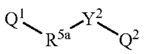 |
| G | 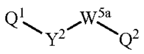 |
| H | 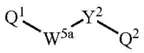 |
TABLE 10.1-continued
| | |
|---|---|
| I | 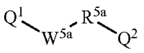 |
| J | 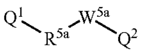 |
| K | 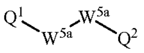 |
| L | 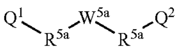 |
| M | 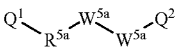 |
| N | 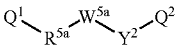 |
| O | 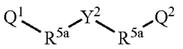 |
TABLE 10.2
| | |
|---|---|
| P | 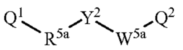 |
| Q | 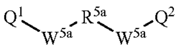 |
| R | 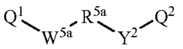 |
| S | 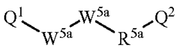 |
| T | 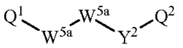 |
| U | 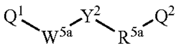 |
| V | 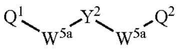 |
| W | 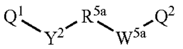 |
| X | 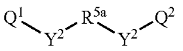 |
| Y | 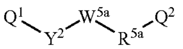 |
| Z | 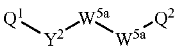 |
| AA | 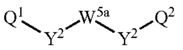 |
TABLE 10.3
| | |
|---|---|
| AB | 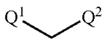 |
| AC | 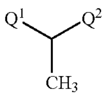 |

TABLE 10.3-continued
| | |
|---|---|
| AD | 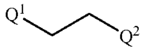 |
| AE | 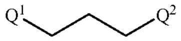 |
| AF | 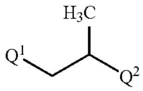 |
| AG | 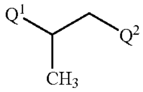 |
| AH | 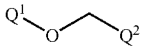 |
| AI | 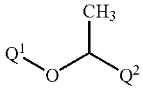 |
| AJ | 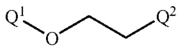 |
| AK | 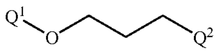 |
| AL | 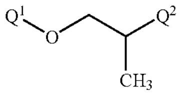 |
| AM | 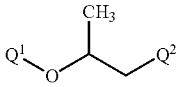 |
TABLE 10.4
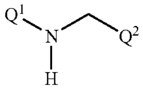
AN
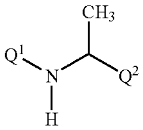
AO
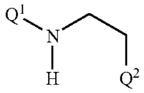
AP
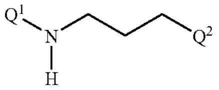
AQ
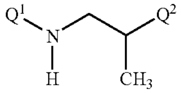
AR
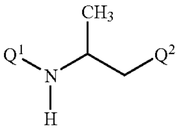
AS
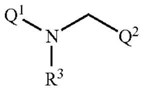
AT
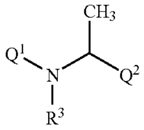
AU
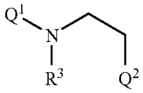
AV
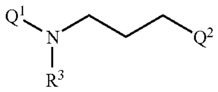
AW
TABLE 10.4-continued
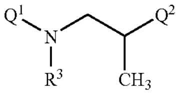
AX
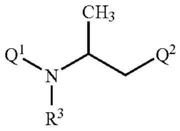
AY
TABLE 10.5
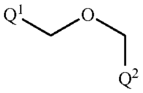
AZ
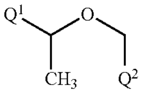
BA
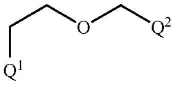
BB
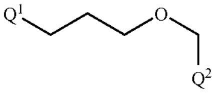
BC
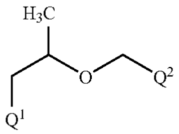
BD
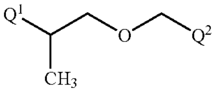
BE
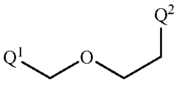
BF
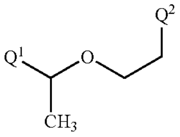
BG
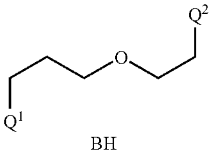
BH
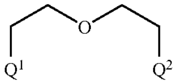
BI
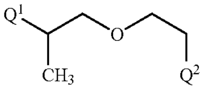
BJ1
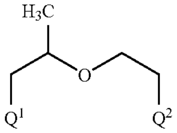
BJ2
TABLE 10.6
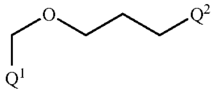
BK
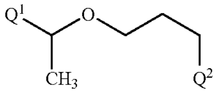
BL
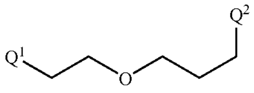
BM
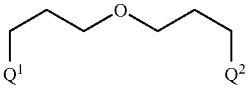
BN
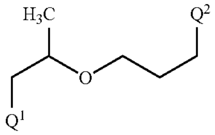
BO
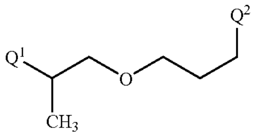
BP TABLE 10.7
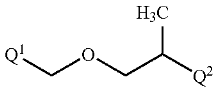
BQ
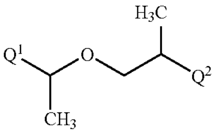
BR
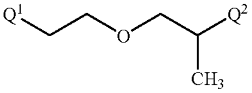
BS
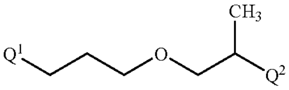
BT
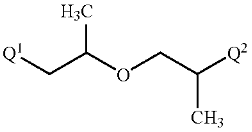
BU
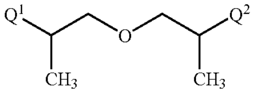
BV
TABLE 10.8
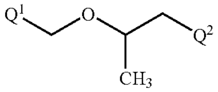
BW
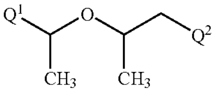
BX
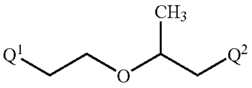
BY
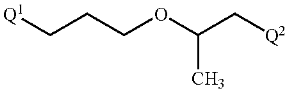
BZ
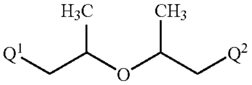
CA
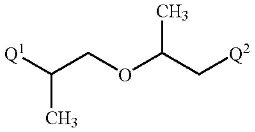
CB
TABLE 10.9
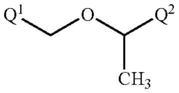
CC
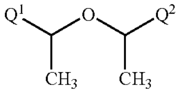
CD
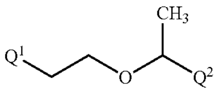
CE
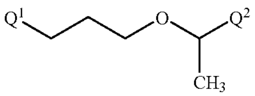
CF
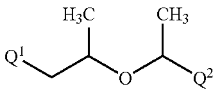
CG
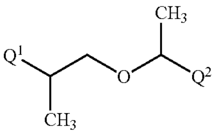
CH
TABLE 10.10
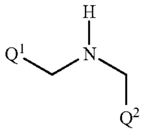
CI
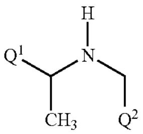
CJ
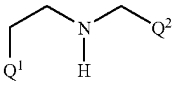
CK
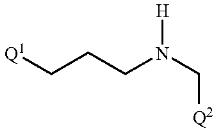
CL
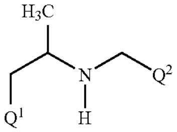
CM
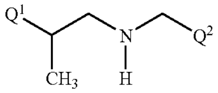
CN
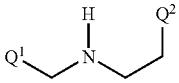
CO
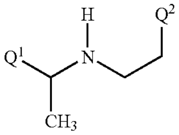
CP
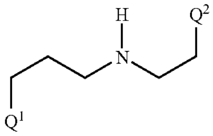
CQ
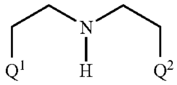
CR
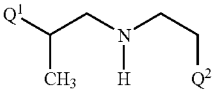
CS
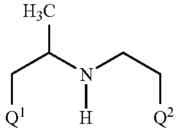
CT
TABLE 10.11
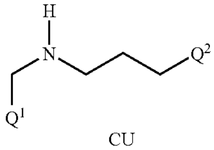
CU
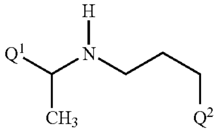
CV
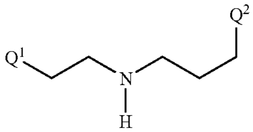
CW
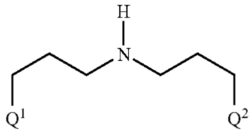
CX TABLE 10.11-continued
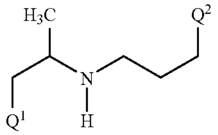
CY
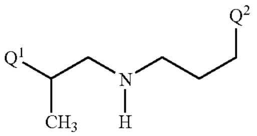
CZ
TABLE 10.12
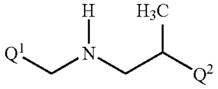
DA
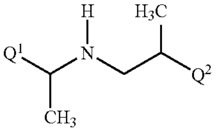
DB
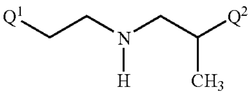
DC
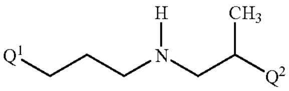
DD
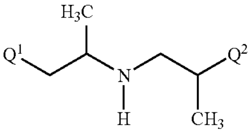
DE
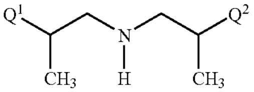
DF
TABLE 10.13
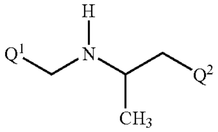
DG
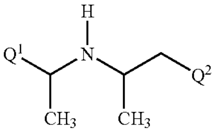
DH
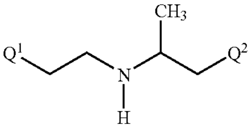
DI
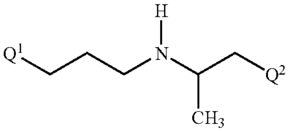
DJ
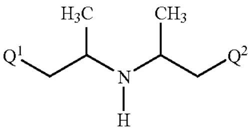
DK
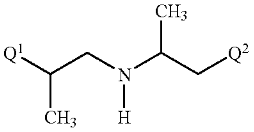
DL
TABLE 10.14
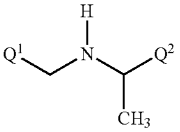
DM
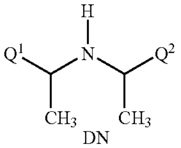
DN
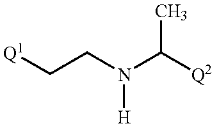
DO
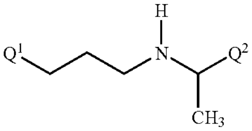
DP
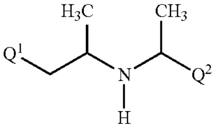
DQ
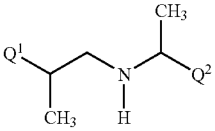
DR
TABLE 10.15
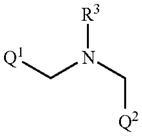
DS
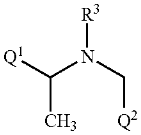
DT
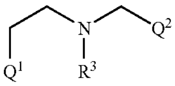
DU
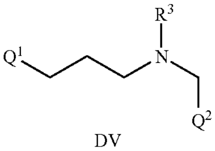
DV
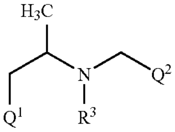
DW
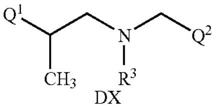
DX
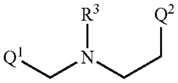
DY
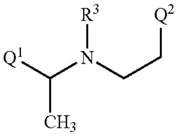
DZ
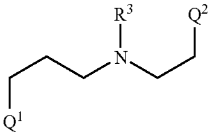
EA
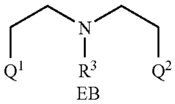
EB
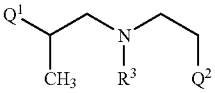
EC TABLE 10.15-continued
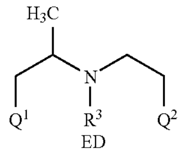
ED
TABLE 10.16
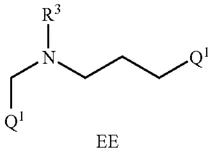
EE
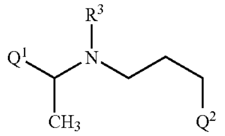
EF
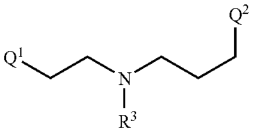
EG
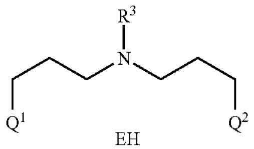
EH
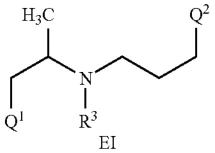
EI
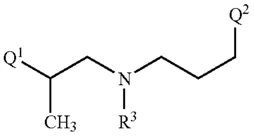
EJ
TABLE 10.17
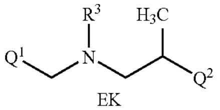
EK
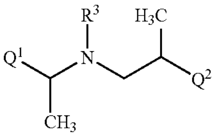
EL
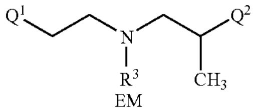
EM
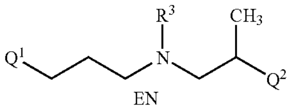
EN
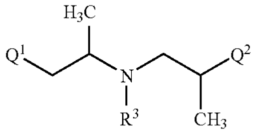
EO
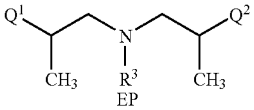
EP
TABLE 10.18
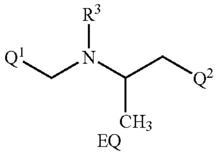
EQ
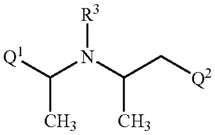
ER
TABLE 10.18-continued
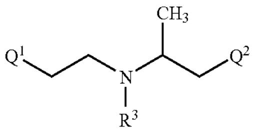
ES
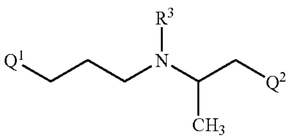
ET
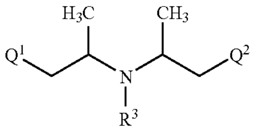
EU
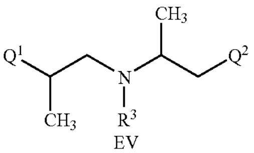
EV
TABLE 10.19
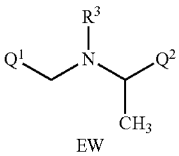
EW
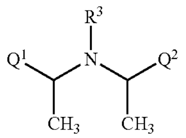
EX
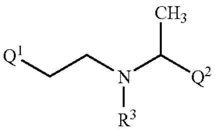
EY
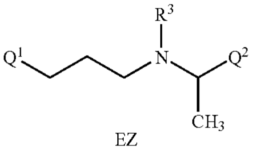
EZ
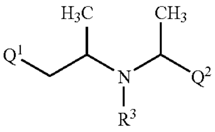
FA
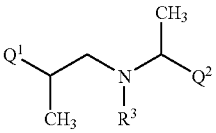
FB
TABLE 20.1
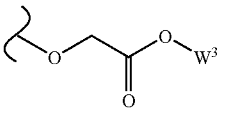
1
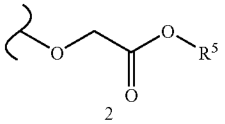
2
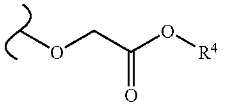
3
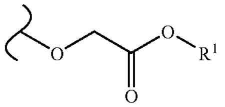
4

TABLE 20.1-continued
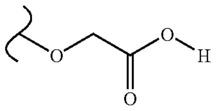
5
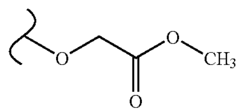
6
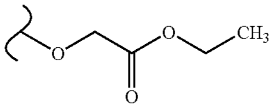
7
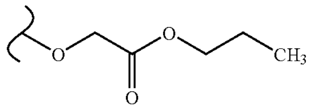
8
TABLE 20.2
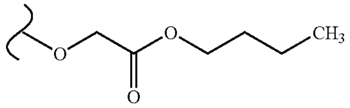
9
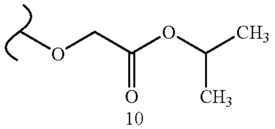
10
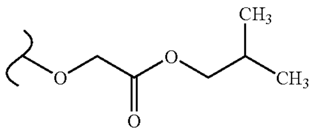
11
TABLE 20.3
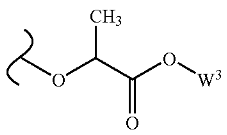
12
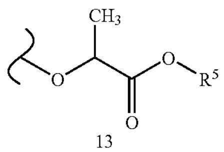
13
TABLE 20.3-continued
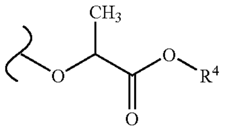
14
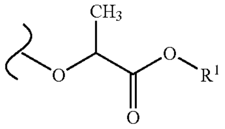
15
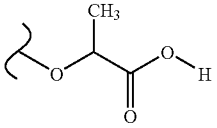
16
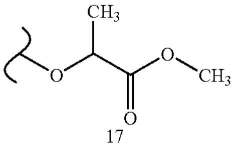
17
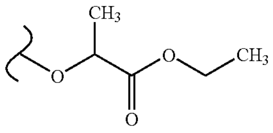
18
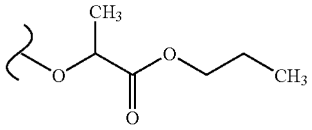
19
TABLE 20.4
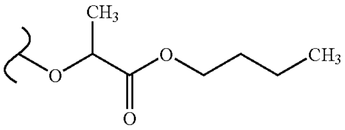
20
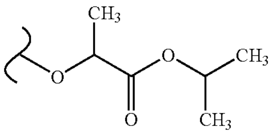
21

TABLE 20.4-continued
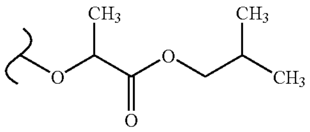
22
TABLE 20.5
23 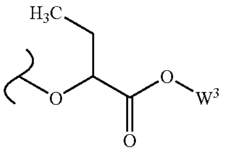
24 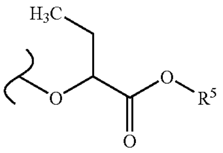
25 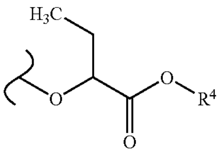
26 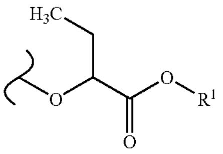
27 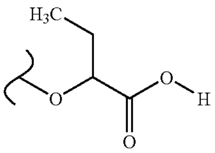
28 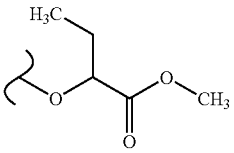
29 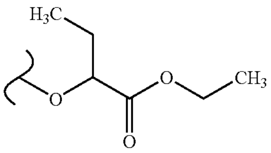
TABLE 20.5-continued
30 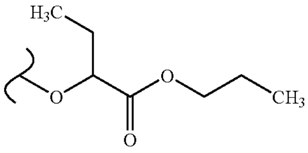
TABLE 20.6
31 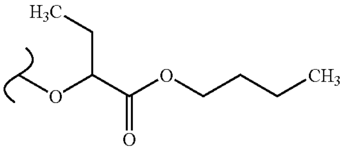
32 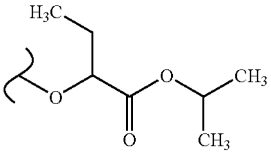
33 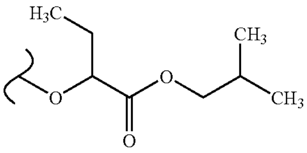
TABLE 20.7
34 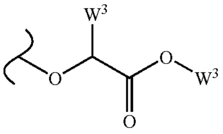
35 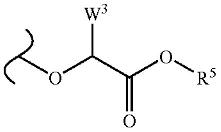
36 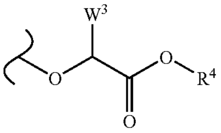
37 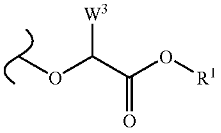
38 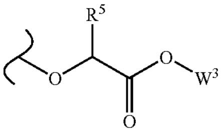

TABLE 20.7-continued
| | |
|---|---|
| 39 | 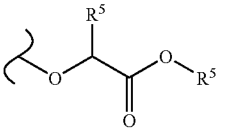 |
| 40 | 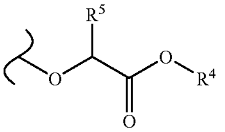 |
| 41 | 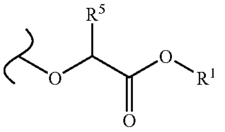 |
TABLE 20.8
| | |
|---|---|
| 42 | 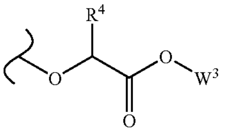 |
| 43 | 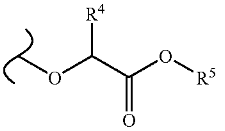 |
| 44 | 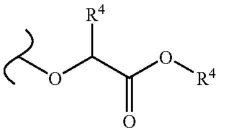 |
| 45 | 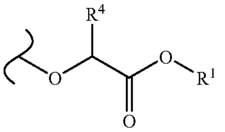 |
| 46 | 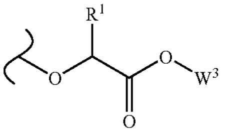 |
| 47 | 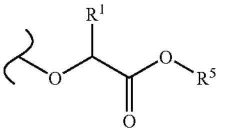 |
| 48 | 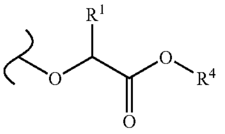 |
TABLE 20.8-continued
| | |
|---|---|
| 49 | 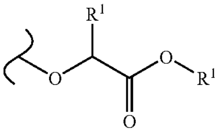 |
TABLE 20.9
| | |
|---|---|
| 50 | 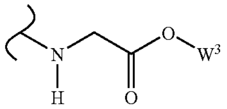 |
| 51 | 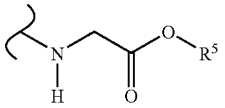 |
| 52 | 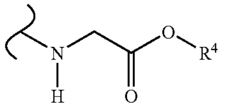 |
| 53 | 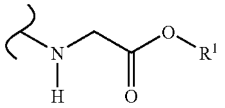 |
| 54 | 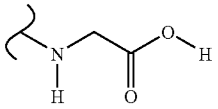 |
| 55 | 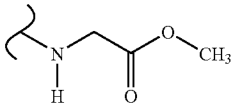 |
| 56 | 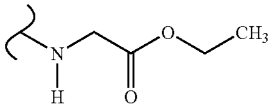 |
| 57 | 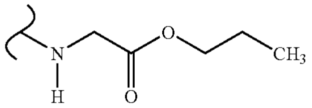 |
TABLE 20.10
| | |
|---|---|
| 58 | 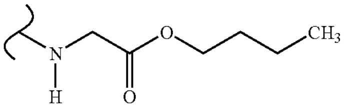 |
| 59 | 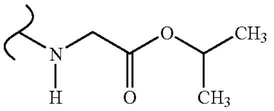 |

TABLE 20.10-continued
| | |
|---|---|
| 60 | 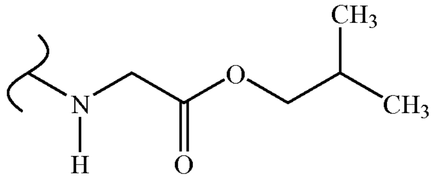 |
TABLE 20.11
| | |
|---|---|
| 61 | 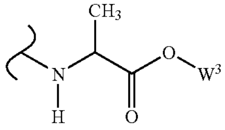 |
| 62 | 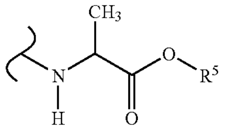 |
| 63 | 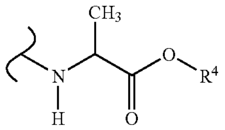 |
| 64 | 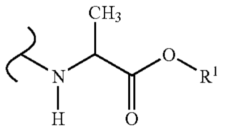 |
| 65 | 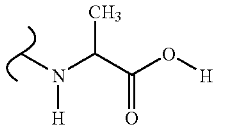 |
| 66 | 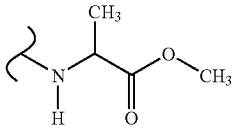 |
| 67 | 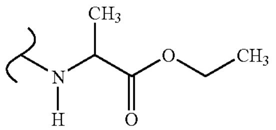 |
| 68 | 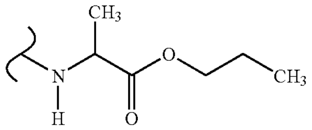 |
TABLE 20.12
| | |
|---|---|
| 69 | 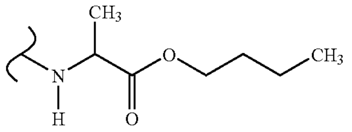 |
| 70 | 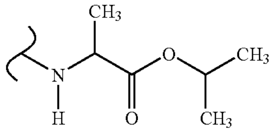 |
| 71 | 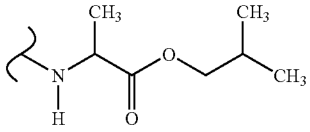 |
TABLE 20.13
| | |
|---|---|
| 72 | 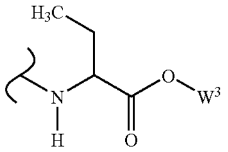 |
| 73 | 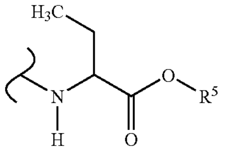 |
| 74 | 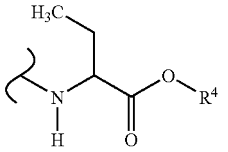 |
| 75 | 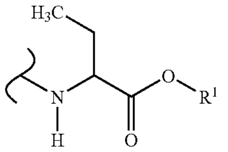 |
| 76 | 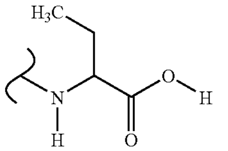 |
| 77 | 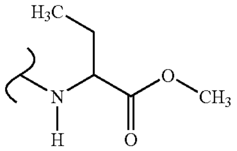 |

TABLE 20.13-continued
| | |
|---|---|
| 78 | 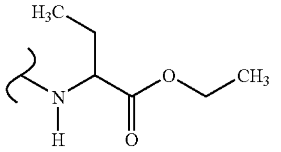 |
| 79 | 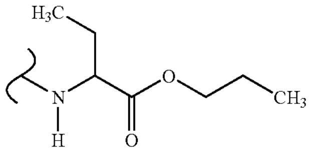 |
TABLE 20.14
| | |
|---|---|
| 80 | 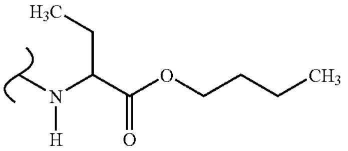 |
| 81 | 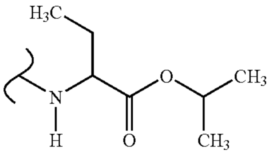 |
| 82 | 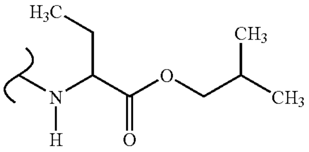 |
TABLE 20.15
| | |
|---|---|
| 83 | 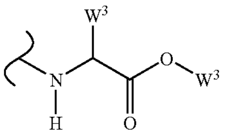 |
| 84 | 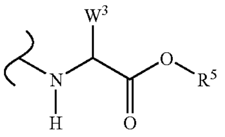 |
| 85 | 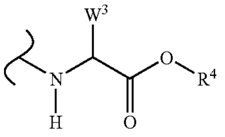 |
| 86 | 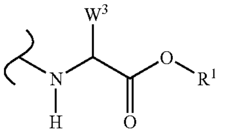 |
TABLE 20.15-continued
| | |
|---|---|
| 87 | 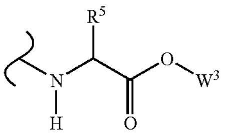 |
| 88 | 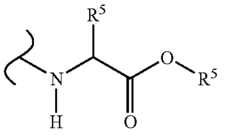 |
| 89 | 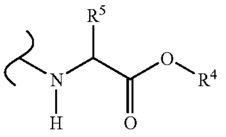 |
| 90 | 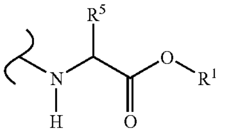 |
TABLE 20.16
| | |
|---|---|
| 91 | 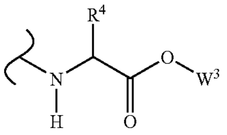 |
| 92 | 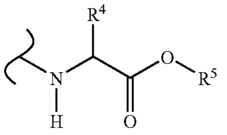 |
| 93 | 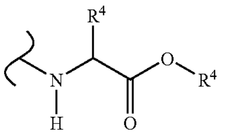 |
| 94 | 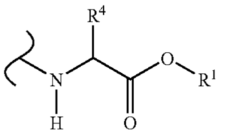 |
| 95 | 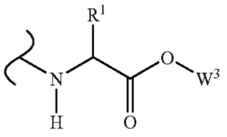 |
| 96 | 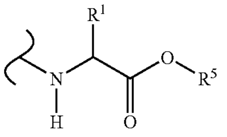 |

TABLE 20.16-continued
| | |
|---|---|
| 97 | 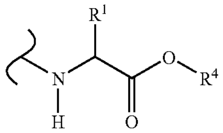 |
| 98 | 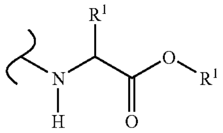 |
TABLE 20.17
| | |
|---|---|
| 99 | 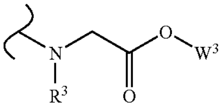 |
| 100 | 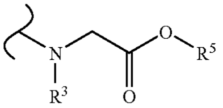 |
| 101 | 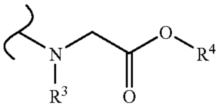 |
| 102 | 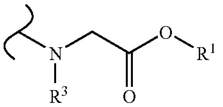 |
| 103 | 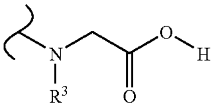 |
| 104 | 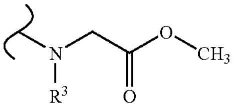 |
| 105 | 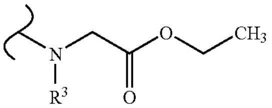 |
| 106 | 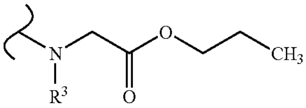 |
TABLE 20.18
| | |
|---|---|
| 107 | 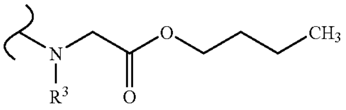 |
TABLE 20.18-continued
| | |
|---|---|
| 108 | 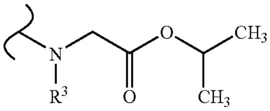 |
| 109 | 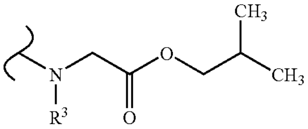 |
TABLE 20.19
| | |
|---|---|
| 110 | 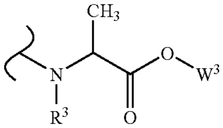 |
| 111 | 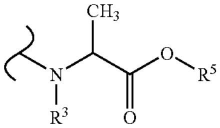 |
| 112 | 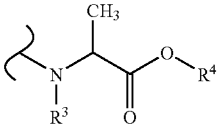 |
| 113 | 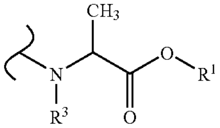 |
| 114 | 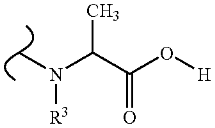 |
| 115 | 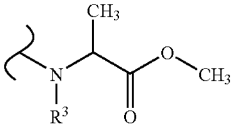 |
| 116 | 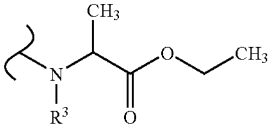 |
| 117 | 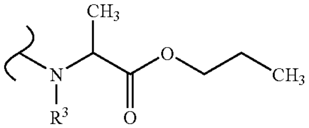 |

TABLE 20.20
| | |
|---|---|
| 118 | 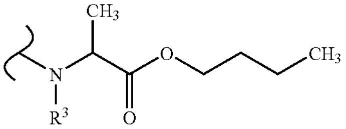 |
| 119 | 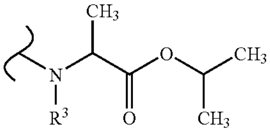 |
| 120 | 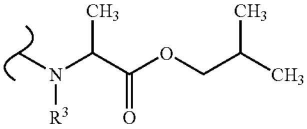 |
TABLE 20.21
| | |
|---|---|
| 121 | 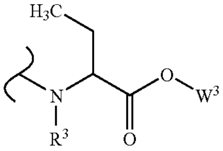 |
| 122 | 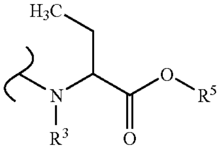 |
| 123 | 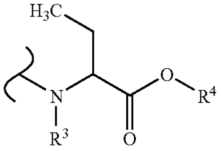 |
| 124 | 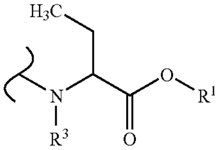 |
| 125 | 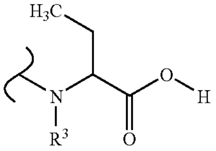 |
| 126 | 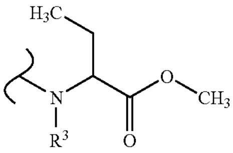 |
TABLE 20.21-continued
| | |
|---|---|
| 127 | 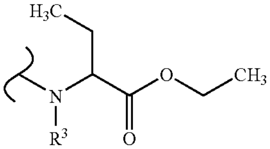 |
| 128 | 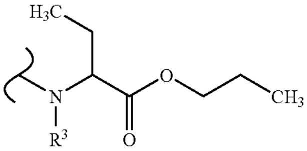 |
TABLE 20.22
| | |
|---|---|
| 129 | 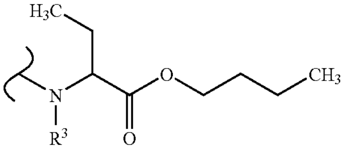 |
| 130 | 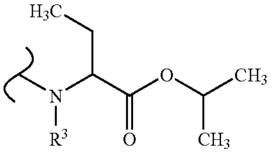 |
| 131 | 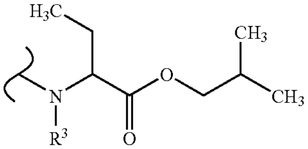 |
TABLE 20.23
| | |
|---|---|
| 132 | 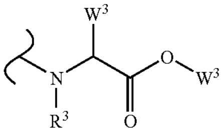 |
| 133 | 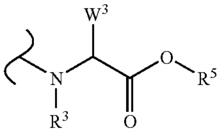 |
| 134 | 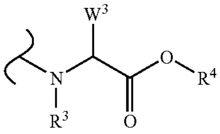 |
| 135 | 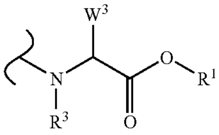 |

TABLE 20.23-continued
| | |
|---|---|
| 136 | 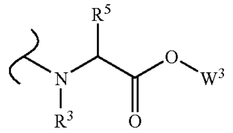 |
| 137 | 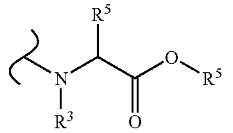 |
| 138 | 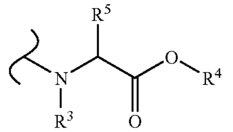 |
| 139 | 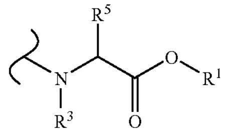 |
TABLE 20.24
| | |
|---|---|
| 140 | 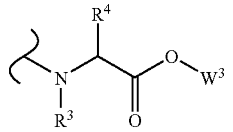 |
| 141 | 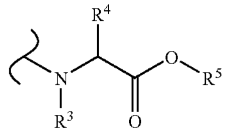 |
| 142 | 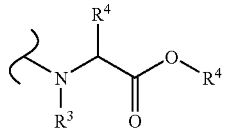 |
| 143 | 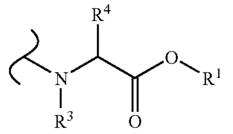 |
| 144 | 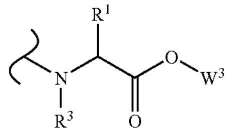 |
| 145 | 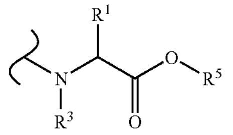 |
TABLE 20.24-continued
| | |
|---|---|
| 146 | 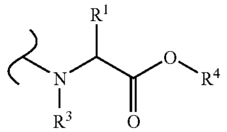 |
| 147 | 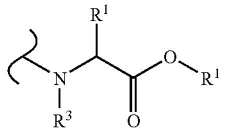 |
TABLE 20.25
| | | |
|---|---|---|
| 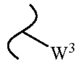 | 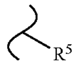 | 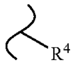 |
| 148 | 149 | 150 |
| 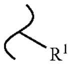 | 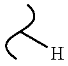 | 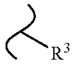 |
| 151 | 152 | 153 |
| 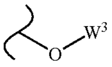 | 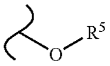 | 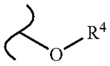 |
| 154 | 155 | 156 |
| 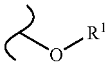 | 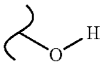 | 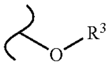 |
| 157 | 158 | 159 |
TABLE 20.26
| | | |
|---|---|---|
| 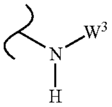 | 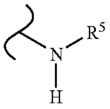 | 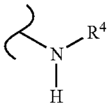 |
| 160 | 161 | 162 |
| 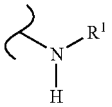 | 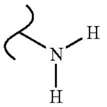 | 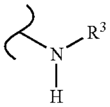 |
| 163 | 164 | 165 |
| 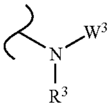 | 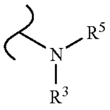 | 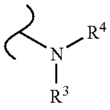 |
| 166 | 167 | 168 |

TABLE 20.26-continued
| | | |
|---|---|---|
| 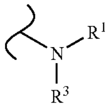 169 | 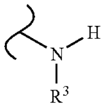 170 | 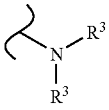 171 |
TABLE 20.27
| | |
|---|---|
| 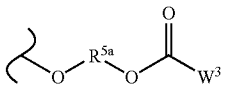 172 | 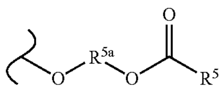 173 |
| 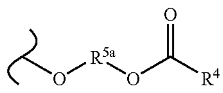 174 | 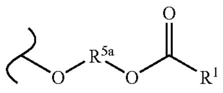 175 |
| 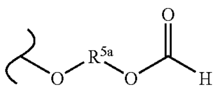 176 | 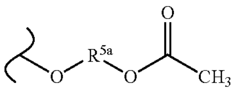 177 |
| 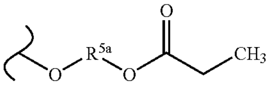 178 | 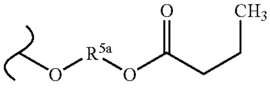 179 |
TABLE 20.28
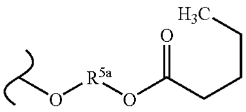
180
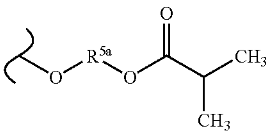
181
TABLE 20.28-continued
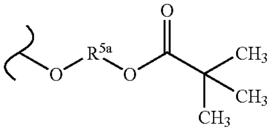
182
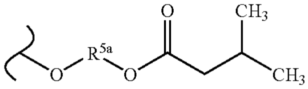
183
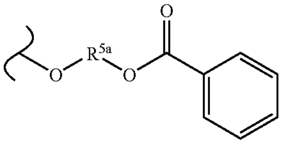
184
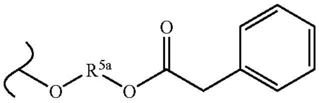
185
TABLE 20.29
| | |
|---|---|
| 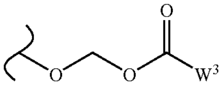 186 | 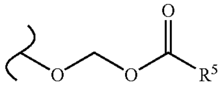 187 |
| 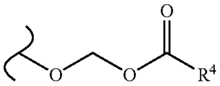 188 | 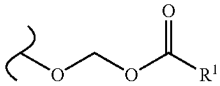 189 |
| 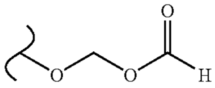 190 | 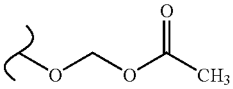 191 |
| 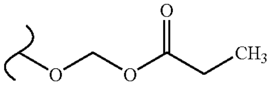 192 | 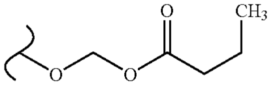 193 |

TABLE 20.30
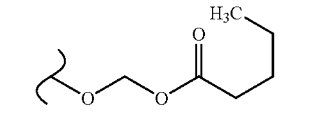
194
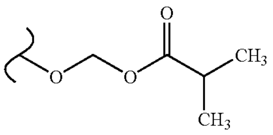
195
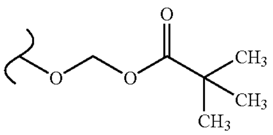
196
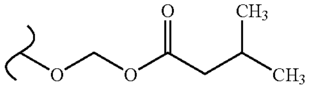
197
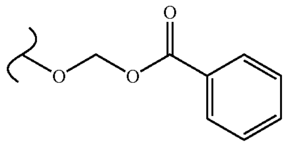
198
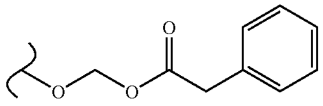
199
TABLE 20.31
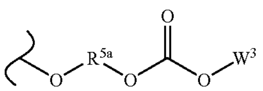
200
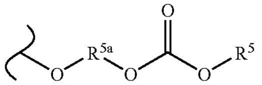
201
TABLE 20.31-continued
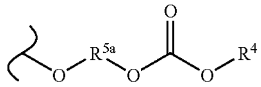
202
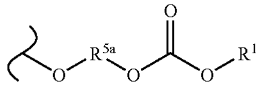
203
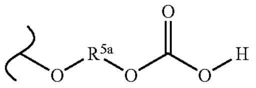
204
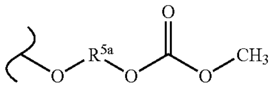
205
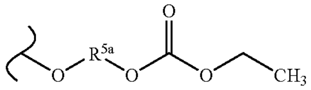
206
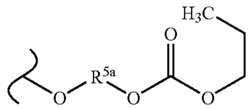
207
TABLE 20.32
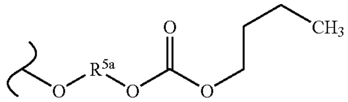
208
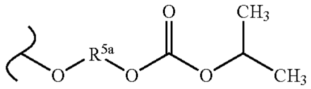
209

TABLE 20.32-continued
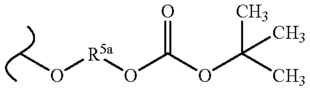
210
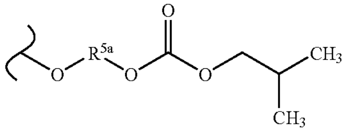
211
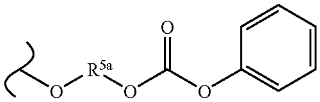
212
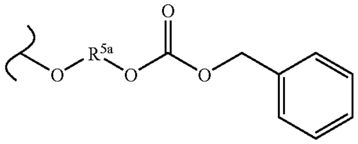
213
TABLE 20.33
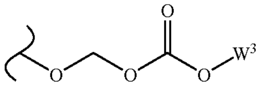
214
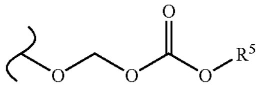
215
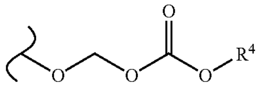
216
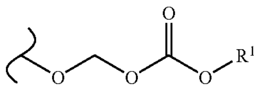
217
TABLE 20.33-continued
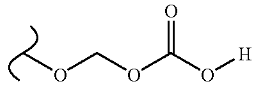
218
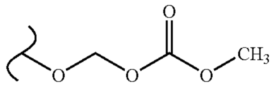
219
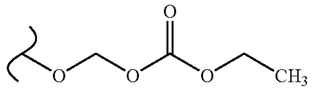
220
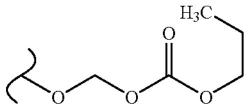
221
TABLE 20.34
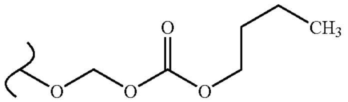
222
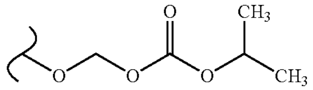
223
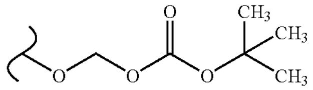
224
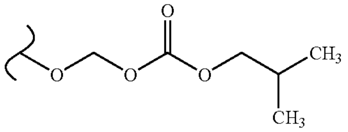
225

TABLE 20.34-continued
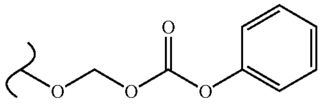
226
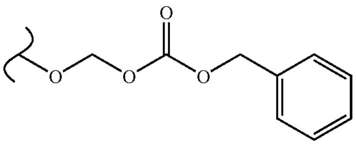
227
TABLE 20.35
228
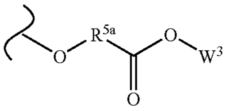
229
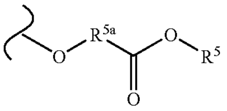
230
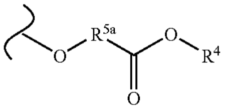
231
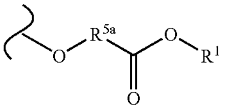
232
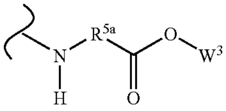
233
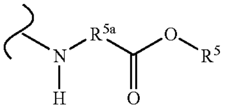
234
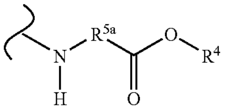
235
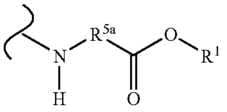
TABLE 20.36
236
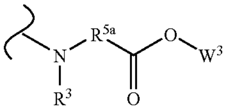
237
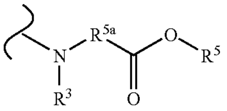
TABLE 20.36-continued
238
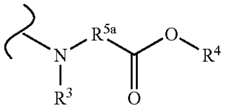
239
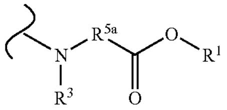
240
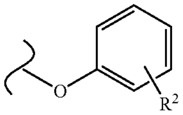
241
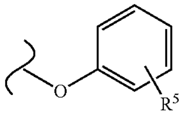
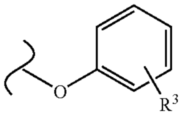
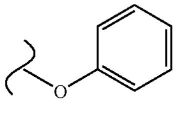
TABLE 20.37
244
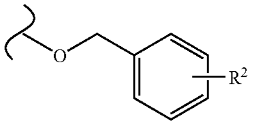
245
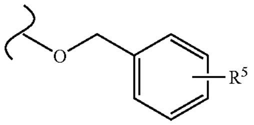
246
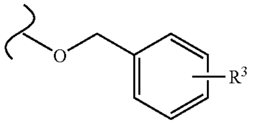
247
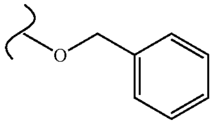
TABLE 100
Prodrugs of 1.B
1.B.228.228; 1.B.228.229; 1.B.228.230; 1.B.228.231; 1.B.228.236; 1.B.228.237; 1.B.228.238; 1.B.228.239; 1.B.228.154; 1.B.228.157; 1.B.228.166; 1.B.228.169; 1.B.228.172; 1.B.228.175; 1.B.228.240; 1.B.228.244; 1.B.229.228; 1.B.229.229; 1.B.229.230; 1.B.229.231; 1.B.229.236; 1.B.229.237; 1.B.229.238; 1.B.229.239; 1.B.229.154; 1.B.229.157; 1.B.229.166; 1.B.229.169; 1.B.229.172; 1.B.229.175; 1.B.229.240; 1.B.229.244; 1.B.230.228; 1.B.230.229; 1.B.230.230; 1.B.230.231; 1.B.230.236; 1.B.230.237; 1.B.230.238; 1.B.230.239; 1.B.230.154; 1.B.230.157; 1.B.230.166; 1.B.230.169; 1.B.230.172; 1.B.230.175; 1.B.230.240; 1.B.230.244; 1.B.231.228; 1.B.231.229; 1.B.231.230; 1.B.231.231; 1.B.231.236; 1.B.231.237; 1.B.231.238; 1.B.231.239; 1.B.231.154; 1.B.231.157; 1.B.231.166;

TABLE 100-continued

1.B.231.169; 1.B.231.172; 1.B.231.175; 1.B.231.240; 1.B.231.244; 1.B.236.228; 1.B.236.229; 1.B.236.230; 1.B.236.231; 1.B.236.236; 1.B.236.237; 1.B.236.238; 1.B.236.239; 1.B.236.154; 1.B.236.157; 1.B.236.166; 1.B.236.169; 1.B.236.172; 1.B.236.175; 1.B.236.240; 1.B.236.244; 1.B.237.228; 1.B.237.229; 1.B.237.230; 1.B.237.231; 1.B.237.236; 1.B.237.237; 1.B.237.238; 1.B.237.239; 1.B.237.154; 1.B.237.157; 1.B.237.166; 1.B.237.169; 1.B.237.172; 1.B.237.175; 1.B.237.240; 1.B.237.244; 1.B.238.228; 1.B.238.229; 1.B.238.230; 1.B.238.231; 1.B.238.236; 1.B.238.237; 1.B.238.238; 1.B.238.239; 1.B.238.154; 1.B.238.157; 1.B.238.166; 1.B.238.169; 1.B.238.172; 1.B.238.175; 1.B.238.240; 1.B.238.244; 1.B.239.228; 1.B.239.229; 1.B.239.230; 1.B.239.231; 1.B.239.236; 1.B.239.237; 1.B.239.238; 1.B.239.239; 1.B.239.154; 1.B.239.157; 1.B.239.166; 1.B.239.169; 1.B.239.172; 1.B.239.175; 1.B.239.240; 1.B.239.244; 1.B.154.228; 1.B.154.229; 1.B.154.230; 1.B.154.231; 1.B.154.236; 1.B.154.237; 1.B.154.238; 1.B.154.239; 1.B.154.154; 1.B.154.157; 1.B.154.166; 1.B.154.169; 1.B.154.172; 1.B.154.175; 1.B.154.240; 1.B.154.244; 1.B.157.228; 1.B.157.229; 1.B.157.230; 1.B.157.231; 1.B.157.236; 1.B.157.237; 1.B.157.238; 1.B.157.239; 1.B.157.154; 1.B.157.157; 1.B.157.166; 1.B.157.169; 1.B.157.172; 1.B.157.175; 1.B.157.240; 1.B.157.244; 1.B.166.228; 1.B.166.229; 1.B.166.230; 1.B.166.231; 1.B.166.236; 1.B.166.237; 1.B.166.238; 1.B.166.239; 1.B.166.154; 1.B.166.157; 1.B.166.166; 1.B.166.169; 1.B.166.172; 1.B.166.175; 1.B.166.240; 1.B.166.244; 1.B.169.228; 1.B.169.229; 1.B.169.230; 1.B.169.231; 1.B.169.236; 1.B.169.237; 1.B.169.238; 1.B.169.239; 1.B.169.154; 1.B.169.157; 1.B.169.166; 1.B.169.169; 1.B.169.172; 1.B.169.175; 1.B.169.240; 1.B.169.244; 1.B.172.228; 1.B.172.229; 1.B.172.230; 1.B.172.231; 1.B.172.236; 1.B.172.237; 1.B.172.238; 1.B.172.239; 1.B.172.154; 1.B.172.157; 1.B.172.166; 1.B.172.169; 1.B.172.172; 1.B.172.175; 1.B.172.240; 1.B.172.244; 1.B.175.228; 1.B.175.229; 1.B.175.230; 1.B.175.231; 1.B.175.236; 1.B.175.237; 1.B.175.238; 1.B.175.239; 1.B.175.154; 1.B.175.157; 1.B.175.166; 1.B.175.169; 1.B.175.172; 1.B.175.175; 1.B.175.240; 1.B.175.244; 1.B.240.228; 1.B.240.229; 1.B.240.230; 1.B.240.231; 1.B.240.236; 1.B.240.237; 1.B.240.238; 1.B.240.239; 1.B.240.154; 1.B.240.157; 1.B.240.166; 1.B.240.169; 1.B.240.172; 1.B.240.175; 1.B.240.240; 1.B.240.244; 1.B.244.228; 1.B.244.229; 1.B.244.230; 1.B.244.231; 1.B.244.236; 1.B.244.237; 1.B.244.238; 1.B.244.239; 1.B.244.154; 1.B.244.157; 1.B.244.166; 1.B.244.169; 1.B.244.172; 1.B.244.175; 1.B.244.240; 1.B.244.244;

Prodrugs of 1.D

1.D.228.228; 1.D.228.229; 1.D.228.230; 1.D.228.231; 1.D.228.236; 1.D.228.237; 1.D.228.238; 1.D.228.239; 1.D.228.154; 1.D.228.157; 1.D.228.166; 1.D.228.169; 1.D.228.172; 1.D.228.175; 1.D.228.240; 1.D.228.244; 1.D.229.228; 1.D.229.229; 1.D.229.230; 1.D.229.231; 1.D.229.236; 1.D.229.237; 1.D.229.238; 1.D.229.239; 1.D.229.154; 1.D.229.157; 1.D.229.166; 1.D.229.169; 1.D.229.172; 1.D.229.175; 1.D.229.240; 1.D.229.244; 1.D.230.228; 1.D.230.229; 1.D.230.230; 1.D.230.231; 1.D.230.236; 1.D.230.237; 1.D.230.238; 1.D.230.239; 1.D.230.154; 1.D.230.157; 1.D.230.166; 1.D.230.169; 1.D.230.172; 1.D.230.175; 1.D.230.240; 1.D.230.244; 1.D.231.228; 1.D.231.229; 1.D.231.230; 1.D.231.231; 1.D.231.236; 1.D.231.237; 1.D.231.238; 1.D.231.239; 1.D.231.154; 1.D.231.157; 1.D.231.166; 1.D.231.169; 1.D.231.172; 1.D.231.175; 1.D.231.240; 1.D.231.244; 1.D.236.228; 1.D.236.229; 1.D.236.230; 1.D.236.231; 1.D.236.236; 1.D.236.237; 1.D.236.238; 1.D.236.239; 1.D.236.154; 1.D.236.157; 1.D.236.166; 1.D.236.169; 1.D.236.172; 1.D.236.175; 1.D.236.240; 1.D.236.244; 1.D.237.228; 1.D.237.229; 1.D.237.230; 1.D.237.231; 1.D.237.236; 1.D.237.237; 1.D.237.238; 1.D.237.239; 1.D.237.154; 1.D.237.157; 1.D.237.166; 1.D.237.169; 1.D.237.172; 1.D.237.175; 1.D.237.240; 1.D.237.244; 1.D.238.228; 1.D.238.229; 1.D.238.230; 1.D.238.231; 1.D.238.236; 1.D.238.237; 1.D.238.238; 1.D.238.239; 1.D.238.154; 1.D.238.157; 1.D.238.166; 1.D.238.169; 1.D.238.172; 1.D.238.175; 1.D.238.240; 1.D.238.244; 1.D.239.228; 1.D.239.229; 1.D.239.230; 1.D.239.231; 1.D.239.236; 1.D.239.237; 1.D.239.238; 1.D.239.239; 1.D.239.154; 1.D.239.157; 1.D.239.166; 1.D.239.169; 1.D.239.172; 1.D.239.175; 1.D.239.240; 1.D.239.244; 1.D.154.228; 1.D.154.229; 1.D.154.230; 1.D.154.231; 1.D.154.236; 1.D.154.237; 1.D.154.238; 1.D.154.239; 1.D.154.154; 1.D.154.157; 1.D.154.166; 1.D.154.169; 1.D.154.172; 1.D.154.175; 1.D.154.240; 1.D.154.244; 1.D.157.228; 1.D.157.229; 1.D.157.230; 1.D.157.231; 1.D.157.236; 1.D.157.237; 1.D.157.238; 1.D.157.239; 1.D.157.154; 1.D.157.157; 1.D.157.166; 1.D.157.169; 1.D.157.172; 1.D.157.175; 1.D.157.240; 1.D.157.244; 1.D.166.228; 1.D.166.229; 1.D.166.230; 1.D.166.231; 1.D.166.236; 1.D.166.237; 1.D.166.238; 1.D.166.239; 1.D.166.154; 1.D.166.157; 1.D.166.166; 1.D.166.169; 1.D.166.172; 1.D.166.175; 1.D.166.240; 1.D.166.244; 1.D.169.228; 1.D.169.229; 1.D.169.230; 1.D.169.231; 1.D.169.236; 1.D.169.237; 1.D.169.238; 1.D.169.239; 1.D.169.154; 1.D.169.157; 1.D.169.166; 1.D.169.169; 1.D.169.172; 1.D.169.175; 1.D.169.240; 1.D.169.244; 1.D.172.228; 1.D.172.229; 1.D.172.230; 1.D.172.231; 1.D.172.236; 1.D.172.237; 1.D.172.238; 1.D.172.239; 1.D.172.154; 1.D.172.157; 1.D.172.166; 1.D.172.169; 1.D.172.172; 1.D.172.175; 1.D.172.240; 1.D.172.244; 1.D.175.228; 1.D.175.229; 1.D.175.230; 1.D.175.231; 1.D.175.236; 1.D.175.237; 1.D.175.238; 1.D.175.239; 1.D.175.154; 1.D.175.157; 1.D.175.166; 1.D.175.169;

TABLE 100-continued

1.D.175.172; 1.D.175.175; 1.D.175.240; 1.D.175.244; 1.D.240.228; 1.D.240.229; 1.D.240.230; 1.D.240.231; 1.D.240.236; 1.D.240.237; 1.D.240.238; 1.D.240.239; 1.D.240.154; 1.D.240.157; 1.D.240.166; 1.D.240.169; 1.D.240.172; 1.D.240.175; 1.D.240.240; 1.D.240.244; 1.D.244.228; 1.D.244.229; 1.D.244.230; 1.D.244.231; 1.D.244.236; 1.D.244.237; 1.D.244.238; 1.D.244.239; 1.D.244.154; 1.D.244.157; 1.D.244.166; 1.D.244.169; 1.D.244.172; 1.D.244.175; 1.D.244.240; 1.D.244.244;

Prodrugs of 1.E

1.E.228.228; 1.E.228.229; 1.E.228.230; 1.E.228.231; 1.E.228.236; 1.E.228.237; 1.E.228.238; 1.E.228.239; 1.E.228.154; 1.E.228.157; 1.E.228.166; 1.E.228.169; 1.E.228.172; 1.E.228.175; 1.E.228.240; 1.E.228.244; 1.E.229.228; 1.E.229.229; 1.E.229.230; 1.E.229.231; 1.E.229.236; 1.E.229.237; 1.E.229.238; 1.E.229.239; 1.E.229.154; 1.E.229.157; 1.E.229.166; 1.E.229.169; 1.E.229.172; 1.E.229.175; 1.E.229.240; 1.E.229.244; 1.E.230.228; 1.E.230.229; 1.E.230.230; 1.E.230.231; 1.E.230.236; 1.E.230.237; 1.E.230.238; 1.E.230.239; 1.E.230.154; 1.E.230.157; 1.E.230.166; 1.E.230.169; 1.E.230.172; 1.E.230.175; 1.E.230.240; 1.E.230.244; 1.E.231.228; 1.E.231.229; 1.E.231.230; 1.E.231.231; 1.E.231.236; 1.E.231.237; 1.E.231.238; 1.E.231.239; 1.E.231.154; 1.E.231.157; 1.E.231.166; 1.E.231.169; 1.E.231.172; 1.E.231.175; 1.E.231.240; 1.E.231.244; 1.E.236.228; 1.E.236.229; 1.E.236.230; 1.E.236.231; 1.E.236.236; 1.E.236.237; 1.E.236.238; 1.E.236.239; 1.E.236.154; 1.E.236.157; 1.E.236.166; 1.E.236.169; 1.E.236.172; 1.E.236.175; 1.E.236.240; 1.E.236.244; 1.E.237.228; 1.E.237.229; 1.E.237.230; 1.E.237.231; 1.E.237.236; 1.E.237.237; 1.E.237.238; 1.E.237.239; 1.E.237.154; 1.E.237.157; 1.E.237.166; 1.E.237.169; 1.E.237.172; 1.E.237.175; 1.E.237.240; 1.E.237.244; 1.E.238.228; 1.E.238.229; 1.E.238.230; 1.E.238.231; 1.E.238.236; 1.E.238.237; 1.E.238.238; 1.E.238.239; 1.E.238.154; 1.E.238.157; 1.E.238.166; 1.E.238.169; 1.E.238.172; 1.E.238.175; 1.E.238.240; 1.E.238.244; 1.E.239.228; 1.E.239.229; 1.E.239.230; 1.E.239.231; 1.E.239.236; 1.E.239.237; 1.E.239.238; 1.E.239.239; 1.E.239.154; 1.E.239.157; 1.E.239.166; 1.E.239.169; 1.E.239.172; 1.E.239.175; 1.E.239.240; 1.E.239.244; 1.E.154.228; 1.E.154.229; 1.E.154.230; 1.E.154.231; 1.E.154.236; 1.E.154.237; 1.E.154.238; 1.E.154.239; 1.E.154.154; 1.E.154.157; 1.E.154.166; 1.E.154.169; 1.E.154.172; 1.E.154.175; 1.E.154.240; 1.E.154.244; 1.E.157.228; 1.E.157.229; 1.E.157.230; 1.E.157.231; 1.E.157.236; 1.E.157.237; 1.E.157.238; 1.E.157.239; 1.E.157.154; 1.E.157.157; 1.E.157.166; 1.E.157.169; 1.E.157.172; 1.E.157.175; 1.E.157.240; 1.E.157.244; 1.E.166.228; 1.E.166.229; 1.E.166.230; 1.E.166.231; 1.E.166.236; 1.E.166.237; 1.E.166.238; 1.E.166.239; 1.E.166.154; 1.E.166.157; 1.E.166.166; 1.E.166.169; 1.E.166.172; 1.E.166.175; 1.E.166.240; 1.E.166.244; 1.E.169.228; 1.E.169.229; 1.E.169.230; 1.E.169.231; 1.E.169.236; 1.E.169.237; 1.E.169.238; 1.E.169.239; 1.E.169.154; 1.E.169.157; 1.E.169.166; 1.E.169.169; 1.E.169.172; 1.E.169.175; 1.E.169.240; 1.E.169.244; 1.E.172.228; 1.E.172.229; 1.E.172.230; 1.E.172.231; 1.E.172.236; 1.E.172.237; 1.E.172.238; 1.E.172.239; 1.E.172.154; 1.E.172.157; 1.E.172.166; 1.E.172.169; 1.E.172.172; 1.E.172.175; 1.E.172.240; 1.E.172.244; 1.E.175.228; 1.E.175.229; 1.E.175.230; 1.E.175.231; 1.E.175.236; 1.E.175.237; 1.E.175.238; 1.E.175.239; 1.E.175.154; 1.E.175.157; 1.E.175.166; 1.E.175.169; 1.E.175.172; 1.E.175.175; 1.E.175.240; 1.E.175.244; 1.E.240.228; 1.E.240.229; 1.E.240.230; 1.E.240.231; 1.E.240.236; 1.E.240.237; 1.E.240.238; 1.E.240.239; 1.E.240.154; 1.E.240.157; 1.E.240.166; 1.E.240.169; 1.E.240.172; 1.E.240.175; 1.E.240.240; 1.E.240.244; 1.E.244.228; 1.E.244.229; 1.E.244.230; 1.E.244.231; 1.E.244.236; 1.E.244.237; 1.E.244.238; 1.E.244.239; 1.E.244.154; 1.E.244.157; 1.E.244.166; 1.E.244.169; 1.E.244.172; 1.E.244.175; 1.E.244.240; 1.E.244.244;

Prodrugs of 1.G

1.G.228.228; 1.G.228.229; 1.G.228.230; 1.G.228.231; 1.G.228.236; 1.G.228.237; 1.G.228.238; 1.G.228.239; 1.G.228.154; 1.G.228.157; 1.G.228.166; 1.G.228.169; 1.G.228.172; 1.G.228.175; 1.G.228.240; 1.G.228.244; 1.G.229.228; 1.G.229.229; 1.G.229.230; 1.G.229.231; 1.G.229.236; 1.G.229.237; 1.G.229.238; 1.G.229.239; 1.G.229.154; 1.G.229.157; 1.G.229.166; 1.G.229.169; 1.G.229.172; 1.G.229.175; 1.G.229.240; 1.G.229.244; 1.G.230.228; 1.G.230.229; 1.G.230.230; 1.G.230.231; 1.G.230.236; 1.G.230.237; 1.G.230.238; 1.G.230.239; 1.G.230.154; 1.G.230.157; 1.G.230.166; 1.G.230.169; 1.G.230.172; 1.G.230.175; 1.G.230.240; 1.G.230.244; 1.G.231.228; 1.G.231.229; 1.G.231.230; 1.G.231.231; 1.G.231.236; 1.G.231.237; 1.G.231.238; 1.G.231.239; 1.G.231.154; 1.G.231.157; 1.G.231.166; 1.G.231.169; 1.G.231.172; 1.G.231.175; 1.G.231.240; 1.G.231.244; 1.G.236.228; 1.G.236.229; 1.G.236.230; 1.G.236.231; 1.G.236.236; 1.G.236.237; 1.G.236.238; 1.G.236.239; 1.G.236.154; 1.G.236.157; 1.G.236.166; 1.G.236.169; 1.G.236.172; 1.G.236.175; 1.G.236.240; 1.G.236.244; 1.G.237.228; 1.G.237.229; 1.G.237.230; 1.G.237.231; 1.G.237.236; 1.G.237.237; 1.G.237.238; 1.G.237.239; 1.G.237.154; 1.G.237.157; 1.G.237.166; 1.G.237.169; 1.G.237.172; 1.G.237.175; 1.G.237.240; 1.G.237.244; 1.G.238.228; 1.G.238.229; 1.G.238.230; 1.G.238.231; 1.G.238.236; 1.G.238.237; 1.G.238.238; 1.G.238.239; 1.G.238.154; 1.G.238.157; 1.G.238.166; 1.G.238.169; 1.G.238.172; 1.G.238.175; 1.G.238.240; 1.G.238.244; 1.G.239.228; 1.G.239.229; 1.G.239.230; 1.G.239.231; 1.G.239.236; 1.G.239.237; 1.G.239.238; 1.G.239.239;

TABLE 100-continued

1.G.239.154; 1.G.239.157; 1.G.239.166; 1.G.239.169; 1.G.239.172; 1.G.239.175; 1.G.239.240; 1.G.239.244; 1.G.154.228; 1.G.154.229; 1.G.154.230; 1.G.154.231; 1.G.154.236; 1.G.154.237; 1.G.154.238; 1.G.154.239; 1.G.154.154; 1.G.154.157; 1.G.154.166; 1.G.154.169; 1.G.154.172; 1.G.154.175; 1.G.154.240; 1.G.154.244; 1.G.157.228; 1.G.157.229; 1.G.157.230; 1.G.157.231; 1.G.157.236; 1.G.157.237; 1.G.157.238; 1.G.157.239; 1.G.157.154; 1.G.157.157; 1.G.157.166; 1.G.157.169; 1.G.157.172; 1.G.157.175; 1.G.157.240; 1.G.157.244; 1.G.166.228; 1.G.166.229; 1.G.166.230; 1.G.166.231; 1.G.166.236; 1.G.166.237; 1.G.166.238; 1.G.166.239; 1.G.166.154; 1.G.166.157; 1.G.166.166; 1.G.166.169; 1.G.166.172; 1.G.166.175; 1.G.166.240; 1.G.166.244; 1.G.169.228; 1.G.169.229; 1.G.169.230; 1.G.169.231; 1.G.169.236; 1.G.169.237; 1.G.169.238; 1.G.169.239; 1.G.169.154; 1.G.169.157; 1.G.169.166; 1.G.169.169; 1.G.169.172; 1.G.169.175; 1.G.169.240; 1.G.169.244; 1.G.172.228; 1.G.172.229; 1.G.172.230; 1.G.172.231; 1.G.172.236; 1.G.172.237; 1.G.172.238; 1.G.172.239; 1.G.172.154; 1.G.172.157; 1.G.172.166; 1.G.172.169; 1.G.172.172; 1.G.172.175; 1.G.172.240; 1.G.172.244; 1.G.175.228; 1.G.175.229; 1.G.175.230; 1.G.175.231; 1.G.175.236; 1.G.175.237; 1.G.175.238; 1.G.175.239; 1.G.175.154; 1.G.175.157; 1.G.175.166; 1.G.175.169; 1.G.175.172; 1.G.175.175; 1.G.175.240; 1.G.175.244; 1.G.240.228; 1.G.240.229; 1.G.240.230; 1.G.240.231; 1.G.240.236; 1.G.240.237; 1.G.240.238; 1.G.240.239; 1.G.240.154; 1.G.240.157; 1.G.240.166; 1.G.240.169; 1.G.240.172; 1.G.240.175; 1.G.240.240; 1.G.240.244; 1.G.244.228; 1.G.244.229; 1.G.244.230; 1.G.244.231; 1.G.244.236; 1.G.244.237; 1.G.244.238; 1.G.244.239; 1.G.244.154; 1.G.244.157; 1.G.244.166; 1.G.244.169; 1.G.244.172; 1.G.244.175; 1.G.244.240; 1.G.244.244;

Prodrugs of 1.I

1.I.228.228; 1.I.228.229; 1.I.228.230; 1.I.228.231; 1.I.228.236; 1.I.228.237; 1.I.228.238; 1.I.228.239; 1.I.228.154; 1.I.228.157; 1.I.228.166; 1.I.228.169; 1.I.228.172; 1.I.228.175; 1.I.228.240; 1.I.228.244; 1.I.229.228; 1.I.229.229; 1.I.229.230; 1.I.229.231; 1.I.229.236; 1.I.229.237; 1.I.229.238; 1.I.229.239; 1.I.229.154; 1.I.229.157; 1.I.229.166; 1.I.229.169; 1.I.229.172; 1.I.229.175; 1.I.229.240; 1.I.229.244; 1.I.230.228; 1.I.230.229; 1.I.230.230; 1.I.230.231; 1.I.230.236; 1.I.230.237; 1.I.230.238; 1.I.230.239; 1.I.230.154; 1.I.230.157; 1.I.230.166; 1.I.230.169; 1.I.230.172; 1.I.230.175; 1.I.230.240; 1.I.230.244; 1.I.231.228; 1.I.231.229; 1.I.231.230; 1.I.231.231; 1.I.231.236; 1.I.231.237; 1.I.231.238; 1.I.231.239; 1.I.231.154; 1.I.231.157; 1.I.231.166; 1.I.231.169; 1.I.231.172; 1.I.231.175; 1.I.231.240; 1.I.231.244; 1.I.236.228; 1.I.236.229; 1.I.236.230; 1.I.236.231; 1.I.236.236; 1.I.236.237; 1.I.236.238; 1.I.236.239; 1.I.236.154; 1.I.236.157; 1.I.236.166; 1.I.236.169; 1.I.236.172; 1.I.236.175; 1.I.236.240; 1.I.236.244; 1.I.237.228; 1.I.237.229; 1.I.237.230; 1.I.237.231; 1.I.237.236; 1.I.237.237; 1.I.237.238; 1.I.237.239; 1.I.237.154; 1.I.237.157; 1.I.237.166; 1.I.237.169; 1.I.237.172; 1.I.237.175; 1.I.237.240; 1.I.237.244; 1.I.238.228; 1.I.238.229; 1.I.238.230; 1.I.238.231; 1.I.238.236; 1.I.238.237; 1.I.238.238; 1.I.238.239; 1.I.238.154; 1.I.238.157; 1.I.238.166; 1.I.238.169; 1.I.238.172; 1.I.238.175; 1.I.238.240; 1.I.238.244; 1.I.239.228; 1.I.239.229; 1.I.239.230; 1.I.239.231; 1.I.239.236; 1.I.239.237; 1.I.239.238; 1.I.239.239; 1.I.239.154; 1.I.239.157; 1.I.239.166; 1.I.239.169; 1.I.239.172; 1.I.239.175; 1.I.239.240; 1.I.239.244; 1.I.154.228; 1.I.154.229; 1.I.154.230; 1.I.154.231; 1.I.154.236; 1.I.154.237; 1.I.154.238; 1.I.154.239; 1.I.154.154; 1.I.154.157; 1.I.154.166; 1.I.154.169; 1.I.154.172; 1.I.154.175; 1.I.154.240; 1.I.154.244; 1.I.157.228; 1.I.157.229; 1.I.157.230; 1.I.157.231; 1.I.157.236; 1.I.157.237; 1.I.157.238; 1.I.157.239; 1.I.157.154; 1.I.157.157; 1.I.157.166; 1.I.157.169; 1.I.157.172; 1.I.157.175; 1.I.157.240; 1.I.157.244; 1.I.166.228; 1.I.166.229; 1.I.166.230; 1.I.166.231; 1.I.166.236; 1.I.166.237; 1.I.166.238; 1.I.166.239; 1.I.166.154; 1.I.166.157; 1.I.166.166; 1.I.166.169; 1.I.166.172; 1.I.166.175; 1.I.166.240; 1.I.166.244; 1.I.169.228; 1.I.169.229; 1.I.169.230; 1.I.169.231; 1.I.169.236; 1.I.169.237; 1.I.169.238; 1.I.169.239; 1.I.169.154; 1.I.169.157; 1.I.169.166; 1.I.169.169; 1.I.169.172; 1.I.169.175; 1.I.169.240; 1.I.169.244; 1.I.172.228; 1.I.172.229; 1.I.172.230; 1.I.172.231; 1.I.172.236; 1.I.172.237; 1.I.172.238; 1.I.172.239; 1.I.172.154; 1.I.172.157; 1.I.172.166; 1.I.172.169; 1.I.172.172; 1.I.172.175; 1.I.172.240; 1.I.172.244; 1.I.175.228; 1.I.175.229; 1.I.175.230; 1.I.175.231; 1.I.175.236; 1.I.175.237; 1.I.175.238; 1.I.175.239; 1.I.175.154; 1.I.175.157; 1.I.175.166; 1.I.175.169; 1.I.175.172; 1.I.175.175; 1.I.175.240; 1.I.175.244; 1.I.240.228; 1.I.240.229; 1.I.240.230; 1.I.240.231; 1.I.240.236; 1.I.240.237; 1.I.240.238; 1.I.240.239; 1.I.240.154; 1.I.240.157; 1.I.240.166; 1.I.240.169; 1.I.240.172; 1.I.240.175; 1.I.240.240; 1.I.240.244; 1.I.244.228; 1.I.244.229; 1.I.244.230; 1.I.244.231; 1.I.244.236; 1.I.244.237; 1.I.244.238; 1.I.244.239; 1.I.244.154; 1.I.244.157; 1.I.244.166; 1.I.244.169; 1.I.244.172; 1.I.244.175; 1.I.244.240; 1.I.244.244;

Prodrugs of 1.J

1.J.228.228; 1.J.228.229; 1.J.228.230; 1.J.228.231; 1.J.228.236; 1.J.228.237; 1.J.228.238; 1.J.228.239; 1.J.228.154; 1.J.228.157; 1.J.228.166; 1.J.228.169; 1.J.228.172; 1.J.228.175; 1.J.228.240; 1.J.228.244; 1.J.229.228; 1.J.229.229; 1.J.229.230; 1.J.229.231; 1.J.229.236; 1.J.229.237; 1.J.229.238; 1.J.229.239;

TABLE 100-continued

1.J.229.154; 1.J.229.157; 1.J.229.166; 1.J.229.169; 1.J.229.172; 1.J.229.175;
1.J.229.240; 1.J.229.244; 1.J.230.228; 1.J.230.229; 1.J.230.230; 1.J.230.231;
1.J.230.236; 1.J.230.237; 1.J.230.238; 1.J.230.239; 1.J.230.154; 1.J.230.157;
1.J.230.166; 1.J.230.169; 1.J.230.172; 1.J.230.175; 1.J.230.240; 1.J.230.244;
1.J.231.228; 1.J.231.229; 1.J.231.230; 1.J.231.231; 1.J.231.236; 1.J.231.237;
1.J.231.238; 1.J.231.239; 1.J.231.154; 1.J.231.157; 1.J.231.166; 1.J.231.169;
1.J.231.172; 1.J.231.175; 1.J.231.240; 1.J.231.244; 1.J.236.228; 1.J.236.229;
1.J.236.230; 1.J.236.231; 1.J.236.236; 1.J.236.237; 1.J.236.238; 1.J.236.239;
1.J.236.154; 1.J.236.157; 1.J.236.166; 1.J.236.169; 1.J.236.172; 1.J.236.175;
1.J.236.240; 1.J.236.244; 1.J.237.228; 1.J.237.229; 1.J.237.230; 1.J.237.231;
1.J.237.236; 1.J.237.237; 1.J.237.238; 1.J.237.239; 1.J.237.154; 1.J.237.157;
1.J.237.166; 1.J.237.169; 1.J.237.172; 1.J.237.175; 1.J.237.240; 1.J.237.244;
1.J.238.228; 1.J.238.229; 1.J.238.230; 1.J.238.231; 1.J.238.236; 1.J.238.237;
1.J.238.238; 1.J.238.239; 1.J.238.154; 1.J.238.157; 1.J.238.166; 1.J.238.169;
1.J.238.172; 1.J.238.175; 1.J.238.240; 1.J.238.244; 1.J.239.228; 1.J.239.229;
1.J.239.230; 1.J.239.231; 1.J.239.236; 1.J.239.237; 1.J.239.238; 1.J.239.239;
1.J.239.154; 1.J.239.157; 1.J.239.166; 1.J.239.169; 1.J.239.172; 1.J.239.175;
1.J.239.240; 1.J.239.244; 1.J.154.228; 1.J.154.229; 1.J.154.230; 1.J.154.231;
1.J.154.236; 1.J.154.237; 1.J.154.238; 1.J.154.239; 1.J.154.154; 1.J.154.157;
1.J.154.166; 1.J.154.169; 1.J.154.172; 1.J.154.175; 1.J.154.240; 1.J.154.244;
1.J.157.228; 1.J.157.229; 1.J.157.230; 1.J.157.231; 1.J.157.236; 1.J.157.237;
1.J.157.238; 1.J.157.239; 1.J.157.154; 1.J.157.157; 1.J.157.166; 1.J.157.169;
1.J.157.172; 1.J.157.175; 1.J.157.240; 1.J.157.244; 1.J.166.228; 1.J.166.229;
1.J.166.230; 1.J.166.231; 1.J.166.236; 1.J.166.237; 1.J.166.238; 1.J.166.239;
1.J.166.154; 1.J.166.157; 1.J.166.166; 1.J.166.169; 1.J.166.172; 1.J.166.175;
1.J.166.240; 1.J.166.244; 1.J.169.228; 1.J.169.229; 1.J.169.230; 1.J.169.231;
1.J.169.236; 1.J.169.237; 1.J.169.238; 1.J.169.239; 1.J.169.154; 1.J.169.157;
1.J.169.166; 1.J.169.169; 1.J.169.172; 1.J.169.175; 1.J.169.240; 1.J.169.244;
1.J.172.228; 1.J.172.229; 1.J.172.230; 1.J.172.231; 1.J.172.236; 1.J.172.237;
1.J.172.238; 1.J.172.239; 1.J.172.154; 1.J.172.157; 1.J.172.166; 1.J.172.169;
1.J.172.172; 1.J.172.175; 1.J.172.240; 1.J.172.244; 1.J.175.228; 1.J.175.229;
1.J.175.230; 1.J.175.231; 1.J.175.236; 1.J.175.237; 1.J.175.238; 1.J.175.239;
1.J.175.154; 1.J.175.157; 1.J.175.166; 1.J.175.169; 1.J.175.172; 1.J.175.175;
1.J.175.240; 1.J.175.244; 1.J.240.228; 1.J.240.229; 1.J.240.230; 1.J.240.231;
1.J.240.236; 1.J.240.237; 1.J.240.238; 1.J.240.239; 1.J.240.154; 1.J.240.157;
1.J.240.166; 1.J.240.169; 1.J.240.172; 1.J.240.175; 1.J.240.240; 1.J.240.244;
1.J.244.228; 1.J.244.229; 1.J.244.230; 1.J.244.231; 1.J.244.236; 1.J.244.237;
1.J.244.238; 1.J.244.239; 1.J.244.154; 1.J.244.157; 1.J.244.166; 1.J.244.169;
1.J.244.172; 1.J.244.175; 1.J.244.240; 1.J.244.244;

Prodrugs of 1.L

1.L.228.228; 1.L.228.229; 1.L.228.230; 1.L.228.231; 1.L.228.236;
1.L.228.237; 1.L.228.238; 1.L.228.239; 1.L.228.154; 1.L.228.157; 1.L.228.166;
1.L.228.169; 1.L.228.172; 1.L.228.175; 1.L.228.240; 1.L.228.244; 1.L.229.228;
1.L.229.229; 1.L.229.230; 1.L.229.231; 1.L.229.236; 1.L.229.237; 1.L.229.238;
1.L.229.239; 1.L.229.154; 1.L.229.157; 1.L.229.166; 1.L.229.169; 1.L.229.172;
1.L.229.175; 1.L.229.240; 1.L.229.244; 1.L.230.228; 1.L.230.229; 1.L.230.230;
1.L.230.231; 1.L.230.236; 1.L.230.237; 1.L.230.238; 1.L.230.239; 1.L.230.154;
1.L.230.157; 1.L.230.166; 1.L.230.169; 1.L.230.172; 1.L.230.175; 1.L.230.240;
1.L.230.244; 1.L.231.228; 1.L.231.229; 1.L.231.230; 1.L.231.231; 1.L.231.236;
1.L.231.237; 1.L.231.238; 1.L.231.239; 1.L.231.154; 1.L.231.157; 1.L.231.166;
1.L.231.169; 1.L.231.172; 1.L.231.175; 1.L.231.240; 1.L.231.244; 1.L.236.228;
1.L.236.229; 1.L.236.230; 1.L.236.231; 1.L.236.236; 1.L.236.237; 1.L.236.238;
1.L.236.239; 1.L.236.154; 1.L.236.157; 1.L.236.166; 1.L.236.169; 1.L.236.172;
1.L.236.175; 1.L.236.240; 1.L.236.244; 1.L.237.228; 1.L.237.229; 1.L.237.230;
1.L.237.231; 1.L.237.236; 1.L.237.237; 1.L.237.238; 1.L.237.239; 1.L.237.154;
1.L.237.157; 1.L.237.166; 1.L.237.169; 1.L.237.172; 1.L.237.175; 1.L.237.240;
1.L.237.244; 1.L.238.228; 1.L.238.229; 1.L.238.230; 1.L.238.231; 1.L.238.236;
1.L.238.237; 1.L.238.238; 1.L.238.239; 1.L.238.154; 1.L.238.157; 1.L.238.166;
1.L.238.169; 1.L.238.172; 1.L.238.175; 1.L.238.240; 1.L.238.244; 1.L.239.228;
1.L.239.229; 1.L.239.230; 1.L.239.231; 1.L.239.236; 1.L.239.237; 1.L.239.238;
1.L.239.239; 1.L.239.154; 1.L.239.157; 1.L.239.166; 1.L.239.169; 1.L.239.172;
1.L.239.175; 1.L.239.240; 1.L.239.244; 1.L.154.228; 1.L.154.229; 1.L.154.230;
1.L.154.231; 1.L.154.236; 1.L.154.237; 1.L.154.238; 1.L.154.239; 1.L.154.154;
1.L.154.157; 1.L.154.166; 1.L.154.169; 1.L.154.172; 1.L.154.175; 1.L.154.240;
1.L.154.244; 1.L.157.228; 1.L.157.229; 1.L.157.230; 1.L.157.231; 1.L.157.236;
1.L.157.237; 1.L.157.238; 1.L.157.239; 1.L.157.154; 1.L.157.157; 1.L.157.166;
1.L.157.169; 1.L.157.172; 1.L.157.175; 1.L.157.240; 1.L.157.244; 1.L.166.228;
1.L.166.229; 1.L.166.230; 1.L.166.231; 1.L.166.236; 1.L.166.237; 1.L.166.238;
1.L.166.239; 1.L.166.154; 1.L.166.157; 1.L.166.166; 1.L.166.169; 1.L.166.172;
1.L.166.175; 1.L.166.240; 1.L.166.244; 1.L.169.228; 1.L.169.229; 1.L.169.230;
1.L.169.231; 1.L.169.236; 1.L.169.237; 1.L.169.238; 1.L.169.239; 1.L.169.154;
1.L.169.157; 1.L.169.166; 1.L.169.169; 1.L.169.172; 1.L.169.175; 1.L.169.240;
1.L.169.244; 1.L.172.228; 1.L.172.229; 1.L.172.230; 1.L.172.231; 1.L.172.236;
1.L.172.237; 1.L.172.238; 1.L.172.239; 1.L.172.154; 1.L.172.157; 1.L.172.166;
1.L.172.169; 1.L.172.172; 1.L.172.175; 1.L.172.240; 1.L.172.244; 1.L.175.228;
1.L.175.229; 1.L.175.230; 1.L.175.231; 1.L.175.236; 1.L.175.237; 1.L.175.238;
1.L.175.239; 1.L.175.154; 1.L.175.157; 1.L.175.166; 1.L.175.169; 1.L.175.172;
1.L.175.175; 1.L.175.240; 1.L.175.244; 1.L.240.228; 1.L.240.229; 1.L.240.230;

TABLE 100-continued

1.L.240.231; 1.L.240.236; 1.L.240.237; 1.L.240.238; 1.L.240.239; 1.L.240.154; 1.L.240.157; 1.L.240.166; 1.L.240.169; 1.L.240.172; 1.L.240.175; 1.L.240.240; 1.L.240.244; 1.L.244.228; 1.L.244.229; 1.L.244.230; 1.L.244.231; 1.L.244.236; 1.L.244.237; 1.L.244.238; 1.L.244.239; 1.L.244.154; 1.L.244.157; 1.L.244.166; 1.L.244.169; 1.L.244.172; 1.L.244.175; 1.L.244.240; 1.L.244.244;

Prodrugs of 1.O

1.O.228.228; 1.O.228.229; 1.O.228.230; 1.O.228.231; 1.O.228.236; 1.O.228.237; 1.O.228.238; 1.O.228.239; 1.O.228.154; 1.O.228.157; 1.O.228.166; 1.O.228.169; 1.O.228.172; 1.O.228.175; 1.O.228.240; 1.O.228.244; 1.O.229.228; 1.O.229.229; 1.O.229.230; 1.O.229.231; 1.O.229.236; 1.O.229.237; 1.O.229.238; 1.O.229.239; 1.O.229.154; 1.O.229.157; 1.O.229.166; 1.O.229.169; 1.O.229.172; 1.O.229.175; 1.O.229.240; 1.O.229.244; 1.O.230.228; 1.O.230.229; 1.O.230.230; 1.O.230.231; 1.O.230.236; 1.O.230.237; 1.O.230.238; 1.O.230.239; 1.O.230.154; 1.O.230.157; 1.O.230.166; 1.O.230.169; 1.O.230.172; 1.O.230.175; 1.O.230.240; 1.O.230.244; 1.O.231.228; 1.O.231.229; 1.O.231.230; 1.O.231.231; 1.O.231.236; 1.O.231.237; 1.O.231.238; 1.O.231.239; 1.O.231.154; 1.O.231.157; 1.O.231.166; 1.O.231.169; 1.O.231.172; 1.O.231.175; 1.O.231.240; 1.O.231.244; 1.O.236.228; 1.O.236.229; 1.O.236.230; 1.O.236.231; 1.O.236.236; 1.O.236.237; 1.O.236.238; 1.O.236.239; 1.O.236.154; 1.O.236.157; 1.O.236.166; 1.O.236.169; 1.O.236.172; 1.O.236.175; 1.O.236.240; 1.O.236.244; 1.O.237.228; 1.O.237.229; 1.O.237.230; 1.O.237.231; 1.O.237.236; 1.O.237.237; 1.O.237.238; 1.O.237.239; 1.O.237.154; 1.O.237.157; 1.O.237.166; 1.O.237.169; 1.O.237.172; 1.O.237.175; 1.O.237.240; 1.O.237.244; 1.O.238.228; 1.O.238.229; 1.O.238.230; 1.O.238.231; 1.O.238.236; 1.O.238.237; 1.O.238.238; 1.O.238.239; 1.O.238.154; 1.O.238.157; 1.O.238.166; 1.O.238.169; 1.O.238.172; 1.O.238.175; 1.O.238.240; 1.O.238.244; 1.O.239.228; 1.O.239.229; 1.O.239.230; 1.O.239.231; 1.O.239.236; 1.O.239.237; 1.O.239.238; 1.O.239.239; 1.O.239.154; 1.O.239.157; 1.O.239.166; 1.O.239.169; 1.O.239.172; 1.O.239.175; 1.O.239.240; 1.O.239.244; 1.O.154.228; 1.O.154.229; 1.O.154.230; 1.O.154.231; 1.O.154.236; 1.O.154.237; 1.O.154.238; 1.O.154.239; 1.O.154.154; 1.O.154.157; 1.O.154.166; 1.O.154.169; 1.O.154.172; 1.O.154.175; 1.O.154.240; 1.O.154.244; 1.O.157.228; 1.O.157.229; 1.O.157.230; 1.O.157.231; 1.O.157.236; 1.O.157.237; 1.O.157.238; 1.O.157.239; 1.O.157.154; 1.O.157.157; 1.O.157.166; 1.O.157.169; 1.O.157.172; 1.O.157.175; 1.O.157.240; 1.O.157.244; 1.O.166.228; 1.O.166.229; 1.O.166.230; 1.O.166.231; 1.O.166.236; 1.O.166.237; 1.O.166.238; 1.O.166.239; 1.O.166.154; 1.O.166.157; 1.O.166.166; 1.O.166.169; 1.O.166.172; 1.O.166.175; 1.O.166.240; 1.O.166.244; 1.O.169.228; 1.O.169.229; 1.O.169.230; 1.O.169.231; 1.O.169.236; 1.O.169.237; 1.O.169.238; 1.O.169.239; 1.O.169.154; 1.O.169.157; 1.O.169.166; 1.O.169.169; 1.O.169.172; 1.O.169.175; 1.O.169.240; 1.O.169.244; 1.O.172.228; 1.O.172.229; 1.O.172.230; 1.O.172.231; 1.O.172.236; 1.O.172.237; 1.O.172.238; 1.O.172.239; 1.O.172.154; 1.O.172.157; 1.O.172.166; 1.O.172.169; 1.O.172.172; 1.O.172.175; 1.O.172.240; 1.O.172.244; 1.O.175.228; 1.O.175.229; 1.O.175.230; 1.O.175.231; 1.O.175.236; 1.O.175.237; 1.O.175.238; 1.O.175.239; 1.O.175.154; 1.O.175.157; 1.O.175.166; 1.O.175.169; 1.O.175.172; 1.O.175.175; 1.O.175.240; 1.O.175.244; 1.O.240.228; 1.O.240.229; 1.O.240.230; 1.O.240.231; 1.O.240.236; 1.O.240.237; 1.O.240.238; 1.O.240.239; 1.O.240.154; 1.O.240.157; 1.O.240.166; 1.O.240.169; 1.O.240.172; 1.O.240.175; 1.O.240.240; 1.O.240.244; 1.O.244.228; 1.O.244.229; 1.O.244.230; 1.O.244.231; 1.O.244.236; 1.O.244.237; 1.O.244.238; 1.O.244.239; 1.O.244.154; 1.O.244.157; 1.O.244.166; 1.O.244.169; 1.O.244.172; 1.O.244.175; 1.O.244.240; 1.O.244.244;

Prodrugs of 1.P

1.P.228.228; 1.P.228.229; 1.P.228.230; 1.P.228.231; 1.P.228.236; 1.P.228.237; 1.P.228.238; 1.P.228.239; 1.P.228.154; 1.P.228.157; 1.P.228.166; 1.P.228.169; 1.P.228.172; 1.P.228.175; 1.P.228.240; 1.P.228.244; 1.P.229.228; 1.P.229.229; 1.P.229.230; 1.P.229.231; 1.P.229.236; 1.P.229.237; 1.P.229.238; 1.P.229.239; 1.P.229.154; 1.P.229.157; 1.P.229.166; 1.P.229.169; 1.P.229.172; 1.P.229.175; 1.P.229.240; 1.P.229.244; 1.P.230.228; 1.P.230.229; 1.P.230.230; 1.P.230.231; 1.P.230.236; 1.P.230.237; 1.P.230.238; 1.P.230.239; 1.P.230.154; 1.P.230.157; 1.P.230.166; 1.P.230.169; 1.P.230.172; 1.P.230.175; 1.P.230.240; 1.P.230.244; 1.P.231.228; 1.P.231.229; 1.P.231.230; 1.P.231.231; 1.P.231.236; 1.P.231.237; 1.P.231.238; 1.P.231.239; 1.P.231.154; 1.P.231.157; 1.P.231.166; 1.P.231.169; 1.P.231.172; 1.P.231.175; 1.P.231.240; 1.P.231.244; 1.P.236.228; 1.P.236.229; 1.P.236.230; 1.P.236.231; 1.P.236.236; 1.P.236.237; 1.P.236.238; 1.P.236.239; 1.P.236.154; 1.P.236.157; 1.P.236.166; 1.P.236.169; 1.P.236.172; 1.P.236.175; 1.P.236.240; 1.P.236.244; 1.P.237.228; 1.P.237.229; 1.P.237.230; 1.P.237.231; 1.P.237.236; 1.P.237.237; 1.P.237.238; 1.P.237.239; 1.P.237.154; 1.P.237.157; 1.P.237.166; 1.P.237.169; 1.P.237.172; 1.P.237.175; 1.P.237.240; 1.P.237.244; 1.P.238.228; 1.P.238.229; 1.P.238.230; 1.P.238.231; 1.P.238.236; 1.P.238.237; 1.P.238.238; 1.P.238.239; 1.P.238.154; 1.P.238.157; 1.P.238.166;

TABLE 100-continued

1.P.238.169; 1.P.238.172; 1.P.238.175; 1.P.238.240; 1.P.238.244; 1.P.239.228; 1.P.239.229; 1.P.239.230; 1.P.239.231; 1.P.239.236; 1.P.239.237; 1.P.239.238; 1.P.239.239; 1.P.239.154; 1.P.239.157; 1.P.239.166; 1.P.239.169; 1.P.239.172; 1.P.239.175; 1.P.239.240; 1.P.239.244; 1.P.154.228; 1.P.154.229; 1.P.154.230; 1.P.154.231; 1.P.154.236; 1.P.154.237; 1.P.154.238; 1.P.154.239; 1.P.154.154; 1.P.154.157; 1.P.154.166; 1.P.154.169; 1.P.154.172; 1.P.154.175; 1.P.154.240; 1.P.154.244; 1.P.157.228; 1.P.157.229; 1.P.157.230; 1.P.157.231; 1.P.157.236; 1.P.157.237; 1.P.157.238; 1.P.157.239; 1.P.157.154; 1.P.157.157; 1.P.157.166; 1.P.157.169; 1.P.157.172; 1.P.157.175; 1.P.157.240; 1.P.157.244; 1.P.166.228; 1.P.166.229; 1.P.166.230; 1.P.166.231; 1.P.166.236; 1.P.166.237; 1.P.166.238; 1.P.166.239; 1.P.166.154; 1.P.166.157; 1.P.166.166; 1.P.166.169; 1.P.166.172; 1.P.166.175; 1.P.166.240; 1.P.166.244; 1.P.169.228; 1.P.169.229; 1.P.169.230; 1.P.169.231; 1.P.169.236; 1.P.169.237; 1.P.169.238; 1.P.169.239; 1.P.169.154; 1.P.169.157; 1.P.169.166; 1.P.169.169; 1.P.169.172; 1.P.169.175; 1.P.169.240; 1.P.169.244; 1.P.172.228; 1.P.172.229; 1.P.172.230; 1.P.172.231; 1.P.172.236; 1.P.172.237; 1.P.172.238; 1.P.172.239; 1.P.172.154; 1.P.172.157; 1.P.172.166; 1.P.172.169; 1.P.172.172; 1.P.172.175; 1.P.172.240; 1.P.172.244; 1.P.175.228; 1.P.175.229; 1.P.175.230; 1.P.175.231; 1.P.175.236; 1.P.175.237; 1.P.175.238; 1.P.175.239; 1.P.175.154; 1.P.175.157; 1.P.175.166; 1.P.175.169; 1.P.175.172; 1.P.175.175; 1.P.175.240; 1.P.175.244; 1.P.240.228; 1.P.240.229; 1.P.240.230; 1.P.240.231; 1.P.240.236; 1.P.240.237; 1.P.240.238; 1.P.240.239; 1.P.240.154; 1.P.240.157; 1.P.240.166; 1.P.240.169; 1.P.240.172; 1.P.240.175; 1.P.240.240; 1.P.240.244; 1.P.244.228; 1.P.244.229; 1.P.244.230; 1.P.244.231; 1.P.244.236; 1.P.244.237; 1.P.244.238; 1.P.244.239; 1.P.244.154; 1.P.244.157; 1.P.244.166; 1.P.244.169; 1.P.244.172; 1.P.244.175; 1.P.244.240; 1.P.244.244;

Prodrugs of 1.U

1.U.228.228; 1.U.228.229; 1.U.228.230; 1.U.228.231; 1.U.228.236; 1.U.228.237; 1.U.228.238; 1.U.228.239; 1.U.228.154; 1.U.228.157; 1.U.228.166; 1.U.228.169; 1.U.228.172; 1.U.228.175; 1.U.228.240; 1.U.228.244; 1.U.229.228; 1.U.229.229; 1.U.229.230; 1.U.229.231; 1.U.229.236; 1.U.229.237; 1.U.229.238; 1.U.229.239; 1.U.229.154; 1.U.229.157; 1.U.229.166; 1.U.229.169; 1.U.229.172; 1.U.229.175; 1.U.229.240; 1.U.229.244; 1.U.230.228; 1.U.230.229; 1.U.230.230; 1.U.230.231; 1.U.230.236; 1.U.230.237; 1.U.230.238; 1.U.230.239; 1.U.230.154; 1.U.230.157; 1.U.230.166; 1.U.230.169; 1.U.230.172; 1.U.230.175; 1.U.230.240; 1.U.230.244; 1.U.231.228; 1.U.231.229; 1.U.231.230; 1.U.231.231; 1.U.231.236; 1.U.231.237; 1.U.231.238; 1.U.231.239; 1.U.231.154; 1.U.231.157; 1.U.231.166; 1.U.231.169; 1.U.231.172; 1.U.231.175; 1.U.231.240; 1.U.231.244; 1.U.236.228; 1.U.236.229; 1.U.236.230; 1.U.236.231; 1.U.236.236; 1.U.236.237; 1.U.236.238; 1.U.236.239; 1.U.236.154; 1.U.236.157; 1.U.236.166; 1.U.236.169; 1.U.236.172; 1.U.236.175; 1.U.236.240; 1.U.236.244; 1.U.237.228; 1.U.237.229; 1.U.237.230; 1.U.237.231; 1.U.237.236; 1.U.237.237; 1.U.237.238; 1.U.237.239; 1.U.237.154; 1.U.237.157; 1.U.237.166; 1.U.237.169; 1.U.237.172; 1.U.237.175; 1.U.237.240; 1.U.237.244; 1.U.238.228; 1.U.238.229; 1.U.238.230; 1.U.238.231; 1.U.238.236; 1.U.238.237; 1.U.238.238; 1.U.238.239; 1.U.238.154; 1.U.238.157; 1.U.238.166; 1.U.238.169; 1.U.238.172; 1.U.238.175; 1.U.238.240; 1.U.238.244; 1.U.239.228; 1.U.239.229; 1.U.239.230; 1.U.239.231; 1.U.239.236; 1.U.239.237; 1.U.239.238; 1.U.239.239; 1.U.239.154; 1.U.239.157; 1.U.239.166; 1.U.239.169; 1.U.239.172; 1.U.239.175; 1.U.239.240; 1.U.239.244; 1.U.154.228; 1.U.154.229; 1.U.154.230; 1.U.154.231; 1.U.154.236; 1.U.154.237; 1.U.154.238; 1.U.154.239; 1.U.154.154; 1.U.154.157; 1.U.154.166; 1.U.154.169; 1.U.154.172; 1.U.154.175; 1.U.154.240; 1.U.154.244; 1.U.157.228; 1.U.157.229; 1.U.157.230; 1.U.157.231; 1.U.157.236; 1.U.157.237; 1.U.157.238; 1.U.157.239; 1.U.157.154; 1.U.157.157; 1.U.157.166; 1.U.157.169; 1.U.157.172; 1.U.157.175; 1.U.157.240; 1.U.157.244; 1.U.166.228; 1.U.166.229; 1.U.166.230; 1.U.166.231; 1.U.166.236; 1.U.166.237; 1.U.166.238; 1.U.166.239; 1.U.166.154; 1.U.166.157; 1.U.166.166; 1.U.166.169; 1.U.166.172; 1.U.166.175; 1.U.166.240; 1.U.166.244; 1.U.169.228; 1.U.169.229; 1.U.169.230; 1.U.169.231; 1.U.169.236; 1.U.169.237; 1.U.169.238; 1.U.169.239; 1.U.169.154; 1.U.169.157; 1.U.169.166; 1.U.169.169; 1.U.169.172; 1.U.169.175; 1.U.169.240; 1.U.169.244; 1.U.172.228; 1.U.172.229; 1.U.172.230; 1.U.172.231; 1.U.172.236; 1.U.172.237; 1.U.172.238; 1.U.172.239; 1.U.172.154; 1.U.172.157; 1.U.172.166; 1.U.172.169; 1.U.172.172; 1.U.172.175; 1.U.172.240; 1.U.172.244; 1.U.175.228; 1.U.175.229; 1.U.175.230; 1.U.175.231; 1.U.175.236; 1.U.175.237; 1.U.175.238; 1.U.175.239; 1.U.175.154; 1.U.175.157; 1.U.175.166; 1.U.175.169; 1.U.175.172; 1.U.175.175; 1.U.175.240; 1.U.175.244; 1.U.240.228; 1.U.240.229; 1.U.240.230; 1.U.240.231; 1.U.240.236; 1.U.240.237; 1.U.240.238; 1.U.240.239; 1.U.240.154; 1.U.240.157; 1.U.240.166; 1.U.240.169; 1.U.240.172; 1.U.240.175; 1.U.240.240; 1.U.240.244; 1.U.244.228; 1.U.244.229; 1.U.244.230; 1.U.244.231; 1.U.244.236; 1.U.244.237; 1.U.244.238; 1.U.244.239; 1.U.244.154; 1.U.244.157; 1.U.244.166; 1.U.244.169; 1.U.244.172; 1.U.244.175; 1.U.244.240; 1.U.244.244;

TABLE 100-continued

Prodrugs of 1.W

1.W.228.228; 1.W.228.229; 1.W.228.230; 1.W.228.231; 1.W.228.236; 1.W.228.237; 1.W.228.238; 1.W.228.239; 1.W.228.154; 1.W.228.157; 1.W.228.166; 1.W.228.169; 1.W.228.172; 1.W.228.175; 1.W.228.240; 1.W.228.244; 1.W.229.228; 1.W.229.229; 1.W.229.230; 1.W.229.231; 1.W.229.236; 1.W.229.237; 1.W.229.238; 1.W.229.239; 1.W.229.154; 1.W.229.157; 1.W.229.166; 1.W.229.169; 1.W.229.172; 1.W.229.175; 1.W.229.240; 1.W.229.244; 1.W.230.228; 1.W.230.229; 1.W.230.230; 1.W.230.231; 1.W.230.236; 1.W.230.237; 1.W.230.238; 1.W.230.239; 1.W.230.154; 1.W.230.157; 1.W.230.166; 1.W.230.169; 1.W.230.172; 1.W.230.175; 1.W.230.240; 1.W.230.244; 1.W.231.228; 1.W.231.229; 1.W.231.230; 1.W.231.231; 1.W.231.236; 1.W.231.237; 1.W.231.238; 1.W.231.239; 1.W.231.154; 1.W.231.157; 1.W.231.166; 1.W.231.169; 1.W.231.172; 1.W.231.175; 1.W.231.240; 1.W.231.244; 1.W.236.228; 1.W.236.229; 1.W.236.230; 1.W.236.231; 1.W.236.236; 1.W.236.237; 1.W.236.238; 1.W.236.239; 1.W.236.154; 1.W.236.157; 1.W.236.166; 1.W.236.169; 1.W.236.172; 1.W.236.175; 1.W.236.240; 1.W.236.244; 1.W.237.228; 1.W.237.229; 1.W.237.230; 1.W.237.231; 1.W.237.236; 1.W.237.237; 1.W.237.238; 1.W.237.239; 1.W.237.154; 1.W.237.157; 1.W.237.166; 1.W.237.169; 1.W.237.172; 1.W.237.175; 1.W.237.240; 1.W.237.244; 1.W.238.228; 1.W.238.229; 1.W.238.230; 1.W.238.231; 1.W.238.236; 1.W.238.237; 1.W.238.238; 1.W.238.239; 1.W.238.154; 1.W.238.157; 1.W.238.166; 1.W.238.169; 1.W.238.172; 1.W.238.175; 1.W.238.240; 1.W.238.244; 1.W.239.228; 1.W.239.229; 1.W.239.230; 1.W.239.231; 1.W.239.236; 1.W.239.237; 1.W.239.238; 1.W.239.239; 1.W.239.154; 1.W.239.157; 1.W.239.166; 1.W.239.169; 1.W.239.172; 1.W.239.175; 1.W.239.240; 1.W.239.244; 1.W.154.228; 1.W.154.229; 1.W.154.230; 1.W.154.231; 1.W.154.236; 1.W.154.237; 1.W.154.238; 1.W.154.239; 1.W.154.154; 1.W.154.157; 1.W.154.166; 1.W.154.169; 1.W.154.172; 1.W.154.175; 1.W.154.240; 1.W.154.244; 1.W.157.228; 1.W.157.229; 1.W.157.230; 1.W.157.231; 1.W.157.236; 1.W.157.237; 1.W.157.238; 1.W.157.239; 1.W.157.154; 1.W.157.157; 1.W.157.166; 1.W.157.169; 1.W.157.172; 1.W.157.175; 1.W.157.240; 1.W.157.244; 1.W.166.228; 1.W.166.229; 1.W.166.230; 1.W.166.231; 1.W.166.236; 1.W.166.237; 1.W.166.238; 1.W.166.239; 1.W.166.154; 1.W.166.157; 1.W.166.166; 1.W.166.169; 1.W.166.172; 1.W.166.175; 1.W.166.240; 1.W.166.244; 1.W.169.228; 1.W.169.229; 1.W.169.230; 1.W.169.231; 1.W.169.236; 1.W.169.237; 1.W.169.238; 1.W.169.239; 1.W.169.154; 1.W.169.157; 1.W.169.166; 1.W.169.169; 1.W.169.172; 1.W.169.175; 1.W.169.240; 1.W.169.244; 1.W.172.228; 1.W.172.229; 1.W.172.230; 1.W.172.231; 1.W.172.236; 1.W.172.237; 1.W.172.238; 1.W.172.239; 1.W.172.154; 1.W.172.157; 1.W.172.166; 1.W.172.169; 1.W.172.172; 1.W.172.175; 1.W.172.240; 1.W.172.244; 1.W.175.228; 1.W.175.229; 1.W.175.230; 1.W.175.231; 1.W.175.236; 1.W.175.237; 1.W.175.238; 1.W.175.239; 1.W.175.154; 1.W.175.157; 1.W.175.166; 1.W.175.169; 1.W.175.172; 1.W.175.175; 1.W.175.240; 1.W.175.244; 1.W.240.228; 1.W.240.229; 1.W.240.230; 1.W.240.231; 1.W.240.236; 1.W.240.237; 1.W.240.238; 1.W.240.239; 1.W.240.154; 1.W.240.157; 1.W.240.166; 1.W.240.169; 1.W.240.172; 1.W.240.175; 1.W.240.240; 1.W.240.244; 1.W.244.228; 1.W.244.229; 1.W.244.230; 1.W.244.231; 1.W.244.236; 1.W.244.237; 1.W.244.238; 1.W.244.239; 1.W.244.154; 1.W.244.157; 1.W.244.166; 1.W.244.169; 1.W.244.172; 1.W.244.175; 1.W.244.240; 1.W.244.244;

Prodrugs of 1.Y

1.Y.228.228; 1.Y.228.229; 1.Y.228.230; 1.Y.228.231; 1.Y.228.236; 1.Y.228.237; 1.Y.228.238; 1.Y.228.239; 1.Y.228.154; 1.Y.228.157; 1.Y.228.166; 1.Y.228.169; 1.Y.228.172; 1.Y.228.175; 1.Y.228.240; 1.Y.228.244; 1.Y.229.228; 1.Y.229.229; 1.Y.229.230; 1.Y.229.231; 1.Y.229.236; 1.Y.229.237; 1.Y.229.238; 1.Y.229.239; 1.Y.229.154; 1.Y.229.157; 1.Y.229.166; 1.Y.229.169; 1.Y.229.172; 1.Y.229.175; 1.Y.229.240; 1.Y.229.244; 1.Y.230.228; 1.Y.230.229; 1.Y.230.230; 1.Y.230.231; 1.Y.230.236; 1.Y.230.237; 1.Y.230.238; 1.Y.230.239; 1.Y.230.154; 1.Y.230.157; 1.Y.230.166; 1.Y.230.169; 1.Y.230.172; 1.Y.230.175; 1.Y.230.240; 1.Y.230.244; 1.Y.231.228; 1.Y.231.229; 1.Y.231.230; 1.Y.231.231; 1.Y.231.236; 1.Y.231.237; 1.Y.231.238; 1.Y.231.239; 1.Y.231.154; 1.Y.231.157; 1.Y.231.166; 1.Y.231.169; 1.Y.231.172; 1.Y.231.175; 1.Y.231.240; 1.Y.231.244; 1.Y.236.228; 1.Y.236.229; 1.Y.236.230; 1.Y.236.231; 1.Y.236.236; 1.Y.236.237; 1.Y.236.238; 1.Y.236.239; 1.Y.236.154; 1.Y.236.157; 1.Y.236.166; 1.Y.236.169; 1.Y.236.172; 1.Y.236.175; 1.Y.236.240; 1.Y.236.244; 1.Y.237.228; 1.Y.237.229; 1.Y.237.230; 1.Y.237.231; 1.Y.237.236; 1.Y.237.237; 1.Y.237.238; 1.Y.237.239; 1.Y.237.154; 1.Y.237.157; 1.Y.237.166; 1.Y.237.169; 1.Y.237.172; 1.Y.237.175; 1.Y.237.240; 1.Y.237.244; 1.Y.238.228; 1.Y.238.229; 1.Y.238.230; 1.Y.238.231; 1.Y.238.236; 1.Y.238.237; 1.Y.238.238; 1.Y.238.239; 1.Y.238.154; 1.Y.238.157; 1.Y.238.166; 1.Y.238.169; 1.Y.238.172; 1.Y.238.175; 1.Y.238.240; 1.Y.238.244; 1.Y.239.228; 1.Y.239.229; 1.Y.239.230; 1.Y.239.231; 1.Y.239.236; 1.Y.239.237; 1.Y.239.238; 1.Y.239.239; 1.Y.239.154; 1.Y.239.157; 1.Y.239.166; 1.Y.239.169; 1.Y.239.172; 1.Y.239.175; 1.Y.239.240; 1.Y.239.244; 1.Y.154.228; 1.Y.154.229; 1.Y.154.230; 1.Y.154.231; 1.Y.154.236; 1.Y.154.237; 1.Y.154.238; 1.Y.154.239; 1.Y.154.154;

TABLE 100-continued

1.Y.154.157; 1.Y.154.166; 1.Y.154.169; 1.Y.154.172; 1.Y.154.175; 1.Y.154.240; 1.Y.154.244; 1.Y.157.228; 1.Y.157.229; 1.Y.157.230; 1.Y.157.231; 1.Y.157.236; 1.Y.157.237; 1.Y.157.238; 1.Y.157.239; 1.Y.157.154; 1.Y.157.157; 1.Y.157.166; 1.Y.157.169; 1.Y.157.172; 1.Y.157.175; 1.Y.157.240; 1.Y.157.244; 1.Y.166.228; 1.Y.166.229; 1.Y.166.230; 1.Y.166.231; 1.Y.166.236; 1.Y.166.237; 1.Y.166.238; 1.Y.166.239; 1.Y.166.154; 1.Y.166.157; 1.Y.166.166; 1.Y.166.169; 1.Y.166.172; 1.Y.166.175; 1.Y.166.240; 1.Y.166.244; 1.Y.169.228; 1.Y.169.229; 1.Y.169.230; 1.Y.169.231; 1.Y.169.236; 1.Y.169.237; 1.Y.169.238; 1.Y.169.239; 1.Y.169.154; 1.Y.169.157; 1.Y.169.166; 1.Y.169.169; 1.Y.169.172; 1.Y.169.175; 1.Y.169.240; 1.Y.169.244; 1.Y.172.228; 1.Y.172.229; 1.Y.172.230; 1.Y.172.231; 1.Y.172.236; 1.Y.172.237; 1.Y.172.238; 1.Y.172.239; 1.Y.172.154; 1.Y.172.157; 1.Y.172.166; 1.Y.172.169; 1.Y.172.172; 1.Y.172.175; 1.Y.172.240; 1.Y.172.244; 1.Y.175.228; 1.Y.175.229; 1.Y.175.230; 1.Y.175.231; 1.Y.175.236; 1.Y.175.237; 1.Y.175.238; 1.Y.175.239; 1.Y.175.154; 1.Y.175.157; 1.Y.175.166; 1.Y.175.169; 1.Y.175.172; 1.Y.175.175; 1.Y.175.240; 1.Y.175.244; 1.Y.240.228; 1.Y.240.229; 1.Y.240.230; 1.Y.240.231; 1.Y.240.236; 1.Y.240.237; 1.Y.240.238; 1.Y.240.239; 1.Y.240.154; 1.Y.240.157; 1.Y.240.166; 1.Y.240.169; 1.Y.240.172; 1.Y.240.175; 1.Y.240.240; 1.Y.240.244; 1.Y.244.228; 1.Y.244.229; 1.Y.244.230; 1.Y.244.231; 1.Y.244.236; 1.Y.244.237; 1.Y.244.238; 1.Y.244.239; 1.Y.244.154; 1.Y.244.157; 1.Y.244.166; 1.Y.244.169; 1.Y.244.172; 1.Y.244.175; 1.Y.244.240; 1.Y.244.244;

Prodrugs of 2.B

2.B.228.228; 2.B.228.229; 2.B.228.230; 2.B.228.231; 2.B.228.236; 2.B.228.237; 2.B.228.238; 2.B.228.239; 2.B.228.154; 2.B.228.157; 2.B.228.166; 2.B.228.169; 2.B.228.172; 2.B.228.175; 2.B.228.240; 2.B.228.244; 2.B.229.228; 2.B.229.229; 2.B.229.230; 2.B.229.231; 2.B.229.236; 2.B.229.237; 2.B.229.238; 2.B.229.239; 2.B.229.154; 2.B.229.157; 2.B.229.166; 2.B.229.169; 2.B.229.172; 2.B.229.175; 2.B.229.240; 2.B.229.244; 2.B.230.228; 2.B.230.229; 2.B.230.230; 2.B.230.231; 2.B.230.236; 2.B.230.237; 2.B.230.238; 2.B.230.239; 2.B.230.154; 2.B.230.157; 2.B.230.166; 2.B.230.169; 2.B.230.172; 2.B.230.175; 2.B.230.240; 2.B.230.244; 2.B.231.228; 2.B.231.229; 2.B.231.230; 2.B.231.231; 2.B.231.236; 2.B.231.237; 2.B.231.238; 2.B.231.239; 2.B.231.154; 2.B.231.157; 2.B.231.166; 2.B.231.169; 2.B.231.172; 2.B.231.175; 2.B.231.240; 2.B.231.244; 2.B.236.228; 2.B.236.229; 2.B.236.230; 2.B.236.231; 2.B.236.236; 2.B.236.237; 2.B.236.238; 2.B.236.239; 2.B.236.154; 2.B.236.157; 2.B.236.166; 2.B.236.169; 2.B.236.172; 2.B.236.175; 2.B.236.240; 2.B.236.244; 2.B.237.228; 2.B.237.229; 2.B.237.230; 2.B.237.231; 2.B.237.236; 2.B.237.237; 2.B.237.238; 2.B.237.239; 2.B.237.154; 2.B.237.157; 2.B.237.166; 2.B.237.169; 2.B.237.172; 2.B.237.175; 2.B.237.240; 2.B.237.244; 2.B.238.228; 2.B.238.229; 2.B.238.230; 2.B.238.231; 2.B.238.236; 2.B.238.237; 2.B.238.238; 2.B.238.239; 2.B.238.154; 2.B.238.157; 2.B.238.166; 2.B.238.169; 2.B.238.172; 2.B.238.175; 2.B.238.240; 2.B.238.244; 2.B.239.228; 2.B.239.229; 2.B.239.230; 2.B.239.231; 2.B.239.236; 2.B.239.237; 2.B.239.238; 2.B.239.239; 2.B.239.154; 2.B.239.157; 2.B.239.166; 2.B.239.169; 2.B.239.172; 2.B.239.175; 2.B.239.240; 2.B.239.244; 2.B.154.228; 2.B.154.229; 2.B.154.230; 2.B.154.231; 2.B.154.236; 2.B.154.237; 2.B.154.238; 2.B.154.239; 2.B.154.154; 2.B.154.157; 2.B.154.166; 2.B.154.169; 2.B.154.172; 2.B.154.175; 2.B.154.240; 2.B.154.244; 2.B.157.228; 2.B.157.229; 2.B.157.230; 2.B.157.231; 2.B.157.236; 2.B.157.237; 2.B.157.238; 2.B.157.239; 2.B.157.154; 2.B.157.157; 2.B.157.166; 2.B.157.169; 2.B.157.172; 2.B.157.175; 2.B.157.240; 2.B.157.244; 2.B.166.228; 2.B.166.229; 2.B.166.230; 2.B.166.231; 2.B.166.236; 2.B.166.237; 2.B.166.238; 2.B.166.239; 2.B.166.154; 2.B.166.157; 2.B.166.166; 2.B.166.169; 2.B.166.172; 2.B.166.175; 2.B.166.240; 2.B.166.244; 2.B.169.228; 2.B.169.229; 2.B.169.230; 2.B.169.231; 2.B.169.236; 2.B.169.237; 2.B.169.238; 2.B.169.239; 2.B.169.154; 2.B.169.157; 2.B.169.166; 2.B.169.169; 2.B.169.172; 2.B.169.175; 2.B.169.240; 2.B.169.244; 2.B.172.228; 2.B.172.229; 2.B.172.230; 2.B.172.231; 2.B.172.236; 2.B.172.237; 2.B.172.238; 2.B.172.239; 2.B.172.154; 2.B.172.157; 2.B.172.166; 2.B.172.169; 2.B.172.172; 2.B.172.175; 2.B.172.240; 2.B.172.244; 2.B.175.228; 2.B.175.229; 2.B.175.230; 2.B.175.231; 2.B.175.236; 2.B.175.237; 2.B.175.238; 2.B.175.239; 2.B.175.154; 2.B.175.157; 2.B.175.166; 2.B.175.169; 2.B.175.172; 2.B.175.175; 2.B.175.240; 2.B.175.244; 2.B.240.228; 2.B.240.229; 2.B.240.230; 2.B.240.231; 2.B.240.236; 2.B.240.237; 2.B.240.238; 2.B.240.239; 2.B.240.154; 2.B.240.157; 2.B.240.166; 2.B.240.169; 2.B.240.172; 2.B.240.175; 2.B.240.240; 2.B.240.244; 2.B.244.228; 2.B.244.229; 2.B.244.230; 2.B.244.231; 2.B.244.236; 2.B.244.237; 2.B.244.238; 2.B.244.239; 2.B.244.154; 2.B.244.157; 2.B.244.166; 2.B.244.169; 2.B.244.172; 2.B.244.175; 2.B.244.240; 2.B.244.244;

Prodrugs of 2.D

2.D.228.228; 2.D.228.229; 2.D.228.230; 2.D.228.231; 2.D.228.236; 2.D.228.237; 2.D.228.238; 2.D.228.239; 2.D.228.154; 2.D.228.157; 2.D.228.166; 2.D.228.169; 2.D.228.172; 2.D.228.175; 2.D.228.240; 2.D.228.244; 2.D.229.228; 2.D.229.229; 2.D.229.230; 2.D.229.231; 2.D.229.236; 2.D.229.237; 2.D.229.238; 2.D.229.239; 2.D.229.154; 2.D.229.157; 2.D.229.166; 2.D.229.169; 2.D.229.172; 2.D.229.175; 2.D.229.240; 2.D.229.244; 2.D.230.228; 2.D.230.229; 2.D.230.230; 2.D.230.231; 2.D.230.236; 2.D.230.237; 2.D.230.238; 2.D.230.239; 2.D.230.154; 2.D.230.157; 2.D.230.166; 2.D.230.169; 2.D.230.172; 2.D.230.175; 2.D.230.240; 2.D.230.244; 2.D.231.228; 2.D.231.229; 2.D.231.230; 2.D.231.231; 2.D.231.236; 2.D.231.237; 2.D.231.238; 2.D.231.239; 2.D.231.154; 2.D.231.157; 2.D.231.166; 2.D.231.169;

TABLE 100-continued

2.D.231.172; 2.D.231.175; 2.D.231.240; 2.D.231.244; 2.D.236.228; 2.D.236.229; 2.D.236.230; 2.D.236.231; 2.D.236.236; 2.D.236.237; 2.D.236.238; 2.D.236.239; 2.D.236.154; 2.D.236.157; 2.D.236.166; 2.D.236.169; 2.D.236.172; 2.D.236.175; 2.D.236.240; 2.D.236.244; 2.D.237.228; 2.D.237.229; 2.D.237.230; 2.D.237.231; 2.D.237.236; 2.D.237.237; 2.D.237.238; 2.D.237.239; 2.D.237.154; 2.D.237.157; 2.D.237.166; 2.D.237.169; 2.D.237.172; 2.D.237.175; 2.D.237.240; 2.D.237.244; 2.D.238.228; 2.D.238.229; 2.D.238.230; 2.D.238.231; 2.D.238.236; 2.D.238.237; 2.D.238.238; 2.D.238.239; 2.D.238.154; 2.D.238.157; 2.D.238.166; 2.D.238.169; 2.D.238.172; 2.D.238.175; 2.D.238.240; 2.D.238.244; 2.D.239.228; 2.D.239.229; 2.D.239.230; 2.D.239.231; 2.D.239.236; 2.D.239.237; 2.D.239.238; 2.D.239.239; 2.D.239.154; 2.D.239.157; 2.D.239.166; 2.D.239.169; 2.D.239.172; 2.D.239.175; 2.D.239.240; 2.D.239.244; 2.D.154.228; 2.D.154.229; 2.D.154.230; 2.D.154.231; 2.D.154.236; 2.D.154.237; 2.D.154.238; 2.D.154.239; 2.D.154.154; 2.D.154.157; 2.D.154.166; 2.D.154.169; 2.D.154.172; 2.D.154.175; 2.D.154.240; 2.D.154.244; 2.D.157.228; 2.D.157.229; 2.D.157.230; 2.D.157.231; 2.D.157.236; 2.D.157.237; 2.D.157.238; 2.D.157.239; 2.D.157.154; 2.D.157.157; 2.D.157.166; 2.D.157.169; 2.D.157.172; 2.D.157.175; 2.D.157.240; 2.D.157.244; 2.D.166.228; 2.D.166.229; 2.D.166.230; 2.D.166.231; 2.D.166.236; 2.D.166.237; 2.D.166.238; 2.D.166.239; 2.D.166.154; 2.D.166.157; 2.D.166.166; 2.D.166.169; 2.D.166.172; 2.D.166.175; 2.D.166.240; 2.D.166.244; 2.D.169.228; 2.D.169.229; 2.D.169.230; 2.D.169.231; 2.D.169.236; 2.D.169.237; 2.D.169.238; 2.D.169.239; 2.D.169.154; 2.D.169.157; 2.D.169.166; 2.D.169.169; 2.D.169.172; 2.D.169.175; 2.D.169.240; 2.D.169.244; 2.D.172.228; 2.D.172.229; 2.D.172.230; 2.D.172.231; 2.D.172.236; 2.D.172.237; 2.D.172.238; 2.D.172.239; 2.D.172.154; 2.D.172.157; 2.D.172.166; 2.D.172.169; 2.D.172.172; 2.D.172.175; 2.D.172.240; 2.D.172.244; 2.D.175.228; 2.D.175.229; 2.D.175.230; 2.D.175.231; 2.D.175.236; 2.D.175.237; 2.D.175.238; 2.D.175.239; 2.D.175.154; 2.D.175.157; 2.D.175.166; 2.D.175.169; 2.D.175.172; 2.D.175.175; 2.D.175.240; 2.D.175.244; 2.D.240.228; 2.D.240.229; 2.D.240.230; 2.D.240.231; 2.D.240.236; 2.D.240.237; 2.D.240.238; 2.D.240.239; 2.D.240.154; 2.D.240.157; 2.D.240.166; 2.D.240.169; 2.D.240.172; 2.D.240.175; 2.D.240.240; 2.D.240.244; 2.D.244.228; 2.D.244.229; 2.D.244.230; 2.D.244.231; 2.D.244.236; 2.D.244.237; 2.D.244.238; 2.D.244.239; 2.D.244.154; 2.D.244.157; 2.D.244.166; 2.D.244.169; 2.D.244.172; 2.D.244.175; 2.D.244.240; 2.D.244.244;

Prodrugs of 2.E

2.E.228.228; 2.E.228.229; 2.E.228.230; 2.E.228.231; 2.E.228.236; 2.E.228.237; 2.E.228.238; 2.E.228.239; 2.E.228.154; 2.E.228.157; 2.E.228.166; 2.E.228.169; 2.E.228.172; 2.E.228.175; 2.E.228.240; 2.E.228.244; 2.E.229.228; 2.E.229.229; 2.E.229.230; 2.E.229.231; 2.E.229.236; 2.E.229.237; 2.E.229.238; 2.E.229.239; 2.E.229.154; 2.E.229.157; 2.E.229.166; 2.E.229.169; 2.E.229.172; 2.E.229.175; 2.E.229.240; 2.E.229.244; 2.E.230.228; 2.E.230.229; 2.E.230.230; 2.E.230.231; 2.E.230.236; 2.E.230.237; 2.E.230.238; 2.E.230.239; 2.E.230.154; 2.E.230.157; 2.E.230.166; 2.E.230.169; 2.E.230.172; 2.E.230.175; 2.E.230.240; 2.E.230.244; 2.E.231.228; 2.E.231.229; 2.E.231.230; 2.E.231.231; 2.E.231.236; 2.E.231.237; 2.E.231.238; 2.E.231.239; 2.E.231.154; 2.E.231.157; 2.E.231.166; 2.E.231.169; 2.E.231.172; 2.E.231.175; 2.E.231.240; 2.E.231.244; 2.E.236.228; 2.E.236.229; 2.E.236.230; 2.E.236.231; 2.E.236.236; 2.E.236.237; 2.E.236.238; 2.E.236.239; 2.E.236.154; 2.E.236.157; 2.E.236.166; 2.E.236.169; 2.E.236.172; 2.E.236.175; 2.E.236.240; 2.E.236.244; 2.E.237.228; 2.E.237.229; 2.E.237.230; 2.E.237.231; 2.E.237.236; 2.E.237.237; 2.E.237.238; 2.E.237.239; 2.E.237.154; 2.E.237.157; 2.E.237.166; 2.E.237.169; 2.E.237.172; 2.E.237.175; 2.E.237.240; 2.E.237.244; 2.E.238.228; 2.E.238.229; 2.E.238.230; 2.E.238.231; 2.E.238.236; 2.E.238.237; 2.E.238.238; 2.E.238.239; 2.E.238.154; 2.E.238.157; 2.E.238.166; 2.E.238.169; 2.E.238.172; 2.E.238.175; 2.E.238.240; 2.E.238.244; 2.E.239.228; 2.E.239.229; 2.E.239.230; 2.E.239.231; 2.E.239.236; 2.E.239.237; 2.E.239.238; 2.E.239.239; 2.E.239.154; 2.E.239.157; 2.E.239.166; 2.E.239.169; 2.E.239.172; 2.E.239.175; 2.E.239.240; 2.E.239.244; 2.E.154.228; 2.E.154.229; 2.E.154.230; 2.E.154.231; 2.E.154.236; 2.E.154.237; 2.E.154.238; 2.E.154.239; 2.E.154.154; 2.E.154.157; 2.E.154.166; 2.E.154.169; 2.E.154.172; 2.E.154.175; 2.E.154.240; 2.E.154.244; 2.E.157.228; 2.E.157.229; 2.E.157.230; 2.E.157.231; 2.E.157.236; 2.E.157.237; 2.E.157.238; 2.E.157.239; 2.E.157.154; 2.E.157.157; 2.E.157.166; 2.E.157.169; 2.E.157.172; 2.E.157.175; 2.E.157.240; 2.E.157.244; 2.E.166.228; 2.E.166.229; 2.E.166.230; 2.E.166.231; 2.E.166.236; 2.E.166.237; 2.E.166.238; 2.E.166.239; 2.E.166.154; 2.E.166.157; 2.E.166.166; 2.E.166.169; 2.E.166.172; 2.E.166.175; 2.E.166.240; 2.E.166.244; 2.E.169.228; 2.E.169.229; 2.E.169.230; 2.E.169.231; 2.E.169.236; 2.E.169.237; 2.E.169.238; 2.E.169.239; 2.E.169.154; 2.E.169.157; 2.E.169.166; 2.E.169.169; 2.E.169.172; 2.E.169.175; 2.E.169.240; 2.E.169.244; 2.E.172.228; 2.E.172.229; 2.E.172.230; 2.E.172.231; 2.E.172.236; 2.E.172.237; 2.E.172.238; 2.E.172.239; 2.E.172.154; 2.E.172.157; 2.E.172.166; 2.E.172.169; 2.E.172.172; 2.E.172.175; 2.E.172.240; 2.E.172.244; 2.E.175.228; 2.E.175.229; 2.E.175.230; 2.E.175.231; 2.E.175.236; 2.E.175.237; 2.E.175.238; 2.E.175.239; 2.E.175.154; 2.E.175.157; 2.E.175.166; 2.E.175.169; 2.E.175.172;

TABLE 100-continued

2.E.175.175; 2.E.175.240; 2.E.175.244; 2.E.240.228; 2.E.240.229; 2.E.240.230;
2.E.240.231; 2.E.240.236; 2.E.240.237; 2.E.240.238; 2.E.240.239; 2.E.240.154;
2.E.240.157; 2.E.240.166; 2.E.240.169; 2.E.240.172; 2.E.240.175; 2.E.240.240;
2.E.240.244; 2.E.244.228; 2.E.244.229; 2.E.244.230; 2.E.244.231; 2.E.244.236;
2.E.244.237; 2.E.244.238; 2.E.244.239; 2.E.244.154; 2.E.244.157; 2.E.244.166;
2.E.244.169; 2.E.244.172; 2.E.244.175; 2.E.244.240; 2.E.244.244;

Prodrugs of 2.G

2.G.228.228; 2.G.228.229; 2.G.228.230; 2.G.228.231; 2.G.228.236;
2.G.228.237; 2.G.228.238; 2.G.228.239; 2.G.228.154; 2.G.228.157;
2.G.228.166; 2.G.228.169; 2.G.228.172; 2.G.228.175; 2.G.228.240;
2.G.228.244; 2.G.229.228; 2.G.229.229; 2.G.229.230; 2.G.229.231;
2.G.229.236; 2.G.229.237; 2.G.229.238; 2.G.229.239; 2.G.229.154;
2.G.229.157; 2.G.229.166; 2.G.229.169; 2.G.229.172; 2.G.229.175;
2.G.229.240; 2.G.229.244; 2.G.230.228; 2.G.230.229; 2.G.230.230;
2.G.230.231; 2.G.230.236; 2.G.230.237; 2.G.230.238; 2.G.230.239;
2.G.230.154; 2.G.230.157; 2.G.230.166; 2.G.230.169; 2.G.230.172;
2.G.230.175; 2.G.230.240; 2.G.230.244; 2.G.231.228; 2.G.231.229;
2.G.231.230; 2.G.231.231; 2.G.231.236; 2.G.231.237; 2.G.231.238;
2.G.231.239; 2.G.231.154; 2.G.231.157; 2.G.231.166; 2.G.231.169;
2.G.231.172; 2.G.231.175; 2.G.231.240; 2.G.231.244; 2.G.236.228;
2.G.236.229; 2.G.236.230; 2.G.236.231; 2.G.236.236; 2.G.236.237;
2.G.236.238; 2.G.236.239; 2.G.236.154; 2.G.236.157; 2.G.236.166;
2.G.236.169; 2.G.236.172; 2.G.236.175; 2.G.236.240; 2.G.236.244;
2.G.237.228; 2.G.237.229; 2.G.237.230; 2.G.237.231; 2.G.237.236;
2.G.237.237; 2.G.237.238; 2.G.237.239; 2.G.237.154; 2.G.237.157;
2.G.237.166; 2.G.237.169; 2.G.237.172; 2.G.237.175; 2.G.237.240;
2.G.237.244; 2.G.238.228; 2.G.238.229; 2.G.238.230; 2.G.238.231;
2.G.238.236; 2.G.238.237; 2.G.238.238; 2.G.238.239; 2.G.238.154;
2.G.238.157; 2.G.238.166; 2.G.238.169; 2.G.238.172; 2.G.238.175;
2.G.238.240; 2.G.238.244; 2.G.239.228; 2.G.239.229; 2.G.239.230;
2.G.239.231; 2.G.239.236; 2.G.239.237; 2.G.239.238; 2.G.239.239;
2.G.239.154; 2.G.239.157; 2.G.239.166; 2.G.239.169; 2.G.239.172;
2.G.239.175; 2.G.239.240; 2.G.239.244; 2.G.154.228; 2.G.154.229;
2.G.154.230; 2.G.154.231; 2.G.154.236; 2.G.154.237; 2.G.154.238;
2.G.154.239; 2.G.154.154; 2.G.154.157; 2.G.154.166; 2.G.154.169;
2.G.154.172; 2.G.154.175; 2.G.154.240; 2.G.154.244; 2.G.157.228;
2.G.157.229; 2.G.157.230; 2.G.157.231; 2.G.157.236; 2.G.157.237;
2.G.157.238; 2.G.157.239; 2.G.157.154; 2.G.157.157; 2.G.157.166;
2.G.157.169; 2.G.157.172; 2.G.157.175; 2.G.157.240; 2.G.157.244;
2.G.166.228; 2.G.166.229; 2.G.166.230; 2.G.166.231; 2.G.166.236;
2.G.166.237; 2.G.166.238; 2.G.166.239; 2.G.166.154; 2.G.166.157;
2.G.166.166; 2.G.166.169; 2.G.166.172; 2.G.166.175; 2.G.166.240;
2.G.166.244; 2.G.169.228; 2.G.169.229; 2.G.169.230; 2.G.169.231;
2.G.169.236; 2.G.169.237; 2.G.169.238; 2.G.169.239; 2.G.169.154;
2.G.169.157; 2.G.169.166; 2.G.169.169; 2.G.169.172; 2.G.169.175;
2.G.169.240; 2.G.169.244; 2.G.172.228; 2.G.172.229; 2.G.172.230;
2.G.172.231; 2.G.172.236; 2.G.172.237; 2.G.172.238; 2.G.172.239;
2.G.172.154; 2.G.172.157; 2.G.172.166; 2.G.172.169; 2.G.172.172;
2.G.172.175; 2.G.172.240; 2.G.172.244; 2.G.175.228; 2.G.175.229;
2.G.175.230; 2.G.175.231; 2.G.175.236; 2.G.175.237; 2.G.175.238;
2.G.175.239; 2.G.175.154; 2.G.175.157; 2.G.175.166; 2.G.175.169;
2.G.175.172; 2.G.175.175; 2.G.175.240; 2.G.175.244; 2.G.240.228;
2.G.240.229; 2.G.240.230; 2.G.240.231; 2.G.240.236; 2.G.240.237;
2.G.240.238; 2.G.240.239; 2.G.240.154; 2.G.240.157; 2.G.240.166;
2.G.240.169; 2.G.240.172; 2.G.240.175; 2.G.240.240; 2.G.240.244;
2.G.244.228; 2.G.244.229; 2.G.244.230; 2.G.244.231; 2.G.244.236;
2.G.244.237; 2.G.244.238; 2.G.244.239; 2.G.244.154; 2.G.244.157;
2.G.244.166; 2.G.244.169; 2.G.244.172; 2.G.244.175; 2.G.244.240;
2.G.244.244;

Prodrugs of 2.I

2.I.228.228; 2.I.228.229; 2.I.228.230; 2.I.228.231; 2.I.228.236; 2.I.228.237;
2.I.228.238; 2.I.228.239; 2.I.228.154; 2.I.228.157; 2.I.228.166; 2.I.228.169;
2.I.228.172; 2.I.228.175; 2.I.228.240; 2.I.228.244; 2.I.229.228; 2.I.229.229;
2.I.229.230; 2.I.229.231; 2.I.229.236; 2.I.229.237; 2.I.229.238; 2.I.229.239;
2.I.229.154; 2.I.229.157; 2.I.229.166; 2.I.229.169; 2.I.229.172; 2.I.229.175;
2.I.229.240; 2.I.229.244; 2.I.230.228; 2.I.230.229; 2.I.230.230; 2.I.230.231;
2.I.230.236; 2.I.230.237; 2.I.230.238; 2.I.230.239; 2.I.230.154; 2.I.230.157;
2.I.230.166; 2.I.230.169; 2.I.230.172; 2.I.230.175; 2.I.230.240; 2.I.230.244;
2.I.231.228; 2.I.231.229; 2.I.231.230; 2.I.231.231; 2.I.231.236; 2.I.231.237;
2.I.231.238; 2.I.231.239; 2.I.231.154; 2.I.231.157; 2.I.231.166; 2.I.231.169;
2.I.231.172; 2.I.231.175; 2.I.231.240; 2.I.231.244; 2.I.236.228; 2.I.236.229;
2.I.236.230; 2.I.236.231; 2.I.236.236; 2.I.236.237; 2.I.236.238; 2.I.236.239;
2.I.236.154; 2.I.236.157; 2.I.236.166; 2.I.236.169; 2.I.236.172; 2.I.236.175;
2.I.236.240; 2.I.236.244; 2.I.237.228; 2.I.237.229; 2.I.237.230; 2.I.237.231;
2.I.237.236; 2.I.237.237; 2.I.237.238; 2.I.237.239; 2.I.237.154; 2.I.237.157;
2.I.237.166; 2.I.237.169; 2.I.237.172; 2.I.237.175; 2.I.237.240; 2.I.237.244;
2.I.238.228; 2.I.238.229; 2.I.238.230; 2.I.238.231; 2.I.238.236; 2.I.238.237;

TABLE 100-continued

2.I.238.238; 2.I.238.239; 2.I.238.154; 2.I.238.157; 2.I.238.166; 2.I.238.169; 2.I.238.172; 2.I.238.175; 2.I.238.240; 2.I.238.244; 2.I.239.228; 2.I.239.229; 2.I.239.230; 2.I.239.231; 2.I.239.236; 2.I.239.237; 2.I.239.238; 2.I.239.239; 2.I.239.154; 2.I.239.157; 2.I.239.166; 2.I.239.169; 2.I.239.172; 2.I.239.175; 2.I.239.240; 2.I.239.244; 2.I.154.228; 2.I.154.229; 2.I.154.230; 2.I.154.231; 2.I.154.236; 2.I.154.237; 2.I.154.238; 2.I.154.239; 2.I.154.154; 2.I.154.157; 2.I.154.166; 2.I.154.169; 2.I.154.172; 2.I.154.175; 2.I.154.240; 2.I.154.244; 2.I.157.228; 2.I.157.229; 2.I.157.230; 2.I.157.231; 2.I.157.236; 2.I.157.237; 2.I.157.238; 2.I.157.239; 2.I.157.154; 2.I.157.157; 2.I.157.166; 2.I.157.169; 2.I.157.172; 2.I.157.175; 2.I.157.240; 2.I.157.244; 2.I.166.228; 2.I.166.229; 2.I.166.230; 2.I.166.231; 2.I.166.236; 2.I.166.237; 2.I.166.238; 2.I.166.239; 2.I.166.154; 2.I.166.157; 2.I.166.166; 2.I.166.169; 2.I.166.172; 2.I.166.175; 2.I.166.240; 2.I.166.244; 2.I.169.228; 2.I.169.229; 2.I.169.230; 2.I.169.231; 2.I.169.236; 2.I.169.237; 2.I.169.238; 2.I.169.239; 2.I.169.154; 2.I.169.157; 2.I.169.166; 2.I.169.169; 2.I.169.172; 2.I.169.175; 2.I.169.240; 2.I.169.244; 2.I.172.228; 2.I.172.229; 2.I.172.230; 2.I.172.231; 2.I.172.236; 2.I.172.237; 2.I.172.238; 2.I.172.239; 2.I.172.154; 2.I.172.157; 2.I.172.166; 2.I.172.169; 2.I.172.172; 2.I.172.175; 2.I.172.240; 2.I.172.244; 2.I.175.228; 2.I.175.229; 2.I.175.230; 2.I.175.231; 2.I.175.236; 2.I.175.237; 2.I.175.238; 2.I.175.239; 2.I.175.154; 2.I.175.157; 2.I.175.166; 2.I.175.169; 2.I.175.172; 2.I.175.175; 2.I.175.240; 2.I.175.244; 2.I.240.228; 2.I.240.229; 2.I.240.230; 2.I.240.231; 2.I.240.236; 2.I.240.237; 2.I.240.238; 2.I.240.239; 2.I.240.154; 2.I.240.157; 2.I.240.166; 2.I.240.169; 2.I.240.172; 2.I.240.175; 2.I.240.240; 2.I.240.244; 2.I.244.228; 2.I.244.229; 2.I.244.230; 2.I.244.231; 2.I.244.236; 2.I.244.237; 2.I.244.238; 2.I.244.239; 2.I.244.154; 2.I.244.157; 2.I.244.166; 2.I.244.169; 2.I.244.172; 2.I.244.175; 2.I.244.240; 2.I.244.244;

Prodrugs of 2.J

2.J.228.228; 2.J.228.229; 2.J.228.230; 2.J.228.231; 2.J.228.236; 2.J.228.237; 2.J.228.238; 2.J.228.239; 2.J.228.154; 2.J.228.157; 2.J.228.166; 2.J.228.169; 2.J.228.172; 2.J.228.175; 2.J.228.240; 2.J.228.244; 2.J.229.228; 2.J.229.229; 2.J.229.230; 2.J.229.231; 2.J.229.236; 2.J.229.237; 2.J.229.238; 2.J.229.239; 2.J.229.154; 2.J.229.157; 2.J.229.166; 2.J.229.169; 2.J.229.172; 2.J.229.175; 2.J.229.240; 2.J.229.244; 2.J.230.228; 2.J.230.229; 2.J.230.230; 2.J.230.231; 2.J.230.236; 2.J.230.237; 2.J.230.238; 2.J.230.239; 2.J.230.154; 2.J.230.157; 2.J.230.166; 2.J.230.169; 2.J.230.172; 2.J.230.175; 2.J.230.240; 2.J.230.244; 2.J.231.228; 2.J.231.229; 2.J.231.230; 2.J.231.231; 2.J.231.236; 2.J.231.237; 2.J.231.238; 2.J.231.239; 2.J.231.154; 2.J.231.157; 2.J.231.166; 2.J.231.169; 2.J.231.172; 2.J.231.175; 2.J.231.240; 2.J.231.244; 2.J.236.228; 2.J.236.229; 2.J.236.230; 2.J.236.231; 2.J.236.236; 2.J.236.237; 2.J.236.238; 2.J.236.239; 2.J.236.154; 2.J.236.157; 2.J.236.166; 2.J.236.169; 2.J.236.172; 2.J.236.175; 2.J.236.240; 2.J.236.244; 2.J.237.228; 2.J.237.229; 2.J.237.230; 2.J.237.231; 2.J.237.236; 2.J.237.237; 2.J.237.238; 2.J.237.239; 2.J.237.154; 2.J.237.157; 2.J.237.166; 2.J.237.169; 2.J.237.172; 2.J.237.175; 2.J.237.240; 2.J.237.244; 2.J.238.228; 2.J.238.229; 2.J.238.230; 2.J.238.231; 2.J.238.236; 2.J.238.237; 2.J.238.238; 2.J.238.239; 2.J.238.154; 2.J.238.157; 2.J.238.166; 2.J.238.169; 2.J.238.172; 2.J.238.175; 2.J.238.240; 2.J.238.244; 2.J.239.228; 2.J.239.229; 2.J.239.230; 2.J.239.231; 2.J.239.236; 2.J.239.237; 2.J.239.238; 2.J.239.239; 2.J.239.154; 2.J.239.157; 2.J.239.166; 2.J.239.169; 2.J.239.172; 2.J.239.175; 2.J.239.240; 2.J.239.244; 2.J.154.228; 2.J.154.229; 2.J.154.230; 2.J.154.231; 2.J.154.236; 2.J.154.237; 2.J.154.238; 2.J.154.239; 2.J.154.154; 2.J.154.157; 2.J.154.166; 2.J.154.169; 2.J.154.172; 2.J.154.175; 2.J.154.240; 2.J.154.244; 2.J.157.228; 2.J.157.229; 2.J.157.230; 2.J.157.231; 2.J.157.236; 2.J.157.237; 2.J.157.238; 2.J.157.239; 2.J.157.154; 2.J.157.157; 2.J.157.166; 2.J.157.169; 2.J.157.172; 2.J.157.175; 2.J.157.240; 2.J.157.244; 2.J.166.228; 2.J.166.229; 2.J.166.230; 2.J.166.231; 2.J.166.236; 2.J.166.237; 2.J.166.238; 2.J.166.239; 2.J.166.154; 2.J.166.157; 2.J.166.166; 2.J.166.169; 2.J.166.172; 2.J.166.175; 2.J.166.240; 2.J.166.244; 2.J.169.228; 2.J.169.229; 2.J.169.230; 2.J.169.231; 2.J.169.236; 2.J.169.237; 2.J.169.238; 2.J.169.239; 2.J.169.154; 2.J.169.157; 2.J.169.166; 2.J.169.169; 2.J.169.172; 2.J.169.175; 2.J.169.240; 2.J.169.244; 2.J.172.228; 2.J.172.229; 2.J.172.230; 2.J.172.231; 2.J.172.236; 2.J.172.237; 2.J.172.238; 2.J.172.239; 2.J.172.154; 2.J.172.157; 2.J.172.166; 2.J.172.169; 2.J.172.172; 2.J.172.175; 2.J.172.240; 2.J.172.244; 2.J.175.228; 2.J.175.229; 2.J.175.230; 2.J.175.231; 2.J.175.236; 2.J.175.237; 2.J.175.238; 2.J.175.239; 2.J.175.154; 2.J.175.157; 2.J.175.166; 2.J.175.169; 2.J.175.172; 2.J.175.175; 2.J.175.240; 2.J.175.244; 2.J.240.228; 2.J.240.229; 2.J.240.230; 2.J.240.231; 2.J.240.236; 2.J.240.237; 2.J.240.238; 2.J.240.239; 2.J.240.154; 2.J.240.157; 2.J.240.166; 2.J.240.169; 2.J.240.172; 2.J.240.175; 2.J.240.240; 2.J.240.244; 2.J.244.228; 2.J.244.229; 2.J.244.230; 2.J.244.231; 2.J.244.236; 2.J.244.237; 2.J.244.238; 2.J.244.239; 2.J.244.154; 2.J.244.157; 2.J.244.166; 2.J.244.169; 2.J.244.172; 2.J.244.175; 2.J.244.240; 2.J.244.244;

Prodrugs of 2.L

2.L.228.228; 2.L.228.229; 2.L.228.230; 2.L.228.231; 2.L.228.236; 2.L.228.237; 2.L.228.238; 2.L.228.239; 2.L.228.154; 2.L.228.157; 2.L.228.166; 2.L.228.169; 2.L.228.172; 2.L.228.175; 2.L.228.240; 2.L.228.244; 2.L.229.228; 2.L.229.229; 2.L.229.230; 2.L.229.231; 2.L.229.236; 2.L.229.237; 2.L.229.238; 2.L.229.239; 2.L.229.154; 2.L.229.157; 2.L.229.166; 2.L.229.169; 2.L.229.172; 2.L.229.175; 2.L.229.240; 2.L.229.244; 2.L.230.228; 2.L.230.229; 2.L.230.230;

TABLE 100-continued

2.L.230.231; 2.L.230.236; 2.L.230.237; 2.L.230.238; 2.L.230.239; 2.L.230.154; 2.L.230.157; 2.L.230.166; 2.L.230.169; 2.L.230.172; 2.L.230.175; 2.L.230.240; 2.L.230.244; 2.L.231.228; 2.L.231.229; 2.L.231.230; 2.L.231.231; 2.L.231.236; 2.L.231.237; 2.L.231.238; 2.L.231.239; 2.L.231.154; 2.L.231.157; 2.L.231.166; 2.L.231.169; 2.L.231.172; 2.L.231.175; 2.L.231.240; 2.L.231.244; 2.L.236.228; 2.L.236.229; 2.L.236.230; 2.L.236.231; 2.L.236.236; 2.L.236.237; 2.L.236.238; 2.L.236.239; 2.L.236.154; 2.L.236.157; 2.L.236.166; 2.L.236.169; 2.L.236.172; 2.L.236.175; 2.L.236.240; 2.L.236.244; 2.L.237.228; 2.L.237.229; 2.L.237.230; 2.L.237.231; 2.L.237.236; 2.L.237.237; 2.L.237.238; 2.L.237.239; 2.L.237.154; 2.L.237.157; 2.L.237.166; 2.L.237.169; 2.L.237.172; 2.L.237.175; 2.L.237.240; 2.L.237.244; 2.L.238.228; 2.L.238.229; 2.L.238.230; 2.L.238.231; 2.L.238.236; 2.L.238.237; 2.L.238.238; 2.L.238.239; 2.L.238.154; 2.L.238.157; 2.L.238.166; 2.L.238.169; 2.L.238.172; 2.L.238.175; 2.L.238.240; 2.L.238.244; 2.L.239.228; 2.L.239.229; 2.L.239.230; 2.L.239.231; 2.L.239.236; 2.L.239.237; 2.L.239.238; 2.L.239.239; 2.L.239.154; 2.L.239.157; 2.L.239.166; 2.L.239.169; 2.L.239.172; 2.L.239.175; 2.L.239.240; 2.L.239.244; 2.L.154.228; 2.L.154.229; 2.L.154.230; 2.L.154.231; 2.L.154.236; 2.L.154.237; 2.L.154.238; 2.L.154.239; 2.L.154.154; 2.L.154.157; 2.L.154.166; 2.L.154.169; 2.L.154.172; 2.L.154.175; 2.L.154.240; 2.L.154.244; 2.L.157.228; 2.L.157.229; 2.L.157.230; 2.L.157.231; 2.L.157.236; 2.L.157.237; 2.L.157.238; 2.L.157.239; 2.L.157.154; 2.L.157.157; 2.L.157.166; 2.L.157.169; 2.L.157.172; 2.L.157.175; 2.L.157.240; 2.L.157.244; 2.L.166.228; 2.L.166.229; 2.L.166.230; 2.L.166.231; 2.L.166.236; 2.L.166.237; 2.L.166.238; 2.L.166.239; 2.L.166.154; 2.L.166.157; 2.L.166.166; 2.L.166.169; 2.L.166.172; 2.L.166.175; 2.L.166.240; 2.L.166.244; 2.L.169.228; 2.L.169.229; 2.L.169.230; 2.L.169.231; 2.L.169.236; 2.L.169.237; 2.L.169.238; 2.L.169.239; 2.L.169.154; 2.L.169.157; 2.L.169.166; 2.L.169.169; 2.L.169.172; 2.L.169.175; 2.L.169.240; 2.L.169.244; 2.L.172.228; 2.L.172.229; 2.L.172.230; 2.L.172.231; 2.L.172.236; 2.L.172.237; 2.L.172.238; 2.L.172.239; 2.L.172.154; 2.L.172.157; 2.L.172.166; 2.L.172.169; 2.L.172.172; 2.L.172.175; 2.L.172.240; 2.L.172.244; 2.L.175.228; 2.L.175.229; 2.L.175.230; 2.L.175.231; 2.L.175.236; 2.L.175.237; 2.L.175.238; 2.L.175.239; 2.L.175.154; 2.L.175.157; 2.L.175.166; 2.L.175.169; 2.L.175.172; 2.L.175.175; 2.L.175.240; 2.L.175.244; 2.L.240.228; 2.L.240.229; 2.L.240.230; 2.L.240.231; 2.L.240.236; 2.L.240.237; 2.L.240.238; 2.L.240.239; 2.L.240.154; 2.L.240.157; 2.L.240.166; 2.L.240.169; 2.L.240.172; 2.L.240.175; 2.L.240.240; 2.L.240.244; 2.L.244.228; 2.L.244.229; 2.L.244.230; 2.L.244.231; 2.L.244.236; 2.L.244.237; 2.L.244.238; 2.L.244.239; 2.L.244.154; 2.L.244.157; 2.L.244.166; 2.L.244.169; 2.L.244.172; 2.L.244.175; 2.L.244.240; 2.L.244.244;

Prodrugs of 2.O

2.O.228.228; 2.O.228.229; 2.O.228.230; 2.O.228.231; 2.O.228.236; 2.O.228.237; 2.O.228.238; 2.O.228.239; 2.O.228.154; 2.O.228.157; 2.O.228.166; 2.O.228.169; 2.O.228.172; 2.O.228.175; 2.O.228.240; 2.O.228.244; 2.O.229.228; 2.O.229.229; 2.O.229.230; 2.O.229.231; 2.O.229.236; 2.O.229.237; 2.O.229.238; 2.O.229.239; 2.O.229.154; 2.O.229.157; 2.O.229.166; 2.O.229.169; 2.O.229.172; 2.O.229.175; 2.O.229.240; 2.O.229.244; 2.O.230.228; 2.O.230.229; 2.O.230.230; 2.O.230.231; 2.O.230.236; 2.O.230.237; 2.O.230.238; 2.O.230.239; 2.O.230.154; 2.O.230.157; 2.O.230.166; 2.O.230.169; 2.O.230.172; 2.O.230.175; 2.O.230.240; 2.O.230.244; 2.O.231.228; 2.O.231.229; 2.O.231.230; 2.O.231.231; 2.O.231.236; 2.O.231.237; 2.O.231.238; 2.O.231.239; 2.O.231.154; 2.O.231.157; 2.O.231.166; 2.O.231.169; 2.O.231.172; 2.O.231.175; 2.O.231.240; 2.O.231.244; 2.O.236.228; 2.O.236.229; 2.O.236.230; 2.O.236.231; 2.O.236.236; 2.O.236.237; 2.O.236.238; 2.O.236.239; 2.O.236.154; 2.O.236.157; 2.O.236.166; 2.O.236.169; 2.O.236.172; 2.O.236.175; 2.O.236.240; 2.O.236.244; 2.O.237.228; 2.O.237.229; 2.O.237.230; 2.O.237.231; 2.O.237.236; 2.O.237.237; 2.O.237.238; 2.O.237.239; 2.O.237.154; 2.O.237.157; 2.O.237.166; 2.O.237.169; 2.O.237.172; 2.O.237.175; 2.O.237.240; 2.O.237.244; 2.O.238.228; 2.O.238.229; 2.O.238.230; 2.O.238.231; 2.O.238.236; 2.O.238.237; 2.O.238.238; 2.O.238.239; 2.O.238.154; 2.O.238.157; 2.O.238.166; 2.O.238.169; 2.O.238.172; 2.O.238.175; 2.O.238.240; 2.O.238.244; 2.O.239.228; 2.O.239.229; 2.O.239.230; 2.O.239.231; 2.O.239.236; 2.O.239.237; 2.O.239.238; 2.O.239.239; 2.O.239.154; 2.O.239.157; 2.O.239.166; 2.O.239.169; 2.O.239.172; 2.O.239.175; 2.O.239.240; 2.O.239.244; 2.O.154.228; 2.O.154.229; 2.O.154.230; 2.O.154.231; 2.O.154.236; 2.O.154.237; 2.O.154.238; 2.O.154.239; 2.O.154.154; 2.O.154.157; 2.O.154.166; 2.O.154.169; 2.O.154.172; 2.O.154.175; 2.O.154.240; 2.O.154.244; 2.O.157.228; 2.O.157.229; 2.O.157.230; 2.O.157.231; 2.O.157.236; 2.O.157.237; 2.O.157.238; 2.O.157.239; 2.O.157.154; 2.O.157.157; 2.O.157.166; 2.O.157.169; 2.O.157.172; 2.O.157.175; 2.O.157.240; 2.O.157.244; 2.O.166.228; 2.O.166.229; 2.O.166.230; 2.O.166.231; 2.O.166.236; 2.O.166.237; 2.O.166.238; 2.O.166.239; 2.O.166.154; 2.O.166.157; 2.O.166.166; 2.O.166.169; 2.O.166.172; 2.O.166.175; 2.O.166.240; 2.O.166.244; 2.O.169.228; 2.O.169.229; 2.O.169.230; 2.O.169.231; 2.O.169.236; 2.O.169.237; 2.O.169.238; 2.O.169.239; 2.O.169.154; 2.O.169.157; 2.O.169.166; 2.O.169.169; 2.O.169.172; 2.O.169.175; 2.O.169.240; 2.O.169.244; 2.O.172.228; 2.O.172.229; 2.O.172.230; 2.O.172.231; 2.O.172.236; 2.O.172.237; 2.O.172.238; 2.O.172.239;

TABLE 100-continued

2.O.172.154; 2.O.172.157; 2.O.172.166; 2.O.172.169; 2.O.172.172;
2.O.172.175; 2.O.172.240; 2.O.172.244; 2.O.175.228; 2.O.175.229;
2.O.175.230; 2.O.175.231; 2.O.175.236; 2.O.175.237; 2.O.175.238;
2.O.175.239; 2.O.175.154; 2.O.175.157; 2.O.175.166; 2.O.175.169;
2.O.175.172; 2.O.175.175; 2.O.175.240; 2.O.175.244; 2.O.240.228;
2.O.240.229; 2.O.240.230; 2.O.240.231; 2.O.240.236; 2.O.240.237;
2.O.240.238; 2.O.240.239; 2.O.240.154; 2.O.240.157; 2.O.240.166;
2.O.240.169; 2.O.240.172; 2.O.240.175; 2.O.240.240; 2.O.240.244;
2.O.244.228; 2.O.244.229; 2.O.244.230; 2.O.244.231; 2.O.244.236;
2.O.244.237; 2.O.244.238; 2.O.244.239; 2.O.244.154; 2.O.244.157;
2.O.244.166; 2.O.244.169; 2.O.244.172; 2.O.244.175; 2.O.244.240;
2.O.244.244;

Prodrugs of 2.P

2.P.228.228; 2.P.228.229; 2.P.228.230; 2.P.228.231; 2.P.228.236;
2.P.228.237; 2.P.228.238; 2.P.228.239; 2.P.228.154; 2.P.228.157; 2.P.228.166;
2.P.228.169; 2.P.228.172; 2.P.228.175; 2.P.228.240; 2.P.228.244; 2.P.229.228;
2.P.229.229; 2.P.229.230; 2.P.229.231; 2.P.229.236; 2.P.229.237; 2.P.229.238;
2.P.229.239; 2.P.229.154; 2.P.229.157; 2.P.229.166; 2.P.229.169; 2.P.229.172;
2.P.229.175; 2.P.229.240; 2.P.229.244; 2.P.230.228; 2.P.230.229; 2.P.230.230;
2.P.230.231; 2.P.230.236; 2.P.230.237; 2.P.230.238; 2.P.230.239; 2.P.230.154;
2.P.230.157; 2.P.230.166; 2.P.230.169; 2.P.230.172; 2.P.230.175; 2.P.230.240;
2.P.230.244; 2.P.231.228; 2.P.231.229; 2.P.231.230; 2.P.231.231; 2.P.231.236;
2.P.231.237; 2.P.231.238; 2.P.231.239; 2.P.231.154; 2.P.231.157; 2.P.231.166;
2.P.231.169; 2.P.231.172; 2.P.231.175; 2.P.231.240; 2.P.231.244; 2.P.236.228;
2.P.236.229; 2.P.236.230; 2.P.236.231; 2.P.236.236; 2.P.236.237; 2.P.236.238;
2.P.236.239; 2.P.236.154; 2.P.236.157; 2.P.236.166; 2.P.236.169; 2.P.236.172;
2.P.236.175; 2.P.236.240; 2.P.236.244; 2.P.237.228; 2.P.237.229; 2.P.237.230;
2.P.237.231; 2.P.237.236; 2.P.237.237; 2.P.237.238; 2.P.237.239; 2.P.237.154;
2.P.237.157; 2.P.237.166; 2.P.237.169; 2.P.237.172; 2.P.237.175; 2.P.237.240;
2.P.237.244; 2.P.238.228; 2.P.238.229; 2.P.238.230; 2.P.238.231; 2.P.238.236;
2.P.238.237; 2.P.238.238; 2.P.238.239; 2.P.238.154; 2.P.238.157; 2.P.238.166;
2.P.238.169; 2.P.238.172; 2.P.238.175; 2.P.238.240; 2.P.238.244; 2.P.239.228;
2.P.239.229; 2.P.239.230; 2.P.239.231; 2.P.239.236; 2.P.239.237; 2.P.239.238;
2.P.239.239; 2.P.239.154; 2.P.239.157; 2.P.239.166; 2.P.239.169; 2.P.239.172;
2.P.239.175; 2.P.239.240; 2.P.239.244; 2.P.154.228; 2.P.154.229; 2.P.154.230;
2.P.154.231; 2.P.154.236; 2.P.154.237; 2.P.154.238; 2.P.154.239; 2.P.154.154;
2.P.154.157; 2.P.154.166; 2.P.154.169; 2.P.154.172; 2.P.154.175; 2.P.154.240;
2.P.154.244; 2.P.157.228; 2.P.157.229; 2.P.157.230; 2.P.157.231; 2.P.157.236;
2.P.157.237; 2.P.157.238; 2.P.157.239; 2.P.157.154; 2.P.157.157; 2.P.157.166;
2.P.157.169; 2.P.157.172; 2.P.157.175; 2.P.157.240; 2.P.157.244; 2.P.166.228;
2.P.166.229; 2.P.166.230; 2.P.166.231; 2.P.166.236; 2.P.166.237; 2.P.166.238;
2.P.166.239; 2.P.166.154; 2.P.166.157; 2.P.166.166; 2.P.166.169; 2.P.166.172;
2.P.166.175; 2.P.166.240; 2.P.166.244; 2.P.169.228; 2.P.169.229; 2.P.169.230;
2.P.169.231; 2.P.169.236; 2.P.169.237; 2.P.169.238; 2.P.169.239; 2.P.169.154;
2.P.169.157; 2.P.169.166; 2.P.169.169; 2.P.169.172; 2.P.169.175; 2.P.169.240;
2.P.169.244; 2.P.172.228; 2.P.172.229; 2.P.172.230; 2.P.172.231; 2.P.172.236;
2.P.172.237; 2.P.172.238; 2.P.172.239; 2.P.172.154; 2.P.172.157; 2.P.172.166;
2.P.172.169; 2.P.172.172; 2.P.172.175; 2.P.172.240; 2.P.172.244; 2.P.175.228;
2.P.175.229; 2.P.175.230; 2.P.175.231; 2.P.175.236; 2.P.175.237; 2.P.175.238;
2.P.175.239; 2.P.175.154; 2.P.175.157; 2.P.175.166; 2.P.175.169; 2.P.175.172;
2.P.175.175; 2.P.175.240; 2.P.175.244; 2.P.240.228; 2.P.240.229; 2.P.240.230;
2.P.240.231; 2.P.240.236; 2.P.240.237; 2.P.240.238; 2.P.240.239; 2.P.240.154;
2.P.240.157; 2.P.240.166; 2.P.240.169; 2.P.240.172; 2.P.240.175; 2.P.240.240;
2.P.240.244; 2.P.244.228; 2.P.244.229; 2.P.244.230; 2.P.244.231; 2.P.244.236;
2.P.244.237; 2.P.244.238; 2.P.244.239; 2.P.244.154; 2.P.244.157; 2.P.244.166;
2.P.244.169; 2.P.244.172; 2.P.244.175; 2.P.244.240; 2.P.244.244;

Prodrugs of 2.U

2.U.228.228; 2.U.228.229; 2.U.228.230; 2.U.228.231; 2.U.228.236;
2.U.228.237; 2.U.228.238; 2.U.228.239; 2.U.228.154; 2.U.228.157;
2.U.228.166; 2.U.228.169; 2.U.228.172; 2.U.228.175; 2.U.228.240;
2.U.228.244; 2.U.229.228; 2.U.229.229; 2.U.229.230; 2.U.229.231;
2.U.229.236; 2.U.229.237; 2.U.229.238; 2.U.229.239; 2.U.229.154;
2.U.229.157; 2.U.229.166; 2.U.229.169; 2.U.229.172; 2.U.229.175;
2.U.229.240; 2.U.229.244; 2.U.230.228; 2.U.230.229; 2.U.230.230;
2.U.230.231; 2.U.230.236; 2.U.230.237; 2.U.230.238; 2.U.230.239;
2.U.230.154; 2.U.230.157; 2.U.230.166; 2.U.230.169; 2.U.230.172;
2.U.230.175; 2.U.230.240; 2.U.230.244; 2.U.231.228; 2.U.231.229;
2.U.231.230; 2.U.231.231; 2.U.231.236; 2.U.231.237; 2.U.231.238;
2.U.231.239; 2.U.231.154; 2.U.231.157; 2.U.231.166; 2.U.231.169;
2.U.231.172; 2.U.231.175; 2.U.231.240; 2.U.231.244; 2.U.236.228;
2.U.236.229; 2.U.236.230; 2.U.236.231; 2.U.236.236; 2.U.236.237;
2.U.236.238; 2.U.236.239; 2.U.236.154; 2.U.236.157; 2.U.236.166;
2.U.236.169; 2.U.236.172; 2.U.236.175; 2.U.236.240; 2.U.236.244;
2.U.237.228; 2.U.237.229; 2.U.237.230; 2.U.237.231; 2.U.237.236;
2.U.237.237; 2.U.237.238; 2.U.237.239; 2.U.237.154; 2.U.237.157;
2.U.237.166; 2.U.237.169; 2.U.237.172; 2.U.237.175; 2.U.237.240;
2.U.237.244; 2.U.238.228; 2.U.238.229; 2.U.238.230; 2.U.238.231;

TABLE 100-continued

2.U.238.236; 2.U.238.237; 2.U.238.238; 2.U.238.239; 2.U.238.154; 2.U.238.157; 2.U.238.166; 2.U.238.169; 2.U.238.172; 2.U.238.175; 2.U.238.240; 2.U.238.244; 2.U.239.228; 2.U.239.229; 2.U.239.230; 2.U.239.231; 2.U.239.236; 2.U.239.237; 2.U.239.238; 2.U.239.239; 2.U.239.154; 2.U.239.157; 2.U.239.166; 2.U.239.169; 2.U.239.172; 2.U.239.175; 2.U.239.240; 2.U.239.244; 2.U.154.228; 2.U.154.229; 2.U.154.230; 2.U.154.231; 2.U.154.236; 2.U.154.237; 2.U.154.238; 2.U.154.239; 2.U.154.154; 2.U.154.157; 2.U.154.166; 2.U.154.169; 2.U.154.172; 2.U.154.175; 2.U.154.240; 2.U.154.244; 2.U.157.228; 2.U.157.229; 2.U.157.230; 2.U.157.231; 2.U.157.236; 2.U.157.237; 2.U.157.238; 2.U.157.239; 2.U.157.154; 2.U.157.157; 2.U.157.166; 2.U.157.169; 2.U.157.172; 2.U.157.175; 2.U.157.240; 2.U.157.244; 2.U.166.228; 2.U.166.229; 2.U.166.230; 2.U.166.231; 2.U.166.236; 2.U.166.237; 2.U.166.238; 2.U.166.239; 2.U.166.154; 2.U.166.157; 2.U.166.166; 2.U.166.169; 2.U.166.172; 2.U.166.175; 2.U.166.240; 2.U.166.244; 2.U.169.228; 2.U.169.229; 2.U.169.230; 2.U.169.231; 2.U.169.236; 2.U.169.237; 2.U.169.238; 2.U.169.239; 2.U.169.154; 2.U.169.157; 2.U.169.166; 2.U.169.169; 2.U.169.172; 2.U.169.175; 2.U.169.240; 2.U.169.244; 2.U.172.228; 2.U.172.229; 2.U.172.230; 2.U.172.231; 2.U.172.236; 2.U.172.237; 2.U.172.238; 2.U.172.239; 2.U.172.154; 2.U.172.157; 2.U.172.166; 2.U.172.169; 2.U.172.172; 2.U.172.175; 2.U.172.240; 2.U.172.244; 2.U.175.228; 2.U.175.229; 2.U.175.230; 2.U.175.231; 2.U.175.236; 2.U.175.237; 2.U.175.238; 2.U.175.239; 2.U.175.154; 2.U.175.157; 2.U.175.166; 2.U.175.169; 2.U.175.172; 2.U.175.175; 2.U.175.240; 2.U.175.244; 2.U.240.228; 2.U.240.229; 2.U.240.230; 2.U.240.231; 2.U.240.236; 2.U.240.237; 2.U.240.238; 2.U.240.239; 2.U.240.154; 2.U.240.157; 2.U.240.166; 2.U.240.169; 2.U.240.172; 2.U.240.175; 2.U.240.240; 2.U.240.244; 2.U.244.228; 2.U.244.229; 2.U.244.230; 2.U.244.231; 2.U.244.236; 2.U.244.237; 2.U.244.238; 2.U.244.239; 2.U.244.154; 2.U.244.157; 2.U.244.166; 2.U.244.169; 2.U.244.172; 2.U.244.175; 2.U.244.240; 2.U.244.244;

Prodrugs of 2.W

2.W.228.228; 2.W.228.229; 2.W.228.230; 2.W.228.231; 2.W.228.236; 2.W.228.237; 2.W.228.238; 2.W.228.239; 2.W.228.154; 2.W.228.157; 2.W.228.166; 2.W.228.169; 2.W.228.172; 2.W.228.175; 2.W.228.240; 2.W.228.244; 2.W.229.228; 2.W.229.229; 2.W.229.230; 2.W.229.231; 2.W.229.236; 2.W.229.237; 2.W.229.238; 2.W.229.239; 2.W.229.154; 2.W.229.157; 2.W.229.166; 2.W.229.169; 2.W.229.172; 2.W.229.175; 2.W.229.240; 2.W.229.244; 2.W.230.228; 2.W.230.229; 2.W.230.230; 2.W.230.231; 2.W.230.236; 2.W.230.237; 2.W.230.238; 2.W.230.239; 2.W.230.154; 2.W.230.157; 2.W.230.166; 2.W.230.169; 2.W.230.172; 2.W.230.175; 2.W.230.240; 2.W.230.244; 2.W.231.228; 2.W.231.229; 2.W.231.230; 2.W.231.231; 2.W.231.236; 2.W.231.237; 2.W.231.238; 2.W.231.239; 2.W.231.154; 2.W.231.157; 2.W.231.166; 2.W.231.169; 2.W.231.172; 2.W.231.175; 2.W.231.240; 2.W.231.244; 2.W.236.228; 2.W.236.229; 2.W.236.230; 2.W.236.231; 2.W.236.236; 2.W.236.237; 2.W.236.238; 2.W.236.239; 2.W.236.154; 2.W.236.157; 2.W.236.166; 2.W.236.169; 2.W.236.172; 2.W.236.175; 2.W.236.240; 2.W.236.244; 2.W.237.228; 2.W.237.229; 2.W.237.230; 2.W.237.231; 2.W.237.236; 2.W.237.237; 2.W.237.238; 2.W.237.239; 2.W.237.154; 2.W.237.157; 2.W.237.166; 2.W.237.169; 2.W.237.172; 2.W.237.175; 2.W.237.240; 2.W.237.244; 2.W.238.228; 2.W.238.229; 2.W.238.230; 2.W.238.231; 2.W.238.236; 2.W.238.237; 2.W.238.238; 2.W.238.239; 2.W.238.154; 2.W.238.157; 2.W.238.166; 2.W.238.169; 2.W.238.172; 2.W.238.175; 2.W.238.240; 2.W.238.244; 2.W.239.228; 2.W.239.229; 2.W.239.230; 2.W.239.231; 2.W.239.236; 2.W.239.237; 2.W.239.238; 2.W.239.239; 2.W.239.154; 2.W.239.157; 2.W.239.166; 2.W.239.169; 2.W.239.172; 2.W.239.175; 2.W.239.240; 2.W.239.244; 2.W.154.228; 2.W.154.229; 2.W.154.230; 2.W.154.231; 2.W.154.236; 2.W.154.237; 2.W.154.238; 2.W.154.239; 2.W.154.154; 2.W.154.157; 2.W.154.166; 2.W.154.169; 2.W.154.172; 2.W.154.175; 2.W.154.240; 2.W.154.244; 2.W.157.228; 2.W.157.229; 2.W.157.230; 2.W.157.231; 2.W.157.236; 2.W.157.237; 2.W.157.238; 2.W.157.239; 2.W.157.154; 2.W.157.157; 2.W.157.166; 2.W.157.169; 2.W.157.172; 2.W.157.175; 2.W.157.240; 2.W.157.244; 2.W.166.228; 2.W.166.229; 2.W.166.230; 2.W.166.231; 2.W.166.236; 2.W.166.237; 2.W.166.238; 2.W.166.239; 2.W.166.154; 2.W.166.157; 2.W.166.166; 2.W.166.169; 2.W.166.172; 2.W.166.175; 2.W.166.240; 2.W.166.244; 2.W.169.228; 2.W.169.229; 2.W.169.230; 2.W.169.231; 2.W.169.236; 2.W.169.237; 2.W.169.238; 2.W.169.239; 2.W.169.154; 2.W.169.157; 2.W.169.166; 2.W.169.169; 2.W.169.172; 2.W.169.175; 2.W.169.240; 2.W.169.244; 2.W.172.228; 2.W.172.229; 2.W.172.230; 2.W.172.231; 2.W.172.236; 2.W.172.237; 2.W.172.238; 2.W.172.239; 2.W.172.154; 2.W.172.157; 2.W.172.166; 2.W.172.169; 2.W.172.172; 2.W.172.175; 2.W.172.240; 2.W.172.244; 2.W.175.228; 2.W.175.229; 2.W.175.230; 2.W.175.231; 2.W.175.236; 2.W.175.237; 2.W.175.238; 2.W.175.239; 2.W.175.154; 2.W.175.157; 2.W.175.166; 2.W.175.169; 2.W.175.172; 2.W.175.175; 2.W.175.240; 2.W.175.244; 2.W.240.228;

TABLE 100-continued

2.W.240.229; 2.W.240.230; 2.W.240.231; 2.W.240.236; 2.W.240.237; 2.W.240.238; 2.W.240.239; 2.W.240.154; 2.W.240.157; 2.W.240.166; 2.W.240.169; 2.W.240.172; 2.W.240.175; 2.W.240.240; 2.W.240.244; 2.W.244.228; 2.W.244.229; 2.W.244.230; 2.W.244.231; 2.W.244.236; 2.W.244.237; 2.W.244.238; 2.W.244.239; 2.W.244.154; 2.W.244.157; 2.W.244.166; 2.W.244.169; 2.W.244.172; 2.W.244.175; 2.W.244.240; 2.W.244.244;

Prodrugs of 2.Y

2.Y.228.228; 2.Y.228.229; 2.Y.228.230; 2.Y.228.231; 2.Y.228.236; 2.Y.228.237; 2.Y.228.238; 2.Y.228.239; 2.Y.228.154; 2.Y.228.157; 2.Y.228.166; 2.Y.228.169; 2.Y.228.172; 2.Y.228.175; 2.Y.228.240; 2.Y.228.244; 2.Y.229.228; 2.Y.229.229; 2.Y.229.230; 2.Y.229.231; 2.Y.229.236; 2.Y.229.237; 2.Y.229.238; 2.Y.229.239; 2.Y.229.154; 2.Y.229.157; 2.Y.229.166; 2.Y.229.169; 2.Y.229.172; 2.Y.229.175; 2.Y.229.240; 2.Y.229.244; 2.Y.230.228; 2.Y.230.229; 2.Y.230.230; 2.Y.230.231; 2.Y.230.236; 2.Y.230.237; 2.Y.230.238; 2.Y.230.239; 2.Y.230.154; 2.Y.230.157; 2.Y.230.166; 2.Y.230.169; 2.Y.230.172; 2.Y.230.175; 2.Y.230.240; 2.Y.230.244; 2.Y.231.228; 2.Y.231.229; 2.Y.231.230; 2.Y.231.231; 2.Y.231.236; 2.Y.231.237; 2.Y.231.238; 2.Y.231.239; 2.Y.231.154; 2.Y.231.157; 2.Y.231.166; 2.Y.231.169; 2.Y.231.172; 2.Y.231.175; 2.Y.231.240; 2.Y.231.244; 2.Y.236.228; 2.Y.236.229; 2.Y.236.230; 2.Y.236.231; 2.Y.236.236; 2.Y.236.237; 2.Y.236.238; 2.Y.236.239; 2.Y.236.154; 2.Y.236.157; 2.Y.236.166; 2.Y.236.169; 2.Y.236.172; 2.Y.236.175; 2.Y.236.240; 2.Y.236.244; 2.Y.237.228; 2.Y.237.229; 2.Y.237.230; 2.Y.237.231; 2.Y.237.236; 2.Y.237.237; 2.Y.237.238; 2.Y.237.239; 2.Y.237.154; 2.Y.237.157; 2.Y.237.166; 2.Y.237.169; 2.Y.237.172; 2.Y.237.175; 2.Y.237.240; 2.Y.237.244; 2.Y.238.228; 2.Y.238.229; 2.Y.238.230; 2.Y.238.231; 2.Y.238.236; 2.Y.238.237; 2.Y.238.238; 2.Y.238.239; 2.Y.238.154; 2.Y.238.157; 2.Y.238.166; 2.Y.238.169; 2.Y.238.172; 2.Y.238.175; 2.Y.238.240; 2.Y.238.244; 2.Y.239.228; 2.Y.239.229; 2.Y.239.230; 2.Y.239.231; 2.Y.239.236; 2.Y.239.237; 2.Y.239.238; 2.Y.239.239; 2.Y.239.154; 2.Y.239.157; 2.Y.239.166; 2.Y.239.169; 2.Y.239.172; 2.Y.239.175; 2.Y.239.240; 2.Y.239.244; 2.Y.154.228; 2.Y.154.229; 2.Y.154.230; 2.Y.154.231; 2.Y.154.236; 2.Y.154.237; 2.Y.154.238; 2.Y.154.239; 2.Y.154.154; 2.Y.154.157; 2.Y.154.166; 2.Y.154.169; 2.Y.154.172; 2.Y.154.175; 2.Y.154.240; 2.Y.154.244; 2.Y.157.228; 2.Y.157.229; 2.Y.157.230; 2.Y.157.231; 2.Y.157.236; 2.Y.157.237; 2.Y.157.238; 2.Y.157.239; 2.Y.157.154; 2.Y.157.157; 2.Y.157.166; 2.Y.157.169; 2.Y.157.172; 2.Y.157.175; 2.Y.157.240; 2.Y.157.244; 2.Y.166.228; 2.Y.166.229; 2.Y.166.230; 2.Y.166.231; 2.Y.166.236; 2.Y.166.237; 2.Y.166.238; 2.Y.166.239; 2.Y.166.154; 2.Y.166.157; 2.Y.166.166; 2.Y.166.169; 2.Y.166.172; 2.Y.166.175; 2.Y.166.240; 2.Y.166.244; 2.Y.169.228; 2.Y.169.229; 2.Y.169.230; 2.Y.169.231; 2.Y.169.236; 2.Y.169.237; 2.Y.169.238; 2.Y.169.239; 2.Y.169.154; 2.Y.169.157; 2.Y.169.166; 2.Y.169.169; 2.Y.169.172; 2.Y.169.175; 2.Y.169.240; 2.Y.169.244; 2.Y.172.228; 2.Y.172.229; 2.Y.172.230; 2.Y.172.231; 2.Y.172.236; 2.Y.172.237; 2.Y.172.238; 2.Y.172.239; 2.Y.172.154; 2.Y.172.157; 2.Y.172.166; 2.Y.172.169; 2.Y.172.172; 2.Y.172.175; 2.Y.172.240; 2.Y.172.244; 2.Y.175.228; 2.Y.175.229; 2.Y.175.230; 2.Y.175.231; 2.Y.175.236; 2.Y.175.237; 2.Y.175.238; 2.Y.175.239; 2.Y.175.154; 2.Y.175.157; 2.Y.175.166; 2.Y.175.169; 2.Y.175.172; 2.Y.175.175; 2.Y.175.240; 2.Y.175.244; 2.Y.240.228; 2.Y.240.229; 2.Y.240.230; 2.Y.240.231; 2.Y.240.236; 2.Y.240.237; 2.Y.240.238; 2.Y.240.239; 2.Y.240.154; 2.Y.240.157; 2.Y.240.166; 2.Y.240.169; 2.Y.240.172; 2.Y.240.175; 2.Y.240.240; 2.Y.240.244; 2.Y.244.228; 2.Y.244.229; 2.Y.244.230; 2.Y.244.231; 2.Y.244.236; 2.Y.244.237; 2.Y.244.238; 2.Y.244.239; 2.Y.244.154; 2.Y.244.157; 2.Y.244.166; 2.Y.244.169; 2.Y.244.172; 2.Y.244.175; 2.Y.244.240; 2.Y.244.244;

Prodrugs of 3.B

3.B.228.228; 3.B.228.229; 3.B.228.230; 3.B.228.231; 3.B.228.236; 3.B.228.237; 3.B.228.238; 3.B.228.239; 3.B.228.154; 3.B.228.157; 3.B.228.166; 3.B.228.169; 3.B.228.172; 3.B.228.175; 3.B.228.240; 3.B.228.244; 3.B.229.228; 3.B.229.229; 3.B.229.230; 3.B.229.231; 3.B.229.236; 3.B.229.237; 3.B.229.238; 3.B.229.239; 3.B.229.154; 3.B.229.157; 3.B.229.166; 3.B.229.169; 3.B.229.172; 3.B.229.175; 3.B.229.240; 3.B.229.244; 3.B.230.228; 3.B.230.229; 3.B.230.230; 3.B.230.231; 3.B.230.236; 3.B.230.237; 3.B.230.238; 3.B.230.239; 3.B.230.154; 3.B.230.157; 3.B.230.166; 3.B.230.169; 3.B.230.172; 3.B.230.175; 3.B.230.240; 3.B.230.244; 3.B.231.228; 3.B.231.229; 3.B.231.230; 3.B.231.231; 3.B.231.236; 3.B.231.237; 3.B.231.238; 3.B.231.239; 3.B.231.154; 3.B.231.157; 3.B.231.166; 3.B.231.169; 3.B.231.172; 3.B.231.175; 3.B.231.240; 3.B.231.244; 3.B.236.228; 3.B.236.229; 3.B.236.230; 3.B.236.231; 3.B.236.236; 3.B.236.237; 3.B.236.238; 3.B.236.239; 3.B.236.154; 3.B.236.157; 3.B.236.166; 3.B.236.169; 3.B.236.172; 3.B.236.175; 3.B.236.240; 3.B.236.244; 3.B.237.228; 3.B.237.229; 3.B.237.230; 3.B.237.231; 3.B.237.236; 3.B.237.237; 3.B.237.238; 3.B.237.239; 3.B.237.154; 3.B.237.157; 3.B.237.166; 3.B.237.169; 3.B.237.172; 3.B.237.175; 3.B.237.240; 3.B.237.244; 3.B.238.228; 3.B.238.229; 3.B.238.230; 3.B.238.231; 3.B.238.236; 3.B.238.237; 3.B.238.238; 3.B.238.239; 3.B.238.154; 3.B.238.157; 3.B.238.166; 3.B.238.169; 3.B.238.172; 3.B.238.175; 3.B.238.240; 3.B.238.244; 3.B.239.228; 3.B.239.229; 3.B.239.230; 3.B.239.231; 3.B.239.236; 3.B.239.237; 3.B.239.238; 3.B.239.239; 3.B.239.154; 3.B.239.157; 3.B.239.166; 3.B.239.169; 3.B.239.172; 3.B.239.175; 3.B.239.240; 3.B.239.244; 3.B.154.228; 3.B.154.229; 3.B.154.230; 3.B.154.231; 3.B.154.236; 3.B.154.237; 3.B.154.238; 3.B.154.239; 3.B.154.154; 3.B.154.157; 3.B.154.166; 3.B.154.169; 3.B.154.172; 3.B.154.175; 3.B.154.240; 3.B.154.244; 3.B.157.228; 3.B.157.229; 3.B.157.230; 3.B.157.231; 3.B.157.236;

TABLE 100-continued

3.B.157.237; 3.B.157.238; 3.B.157.239; 3.B.157.154; 3.B.157.157; 3.B.157.166;
3.B.157.169; 3.B.157.172; 3.B.157.175; 3.B.157.240; 3.B.157.244; 3.B.166.228;
3.B.166.229; 3.B.166.230; 3.B.166.231; 3.B.166.236; 3.B.166.237; 3.B.166.238;
3.B.166.239; 3.B.166.154; 3.B.166.157; 3.B.166.166; 3.B.166.169; 3.B.166.172;
3.B.166.175; 3.B.166.240; 3.B.166.244; 3.B.169.228; 3.B.169.229; 3.B.169.230;
3.B.169.231; 3.B.169.236; 3.B.169.237; 3.B.169.238; 3.B.169.239; 3.B.169.154;
3.B.169.157; 3.B.169.166; 3.B.169.169; 3.B.169.172; 3.B.169.175; 3.B.169.240;
3.B.169.244; 3.B.172.228; 3.B.172.229; 3.B.172.230; 3.B.172.231; 3.B.172.236;
3.B.172.237; 3.B.172.238; 3.B.172.239; 3.B.172.154; 3.B.172.157; 3.B.172.166;
3.B.172.169; 3.B.172.172; 3.B.172.175; 3.B.172.240; 3.B.172.244; 3.B.175.228;
3.B.175.229; 3.B.175.230; 3.B.175.231; 3.B.175.236; 3.B.175.237; 3.B.175.238;
3.B.175.239; 3.B.175.154; 3.B.175.157; 3.B.175.166; 3.B.175.169; 3.B.175.172;
3.B.175.175; 3.B.175.240; 3.B.175.244; 3.B.240.228; 3.B.240.229; 3.B.240.230;
3.B.240.231; 3.B.240.236; 3.B.240.237; 3.B.240.238; 3.B.240.239; 3.B.240.154;
3.B.240.157; 3.B.240.166; 3.B.240.169; 3.B.240.172; 3.B.240.175; 3.B.240.240;
3.B.240.244; 3.B.244.228; 3.B.244.229; 3.B.244.230; 3.B.244.231; 3.B.244.236;
3.B.244.237; 3.B.244.238; 3.B.244.239; 3.B.244.154; 3.B.244.157; 3.B.244.166;
3.B.244.169; 3.B.244.172; 3.B.244.175; 3.B.244.240; 3.B.244.244;

Prodrugs of 3.D

3.D.228.228; 3.D.228.229; 3.D.228.230; 3.D.228.231; 3.D.228.236;
3.D.228.237; 3.D.228.238; 3.D.228.239; 3.D.228.154; 3.D.228.157;
3.D.228.166; 3.D.228.169; 3.D.228.172; 3.D.228.175; 3.D.228.240;
3.D.228.244; 3.D.229.228; 3.D.229.229; 3.D.229.230; 3.D.229.231;
3.D.229.236; 3.D.229.237; 3.D.229.238; 3.D.229.239; 3.D.229.154;
3.D.229.157; 3.D.229.166; 3.D.229.169; 3.D.229.172; 3.D.229.175;
3.D.229.240; 3.D.229.244; 3.D.230.228; 3.D.230.229; 3.D.230.230;
3.D.230.231; 3.D.230.236; 3.D.230.237; 3.D.230.238; 3.D.230.239;
3.D.230.154; 3.D.230.157; 3.D.230.166; 3.D.230.169; 3.D.230.172;
3.D.230.175; 3.D.230.240; 3.D.230.244; 3.D.231.228; 3.D.231.229;
3.D.231.230; 3.D.231.231; 3.D.231.236; 3.D.231.237; 3.D.231.238;
3.D.231.239; 3.D.231.154; 3.D.231.157; 3.D.231.166; 3.D.231.169;
3.D.231.172; 3.D.231.175; 3.D.231.240; 3.D.231.244; 3.D.236.228;
3.D.236.229; 3.D.236.230; 3.D.236.231; 3.D.236.236; 3.D.236.237;
3.D.236.238; 3.D.236.239; 3.D.236.154; 3.D.236.157; 3.D.236.166;
3.D.236.169; 3.D.236.172; 3.D.236.175; 3.D.236.240; 3.D.236.244;
3.D.237.228; 3.D.237.229; 3.D.237.230; 3.D.237.231; 3.D.237.236;
3.D.237.237; 3.D.237.238; 3.D.237.239; 3.D.237.154; 3.D.237.157;
3.D.237.166; 3.D.237.169; 3.D.237.172; 3.D.237.175; 3.D.237.240;
3.D.237.244; 3.D.238.228; 3.D.238.229; 3.D.238.230; 3.D.238.231;
3.D.238.236; 3.D.238.237; 3.D.238.238; 3.D.238.239; 3.D.238.154;
3.D.238.157; 3.D.238.166; 3.D.238.169; 3.D.238.172; 3.D.238.175;
3.D.238.240; 3.D.238.244; 3.D.239.228; 3.D.239.229; 3.D.239.230;
3.D.239.231; 3.D.239.236; 3.D.239.237; 3.D.239.238; 3.D.239.239;
3.D.239.154; 3.D.239.157; 3.D.239.166; 3.D.239.169; 3.D.239.172;
3.D.239.175; 3.D.239.240; 3.D.239.244; 3.D.154.228; 3.D.154.229;
3.D.154.230; 3.D.154.231; 3.D.154.236; 3.D.154.237; 3.D.154.238;
3.D.154.239; 3.D.154.154; 3.D.154.157; 3.D.154.166; 3.D.154.169;
3.D.154.172; 3.D.154.175; 3.D.154.240; 3.D.154.244; 3.D.157.228;
3.D.157.229; 3.D.157.230; 3.D.157.231; 3.D.157.236; 3.D.157.237;
3.D.157.238; 3.D.157.239; 3.D.157.154; 3.D.157.157; 3.D.157.166;
3.D.157.169; 3.D.157.172; 3.D.157.175; 3.D.157.240; 3.D.157.244;
3.D.166.228; 3.D.166.229; 3.D.166.230; 3.D.166.231; 3.D.166.236;
3.D.166.237; 3.D.166.238; 3.D.166.239; 3.D.166.154; 3.D.166.157;
3.D.166.166; 3.D.166.169; 3.D.166.172; 3.D.166.175; 3.D.166.240;
3.D.166.244; 3.D.169.228; 3.D.169.229; 3.D.169.230; 3.D.169.231;
3.D.169.236; 3.D.169.237; 3.D.169.238; 3.D.169.239; 3.D.169.154;
3.D.169.157; 3.D.169.166; 3.D.169.169; 3.D.169.172; 3.D.169.175;
3.D.169.240; 3.D.169.244; 3.D.172.228; 3.D.172.229; 3.D.172.230;
3.D.172.231; 3.D.172.236; 3.D.172.237; 3.D.172.238; 3.D.172.239;
3.D.172.154; 3.D.172.157; 3.D.172.166; 3.D.172.169; 3.D.172.172;
3.D.172.175; 3.D.172.240; 3.D.172.244; 3.D.175.228; 3.D.175.229;
3.D.175.230; 3.D.175.231; 3.D.175.236; 3.D.175.237; 3.D.175.238;
3.D.175.239; 3.D.175.154; 3.D.175.157; 3.D.175.166; 3.D.175.169;
3.D.175.172; 3.D.175.175; 3.D.175.240; 3.D.175.244; 3.D.240.228;
3.D.240.229; 3.D.240.230; 3.D.240.231; 3.D.240.236; 3.D.240.237;
3.D.240.238; 3.D.240.239; 3.D.240.154; 3.D.240.157; 3.D.240.166;
3.D.240.169; 3.D.240.172; 3.D.240.175; 3.D.240.240; 3.D.240.244;
3.D.244.228; 3.D.244.229; 3.D.244.230; 3.D.244.231; 3.D.244.236;
3.D.244.237; 3.D.244.238; 3.D.244.239; 3.D.244.154; 3.D.244.157;
3.D.244.166; 3.D.244.169; 3.D.244.172; 3.D.244.175; 3.D.244.240;
3.D.244.244;

Prodrugs of 3.E

3.E.228.228; 3.E.228.229; 3.E.228.230; 3.E.228.231; 3.E.228.236;
3.E.228.237; 3.E.228.238; 3.E.228.239; 3.E.228.154; 3.E.228.157; 3.E.228.166;
3.E.228.169; 3.E.228.172; 3.E.228.175; 3.E.228.240; 3.E.228.244; 3.E.229.228;
3.E.229.229; 3.E.229.230; 3.E.229.231; 3.E.229.236; 3.E.229.237; 3.E.229.238;
3.E.229.239; 3.E.229.154; 3.E.229.157; 3.E.229.166; 3.E.229.169; 3.E.229.172;

TABLE 100-continued

3.E.229.175; 3.E.229.240; 3.E.229.244; 3.E.230.228; 3.E.230.229; 3.E.230.230; 3.E.230.231; 3.E.230.236; 3.E.230.237; 3.E.230.238; 3.E.230.239; 3.E.230.154; 3.E.230.157; 3.E.230.166; 3.E.230.169; 3.E.230.172; 3.E.230.175; 3.E.230.240; 3.E.230.244; 3.E.231.228; 3.E.231.229; 3.E.231.230; 3.E.231.231; 3.E.231.236; 3.E.231.237; 3.E.231.238; 3.E.231.239; 3.E.231.154; 3.E.231.157; 3.E.231.166; 3.E.231.169; 3.E.231.172; 3.E.231.175; 3.E.231.240; 3.E.231.244; 3.E.236.228; 3.E.236.229; 3.E.236.230; 3.E.236.231; 3.E.236.236; 3.E.236.237; 3.E.236.238; 3.E.236.239; 3.E.236.154; 3.E.236.157; 3.E.236.166; 3.E.236.169; 3.E.236.172; 3.E.236.175; 3.E.236.240; 3.E.236.244; 3.E.237.228; 3.E.237.229; 3.E.237.230; 3.E.237.231; 3.E.237.236; 3.E.237.237; 3.E.237.238; 3.E.237.239; 3.E.237.154; 3.E.237.157; 3.E.237.166; 3.E.237.169; 3.E.237.172; 3.E.237.175; 3.E.237.240; 3.E.237.244; 3.E.238.228; 3.E.238.229; 3.E.238.230; 3.E.238.231; 3.E.238.236; 3.E.238.237; 3.E.238.238; 3.E.238.239; 3.E.238.154; 3.E.238.157; 3.E.238.166; 3.E.238.169; 3.E.238.172; 3.E.238.175; 3.E.238.240; 3.E.238.244; 3.E.239.228; 3.E.239.229; 3.E.239.230; 3.E.239.231; 3.E.239.236; 3.E.239.237; 3.E.239.238; 3.E.239.239; 3.E.239.154; 3.E.239.157; 3.E.239.166; 3.E.239.169; 3.E.239.172; 3.E.239.175; 3.E.239.240; 3.E.239.244; 3.E.154.228; 3.E.154.229; 3.E.154.230; 3.E.154.231; 3.E.154.236; 3.E.154.237; 3.E.154.238; 3.E.154.239; 3.E.154.154; 3.E.154.157; 3.E.154.166; 3.E.154.169; 3.E.154.172; 3.E.154.175; 3.E.154.240; 3.E.154.244; 3.E.157.228; 3.E.157.229; 3.E.157.230; 3.E.157.231; 3.E.157.236; 3.E.157.237; 3.E.157.238; 3.E.157.239; 3.E.157.154; 3.E.157.157; 3.E.157.166; 3.E.157.169; 3.E.157.172; 3.E.157.175; 3.E.157.240; 3.E.157.244; 3.E.166.228; 3.E.166.229; 3.E.166.230; 3.E.166.231; 3.E.166.236; 3.E.166.237; 3.E.166.238; 3.E.166.239; 3.E.166.154; 3.E.166.157; 3.E.166.166; 3.E.166.169; 3.E.166.172; 3.E.166.175; 3.E.166.240; 3.E.166.244; 3.E.169.228; 3.E.169.229; 3.E.169.230; 3.E.169.231; 3.E.169.236; 3.E.169.237; 3.E.169.238; 3.E.169.239; 3.E.169.154; 3.E.169.157; 3.E.169.166; 3.E.169.169; 3.E.169.172; 3.E.169.175; 3.E.169.240; 3.E.169.244; 3.E.172.228; 3.E.172.229; 3.E.172.230; 3.E.172.231; 3.E.172.236; 3.E.172.237; 3.E.172.238; 3.E.172.239; 3.E.172.154; 3.E.172.157; 3.E.172.166; 3.E.172.169; 3.E.172.172; 3.E.172.175; 3.E.172.240; 3.E.172.244; 3.E.175.228; 3.E.175.229; 3.E.175.230; 3.E.175.231; 3.E.175.236; 3.E.175.237; 3.E.175.238; 3.E.175.239; 3.E.175.154; 3.E.175.157; 3.E.175.166; 3.E.175.169; 3.E.175.172; 3.E.175.175; 3.E.175.240; 3.E.175.244; 3.E.240.228; 3.E.240.229; 3.E.240.230; 3.E.240.231; 3.E.240.236; 3.E.240.237; 3.E.240.238; 3.E.240.239; 3.E.240.154; 3.E.240.157; 3.E.240.166; 3.E.240.169; 3.E.240.172; 3.E.240.175; 3.E.240.240; 3.E.240.244; 3.E.244.228; 3.E.244.229; 3.E.244.230; 3.E.244.231; 3.E.244.236; 3.E.244.237; 3.E.244.238; 3.E.244.239; 3.E.244.154; 3.E.244.157; 3.E.244.166; 3.E.244.169; 3.E.244.172; 3.E.244.175; 3.E.244.240; 3.E.244.244;

Prodrugs of 3.G

3.G.228.228; 3.G.228.229; 3.G.228.230; 3.G.228.231; 3.G.228.236; 3.G.228.237; 3.G.228.238; 3.G.228.239; 3.G.228.154; 3.G.228.157; 3.G.228.166; 3.G.228.169; 3.G.228.172; 3.G.228.175; 3.G.228.240; 3.G.228.244; 3.G.229.228; 3.G.229.229; 3.G.229.230; 3.G.229.231; 3.G.229.236; 3.G.229.237; 3.G.229.238; 3.G.229.239; 3.G.229.154; 3.G.229.157; 3.G.229.166; 3.G.229.169; 3.G.229.172; 3.G.229.175; 3.G.229.240; 3.G.229.244; 3.G.230.228; 3.G.230.229; 3.G.230.230; 3.G.230.231; 3.G.230.236; 3.G.230.237; 3.G.230.238; 3.G.230.239; 3.G.230.154; 3.G.230.157; 3.G.230.166; 3.G.230.169; 3.G.230.172; 3.G.230.175; 3.G.230.240; 3.G.230.244; 3.G.231.228; 3.G.231.229; 3.G.231.230; 3.G.231.231; 3.G.231.236; 3.G.231.237; 3.G.231.238; 3.G.231.239; 3.G.231.154; 3.G.231.157; 3.G.231.166; 3.G.231.169; 3.G.231.172; 3.G.231.175; 3.G.231.240; 3.G.231.244; 3.G.236.228; 3.G.236.229; 3.G.236.230; 3.G.236.231; 3.G.236.236; 3.G.236.237; 3.G.236.238; 3.G.236.239; 3.G.236.154; 3.G.236.157; 3.G.236.166; 3.G.236.169; 3.G.236.172; 3.G.236.175; 3.G.236.240; 3.G.236.244; 3.G.237.228; 3.G.237.229; 3.G.237.230; 3.G.237.231; 3.G.237.236; 3.G.237.237; 3.G.237.238; 3.G.237.239; 3.G.237.154; 3.G.237.157; 3.G.237.166; 3.G.237.169; 3.G.237.172; 3.G.237.175; 3.G.237.240; 3.G.237.244; 3.G.238.228; 3.G.238.229; 3.G.238.230; 3.G.238.231; 3.G.238.236; 3.G.238.237; 3.G.238.238; 3.G.238.239; 3.G.238.154; 3.G.238.157; 3.G.238.166; 3.G.238.169; 3.G.238.172; 3.G.238.175; 3.G.238.240; 3.G.238.244; 3.G.239.228; 3.G.239.229; 3.G.239.230; 3.G.239.231; 3.G.239.236; 3.G.239.237; 3.G.239.238; 3.G.239.239; 3.G.239.154; 3.G.239.157; 3.G.239.166; 3.G.239.169; 3.G.239.172; 3.G.239.175; 3.G.239.240; 3.G.239.244; 3.G.154.228; 3.G.154.229; 3.G.154.230; 3.G.154.231; 3.G.154.236; 3.G.154.237; 3.G.154.238; 3.G.154.239; 3.G.154.154; 3.G.154.157; 3.G.154.166; 3.G.154.169; 3.G.154.172; 3.G.154.175; 3.G.154.240; 3.G.154.244; 3.G.157.228; 3.G.157.229; 3.G.157.230; 3.G.157.231; 3.G.157.236; 3.G.157.237; 3.G.157.238; 3.G.157.239; 3.G.157.154; 3.G.157.157; 3.G.157.166; 3.G.157.169; 3.G.157.172; 3.G.157.175; 3.G.157.240; 3.G.157.244; 3.G.166.228; 3.G.166.229; 3.G.166.230; 3.G.166.231; 3.G.166.236; 3.G.166.237; 3.G.166.238; 3.G.166.239; 3.G.166.154; 3.G.166.157; 3.G.166.166; 3.G.166.169; 3.G.166.172; 3.G.166.175; 3.G.166.240; 3.G.166.244; 3.G.169.228; 3.G.169.229; 3.G.169.230; 3.G.169.231; 3.G.169.236; 3.G.169.237; 3.G.169.238; 3.G.169.239; 3.G.169.154; 3.G.169.157; 3.G.169.166; 3.G.169.169; 3.G.169.172; 3.G.169.175; 3.G.169.240; 3.G.169.244; 3.G.172.228; 3.G.172.229; 3.G.172.230;

TABLE 100-continued

3.G.172.231; 3.G.172.236; 3.G.172.237; 3.G.172.238; 3.G.172.239; 3.G.172.154; 3.G.172.157; 3.G.172.166; 3.G.172.169; 3.G.172.172; 3.G.172.175; 3.G.172.240; 3.G.172.244; 3.G.175.228; 3.G.175.229; 3.G.175.230; 3.G.175.231; 3.G.175.236; 3.G.175.237; 3.G.175.238; 3.G.175.239; 3.G.175.154; 3.G.175.157; 3.G.175.166; 3.G.175.169; 3.G.175.172; 3.G.175.175; 3.G.175.240; 3.G.175.244; 3.G.240.228; 3.G.240.229; 3.G.240.230; 3.G.240.231; 3.G.240.236; 3.G.240.237; 3.G.240.238; 3.G.240.239; 3.G.240.154; 3.G.240.157; 3.G.240.166; 3.G.240.169; 3.G.240.172; 3.G.240.175; 3.G.240.240; 3.G.240.244; 3.G.244.228; 3.G.244.229; 3.G.244.230; 3.G.244.231; 3.G.244.236; 3.G.244.237; 3.G.244.238; 3.G.244.239; 3.G.244.154; 3.G.244.157; 3.G.244.166; 3.G.244.169; 3.G.244.172; 3.G.244.175; 3.G.244.240; 3.G.244.244;

Prodrugs of 3.I

3.I.228.228; 3.I.228.229; 3.I.228.230; 3.I.228.231; 3.I.228.236; 3.I.228.237; 3.I.228.238; 3.I.228.239; 3.I.228.154; 3.I.228.157; 3.I.228.166; 3.I.228.169; 3.I.228.172; 3.I.228.175; 3.I.228.240; 3.I.228.244; 3.I.229.228; 3.I.229.229; 3.I.229.230; 3.I.229.231; 3.I.229.236; 3.I.229.237; 3.I.229.238; 3.I.229.239; 3.I.229.154; 3.I.229.157; 3.I.229.166; 3.I.229.169; 3.I.229.172; 3.I.229.175; 3.I.229.240; 3.I.229.244; 3.I.230.228; 3.I.230.229; 3.I.230.230; 3.I.230.231; 3.I.230.236; 3.I.230.237; 3.I.230.238; 3.I.230.239; 3.I.230.154; 3.I.230.157; 3.I.230.166; 3.I.230.169; 3.I.230.172; 3.I.230.175; 3.I.230.240; 3.I.230.244; 3.I.231.228; 3.I.231.229; 3.I.231.230; 3.I.231.231; 3.I.231.236; 3.I.231.237; 3.I.231.238; 3.I.231.239; 3.I.231.154; 3.I.231.157; 3.I.231.166; 3.I.231.169; 3.I.231.172; 3.I.231.175; 3.I.231.240; 3.I.231.244; 3.I.236.228; 3.I.236.229; 3.I.236.230; 3.I.236.231; 3.I.236.236; 3.I.236.237; 3.I.236.238; 3.I.236.239; 3.I.236.154; 3.I.236.157; 3.I.236.166; 3.I.236.169; 3.I.236.172; 3.I.236.175; 3.I.236.240; 3.I.236.244; 3.I.237.228; 3.I.237.229; 3.I.237.230; 3.I.237.231; 3.I.237.236; 3.I.237.237; 3.I.237.238; 3.I.237.239; 3.I.237.154; 3.I.237.157; 3.I.237.166; 3.I.237.169; 3.I.237.172; 3.I.237.175; 3.I.237.240; 3.I.237.244; 3.I.238.228; 3.I.238.229; 3.I.238.230; 3.I.238.231; 3.I.238.236; 3.I.238.237; 3.I.238.238; 3.I.238.239; 3.I.238.154; 3.I.238.157; 3.I.238.166; 3.I.238.169; 3.I.238.172; 3.I.238.175; 3.I.238.240; 3.I.238.244; 3.I.239.228; 3.I.239.229; 3.I.239.230; 3.I.239.231; 3.I.239.236; 3.I.239.237; 3.I.239.238; 3.I.239.239; 3.I.239.154; 3.I.239.157; 3.I.239.166; 3.I.239.169; 3.I.239.172; 3.I.239.175; 3.I.239.240; 3.I.239.244; 3.I.154.228; 3.I.154.229; 3.I.154.230; 3.I.154.231; 3.I.154.236; 3.I.154.237; 3.I.154.238; 3.I.154.239; 3.I.154.154; 3.I.154.157; 3.I.154.166; 3.I.154.169; 3.I.154.172; 3.I.154.175; 3.I.154.240; 3.I.154.244; 3.I.157.228; 3.I.157.229; 3.I.157.230; 3.I.157.231; 3.I.157.236; 3.I.157.237; 3.I.157.238; 3.I.157.239; 3.I.157.154; 3.I.157.157; 3.I.157.166; 3.I.157.169; 3.I.157.172; 3.I.157.175; 3.I.157.240; 3.I.157.244; 3.I.166.228; 3.I.166.229; 3.I.166.230; 3.I.166.231; 3.I.166.236; 3.I.166.237; 3.I.166.238; 3.I.166.239; 3.I.166.154; 3.I.166.157; 3.I.166.166; 3.I.166.169; 3.I.166.172; 3.I.166.175; 3.I.166.240; 3.I.166.244; 3.I.169.228; 3.I.169.229; 3.I.169.230; 3.I.169.231; 3.I.169.236; 3.I.169.237; 3.I.169.238; 3.I.169.239; 3.I.169.154; 3.I.169.157; 3.I.169.166; 3.I.169.169; 3.I.169.172; 3.I.169.175; 3.I.169.240; 3.I.169.244; 3.I.172.228; 3.I.172.229; 3.I.172.230; 3.I.172.231; 3.I.172.236; 3.I.172.237; 3.I.172.238; 3.I.172.239; 3.I.172.154; 3.I.172.157; 3.I.172.166; 3.I.172.169; 3.I.172.172; 3.I.172.175; 3.I.172.240; 3.I.172.244; 3.I.175.228; 3.I.175.229; 3.I.175.230; 3.I.175.231; 3.I.175.236; 3.I.175.237; 3.I.175.238; 3.I.175.239; 3.I.175.154; 3.I.175.157; 3.I.175.166; 3.I.175.169; 3.I.175.172; 3.I.175.175; 3.I.175.240; 3.I.175.244; 3.I.240.228; 3.I.240.229; 3.I.240.230; 3.I.240.231; 3.I.240.236; 3.I.240.237; 3.I.240.238; 3.I.240.239; 3.I.240.154; 3.I.240.157; 3.I.240.166; 3.I.240.169; 3.I.240.172; 3.I.240.175; 3.I.240.240; 3.I.240.244; 3.I.244.228; 3.I.244.229; 3.I.244.230; 3.I.244.231; 3.I.244.236; 3.I.244.237; 3.I.244.238; 3.I.244.239; 3.I.244.154; 3.I.244.157; 3.I.244.166; 3.I.244.169; 3.I.244.172; 3.I.244.175; 3.I.244.240; 3.I.244.244;

Prodrugs of 3.J

3.J.228.228; 3.J.228.229; 3.J.228.230; 3.J.228.231; 3.J.228.236; 3.J.228.237; 3.J.228.238; 3.J.228.239; 3.J.228.154; 3.J.228.157; 3.J.228.166; 3.J.228.169; 3.J.228.172; 3.J.228.175; 3.J.228.240; 3.J.228.244; 3.J.229.228; 3.J.229.229; 3.J.229.230; 3.J.229.231; 3.J.229.236; 3.J.229.237; 3.J.229.238; 3.J.229.239; 3.J.229.154; 3.J.229.157; 3.J.229.166; 3.J.229.169; 3.J.229.172; 3.J.229.175; 3.J.229.240; 3.J.229.244; 3.J.230.228; 3.J.230.229; 3.J.230.230; 3.J.230.231; 3.J.230.236; 3.J.230.237; 3.J.230.238; 3.J.230.239; 3.J.230.154; 3.J.230.157; 3.J.230.166; 3.J.230.169; 3.J.230.172; 3.J.230.175; 3.J.230.240; 3.J.230.244; 3.J.231.228; 3.J.231.229; 3.J.231.230; 3.J.231.231; 3.J.231.236; 3.J.231.237; 3.J.231.238; 3.J.231.239; 3.J.231.154; 3.J.231.157; 3.J.231.166; 3.J.231.169; 3.J.231.172; 3.J.231.175; 3.J.231.240; 3.J.231.244; 3.J.236.228; 3.J.236.229; 3.J.236.230; 3.J.236.231; 3.J.236.236; 3.J.236.237; 3.J.236.238; 3.J.236.239; 3.J.236.154; 3.J.236.157; 3.J.236.166; 3.J.236.169; 3.J.236.172; 3.J.236.175; 3.J.236.240; 3.J.236.244; 3.J.237.228; 3.J.237.229; 3.J.237.230; 3.J.237.231; 3.J.237.236; 3.J.237.237; 3.J.237.238; 3.J.237.239; 3.J.237.154; 3.J.237.157; 3.J.237.166; 3.J.237.169; 3.J.237.172; 3.J.237.175; 3.J.237.240; 3.J.237.244; 3.J.238.228; 3.J.238.229; 3.J.238.230; 3.J.238.231; 3.J.238.236; 3.J.238.237; 3.J.238.238; 3.J.238.239; 3.J.238.154; 3.J.238.157; 3.J.238.166; 3.J.238.169; 3.J.238.172; 3.J.238.175; 3.J.238.240; 3.J.238.244; 3.J.239.228; 3.J.239.229;

TABLE 100-continued

3.J.239.230; 3.J.239.231; 3.J.239.236; 3.J.239.237; 3.J.239.238; 3.J.239.239; 3.J.239.154; 3.J.239.157; 3.J.239.166; 3.J.239.169; 3.J.239.172; 3.J.239.175; 3.J.239.240; 3.J.239.244; 3.J.154.228; 3.J.154.229; 3.J.154.230; 3.J.154.231; 3.J.154.236; 3.J.154.237; 3.J.154.238; 3.J.154.239; 3.J.154.154; 3.J.154.157; 3.J.154.166; 3.J.154.169; 3.J.154.172; 3.J.154.175; 3.J.154.240; 3.J.154.244; 3.J.157.228; 3.J.157.229; 3.J.157.230; 3.J.157.231; 3.J.157.236; 3.J.157.237; 3.J.157.238; 3.J.157.239; 3.J.157.154; 3.J.157.157; 3.J.157.166; 3.J.157.169; 3.J.157.172; 3.J.157.175; 3.J.157.240; 3.J.157.244; 3.J.166.228; 3.J.166.229; 3.J.166.230; 3.J.166.231; 3.J.166.236; 3.J.166.237; 3.J.166.238; 3.J.166.239; 3.J.166.154; 3.J.166.157; 3.J.166.166; 3.J.166.169; 3.J.166.172; 3.J.166.175; 3.J.166.240; 3.J.166.244; 3.J.169.228; 3.J.169.229; 3.J.169.230; 3.J.169.231; 3.J.169.236; 3.J.169.237; 3.J.169.238; 3.J.169.239; 3.J.169.154; 3.J.169.157; 3.J.169.166; 3.J.169.169; 3.J.169.172; 3.J.169.175; 3.J.169.240; 3.J.169.244; 3.J.172.228; 3.J.172.229; 3.J.172.230; 3.J.172.231; 3.J.172.236; 3.J.172.237; 3.J.172.238; 3.J.172.239; 3.J.172.154; 3.J.172.157; 3.J.172.166; 3.J.172.169; 3.J.172.172; 3.J.172.175; 3.J.172.240; 3.J.172.244; 3.J.175.228; 3.J.175.229; 3.J.175.230; 3.J.175.231; 3.J.175.236; 3.J.175.237; 3.J.175.238; 3.J.175.239; 3.J.175.154; 3.J.175.157; 3.J.175.166; 3.J.175.169; 3.J.175.172; 3.J.175.175; 3.J.175.240; 3.J.175.244; 3.J.240.228; 3.J.240.229; 3.J.240.230; 3.J.240.231; 3.J.240.236; 3.J.240.237; 3.J.240.238; 3.J.240.239; 3.J.240.154; 3.J.240.157; 3.J.240.166; 3.J.240.169; 3.J.240.172; 3.J.240.175; 3.J.240.240; 3.J.240.244; 3.J.244.228; 3.J.244.229; 3.J.244.230; 3.J.244.231; 3.J.244.236; 3.J.244.237; 3.J.244.238; 3.J.244.239; 3.J.244.154; 3.J.244.157; 3.J.244.166; 3.J.244.169; 3.J.244.172; 3.J.244.175; 3.J.244.240; 3.J.244.244;

Prodrugs of 3.L

3.L.228.228; 3.L.228.229; 3.L.228.230; 3.L.228.231; 3.L.228.236; 3.L.228.237; 3.L.228.238; 3.L.228.239; 3.L.228.154; 3.L.228.157; 3.L.228.166; 3.L.228.169; 3.L.228.172; 3.L.228.175; 3.L.228.240; 3.L.228.244; 3.L.229.228; 3.L.229.229; 3.L.229.230; 3.L.229.231; 3.L.229.236; 3.L.229.237; 3.L.229.238; 3.L.229.239; 3.L.229.154; 3.L.229.157; 3.L.229.166; 3.L.229.169; 3.L.229.172; 3.L.229.175; 3.L.229.240; 3.L.229.244; 3.L.230.228; 3.L.230.229; 3.L.230.230; 3.L.230.231; 3.L.230.236; 3.L.230.237; 3.L.230.238; 3.L.230.239; 3.L.230.154; 3.L.230.157; 3.L.230.166; 3.L.230.169; 3.L.230.172; 3.L.230.175; 3.L.230.240; 3.L.230.244; 3.L.231.228; 3.L.231.229; 3.L.231.230; 3.L.231.231; 3.L.231.236; 3.L.231.237; 3.L.231.238; 3.L.231.239; 3.L.231.154; 3.L.231.157; 3.L.231.166; 3.L.231.169; 3.L.231.172; 3.L.231.175; 3.L.231.240; 3.L.231.244; 3.L.236.228; 3.L.236.229; 3.L.236.230; 3.L.236.231; 3.L.236.236; 3.L.236.237; 3.L.236.238; 3.L.236.239; 3.L.236.154; 3.L.236.157; 3.L.236.166; 3.L.236.169; 3.L.236.172; 3.L.236.175; 3.L.236.240; 3.L.236.244; 3.L.237.228; 3.L.237.229; 3.L.237.230; 3.L.237.231; 3.L.237.236; 3.L.237.237; 3.L.237.238; 3.L.237.239; 3.L.237.154; 3.L.237.157; 3.L.237.166; 3.L.237.169; 3.L.237.172; 3.L.237.175; 3.L.237.240; 3.L.237.244; 3.L.238.228; 3.L.238.229; 3.L.238.230; 3.L.238.231; 3.L.238.236; 3.L.238.237; 3.L.238.238; 3.L.238.239; 3.L.238.154; 3.L.238.157; 3.L.238.166; 3.L.238.169; 3.L.238.172; 3.L.238.175; 3.L.238.240; 3.L.238.244; 3.L.239.228; 3.L.239.229; 3.L.239.230; 3.L.239.231; 3.L.239.236; 3.L.239.237; 3.L.239.238; 3.L.239.239; 3.L.239.154; 3.L.239.157; 3.L.239.166; 3.L.239.169; 3.L.239.172; 3.L.239.175; 3.L.239.240; 3.L.239.244; 3.L.154.228; 3.L.154.229; 3.L.154.230; 3.L.154.231; 3.L.154.236; 3.L.154.237; 3.L.154.238; 3.L.154.239; 3.L.154.154; 3.L.154.157; 3.L.154.166; 3.L.154.169; 3.L.154.172; 3.L.154.175; 3.L.154.240; 3.L.154.244; 3.L.157.228; 3.L.157.229; 3.L.157.230; 3.L.157.231; 3.L.157.236; 3.L.157.237; 3.L.157.238; 3.L.157.239; 3.L.157.154; 3.L.157.157; 3.L.157.166; 3.L.157.169; 3.L.157.172; 3.L.157.175; 3.L.157.240; 3.L.157.244; 3.L.166.228; 3.L.166.229; 3.L.166.230; 3.L.166.231; 3.L.166.236; 3.L.166.237; 3.L.166.238; 3.L.166.239; 3.L.166.154; 3.L.166.157; 3.L.166.166; 3.L.166.169; 3.L.166.172; 3.L.166.175; 3.L.166.240; 3.L.166.244; 3.L.169.228; 3.L.169.229; 3.L.169.230; 3.L.169.231; 3.L.169.236; 3.L.169.237; 3.L.169.238; 3.L.169.239; 3.L.169.154; 3.L.169.157; 3.L.169.166; 3.L.169.169; 3.L.169.172; 3.L.169.175; 3.L.169.240; 3.L.169.244; 3.L.172.228; 3.L.172.229; 3.L.172.230; 3.L.172.231; 3.L.172.236; 3.L.172.237; 3.L.172.238; 3.L.172.239; 3.L.172.154; 3.L.172.157; 3.L.172.166; 3.L.172.169; 3.L.172.172; 3.L.172.175; 3.L.172.240; 3.L.172.244; 3.L.175.228; 3.L.175.229; 3.L.175.230; 3.L.175.231; 3.L.175.236; 3.L.175.237; 3.L.175.238; 3.L.175.239; 3.L.175.154; 3.L.175.157; 3.L.175.166; 3.L.175.169; 3.L.175.172; 3.L.175.175; 3.L.175.240; 3.L.175.244; 3.L.240.228; 3.L.240.229; 3.L.240.230; 3.L.240.231; 3.L.240.236; 3.L.240.237; 3.L.240.238; 3.L.240.239; 3.L.240.154; 3.L.240.157; 3.L.240.166; 3.L.240.169; 3.L.240.172; 3.L.240.175; 3.L.240.240; 3.L.240.244; 3.L.244.228; 3.L.244.229; 3.L.244.230; 3.L.244.231; 3.L.244.236; 3.L.244.237; 3.L.244.238; 3.L.244.239; 3.L.244.154; 3.L.244.157; 3.L.244.166; 3.L.244.169; 3.L.244.172; 3.L.244.175; 3.L.244.240; 3.L.244.244;

Prodrugs of 3.O

3.O.228.228; 3.O.228.229; 3.O.228.230; 3.O.228.231; 3.O.228.236; 3.O.228.237; 3.O.228.238; 3.O.228.239; 3.O.228.154; 3.O.228.157; 3.O.228.166; 3.O.228.169; 3.O.228.172; 3.O.228.175; 3.O.228.240; 3.O.228.244; 3.O.229.228; 3.O.229.229; 3.O.229.230; 3.O.229.231; 3.O.229.236; 3.O.229.237; 3.O.229.238; 3.O.229.239; 3.O.229.154; 3.O.229.157; 3.O.229.166; 3.O.229.169; 3.O.229.172; 3.O.229.175; 3.O.229.240; 3.O.229.244; 3.O.230.228; 3.O.230.229; 3.O.230.230; 3.O.230.231; 3.O.230.236; 3.O.230.237; 3.O.230.238; 3.O.230.239;

TABLE 100-continued

3.O.230.154; 3.O.230.157; 3.O.230.166; 3.O.230.169; 3.O.230.172; 3.O.230.175; 3.O.230.240; 3.O.230.244; 3.O.231.228; 3.O.231.229; 3.O.231.230; 3.O.231.231; 3.O.231.236; 3.O.231.237; 3.O.231.238; 3.O.231.239; 3.O.231.154; 3.O.231.157; 3.O.231.166; 3.O.231.169; 3.O.231.172; 3.O.231.175; 3.O.231.240; 3.O.231.244; 3.O.236.228; 3.O.236.229; 3.O.236.230; 3.O.236.231; 3.O.236.236; 3.O.236.237; 3.O.236.238; 3.O.236.239; 3.O.236.154; 3.O.236.157; 3.O.236.166; 3.O.236.169; 3.O.236.172; 3.O.236.175; 3.O.236.240; 3.O.236.244; 3.O.237.228; 3.O.237.229; 3.O.237.230; 3.O.237.231; 3.O.237.236; 3.O.237.237; 3.O.237.238; 3.O.237.239; 3.O.237.154; 3.O.237.157; 3.O.237.166; 3.O.237.169; 3.O.237.172; 3.O.237.175; 3.O.237.240; 3.O.237.244; 3.O.238.228; 3.O.238.229; 3.O.238.230; 3.O.238.231; 3.O.238.236; 3.O.238.237; 3.O.238.238; 3.O.238.239; 3.O.238.154; 3.O.238.157; 3.O.238.166; 3.O.238.169; 3.O.238.172; 3.O.238.175; 3.O.238.240; 3.O.238.244; 3.O.239.228; 3.O.239.229; 3.O.239.230; 3.O.239.231; 3.O.239.236; 3.O.239.237; 3.O.239.238; 3.O.239.239; 3.O.239.154; 3.O.239.157; 3.O.239.166; 3.O.239.169; 3.O.239.172; 3.O.239.175; 3.O.239.240; 3.O.239.244; 3.O.154.228; 3.O.154.229; 3.O.154.230; 3.O.154.231; 3.O.154.236; 3.O.154.237; 3.O.154.238; 3.O.154.239; 3.O.154.154; 3.O.154.157; 3.O.154.166; 3.O.154.169; 3.O.154.172; 3.O.154.175; 3.O.154.240; 3.O.154.244; 3.O.157.228; 3.O.157.229; 3.O.157.230; 3.O.157.231; 3.O.157.236; 3.O.157.237; 3.O.157.238; 3.O.157.239; 3.O.157.154; 3.O.157.157; 3.O.157.166; 3.O.157.169; 3.O.157.172; 3.O.157.175; 3.O.157.240; 3.O.157.244; 3.O.166.228; 3.O.166.229; 3.O.166.230; 3.O.166.231; 3.O.166.236; 3.O.166.237; 3.O.166.238; 3.O.166.239; 3.O.166.154; 3.O.166.157; 3.O.166.166; 3.O.166.169; 3.O.166.172; 3.O.166.175; 3.O.166.240; 3.O.166.244; 3.O.169.228; 3.O.169.229; 3.O.169.230; 3.O.169.231; 3.O.169.236; 3.O.169.237; 3.O.169.238; 3.O.169.239; 3.O.169.154; 3.O.169.157; 3.O.169.166; 3.O.169.169; 3.O.169.172; 3.O.169.175; 3.O.169.240; 3.O.169.244; 3.O.172.228; 3.O.172.229; 3.O.172.230; 3.O.172.231; 3.O.172.236; 3.O.172.237; 3.O.172.238; 3.O.172.239; 3.O.172.154; 3.O.172.157; 3.O.172.166; 3.O.172.169; 3.O.172.172; 3.O.172.175; 3.O.172.240; 3.O.172.244; 3.O.175.228; 3.O.175.229; 3.O.175.230; 3.O.175.231; 3.O.175.236; 3.O.175.237; 3.O.175.238; 3.O.175.239; 3.O.175.154; 3.O.175.157; 3.O.175.166; 3.O.175.169; 3.O.175.172; 3.O.175.175; 3.O.175.240; 3.O.175.244; 3.O.240.228; 3.O.240.229; 3.O.240.230; 3.O.240.231; 3.O.240.236; 3.O.240.237; 3.O.240.238; 3.O.240.239; 3.O.240.154; 3.O.240.157; 3.O.240.166; 3.O.240.169; 3.O.240.172; 3.O.240.175; 3.O.240.240; 3.O.240.244; 3.O.244.228; 3.O.244.229; 3.O.244.230; 3.O.244.231; 3.O.244.236; 3.O.244.237; 3.O.244.238; 3.O.244.239; 3.O.244.154; 3.O.244.157; 3.O.244.166; 3.O.244.169; 3.O.244.172; 3.O.244.175; 3.O.244.240; 3.O.244.244;

Prodrugs of 3.P

3.P.228.228; 3.P.228.229; 3.P.228.230; 3.P.228.231; 3.P.228.236; 3.P.228.237; 3.P.228.238; 3.P.228.239; 3.P.228.154; 3.P.228.157; 3.P.228.166; 3.P.228.169; 3.P.228.172; 3.P.228.175; 3.P.228.240; 3.P.228.244; 3.P.229.228; 3.P.229.229; 3.P.229.230; 3.P.229.231; 3.P.229.236; 3.P.229.237; 3.P.229.238; 3.P.229.239; 3.P.229.154; 3.P.229.157; 3.P.229.166; 3.P.229.169; 3.P.229.172; 3.P.229.175; 3.P.229.240; 3.P.229.244; 3.P.230.228; 3.P.230.229; 3.P.230.230; 3.P.230.231; 3.P.230.236; 3.P.230.237; 3.P.230.238; 3.P.230.239; 3.P.230.154; 3.P.230.157; 3.P.230.166; 3.P.230.169; 3.P.230.172; 3.P.230.175; 3.P.230.240; 3.P.230.244; 3.P.231.228; 3.P.231.229; 3.P.231.230; 3.P.231.231; 3.P.231.236; 3.P.231.237; 3.P.231.238; 3.P.231.239; 3.P.231.154; 3.P.231.157; 3.P.231.166; 3.P.231.169; 3.P.231.172; 3.P.231.175; 3.P.231.240; 3.P.231.244; 3.P.236.228; 3.P.236.229; 3.P.236.230; 3.P.236.231; 3.P.236.236; 3.P.236.237; 3.P.236.238; 3.P.236.239; 3.P.236.154; 3.P.236.157; 3.P.236.166; 3.P.236.169; 3.P.236.172; 3.P.236.175; 3.P.236.240; 3.P.236.244; 3.P.237.228; 3.P.237.229; 3.P.237.230; 3.P.237.231; 3.P.237.236; 3.P.237.237; 3.P.237.238; 3.P.237.239; 3.P.237.154; 3.P.237.157; 3.P.237.166; 3.P.237.169; 3.P.237.172; 3.P.237.175; 3.P.237.240; 3.P.237.244; 3.P.238.228; 3.P.238.229; 3.P.238.230; 3.P.238.231; 3.P.238.236; 3.P.238.237; 3.P.238.238; 3.P.238.239; 3.P.238.154; 3.P.238.157; 3.P.238.166; 3.P.238.169; 3.P.238.172; 3.P.238.175; 3.P.238.240; 3.P.238.244; 3.P.239.228; 3.P.239.229; 3.P.239.230; 3.P.239.231; 3.P.239.236; 3.P.239.237; 3.P.239.238; 3.P.239.239; 3.P.239.154; 3.P.239.157; 3.P.239.166; 3.P.239.169; 3.P.239.172; 3.P.239.175; 3.P.239.240; 3.P.239.244; 3.P.154.228; 3.P.154.229; 3.P.154.230; 3.P.154.231; 3.P.154.236; 3.P.154.237; 3.P.154.238; 3.P.154.239; 3.P.154.154; 3.P.154.157; 3.P.154.166; 3.P.154.169; 3.P.154.172; 3.P.154.175; 3.P.154.240; 3.P.154.244; 3.P.157.228; 3.P.157.229; 3.P.157.230; 3.P.157.231; 3.P.157.236; 3.P.157.237; 3.P.157.238; 3.P.157.239; 3.P.157.154; 3.P.157.157; 3.P.157.166; 3.P.157.169; 3.P.157.172; 3.P.157.175; 3.P.157.240; 3.P.157.244; 3.P.166.228; 3.P.166.229; 3.P.166.230; 3.P.166.231; 3.P.166.236; 3.P.166.237; 3.P.166.238; 3.P.166.239; 3.P.166.154; 3.P.166.157; 3.P.166.166; 3.P.166.169; 3.P.166.172; 3.P.166.175; 3.P.166.240; 3.P.166.244; 3.P.169.228; 3.P.169.229; 3.P.169.230; 3.P.169.231; 3.P.169.236; 3.P.169.237; 3.P.169.238; 3.P.169.239; 3.P.169.154; 3.P.169.157; 3.P.169.166; 3.P.169.169; 3.P.169.172; 3.P.169.175; 3.P.169.240; 3.P.169.244; 3.P.172.228; 3.P.172.229; 3.P.172.230; 3.P.172.231; 3.P.172.236;

TABLE 100-continued

3.P.172.237; 3.P.172.238; 3.P.172.239; 3.P.172.154; 3.P.172.157; 3.P.172.166; 3.P.172.169; 3.P.172.172; 3.P.172.175; 3.P.172.240; 3.P.172.244; 3.P.175.228; 3.P.175.229; 3.P.175.230; 3.P.175.231; 3.P.175.236; 3.P.175.237; 3.P.175.238; 3.P.175.239; 3.P.175.154; 3.P.175.157; 3.P.175.166; 3.P.175.169; 3.P.175.172; 3.P.175.175; 3.P.175.240; 3.P.175.244; 3.P.240.228; 3.P.240.229; 3.P.240.230; 3.P.240.231; 3.P.240.236; 3.P.240.237; 3.P.240.238; 3.P.240.239; 3.P.240.154; 3.P.240.157; 3.P.240.166; 3.P.240.169; 3.P.240.172; 3.P.240.175; 3.P.240.240; 3.P.240.244; 3.P.244.228; 3.P.244.229; 3.P.244.230; 3.P.244.231; 3.P.244.236; 3.P.244.237; 3.P.244.238; 3.P.244.239; 3.P.244.154; 3.P.244.157; 3.P.244.166; 3.P.244.169; 3.P.244.172; 3.P.244.175; 3.P.244.240; 3.P.244.244;

Prodrugs of 3.U

3.U.228.228; 3.U.228.229; 3.U.228.230; 3.U.228.231; 3.U.228.236; 3.U.228.237; 3.U.228.238; 3.U.228.239; 3.U.228.154; 3.U.228.157; 3.U.228.166; 3.U.228.169; 3.U.228.172; 3.U.228.175; 3.U.228.240; 3.U.228.244; 3.U.229.228; 3.U.229.229; 3.U.229.230; 3.U.229.231; 3.U.229.236; 3.U.229.237; 3.U.229.238; 3.U.229.239; 3.U.229.154; 3.U.229.157; 3.U.229.166; 3.U.229.169; 3.U.229.172; 3.U.229.175; 3.U.229.240; 3.U.229.244; 3.U.230.228; 3.U.230.229; 3.U.230.230; 3.U.230.231; 3.U.230.236; 3.U.230.237; 3.U.230.238; 3.U.230.239; 3.U.230.154; 3.U.230.157; 3.U.230.166; 3.U.230.169; 3.U.230.172; 3.U.230.175; 3.U.230.240; 3.U.230.244; 3.U.231.228; 3.U.231.229; 3.U.231.230; 3.U.231.231; 3.U.231.236; 3.U.231.237; 3.U.231.238; 3.U.231.239; 3.U.231.154; 3.U.231.157; 3.U.231.166; 3.U.231.169; 3.U.231.172; 3.U.231.175; 3.U.231.240; 3.U.231.244; 3.U.236.228; 3.U.236.229; 3.U.236.230; 3.U.236.231; 3.U.236.236; 3.U.236.237; 3.U.236.238; 3.U.236.239; 3.U.236.154; 3.U.236.157; 3.U.236.166; 3.U.236.169; 3.U.236.172; 3.U.236.175; 3.U.236.240; 3.U.236.244; 3.U.237.228; 3.U.237.229; 3.U.237.230; 3.U.237.231; 3.U.237.236; 3.U.237.237; 3.U.237.238; 3.U.237.239; 3.U.237.154; 3.U.237.157; 3.U.237.166; 3.U.237.169; 3.U.237.172; 3.U.237.175; 3.U.237.240; 3.U.237.244; 3.U.238.228; 3.U.238.229; 3.U.238.230; 3.U.238.231; 3.U.238.236; 3.U.238.237; 3.U.238.238; 3.U.238.239; 3.U.238.154; 3.U.238.157; 3.U.238.166; 3.U.238.169; 3.U.238.172; 3.U.238.175; 3.U.238.240; 3.U.238.244; 3.U.239.228; 3.U.239.229; 3.U.239.230; 3.U.239.231; 3.U.239.236; 3.U.239.237; 3.U.239.238; 3.U.239.239; 3.U.239.154; 3.U.239.157; 3.U.239.166; 3.U.239.169; 3.U.239.172; 3.U.239.175; 3.U.239.240; 3.U.239.244; 3.U.154.228; 3.U.154.229; 3.U.154.230; 3.U.154.231; 3.U.154.236; 3.U.154.237; 3.U.154.238; 3.U.154.239; 3.U.154.154; 3.U.154.157; 3.U.154.166; 3.U.154.169; 3.U.154.172; 3.U.154.175; 3.U.154.240; 3.U.154.244; 3.U.157.228; 3.U.157.229; 3.U.157.230; 3.U.157.231; 3.U.157.236; 3.U.157.237; 3.U.157.238; 3.U.157.239; 3.U.157.154; 3.U.157.157; 3.U.157.166; 3.U.157.169; 3.U.157.172; 3.U.157.175; 3.U.157.240; 3.U.157.244; 3.U.166.228; 3.U.166.229; 3.U.166.230; 3.U.166.231; 3.U.166.236; 3.U.166.237; 3.U.166.238; 3.U.166.239; 3.U.166.154; 3.U.166.157; 3.U.166.166; 3.U.166.169; 3.U.166.172; 3.U.166.175; 3.U.166.240; 3.U.166.244; 3.U.169.228; 3.U.169.229; 3.U.169.230; 3.U.169.231; 3.U.169.236; 3.U.169.237; 3.U.169.238; 3.U.169.239; 3.U.169.154; 3.U.169.157; 3.U.169.166; 3.U.169.169; 3.U.169.172; 3.U.169.175; 3.U.169.240; 3.U.169.244; 3.U.172.228; 3.U.172.229; 3.U.172.230; 3.U.172.231; 3.U.172.236; 3.U.172.237; 3.U.172.238; 3.U.172.239; 3.U.172.154; 3.U.172.157; 3.U.172.166; 3.U.172.169; 3.U.172.172; 3.U.172.175; 3.U.172.240; 3.U.172.244; 3.U.175.228; 3.U.175.229; 3.U.175.230; 3.U.175.231; 3.U.175.236; 3.U.175.237; 3.U.175.238; 3.U.175.239; 3.U.175.154; 3.U.175.157; 3.U.175.166; 3.U.175.169; 3.U.175.172; 3.U.175.175; 3.U.175.240; 3.U.175.244; 3.U.240.228; 3.U.240.229; 3.U.240.230; 3.U.240.231; 3.U.240.236; 3.U.240.237; 3.U.240.238; 3.U.240.239; 3.U.240.154; 3.U.240.157; 3.U.240.166; 3.U.240.169; 3.U.240.172; 3.U.240.175; 3.U.240.240; 3.U.240.244; 3.U.244.228; 3.U.244.229; 3.U.244.230; 3.U.244.231; 3.U.244.236; 3.U.244.237; 3.U.244.238; 3.U.244.239; 3.U.244.154; 3.U.244.157; 3.U.244.166; 3.U.244.169; 3.U.244.172; 3.U.244.175; 3.U.244.240; 3.U.244.244;

Prodrugs of 3.W

3.W.228.228; 3.W.228.229; 3.W.228.230; 3.W.228.231; 3.W.228.236; 3.W.228.237; 3.W.228.238; 3.W.228.239; 3.W.228.154; 3.W.228.157; 3.W.228.166; 3.W.228.169; 3.W.228.172; 3.W.228.175; 3.W.228.240; 3.W.228.244; 3.W.229.228; 3.W.229.229; 3.W.229.230; 3.W.229.231; 3.W.229.236; 3.W.229.237; 3.W.229.238; 3.W.229.239; 3.W.229.154; 3.W.229.157; 3.W.229.166; 3.W.229.169; 3.W.229.172; 3.W.229.175; 3.W.229.240; 3.W.229.244; 3.W.230.228; 3.W.230.229; 3.W.230.230; 3.W.230.231; 3.W.230.236; 3.W.230.237; 3.W.230.238; 3.W.230.239; 3.W.230.154; 3.W.230.157; 3.W.230.166; 3.W.230.169; 3.W.230.172; 3.W.230.175; 3.W.230.240; 3.W.230.244; 3.W.231.228; 3.W.231.229; 3.W.231.230; 3.W.231.231; 3.W.231.236; 3.W.231.237; 3.W.231.238; 3.W.231.239; 3.W.231.154; 3.W.231.157; 3.W.231.166; 3.W.231.169; 3.W.231.172; 3.W.231.175; 3.W.231.240; 3.W.231.244; 3.W.236.228;

TABLE 100-continued

3.W.236.229; 3.W.236.230; 3.W.236.231; 3.W.236.236; 3.W.236.237;
3.W.236.238; 3.W.236.239; 3.W.236.154; 3.W.236.157; 3.W.236.166;
3.W.236.169; 3.W.236.172; 3.W.236.175; 3.W.236.240; 3.W.236.244;
3.W.237.228; 3.W.237.229; 3.W.237.230; 3.W.237.231; 3.W.237.236;
3.W.237.237; 3.W.237.238; 3.W.237.239; 3.W.237.154; 3.W.237.157;
3.W.237.166; 3.W.237.169; 3.W.237.172; 3.W.237.175; 3.W.237.240;
3.W.237.244; 3.W.238.228; 3.W.238.229; 3.W.238.230; 3.W.238.231;
3.W.238.236; 3.W.238.237; 3.W.238.238; 3.W.238.239; 3.W.238.154;
3.W.238.157; 3.W.238.166; 3.W.238.169; 3.W.238.172; 3.W.238.175;
3.W.238.240; 3.W.238.244; 3.W.239.228; 3.W.239.229; 3.W.239.230;
3.W.239.231; 3.W.239.236; 3.W.239.237; 3.W.239.238; 3.W.239.239;
3.W.239.154; 3.W.239.157; 3.W.239.166; 3.W.239.169; 3.W.239.172;
3.W.239.175; 3.W.239.240; 3.W.239.244; 3.W.154.228; 3.W.154.229;
3.W.154.230; 3.W.154.231; 3.W.154.236; 3.W.154.237; 3.W.154.238;
3.W.154.239; 3.W.154.154; 3.W.154.157; 3.W.154.166; 3.W.154.169;
3.W.154.172; 3.W.154.175; 3.W.154.240; 3.W.154.244; 3.W.157.228;
3.W.157.229; 3.W.157.230; 3.W.157.231; 3.W.157.236; 3.W.157.237;
3.W.157.238; 3.W.157.239; 3.W.157.154; 3.W.157.157; 3.W.157.166;
3.W.157.169; 3.W.157.172; 3.W.157.175; 3.W.157.240; 3.W.157.244;
3.W.166.228; 3.W.166.229; 3.W.166.230; 3.W.166.231; 3.W.166.236;
3.W.166.237; 3.W.166.238; 3.W.166.239; 3.W.166.154; 3.W.166.157;
3.W.166.166; 3.W.166.169; 3.W.166.172; 3.W.166.175; 3.W.166.240;
3.W.166.244; 3.W.169.228; 3.W.169.229; 3.W.169.230; 3.W.169.231;
3.W.169.236; 3.W.169.237; 3.W.169.238; 3.W.169.239; 3.W.169.154;
3.W.169.157; 3.W.169.166; 3.W.169.169; 3.W.169.172; 3.W.169.175;
3.W.169.240; 3.W.169.244; 3.W.172.228; 3.W.172.229; 3.W.172.230;
3.W.172.231; 3.W.172.236; 3.W.172.237; 3.W.172.238; 3.W.172.239;
3.W.172.154; 3.W.172.157; 3.W.172.166; 3.W.172.169; 3.W.172.172;
3.W.172.175; 3.W.172.240; 3.W.172.244; 3.W.175.228; 3.W.175.229;
3.W.175.230; 3.W.175.231; 3.W.175.236; 3.W.175.237; 3.W.175.238;
3.W.175.239; 3.W.175.154; 3.W.175.157; 3.W.175.166; 3.W.175.169;
3.W.175.172; 3.W.175.175; 3.W.175.240; 3.W.175.244; 3.W.240.228;
3.W.240.229; 3.W.240.230; 3.W.240.231; 3.W.240.236; 3.W.240.237;
3.W.240.238; 3.W.240.239; 3.W.240.154; 3.W.240.157; 3.W.240.166;
3.W.240.169; 3.W.240.172; 3.W.240.175; 3.W.240.240; 3.W.240.244;
3.W.244.228; 3.W.244.229; 3.W.244.230; 3.W.244.231; 3.W.244.236;
3.W.244.237; 3.W.244.238; 3.W.244.239; 3.W.244.154; 3.W.244.157;
3.W.244.166; 3.W.244.169; 3.W.244.172; 3.W.244.175; 3.W.244.240;
3.W.244.244;

Prodrugs of 3.Y

3.Y.228.228; 3.Y.228.229; 3.Y.228.230; 3.Y.228.231; 3.Y.228.236;
3.Y.228.237; 3.Y.228.238; 3.Y.228.239; 3.Y.228.154; 3.Y.228.157; 3.Y.228.166;
3.Y.228.169; 3.Y.228.172; 3.Y.228.175; 3.Y.228.240; 3.Y.228.244; 3.Y.229.228;
3.Y.229.229; 3.Y.229.230; 3.Y.229.231; 3.Y.229.236; 3.Y.229.237; 3.Y.229.238;
3.Y.229.239; 3.Y.229.154; 3.Y.229.157; 3.Y.229.166; 3.Y.229.169; 3.Y.229.172;
3.Y.229.175; 3.Y.229.240; 3.Y.229.244; 3.Y.230.228; 3.Y.230.229; 3.Y.230.230;
3.Y.230.231; 3.Y.230.236; 3.Y.230.237; 3.Y.230.238; 3.Y.230.239; 3.Y.230.154;
3.Y.230.157; 3.Y.230.166; 3.Y.230.169; 3.Y.230.172; 3.Y.230.175; 3.Y.230.240;
3.Y.230.244; 3.Y.231.228; 3.Y.231.229; 3.Y.231.230; 3.Y.231.231; 3.Y.231.236;
3.Y.231.237; 3.Y.231.238; 3.Y.231.239; 3.Y.231.154; 3.Y.231.157; 3.Y.231.166;
3.Y.231.169; 3.Y.231.172; 3.Y.231.175; 3.Y.231.240; 3.Y.231.244; 3.Y.236.228;
3.Y.236.229; 3.Y.236.230; 3.Y.236.231; 3.Y.236.236; 3.Y.236.237; 3.Y.236.238;
3.Y.236.239; 3.Y.236.154; 3.Y.236.157; 3.Y.236.166; 3.Y.236.169; 3.Y.236.172;
3.Y.236.175; 3.Y.236.240; 3.Y.236.244; 3.Y.237.228; 3.Y.237.229; 3.Y.237.230;
3.Y.237.231; 3.Y.237.236; 3.Y.237.237; 3.Y.237.238; 3.Y.237.239; 3.Y.237.154;
3.Y.237.157; 3.Y.237.166; 3.Y.237.169; 3.Y.237.172; 3.Y.237.175; 3.Y.237.240;
3.Y.237.244; 3.Y.238.228; 3.Y.238.229; 3.Y.238.230; 3.Y.238.231; 3.Y.238.236;
3.Y.238.237; 3.Y.238.238; 3.Y.238.239; 3.Y.238.154; 3.Y.238.157; 3.Y.238.166;
3.Y.238.169; 3.Y.238.172; 3.Y.238.175; 3.Y.238.240; 3.Y.238.244; 3.Y.239.228;
3.Y.239.229; 3.Y.239.230; 3.Y.239.231; 3.Y.239.236; 3.Y.239.237; 3.Y.239.238;
3.Y.239.239; 3.Y.239.154; 3.Y.239.157; 3.Y.239.166; 3.Y.239.169; 3.Y.239.172;
3.Y.239.175; 3.Y.239.240; 3.Y.239.244; 3.Y.154.228; 3.Y.154.229; 3.Y.154.230;
3.Y.154.231; 3.Y.154.236; 3.Y.154.237; 3.Y.154.238; 3.Y.154.239; 3.Y.154.154;
3.Y.154.157; 3.Y.154.166; 3.Y.154.169; 3.Y.154.172; 3.Y.154.175; 3.Y.154.240;
3.Y.154.244; 3.Y.157.228; 3.Y.157.229; 3.Y.157.230; 3.Y.157.231; 3.Y.157.236;
3.Y.157.237; 3.Y.157.238; 3.Y.157.239; 3.Y.157.154; 3.Y.157.157; 3.Y.157.166;
3.Y.157.169; 3.Y.157.172; 3.Y.157.175; 3.Y.157.240; 3.Y.157.244; 3.Y.166.228;
3.Y.166.229; 3.Y.166.230; 3.Y.166.231; 3.Y.166.236; 3.Y.166.237; 3.Y.166.238;
3.Y.166.239; 3.Y.166.154; 3.Y.166.157; 3.Y.166.166; 3.Y.166.169; 3.Y.166.172;
3.Y.166.175; 3.Y.166.240; 3.Y.166.244; 3.Y.169.228; 3.Y.169.229; 3.Y.169.230;
3.Y.169.231; 3.Y.169.236; 3.Y.169.237; 3.Y.169.238; 3.Y.169.239; 3.Y.169.154;
3.Y.169.157; 3.Y.169.166; 3.Y.169.169; 3.Y.169.172; 3.Y.169.175; 3.Y.169.240;
3.Y.169.244; 3.Y.172.228; 3.Y.172.229; 3.Y.172.230; 3.Y.172.231; 3.Y.172.236;
3.Y.172.237; 3.Y.172.238; 3.Y.172.239; 3.Y.172.154; 3.Y.172.157; 3.Y.172.166;
3.Y.172.169; 3.Y.172.172; 3.Y.172.175; 3.Y.172.240; 3.Y.172.244; 3.Y.175.228;
3.Y.175.229; 3.Y.175.230; 3.Y.175.231; 3.Y.175.236; 3.Y.175.237; 3.Y.175.238;
3.Y.175.239; 3.Y.175.154; 3.Y.175.157; 3.Y.175.166; 3.Y.175.169; 3.Y.175.172;
3.Y.175.175; 3.Y.175.240; 3.Y.175.244; 3.Y.240.228; 3.Y.240.229; 3.Y.240.230;

TABLE 100-continued

3.Y.240.231; 3.Y.240.236; 3.Y.240.237; 3.Y.240.238; 3.Y.240.239; 3.Y.240.154; 3.Y.240.157; 3.Y.240.166; 3.Y.240.169; 3.Y.240.172; 3.Y.240.175; 3.Y.240.240; 3.Y.240.244; 3.Y.244.228; 3.Y.244.229; 3.Y.244.230; 3.Y.244.231; 3.Y.244.236; 3.Y.244.237; 3.Y.244.238; 3.Y.244.239; 3.Y.244.154; 3.Y.244.157; 3.Y.244.166; 3.Y.244.169; 3.Y.244.172; 3.Y.244.175; 3.Y.244.240; 3.Y.244.244;

Prodrugs of 4.B

4.B.228.228; 4.B.228.229; 4.B.228.230; 4.B.228.231; 4.B.228.236; 4.B.228.237; 4.B.228.238; 4.B.228.239; 4.B.228.154; 4.B.228.157; 4.B.228.166; 4.B.228.169; 4.B.228.172; 4.B.228.175; 4.B.228.240; 4.B.228.244; 4.B.229.228; 4.B.229.229; 4.B.229.230; 4.B.229.231; 4.B.229.236; 4.B.229.237; 4.B.229.238; 4.B.229.239; 4.B.229.154; 4.B.229.157; 4.B.229.166; 4.B.229.169; 4.B.229.172; 4.B.229.175; 4.B.229.240; 4.B.229.244; 4.B.230.228; 4.B.230.229; 4.B.230.230; 4.B.230.231; 4.B.230.236; 4.B.230.237; 4.B.230.238; 4.B.230.239; 4.B.230.154; 4.B.230.157; 4.B.230.166; 4.B.230.169; 4.B.230.172; 4.B.230.175; 4.B.230.240; 4.B.230.244; 4.B.231.228; 4.B.231.229; 4.B.231.230; 4.B.231.231; 4.B.231.236; 4.B.231.237; 4.B.231.238; 4.B.231.239; 4.B.231.154; 4.B.231.157; 4.B.231.166; 4.B.231.169; 4.B.231.172; 4.B.231.175; 4.B.231.240; 4.B.231.244; 4.B.236.228; 4.B.236.229; 4.B.236.230; 4.B.236.231; 4.B.236.236; 4.B.236.237; 4.B.236.238; 4.B.236.239; 4.B.236.154; 4.B.236.157; 4.B.236.166; 4.B.236.169; 4.B.236.172; 4.B.236.175; 4.B.236.240; 4.B.236.244; 4.B.237.228; 4.B.237.229; 4.B.237.230; 4.B.237.231; 4.B.237.236; 4.B.237.237; 4.B.237.238; 4.B.237.239; 4.B.237.154; 4.B.237.157; 4.B.237.166; 4.B.237.169; 4.B.237.172; 4.B.237.175; 4.B.237.240; 4.B.237.244; 4.B.238.228; 4.B.238.229; 4.B.238.230; 4.B.238.231; 4.B.238.236; 4.B.238.237; 4.B.238.238; 4.B.238.239; 4.B.238.154; 4.B.238.157; 4.B.238.166; 4.B.238.169; 4.B.238.172; 4.B.238.175; 4.B.238.240; 4.B.238.244; 4.B.239.228; 4.B.239.229; 4.B.239.230; 4.B.239.231; 4.B.239.236; 4.B.239.237; 4.B.239.238; 4.B.239.239; 4.B.239.154; 4.B.239.157; 4.B.239.166; 4.B.239.169; 4.B.239.172; 4.B.239.175; 4.B.239.240; 4.B.239.244; 4.B.154.228; 4.B.154.229; 4.B.154.230; 4.B.154.231; 4.B.154.236; 4.B.154.237; 4.B.154.238; 4.B.154.239; 4.B.154.154; 4.B.154.157; 4.B.154.166; 4.B.154.169; 4.B.154.172; 4.B.154.175; 4.B.154.240; 4.B.154.244; 4.B.157.228; 4.B.157.229; 4.B.157.230; 4.B.157.231; 4.B.157.236; 4.B.157.237; 4.B.157.238; 4.B.157.239; 4.B.157.154; 4.B.157.157; 4.B.157.166; 4.B.157.169; 4.B.157.172; 4.B.157.175; 4.B.157.240; 4.B.157.244; 4.B.166.228; 4.B.166.229; 4.B.166.230; 4.B.166.231; 4.B.166.236; 4.B.166.237; 4.B.166.238; 4.B.166.239; 4.B.166.154; 4.B.166.157; 4.B.166.166; 4.B.166.169; 4.B.166.172; 4.B.166.175; 4.B.166.240; 4.B.166.244; 4.B.169.228; 4.B.169.229; 4.B.169.230; 4.B.169.231; 4.B.169.236; 4.B.169.237; 4.B.169.238; 4.B.169.239; 4.B.169.154; 4.B.169.157; 4.B.169.166; 4.B.169.169; 4.B.169.172; 4.B.169.175; 4.B.169.240; 4.B.169.244; 4.B.172.228; 4.B.172.229; 4.B.172.230; 4.B.172.231; 4.B.172.236; 4.B.172.237; 4.B.172.238; 4.B.172.239; 4.B.172.154; 4.B.172.157; 4.B.172.166; 4.B.172.169; 4.B.172.172; 4.B.172.175; 4.B.172.240; 4.B.172.244; 4.B.175.228; 4.B.175.229; 4.B.175.230; 4.B.175.231; 4.B.175.236; 4.B.175.237; 4.B.175.238; 4.B.175.239; 4.B.175.154; 4.B.175.157; 4.B.175.166; 4.B.175.169; 4.B.175.172; 4.B.175.175; 4.B.175.240; 4.B.175.244; 4.B.240.228; 4.B.240.229; 4.B.240.230; 4.B.240.231; 4.B.240.236; 4.B.240.237; 4.B.240.238; 4.B.240.239; 4.B.240.154; 4.B.240.157; 4.B.240.166; 4.B.240.169; 4.B.240.172; 4.B.240.175; 4.B.240.240; 4.B.240.244; 4.B.244.228; 4.B.244.229; 4.B.244.230; 4.B.244.231; 4.B.244.236; 4.B.244.237; 4.B.244.238; 4.B.244.239; 4.B.244.154; 4.B.244.157; 4.B.244.166; 4.B.244.169; 4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236; 4.D.228.237; 4.D.228.238; 4.D.228.239; 4.D.228.154; 4.D.228.157; 4.D.228.166; 4.D.228.169; 4.D.228.172; 4.D.228.175; 4.D.228.240; 4.D.228.244; 4.D.229.228; 4.D.229.229; 4.D.229.230; 4.D.229.231; 4.D.229.236; 4.D.229.237; 4.D.229.238; 4.D.229.239; 4.D.229.154; 4.D.229.157; 4.D.229.166; 4.D.229.169; 4.D.229.172; 4.D.229.175; 4.D.229.240; 4.D.229.244; 4.D.230.228; 4.D.230.229; 4.D.230.230; 4.D.230.231; 4.D.230.236; 4.D.230.237; 4.D.230.238; 4.D.230.239; 4.D.230.154; 4.D.230.157; 4.D.230.166; 4.D.230.169; 4.D.230.172; 4.D.230.175; 4.D.230.240; 4.D.230.244; 4.D.231.228; 4.D.231.229; 4.D.231.230; 4.D.231.231; 4.D.231.236; 4.D.231.237; 4.D.231.238; 4.D.231.239; 4.D.231.154; 4.D.231.157; 4.D.231.166; 4.D.231.169; 4.D.231.172; 4.D.231.175; 4.D.231.240; 4.D.231.244; 4.D.236.228; 4.D.236.229; 4.D.236.230; 4.D.236.231; 4.D.236.236; 4.D.236.237; 4.D.236.238; 4.D.236.239; 4.D.236.154; 4.D.236.157; 4.D.236.166; 4.D.236.169; 4.D.236.172; 4.D.236.175; 4.D.236.240; 4.D.236.244; 4.D.237.228; 4.D.237.229; 4.D.237.230; 4.D.237.231; 4.D.237.236; 4.D.237.237; 4.D.237.238; 4.D.237.239; 4.D.237.154; 4.D.237.157; 4.D.237.166; 4.D.237.169; 4.D.237.172; 4.D.237.175; 4.D.237.240; 4.D.237.244; 4.D.238.228; 4.D.238.229; 4.D.238.230; 4.D.238.231; 4.D.238.236; 4.D.238.237; 4.D.238.238; 4.D.238.239; 4.D.238.154; 4.D.238.157; 4.D.238.166; 4.D.238.169; 4.D.238.172; 4.D.238.175; 4.D.238.240; 4.D.238.244; 4.D.239.228; 4.D.239.229; 4.D.239.230; 4.D.239.231; 4.D.239.236; 4.D.239.237; 4.D.239.238; 4.D.239.239; 4.D.239.154; 4.D.239.157; 4.D.239.166; 4.D.239.169; 4.D.239.172; 4.D.239.175; 4.D.239.240; 4.D.239.244; 4.D.154.228; 4.D.154.229; 4.D.154.230; 4.D.154.231; 4.D.154.236; 4.D.154.237; 4.D.154.238;

TABLE 100-continued

4.D.154.239; 4.D.154.154; 4.D.154.157; 4.D.154.166; 4.D.154.169; 4.D.154.172; 4.D.154.175; 4.D.154.240; 4.D.154.244; 4.D.157.228; 4.D.157.229; 4.D.157.230; 4.D.157.231; 4.D.157.236; 4.D.157.237; 4.D.157.238; 4.D.157.239; 4.D.157.154; 4.D.157.157; 4.D.157.166; 4.D.157.169; 4.D.157.172; 4.D.157.175; 4.D.157.240; 4.D.157.244; 4.D.166.228; 4.D.166.229; 4.D.166.230; 4.D.166.231; 4.D.166.236; 4.D.166.237; 4.D.166.238; 4.D.166.239; 4.D.166.154; 4.D.166.157; 4.D.166.166; 4.D.166.169; 4.D.166.172; 4.D.166.175; 4.D.166.240; 4.D.166.244; 4.D.169.228; 4.D.169.229; 4.D.169.230; 4.D.169.231; 4.D.169.236; 4.D.169.237; 4.D.169.238; 4.D.169.239; 4.D.169.154; 4.D.169.157; 4.D.169.166; 4.D.169.169; 4.D.169.172; 4.D.169.175; 4.D.169.240; 4.D.169.244; 4.D.172.228; 4.D.172.229; 4.D.172.230; 4.D.172.231; 4.D.172.236; 4.D.172.237; 4.D.172.238; 4.D.172.239; 4.D.172.154; 4.D.172.157; 4.D.172.166; 4.D.172.169; 4.D.172.172; 4.D.172.175; 4.D.172.240; 4.D.172.244; 4.D.175.228; 4.D.175.229; 4.D.175.230; 4.D.175.231; 4.D.175.236; 4.D.175.237; 4.D.175.238; 4.D.175.239; 4.D.175.154; 4.D.175.157; 4.D.175.166; 4.D.175.169; 4.D.175.172; 4.D.175.175; 4.D.175.240; 4.D.175.244; 4.D.240.228; 4.D.240.229; 4.D.240.230; 4.D.240.231; 4.D.240.236; 4.D.240.237; 4.D.240.238; 4.D.240.239; 4.D.240.154; 4.D.240.157; 4.D.240.166; 4.D.240.169; 4.D.240.172; 4.D.240.175; 4.D.240.240; 4.D.240.244; 4.D.244.228; 4.D.244.229; 4.D.244.230; 4.D.244.231; 4.D.244.236; 4.D.244.237; 4.D.244.238; 4.D.244.239; 4.D.244.154; 4.D.244.157; 4.D.244.166; 4.D.244.169; 4.D.244.172; 4.D.244.175; 4.D.244.240; 4.D.244.244;

Prodrugs of 4.E

4.E.228.228; 4.E.228.229; 4.E.228.230; 4.E.228.231; 4.E.228.236; 4.E.228.237; 4.E.228.238; 4.E.228.239; 4.E.228.154; 4.E.228.157; 4.E.228.166; 4.E.228.169; 4.E.228.172; 4.E.228.175; 4.E.228.240; 4.E.228.244; 4.E.229.228; 4.E.229.229; 4.E.229.230; 4.E.229.231; 4.E.229.236; 4.E.229.237; 4.E.229.238; 4.E.229.239; 4.E.229.154; 4.E.229.157; 4.E.229.166; 4.E.229.169; 4.E.229.172; 4.E.229.175; 4.E.229.240; 4.E.229.244; 4.E.230.228; 4.E.230.229; 4.E.230.230; 4.E.230.231; 4.E.230.236; 4.E.230.237; 4.E.230.238; 4.E.230.239; 4.E.230.154; 4.E.230.157; 4.E.230.166; 4.E.230.169; 4.E.230.172; 4.E.230.175; 4.E.230.240; 4.E.230.244; 4.E.231.228; 4.E.231.229; 4.E.231.230; 4.E.231.231; 4.E.231.236; 4.E.231.237; 4.E.231.238; 4.E.231.239; 4.E.231.154; 4.E.231.157; 4.E.231.166; 4.E.231.169; 4.E.231.172; 4.E.231.175; 4.E.231.240; 4.E.231.244; 4.E.236.228; 4.E.236.229; 4.E.236.230; 4.E.236.231; 4.E.236.236; 4.E.236.237; 4.E.236.238; 4.E.236.239; 4.E.236.154; 4.E.236.157; 4.E.236.166; 4.E.236.169; 4.E.236.172; 4.E.236.175; 4.E.236.240; 4.E.236.244; 4.E.237.228; 4.E.237.229; 4.E.237.230; 4.E.237.231; 4.E.237.236; 4.E.237.237; 4.E.237.238; 4.E.237.239; 4.E.237.154; 4.E.237.157; 4.E.237.166; 4.E.237.169; 4.E.237.172; 4.E.237.175; 4.E.237.240; 4.E.237.244; 4.E.238.228; 4.E.238.229; 4.E.238.230; 4.E.238.231; 4.E.238.236; 4.E.238.237; 4.E.238.238; 4.E.238.239; 4.E.238.154; 4.E.238.157; 4.E.238.166; 4.E.238.169; 4.E.238.172; 4.E.238.175; 4.E.238.240; 4.E.238.244; 4.E.239.228; 4.E.239.229; 4.E.239.230; 4.E.239.231; 4.E.239.236; 4.E.239.237; 4.E.239.238; 4.E.239.239; 4.E.239.154; 4.E.239.157; 4.E.239.166; 4.E.239.169; 4.E.239.172; 4.E.239.175; 4.E.239.240; 4.E.239.244; 4.E.154.228; 4.E.154.229; 4.E.154.230; 4.E.154.231; 4.E.154.236; 4.E.154.237; 4.E.154.238; 4.E.154.239; 4.E.154.154; 4.E.154.157; 4.E.154.166; 4.E.154.169; 4.E.154.172; 4.E.154.175; 4.E.154.240; 4.E.154.244; 4.E.157.228; 4.E.157.229; 4.E.157.230; 4.E.157.231; 4.E.157.236; 4.E.157.237; 4.E.157.238; 4.E.157.239; 4.E.157.154; 4.E.157.157; 4.E.157.166; 4.E.157.169; 4.E.157.172; 4.E.157.175; 4.E.157.240; 4.E.157.244; 4.E.166.228; 4.E.166.229; 4.E.166.230; 4.E.166.231; 4.E.166.236; 4.E.166.237; 4.E.166.238; 4.E.166.239; 4.E.166.154; 4.E.166.157; 4.E.166.166; 4.E.166.169; 4.E.166.172; 4.E.166.175; 4.E.166.240; 4.E.166.244; 4.E.169.228; 4.E.169.229; 4.E.169.230; 4.E.169.231; 4.E.169.236; 4.E.169.237; 4.E.169.238; 4.E.169.239; 4.E.169.154; 4.E.169.157; 4.E.169.166; 4.E.169.169; 4.E.169.172; 4.E.169.175; 4.E.169.240; 4.E.169.244; 4.E.172.228; 4.E.172.229; 4.E.172.230; 4.E.172.231; 4.E.172.236; 4.E.172.237; 4.E.172.238; 4.E.172.239; 4.E.172.154; 4.E.172.157; 4.E.172.166; 4.E.172.169; 4.E.172.172; 4.E.172.175; 4.E.172.240; 4.E.172.244; 4.E.175.228; 4.E.175.229; 4.E.175.230; 4.E.175.231; 4.E.175.236; 4.E.175.237; 4.E.175.238; 4.E.175.239; 4.E.175.154; 4.E.175.157; 4.E.175.166; 4.E.175.169; 4.E.175.172; 4.E.175.175; 4.E.175.240; 4.E.175.244; 4.E.240.228; 4.E.240.229; 4.E.240.230; 4.E.240.231; 4.E.240.236; 4.E.240.237; 4.E.240.238; 4.E.240.239; 4.E.240.154; 4.E.240.157; 4.E.240.166; 4.E.240.169; 4.E.240.172; 4.E.240.175; 4.E.240.240; 4.E.240.244; 4.E.244.228; 4.E.244.229; 4.E.244.230; 4.E.244.231; 4.E.244.236; 4.E.244.237; 4.E.244.238; 4.E.244.239; 4.E.244.154; 4.E.244.157; 4.E.244.166; 4.E.244.169; 4.E.244.172; 4.E.244.175; 4.E.244.240; 4.E.244.244;

Prodrugs of 4.G

4.G.228.228; 4.G.228.229; 4.G.228.230; 4.G.228.231; 4.G.228.236; 4.G.228.237; 4.G.228.238; 4.G.228.239; 4.G.228.154; 4.G.228.157; 4.G.228.166; 4.G.228.169; 4.G.228.172; 4.G.228.175; 4.G.228.240; 4.G.228.244; 4.G.229.228; 4.G.229.229; 4.G.229.230; 4.G.229.231; 4.G.229.236; 4.G.229.237; 4.G.229.238; 4.G.229.239; 4.G.229.154; 4.G.229.157; 4.G.229.166; 4.G.229.169; 4.G.229.172; 4.G.229.175; 4.G.229.240; 4.G.229.244; 4.G.230.228; 4.G.230.229; 4.G.230.230;

TABLE 100-continued

4.G.230.231; 4.G.230.236; 4.G.230.237; 4.G.230.238; 4.G.230.239; 4.G.230.154; 4.G.230.157; 4.G.230.166; 4.G.230.169; 4.G.230.172; 4.G.230.175; 4.G.230.240; 4.G.230.244; 4.G.231.228; 4.G.231.229; 4.G.231.230; 4.G.231.231; 4.G.231.236; 4.G.231.237; 4.G.231.238; 4.G.231.239; 4.G.231.154; 4.G.231.157; 4.G.231.166; 4.G.231.169; 4.G.231.172; 4.G.231.175; 4.G.231.240; 4.G.231.244; 4.G.236.228; 4.G.236.229; 4.G.236.230; 4.G.236.231; 4.G.236.236; 4.G.236.237; 4.G.236.238; 4.G.236.239; 4.G.236.154; 4.G.236.157; 4.G.236.166; 4.G.236.169; 4.G.236.172; 4.G.236.175; 4.G.236.240; 4.G.236.244; 4.G.237.228; 4.G.237.229; 4.G.237.230; 4.G.237.231; 4.G.237.236; 4.G.237.237; 4.G.237.238; 4.G.237.239; 4.G.237.154; 4.G.237.157; 4.G.237.166; 4.G.237.169; 4.G.237.172; 4.G.237.175; 4.G.237.240; 4.G.237.244; 4.G.238.228; 4.G.238.229; 4.G.238.230; 4.G.238.231; 4.G.238.236; 4.G.238.237; 4.G.238.238; 4.G.238.239; 4.G.238.154; 4.G.238.157; 4.G.238.166; 4.G.238.169; 4.G.238.172; 4.G.238.175; 4.G.238.240; 4.G.238.244; 4.G.239.228; 4.G.239.229; 4.G.239.230; 4.G.239.231; 4.G.239.236; 4.G.239.237; 4.G.239.238; 4.G.239.239; 4.G.239.154; 4.G.239.157; 4.G.239.166; 4.G.239.169; 4.G.239.172; 4.G.239.175; 4.G.239.240; 4.G.239.244; 4.G.154.228; 4.G.154.229; 4.G.154.230; 4.G.154.231; 4.G.154.236; 4.G.154.237; 4.G.154.238; 4.G.154.239; 4.G.154.154; 4.G.154.157; 4.G.154.166; 4.G.154.169; 4.G.154.172; 4.G.154.175; 4.G.154.240; 4.G.154.244; 4.G.157.228; 4.G.157.229; 4.G.157.230; 4.G.157.231; 4.G.157.236; 4.G.157.237; 4.G.157.238; 4.G.157.239; 4.G.157.154; 4.G.157.157; 4.G.157.166; 4.G.157.169; 4.G.157.172; 4.G.157.175; 4.G.157.240; 4.G.157.244; 4.G.166.228; 4.G.166.229; 4.G.166.230; 4.G.166.231; 4.G.166.236; 4.G.166.237; 4.G.166.238; 4.G.166.239; 4.G.166.154; 4.G.166.157; 4.G.166.166; 4.G.166.169; 4.G.166.172; 4.G.166.175; 4.G.166.240; 4.G.166.244; 4.G.169.228; 4.G.169.229; 4.G.169.230; 4.G.169.231; 4.G.169.236; 4.G.169.237; 4.G.169.238; 4.G.169.239; 4.G.169.154; 4.G.169.157; 4.G.169.166; 4.G.169.169; 4.G.169.172; 4.G.169.175; 4.G.169.240; 4.G.169.244; 4.G.172.228; 4.G.172.229; 4.G.172.230; 4.G.172.231; 4.G.172.236; 4.G.172.237; 4.G.172.238; 4.G.172.239; 4.G.172.154; 4.G.172.157; 4.G.172.166; 4.G.172.169; 4.G.172.172; 4.G.172.175; 4.G.172.240; 4.G.172.244; 4.G.175.228; 4.G.175.229; 4.G.175.230; 4.G.175.231; 4.G.175.236; 4.G.175.237; 4.G.175.238; 4.G.175.239; 4.G.175.154; 4.G.175.157; 4.G.175.166; 4.G.175.169; 4.G.175.172; 4.G.175.175; 4.G.175.240; 4.G.175.244; 4.G.240.228; 4.G.240.229; 4.G.240.230; 4.G.240.231; 4.G.240.236; 4.G.240.237; 4.G.240.238; 4.G.240.239; 4.G.240.154; 4.G.240.157; 4.G.240.166; 4.G.240.169; 4.G.240.172; 4.G.240.175; 4.G.240.240; 4.G.240.244; 4.G.244.228; 4.G.244.229; 4.G.244.230; 4.G.244.231; 4.G.244.236; 4.G.244.237; 4.G.244.238; 4.G.244.239; 4.G.244.154; 4.G.244.157; 4.G.244.166; 4.G.244.169; 4.G.244.172; 4.G.244.175; 4.G.244.240; 4.G.244.244;

Prodrugs of 4.I

4.I.228.228; 4.I.228.229; 4.I.228.230; 4.I.228.231; 4.I.228.236; 4.I.228.237; 4.I.228.238; 4.I.228.239; 4.I.228.154; 4.I.228.157; 4.I.228.166; 4.I.228.169; 4.I.228.172; 4.I.228.175; 4.I.228.240; 4.I.228.244; 4.I.229.228; 4.I.229.229; 4.I.229.230; 4.I.229.231; 4.I.229.236; 4.I.229.237; 4.I.229.238; 4.I.229.239; 4.I.229.154; 4.I.229.157; 4.I.229.166; 4.I.229.169; 4.I.229.172; 4.I.229.175; 4.I.229.240; 4.I.229.244; 4.I.230.228; 4.I.230.229; 4.I.230.230; 4.I.230.231; 4.I.230.236; 4.I.230.237; 4.I.230.238; 4.I.230.239; 4.I.230.154; 4.I.230.157; 4.I.230.166; 4.I.230.169; 4.I.230.172; 4.I.230.175; 4.I.230.240; 4.I.230.244; 4.I.231.228; 4.I.231.229; 4.I.231.230; 4.I.231.231; 4.I.231.236; 4.I.231.237; 4.I.231.238; 4.I.231.239; 4.I.231.154; 4.I.231.157; 4.I.231.166; 4.I.231.169; 4.I.231.172; 4.I.231.175; 4.I.231.240; 4.I.231.244; 4.I.236.228; 4.I.236.229; 4.I.236.230; 4.I.236.231; 4.I.236.236; 4.I.236.237; 4.I.236.238; 4.I.236.239; 4.I.236.154; 4.I.236.157; 4.I.236.166; 4.I.236.169; 4.I.236.172; 4.I.236.175; 4.I.236.240; 4.I.236.244; 4.I.237.228; 4.I.237.229; 4.I.237.230; 4.I.237.231; 4.I.237.236; 4.I.237.237; 4.I.237.238; 4.I.237.239; 4.I.237.154; 4.I.237.157; 4.I.237.166; 4.I.237.169; 4.I.237.172; 4.I.237.175; 4.I.237.240; 4.I.237.244; 4.I.238.228; 4.I.238.229; 4.I.238.230; 4.I.238.231; 4.I.238.236; 4.I.238.237; 4.I.238.238; 4.I.238.239; 4.I.238.154; 4.I.238.157; 4.I.238.166; 4.I.238.169; 4.I.238.172; 4.I.238.175; 4.I.238.240; 4.I.238.244; 4.I.239.228; 4.I.239.229; 4.I.239.230; 4.I.239.231; 4.I.239.236; 4.I.239.237; 4.I.239.238; 4.I.239.239; 4.I.239.154; 4.I.239.157; 4.I.239.166; 4.I.239.169; 4.I.239.172; 4.I.239.175; 4.I.239.240; 4.I.239.244; 4.I.154.228; 4.I.154.229; 4.I.154.230; 4.I.154.231; 4.I.154.236; 4.I.154.237; 4.I.154.238; 4.I.154.239; 4.I.154.154; 4.I.154.157; 4.I.154.166; 4.I.154.169; 4.I.154.172; 4.I.154.175; 4.I.154.240; 4.I.154.244; 4.I.157.228; 4.I.157.229; 4.I.157.230; 4.I.157.231; 4.I.157.236; 4.I.157.237; 4.I.157.238; 4.I.157.239; 4.I.157.154; 4.I.157.157; 4.I.157.166; 4.I.157.169; 4.I.157.172; 4.I.157.175; 4.I.157.240; 4.I.157.244; 4.I.166.228; 4.I.166.229; 4.I.166.230; 4.I.166.231; 4.I.166.236; 4.I.166.237; 4.I.166.238; 4.I.166.239; 4.I.166.154; 4.I.166.157; 4.I.166.166; 4.I.166.169; 4.I.166.172; 4.I.166.175; 4.I.166.240; 4.I.166.244; 4.I.169.228; 4.I.169.229; 4.I.169.230; 4.I.169.231; 4.I.169.236; 4.I.169.237; 4.I.169.238; 4.I.169.239; 4.I.169.154; 4.I.169.157; 4.I.169.166; 4.I.169.169; 4.I.169.172; 4.I.169.175; 4.I.169.240; 4.I.169.244;

TABLE 100-continued

4.I.172.228; 4.I.172.229; 4.I.172.230; 4.I.172.231; 4.I.172.236; 4.I.172.237; 4.I.172.238; 4.I.172.239; 4.I.172.154; 4.I.172.157; 4.I.172.166; 4.I.172.169; 4.I.172.172; 4.I.172.175; 4.I.172.240; 4.I.172.244; 4.I.175.228; 4.I.175.229; 4.I.175.230; 4.I.175.231; 4.I.175.236; 4.I.175.237; 4.I.175.238; 4.I.175.239; 4.I.175.154; 4.I.175.157; 4.I.175.166; 4.I.175.169; 4.I.175.172; 4.I.175.175; 4.I.175.240; 4.I.175.244; 4.I.240.228; 4.I.240.229; 4.I.240.230; 4.I.240.231; 4.I.240.236; 4.I.240.237; 4.I.240.238; 4.I.240.239; 4.I.240.154; 4.I.240.157; 4.I.240.166; 4.I.240.169; 4.I.240.172; 4.I.240.175; 4.I.240.240; 4.I.240.244; 4.I.244.228; 4.I.244.229; 4.I.244.230; 4.I.244.231; 4.I.244.236; 4.I.244.237; 4.I.244.238; 4.I.244.239; 4.I.244.154; 4.I.244.157; 4.I.244.166; 4.I.244.169; 4.I.244.172; 4.I.244.175; 4.I.244.240; 4.I.244.244;

Prodrugs of 4.J

4.J.228.228; 4.J.228.229; 4.J.228.230; 4.J.228.231; 4.J.228.236; 4.J.228.237; 4.J.228.238; 4.J.228.239; 4.J.228.154; 4.J.228.157; 4.J.228.166; 4.J.228.169; 4.J.228.172; 4.J.228.175; 4.J.228.240; 4.J.228.244; 4.J.229.228; 4.J.229.229; 4.J.229.230; 4.J.229.231; 4.J.229.236; 4.J.229.237; 4.J.229.238; 4.J.229.239; 4.J.229.154; 4.J.229.157; 4.J.229.166; 4.J.229.169; 4.J.229.172; 4.J.229.175; 4.J.229.240; 4.J.229.244; 4.J.230.228; 4.J.230.229; 4.J.230.230; 4.J.230.231; 4.J.230.236; 4.J.230.237; 4.J.230.238; 4.J.230.239; 4.J.230.154; 4.J.230.157; 4.J.230.166; 4.J.230.169; 4.J.230.172; 4.J.230.175; 4.J.230.240; 4.J.230.244; 4.J.231.228; 4.J.231.229; 4.J.231.230; 4.J.231.231; 4.J.231.236; 4.J.231.237; 4.J.231.238; 4.J.231.239; 4.J.231.154; 4.J.231.157; 4.J.231.166; 4.J.231.169; 4.J.231.172; 4.J.231.175; 4.J.231.240; 4.J.231.244; 4.J.236.228; 4.J.236.229; 4.J.236.230; 4.J.236.231; 4.J.236.236; 4.J.236.237; 4.J.236.238; 4.J.236.239; 4.J.236.154; 4.J.236.157; 4.J.236.166; 4.J.236.169; 4.J.236.172; 4.J.236.175; 4.J.236.240; 4.J.236.244; 4.J.237.228; 4.J.237.229; 4.J.237.230; 4.J.237.231; 4.J.237.236; 4.J.237.237; 4.J.237.238; 4.J.237.239; 4.J.237.154; 4.J.237.157; 4.J.237.166; 4.J.237.169; 4.J.237.172; 4.J.237.175; 4.J.237.240; 4.J.237.244; 4.J.238.228; 4.J.238.229; 4.J.238.230; 4.J.238.231; 4.J.238.236; 4.J.238.237; 4.J.238.238; 4.J.238.239; 4.J.238.154; 4.J.238.157; 4.J.238.166; 4.J.238.169; 4.J.238.172; 4.J.238.175; 4.J.238.240; 4.J.238.244; 4.J.239.228; 4.J.239.229; 4.J.239.230; 4.J.239.231; 4.J.239.236; 4.J.239.237; 4.J.239.238; 4.J.239.239; 4.J.239.154; 4.J.239.157; 4.J.239.166; 4.J.239.169; 4.J.239.172; 4.J.239.175; 4.J.239.240; 4.J.239.244; 4.J.154.228; 4.J.154.229; 4.J.154.230; 4.J.154.231; 4.J.154.236; 4.J.154.237; 4.J.154.238; 4.J.154.239; 4.J.154.154; 4.J.154.157; 4.J.154.166; 4.J.154.169; 4.J.154.172; 4.J.154.175; 4.J.154.240; 4.J.154.244; 4.J.157.228; 4.J.157.229; 4.J.157.230; 4.J.157.231; 4.J.157.236; 4.J.157.237; 4.J.157.238; 4.J.157.239; 4.J.157.154; 4.J.157.157; 4.J.157.166; 4.J.157.169; 4.J.157.172; 4.J.157.175; 4.J.157.240; 4.J.157.244; 4.J.166.228; 4.J.166.229; 4.J.166.230; 4.J.166.231; 4.J.166.236; 4.J.166.237; 4.J.166.238; 4.J.166.239; 4.J.166.154; 4.J.166.157; 4.J.166.166; 4.J.166.169; 4.J.166.172; 4.J.166.175; 4.J.166.240; 4.J.166.244; 4.J.169.228; 4.J.169.229; 4.J.169.230; 4.J.169.231; 4.J.169.236; 4.J.169.237; 4.J.169.238; 4.J.169.239; 4.J.169.154; 4.J.169.157; 4.J.169.166; 4.J.169.169; 4.J.169.172; 4.J.169.175; 4.J.169.240; 4.J.169.244; 4.J.172.228; 4.J.172.229; 4.J.172.230; 4.J.172.231; 4.J.172.236; 4.J.172.237; 4.J.172.238; 4.J.172.239; 4.J.172.154; 4.J.172.157; 4.J.172.166; 4.J.172.169; 4.J.172.172; 4.J.172.175; 4.J.172.240; 4.J.172.244; 4.J.175.228; 4.J.175.229; 4.J.175.230; 4.J.175.231; 4.J.175.236; 4.J.175.237; 4.J.175.238; 4.J.175.239; 4.J.175.154; 4.J.175.157; 4.J.175.166; 4.J.175.169; 4.J.175.172; 4.J.175.175; 4.J.175.240; 4.J.175.244; 4.J.240.228; 4.J.240.229; 4.J.240.230; 4.J.240.231; 4.J.240.236; 4.J.240.237; 4.J.240.238; 4.J.240.239; 4.J.240.154; 4.J.240.157; 4.J.240.166; 4.J.240.169; 4.J.240.172; 4.J.240.175; 4.J.240.240; 4.J.240.244; 4.J.244.228; 4.J.244.229; 4.J.244.230; 4.J.244.231; 4.J.244.236; 4.J.244.237; 4.J.244.238; 4.J.244.239; 4.J.244.154; 4.J.244.157; 4.J.244.166; 4.J.244.169; 4.J.244.172; 4.J.244.175; 4.J.244.240; 4.J.244.244;

Prodrugs of 4.L

4.L.228.228; 4.L.228.229; 4.L.228.230; 4.L.228.231; 4.L.228.236; 4.L.228.237; 4.L.228.238; 4.L.228.239; 4.L.228.154; 4.L.228.157; 4.L.228.166; 4.L.228.169; 4.L.228.172; 4.L.228.175; 4.L.228.240; 4.L.228.244; 4.L.229.228; 4.L.229.229; 4.L.229.230; 4.L.229.231; 4.L.229.236; 4.L.229.237; 4.L.229.238; 4.L.229.239; 4.L.229.154; 4.L.229.157; 4.L.229.166; 4.L.229.169; 4.L.229.172; 4.L.229.175; 4.L.229.240; 4.L.229.244; 4.L.230.228; 4.L.230.229; 4.L.230.230; 4.L.230.231; 4.L.230.236; 4.L.230.237; 4.L.230.238; 4.L.230.239; 4.L.230.154; 4.L.230.157; 4.L.230.166; 4.L.230.169; 4.L.230.172; 4.L.230.175; 4.L.230.240; 4.L.230.244; 4.L.231.228; 4.L.231.229; 4.L.231.230; 4.L.231.231; 4.L.231.236; 4.L.231.237; 4.L.231.238; 4.L.231.239; 4.L.231.154; 4.L.231.157; 4.L.231.166; 4.L.231.169; 4.L.231.172; 4.L.231.175; 4.L.231.240; 4.L.231.244; 4.L.236.228; 4.L.236.229; 4.L.236.230; 4.L.236.231; 4.L.236.236; 4.L.236.237; 4.L.236.238; 4.L.236.239; 4.L.236.154; 4.L.236.157; 4.L.236.166; 4.L.236.169; 4.L.236.172; 4.L.236.175; 4.L.236.240; 4.L.236.244; 4.L.237.228; 4.L.237.229; 4.L.237.230; 4.L.237.231; 4.L.237.236; 4.L.237.237; 4.L.237.238; 4.L.237.239; 4.L.237.154; 4.L.237.157; 4.L.237.166; 4.L.237.169; 4.L.237.172; 4.L.237.175; 4.L.237.240; 4.L.237.244; 4.L.238.228; 4.L.238.229; 4.L.238.230; 4.L.238.231; 4.L.238.236; 4.L.238.237; 4.L.238.238; 4.L.238.239; 4.L.238.154; 4.L.238.157; 4.L.238.166; 4.L.238.169; 4.L.238.172; 4.L.238.175; 4.L.238.240; 4.L.238.244; 4.L.239.228; 4.L.239.229; 4.L.239.230; 4.L.239.231; 4.L.239.236; 4.L.239.237; 4.L.239.238; 4.L.239.239; 4.L.239.154; 4.L.239.157; 4.L.239.166; 4.L.239.169; 4.L.239.172;

TABLE 100-continued

4.L.239.175; 4.L.239.240; 4.L.239.244; 4.L.154.228; 4.L.154.229; 4.L.154.230; 4.L.154.231; 4.L.154.236; 4.L.154.237; 4.L.154.238; 4.L.154.239; 4.L.154.154; 4.L.154.157; 4.L.154.166; 4.L.154.169; 4.L.154.172; 4.L.154.175; 4.L.154.240; 4.L.154.244; 4.L.157.228; 4.L.157.229; 4.L.157.230; 4.L.157.231; 4.L.157.236; 4.L.157.237; 4.L.157.238; 4.L.157.239; 4.L.157.154; 4.L.157.157; 4.L.157.166; 4.L.157.169; 4.L.157.172; 4.L.157.175; 4.L.157.240; 4.L.157.244; 4.L.166.228; 4.L.166.229; 4.L.166.230; 4.L.166.231; 4.L.166.236; 4.L.166.237; 4.L.166.238; 4.L.166.239; 4.L.166.154; 4.L.166.157; 4.L.166.166; 4.L.166.169; 4.L.166.172; 4.L.166.175; 4.L.166.240; 4.L.166.244; 4.L.169.228; 4.L.169.229; 4.L.169.230; 4.L.169.231; 4.L.169.236; 4.L.169.237; 4.L.169.238; 4.L.169.239; 4.L.169.154; 4.L.169.157; 4.L.169.166; 4.L.169.169; 4.L.169.172; 4.L.169.175; 4.L.169.240; 4.L.169.244; 4.L.172.228; 4.L.172.229; 4.L.172.230; 4.L.172.231; 4.L.172.236; 4.L.172.237; 4.L.172.238; 4.L.172.239; 4.L.172.154; 4.L.172.157; 4.L.172.166; 4.L.172.169; 4.L.172.172; 4.L.172.175; 4.L.172.240; 4.L.172.244; 4.L.175.228; 4.L.175.229; 4.L.175.230; 4.L.175.231; 4.L.175.236; 4.L.175.237; 4.L.175.238; 4.L.175.239; 4.L.175.154; 4.L.175.157; 4.L.175.166; 4.L.175.169; 4.L.175.172; 4.L.175.175; 4.L.175.240; 4.L.175.244; 4.L.240.228; 4.L.240.229; 4.L.240.230; 4.L.240.231; 4.L.240.236; 4.L.240.237; 4.L.240.238; 4.L.240.239; 4.L.240.154; 4.L.240.157; 4.L.240.166; 4.L.240.169; 4.L.240.172; 4.L.240.175; 4.L.240.240; 4.L.240.244; 4.L.244.228; 4.L.244.229; 4.L.244.230; 4.L.244.231; 4.L.244.236; 4.L.244.237; 4.L.244.238; 4.L.244.239; 4.L.244.154; 4.L.244.157; 4.L.244.166; 4.L.244.169; 4.L.244.172; 4.L.244.175; 4.L.244.240; 4.L.244.244;

Prodrugs of 4.O

4.O.228.228; 4.O.228.229; 4.O.228.230; 4.O.228.231; 4.O.228.236; 4.O.228.237; 4.O.228.238; 4.O.228.239; 4.O.228.154; 4.O.228.157; 4.O.228.166; 4.O.228.169; 4.O.228.172; 4.O.228.175; 4.O.228.240; 4.O.228.244; 4.O.229.228; 4.O.229.229; 4.O.229.230; 4.O.229.231; 4.O.229.236; 4.O.229.237; 4.O.229.238; 4.O.229.239; 4.O.229.154; 4.O.229.157; 4.O.229.166; 4.O.229.169; 4.O.229.172; 4.O.229.175; 4.O.229.240; 4.O.229.244; 4.O.230.228; 4.O.230.229; 4.O.230.230; 4.O.230.231; 4.O.230.236; 4.O.230.237; 4.O.230.238; 4.O.230.239; 4.O.230.154; 4.O.230.157; 4.O.230.166; 4.O.230.169; 4.O.230.172; 4.O.230.175; 4.O.230.240; 4.O.230.244; 4.O.231.228; 4.O.231.229; 4.O.231.230; 4.O.231.231; 4.O.231.236; 4.O.231.237; 4.O.231.238; 4.O.231.239; 4.O.231.154; 4.O.231.157; 4.O.231.166; 4.O.231.169; 4.O.231.172; 4.O.231.175; 4.O.231.240; 4.O.231.244; 4.O.236.228; 4.O.236.229; 4.O.236.230; 4.O.236.231; 4.O.236.236; 4.O.236.237; 4.O.236.238; 4.O.236.239; 4.O.236.154; 4.O.236.157; 4.O.236.166; 4.O.236.169; 4.O.236.172; 4.O.236.175; 4.O.236.240; 4.O.236.244; 4.O.237.228; 4.O.237.229; 4.O.237.230; 4.O.237.231; 4.O.237.236; 4.O.237.237; 4.O.237.238; 4.O.237.239; 4.O.237.154; 4.O.237.157; 4.O.237.166; 4.O.237.169; 4.O.237.172; 4.O.237.175; 4.O.237.240; 4.O.237.244; 4.O.238.228; 4.O.238.229; 4.O.238.230; 4.O.238.231; 4.O.238.236; 4.O.238.237; 4.O.238.238; 4.O.238.239; 4.O.238.154; 4.O.238.157; 4.O.238.166; 4.O.238.169; 4.O.238.172; 4.O.238.175; 4.O.238.240; 4.O.238.244; 4.O.239.228; 4.O.239.229; 4.O.239.230; 4.O.239.231; 4.O.239.236; 4.O.239.237; 4.O.239.238; 4.O.239.239; 4.O.239.154; 4.O.239.157; 4.O.239.166; 4.O.239.169; 4.O.239.172; 4.O.239.175; 4.O.239.240; 4.O.239.244; 4.O.154.228; 4.O.154.229; 4.O.154.230; 4.O.154.231; 4.O.154.236; 4.O.154.237; 4.O.154.238; 4.O.154.239; 4.O.154.154; 4.O.154.157; 4.O.154.166; 4.O.154.169; 4.O.154.172; 4.O.154.175; 4.O.154.240; 4.O.154.244; 4.O.157.228; 4.O.157.229; 4.O.157.230; 4.O.157.231; 4.O.157.236; 4.O.157.237; 4.O.157.238; 4.O.157.239; 4.O.157.154; 4.O.157.157; 4.O.157.166; 4.O.157.169; 4.O.157.172; 4.O.157.175; 4.O.157.240; 4.O.157.244; 4.O.166.228; 4.O.166.229; 4.O.166.230; 4.O.166.231; 4.O.166.236; 4.O.166.237; 4.O.166.238; 4.O.166.239; 4.O.166.154; 4.O.166.157; 4.O.166.166; 4.O.166.169; 4.O.166.172; 4.O.166.175; 4.O.166.240; 4.O.166.244; 4.O.169.228; 4.O.169.229; 4.O.169.230; 4.O.169.231; 4.O.169.236; 4.O.169.237; 4.O.169.238; 4.O.169.239; 4.O.169.154; 4.O.169.157; 4.O.169.166; 4.O.169.169; 4.O.169.172; 4.O.169.175; 4.O.169.240; 4.O.169.244; 4.O.172.228; 4.O.172.229; 4.O.172.230; 4.O.172.231; 4.O.172.236; 4.O.172.237; 4.O.172.238; 4.O.172.239; 4.O.172.154; 4.O.172.157; 4.O.172.166; 4.O.172.169; 4.O.172.172; 4.O.172.175; 4.O.172.240; 4.O.172.244; 4.O.175.228; 4.O.175.229; 4.O.175.230; 4.O.175.231; 4.O.175.236; 4.O.175.237; 4.O.175.238; 4.O.175.239; 4.O.175.154; 4.O.175.157; 4.O.175.166; 4.O.175.169; 4.O.175.172; 4.O.175.175; 4.O.175.240; 4.O.175.244; 4.O.240.228; 4.O.240.229; 4.O.240.230; 4.O.240.231; 4.O.240.236; 4.O.240.237; 4.O.240.238; 4.O.240.239; 4.O.240.154; 4.O.240.157; 4.O.240.166; 4.O.240.169; 4.O.240.172; 4.O.240.175; 4.O.240.240; 4.O.240.244; 4.O.244.228; 4.O.244.229; 4.O.244.230; 4.O.244.231; 4.O.244.236; 4.O.244.237; 4.O.244.238; 4.O.244.239; 4.O.244.154; 4.O.244.157; 4.O.244.166; 4.O.244.169; 4.O.244.172; 4.O.244.175; 4.O.244.240; 4.O.244.244;

TABLE 100-continued

Prodrugs of 4.P

4.P.228.228; 4.P.228.229; 4.P.228.230; 4.P.228.231; 4.P.228.236; 4.P.228.237; 4.P.228.238; 4.P.228.239; 4.P.228.154; 4.P.228.157; 4.P.228.166; 4.P.228.169; 4.P.228.172; 4.P.228.175; 4.P.228.240; 4.P.228.244; 4.P.229.228; 4.P.229.229; 4.P.229.230; 4.P.229.231; 4.P.229.236; 4.P.229.237; 4.P.229.238; 4.P.229.239; 4.P.229.154; 4.P.229.157; 4.P.229.166; 4.P.229.169; 4.P.229.172; 4.P.229.175; 4.P.229.240; 4.P.229.244; 4.P.230.228; 4.P.230.229; 4.P.230.230; 4.P.230.231; 4.P.230.236; 4.P.230.237; 4.P.230.238; 4.P.230.239; 4.P.230.154; 4.P.230.157; 4.P.230.166; 4.P.230.169; 4.P.230.172; 4.P.230.175; 4.P.230.240; 4.P.230.244; 4.P.231.228; 4.P.231.229; 4.P.231.230; 4.P.231.231; 4.P.231.236; 4.P.231.237; 4.P.231.238; 4.P.231.239; 4.P.231.154; 4.P.231.157; 4.P.231.166; 4.P.231.169; 4.P.231.172; 4.P.231.175; 4.P.231.240; 4.P.231.244; 4.P.236.228; 4.P.236.229; 4.P.236.230; 4.P.236.231; 4.P.236.236; 4.P.236.237; 4.P.236.238; 4.P.236.239; 4.P.236.154; 4.P.236.157; 4.P.236.166; 4.P.236.169; 4.P.236.172; 4.P.236.175; 4.P.236.240; 4.P.236.244; 4.P.237.228; 4.P.237.229; 4.P.237.230; 4.P.237.231; 4.P.237.236; 4.P.237.237; 4.P.237.238; 4.P.237.239; 4.P.237.154; 4.P.237.157; 4.P.237.166; 4.P.237.169; 4.P.237.172; 4.P.237.175; 4.P.237.240; 4.P.237.244; 4.P.238.228; 4.P.238.229; 4.P.238.230; 4.P.238.231; 4.P.238.236; 4.P.238.237; 4.P.238.238; 4.P.238.239; 4.P.238.154; 4.P.238.157; 4.P.238.166; 4.P.238.169; 4.P.238.172; 4.P.238.175; 4.P.238.240; 4.P.238.244; 4.P.239.228; 4.P.239.229; 4.P.239.230; 4.P.239.231; 4.P.239.236; 4.P.239.237; 4.P.239.238; 4.P.239.239; 4.P.239.154; 4.P.239.157; 4.P.239.166; 4.P.239.169; 4.P.239.172; 4.P.239.175; 4.P.239.240; 4.P.239.244; 4.P.154.228; 4.P.154.229; 4.P.154.230; 4.P.154.231; 4.P.154.236; 4.P.154.237; 4.P.154.238; 4.P.154.239; 4.P.154.154; 4.P.154.157; 4.P.154.166; 4.P.154.169; 4.P.154.172; 4.P.154.175; 4.P.154.240; 4.P.154.244; 4.P.157.228; 4.P.157.229; 4.P.157.230; 4.P.157.231; 4.P.157.236; 4.P.157.237; 4.P.157.238; 4.P.157.239; 4.P.157.154; 4.P.157.157; 4.P.157.166; 4.P.157.169; 4.P.157.172; 4.P.157.175; 4.P.157.240; 4.P.157.244; 4.P.166.228; 4.P.166.229; 4.P.166.230; 4.P.166.231; 4.P.166.236; 4.P.166.237; 4.P.166.238; 4.P.166.239; 4.P.166.154; 4.P.166.157; 4.P.166.166; 4.P.166.169; 4.P.166.172; 4.P.166.175; 4.P.166.240; 4.P.166.244; 4.P.169.228; 4.P.169.229; 4.P.169.230; 4.P.169.231; 4.P.169.236; 4.P.169.237; 4.P.169.238; 4.P.169.239; 4.P.169.154; 4.P.169.157; 4.P.169.166; 4.P.169.169; 4.P.169.172; 4.P.169.175; 4.P.169.240; 4.P.169.244; 4.P.172.228; 4.P.172.229; 4.P.172.230; 4.P.172.231; 4.P.172.236; 4.P.172.237; 4.P.172.238; 4.P.172.239; 4.P.172.154; 4.P.172.157; 4.P.172.166; 4.P.172.169; 4.P.172.172; 4.P.172.175; 4.P.172.240; 4.P.172.244; 4.P.175.228; 4.P.175.229; 4.P.175.230; 4.P.175.231; 4.P.175.236; 4.P.175.237; 4.P.175.238; 4.P.175.239; 4.P.175.154; 4.P.175.157; 4.P.175.166; 4.P.175.169; 4.P.175.172; 4.P.175.175; 4.P.175.240; 4.P.175.244; 4.P.240.228; 4.P.240.229; 4.P.240.230; 4.P.240.231; 4.P.240.236; 4.P.240.237; 4.P.240.238; 4.P.240.239; 4.P.240.154; 4.P.240.157; 4.P.240.166; 4.P.240.169; 4.P.240.172; 4.P.240.175; 4.P.240.240; 4.P.240.244; 4.P.244.228; 4.P.244.229; 4.P.244.230; 4.P.244.231; 4.P.244.236; 4.P.244.237; 4.P.244.238; 4.P.244.239; 4.P.244.154; 4.P.244.157; 4.P.244.166; 4.P.244.169; 4.P.244.172; 4.P.244.175; 4.P.244.240; 4.P.244.244;

Prodrugs of 4.U

4.U.228.228; 4.U.228.229; 4.U.228.230; 4.U.228.231; 4.U.228.236; 4.U.228.237; 4.U.228.238; 4.U.228.239; 4.U.228.154; 4.U.228.157; 4.U.228.166; 4.U.228.169; 4.U.228.172; 4.U.228.175; 4.U.228.240; 4.U.228.244; 4.U.229.228; 4.U.229.229; 4.U.229.230; 4.U.229.231; 4.U.229.236; 4.U.229.237; 4.U.229.238; 4.U.229.239; 4.U.229.154; 4.U.229.157; 4.U.229.166; 4.U.229.169; 4.U.229.172; 4.U.229.175; 4.U.229.240; 4.U.229.244; 4.U.230.228; 4.U.230.229; 4.U.230.230; 4.U.230.231; 4.U.230.236; 4.U.230.237; 4.U.230.238; 4.U.230.239; 4.U.230.154; 4.U.230.157; 4.U.230.166; 4.U.230.169; 4.U.230.172; 4.U.230.175; 4.U.230.240; 4.U.230.244; 4.U.231.228; 4.U.231.229; 4.U.231.230; 4.U.231.231; 4.U.231.236; 4.U.231.237; 4.U.231.238; 4.U.231.239; 4.U.231.154; 4.U.231.157; 4.U.231.166; 4.U.231.169; 4.U.231.172; 4.U.231.175; 4.U.231.240; 4.U.231.244; 4.U.236.228; 4.U.236.229; 4.U.236.230; 4.U.236.231; 4.U.236.236; 4.U.236.237; 4.U.236.238; 4.U.236.239; 4.U.236.154; 4.U.236.157; 4.U.236.166; 4.U.236.169; 4.U.236.172; 4.U.236.175; 4.U.236.240; 4.U.236.244; 4.U.237.228; 4.U.237.229; 4.U.237.230; 4.U.237.231; 4.U.237.236; 4.U.237.237; 4.U.237.238; 4.U.237.239; 4.U.237.154; 4.U.237.157; 4.U.237.166; 4.U.237.169; 4.U.237.172; 4.U.237.175; 4.U.237.240; 4.U.237.244; 4.U.238.228; 4.U.238.229; 4.U.238.230; 4.U.238.231; 4.U.238.236; 4.U.238.237; 4.U.238.238; 4.U.238.239; 4.U.238.154; 4.U.238.157; 4.U.238.166; 4.U.238.169; 4.U.238.172; 4.U.238.175; 4.U.238.240; 4.U.238.244; 4.U.239.228; 4.U.239.229; 4.U.239.230; 4.U.239.231; 4.U.239.236; 4.U.239.237; 4.U.239.238; 4.U.239.239; 4.U.239.154; 4.U.239.157; 4.U.239.166; 4.U.239.169; 4.U.239.172; 4.U.239.175; 4.U.239.240; 4.U.239.244; 4.U.154.228; 4.U.154.229; 4.U.154.230; 4.U.154.231; 4.U.154.236; 4.U.154.237; 4.U.154.238; 4.U.154.239; 4.U.154.154; 4.U.154.157; 4.U.154.166; 4.U.154.169; 4.U.154.172; 4.U.154.175; 4.U.154.240; 4.U.154.244; 4.U.157.228; 4.U.157.229; 4.U.157.230; 4.U.157.231; 4.U.157.236; 4.U.157.237; 4.U.157.238; 4.U.157.239; 4.U.157.154; 4.U.157.157; 4.U.157.166; 4.U.157.169; 4.U.157.172; 4.U.157.175; 4.U.157.240; 4.U.157.244;

TABLE 100-continued

4.U.166.228; 4.U.166.229; 4.U.166.230; 4.U.166.231; 4.U.166.236; 4.U.166.237; 4.U.166.238; 4.U.166.239; 4.U.166.154; 4.U.166.157; 4.U.166.166; 4.U.166.169; 4.U.166.172; 4.U.166.175; 4.U.166.240; 4.U.166.244; 4.U.169.228; 4.U.169.229; 4.U.169.230; 4.U.169.231; 4.U.169.236; 4.U.169.237; 4.U.169.238; 4.U.169.239; 4.U.169.154; 4.U.169.157; 4.U.169.166; 4.U.169.169; 4.U.169.172; 4.U.169.175; 4.U.169.240; 4.U.169.244; 4.U.172.228; 4.U.172.229; 4.U.172.230; 4.U.172.231; 4.U.172.236; 4.U.172.237; 4.U.172.238; 4.U.172.239; 4.U.172.154; 4.U.172.157; 4.U.172.166; 4.U.172.169; 4.U.172.172; 4.U.172.175; 4.U.172.240; 4.U.172.244; 4.U.175.228; 4.U.175.229; 4.U.175.230; 4.U.175.231; 4.U.175.236; 4.U.175.237; 4.U.175.238; 4.U.175.239; 4.U.175.154; 4.U.175.157; 4.U.175.166; 4.U.175.169; 4.U.175.172; 4.U.175.175; 4.U.175.240; 4.U.175.244; 4.U.240.228; 4.U.240.229; 4.U.240.230; 4.U.240.231; 4.U.240.236; 4.U.240.237; 4.U.240.238; 4.U.240.239; 4.U.240.154; 4.U.240.157; 4.U.240.166; 4.U.240.169; 4.U.240.172; 4.U.240.175; 4.U.240.240; 4.U.240.244; 4.U.244.228; 4.U.244.229; 4.U.244.230; 4.U.244.231; 4.U.244.236; 4.U.244.237; 4.U.244.238; 4.U.244.239; 4.U.244.154; 4.U.244.157; 4.U.244.166; 4.U.244.169; 4.U.244.172; 4.U.244.175; 4.U.244.240; 4.U.244.244;

Prodrugs of 4.W

4.W.228.228; 4.W.228.229; 4.W.228.230; 4.W.228.231; 4.W.228.236; 4.W.228.237; 4.W.228.238; 4.W.228.239; 4.W.228.154; 4.W.228.157; 4.W.228.166; 4.W.228.169; 4.W.228.172; 4.W.228.175; 4.W.228.240; 4.W.228.244; 4.W.229.228; 4.W.229.229; 4.W.229.230; 4.W.229.231; 4.W.229.236; 4.W.229.237; 4.W.229.238; 4.W.229.239; 4.W.229.154; 4.W.229.157; 4.W.229.166; 4.W.229.169; 4.W.229.172; 4.W.229.175; 4.W.229.240; 4.W.229.244; 4.W.230.228; 4.W.230.229; 4.W.230.230; 4.W.230.231; 4.W.230.236; 4.W.230.237; 4.W.230.238; 4.W.230.239; 4.W.230.154; 4.W.230.157; 4.W.230.166; 4.W.230.169; 4.W.230.172; 4.W.230.175; 4.W.230.240; 4.W.230.244; 4.W.231.228; 4.W.231.229; 4.W.231.230; 4.W.231.231; 4.W.231.236; 4.W.231.237; 4.W.231.238; 4.W.231.239; 4.W.231.154; 4.W.231.157; 4.W.231.166; 4.W.231.169; 4.W.231.172; 4.W.231.175; 4.W.231.240; 4.W.231.244; 4.W.236.228; 4.W.236.229; 4.W.236.230; 4.W.236.231; 4.W.236.236; 4.W.236.237; 4.W.236.238; 4.W.236.239; 4.W.236.154; 4.W.236.157; 4.W.236.166; 4.W.236.169; 4.W.236.172; 4.W.236.175; 4.W.236.240; 4.W.236.244; 4.W.237.228; 4.W.237.229; 4.W.237.230; 4.W.237.231; 4.W.237.236; 4.W.237.237; 4.W.237.238; 4.W.237.239; 4.W.237.154; 4.W.237.157; 4.W.237.166; 4.W.237.169; 4.W.237.172; 4.W.237.175; 4.W.237.240; 4.W.237.244; 4.W.238.228; 4.W.238.229; 4.W.238.230; 4.W.238.231; 4.W.238.236; 4.W.238.237; 4.W.238.238; 4.W.238.239; 4.W.238.154; 4.W.238.157; 4.W.238.166; 4.W.238.169; 4.W.238.172; 4.W.238.175; 4.W.238.240; 4.W.238.244; 4.W.239.228; 4.W.239.229; 4.W.239.230; 4.W.239.231; 4.W.239.236; 4.W.239.237; 4.W.239.238; 4.W.239.239; 4.W.239.154; 4.W.239.157; 4.W.239.166; 4.W.239.169; 4.W.239.172; 4.W.239.175; 4.W.239.240; 4.W.239.244; 4.W.154.228; 4.W.154.229; 4.W.154.230; 4.W.154.231; 4.W.154.236; 4.W.154.237; 4.W.154.238; 4.W.154.239; 4.W.154.154; 4.W.154.157; 4.W.154.166; 4.W.154.169; 4.W.154.172; 4.W.154.175; 4.W.154.240; 4.W.154.244; 4.W.157.228; 4.W.157.229; 4.W.157.230; 4.W.157.231; 4.W.157.236; 4.W.157.237; 4.W.157.238; 4.W.157.239; 4.W.157.154; 4.W.157.157; 4.W.157.166; 4.W.157.169; 4.W.157.172; 4.W.157.175; 4.W.157.240; 4.W.157.244; 4.W.166.228; 4.W.166.229; 4.W.166.230; 4.W.166.231; 4.W.166.236; 4.W.166.237; 4.W.166.238; 4.W.166.239; 4.W.166.154; 4.W.166.157; 4.W.166.166; 4.W.166.169; 4.W.166.172; 4.W.166.175; 4.W.166.240; 4.W.166.244; 4.W.169.228; 4.W.169.229; 4.W.169.230; 4.W.169.231; 4.W.169.236; 4.W.169.237; 4.W.169.238; 4.W.169.239; 4.W.169.154; 4.W.169.157; 4.W.169.166; 4.W.169.169; 4.W.169.172; 4.W.169.175; 4.W.169.240; 4.W.169.244; 4.W.172.228; 4.W.172.229; 4.W.172.230; 4.W.172.231; 4.W.172.236; 4.W.172.237; 4.W.172.238; 4.W.172.239; 4.W.172.154; 4.W.172.157; 4.W.172.166; 4.W.172.169; 4.W.172.172; 4.W.172.175; 4.W.172.240; 4.W.172.244; 4.W.175.228; 4.W.175.229; 4.W.175.230; 4.W.175.231; 4.W.175.236; 4.W.175.237; 4.W.175.238; 4.W.175.239; 4.W.175.154; 4.W.175.157; 4.W.175.166; 4.W.175.169; 4.W.175.172; 4.W.175.175; 4.W.175.240; 4.W.175.244; 4.W.240.228; 4.W.240.229; 4.W.240.230; 4.W.240.231; 4.W.240.236; 4.W.240.237; 4.W.240.238; 4.W.240.239; 4.W.240.154; 4.W.240.157; 4.W.240.166; 4.W.240.169; 4.W.240.172; 4.W.240.175; 4.W.240.240; 4.W.240.244; 4.W.244.228; 4.W.244.229; 4.W.244.230; 4.W.244.231; 4.W.244.236; 4.W.244.237; 4.W.244.238; 4.W.244.239; 4.W.244.154; 4.W.244.157; 4.W.244.166; 4.W.244.169; 4.W.244.172; 4.W.244.175; 4.W.244.240; 4.W.244.244;

Prodrugs of 4.Y

4.Y.228.228; 4.Y.228.229; 4.Y.228.230; 4.Y.228.231; 4.Y.228.236; 4.Y.228.237; 4.Y.228.238; 4.Y.228.239; 4.Y.228.154; 4.Y.228.157; 4.Y.228.166; 4.Y.228.169; 4.Y.228.172; 4.Y.228.175; 4.Y.228.240; 4.Y.228.244; 4.Y.229.228;

TABLE 100-continued

4.Y.229.229; 4.Y.229.230; 4.Y.229.231; 4.Y.229.236; 4.Y.229.237; 4.Y.229.238;
4.Y.229.239; 4.Y.229.154; 4.Y.229.157; 4.Y.229.166; 4.Y.229.169; 4.Y.229.172;
4.Y.229.175; 4.Y.229.240; 4.Y.229.244; 4.Y.230.228; 4.Y.230.229; 4.Y.230.230;
4.Y.230.231; 4.Y.230.236; 4.Y.230.237; 4.Y.230.238; 4.Y.230.239; 4.Y.230.154;
4.Y.230.157; 4.Y.230.166; 4.Y.230.169; 4.Y.230.172; 4.Y.230.175; 4.Y.230.240;
4.Y.230.244; 4.Y.231.228; 4.Y.231.229; 4.Y.231.230; 4.Y.231.231; 4.Y.231.236;
4.Y.231.237; 4.Y.231.238; 4.Y.231.239; 4.Y.231.154; 4.Y.231.157; 4.Y.231.166;
4.Y.231.169; 4.Y.231.172; 4.Y.231.175; 4.Y.231.240; 4.Y.231.244; 4.Y.236.228;
4.Y.236.229; 4.Y.236.230; 4.Y.236.231; 4.Y.236.236; 4.Y.236.237; 4.Y.236.238;
4.Y.236.239; 4.Y.236.154; 4.Y.236.157; 4.Y.236.166; 4.Y.236.169; 4.Y.236.172;
4.Y.236.175; 4.Y.236.240; 4.Y.236.244; 4.Y.237.228; 4.Y.237.229; 4.Y.237.230;
4.Y.237.231; 4.Y.237.236; 4.Y.237.237; 4.Y.237.238; 4.Y.237.239; 4.Y.237.154;
4.Y.237.157; 4.Y.237.166; 4.Y.237.169; 4.Y.237.172; 4.Y.237.175; 4.Y.237.240;
4.Y.237.244; 4.Y.238.228; 4.Y.238.229; 4.Y.238.230; 4.Y.238.231; 4.Y.238.236;
4.Y.238.237; 4.Y.238.238; 4.Y.238.239; 4.Y.238.154; 4.Y.238.157; 4.Y.238.166;
4.Y.238.169; 4.Y.238.172; 4.Y.238.175; 4.Y.238.240; 4.Y.238.244; 4.Y.239.228;
4.Y.239.229; 4.Y.239.230; 4.Y.239.231; 4.Y.239.236; 4.Y.239.237; 4.Y.239.238;
4.Y.239.239; 4.Y.239.154; 4.Y.239.157; 4.Y.239.166; 4.Y.239.169; 4.Y.239.172;
4.Y.239.175; 4.Y.239.240; 4.Y.239.244; 4.Y.154.228; 4.Y.154.229; 4.Y.154.230;
4.Y.154.231; 4.Y.154.236; 4.Y.154.237; 4.Y.154.238; 4.Y.154.239; 4.Y.154.154;
4.Y.154.157; 4.Y.154.166; 4.Y.154.169; 4.Y.154.172; 4.Y.154.175; 4.Y.154.240;
4.Y.154.244; 4.Y.157.228; 4.Y.157.229; 4.Y.157.230; 4.Y.157.231; 4.Y.157.236;
4.Y.157.237; 4.Y.157.238; 4.Y.157.239; 4.Y.157.154; 4.Y.157.157; 4.Y.157.166;
4.Y.157.169; 4.Y.157.172; 4.Y.157.175; 4.Y.157.240; 4.Y.157.244; 4.Y.166.228;
4.Y.166.229; 4.Y.166.230; 4.Y.166.231; 4.Y.166.236; 4.Y.166.237; 4.Y.166.238;
4.Y.166.239; 4.Y.166.154; 4.Y.166.157; 4.Y.166.166; 4.Y.166.169; 4.Y.166.172;
4.Y.166.175; 4.Y.166.240; 4.Y.166.244; 4.Y.169.228; 4.Y.169.229; 4.Y.169.230;
4.Y.169.231; 4.Y.169.236; 4.Y.169.237; 4.Y.169.238; 4.Y.169.239; 4.Y.169.154;
4.Y.169.157; 4.Y.169.166; 4.Y.169.169; 4.Y.169.172; 4.Y.169.175; 4.Y.169.240;
4.Y.169.244; 4.Y.172.228; 4.Y.172.229; 4.Y.172.230; 4.Y.172.231; 4.Y.172.236;
4.Y.172.237; 4.Y.172.238; 4.Y.172.239; 4.Y.172.154; 4.Y.172.157; 4.Y.172.166;
4.Y.172.169; 4.Y.172.172; 4.Y.172.175; 4.Y.172.240; 4.Y.172.244; 4.Y.175.228;
4.Y.175.229; 4.Y.175.230; 4.Y.175.231; 4.Y.175.236; 4.Y.175.237; 4.Y.175.238;
4.Y.175.239; 4.Y.175.154; 4.Y.175.157; 4.Y.175.166; 4.Y.175.169; 4.Y.175.172;
4.Y.175.175; 4.Y.175.240; 4.Y.175.244; 4.Y.240.228; 4.Y.240.229; 4.Y.240.230;
4.Y.240.231; 4.Y.240.236; 4.Y.240.237; 4.Y.240.238; 4.Y.240.239; 4.Y.240.154;
4.Y.240.157; 4.Y.240.166; 4.Y.240.169; 4.Y.240.172; 4.Y.240.175; 4.Y.240.240;
4.Y.240.244; 4.Y.244.228; 4.Y.244.229; 4.Y.244.230; 4.Y.244.231; 4.Y.244.236;
4.Y.244.237; 4.Y.244.238; 4.Y.244.239; 4.Y.244.154; 4.Y.244.157; 4.Y.244.166;
4.Y.244.169; 4.Y.244.172; 4.Y.244.175; 4.Y.244.240; 4.Y.244.244;

Prodrugs of 5.B

5.B.228.228; 5.B.228.229; 5.B.228.230; 5.B.228.231; 5.B.228.236;
5.B.228.237; 5.B.228.238; 5.B.228.239; 5.B.228.154; 5.B.228.157; 5.B.228.166;
5.B.228.169; 5.B.228.172; 5.B.228.175; 5.B.228.240; 5.B.228.244; 5.B.229.228;
5.B.229.229; 5.B.229.230; 5.B.229.231; 5.B.229.236; 5.B.229.237; 5.B.229.238;
5.B.229.239; 5.B.229.154; 5.B.229.157; 5.B.229.166; 5.B.229.169; 5.B.229.172;
5.B.229.175; 5.B.229.240; 5.B.229.244; 5.B.230.228; 5.B.230.229; 5.B.230.230;
5.B.230.231; 5.B.230.236; 5.B.230.237; 5.B.230.238; 5.B.230.239; 5.B.230.154;
5.B.230.157; 5.B.230.166; 5.B.230.169; 5.B.230.172; 5.B.230.175; 5.B.230.240;
5.B.230.244; 5.B.231.228; 5.B.231.229; 5.B.231.230; 5.B.231.231; 5.B.231.236;
5.B.231.237; 5.B.231.238; 5.B.231.239; 5.B.231.154; 5.B.231.157; 5.B.231.166;
5.B.231.169; 5.B.231.172; 5.B.231.175; 5.B.231.240; 5.B.231.244; 5.B.236.228;
5.B.236.229; 5.B.236.230; 5.B.236.231; 5.B.236.236; 5.B.236.237; 5.B.236.238;
5.B.236.239; 5.B.236.154; 5.B.236.157; 5.B.236.166; 5.B.236.169; 5.B.236.172;
5.B.236.175; 5.B.236.240; 5.B.236.244; 5.B.237.228; 5.B.237.229; 5.B.237.230;
5.B.237.231; 5.B.237.236; 5.B.237.237; 5.B.237.238; 5.B.237.239; 5.B.237.154;
5.B.237.157; 5.B.237.166; 5.B.237.169; 5.B.237.172; 5.B.237.175; 5.B.237.240;
5.B.237.244; 5.B.238.228; 5.B.238.229; 5.B.238.230; 5.B.238.231; 5.B.238.236;
5.B.238.237; 5.B.238.238; 5.B.238.239; 5.B.238.154; 5.B.238.157; 5.B.238.166;
5.B.238.169; 5.B.238.172; 5.B.238.175; 5.B.238.240; 5.B.238.244; 5.B.239.228;
5.B.239.229; 5.B.239.230; 5.B.239.231; 5.B.239.236; 5.B.239.237; 5.B.239.238;
5.B.239.239; 5.B.239.154; 5.B.239.157; 5.B.239.166; 5.B.239.169; 5.B.239.172;
5.B.239.175; 5.B.239.240; 5.B.239.244; 5.B.154.228; 5.B.154.229; 5.B.154.230;
5.B.154.231; 5.B.154.236; 5.B.154.237; 5.B.154.238; 5.B.154.239; 5.B.154.154;
5.B.154.157; 5.B.154.166; 5.B.154.169; 5.B.154.172; 5.B.154.175; 5.B.154.240;
5.B.154.244; 5.B.157.228; 5.B.157.229; 5.B.157.230; 5.B.157.231; 5.B.157.236;
5.B.157.237; 5.B.157.238; 5.B.157.239; 5.B.157.154; 5.B.157.157; 5.B.157.166;
5.B.157.169; 5.B.157.172; 5.B.157.175; 5.B.157.240; 5.B.157.244; 5.B.166.228;
5.B.166.229; 5.B.166.230; 5.B.166.231; 5.B.166.236; 5.B.166.237; 5.B.166.238;
5.B.166.239; 5.B.166.154; 5.B.166.157; 5.B.166.166; 5.B.166.169; 5.B.166.172;
5.B.166.175; 5.B.166.240; 5.B.166.244; 5.B.169.228; 5.B.169.229; 5.B.169.230;
5.B.169.231; 5.B.169.236; 5.B.169.237; 5.B.169.238; 5.B.169.239; 5.B.169.154;
5.B.169.157; 5.B.169.166; 5.B.169.169; 5.B.169.172; 5.B.169.175; 5.B.169.240;
5.B.169.244; 5.B.172.228; 5.B.172.229; 5.B.172.230; 5.B.172.231; 5.B.172.236;
5.B.172.237; 5.B.172.238; 5.B.172.239; 5.B.172.154; 5.B.172.157; 5.B.172.166;
5.B.172.169; 5.B.172.172; 5.B.172.175; 5.B.172.240; 5.B.172.244; 5.B.175.228;
5.B.175.229; 5.B.175.230; 5.B.175.231; 5.B.175.236; 5.B.175.237; 5.B.175.238;
5.B.175.239; 5.B.175.154; 5.B.175.157; 5.B.175.166; 5.B.175.169; 5.B.175.172;

TABLE 100-continued

5.B.175.175; 5.B.175.240; 5.B.175.244; 5.B.240.228; 5.B.240.229; 5.B.240.230; 5.B.240.231; 5.B.240.236; 5.B.240.237; 5.B.240.238; 5.B.240.239; 5.B.240.154; 5.B.240.157; 5.B.240.166; 5.B.240.169; 5.B.240.172; 5.B.240.175; 5.B.240.240; 5.B.240.244; 5.B.244.228; 5.B.244.229; 5.B.244.230; 5.B.244.231; 5.B.244.236; 5.B.244.237; 5.B.244.238; 5.B.244.239; 5.B.244.154; 5.B.244.157; 5.B.244.166; 5.B.244.169; 5.B.244.172; 5.B.244.175; 5.B.244.240; 5.B.244.244;

Prodrugs of 5.D

5.D.228.228; 5.D.228.229; 5.D.228.230; 5.D.228.231; 5.D.228.236; 5.D.228.237; 5.D.228.238; 5.D.228.239; 5.D.228.154; 5.D.228.157; 5.D.228.166; 5.D.228.169; 5.D.228.172; 5.D.228.175; 5.D.228.240; 5.D.228.244; 5.D.229.228; 5.D.229.229; 5.D.229.230; 5.D.229.231; 5.D.229.236; 5.D.229.237; 5.D.229.238; 5.D.229.239; 5.D.229.154; 5.D.229.157; 5.D.229.166; 5.D.229.169; 5.D.229.172; 5.D.229.175; 5.D.229.240; 5.D.229.244; 5.D.230.228; 5.D.230.229; 5.D.230.230; 5.D.230.231; 5.D.230.236; 5.D.230.237; 5.D.230.238; 5.D.230.239; 5.D.230.154; 5.D.230.157; 5.D.230.166; 5.D.230.169; 5.D.230.172; 5.D.230.175; 5.D.230.240; 5.D.230.244; 5.D.231.228; 5.D.231.229; 5.D.231.230; 5.D.231.231; 5.D.231.236; 5.D.231.237; 5.D.231.238; 5.D.231.239; 5.D.231.154; 5.D.231.157; 5.D.231.166; 5.D.231.169; 5.D.231.172; 5.D.231.175; 5.D.231.240; 5.D.231.244; 5.D.236.228; 5.D.236.229; 5.D.236.230; 5.D.236.231; 5.D.236.236; 5.D.236.237; 5.D.236.238; 5.D.236.239; 5.D.236.154; 5.D.236.157; 5.D.236.166; 5.D.236.169; 5.D.236.172; 5.D.236.175; 5.D.236.240; 5.D.236.244; 5.D.237.228; 5.D.237.229; 5.D.237.230; 5.D.237.231; 5.D.237.236; 5.D.237.237; 5.D.237.238; 5.D.237.239; 5.D.237.154; 5.D.237.157; 5.D.237.166; 5.D.237.169; 5.D.237.172; 5.D.237.175; 5.D.237.240; 5.D.237.244; 5.D.238.228; 5.D.238.229; 5.D.238.230; 5.D.238.231; 5.D.238.236; 5.D.238.237; 5.D.238.238; 5.D.238.239; 5.D.238.154; 5.D.238.157; 5.D.238.166; 5.D.238.169; 5.D.238.172; 5.D.238.175; 5.D.238.240; 5.D.238.244; 5.D.239.228; 5.D.239.229; 5.D.239.230; 5.D.239.231; 5.D.239.236; 5.D.239.237; 5.D.239.238; 5.D.239.239; 5.D.239.154; 5.D.239.157; 5.D.239.166; 5.D.239.169; 5.D.239.172; 5.D.239.175; 5.D.239.240; 5.D.239.244; 5.D.154.228; 5.D.154.229; 5.D.154.230; 5.D.154.231; 5.D.154.236; 5.D.154.237; 5.D.154.238; 5.D.154.239; 5.D.154.154; 5.D.154.157; 5.D.154.166; 5.D.154.169; 5.D.154.172; 5.D.154.175; 5.D.154.240; 5.D.154.244; 5.D.157.228; 5.D.157.229; 5.D.157.230; 5.D.157.231; 5.D.157.236; 5.D.157.237; 5.D.157.238; 5.D.157.239; 5.D.157.154; 5.D.157.157; 5.D.157.166; 5.D.157.169; 5.D.157.172; 5.D.157.175; 5.D.157.240; 5.D.157.244; 5.D.166.228; 5.D.166.229; 5.D.166.230; 5.D.166.231; 5.D.166.236; 5.D.166.237; 5.D.166.238; 5.D.166.239; 5.D.166.154; 5.D.166.157; 5.D.166.166; 5.D.166.169; 5.D.166.172; 5.D.166.175; 5.D.166.240; 5.D.166.244; 5.D.169.228; 5.D.169.229; 5.D.169.230; 5.D.169.231; 5.D.169.236; 5.D.169.237; 5.D.169.238; 5.D.169.239; 5.D.169.154; 5.D.169.157; 5.D.169.166; 5.D.169.169; 5.D.169.172; 5.D.169.175; 5.D.169.240; 5.D.169.244; 5.D.172.228; 5.D.172.229; 5.D.172.230; 5.D.172.231; 5.D.172.236; 5.D.172.237; 5.D.172.238; 5.D.172.239; 5.D.172.154; 5.D.172.157; 5.D.172.166; 5.D.172.169; 5.D.172.172; 5.D.172.175; 5.D.172.240; 5.D.172.244; 5.D.175.228; 5.D.175.229; 5.D.175.230; 5.D.175.231; 5.D.175.236; 5.D.175.237; 5.D.175.238; 5.D.175.239; 5.D.175.154; 5.D.175.157; 5.D.175.166; 5.D.175.169; 5.D.175.172; 5.D.175.175; 5.D.175.240; 5.D.175.244; 5.D.240.228; 5.D.240.229; 5.D.240.230; 5.D.240.231; 5.D.240.236; 5.D.240.237; 5.D.240.238; 5.D.240.239; 5.D.240.154; 5.D.240.157; 5.D.240.166; 5.D.240.169; 5.D.240.172; 5.D.240.175; 5.D.240.240; 5.D.240.244; 5.D.244.228; 5.D.244.229; 5.D.244.230; 5.D.244.231; 5.D.244.236; 5.D.244.237; 5.D.244.238; 5.D.244.239; 5.D.244.154; 5.D.244.157; 5.D.244.166; 5.D.244.169; 5.D.244.172; 5.D.244.175; 5.D.244.240; 5.D.244.244;

Prodrugs of 5.E

5.E.228.228; 5.E.228.229; 5.E.228.230; 5.E.228.231; 5.E.228.236; 5.E.228.237; 5.E.228.238; 5.E.228.239; 5.E.228.154; 5.E.228.157; 5.E.228.166; 5.E.228.169; 5.E.228.172; 5.E.228.175; 5.E.228.240; 5.E.228.244; 5.E.229.228; 5.E.229.229; 5.E.229.230; 5.E.229.231; 5.E.229.236; 5.E.229.237; 5.E.229.238; 5.E.229.239; 5.E.229.154; 5.E.229.157; 5.E.229.166; 5.E.229.169; 5.E.229.172; 5.E.229.175; 5.E.229.240; 5.E.229.244; 5.E.230.228; 5.E.230.229; 5.E.230.230; 5.E.230.231; 5.E.230.236; 5.E.230.237; 5.E.230.238; 5.E.230.239; 5.E.230.154; 5.E.230.157; 5.E.230.166; 5.E.230.169; 5.E.230.172; 5.E.230.175; 5.E.230.240; 5.E.230.244; 5.E.231.228; 5.E.231.229; 5.E.231.230; 5.E.231.231; 5.E.231.236; 5.E.231.237; 5.E.231.238; 5.E.231.239; 5.E.231.154; 5.E.231.157; 5.E.231.166; 5.E.231.169; 5.E.231.172; 5.E.231.175; 5.E.231.240; 5.E.231.244; 5.E.236.228; 5.E.236.229; 5.E.236.230; 5.E.236.231; 5.E.236.236; 5.E.236.237; 5.E.236.238; 5.E.236.239; 5.E.236.154; 5.E.236.157; 5.E.236.166; 5.E.236.169; 5.E.236.172; 5.E.236.175; 5.E.236.240; 5.E.236.244; 5.E.237.228; 5.E.237.229; 5.E.237.230; 5.E.237.231; 5.E.237.236; 5.E.237.237; 5.E.237.238; 5.E.237.239; 5.E.237.154; 5.E.237.157; 5.E.237.166; 5.E.237.169; 5.E.237.172; 5.E.237.175; 5.E.237.240; 5.E.237.244; 5.E.238.228; 5.E.238.229; 5.E.238.230; 5.E.238.231; 5.E.238.236;

TABLE 100-continued

5.E.238.237; 5.E.238.238; 5.E.238.239; 5.E.238.154; 5.E.238.157; 5.E.238.166; 5.E.238.169; 5.E.238.172; 5.E.238.175; 5.E.238.240; 5.E.238.244; 5.E.239.228; 5.E.239.229; 5.E.239.230; 5.E.239.231; 5.E.239.236; 5.E.239.237; 5.E.239.238; 5.E.239.239; 5.E.239.154; 5.E.239.157; 5.E.239.166; 5.E.239.169; 5.E.239.172; 5.E.239.175; 5.E.239.240; 5.E.239.244; 5.E.154.228; 5.E.154.229; 5.E.154.230; 5.E.154.231; 5.E.154.236; 5.E.154.237; 5.E.154.238; 5.E.154.239; 5.E.154.154; 5.E.154.157; 5.E.154.166; 5.E.154.169; 5.E.154.172; 5.E.154.175; 5.E.154.240; 5.E.154.244; 5.E.157.228; 5.E.157.229; 5.E.157.230; 5.E.157.231; 5.E.157.236; 5.E.157.237; 5.E.157.238; 5.E.157.239; 5.E.157.154; 5.E.157.157; 5.E.157.166; 5.E.157.169; 5.E.157.172; 5.E.157.175; 5.E.157.240; 5.E.157.244; 5.E.166.228; 5.E.166.229; 5.E.166.230; 5.E.166.231; 5.E.166.236; 5.E.166.237; 5.E.166.238; 5.E.166.239; 5.E.166.154; 5.E.166.157; 5.E.166.166; 5.E.166.169; 5.E.166.172; 5.E.166.175; 5.E.166.240; 5.E.166.244; 5.E.169.228; 5.E.169.229; 5.E.169.230; 5.E.169.231; 5.E.169.236; 5.E.169.237; 5.E.169.238; 5.E.169.239; 5.E.169.154; 5.E.169.157; 5.E.169.166; 5.E.169.169; 5.E.169.172; 5.E.169.175; 5.E.169.240; 5.E.169.244; 5.E.172.228; 5.E.172.229; 5.E.172.230; 5.E.172.231; 5.E.172.236; 5.E.172.237; 5.E.172.238; 5.E.172.239; 5.E.172.154; 5.E.172.157; 5.E.172.166; 5.E.172.169; 5.E.172.172; 5.E.172.175; 5.E.172.240; 5.E.172.244; 5.E.175.228; 5.E.175.229; 5.E.175.230; 5.E.175.231; 5.E.175.236; 5.E.175.237; 5.E.175.238; 5.E.175.239; 5.E.175.154; 5.E.175.157; 5.E.175.166; 5.E.175.169; 5.E.175.172; 5.E.175.175; 5.E.175.240; 5.E.175.244; 5.E.240.228; 5.E.240.229; 5.E.240.230; 5.E.240.231; 5.E.240.236; 5.E.240.237; 5.E.240.238; 5.E.240.239; 5.E.240.154; 5.E.240.157; 5.E.240.166; 5.E.240.169; 5.E.240.172; 5.E.240.175; 5.E.240.240; 5.E.240.244; 5.E.244.228; 5.E.244.229; 5.E.244.230; 5.E.244.231; 5.E.244.236; 5.E.244.237; 5.E.244.238; 5.E.244.239; 5.E.244.154; 5.E.244.157; 5.E.244.166; 5.E.244.169; 5.E.244.172; 5.E.244.175; 5.E.244.240; 5.E.244.244;

Prodrugs of 5.G

5.G.228.228; 5.G.228.229; 5.G.228.230; 5.G.228.231; 5.G.228.236; 5.G.228.237; 5.G.228.238; 5.G.228.239; 5.G.228.154; 5.G.228.157; 5.G.228.166; 5.G.228.169; 5.G.228.172; 5.G.228.175; 5.G.228.240; 5.G.228.244; 5.G.229.228; 5.G.229.229; 5.G.229.230; 5.G.229.231; 5.G.229.236; 5.G.229.237; 5.G.229.238; 5.G.229.239; 5.G.229.154; 5.G.229.157; 5.G.229.166; 5.G.229.169; 5.G.229.172; 5.G.229.175; 5.G.229.240; 5.G.229.244; 5.G.230.228; 5.G.230.229; 5.G.230.230; 5.G.230.231; 5.G.230.236; 5.G.230.237; 5.G.230.238; 5.G.230.239; 5.G.230.154; 5.G.230.157; 5.G.230.166; 5.G.230.169; 5.G.230.172; 5.G.230.175; 5.G.230.240; 5.G.230.244; 5.G.231.228; 5.G.231.229; 5.G.231.230; 5.G.231.231; 5.G.231.236; 5.G.231.237; 5.G.231.238; 5.G.231.239; 5.G.231.154; 5.G.231.157; 5.G.231.166; 5.G.231.169; 5.G.231.172; 5.G.231.175; 5.G.231.240; 5.G.231.244; 5.G.236.228; 5.G.236.229; 5.G.236.230; 5.G.236.231; 5.G.236.236; 5.G.236.237; 5.G.236.238; 5.G.236.239; 5.G.236.154; 5.G.236.157; 5.G.236.166; 5.G.236.169; 5.G.236.172; 5.G.236.175; 5.G.236.240; 5.G.236.244; 5.G.237.228; 5.G.237.229; 5.G.237.230; 5.G.237.231; 5.G.237.236; 5.G.237.237; 5.G.237.238; 5.G.237.239; 5.G.237.154; 5.G.237.157; 5.G.237.166; 5.G.237.169; 5.G.237.172; 5.G.237.175; 5.G.237.240; 5.G.237.244; 5.G.238.228; 5.G.238.229; 5.G.238.230; 5.G.238.231; 5.G.238.236; 5.G.238.237; 5.G.238.238; 5.G.238.239; 5.G.238.154; 5.G.238.157; 5.G.238.166; 5.G.238.169; 5.G.238.172; 5.G.238.175; 5.G.238.240; 5.G.238.244; 5.G.239.228; 5.G.239.229; 5.G.239.230; 5.G.239.231; 5.G.239.236; 5.G.239.237; 5.G.239.238; 5.G.239.239; 5.G.239.154; 5.G.239.157; 5.G.239.166; 5.G.239.169; 5.G.239.172; 5.G.239.175; 5.G.239.240; 5.G.239.244; 5.G.154.228; 5.G.154.229; 5.G.154.230; 5.G.154.231; 5.G.154.236; 5.G.154.237; 5.G.154.238; 5.G.154.239; 5.G.154.154; 5.G.154.157; 5.G.154.166; 5.G.154.169; 5.G.154.172; 5.G.154.175; 5.G.154.240; 5.G.154.244; 5.G.157.228; 5.G.157.229; 5.G.157.230; 5.G.157.231; 5.G.157.236; 5.G.157.237; 5.G.157.238; 5.G.157.239; 5.G.157.154; 5.G.157.157; 5.G.157.166; 5.G.157.169; 5.G.157.172; 5.G.157.175; 5.G.157.240; 5.G.157.244; 5.G.166.228; 5.G.166.229; 5.G.166.230; 5.G.166.231; 5.G.166.236; 5.G.166.237; 5.G.166.238; 5.G.166.239; 5.G.166.154; 5.G.166.157; 5.G.166.166; 5.G.166.169; 5.G.166.172; 5.G.166.175; 5.G.166.240; 5.G.166.244; 5.G.169.228; 5.G.169.229; 5.G.169.230; 5.G.169.231; 5.G.169.236; 5.G.169.237; 5.G.169.238; 5.G.169.239; 5.G.169.154; 5.G.169.157; 5.G.169.166; 5.G.169.169; 5.G.169.172; 5.G.169.175; 5.G.169.240; 5.G.169.244; 5.G.172.228; 5.G.172.229; 5.G.172.230; 5.G.172.231; 5.G.172.236; 5.G.172.237; 5.G.172.238; 5.G.172.239; 5.G.172.154; 5.G.172.157; 5.G.172.166; 5.G.172.169; 5.G.172.172; 5.G.172.175; 5.G.172.240; 5.G.172.244; 5.G.175.228; 5.G.175.229; 5.G.175.230; 5.G.175.231; 5.G.175.236; 5.G.175.237; 5.G.175.238; 5.G.175.239; 5.G.175.154; 5.G.175.157; 5.G.175.166; 5.G.175.169; 5.G.175.172; 5.G.175.175; 5.G.175.240; 5.G.175.244; 5.G.240.228; 5.G.240.229; 5.G.240.230; 5.G.240.231; 5.G.240.236; 5.G.240.237; 5.G.240.238; 5.G.240.239; 5.G.240.154; 5.G.240.157; 5.G.240.166; 5.G.240.169; 5.G.240.172; 5.G.240.175; 5.G.240.240; 5.G.240.244; 5.G.244.228; 5.G.244.229; 5.G.244.230; 5.G.244.231; 5.G.244.236; 5.G.244.237; 5.G.244.238; 5.G.244.239; 5.G.244.154; 5.G.244.157;

TABLE 100-continued

5.G.244.166; 5.G.244.169; 5.G.244.172; 5.G.244.175; 5.G.244.240;
5.G.244.244;

Prodrugs of 5.I

5.I.228.228; 5.I.228.229; 5.I.228.230; 5.I.228.231; 5.I.228.236; 5.I.228.237;
5.I.228.238; 5.I.228.239; 5.I.228.154; 5.I.228.157; 5.I.228.166; 5.I.228.169;
5.I.228.172; 5.I.228.175; 5.I.228.240; 5.I.228.244; 5.I.229.228; 5.I.229.229;
5.I.229.230; 5.I.229.231; 5.I.229.236; 5.I.229.237; 5.I.229.238; 5.I.229.239;
5.I.229.154; 5.I.229.157; 5.I.229.166; 5.I.229.169; 5.I.229.172; 5.I.229.175;
5.I.229.240; 5.I.229.244; 5.I.230.228; 5.I.230.229; 5.I.230.230; 5.I.230.231;
5.I.230.236; 5.I.230.237; 5.I.230.238; 5.I.230.239; 5.I.230.154; 5.I.230.157;
5.I.230.166; 5.I.230.169; 5.I.230.172; 5.I.230.175; 5.I.230.240; 5.I.230.244;
5.I.231.228; 5.I.231.229; 5.I.231.230; 5.I.231.231; 5.I.231.236; 5.I.231.237;
5.I.231.238; 5.I.231.239; 5.I.231.154; 5.I.231.157; 5.I.231.166; 5.I.231.169;
5.I.231.172; 5.I.231.175; 5.I.231.240; 5.I.231.244; 5.I.236.228; 5.I.236.229;
5.I.236.230; 5.I.236.231; 5.I.236.236; 5.I.236.237; 5.I.236.238; 5.I.236.239;
5.I.236.154; 5.I.236.157; 5.I.236.166; 5.I.236.169; 5.I.236.172; 5.I.236.175;
5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157;
5.I.237.166; 5.I.237.169; 5.I.237.172; 5.I.237.175; 5.I.237.240; 5.I.237.244;
5.I.238.228; 5.I.238.229; 5.I.238.230; 5.I.238.231; 5.I.238.236; 5.I.238.237;
5.I.238.238; 5.I.238.239; 5.I.238.154; 5.I.238.157; 5.I.238.166; 5.I.238.169;
5.I.238.172; 5.I.238.175; 5.I.238.240; 5.I.238.244; 5.I.239.228; 5.I.239.229;
5.I.239.230; 5.I.239.231; 5.I.239.236; 5.I.239.237; 5.I.239.238; 5.I.239.239;
5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231;
5.I.154.236; 5.I.154.237; 5.I.154.238; 5.I.154.239; 5.I.154.154; 5.I.154.157;
5.I.154.166; 5.I.154.169; 5.I.154.172; 5.I.154.175; 5.I.154.240; 5.I.154.244;
5.I.157.228; 5.I.157.229; 5.I.157.230; 5.I.157.231; 5.I.157.236; 5.I.157.237;
5.I.157.238; 5.I.157.239; 5.I.157.154; 5.I.157.157; 5.I.157.166; 5.I.157.169;
5.I.157.172; 5.I.157.175; 5.I.157.240; 5.I.157.244; 5.I.166.228; 5.I.166.229;
5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175;
5.I.166.240; 5.I.166.244; 5.I.169.228; 5.I.169.229; 5.I.169.230; 5.I.169.231;
5.I.169.236; 5.I.169.237; 5.I.169.238; 5.I.169.239; 5.I.169.154; 5.I.169.157;
5.I.169.166; 5.I.169.169; 5.I.169.172; 5.I.169.175; 5.I.169.240; 5.I.169.244;
5.I.172.228; 5.I.172.229; 5.I.172.230; 5.I.172.231; 5.I.172.236; 5.I.172.237;
5.I.172.238; 5.I.172.239; 5.I.172.154; 5.I.172.157; 5.I.172.166; 5.I.172.169;
5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239;
5.I.175.154; 5.I.175.157; 5.I.175.166; 5.I.175.169; 5.I.175.172; 5.I.175.175;
5.I.175.240; 5.I.175.244; 5.I.240.228; 5.I.240.229; 5.I.240.230; 5.I.240.231;
5.I.240.236; 5.I.240.237; 5.I.240.238; 5.I.240.239; 5.I.240.154; 5.I.240.157;
5.I.240.166; 5.I.240.169; 5.I.240.172; 5.I.240.175; 5.I.240.240; 5.I.240.244;
5.I.244.228; 5.I.244.229; 5.I.244.230; 5.I.244.231; 5.I.244.236; 5.I.244.237;
5.I.244.238; 5.I.244.239; 5.I.244.154; 5.I.244.157; 5.I.244.166; 5.I.244.169;
5.I.244.172; 5.I.244.175; 5.I.244.240; 5.I.244.244;

Prodrugs of 5.J

5.J.228.228; 5.J.228.229; 5.J.228.230; 5.J.228.231; 5.J.228.236; 5.J.228.237;
5.J.228.238; 5.J.228.239; 5.J.228.154; 5.J.228.157; 5.J.228.166; 5.J.228.169;
5.J.228.172; 5.J.228.175; 5.J.228.240; 5.J.228.244; 5.J.229.228; 5.J.229.229;
5.J.229.230; 5.J.229.231; 5.J.229.236; 5.J.229.237; 5.J.229.238; 5.J.229.239;
5.J.229.154; 5.J.229.157; 5.J.229.166; 5.J.229.169; 5.J.229.172; 5.J.229.175;
5.J.229.240; 5.J.229.244; 5.J.230.228; 5.J.230.229; 5.J.230.230; 5.J.230.231;
5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244;
5.J.231.228; 5.J.231.229; 5.J.231.230; 5.J.231.231; 5.J.231.236; 5.J.231.237;
5.J.231.238; 5.J.231.239; 5.J.231.154; 5.J.231.157; 5.J.231.166; 5.J.231.169;
5.J.231.172; 5.J.231.175; 5.J.231.240; 5.J.231.244; 5.J.236.228; 5.J.236.229;
5.J.236.230; 5.J.236.231; 5.J.236.236; 5.J.236.237; 5.J.236.238; 5.J.236.239;
5.J.236.154; 5.J.236.157; 5.J.236.166; 5.J.236.169; 5.J.236.172; 5.J.236.175;
5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157;
5.J.237.166; 5.J.237.169; 5.J.237.172; 5.J.237.175; 5.J.237.240; 5.J.237.244;
5.J.238.228; 5.J.238.229; 5.J.238.230; 5.J.238.231; 5.J.238.236; 5.J.238.237;
5.J.238.238; 5.J.238.239; 5.J.238.154; 5.J.238.157; 5.J.238.166; 5.J.238.169;
5.J.238.172; 5.J.238.175; 5.J.238.240; 5.J.238.244; 5.J.239.228; 5.J.239.229;
5.J.239.230; 5.J.239.231; 5.J.239.236; 5.J.239.237; 5.J.239.238; 5.J.239.239;
5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231;
5.J.154.236; 5.J.154.237; 5.J.154.238; 5.J.154.239; 5.J.154.154; 5.J.154.157;
5.J.154.166; 5.J.154.169; 5.J.154.172; 5.J.154.175; 5.J.154.240; 5.J.154.244;
5.J.157.228; 5.J.157.229; 5.J.157.230; 5.J.157.231; 5.J.157.236; 5.J.157.237;
5.J.157.238; 5.J.157.239; 5.J.157.154; 5.J.157.157; 5.J.157.166; 5.J.157.169;
5.J.157.172; 5.J.157.175; 5.J.157.240; 5.J.157.244; 5.J.166.228; 5.J.166.229;
5.J.166.230; 5.J.166.231; 5.I.166.236; 5.J.166.237; 5.J.166.238; 5.J.166.239;
5.J.166.154; 5.J.166.157; 5.J.166.166; 5.J.166.169; 5.J.166.172; 5.J.166.175;
5.J.166.240; 5.J.166.244; 5.J.169.228; 5.J.169.229; 5.J.169.230; 5.J.169.231;

TABLE 100-continued

5.J.169.236; 5.J.169.237; 5.J.169.238; 5.J.169.239; 5.J.169.154; 5.J.169.157; 5.J.169.166; 5.J.169.169; 5.J.169.172; 5.J.169.175; 5.J.169.240; 5.J.169.244; 5.J.172.228; 5.J.172.229; 5.J.172.230; 5.J.172.231; 5.J.172.236; 5.J.172.237; 5.J.172.238; 5.J.172.239; 5.J.172.154; 5.J.172.157; 5.J.172.166; 5.J.172.169; 5.J.172.172; 5.J.172.175; 5.J.172.240; 5.J.172.244; 5.J.175.228; 5.J.175.229; 5.J.175.230; 5.J.175.231; 5.J.175.236; 5.J.175.237; 5.J.175.238; 5.J.175.239; 5.J.175.154; 5.J.175.157; 5.J.175.166; 5.J.175.169; 5.J.175.172; 5.J.175.175; 5.J.175.240; 5.J.175.244; 5.J.240.228; 5.J.240.229; 5.J.240.230; 5.J.240.231; 5.J.240.236; 5.J.240.237; 5.J.240.238; 5.J.240.239; 5.J.240.154; 5.J.240.157; 5.J.240.166; 5.J.240.169; 5.J.240.172; 5.J.240.175; 5.J.240.240; 5.J.240.244; 5.J.244.228; 5.J.244.229; 5.J.244.230; 5.J.244.231; 5.J.244.236; 5.J.244.237; 5.J.244.238; 5.J.244.239; 5.J.244.154; 5.J.244.157; 5.J.244.166; 5.J.244.169; 5.J.244.172; 5.J.244.175; 5.J.244.240; 5.J.244.244;

Prodrugs of 5.L

5.L.228.228; 5.L.228.229; 5.L.228.230; 5.L.228.231; 5.L.228.236; 5.L.228.237; 5.L.228.238; 5.L.228.239; 5.L.228.154; 5.L.228.157; 5.L.228.166; 5.L.228.169; 5.L.228.172; 5.L.228.175; 5.L.228.240; 5.L.228.244; 5.L.229.228; 5.L.229.229; 5.L.229.230; 5.L.229.231; 5.L.229.236; 5.L.229.237; 5.L.229.238; 5.L.229.239; 5.L.229.154; 5.L.229.157; 5.L.229.166; 5.L.229.169; 5.L.229.172; 5.L.229.175; 5.L.229.240; 5.L.229.244; 5.L.230.228; 5.L.230.229; 5.L.230.230; 5.L.230.231; 5.L.230.236; 5.L.230.237; 5.L.230.238; 5.L.230.239; 5.L.230.154; 5.L.230.157; 5.L.230.166; 5.L.230.169; 5.L.230.172; 5.L.230.175; 5.L.230.240; 5.L.230.244; 5.L.231.228; 5.L.231.229; 5.L.231.230; 5.L.231.231; 5.L.231.236; 5.L.231.237; 5.L.231.238; 5.L.231.239; 5.L.231.154; 5.L.231.157; 5.L.231.166; 5.L.231.169; 5.L.231.172; 5.L.231.175; 5.L.231.240; 5.L.231.244; 5.L.236.228; 5.L.236.229; 5.L.236.230; 5.L.236.231; 5.L.236.236; 5.L.236.237; 5.L.236.238; 5.L.236.239; 5.L.236.154; 5.L.236.157; 5.L.236.166; 5.L.236.169; 5.L.236.172; 5.L.236.175; 5.L.236.240; 5.L.236.244; 5.L.237.228; 5.L.237.229; 5.L.237.230; 5.L.237.231; 5.L.237.236; 5.L.237.237; 5.L.237.238; 5.L.237.239; 5.L.237.154; 5.L.237.157; 5.L.237.166; 5.L.237.169; 5.L.237.172; 5.L.237.175; 5.L.237.240; 5.L.237.244; 5.L.238.228; 5.L.238.229; 5.L.238.230; 5.L.238.231; 5.L.238.236; 5.L.238.237; 5.L.238.238; 5.L.238.239; 5.L.238.154; 5.L.238.157; 5.L.238.166; 5.L.238.169; 5.L.238.172; 5.L.238.175; 5.L.238.240; 5.L.238.244; 5.L.239.228; 5.L.239.229; 5.L.239.230; 5.L.239.231; 5.L.239.236; 5.L.239.237; 5.L.239.238; 5.L.239.239; 5.L.239.154; 5.L.239.157; 5.L.239.166; 5.L.239.169; 5.L.239.172; 5.L.239.175; 5.L.239.240; 5.L.239.244; 5.L.154.228; 5.L.154.229; 5.L.154.230; 5.L.154.231; 5.L.154.236; 5.L.154.237; 5.L.154.238; 5.L.154.239; 5.L.154.154; 5.L.154.157; 5.L.154.166; 5.L.154.169; 5.L.154.172; 5.L.154.175; 5.L.154.240; 5.L.154.244; 5.L.157.228; 5.L.157.229; 5.L.157.230; 5.L.157.231; 5.L.157.236; 5.L.157.237; 5.L.157.238; 5.L.157.239; 5.L.157.154; 5.L.157.157; 5.L.157.166; 5.L.157.169; 5.L.157.172; 5.L.157.175; 5.L.157.240; 5.L.157.244; 5.L.166.228; 5.L.166.229; 5.L.166.230; 5.L.166.231; 5.L.166.236; 5.L.166.237; 5.L.166.238; 5.L.166.239; 5.L.166.154; 5.L.166.157; 5.L.166.166; 5.L.166.169; 5.L.166.172; 5.L.166.175; 5.L.166.240; 5.L.166.244; 5.L.169.228; 5.L.169.229; 5.L.169.230; 5.L.169.231; 5.L.169.236; 5.L.169.237; 5.L.169.238; 5.L.169.239; 5.L.169.154; 5.L.169.157; 5.L.169.166; 5.L.169.169; 5.L.169.172; 5.L.169.175; 5.L.169.240; 5.L.169.244; 5.L.172.228; 5.L.172.229; 5.L.172.230; 5.L.172.231; 5.L.172.236; 5.L.172.237; 5.L.172.238; 5.L.172.239; 5.L.172.154; 5.L.172.157; 5.L.172.166; 5.L.172.169; 5.L.172.172; 5.L.172.175; 5.L.172.240; 5.L.172.244; 5.L.175.228; 5.L.175.229; 5.L.175.230; 5.L.175.231; 5.L.175.236; 5.L.175.237; 5.L.175.238; 5.L.175.239; 5.L.175.154; 5.L.175.157; 5.L.175.166; 5.L.175.169; 5.L.175.172; 5.L.175.175; 5.L.175.240; 5.L.175.244; 5.L.240.228; 5.L.240.229; 5.L.240.230; 5.L.240.231; 5.L.240.236; 5.L.240.237; 5.L.240.238; 5.L.240.239; 5.L.240.154; 5.L.240.157; 5.L.240.166; 5.L.240.169; 5.L.240.172; 5.L.240.175; 5.L.240.240; 5.L.240.244; 5.L.244.228; 5.L.244.229; 5.L.244.230; 5.L.244.231; 5.L.244.236; 5.L.244.237; 5.L.244.238; 5.L.244.239; 5.L.244.154; 5.L.244.157; 5.L.244.166; 5.L.244.169; 5.L.244.172; 5.L.244.175; 5.L.244.240; 5.L.244.244;

Prodrugs of 5.O

5.O.228.228; 5.O.228.229; 5.O.228.230; 5.O.228.231; 5.O.228.236; 5.O.228.237; 5.O.228.238; 5.O.228.239; 5.O.228.154; 5.O.228.157; 5.O.228.166; 5.O.228.169; 5.O.228.172; 5.O.228.175; 5.O.228.240; 5.O.228.244; 5.O.229.228; 5.O.229.229; 5.O.229.230; 5.O.229.231; 5.O.229.236; 5.O.229.237; 5.O.229.238; 5.O.229.239; 5.O.229.154; 5.O.229.157; 5.O.229.166; 5.O.229.169; 5.O.229.172; 5.O.229.175; 5.O.229.240; 5.O.229.244; 5.O.230.228; 5.O.230.229; 5.O.230.230; 5.O.230.231; 5.O.230.236; 5.O.230.237; 5.O.230.238; 5.O.230.239; 5.O.230.154; 5.O.230.157; 5.O.230.166; 5.O.230.169; 5.O.230.172; 5.O.230.175; 5.O.230.240; 5.O.230.244; 5.O.231.228; 5.O.231.229; 5.O.231.230; 5.O.231.231; 5.O.231.236; 5.O.231.237; 5.O.231.238; 5.O.231.239; 5.O.231.154; 5.O.231.157; 5.O.231.166; 5.O.231.169; 5.O.231.172; 5.O.231.175; 5.O.231.240; 5.O.231.244; 5.O.236.228; 5.O.236.229; 5.O.236.230; 5.O.236.231; 5.O.236.236; 5.O.236.237; 5.O.236.238; 5.O.236.239; 5.O.236.154; 5.O.236.157; 5.O.236.166; 5.O.236.169; 5.O.236.172; 5.O.236.175; 5.O.236.240; 5.O.236.244; 5.O.237.228; 5.O.237.229; 5.O.237.230; 5.O.237.231; 5.O.237.236; 5.O.237.237; 5.O.237.238; 5.O.237.239; 5.O.237.154; 5.O.237.157; 5.O.237.166; 5.O.237.169; 5.O.237.172; 5.O.237.175; 5.O.237.240;

TABLE 100-continued

5.O.237.244; 5.O.238.228; 5.O.238.229; 5.O.238.230; 5.O.238.231;
5.O.238.236; 5.O.238.237; 5.O.238.238; 5.O.238.239; 5.O.238.154;
5.O.238.157; 5.O.238.166; 5.O.238.169; 5.O.238.172; 5.O.238.175;
5.O.238.240; 5.O.238.244; 5.O.239.228; 5.O.239.229; 5.O.239.230;
5.O.239.231; 5.O.239.236; 5.O.239.237; 5.O.239.238; 5.O.239.239;
5.O.239.154; 5.O.239.157; 5.O.239.166; 5.O.239.169; 5.O.239.172;
5.O.239.175; 5.O.239.240; 5.O.239.244; 5.O.154.228; 5.O.154.229;
5.O.154.230; 5.O.154.231; 5.O.154.236; 5.O.154.237; 5.O.154.238;
5.O.154.239; 5.O.154.154; 5.O.154.157; 5.O.154.166; 5.O.154.169;
5.O.154.172; 5.O.154.175; 5.O.154.240; 5.O.154.244; 5.O.157.228;
5.O.157.229; 5.O.157.230; 5.O.157.231; 5.O.157.236; 5.O.157.237;
5.O.157.238; 5.O.157.239; 5.O.157.154; 5.O.157.157; 5.O.157.166;
5.O.157.169; 5.O.157.172; 5.O.157.175; 5.O.157.240; 5.O.157.244;
5.O.166.228; 5.O.166.229; 5.O.166.230; 5.O.166.231; 5.O.166.236;
5.O.166.237; 5.O.166.238; 5.O.166.239; 5.O.166.154; 5.O.166.157;
5.O.166.166; 5.O.166.169; 5.O.166.172; 5.O.166.175; 5.O.166.240;
5.O.166.244; 5.O.169.228; 5.O.169.229; 5.O.169.230; 5.O.169.231;
5.O.169.236; 5.O.169.237; 5.O.169.238; 5.O.169.239; 5.O.169.154;
5.O.169.157; 5.O.169.166; 5.O.169.169; 5.O.169.172; 5.O.169.175;
5.O.169.240; 5.O.169.244; 5.O.172.228; 5.O.172.229; 5.O.172.230;
5.O.172.231; 5.O.172.236; 5.O.172.237; 5.O.172.238; 5.O.172.239;
5.O.172.154; 5.O.172.157; 5.O.172.166; 5.O.172.169; 5.O.172.172;
5.O.172.175; 5.O.172.240; 5.O.172.244; 5.O.175.228; 5.O.175.229;
5.O.175.230; 5.O.175.231; 5.O.175.236; 5.O.175.237; 5.O.175.238;
5.O.175.239; 5.O.175.154; 5.O.175.157; 5.O.175.166; 5.O.175.169;
5.O.175.172; 5.O.175.175; 5.O.175.240; 5.O.175.244; 5.O.240.228;
5.O.240.229; 5.O.240.230; 5.O.240.231; 5.O.240.236; 5.O.240.237;
5.O.240.238; 5.O.240.239; 5.O.240.154; 5.O.240.157; 5.O.240.166;
5.O.240.169; 5.O.240.172; 5.O.240.175; 5.O.240.240; 5.O.240.244;
5.O.244.228; 5.O.244.229; 5.O.244.230; 5.O.244.231; 5.O.244.236;
5.O.244.237; 5.O.244.238; 5.O.244.239; 5.O.244.154; 5.O.244.157;
5.O.244.166; 5.O.244.169; 5.O.244.172; 5.O.244.175; 5.O.244.240;
5.O.244.244;

Prodrugs of 5.P

5.P.228.228; 5.P.228.229; 5.P.228.230; 5.P.228.231; 5.P.228.236;
5.P.228.237; 5.P.228.238; 5.P.228.239; 5.P.228.154; 5.P.228.157; 5.P.228.166;
5.P.228.169; 5.P.228.172; 5.P.228.175; 5.P.228.240; 5.P.228.244; 5.P.229.228;
5.P.229.229; 5.P.229.230; 5.P.229.231; 5.P.229.236; 5.P.229.237; 5.P.229.238;
5.P.229.239; 5.P.229.154; 5.P.229.157; 5.P.229.166; 5.P.229.169; 5.P.229.172;
5.P.229.175; 5.P.229.240; 5.P.229.244; 5.P.230.228; 5.P.230.229; 5.P.230.230;
5.P.230.231; 5.P.230.236; 5.P.230.237; 5.P.230.238; 5.P.230.239; 5.P.230.154;
5.P.230.157; 5.P.230.166; 5.P.230.169; 5.P.230.172; 5.P.230.175; 5.P.230.240;
5.P.230.244; 5.P.231.228; 5.P.231.229; 5.P.231.230; 5.P.231.231; 5.P.231.236;
5.P.231.237; 5.P.231.238; 5.P.231.239; 5.P.231.154; 5.P.231.157; 5.P.231.166;
5.P.231.169; 5.P.231.172; 5.P.231.175; 5.P.231.240; 5.P.231.244; 5.P.236.228;
5.P.236.229; 5.P.236.230; 5.P.236.231; 5.P.236.236; 5.P.236.237; 5.P.236.238;
5.P.236.239; 5.P.236.154; 5.P.236.157; 5.P.236.166; 5.P.236.169; 5.P.236.172;
5.P.236.175; 5.P.236.240; 5.P.236.244; 5.P.237.228; 5.P.237.229; 5.P.237.230;
5.P.237.231; 5.P.237.236; 5.P.237.237; 5.P.237.238; 5.P.237.239; 5.P.237.154;
5.P.237.157; 5.P.237.166; 5.P.237.169; 5.P.237.172; 5.P.237.175; 5.P.237.240;
5.P.237.244; 5.P.238.228; 5.P.238.229; 5.P.238.230; 5.P.238.231; 5.P.238.236;
5.P.238.237; 5.P.238.238; 5.P.238.239; 5.P.238.154; 5.P.238.157; 5.P.238.166;
5.P.238.169; 5.P.238.172; 5.P.238.175; 5.P.238.240; 5.P.238.244; 5.P.239.228;
5.P.239.229; 5.P.239.230; 5.P.239.231; 5.P.239.236; 5.P.239.237; 5.P.239.238;
5.P.239.239; 5.P.239.154; 5.P.239.157; 5.P.239.166; 5.P.239.169; 5.P.239.172;
5.P.239.175; 5.P.239.240; 5.P.239.244; 5.P.154.228; 5.P.154.229; 5.P.154.230;
5.P.154.231; 5.P.154.236; 5.P.154.237; 5.P.154.238; 5.P.154.239; 5.P.154.154;
5.P.154.157; 5.P.154.166; 5.P.154.169; 5.P.154.172; 5.P.154.175; 5.P.154.240;
5.P.154.244; 5.P.157.228; 5.P.157.229; 5.P.157.230; 5.P.157.231; 5.P.157.236;
5.P.157.237; 5.P.157.238; 5.P.157.239; 5.P.157.154; 5.P.157.157; 5.P.157.166;
5.P.157.169; 5.P.157.172; 5.P.157.175; 5.P.157.240; 5.P.157.244; 5.P.166.228;
5.P.166.229; 5.P.166.230; 5.P.166.231; 5.P.166.236; 5.P.166.237; 5.P.166.238;
5.P.166.239; 5.P.166.154; 5.P.166.157; 5.P.166.166; 5.P.166.169; 5.P.166.172;
5.P.166.175; 5.P.166.240; 5.P.166.244; 5.P.169.228; 5.P.169.229; 5.P.169.230;
5.P.169.231; 5.P.169.236; 5.P.169.237; 5.P.169.238; 5.P.169.239; 5.P.169.154;
5.P.169.157; 5.P.169.166; 5.P.169.169; 5.P.169.172; 5.P.169.175; 5.P.169.240;
5.P.169.244; 5.P.172.228; 5.P.172.229; 5.P.172.230; 5.P.172.231; 5.P.172.236;
5.P.172.237; 5.P.172.238; 5.P.172.239; 5.P.172.154; 5.P.172.157; 5.P.172.166;
5.P.172.169; 5.P.172.172; 5.P.172.175; 5.P.172.240; 5.P.172.244; 5.P.175.228;
5.P.175.229; 5.P.175.230; 5.P.175.231; 5.P.175.236; 5.P.175.237; 5.P.175.238;
5.P.175.239; 5.P.175.154; 5.P.175.157; 5.P.175.166; 5.P.175.169; 5.P.175.172;
5.P.175.175; 5.P.175.240; 5.P.175.244; 5.P.240.228; 5.P.240.229; 5.P.240.230;
5.P.240.231; 5.P.240.236; 5.P.240.237; 5.P.240.238; 5.P.240.239; 5.P.240.154;
5.P.240.157; 5.P.240.166; 5.P.240.169; 5.P.240.172; 5.P.240.175; 5.P.240.240;
5.P.240.244; 5.P.244.228; 5.P.244.229; 5.P.244.230; 5.P.244.231; 5.P.244.236;
5.P.244.237; 5.P.244.238; 5.P.244.239; 5.P.244.154; 5.P.244.157; 5.P.244.166;
5.P.244.169; 5.P.244.172; 5.P.244.175; 5.P.244.240; 5.P.244.244;

TABLE 100-continued

Prodrugs of 5.U

5.U.228.228; 5.U.228.229; 5.U.228.230; 5.U.228.231; 5.U.228.236; 5.U.228.237; 5.U.228.238; 5.U.228.239; 5.U.228.154; 5.U.228.157; 5.U.228.166; 5.U.228.169; 5.U.228.172; 5.U.228.175; 5.U.228.240; 5.U.228.244; 5.U.229.228; 5.U.229.229; 5.U.229.230; 5.U.229.231; 5.U.229.236; 5.U.229.237; 5.U.229.238; 5.U.229.239; 5.U.229.154; 5.U.229.157; 5.U.229.166; 5.U.229.169; 5.U.229.172; 5.U.229.175; 5.U.229.240; 5.U.229.244; 5.U.230.228; 5.U.230.229; 5.U.230.230; 5.U.230.231; 5.U.230.236; 5.U.230.237; 5.U.230.238; 5.U.230.239; 5.U.230.154; 5.U.230.157; 5.U.230.166; 5.U.230.169; 5.U.230.172; 5.U.230.175; 5.U.230.240; 5.U.230.244; 5.U.231.228; 5.U.231.229; 5.U.231.230; 5.U.231.231; 5.U.231.236; 5.U.231.237; 5.U.231.238; 5.U.231.239; 5.U.231.154; 5.U.231.157; 5.U.231.166; 5.U.231.169; 5.U.231.172; 5.U.231.175; 5.U.231.240; 5.U.231.244; 5.U.236.228; 5.U.236.229; 5.U.236.230; 5.U.236.231; 5.U.236.236; 5.U.236.237; 5.U.236.238; 5.U.236.239; 5.U.236.154; 5.U.236.157; 5.U.236.166; 5.U.236.169; 5.U.236.172; 5.U.236.175; 5.U.236.240; 5.U.236.244; 5.U.237.228; 5.U.237.229; 5.U.237.230; 5.U.237.231; 5.U.237.236; 5.U.237.237; 5.U.237.238; 5.U.237.239; 5.U.237.154; 5.U.237.157; 5.U.237.166; 5.U.237.169; 5.U.237.172; 5.U.237.175; 5.U.237.240; 5.U.237.244; 5.U.238.228; 5.U.238.229; 5.U.238.230; 5.U.238.231; 5.U.238.236; 5.U.238.237; 5.U.238.238; 5.U.238.239; 5.U.238.154; 5.U.238.157; 5.U.238.166; 5.U.238.169; 5.U.238.172; 5.U.238.175; 5.U.238.240; 5.U.238.244; 5.U.239.228; 5.U.239.229; 5.U.239.230; 5.U.239.231; 5.U.239.236; 5.U.239.237; 5.U.239.238; 5.U.239.239; 5.U.239.154; 5.U.239.157; 5.U.239.166; 5.U.239.169; 5.U.239.172; 5.U.239.175; 5.U.239.240; 5.U.239.244; 5.U.154.228; 5.U.154.229; 5.U.154.230; 5.U.154.231; 5.U.154.236; 5.U.154.237; 5.U.154.238; 5.U.154.239; 5.U.154.154; 5.U.154.157; 5.U.154.166; 5.U.154.169; 5.U.154.172; 5.U.154.175; 5.U.154.240; 5.U.154.244; 5.U.157.228; 5.U.157.229; 5.U.157.230; 5.U.157.231; 5.U.157.236; 5.U.157.237; 5.U.157.238; 5.U.157.239; 5.U.157.154; 5.U.157.157; 5.U.157.166; 5.U.157.169; 5.U.157.172; 5.U.157.175; 5.U.157.240; 5.U.157.244; 5.U.166.228; 5.U.166.229; 5.U.166.230; 5.U.166.231; 5.U.166.236; 5.U.166.237; 5.U.166.238; 5.U.166.239; 5.U.166.154; 5.U.166.157; 5.U.166.166; 5.U.166.169; 5.U.166.172; 5.U.166.175; 5.U.166.240; 5.U.166.244; 5.U.169.228; 5.U.169.229; 5.U.169.230; 5.U.169.231; 5.U.169.236; 5.U.169.237; 5.U.169.238; 5.U.169.239; 5.U.169.154; 5.U.169.157; 5.U.169.166; 5.U.169.169; 5.U.169.172; 5.U.169.175; 5.U.169.240; 5.U.169.244; 5.U.172.228; 5.U.172.229; 5.U.172.230; 5.U.172.231; 5.U.172.236; 5.U.172.237; 5.U.172.238; 5.U.172.239; 5.U.172.154; 5.U.172.157; 5.U.172.166; 5.U.172.169; 5.U.172.172; 5.U.172.175; 5.U.172.240; 5.U.172.244; 5.U.175.228; 5.U.175.229; 5.U.175.230; 5.U.175.231; 5.U.175.236; 5.U.175.237; 5.U.175.238; 5.U.175.239; 5.U.175.154; 5.U.175.157; 5.U.175.166; 5.U.175.169; 5.U.175.172; 5.U.175.175; 5.U.175.240; 5.U.175.244; 5.U.240.228; 5.U.240.229; 5.U.240.230; 5.U.240.231; 5.U.240.236; 5.U.240.237; 5.U.240.238; 5.U.240.239; 5.U.240.154; 5.U.240.157; 5.U.240.166; 5.U.240.169; 5.U.240.172; 5.U.240.175; 5.U.240.240; 5.U.240.244; 5.U.244.228; 5.U.244.229; 5.U.244.230; 5.U.244.231; 5.U.244.236; 5.U.244.237; 5.U.244.238; 5.U.244.239; 5.U.244.154; 5.U.244.157; 5.U.244.166; 5.U.244.169; 5.U.244.172; 5.U.244.175; 5.U.244.240; 5.U.244.244;

Prodrugs of 5.W

5.W.228.228; 5.W.228.229; 5.W.228.230; 5.W.228.231; 5.W.228.236; 5.W.228.237; 5.W.228.238; 5.W.228.239; 5.W.228.154; 5.W.228.157; 5.W.228.166; 5.W.228.169; 5.W.228.172; 5.W.228.175; 5.W.228.240; 5.W.228.244; 5.W.229.228; 5.W.229.229; 5.W.229.230; 5.W.229.231; 5.W.229.236; 5.W.229.237; 5.W.229.238; 5.W.229.239; 5.W.229.154; 5.W.229.157; 5.W.229.166; 5.W.229.169; 5.W.229.172; 5.W.229.175; 5.W.229.240; 5.W.229.244; 5.W.230.228; 5.W.230.229; 5.W.230.230; 5.W.230.231; 5.W.230.236; 5.W.230.237; 5.W.230.238; 5.W.230.239; 5.W.230.154; 5.W.230.157; 5.W.230.166; 5.W.230.169; 5.W.230.172; 5.W.230.175; 5.W.230.240; 5.W.230.244; 5.W.231.228; 5.W.231.229; 5.W.231.230; 5.W.231.231; 5.W.231.236; 5.W.231.237; 5.W.231.238; 5.W.231.239; 5.W.231.154; 5.W.231.157; 5.W.231.166; 5.W.231.169; 5.W.231.172; 5.W.231.175; 5.W.231.240; 5.W.231.244; 5.W.236.228; 5.W.236.229; 5.W.236.230; 5.W.236.231; 5.W.236.236; 5.W.236.237; 5.W.236.238; 5.W.236.239; 5.W.236.154; 5.W.236.157; 5.W.236.166; 5.W.236.169; 5.W.236.172; 5.W.236.175; 5.W.236.240; 5.W.236.244; 5.W.237.228; 5.W.237.229; 5.W.237.230; 5.W.237.231; 5.W.237.236; 5.W.237.237; 5.W.237.238; 5.W.237.239; 5.W.237.154; 5.W.237.157; 5.W.237.166; 5.W.237.169; 5.W.237.172; 5.W.237.175; 5.W.237.240; 5.W.237.244; 5.W.238.228; 5.W.238.229; 5.W.238.230; 5.W.238.231; 5.W.238.236; 5.W.238.237; 5.W.238.238; 5.W.238.239; 5.W.238.154; 5.W.238.157; 5.W.238.166; 5.W.238.169; 5.W.238.172; 5.W.238.175; 5.W.238.240; 5.W.238.244; 5.W.239.228; 5.W.239.229; 5.W.239.230;

TABLE 100-continued

5.W.239.231; 5.W.239.236; 5.W.239.237; 5.W.239.238; 5.W.239.239; 5.W.239.154; 5.W.239.157; 5.W.239.166; 5.W.239.169; 5.W.239.172; 5.W.239.175; 5.W.239.240; 5.W.239.244; 5.W.154.228; 5.W.154.229; 5.W.154.230; 5.W.154.231; 5.W.154.236; 5.W.154.237; 5.W.154.238; 5.W.154.239; 5.W.154.154; 5.W.154.157; 5.W.154.166; 5.W.154.169; 5.W.154.172; 5.W.154.175; 5.W.154.240; 5.W.154.244; 5.W.157.228; 5.W.157.229; 5.W.157.230; 5.W.157.231; 5.W.157.236; 5.W.157.237; 5.W.157.238; 5.W.157.239; 5.W.157.154; 5.W.157.157; 5.W.157.166; 5.W.157.169; 5.W.157.172; 5.W.157.175; 5.W.157.240; 5.W.157.244; 5.W.166.228; 5.W.166.229; 5.W.166.230; 5.W.166.231; 5.W.166.236; 5.W.166.237; 5.W.166.238; 5.W.166.239; 5.W.166.154; 5.W.166.157; 5.W.166.166; 5.W.166.169; 5.W.166.172; 5.W.166.175; 5.W.166.240; 5.W.166.244; 5.W.169.228; 5.W.169.229; 5.W.169.230; 5.W.169.231; 5.W.169.236; 5.W.169.237; 5.W.169.238; 5.W.169.239; 5.W.169.154; 5.W.169.157; 5.W.169.166; 5.W.169.169; 5.W.169.172; 5.W.169.175; 5.W.169.240; 5.W.169.244; 5.W.172.228; 5.W.172.229; 5.W.172.230; 5.W.172.231; 5.W.172.236; 5.W.172.237; 5.W.172.238; 5.W.172.239; 5.W.172.154; 5.W.172.157; 5.W.172.166; 5.W.172.169; 5.W.172.172; 5.W.172.175; 5.W.172.240; 5.W.172.244; 5.W.175.228; 5.W.175.229; 5.W.175.230; 5.W.175.231; 5.W.175.236; 5.W.175.237; 5.W.175.238; 5.W.175.239; 5.W.175.154; 5.W.175.157; 5.W.175.166; 5.W.175.169; 5.W.175.172; 5.W.175.175; 5.W.175.240; 5.W.175.244; 5.W.240.228; 5.W.240.229; 5.W.240.230; 5.W.240.231; 5.W.240.236; 5.W.240.237; 5.W.240.238; 5.W.240.239; 5.W.240.154; 5.W.240.157; 5.W.240.166; 5.W.240.169; 5.W.240.172; 5.W.240.175; 5.W.240.240; 5.W.240.244; 5.W.244.228; 5.W.244.229; 5.W.244.230; 5.W.244.231; 5.W.244.236; 5.W.244.237; 5.W.244.238; 5.W.244.239; 5.W.244.154; 5.W.244.157; 5.W.244.166; 5.W.244.169; 5.W.244.172; 5.W.244.175; 5.W.244.240; 5.W.244.244;

Prodrugs of 5.Y

5.Y.228.228; 5.Y.228.229; 5.Y.228.230; 5.Y.228.231; 5.Y.228.236; 5.Y.228.237; 5.Y.228.238; 5.Y.228.239; 5.Y.228.154; 5.Y.228.157; 5.Y.228.166; 5.Y.228.169; 5.Y.228.172; 5.Y.228.175; 5.Y.228.240; 5.Y.228.244; 5.Y.229.228; 5.Y.229.229; 5.Y.229.230; 5.Y.229.231; 5.Y.229.236; 5.Y.229.237; 5.Y.229.238; 5.Y.229.239; 5.Y.229.154; 5.Y.229.157; 5.Y.229.166; 5.Y.229.169; 5.Y.229.172; 5.Y.229.175; 5.Y.229.240; 5.Y.229.244; 5.Y.230.228; 5.Y.230.229; 5.Y.230.230; 5.Y.230.231; 5.Y.230.236; 5.Y.230.237; 5.Y.230.238; 5.Y.230.239; 5.Y.230.154; 5.Y.230.157; 5.Y.230.166; 5.Y.230.169; 5.Y.230.172; 5.Y.230.175; 5.Y.230.240; 5.Y.230.244; 5.Y.231.228; 5.Y.231.229; 5.Y.231.230; 5.Y.231.231; 5.Y.231.236; 5.Y.231.237; 5.Y.231.238; 5.Y.231.239; 5.Y.231.154; 5.Y.231.157; 5.Y.231.166; 5.Y.231.169; 5.Y.231.172; 5.Y.231.175; 5.Y.231.240; 5.Y.231.244; 5.Y.236.228; 5.Y.236.229; 5.Y.236.230; 5.Y.236.231; 5.Y.236.236; 5.Y.236.237; 5.Y.236.238; 5.Y.236.239; 5.Y.236.154; 5.Y.236.157; 5.Y.236.166; 5.Y.236.169; 5.Y.236.172; 5.Y.236.175; 5.Y.236.240; 5.Y.236.244; 5.Y.237.228; 5.Y.237.229; 5.Y.237.230; 5.Y.237.231; 5.Y.237.236; 5.Y.237.237; 5.Y.237.238; 5.Y.237.239; 5.Y.237.154; 5.Y.237.157; 5.Y.237.166; 5.Y.237.169; 5.Y.237.172; 5.Y.237.175; 5.Y.237.240; 5.Y.237.244; 5.Y.238.228; 5.Y.238.229; 5.Y.238.230; 5.Y.238.231; 5.Y.238.236; 5.Y.238.237; 5.Y.238.238; 5.Y.238.239; 5.Y.238.154; 5.Y.238.157; 5.Y.238.166; 5.Y.238.169; 5.Y.238.172; 5.Y.238.175; 5.Y.238.240; 5.Y.238.244; 5.Y.239.228; 5.Y.239.229; 5.Y.239.230; 5.Y.239.231; 5.Y.239.236; 5.Y.239.237; 5.Y.239.238; 5.Y.239.239; 5.Y.239.154; 5.Y.239.157; 5.Y.239.166; 5.Y.239.169; 5.Y.239.172; 5.Y.239.175; 5.Y.239.240; 5.Y.239.244; 5.Y.154.228; 5.Y.154.229; 5.Y.154.230; 5.Y.154.231; 5.Y.154.236; 5.Y.154.237; 5.Y.154.238; 5.Y.154.239; 5.Y.154.154; 5.Y.154.157; 5.Y.154.166; 5.Y.154.169; 5.Y.154.172; 5.Y.154.175; 5.Y.154.240; 5.Y.154.244; 5.Y.157.228; 5.Y.157.229; 5.Y.157.230; 5.Y.157.231; 5.Y.157.236; 5.Y.157.237; 5.Y.157.238; 5.Y.157.239; 5.Y.157.154; 5.Y.157.157; 5.Y.157.166; 5.Y.157.169; 5.Y.157.172; 5.Y.157.175; 5.Y.157.240; 5.Y.157.244; 5.Y.166.228; 5.Y.166.229; 5.Y.166.230; 5.Y.166.231; 5.Y.166.236; 5.Y.166.237; 5.Y.166.238; 5.Y.166.239; 5.Y.166.154; 5.Y.166.157; 5.Y.166.166; 5.Y.166.169; 5.Y.166.172; 5.Y.166.175; 5.Y.166.240; 5.Y.166.244; 5.Y.169.228; 5.Y.169.229; 5.Y.169.230; 5.Y.169.231; 5.Y.169.236; 5.Y.169.237; 5.Y.169.238; 5.Y.169.239; 5.Y.169.154; 5.Y.169.157; 5.Y.169.166; 5.Y.169.169; 5.Y.169.172; 5.Y.169.175; 5.Y.169.240; 5.Y.169.244; 5.Y.172.228; 5.Y.172.229; 5.Y.172.230; 5.Y.172.231; 5.Y.172.236; 5.Y.172.237; 5.Y.172.238; 5.Y.172.239; 5.Y.172.154; 5.Y.172.157; 5.Y.172.166; 5.Y.172.169; 5.Y.172.172; 5.Y.172.175; 5.Y.172.240; 5.Y.172.244; 5.Y.175.228; 5.Y.175.229; 5.Y.175.230; 5.Y.175.231; 5.Y.175.236; 5.Y.175.237; 5.Y.175.238; 5.Y.175.239; 5.Y.175.154; 5.Y.175.157; 5.Y.175.166; 5.Y.175.169; 5.Y.175.172; 5.Y.175.175; 5.Y.175.240; 5.Y.175.244; 5.Y.240.228; 5.Y.240.229; 5.Y.240.230; 5.Y.240.231; 5.Y.240.236; 5.Y.240.237; 5.Y.240.238; 5.Y.240.239; 5.Y.240.154; 5.Y.240.157; 5.Y.240.166; 5.Y.240.169; 5.Y.240.172; 5.Y.240.175; 5.Y.240.240; 5.Y.240.244; 5.Y.244.228; 5.Y.244.229; 5.Y.244.230; 5.Y.244.231; 5.Y.244.236; 5.Y.244.237; 5.Y.244.238; 5.Y.244.239; 5.Y.244.154; 5.Y.244.157; 5.Y.244.166; 5.Y.244.169; 5.Y.244.172; 5.Y.244.175; 5.Y.244.240; 5.Y.244.244;

Prodrugs of 6.B

6.B.228.228; 6.B.228.229; 6.B.228.230; 6.B.228.231; 6.B.228.236; 6.B.228.237; 6.B.228.238; 6.B.228.239; 6.B.228.154; 6.B.228.157; 6.B.228.166; 6.B.228.169; 6.B.228.172; 6.B.228.175; 6.B.228.240; 6.B.228.244; 6.B.229.228;

TABLE 100-continued

6.B.229.229; 6.B.229.230; 6.B.229.231; 6.B.229.236; 6.B.229.237; 6.B.229.238;
6.B.229.239; 6.B.229.154; 6.B.229.157; 6.B.229.166; 6.B.229.169; 6.B.229.172;
6.B.229.175; 6.B.229.240; 6.B.229.244; 6.B.230.228; 6.B.230.229; 6.B.230.230;
6.B.230.231; 6.B.230.236; 6.B.230.237; 6.B.230.238; 6.B.230.239; 6.B.230.154;
6.B.230.157; 6.B.230.166; 6.B.230.169; 6.B.230.172; 6.B.230.175; 6.B.230.240;
6.B.230.244; 6.B.231.228; 6.B.231.229; 6.B.231.230; 6.B.231.231; 6.B.231.236;
6.B.231.237; 6.B.231.238; 6.B.231.239; 6.B.231.154; 6.B.231.157; 6.B.231.166;
6.B.231.169; 6.B.231.172; 6.B.231.175; 6.B.231.240; 6.B.231.244; 6.B.236.228;
6.B.236.229; 6.B.236.230; 6.B.236.231; 6.B.236.236; 6.B.236.237; 6.B.236.238;
6.B.236.239; 6.B.236.154; 6.B.236.157; 6.B.236.166; 6.B.236.169; 6.B.236.172;
6.B.236.175; 6.B.236.240; 6.B.236.244; 6.B.237.228; 6.B.237.229; 6.B.237.230;
6.B.237.231; 6.B.237.236; 6.B.237.237; 6.B.237.238; 6.B.237.239; 6.B.237.154;
6.B.237.157; 6.B.237.166; 6.B.237.169; 6.B.237.172; 6.B.237.175; 6.B.237.240;
6.B.237.244; 6.B.238.228; 6.B.238.229; 6.B.238.230; 6.B.238.231; 6.B.238.236;
6.B.238.237; 6.B.238.238; 6.B.238.239; 6.B.238.154; 6.B.238.157; 6.B.238.166;
6.B.238.169; 6.B.238.172; 6.B.238.175; 6.B.238.240; 6.B.238.244; 6.B.239.228;
6.B.239.229; 6.B.239.230; 6.B.239.231; 6.B.239.236; 6.B.239.237; 6.B.239.238;
6.B.239.239; 6.B.239.154; 6.B.239.157; 6.B.239.166; 6.B.239.169; 6.B.239.172;
6.B.239.175; 6.B.239.240; 6.B.239.244; 6.B.154.228; 6.B.154.229; 6.B.154.230;
6.B.154.231; 6.B.154.236; 6.B.154.237; 6.B.154.238; 6.B.154.239; 6.B.154.154;
6.B.154.157; 6.B.154.166; 6.B.154.169; 6.B.154.172; 6.B.154.175; 6.B.154.240;
6.B.154.244; 6.B.157.228; 6.B.157.229; 6.B.157.230; 6.B.157.231; 6.B.157.236;
6.B.157.237; 6.B.157.238; 6.B.157.239; 6.B.157.154; 6.B.157.157; 6.B.157.166;
6.B.157.169; 6.B.157.172; 6.B.157.175; 6.B.157.240; 6.B.157.244; 6.B.166.228;
6.B.166.229; 6.B.166.230; 6.B.166.231; 6.B.166.236; 6.B.166.237; 6.B.166.238;
6.B.166.239; 6.B.166.154; 6.B.166.157; 6.B.166.166; 6.B.166.169; 6.B.166.172;
6.B.166.175; 6.B.166.240; 6.B.166.244; 6.B.169.228; 6.B.169.229; 6.B.169.230;
6.B.169.231; 6.B.169.236; 6.B.169.237; 6.B.169.238; 6.B.169.239; 6.B.169.154;
6.B.169.157; 6.B.169.166; 6.B.169.169; 6.B.169.172; 6.B.169.175; 6.B.169.240;
6.B.169.244; 6.B.172.228; 6.B.172.229; 6.B.172.230; 6.B.172.231; 6.B.172.236;
6.B.172.237; 6.B.172.238; 6.B.172.239; 6.B.172.154; 6.B.172.157; 6.B.172.166;
6.B.172.169; 6.B.172.172; 6.B.172.175; 6.B.172.240; 6.B.172.244; 6.B.175.228;
6.B.175.229; 6.B.175.230; 6.B.175.231; 6.B.175.236; 6.B.175.237; 6.B.175.238;
6.B.175.239; 6.B.175.154; 6.B.175.157; 6.B.175.166; 6.B.175.169; 6.B.175.172;
6.B.175.175; 6.B.175.240; 6.B.175.244; 6.B.240.228; 6.B.240.229; 6.B.240.230;
6.B.240.231; 6.B.240.236; 6.B.240.237; 6.B.240.238; 6.B.240.239; 6.B.240.154;
6.B.240.157; 6.B.240.166; 6.B.240.169; 6.B.240.172; 6.B.240.175; 6.B.240.240;
6.B.240.244; 6.B.244.228; 6.B.244.229; 6.B.244.230; 6.B.244.231; 6.B.244.236;
6.B.244.237; 6.B.244.238; 6.B.244.239; 6.B.244.154; 6.B.244.157; 6.B.244.166;
6.B.244.169; 6.B.244.172; 6.B.244.175; 6.B.244.240; 6.B.244.244;

Prodrugs of 6.D

6.D.228.228; 6.D.228.229; 6.D.228.230; 6.D.228.231; 6.D.228.236;
6.D.228.237; 6.D.228.238; 6.D.228.239; 6.D.228.154; 6.D.228.157;
6.D.228.166; 6.D.228.169; 6.D.228.172; 6.D.228.175; 6.D.228.240;
6.D.228.244; 6.D.229.228; 6.D.229.229; 6.D.229.230; 6.D.229.231;
6.D.229.236; 6.D.229.237; 6.D.229.238; 6.D.229.239; 6.D.229.154;
6.D.229.157; 6.D.229.166; 6.D.229.169; 6.D.229.172; 6.D.229.175;
6.D.229.240; 6.D.229.244; 6.D.230.228; 6.D.230.229; 6.D.230.230;
6.D.230.231; 6.D.230.236; 6.D.230.237; 6.D.230.238; 6.D.230.239;
6.D.230.154; 6.D.230.157; 6.D.230.166; 6.D.230.169; 6.D.230.172;
6.D.230.175; 6.D.230.240; 6.D.230.244; 6.D.231.228; 6.D.231.229;
6.D.231.230; 6.D.231.231; 6.D.231.236; 6.D.231.237; 6.D.231.238;
6.D.231.239; 6.D.231.154; 6.D.231.157; 6.D.231.166; 6.D.231.169;
6.D.231.172; 6.D.231.175; 6.D.231.240; 6.D.231.244; 6.D.236.228;
6.D.236.229; 6.D.236.230; 6.D.236.231; 6.D.236.236; 6.D.236.237;
6.D.236.238; 6.D.236.239; 6.D.236.154; 6.D.236.157; 6.D.236.166;
6.D.236.169; 6.D.236.172; 6.D.236.175; 6.D.236.240; 6.D.236.244;
6.D.237.228; 6.D.237.229; 6.D.237.230; 6.D.237.231; 6.D.237.236;
6.D.237.237; 6.D.237.238; 6.D.237.239; 6.D.237.154; 6.D.237.157;
6.D.237.166; 6.D.237.169; 6.D.237.172; 6.D.237.175; 6.D.237.240;
6.D.237.244; 6.D.238.228; 6.D.238.229; 6.D.238.230; 6.D.238.231;
6.D.238.236; 6.D.238.237; 6.D.238.238; 6.D.238.239; 6.D.238.154;
6.D.238.157; 6.D.238.166; 6.D.238.169; 6.D.238.172; 6.D.238.175;
6.D.238.240; 6.D.238.244; 6.D.239.228; 6.D.239.229; 6.D.239.230;
6.D.239.231; 6.D.239.236; 6.D.239.237; 6.D.239.238; 6.D.239.239;
6.D.239.154; 6.D.239.157; 6.D.239.166; 6.D.239.169; 6.D.239.172;
6.D.239.175; 6.D.239.240; 6.D.239.244; 6.D.154.228; 6.D.154.229;
6.D.154.230; 6.D.154.231; 6.D.154.236; 6.D.154.237; 6.D.154.238;
6.D.154.239; 6.D.154.154; 6.D.154.157; 6.D.154.166; 6.D.154.169;
6.D.154.172; 6.D.154.175; 6.D.154.240; 6.D.154.244; 6.D.157.228;
6.D.157.229; 6.D.157.230; 6.D.157.231; 6.D.157.236; 6.D.157.237;
6.D.157.238; 6.D.157.239; 6.D.157.154; 6.D.157.157; 6.D.157.166;
6.D.157.169; 6.D.157.172; 6.D.157.175; 6.D.157.240; 6.D.157.244;
6.D.166.228; 6.D.166.229; 6.D.166.230; 6.D.166.231; 6.D.166.236;
6.D.166.237; 6.D.166.238; 6.D.166.239; 6.D.166.154; 6.D.166.157;
6.D.166.166; 6.D.166.169; 6.D.166.172; 6.D.166.175; 6.D.166.240;
6.D.166.244; 6.D.169.228; 6.D.169.229; 6.D.169.230; 6.D.169.231;
6.D.169.236; 6.D.169.237; 6.D.169.238; 6.D.169.239; 6.D.169.154;

TABLE 100-continued

6.D.169.157; 6.D.169.166; 6.D.169.169; 6.D.169.172; 6.D.169.175; 6.D.169.240; 6.D.169.244; 6.D.172.228; 6.D.172.229; 6.D.172.230; 6.D.172.231; 6.D.172.236; 6.D.172.237; 6.D.172.238; 6.D.172.239; 6.D.172.154; 6.D.172.157; 6.D.172.166; 6.D.172.169; 6.D.172.172; 6.D.172.175; 6.D.172.240; 6.D.172.244; 6.D.175.228; 6.D.175.229; 6.D.175.230; 6.D.175.231; 6.D.175.236; 6.D.175.237; 6.D.175.238; 6.D.175.239; 6.D.175.154; 6.D.175.157; 6.D.175.166; 6.D.175.169; 6.D.175.172; 6.D.175.175; 6.D.175.240; 6.D.175.244; 6.D.240.228; 6.D.240.229; 6.D.240.230; 6.D.240.231; 6.D.240.236; 6.D.240.237; 6.D.240.238; 6.D.240.239; 6.D.240.154; 6.D.240.157; 6.D.240.166; 6.D.240.169; 6.D.240.172; 6.D.240.175; 6.D.240.240; 6.D.240.244; 6.D.244.228; 6.D.244.229; 6.D.244.230; 6.D.244.231; 6.D.244.236; 6.D.244.237; 6.D.244.238; 6.D.244.239; 6.D.244.154; 6.D.244.157; 6.D.244.166; 6.D.244.169; 6.D.244.172; 6.D.244.175; 6.D.244.240; 6.D.244.244;

Prodrugs of 6.E

6.E.228.228; 6.E.228.229; 6.E.228.230; 6.E.228.231; 6.E.228.236; 6.E.228.237; 6.E.228.238; 6.E.228.239; 6.E.228.154; 6.E.228.157; 6.E.228.166; 6.E.228.169; 6.E.228.172; 6.E.228.175; 6.E.228.240; 6.E.228.244; 6.E.229.228; 6.E.229.229; 6.E.229.230; 6.E.229.231; 6.E.229.236; 6.E.229.237; 6.E.229.238; 6.E.229.239; 6.E.229.154; 6.E.229.157; 6.E.229.166; 6.E.229.169; 6.E.229.172; 6.E.229.175; 6.E.229.240; 6.E.229.244; 6.E.230.228; 6.E.230.229; 6.E.230.230; 6.E.230.231; 6.E.230.236; 6.E.230.237; 6.E.230.238; 6.E.230.239; 6.E.230.154; 6.E.230.157; 6.E.230.166; 6.E.230.169; 6.E.230.172; 6.E.230.175; 6.E.230.240; 6.E.230.244; 6.E.231.228; 6.E.231.229; 6.E.231.230; 6.E.231.231; 6.E.231.236; 6.E.231.237; 6.E.231.238; 6.E.231.239; 6.E.231.154; 6.E.231.157; 6.E.231.166; 6.E.231.169; 6.E.231.172; 6.E.231.175; 6.E.231.240; 6.E.231.244; 6.E.236.228; 6.E.236.229; 6.E.236.230; 6.E.236.231; 6.E.236.236; 6.E.236.237; 6.E.236.238; 6.E.236.239; 6.E.236.154; 6.E.236.157; 6.E.236.166; 6.E.236.169; 6.E.236.172; 6.E.236.175; 6.E.236.240; 6.E.236.244; 6.E.237.228; 6.E.237.229; 6.E.237.230; 6.E.237.231; 6.E.237.236; 6.E.237.237; 6.E.237.238; 6.E.237.239; 6.E.237.154; 6.E.237.157; 6.E.237.166; 6.E.237.169; 6.E.237.172; 6.E.237.175; 6.E.237.240; 6.E.237.244; 6.E.238.228; 6.E.238.229; 6.E.238.230; 6.E.238.231; 6.E.238.236; 6.E.238.237; 6.E.238.238; 6.E.238.239; 6.E.238.154; 6.E.238.157; 6.E.238.166; 6.E.238.169; 6.E.238.172; 6.E.238.175; 6.E.238.240; 6.E.238.244; 6.E.239.228; 6.E.239.229; 6.E.239.230; 6.E.239.231; 6.E.239.236; 6.E.239.237; 6.E.239.238; 6.E.239.239; 6.E.239.154; 6.E.239.157; 6.E.239.166; 6.E.239.169; 6.E.239.172; 6.E.239.175; 6.E.239.240; 6.E.239.244; 6.E.154.228; 6.E.154.229; 6.E.154.230; 6.E.154.231; 6.E.154.236; 6.E.154.237; 6.E.154.238; 6.E.154.239; 6.E.154.154; 6.E.154.157; 6.E.154.166; 6.E.154.169; 6.E.154.172; 6.E.154.175; 6.E.154.240; 6.E.154.244; 6.E.157.228; 6.E.157.229; 6.E.157.230; 6.E.157.231; 6.E.157.236; 6.E.157.237; 6.E.157.238; 6.E.157.239; 6.E.157.154; 6.E.157.157; 6.E.157.166; 6.E.157.169; 6.E.157.172; 6.E.157.175; 6.E.157.240; 6.E.157.244; 6.E.166.228; 6.E.166.229; 6.E.166.230; 6.E.166.231; 6.E.166.236; 6.E.166.237; 6.E.166.238; 6.E.166.239; 6.E.166.154; 6.E.166.157; 6.E.166.166; 6.E.166.169; 6.E.166.172; 6.E.166.175; 6.E.166.240; 6.E.166.244; 6.E.169.228; 6.E.169.229; 6.E.169.230; 6.E.169.231; 6.E.169.236; 6.E.169.237; 6.E.169.238; 6.E.169.239; 6.E.169.154; 6.E.169.157; 6.E.169.166; 6.E.169.169; 6.E.169.172; 6.E.169.175; 6.E.169.240; 6.E.169.244; 6.E.172.228; 6.E.172.229; 6.E.172.230; 6.E.172.231; 6.E.172.236; 6.E.172.237; 6.E.172.238; 6.E.172.239; 6.E.172.154; 6.E.172.157; 6.E.172.166; 6.E.172.169; 6.E.172.172; 6.E.172.175; 6.E.172.240; 6.E.172.244; 6.E.175.228; 6.E.175.229; 6.E.175.230; 6.E.175.231; 6.E.175.236; 6.E.175.237; 6.E.175.238; 6.E.175.239; 6.E.175.154; 6.E.175.157; 6.E.175.166; 6.E.175.169; 6.E.175.172; 6.E.175.175; 6.E.175.240; 6.E.175.244; 6.E.240.228; 6.E.240.229; 6.E.240.230; 6.E.240.231; 6.E.240.236; 6.E.240.237; 6.E.240.238; 6.E.240.239; 6.E.240.154; 6.E.240.157; 6.E.240.166; 6.E.240.169; 6.E.240.172; 6.E.240.175; 6.E.240.240; 6.E.240.244; 6.E.244.228; 6.E.244.229; 6.E.244.230; 6.E.244.231; 6.E.244.236; 6.E.244.237; 6.E.244.238; 6.E.244.239; 6.E.244.154; 6.E.244.157; 6.E.244.166; 6.E.244.169; 6.E.244.172; 6.E.244.175; 6.E.244.240; 6.E.244.244;

Prodrugs of 6.G

6.G.228.228; 6.G.228.229; 6.G.228.230; 6.G.228.231; 6.G.228.236; 6.G.228.237; 6.G.228.238; 6.G.228.239; 6.G.228.154; 6.G.228.157; 6.G.228.166; 6.G.228.169; 6.G.228.172; 6.G.228.175; 6.G.228.240; 6.G.228.244; 6.G.229.228; 6.G.229.229; 6.G.229.230; 6.G.229.231; 6.G.229.236; 6.G.229.237; 6.G.229.238; 6.G.229.239; 6.G.229.154; 6.G.229.157; 6.G.229.166; 6.G.229.169; 6.G.229.172; 6.G.229.175; 6.G.229.240; 6.G.229.244; 6.G.230.228; 6.G.230.229; 6.G.230.230; 6.G.230.231; 6.G.230.236; 6.G.230.237; 6.G.230.238; 6.G.230.239; 6.G.230.154; 6.G.230.157; 6.G.230.166; 6.G.230.169; 6.G.230.172; 6.G.230.175; 6.G.230.240; 6.G.230.244; 6.G.231.228; 6.G.231.229; 6.G.231.230; 6.G.231.231; 6.G.231.236; 6.G.231.237; 6.G.231.238; 6.G.231.239; 6.G.231.154; 6.G.231.157; 6.G.231.166; 6.G.231.169; 6.G.231.172; 6.G.231.175; 6.G.231.240; 6.G.231.244; 6.G.236.228; 6.G.236.229; 6.G.236.230; 6.G.236.231; 6.G.236.236; 6.G.236.237; 6.G.236.238; 6.G.236.239; 6.G.236.154; 6.G.236.157; 6.G.236.166; 6.G.236.169; 6.G.236.172; 6.G.236.175; 6.G.236.240; 6.G.236.244; 6.G.237.228; 6.G.237.229; 6.G.237.230; 6.G.237.231; 6.G.237.236;

TABLE 100-continued

6.G.237.237; 6.G.237.238; 6.G.237.239; 6.G.237.154; 6.G.237.157; 6.G.237.166; 6.G.237.169; 6.G.237.172; 6.G.237.175; 6.G.237.240; 6.G.237.244; 6.G.238.228; 6.G.238.229; 6.G.238.230; 6.G.238.231; 6.G.238.236; 6.G.238.237; 6.G.238.238; 6.G.238.239; 6.G.238.154; 6.G.238.157; 6.G.238.166; 6.G.238.169; 6.G.238.172; 6.G.238.175; 6.G.238.240; 6.G.238.244; 6.G.239.228; 6.G.239.229; 6.G.239.230; 6.G.239.231; 6.G.239.236; 6.G.239.237; 6.G.239.238; 6.G.239.239; 6.G.239.154; 6.G.239.157; 6.G.239.166; 6.G.239.169; 6.G.239.172; 6.G.239.175; 6.G.239.240; 6.G.239.244; 6.G.154.228; 6.G.154.229; 6.G.154.230; 6.G.154.231; 6.G.154.236; 6.G.154.237; 6.G.154.238; 6.G.154.239; 6.G.154.154; 6.G.154.157; 6.G.154.166; 6.G.154.169; 6.G.154.172; 6.G.154.175; 6.G.154.240; 6.G.154.244; 6.G.157.228; 6.G.157.229; 6.G.157.230; 6.G.157.231; 6.G.157.236; 6.G.157.237; 6.G.157.238; 6.G.157.239; 6.G.157.154; 6.G.157.157; 6.G.157.166; 6.G.157.169; 6.G.157.172; 6.G.157.175; 6.G.157.240; 6.G.157.244; 6.G.166.228; 6.G.166.229; 6.G.166.230; 6.G.166.231; 6.G.166.236; 6.G.166.237; 6.G.166.238; 6.G.166.239; 6.G.166.154; 6.G.166.157; 6.G.166.166; 6.G.166.169; 6.G.166.172; 6.G.166.175; 6.G.166.240; 6.G.166.244; 6.G.169.228; 6.G.169.229; 6.G.169.230; 6.G.169.231; 6.G.169.236; 6.G.169.237; 6.G.169.238; 6.G.169.239; 6.G.169.154; 6.G.169.157; 6.G.169.166; 6.G.169.169; 6.G.169.172; 6.G.169.175; 6.G.169.240; 6.G.169.244; 6.G.172.228; 6.G.172.229; 6.G.172.230; 6.G.172.231; 6.G.172.236; 6.G.172.237; 6.G.172.238; 6.G.172.239; 6.G.172.154; 6.G.172.157; 6.G.172.166; 6.G.172.169; 6.G.172.172; 6.G.172.175; 6.G.172.240; 6.G.172.244; 6.G.175.228; 6.G.175.229; 6.G.175.230; 6.G.175.231; 6.G.175.236; 6.G.175.237; 6.G.175.238; 6.G.175.239; 6.G.175.154; 6.G.175.157; 6.G.175.166; 6.G.175.169; 6.G.175.172; 6.G.175.175; 6.G.175.240; 6.G.175.244; 6.G.240.228; 6.G.240.229; 6.G.240.230; 6.G.240.231; 6.G.240.236; 6.G.240.237; 6.G.240.238; 6.G.240.239; 6.G.240.154; 6.G.240.157; 6.G.240.166; 6.G.240.169; 6.G.240.172; 6.G.240.175; 6.G.240.240; 6.G.240.244; 6.G.244.228; 6.G.244.229; 6.G.244.230; 6.G.244.231; 6.G.244.236; 6.G.244.237; 6.G.244.238; 6.G.244.239; 6.G.244.154; 6.G.244.157; 6.G.244.166; 6.G.244.169; 6.G.244.172; 6.G.244.175; 6.G.244.240; 6.G.244.244;

Prodrugs of 6.I

6.I.228.228; 6.I.228.229; 6.I.228.230; 6.I.228.231; 6.I.228.236; 6.I.228.237; 6.I.228.238; 6.I.228.239; 6.I.228.154; 6.I.228.157; 6.I.228.166; 6.I.228.169; 6.I.228.172; 6.I.228.175; 6.I.228.240; 6.I.228.244; 6.I.229.228; 6.I.229.229; 6.I.229.230; 6.I.229.231; 6.I.229.236; 6.I.229.237; 6.I.229.238; 6.I.229.239; 6.I.229.154; 6.I.229.157; 6.I.229.166; 6.I.229.169; 6.I.229.172; 6.I.229.175; 6.I.229.240; 6.I.229.244; 6.I.230.228; 6.I.230.229; 6.I.230.230; 6.I.230.231; 6.I.230.236; 6.I.230.237; 6.I.230.238; 6.I.230.239; 6.I.230.154; 6.I.230.157; 6.I.230.166; 6.I.230.169; 6.I.230.172; 6.I.230.175; 6.I.230.240; 6.I.230.244; 6.I.231.228; 6.I.231.229; 6.I.231.230; 6.I.231.231; 6.I.231.236; 6.I.231.237; 6.I.231.238; 6.I.231.239; 6.I.231.154; 6.I.231.157; 6.I.231.166; 6.I.231.169; 6.I.231.172; 6.I.231.175; 6.I.231.240; 6.I.231.244; 6.I.236.228; 6.I.236.229; 6.I.236.230; 6.I.236.231; 6.I.236.236; 6.I.236.237; 6.I.236.238; 6.I.236.239; 6.I.236.154; 6.I.236.157; 6.I.236.166; 6.I.236.169; 6.I.236.172; 6.I.236.175; 6.I.236.240; 6.I.236.244; 6.I.237.228; 6.I.237.229; 6.I.237.230; 6.I.237.231; 6.I.237.236; 6.I.237.237; 6.I.237.238; 6.I.237.239; 6.I.237.154; 6.I.237.157; 6.I.237.166; 6.I.237.169; 6.I.237.172; 6.I.237.175; 6.I.237.240; 6.I.237.244; 6.I.238.228; 6.I.238.229; 6.I.238.230; 6.I.238.231; 6.I.238.236; 6.I.238.237; 6.I.238.238; 6.I.238.239; 6.I.238.154; 6.I.238.157; 6.I.238.166; 6.I.238.169; 6.I.238.172; 6.I.238.175; 6.I.238.240; 6.I.238.244; 6.I.239.228; 6.I.239.229; 6.I.239.230; 6.I.239.231; 6.I.239.236; 6.I.239.237; 6.I.239.238; 6.I.239.239; 6.I.239.154; 6.I.239.157; 6.I.239.166; 6.I.239.169; 6.I.239.172; 6.I.239.175; 6.I.239.240; 6.I.239.244; 6.I.154.228; 6.I.154.229; 6.I.154.230; 6.I.154.231; 6.I.154.236; 6.I.154.237; 6.I.154.238; 6.I.154.239; 6.I.154.154; 6.I.154.157; 6.I.154.166; 6.I.154.169; 6.I.154.172; 6.I.154.175; 6.I.154.240; 6.I.154.244; 6.I.157.228; 6.I.157.229; 6.I.157.230; 6.I.157.231; 6.I.157.236; 6.I.157.237; 6.I.157.238; 6.I.157.239; 6.I.157.154; 6.I.157.157; 6.I.157.166; 6.I.157.169; 6.I.157.172; 6.I.157.175; 6.I.157.240; 6.I.157.244; 6.I.166.228; 6.I.166.229; 6.I.166.230; 6.I.166.231; 6.I.166.236; 6.I.166.237; 6.I.166.238; 6.I.166.239; 6.I.166.154; 6.I.166.157; 6.I.166.166; 6.I.166.169; 6.I.166.172; 6.I.166.175; 6.I.166.240; 6.I.166.244; 6.I.169.228; 6.I.169.229; 6.I.169.230; 6.I.169.231; 6.I.169.236; 6.I.169.237; 6.I.169.238; 6.I.169.239; 6.I.169.154; 6.I.169.157; 6.I.169.166; 6.I.169.169; 6.I.169.172; 6.I.169.175; 6.I.169.240; 6.I.169.244; 6.I.172.228; 6.I.172.229; 6.I.172.230; 6.I.172.231; 6.I.172.236; 6.I.172.237; 6.I.172.238; 6.I.172.239; 6.I.172.154; 6.I.172.157; 6.I.172.166; 6.I.172.169; 6.I.172.172; 6.I.172.175; 6.I.172.240; 6.I.172.244; 6.I.175.228; 6.I.175.229; 6.I.175.230; 6.I.175.231; 6.I.175.236; 6.I.175.237; 6.I.175.238; 6.I.175.239; 6.I.175.154; 6.I.175.157; 6.I.175.166; 6.I.175.169; 6.I.175.172; 6.I.175.175; 6.I.175.240; 6.I.175.244; 6.I.240.228; 6.I.240.229; 6.I.240.230; 6.I.240.231; 6.I.240.236; 6.I.240.237; 6.I.240.238; 6.I.240.239; 6.I.240.154; 6.I.240.157; 6.I.240.166; 6.I.240.169; 6.I.240.172; 6.I.240.175; 6.I.240.240; 6.I.240.244; 6.I.244.228; 6.I.244.229; 6.I.244.230; 6.I.244.231; 6.I.244.236; 6.I.244.237;

TABLE 100-continued

6.I.244.238; 6.I.244.239; 6.I.244.154; 6.I.244.157; 6.I.244.166; 6.I.244.169; 6.I.244.172; 6.I.244.175; 6.I.244.240; 6.I.244.244;

Prodrugs of 6.J

6.J.228.228; 6.J.228.229; 6.J.228.230; 6.J.228.231; 6.J.228.236; 6.J.228.237; 6.J.228.238; 6.J.228.239; 6.J.228.154; 6.J.228.157; 6.J.228.166; 6.J.228.169; 6.J.228.172; 6.J.228.175; 6.J.228.240; 6.J.228.244; 6.J.229.228; 6.J.229.229; 6.J.229.230; 6.J.229.231; 6.J.229.236; 6.J.229.237; 6.J.229.238; 6.J.229.239; 6.J.229.154; 6.J.229.157; 6.J.229.166; 6.J.229.169; 6.J.229.172; 6.J.229.175; 6.J.229.240; 6.J.229.244; 6.J.230.228; 6.J.230.229; 6.J.230.230; 6.J.230.231; 6.J.230.236; 6.J.230.237; 6.J.230.238; 6.J.230.239; 6.J.230.154; 6.J.230.157; 6.J.230.166; 6.J.230.169; 6.J.230.172; 6.J.230.175; 6.J.230.240; 6.J.230.244; 6.J.231.228; 6.J.231.229; 6.J.231.230; 6.J.231.231; 6.J.231.236; 6.J.231.237; 6.J.231.238; 6.J.231.239; 6.J.231.154; 6.J.231.157; 6.J.231.166; 6.J.231.169; 6.J.231.172; 6.J.231.175; 6.J.231.240; 6.J.231.244; 6.J.236.228; 6.J.236.229; 6.J.236.230; 6.J.236.231; 6.J.236.236; 6.J.236.237; 6.J.236.238; 6.J.236.239; 6.J.236.154; 6.J.236.157; 6.J.236.166; 6.J.236.169; 6.J.236.172; 6.J.236.175; 6.J.236.240; 6.J.236.244; 6.J.237.228; 6.J.237.229; 6.J.237.230; 6.J.237.231; 6.J.237.236; 6.J.237.237; 6.J.237.238; 6.J.237.239; 6.J.237.154; 6.J.237.157; 6.J.237.166; 6.J.237.169; 6.J.237.172; 6.J.237.175; 6.J.237.240; 6.J.237.244; 6.J.238.228; 6.J.238.229; 6.J.238.230; 6.J.238.231; 6.J.238.236; 6.J.238.237; 6.J.238.238; 6.J.238.239; 6.J.238.154; 6.J.238.157; 6.J.238.166; 6.J.238.169; 6.J.238.172; 6.J.238.175; 6.J.238.240; 6.J.238.244; 6.J.239.228; 6.J.239.229; 6.J.239.230; 6.J.239.231; 6.J.239.236; 6.J.239.237; 6.J.239.238; 6.J.239.239; 6.J.239.154; 6.J.239.157; 6.J.239.166; 6.J.239.169; 6.J.239.172; 6.J.239.175; 6.J.239.240; 6.J.239.244; 6.J.154.228; 6.J.154.229; 6.J.154.230; 6.J.154.231; 6.J.154.236; 6.J.154.237; 6.J.154.238; 6.J.154.239; 6.J.154.154; 6.J.154.157; 6.J.154.166; 6.J.154.169; 6.J.154.172; 6.J.154.175; 6.J.154.240; 6.J.154.244; 6.J.157.228; 6.J.157.229; 6.J.157.230; 6.J.157.231; 6.J.157.236; 6.J.157.237; 6.J.157.238; 6.J.157.239; 6.J.157.154; 6.J.157.157; 6.J.157.166; 6.J.157.169; 6.J.157.172; 6.J.157.175; 6.J.157.240; 6.J.157.244; 6.J.166.228; 6.J.166.229; 6.J.166.230; 6.J.166.231; 6.J.166.236; 6.J.166.237; 6.J.166.238; 6.J.166.239; 6.J.166.154; 6.J.166.157; 6.J.166.166; 6.J.166.169; 6.J.166.172; 6.J.166.175; 6.J.166.240; 6.J.166.244; 6.J.169.228; 6.J.169.229; 6.J.169.230; 6.J.169.231; 6.J.169.236; 6.J.169.237; 6.J.169.238; 6.J.169.239; 6.J.169.154; 6.J.169.157; 6.J.169.166; 6.J.169.169; 6.J.169.172; 6.J.169.175; 6.J.169.240; 6.J.169.244; 6.J.172.228; 6.J.172.229; 6.J.172.230; 6.J.172.231; 6.J.172.236; 6.J.172.237; 6.J.172.238; 6.J.172.239; 6.J.172.154; 6.J.172.157; 6.J.172.166; 6.J.172.169; 6.J.172.172; 6.J.172.175; 6.J.172.240; 6.J.172.244; 6.J.175.228; 6.J.175.229; 6.J.175.230; 6.J.175.231; 6.J.175.236; 6.J.175.237; 6.J.175.238; 6.J.175.239; 6.J.175.154; 6.J.175.157; 6.J.175.166; 6.J.175.169; 6.J.175.172; 6.J.175.175; 6.J.175.240; 6.J.175.244; 6.J.240.228; 6.J.240.229; 6.J.240.230; 6.J.240.231; 6.J.240.236; 6.J.240.237; 6.J.240.238; 6.J.240.239; 6.J.240.154; 6.J.240.157; 6.J.240.166; 6.J.240.169; 6.J.240.172; 6.J.240.175; 6.J.240.240; 6.J.240.244; 6.J.244.228; 6.J.244.229; 6.J.244.230; 6.J.244.231; 6.J.244.236; 6.J.244.237; 6.J.244.238; 6.J.244.239; 6.J.244.154; 6.J.244.157; 6.J.244.166; 6.J.244.169; 6.J.244.172; 6.J.244.175; 6.J.244.240; 6.J.244.244;

Prodrugs of 6.L

6.L.228.228; 6.L.228.229; 6.L.228.230; 6.L.228.231; 6.L.228.236; 6.L.228.237; 6.L.228.238; 6.L.228.239; 6.L.228.154; 6.L.228.157; 6.L.228.166; 6.L.228.169; 6.L.228.172; 6.L.228.175; 6.L.228.240; 6.L.228.244; 6.L.229.228; 6.L.229.229; 6.L.229.230; 6.L.229.231; 6.L.229.236; 6.L.229.237; 6.L.229.238; 6.L.229.239; 6.L.229.154; 6.L.229.157; 6.L.229.166; 6.L.229.169; 6.L.229.172; 6.L.229.175; 6.L.229.240; 6.L.229.244; 6.L.230.228; 6.L.230.229; 6.L.230.230; 6.L.230.231; 6.L.230.236; 6.L.230.237; 6.L.230.238; 6.L.230.239; 6.L.230.154; 6.L.230.157; 6.L.230.166; 6.L.230.169; 6.L.230.172; 6.L.230.175; 6.L.230.240; 6.L.230.244; 6.L.231.228; 6.L.231.229; 6.L.231.230; 6.L.231.231; 6.L.231.236; 6.L.231.237; 6.L.231.238; 6.L.231.239; 6.L.231.154; 6.L.231.157; 6.L.231.166; 6.L.231.169; 6.L.231.172; 6.L.231.175; 6.L.231.240; 6.L.231.244; 6.L.236.228; 6.L.236.229; 6.L.236.230; 6.L.236.231; 6.L.236.236; 6.L.236.237; 6.L.236.238; 6.L.236.239; 6.L.236.154; 6.L.236.157; 6.L.236.166; 6.L.236.169; 6.L.236.172; 6.L.236.175; 6.L.236.240; 6.L.236.244; 6.L.237.228; 6.L.237.229; 6.L.237.230; 6.L.237.231; 6.L.237.236; 6.L.237.237; 6.L.237.238; 6.L.237.239; 6.L.237.154; 6.L.237.157; 6.L.237.166; 6.L.237.169; 6.L.237.172; 6.L.237.175; 6.L.237.240; 6.L.237.244; 6.L.238.228; 6.L.238.229; 6.L.238.230; 6.L.238.231; 6.L.238.236; 6.L.238.237; 6.L.238.238; 6.L.238.239; 6.L.238.154; 6.L.238.157; 6.L.238.166; 6.L.238.169; 6.L.238.172; 6.L.238.175; 6.L.238.240; 6.L.238.244; 6.L.239.228; 6.L.239.229; 6.L.239.230; 6.L.239.231; 6.L.239.236; 6.L.239.237; 6.L.239.238; 6.L.239.239; 6.L.239.154; 6.L.239.157; 6.L.239.166; 6.L.239.169; 6.L.239.172; 6.L.239.175; 6.L.239.240; 6.L.239.244; 6.L.154.228; 6.L.154.229; 6.L.154.230; 6.L.154.231; 6.L.154.236; 6.L.154.237; 6.L.154.238; 6.L.154.239; 6.L.154.154; 6.L.154.157; 6.L.154.166; 6.L.154.169; 6.L.154.172; 6.L.154.175; 6.L.154.240; 6.L.154.244; 6.L.157.228; 6.L.157.229; 6.L.157.230; 6.L.157.231; 6.L.157.236; 6.L.157.237; 6.L.157.238; 6.L.157.239; 6.L.157.154; 6.L.157.157; 6.L.157.166; 6.L.157.169; 6.L.157.172; 6.L.157.175; 6.L.157.240; 6.L.157.244; 6.L.166.228; 6.L.166.229; 6.L.166.230; 6.L.166.231; 6.L.166.236; 6.L.166.237; 6.L.166.238; 6.L.166.239; 6.L.166.154; 6.L.166.157; 6.L.166.166; 6.L.166.169; 6.L.166.172; 6.L.166.175; 6.L.166.240; 6.L.166.244; 6.L.169.228; 6.L.169.229; 6.L.169.230;

TABLE 100-continued

6.L.169.231; 6.L.169.236; 6.L.169.237; 6.L.169.238; 6.L.169.239; 6.L.169.154; 6.L.169.157; 6.L.169.166; 6.L.169.169; 6.L.169.172; 6.L.169.175; 6.L.169.240; 6.L.169.244; 6.L.172.228; 6.L.172.229; 6.L.172.230; 6.L.172.231; 6.L.172.236; 6.L.172.237; 6.L.172.238; 6.L.172.239; 6.L.172.154; 6.L.172.157; 6.L.172.166; 6.L.172.169; 6.L.172.172; 6.L.172.175; 6.L.172.240; 6.L.172.244; 6.L.175.228; 6.L.175.229; 6.L.175.230; 6.L.175.231; 6.L.175.236; 6.L.175.237; 6.L.175.238; 6.L.175.239; 6.L.175.154; 6.L.175.157; 6.L.175.166; 6.L.175.169; 6.L.175.172; 6.L.175.175; 6.L.175.240; 6.L.175.244; 6.L.240.228; 6.L.240.229; 6.L.240.230; 6.L.240.231; 6.L.240.236; 6.L.240.237; 6.L.240.238; 6.L.240.239; 6.L.240.154; 6.L.240.157; 6.L.240.166; 6.L.240.169; 6.L.240.172; 6.L.240.175; 6.L.240.240; 6.L.240.244; 6.L.244.228; 6.L.244.229; 6.L.244.230; 6.L.244.231; 6.L.244.236; 6.L.244.237; 6.L.244.238; 6.L.244.239; 6.L.244.154; 6.L.244.157; 6.L.244.166; 6.L.244.169; 6.L.244.172; 6.L.244.175; 6.L.244.240; 6.L.244.244;

Prodrugs of 6.O

6.O.228.228; 6.O.228.229; 6.O.228.230; 6.O.228.231; 6.O.228.236; 6.O.228.237; 6.O.228.238; 6.O.228.239; 6.O.228.154; 6.O.228.157; 6.O.228.166; 6.O.228.169; 6.O.228.172; 6.O.228.175; 6.O.228.240; 6.O.228.244; 6.O.229.228; 6.O.229.229; 6.O.229.230; 6.O.229.231; 6.O.229.236; 6.O.229.237; 6.O.229.238; 6.O.229.239; 6.O.229.154; 6.O.229.157; 6.O.229.166; 6.O.229.169; 6.O.229.172; 6.O.229.175; 6.O.229.240; 6.O.229.244; 6.O.230.228; 6.O.230.229; 6.O.230.230; 6.O.230.231; 6.O.230.236; 6.O.230.237; 6.O.230.238; 6.O.230.239; 6.O.230.154; 6.O.230.157; 6.O.230.166; 6.O.230.169; 6.O.230.172; 6.O.230.175; 6.O.230.240; 6.O.230.244; 6.O.231.228; 6.O.231.229; 6.O.231.230; 6.O.231.231; 6.O.231.236; 6.O.231.237; 6.O.231.238; 6.O.231.239; 6.O.231.154; 6.O.231.157; 6.O.231.166; 6.O.231.169; 6.O.231.172; 6.O.231.175; 6.O.231.240; 6.O.231.244; 6.O.236.228; 6.O.236.229; 6.O.236.230; 6.O.236.231; 6.O.236.236; 6.O.236.237; 6.O.236.238; 6.O.236.239; 6.O.236.154; 6.O.236.157; 6.O.236.166; 6.O.236.169; 6.O.236.172; 6.O.236.175; 6.O.236.240; 6.O.236.244; 6.O.237.228; 6.O.237.229; 6.O.237.230; 6.O.237.231; 6.O.237.236; 6.O.237.237; 6.O.237.238; 6.O.237.239; 6.O.237.154; 6.O.237.157; 6.O.237.166; 6.O.237.169; 6.O.237.172; 6.O.237.175; 6.O.237.240; 6.O.237.244; 6.O.238.228; 6.O.238.229; 6.O.238.230; 6.O.238.231; 6.O.238.236; 6.O.238.237; 6.O.238.238; 6.O.238.239; 6.O.238.154; 6.O.238.157; 6.O.238.166; 6.O.238.169; 6.O.238.172; 6.O.238.175; 6.O.238.240; 6.O.238.244; 6.O.239.228; 6.O.239.229; 6.O.239.230; 6.O.239.231; 6.O.239.236; 6.O.239.237; 6.O.239.238; 6.O.239.239; 6.O.239.154; 6.O.239.157; 6.O.239.166; 6.O.239.169; 6.O.239.172; 6.O.239.175; 6.O.239.240; 6.O.239.244; 6.O.154.228; 6.O.154.229; 6.O.154.230; 6.O.154.231; 6.O.154.236; 6.O.154.237; 6.O.154.238; 6.O.154.239; 6.O.154.154; 6.O.154.157; 6.O.154.166; 6.O.154.169; 6.O.154.172; 6.O.154.175; 6.O.154.240; 6.O.154.244; 6.O.157.228; 6.O.157.229; 6.O.157.230; 6.O.157.231; 6.O.157.236; 6.O.157.237; 6.O.157.238; 6.O.157.239; 6.O.157.154; 6.O.157.157; 6.O.157.166; 6.O.157.169; 6.O.157.172; 6.O.157.175; 6.O.157.240; 6.O.157.244; 6.O.166.228; 6.O.166.229; 6.O.166.230; 6.O.166.231; 6.O.166.236; 6.O.166.237; 6.O.166.238; 6.O.166.239; 6.O.166.154; 6.O.166.157; 6.O.166.166; 6.O.166.169; 6.O.166.172; 6.O.166.175; 6.O.166.240; 6.O.166.244; 6.O.169.228; 6.O.169.229; 6.O.169.230; 6.O.169.231; 6.O.169.236; 6.O.169.237; 6.O.169.238; 6.O.169.239; 6.O.169.154; 6.O.169.157; 6.O.169.166; 6.O.169.169; 6.O.169.172; 6.O.169.175; 6.O.169.240; 6.O.169.244; 6.O.172.228; 6.O.172.229; 6.O.172.230; 6.O.172.231; 6.O.172.236; 6.O.172.237; 6.O.172.238; 6.O.172.239; 6.O.172.154; 6.O.172.157; 6.O.172.166; 6.O.172.169; 6.O.172.172; 6.O.172.175; 6.O.172.240; 6.O.172.244; 6.O.175.228; 6.O.175.229; 6.O.175.230; 6.O.175.231; 6.O.175.236; 6.O.175.237; 6.O.175.238; 6.O.175.239; 6.O.175.154; 6.O.175.157; 6.O.175.166; 6.O.175.169; 6.O.175.172; 6.O.175.175; 6.O.175.240; 6.O.175.244; 6.O.240.228; 6.O.240.229; 6.O.240.230; 6.O.240.231; 6.O.240.236; 6.O.240.237; 6.O.240.238; 6.O.240.239; 6.O.240.154; 6.O.240.157; 6.O.240.166; 6.O.240.169; 6.O.240.172; 6.O.240.175; 6.O.240.240; 6.O.240.244; 6.O.244.228; 6.O.244.229; 6.O.244.230; 6.O.244.231; 6.O.244.236; 6.O.244.237; 6.O.244.238; 6.O.244.239; 6.O.244.154; 6.O.244.157; 6.O.244.166; 6.O.244.169; 6.O.244.172; 6.O.244.175; 6.O.244.240; 6.O.244.244;

Prodrugs of 6.P

6.P.228.228; 6.P.228.229; 6.P.228.230; 6.P.228.231; 6.P.228.236; 6.P.228.237; 6.P.228.238; 6.P.228.239; 6.P.228.154; 6.P.228.157; 6.P.228.166; 6.P.228.169; 6.P.228.172; 6.P.228.175; 6.P.228.240; 6.P.228.244; 6.P.229.228; 6.P.229.229; 6.P.229.230; 6.P.229.231; 6.P.229.236; 6.P.229.237; 6.P.229.238; 6.P.229.239; 6.P.229.154; 6.P.229.157; 6.P.229.166; 6.P.229.169; 6.P.229.172; 6.P.229.175; 6.P.229.240; 6.P.229.244; 6.P.230.228; 6.P.230.229; 6.P.230.230; 6.P.230.231; 6.P.230.236; 6.P.230.237; 6.P.230.238; 6.P.230.239; 6.P.230.154; 6.P.230.157; 6.P.230.166; 6.P.230.169; 6.P.230.172; 6.P.230.175; 6.P.230.240; 6.P.230.244; 6.P.231.228; 6.P.231.229; 6.P.231.230; 6.P.231.231; 6.P.231.236; 6.P.231.237; 6.P.231.238; 6.P.231.239; 6.P.231.154; 6.P.231.157; 6.P.231.166;

TABLE 100-continued

6.P.231.169; 6.P.231.172; 6.P.231.175; 6.P.231.240; 6.P.231.244; 6.P.236.228; 6.P.236.229; 6.P.236.230; 6.P.236.231; 6.P.236.236; 6.P.236.237; 6.P.236.238; 6.P.236.239; 6.P.236.154; 6.P.236.157; 6.P.236.166; 6.P.236.169; 6.P.236.172; 6.P.236.175; 6.P.236.240; 6.P.236.244; 6.P.237.228; 6.P.237.229; 6.P.237.230; 6.P.237.231; 6.P.237.236; 6.P.237.237; 6.P.237.238; 6.P.237.239; 6.P.237.154; 6.P.237.157; 6.P.237.166; 6.P.237.169; 6.P.237.172; 6.P.237.175; 6.P.237.240; 6.P.237.244; 6.P.238.228; 6.P.238.229; 6.P.238.230; 6.P.238.231; 6.P.238.236; 6.P.238.237; 6.P.238.238; 6.P.238.239; 6.P.238.154; 6.P.238.157; 6.P.238.166; 6.P.238.169; 6.P.238.172; 6.P.238.175; 6.P.238.240; 6.P.238.244; 6.P.239.228; 6.P.239.229; 6.P.239.230; 6.P.239.231; 6.P.239.236; 6.P.239.237; 6.P.239.238; 6.P.239.239; 6.P.239.154; 6.P.239.157; 6.P.239.166; 6.P.239.169; 6.P.239.172; 6.P.239.175; 6.P.239.240; 6.P.239.244; 6.P.154.228; 6.P.154.229; 6.P.154.230; 6.P.154.231; 6.P.154.236; 6.P.154.237; 6.P.154.238; 6.P.154.239; 6.P.154.154; 6.P.154.157; 6.P.154.166; 6.P.154.169; 6.P.154.172; 6.P.154.175; 6.P.154.240; 6.P.154.244; 6.P.157.228; 6.P.157.229; 6.P.157.230; 6.P.157.231; 6.P.157.236; 6.P.157.237; 6.P.157.238; 6.P.157.239; 6.P.157.154; 6.P.157.157; 6.P.157.166; 6.P.157.169; 6.P.157.172; 6.P.157.175; 6.P.157.240; 6.P.157.244; 6.P.166.228; 6.P.166.229; 6.P.166.230; 6.P.166.231; 6.P.166.236; 6.P.166.237; 6.P.166.238; 6.P.166.239; 6.P.166.154; 6.P.166.157; 6.P.166.166; 6.P.166.169; 6.P.166.172; 6.P.166.175; 6.P.166.240; 6.P.166.244; 6.P.169.228; 6.P.169.229; 6.P.169.230; 6.P.169.231; 6.P.169.236; 6.P.169.237; 6.P.169.238; 6.P.169.239; 6.P.169.154; 6.P.169.157; 6.P.169.166; 6.P.169.169; 6.P.169.172; 6.P.169.175; 6.P.169.240; 6.P.169.244; 6.P.172.228; 6.P.172.229; 6.P.172.230; 6.P.172.231; 6.P.172.236; 6.P.172.237; 6.P.172.238; 6.P.172.239; 6.P.172.154; 6.P.172.157; 6.P.172.166; 6.P.172.169; 6.P.172.172; 6.P.172.175; 6.P.172.240; 6.P.172.244; 6.P.175.228; 6.P.175.229; 6.P.175.230; 6.P.175.231; 6.P.175.236; 6.P.175.237; 6.P.175.238; 6.P.175.239; 6.P.175.154; 6.P.175.157; 6.P.175.166; 6.P.175.169; 6.P.175.172; 6.P.175.175; 6.P.175.240; 6.P.175.244; 6.P.240.228; 6.P.240.229; 6.P.240.230; 6.P.240.231; 6.P.240.236; 6.P.240.237; 6.P.240.238; 6.P.240.239; 6.P.240.154; 6.P.240.157; 6.P.240.166; 6.P.240.169; 6.P.240.172; 6.P.240.175; 6.P.240.240; 6.P.240.244; 6.P.244.228; 6.P.244.229; 6.P.244.230; 6.P.244.231; 6.P.244.236; 6.P.244.237; 6.P.244.238; 6.P.244.239; 6.P.244.154; 6.P.244.157; 6.P.244.166; 6.P.244.169; 6.P.244.172; 6.P.244.175; 6.P.244.240; 6.P.244.244;

Prodrugs of 6.U

6.U.228.228; 6.U.228.229; 6.U.228.230; 6.U.228.231; 6.U.228.236; 6.U.228.237; 6.U.228.238; 6.U.228.239; 6.U.228.154; 6.U.228.157; 6.U.228.166; 6.U.228.169; 6.U.228.172; 6.U.228.175; 6.U.228.240; 6.U.228.244; 6.U.229.228; 6.U.229.229; 6.U.229.230; 6.U.229.231; 6.U.229.236; 6.U.229.237; 6.U.229.238; 6.U.229.239; 6.U.229.154; 6.U.229.157; 6.U.229.166; 6.U.229.169; 6.U.229.172; 6.U.229.175; 6.U.229.240; 6.U.229.244; 6.U.230.228; 6.U.230.229; 6.U.230.230; 6.U.230.231; 6.U.230.236; 6.U.230.237; 6.U.230.238; 6.U.230.239; 6.U.230.154; 6.U.230.157; 6.U.230.166; 6.U.230.169; 6.U.230.172; 6.U.230.175; 6.U.230.240; 6.U.230.244; 6.U.231.228; 6.U.231.229; 6.U.231.230; 6.U.231.231; 6.U.231.236; 6.U.231.237; 6.U.231.238; 6.U.231.239; 6.U.231.154; 6.U.231.157; 6.U.231.166; 6.U.231.169; 6.U.231.172; 6.U.231.175; 6.U.231.240; 6.U.231.244; 6.U.236.228; 6.U.236.229; 6.U.236.230; 6.U.236.231; 6.U.236.236; 6.U.236.237; 6.U.236.238; 6.U.236.239; 6.U.236.154; 6.U.236.157; 6.U.236.166; 6.U.236.169; 6.U.236.172; 6.U.236.175; 6.U.236.240; 6.U.236.244; 6.U.237.228; 6.U.237.229; 6.U.237.230; 6.U.237.231; 6.U.237.236; 6.U.237.237; 6.U.237.238; 6.U.237.239; 6.U.237.154; 6.U.237.157; 6.U.237.166; 6.U.237.169; 6.U.237.172; 6.U.237.175; 6.U.237.240; 6.U.237.244; 6.U.238.228; 6.U.238.229; 6.U.238.230; 6.U.238.231; 6.U.238.236; 6.U.238.237; 6.U.238.238; 6.U.238.239; 6.U.238.154; 6.U.238.157; 6.U.238.166; 6.U.238.169; 6.U.238.172; 6.U.238.175; 6.U.238.240; 6.U.238.244; 6.U.239.228; 6.U.239.229; 6.U.239.230; 6.U.239.231; 6.U.239.236; 6.U.239.237; 6.U.239.238; 6.U.239.239; 6.U.239.154; 6.U.239.157; 6.U.239.166; 6.U.239.169; 6.U.239.172; 6.U.239.175; 6.U.239.240; 6.U.239.244; 6.U.154.228; 6.U.154.229; 6.U.154.230; 6.U.154.231; 6.U.154.236; 6.U.154.237; 6.U.154.238; 6.U.154.239; 6.U.154.154; 6.U.154.157; 6.U.154.166; 6.U.154.169; 6.U.154.172; 6.U.154.175; 6.U.154.240; 6.U.154.244; 6.U.157.228; 6.U.157.229; 6.U.157.230; 6.U.157.231; 6.U.157.236; 6.U.157.237; 6.U.157.238; 6.U.157.239; 6.U.157.154; 6.U.157.157; 6.U.157.166; 6.U.157.169; 6.U.157.172; 6.U.157.175; 6.U.157.240; 6.U.157.244; 6.U.166.228; 6.U.166.229; 6.U.166.230; 6.U.166.231; 6.U.166.236; 6.U.166.237; 6.U.166.238; 6.U.166.239; 6.U.166.154; 6.U.166.157; 6.U.166.166; 6.U.166.169; 6.U.166.172; 6.U.166.175; 6.U.166.240; 6.U.166.244; 6.U.169.228; 6.U.169.229; 6.U.169.230; 6.U.169.231; 6.U.169.236; 6.U.169.237; 6.U.169.238; 6.U.169.239; 6.U.169.154; 6.U.169.157; 6.U.169.166; 6.U.169.169; 6.U.169.172; 6.U.169.175; 6.U.169.240; 6.U.169.244; 6.U.172.228; 6.U.172.229; 6.U.172.230; 6.U.172.231; 6.U.172.236; 6.U.172.237; 6.U.172.238; 6.U.172.239; 6.U.172.154; 6.U.172.157; 6.U.172.166; 6.U.172.169; 6.U.172.172; 6.U.172.175; 6.U.172.240; 6.U.172.244; 6.U.175.228; 6.U.175.229; 6.U.175.230; 6.U.175.231; 6.U.175.236; 6.U.175.237; 6.U.175.238; 6.U.175.239; 6.U.175.154; 6.U.175.157; 6.U.175.166; 6.U.175.169;

TABLE 100-continued

6.U.175.172; 6.U.175.175; 6.U.175.240; 6.U.175.244; 6.U.240.228; 6.U.240.229; 6.U.240.230; 6.U.240.231; 6.U.240.236; 6.U.240.237; 6.U.240.238; 6.U.240.239; 6.U.240.154; 6.U.240.157; 6.U.240.166; 6.U.240.169; 6.U.240.172; 6.U.240.175; 6.U.240.240; 6.U.240.244; 6.U.244.228; 6.U.244.229; 6.U.244.230; 6.U.244.231; 6.U.244.236; 6.U.244.237; 6.U.244.238; 6.U.244.239; 6.U.244.154; 6.U.244.157; 6.U.244.166; 6.U.244.169; 6.U.244.172; 6.U.244.175; 6.U.244.240; 6.U.244.244;

Prodrugs of 6.W

6.W.228.228; 6.W.228.229; 6.W.228.230; 6.W.228.231; 6.W.228.236; 6.W.228.237; 6.W.228.238; 6.W.228.239; 6.W.228.154; 6.W.228.157; 6.W.228.166; 6.W.228.169; 6.W.228.172; 6.W.228.175; 6.W.228.240; 6.W.228.244; 6.W.229.228; 6.W.229.229; 6.W.229.230; 6.W.229.231; 6.W.229.236; 6.W.229.237; 6.W.229.238; 6.W.229.239; 6.W.229.154; 6.W.229.157; 6.W.229.166; 6.W.229.169; 6.W.229.172; 6.W.229.175; 6.W.229.240; 6.W.229.244; 6.W.230.228; 6.W.230.229; 6.W.230.230; 6.W.230.231; 6.W.230.236; 6.W.230.237; 6.W.230.238; 6.W.230.239; 6.W.230.154; 6.W.230.157; 6.W.230.166; 6.W.230.169; 6.W.230.172; 6.W.230.175; 6.W.230.240; 6.W.230.244; 6.W.231.228; 6.W.231.229; 6.W.231.230; 6.W.231.231; 6.W.231.236; 6.W.231.237; 6.W.231.238; 6.W.231.239; 6.W.231.154; 6.W.231.157; 6.W.231.166; 6.W.231.169; 6.W.231.172; 6.W.231.175; 6.W.231.240; 6.W.231.244; 6.W.236.228; 6.W.236.229; 6.W.236.230; 6.W.236.231; 6.W.236.236; 6.W.236.237; 6.W.236.238; 6.W.236.239; 6.W.236.154; 6.W.236.157; 6.W.236.166; 6.W.236.169; 6.W.236.172; 6.W.236.175; 6.W.236.240; 6.W.236.244; 6.W.237.228; 6.W.237.229; 6.W.237.230; 6.W.237.231; 6.W.237.236; 6.W.237.237; 6.W.237.238; 6.W.237.239; 6.W.237.154; 6.W.237.157; 6.W.237.166; 6.W.237.169; 6.W.237.172; 6.W.237.175; 6.W.237.240; 6.W.237.244; 6.W.238.228; 6.W.238.229; 6.W.238.230; 6.W.238.231; 6.W.238.236; 6.W.238.237; 6.W.238.238; 6.W.238.239; 6.W.238.154; 6.W.238.157; 6.W.238.166; 6.W.238.169; 6.W.238.172; 6.W.238.175; 6.W.238.240; 6.W.238.244; 6.W.239.228; 6.W.239.229; 6.W.239.230; 6.W.239.231; 6.W.239.236; 6.W.239.237; 6.W.239.238; 6.W.239.239; 6.W.239.154; 6.W.239.157; 6.W.239.166; 6.W.239.169; 6.W.239.172; 6.W.239.175; 6.W.239.240; 6.W.239.244; 6.W.154.228; 6.W.154.229; 6.W.154.230; 6.W.154.231; 6.W.154.236; 6.W.154.237; 6.W.154.238; 6.W.154.239; 6.W.154.154; 6.W.154.157; 6.W.154.166; 6.W.154.169; 6.W.154.172; 6.W.154.175; 6.W.154.240; 6.W.154.244; 6.W.157.228; 6.W.157.229; 6.W.157.230; 6.W.157.231; 6.W.157.236; 6.W.157.237; 6.W.157.238; 6.W.157.239; 6.W.157.154; 6.W.157.157; 6.W.157.166; 6.W.157.169; 6.W.157.172; 6.W.157.175; 6.W.157.240; 6.W.157.244; 6.W.166.228; 6.W.166.229; 6.W.166.230; 6.W.166.231; 6.W.166.236; 6.W.166.237; 6.W.166.238; 6.W.166.239; 6.W.166.154; 6.W.166.157; 6.W.166.166; 6.W.166.169; 6.W.166.172; 6.W.166.175; 6.W.166.240; 6.W.166.244; 6.W.169.228; 6.W.169.229; 6.W.169.230; 6.W.169.231; 6.W.169.236; 6.W.169.237; 6.W.169.238; 6.W.169.239; 6.W.169.154; 6.W.169.157; 6.W.169.166; 6.W.169.169; 6.W.169.172; 6.W.169.175; 6.W.169.240; 6.W.169.244; 6.W.172.228; 6.W.172.229; 6.W.172.230; 6.W.172.231; 6.W.172.236; 6.W.172.237; 6.W.172.238; 6.W.172.239; 6.W.172.154; 6.W.172.157; 6.W.172.166; 6.W.172.169; 6.W.172.172; 6.W.172.175; 6.W.172.240; 6.W.172.244; 6.W.175.228; 6.W.175.229; 6.W.175.230; 6.W.175.231; 6.W.175.236; 6.W.175.237; 6.W.175.238; 6.W.175.239; 6.W.175.154; 6.W.175.157; 6.W.175.166; 6.W.175.169; 6.W.175.172; 6.W.175.175; 6.W.175.240; 6.W.175.244; 6.W.240.228; 6.W.240.229; 6.W.240.230; 6.W.240.231; 6.W.240.236; 6.W.240.237; 6.W.240.238; 6.W.240.239; 6.W.240.154; 6.W.240.157; 6.W.240.166; 6.W.240.169; 6.W.240.172; 6.W.240.175; 6.W.240.240; 6.W.240.244; 6.W.244.228; 6.W.244.229; 6.W.244.230; 6.W.244.231; 6.W.244.236; 6.W.244.237; 6.W.244.238; 6.W.244.239; 6.W.244.154; 6.W.244.157; 6.W.244.166; 6.W.244.169; 6.W.244.172; 6.W.244.175; 6.W.244.240; 6.W.244.244;

Prodrugs of 6.Y

6.Y.228.228; 6.Y.228.229; 6.Y.228.230; 6.Y.228.231; 6.Y.228.236; 6.Y.228.237; 6.Y.228.238; 6.Y.228.239; 6.Y.228.154; 6.Y.228.157; 6.Y.228.166; 6.Y.228.169; 6.Y.228.172; 6.Y.228.175; 6.Y.228.240; 6.Y.228.244; 6.Y.229.228; 6.Y.229.229; 6.Y.229.230; 6.Y.229.231; 6.Y.229.236; 6.Y.229.237; 6.Y.229.238; 6.Y.229.239; 6.Y.229.154; 6.Y.229.157; 6.Y.229.166; 6.Y.229.169; 6.Y.229.172; 6.Y.229.175; 6.Y.229.240; 6.Y.229.244; 6.Y.230.228; 6.Y.230.229; 6.Y.230.230; 6.Y.230.231; 6.Y.230.236; 6.Y.230.237; 6.Y.230.238; 6.Y.230.239; 6.Y.230.154; 6.Y.230.157; 6.Y.230.166; 6.Y.230.169; 6.Y.230.172; 6.Y.230.175; 6.Y.230.240; 6.Y.230.244; 6.Y.231.228; 6.Y.231.229; 6.Y.231.230; 6.Y.231.231; 6.Y.231.236; 6.Y.231.237; 6.Y.231.238; 6.Y.231.239; 6.Y.231.154; 6.Y.231.157; 6.Y.231.166; 6.Y.231.169; 6.Y.231.172; 6.Y.231.175; 6.Y.231.240; 6.Y.231.244; 6.Y.236.228; 6.Y.236.229; 6.Y.236.230; 6.Y.236.231; 6.Y.236.236; 6.Y.236.237; 6.Y.236.238; 6.Y.236.239; 6.Y.236.154; 6.Y.236.157; 6.Y.236.166;

TABLE 100-continued

6.Y.236.169; 6.Y.236.172; 6.Y.236.175; 6.Y.236.240; 6.Y.236.244; 6.Y.237.228; 6.Y.237.229; 6.Y.237.230; 6.Y.237.231; 6.Y.237.236; 6.Y.237.237; 6.Y.237.238; 6.Y.237.239; 6.Y.237.154; 6.Y.237.157; 6.Y.237.166; 6.Y.237.169; 6.Y.237.172; 6.Y.237.175; 6.Y.237.240; 6.Y.237.244; 6.Y.238.228; 6.Y.238.229; 6.Y.238.230; 6.Y.238.231; 6.Y.238.236; 6.Y.238.237; 6.Y.238.238; 6.Y.238.239; 6.Y.238.154; 6.Y.238.157; 6.Y.238.166; 6.Y.238.169; 6.Y.238.172; 6.Y.238.175; 6.Y.238.240; 6.Y.238.244; 6.Y.239.228; 6.Y.239.229; 6.Y.239.230; 6.Y.239.231; 6.Y.239.236; 6.Y.239.237; 6.Y.239.238; 6.Y.239.239; 6.Y.239.154; 6.Y.239.157; 6.Y.239.166; 6.Y.239.169; 6.Y.239.172; 6.Y.239.175; 6.Y.239.240; 6.Y.239.244; 6.Y.154.228; 6.Y.154.229; 6.Y.154.230; 6.Y.154.231; 6.Y.154.236; 6.Y.154.237; 6.Y.154.238; 6.Y.154.239; 6.Y.154.154; 6.Y.154.157; 6.Y.154.166; 6.Y.154.169; 6.Y.154.172; 6.Y.154.175; 6.Y.154.240; 6.Y.154.244; 6.Y.157.228; 6.Y.157.229; 6.Y.157.230; 6.Y.157.231; 6.Y.157.236; 6.Y.157.237; 6.Y.157.238; 6.Y.157.239; 6.Y.157.154; 6.Y.157.157; 6.Y.157.166; 6.Y.157.169; 6.Y.157.172; 6.Y.157.175; 6.Y.157.240; 6.Y.157.244; 6.Y.166.228; 6.Y.166.229; 6.Y.166.230; 6.Y.166.231; 6.Y.166.236; 6.Y.166.237; 6.Y.166.238; 6.Y.166.239; 6.Y.166.154; 6.Y.166.157; 6.Y.166.166; 6.Y.166.169; 6.Y.166.172; 6.Y.166.175; 6.Y.166.240; 6.Y.166.244; 6.Y.169.228; 6.Y.169.229; 6.Y.169.230; 6.Y.169.231; 6.Y.169.236; 6.Y.169.237; 6.Y.169.238; 6.Y.169.239; 6.Y.169.154; 6.Y.169.157; 6.Y.169.166; 6.Y.169.169; 6.Y.169.172; 6.Y.169.175; 6.Y.169.240; 6.Y.169.244; 6.Y.172.228; 6.Y.172.229; 6.Y.172.230; 6.Y.172.231; 6.Y.172.236; 6.Y.172.237; 6.Y.172.238; 6.Y.172.239; 6.Y.172.154; 6.Y.172.157; 6.Y.172.166; 6.Y.172.169; 6.Y.172.172; 6.Y.172.175; 6.Y.172.240; 6.Y.172.244; 6.Y.175.228; 6.Y.175.229; 6.Y.175.230; 6.Y.175.231; 6.Y.175.236; 6.Y.175.237; 6.Y.175.238; 6.Y.175.239; 6.Y.175.154; 6.Y.175.157; 6.Y.175.166; 6.Y.175.169; 6.Y.175.172; 6.Y.175.175; 6.Y.175.240; 6.Y.175.244; 6.Y.240.228; 6.Y.240.229; 6.Y.240.230; 6.Y.240.231; 6.Y.240.236; 6.Y.240.237; 6.Y.240.238; 6.Y.240.239; 6.Y.240.154; 6.Y.240.157; 6.Y.240.166; 6.Y.240.169; 6.Y.240.172; 6.Y.240.175; 6.Y.240.240; 6.Y.240.244; 6.Y.244.228; 6.Y.244.229; 6.Y.244.230; 6.Y.244.231; 6.Y.244.236; 6.Y.244.237; 6.Y.244.238; 6.Y.244.239; 6.Y.244.154; 6.Y.244.157; 6.Y.244.166; 6.Y.244.169; 6.Y.244.172; 6.Y.244.175; 6.Y.244.240; 6.Y.244.244;

Prodrugs of 7.AH

7.AH.4.157; 7.AH.4.158; 7.AH.4.196; 7.AH.4.223; 7.AH.4.240; 7.AH.4.244; 7.AH.4.243; 7.AH.4.247; 7.AH.5.157; 7.AH.5.158; 7.AH.5.196; 7.AH.5.223; 7.AH.5.240; 7.AH.5.244; 7.AH.5.243; 7.AH.5.247; 7.AH.7.157; 7.AH.7.158; 7.AH.7.196; 7.AH.7.223; 7.AH.7.240; 7.AH.7.244; 7.AH.7.243; 7.AH.7.247; 7.AH.15.157; 7.AH.15.158; 7.AH.15.196; 7.AH.15.223; 7.AH.15.240; 7.AH.15.244; 7.AH.15.243; 7.AH.15.247; 7.AH.16.157; 7.AH.16.158; 7.AH.16.196; 7.AH.16.223; 7.AH.16.240; 7.AH.16.244; 7.AH.16.243; 7.AH.16.247; 7.AH.18.157; 7.AH.18.158; 7.AH.18.196; 7.AH.18.223; 7.AH.18.240; 7.AH.18.244; 7.AH.18.243; 7.AH.18.247; 7.AH.26.157; 7.AH.26.158; 7.AH.26.196; 7.AH.26.223; 7.AH.26.240; 7.AH.26.244; 7.AH.26.243; 7.AH.26.247; 7.AH.27.157; 7.AH.27.158; 7.AH.27.196; 7.AH.27.223; 7.AH.27.240; 7.AH.27.244; 7.AH.27.243; 7.AH.27.247; 7.AH.29.157; 7.AH.29.158; 7.AH.29.196; 7.AH.29.223; 7.AH.29.240; 7.AH.29.244; 7.AH.29.243; 7.AH.29.247; 7.AH.54.157; 7.AH.54.158; 7.AH.54.196; 7.AH.54.223; 7.AH.54.240; 7.AH.54.244; 7.AH.54.243; 7.AH.54.247; 7.AH.55.157; 7.AH.55.158; 7.AH.55.196; 7.AH.55.223; 7.AH.55.240; 7.AH.55.244; 7.AH.55.243; 7.AH.55.247; 7.AH.56.157; 7.AH.56.158; 7.AH.56.196; 7.AH.56.223; 7.AH.56.240; 7.AH.56.244; 7.AH.56.243; 7.AH.56.247; 7.AH.157.157; 7.AH.157.158; 7.AH.157.196; 7.AH.157.223; 7.AH.157.240; 7.AH.157.244; 7.AH.157.243; 7.AH.157.247; 7.AH.196.157; 7.AH.196.158; 7.AH.196.196; 7.AH.196.223; 7.AH.196.240; 7.AH.196.244; 7.AH.196.243; 7.AH.196.247; 7.AH.223.157; 7.AH.223.158; 7.AH.223.196; 7.AH.223.223; 7.AH.223.240; 7.AH.223.244; 7.AH.223.243; 7.AH.223.247; 7.AH.240.157; 7.AH.240.158; 7.AH.240.196; 7.AH.240.223; 7.AH.240.240; 7.AH.240.244; 7.AH.240.243; 7.AH.240.247; 7.AH.244.157; 7.AH.244.158; 7.AH.244.196; 7.AH.244.223; 7.AH.244.240; 7.AH.244.244; 7.AH.244.243; 7.AH.244.247; 7.AH.247.157; 7.AH.247.158; 7.AH.247.196; 7.AH.247.223; 7.AH.247.240; 7.AH.247.244; 7.AH.247.243; 7.AH.247.247;

Prodrugs of 7.AJ

7.AJ.4.157; 7.AJ.4.158; 7.AJ.4.196; 7.AJ.4.223; 7.AJ.4.240; 7.AJ.4.244; 7.AJ.4.243; 7.AJ.4.247; 7.AJ.5.157; 7.AJ.5.158; 7.AJ.5.196; 7.AJ.5.223; 7.AJ.5.240; 7.AJ.5.244; 7.AJ.5.243; 7.AJ.5.247; 7.AJ.7.157; 7.AJ.7.158; 7.AJ.7.196; 7.AJ.7.223; 7.AJ.7.240; 7.AJ.7.244; 7.AJ.7.243; 7.AJ.7.247; 7.AJ.15.157; 7.AJ.15.158; 7.AJ.15.196; 7.AJ.15.223; 7.AJ.15.240; 7.AJ.15.244; 7.AJ.15.243; 7.AJ.15.247; 7.AJ.16.157; 7.AJ.16.158; 7.AJ.16.196; 7.AJ.16.223; 7.AJ.16.240; 7.AJ.16.244; 7.AJ.16.243; 7.AJ.16.247; 7.AJ.18.157; 7.AJ.18.158; 7.AJ.18.196; 7.AJ.18.223; 7.AJ.18.240; 7.AJ.18.244; 7.AJ.18.243; 7.AJ.18.247; 7.AJ.26.157; 7.AJ.26.158; 7.AJ.26.196; 7.AJ.26.223; 7.AJ.26.240; 7.AJ.26.244; 7.AJ.26.243; 7.AJ.26.247; 7.AJ.27.157; 7.AJ.27.158; 7.AJ.27.196; 7.AJ.27.223;

TABLE 100-continued

7.AJ.27.240; 7.AJ.27.244; 7.AJ.27.243; 7.AJ.27.247; 7.AJ.29.157; 7.AJ.29.158; 7.AJ.29.196; 7.AJ.29.223; 7.AJ.29.240; 7.AJ.29.244; 7.AJ.29.243; 7.AJ.29.247; 7.AJ.54.157; 7.AJ.54.158; 7.AJ.54.196; 7.AJ.54.223; 7.AJ.54.240; 7.AJ.54.244; 7.AJ.54.243; 7.AJ.54.247; 7.AJ.55.157; 7.AJ.55.158; 7.AJ.55.196; 7.AJ.55.223; 7.AJ.55.240; 7.AJ.55.244; 7.AJ.55.243; 7.AJ.55.247; 7.AJ.56.157; 7.AJ.56.158; 7.AJ.56.196; 7.AJ.56.223; 7.AJ.56.240; 7.AJ.56.244; 7.AJ.56.243; 7.AJ.56.247; 7.AJ.157.157; 7.AJ.157.158; 7.AJ.157.196; 7.AJ.157.223; 7.AJ.157.240; 7.AJ.157.244; 7.AJ.157.243; 7.AJ.157.247; 7.AJ.196.157; 7.AJ.196.158; 7.AJ.196.196; 7.AJ.196.223; 7.AJ.196.240; 7.AJ.196.244; 7.AJ.196.243; 7.AJ.196.247; 7.AJ.223.157; 7.AJ.223.158; 7.AJ.223.196; 7.AJ.223.223; 7.AJ.223.240; 7.AJ.223.244; 7.AJ.223.243; 7.AJ.223.247; 7.AJ.240.157; 7.AJ.240.158; 7.AJ.240.196; 7.AJ.240.223; 7.AJ.240.240; 7.AJ.240.244; 7.AJ.240.243; 7.AJ.240.247; 7.AJ.244.157; 7.AJ.244.158; 7.AJ.244.196; 7.AJ.244.223; 7.AJ.244.240; 7.AJ.244.244; 7.AJ.244.243; 7.AJ.244.247; 7.AJ.247.157; 7.AJ.247.158; 7.AJ.247.196; 7.AJ.247.223; 7.AJ.247.240; 7.AJ.247.244; 7.AJ.247.243; 7.AJ.247.247;

Prodrugs of 7.AN

7.AN.4.157; 7.AN.4.158; 7.AN.4.196; 7.AN.4.223; 7.AN.4.240; 7.AN.4.244; 7.AN.4.243; 7.AN.4.247; 7.AN.5.157; 7.AN.5.158; 7.AN.5.196; 7.AN.5.223; 7.AN.5.240; 7.AN.5.244; 7.AN.5.243; 7.AN.5.247; 7.AN.7.157; 7.AN.7.158; 7.AN.7.196; 7.AN.7.223; 7.AN.7.240; 7.AN.7.244; 7.AN.7.243; 7.AN.7.247; 7.AN.15.157; 7.AN.15.158; 7.AN.15.196; 7.AN.15.223; 7.AN.15.240; 7.AN.15.244; 7.AN.15.243; 7.AN.15.247; 7.AN.16.157; 7.AN.16.158; 7.AN.16.196; 7.AN.16.223; 7.AN.16.240; 7.AN.16.244; 7.AN.16.243; 7.AN.16.247; 7.AN.18.157; 7.AN.18.158; 7.AN.18.196; 7.AN.18.223; 7.AN.18.240; 7.AN.18.244; 7.AN.18.243; 7.AN.18.247; 7.AN.26.157; 7.AN.26.158; 7.AN.26.196; 7.AN.26.223; 7.AN.26.240; 7.AN.26.244; 7.AN.26.243; 7.AN.26.247; 7.AN.27.157; 7.AN.27.158; 7.AN.27.196; 7.AN.27.223; 7.AN.27.240; 7.AN.27.244; 7.AN.27.243; 7.AN.27.247; 7.AN.29.157; 7.AN.29.158; 7.AN.29.196; 7.AN.29.223; 7.AN.29.240; 7.AN.29.244; 7.AN.29.243; 7.AN.29.247; 7.AN.54.157; 7.AN.54.158; 7.AN.54.196; 7.AN.54.223; 7.AN.54.240; 7.AN.54.244; 7.AN.54.243; 7.AN.54.247; 7.AN.55.157; 7.AN.55.158; 7.AN.55.196; 7.AN.55.223; 7.AN.55.240; 7.AN.55.244; 7.AN.55.243; 7.AN.55.247; 7.AN.56.157; 7.AN.56.158; 7.AN.56.196; 7.AN.56.223; 7.AN.56.240; 7.AN.56.244; 7.AN.56.243; 7.AN.56.247; 7.AN.157.157; 7.AN.157.158; 7.AN.157.196; 7.AN.157.223; 7.AN.157.240; 7.AN.157.244; 7.AN.157.243; 7.AN.157.247; 7.AN.196.157; 7.AN.196.158; 7.AN.196.196; 7.AN.196.223; 7.AN.196.240; 7.AN.196.244; 7.AN.196.243; 7.AN.196.247; 7.AN.223.157; 7.AN.223.158; 7.AN.223.196; 7.AN.223.223; 7.AN.223.240; 7.AN.223.244; 7.AN.223.243; 7.AN.223.247; 7.AN.240.157; 7.AN.240.158; 7.AN.240.196; 7.AN.240.223; 7.AN.240.240; 7.AN.240.244; 7.AN.240.243; 7.AN.240.247; 7.AN.244.157; 7.AN.244.158; 7.AN.244.196; 7.AN.244.223; 7.AN.244.240; 7.AN.244.244; 7.AN.244.243; 7.AN.244.247; 7.AN.247.157; 7.AN.247.158; 7.AN.247.196; 7.AN.247.223; 7.AN.247.240; 7.AN.247.244; 7.AN.247.243; 7.AN.247.247;

Prodrugs of 7.AP

7.AP.4.157; 7.AP.4.158; 7.AP.4.196; 7.AP.4.223; 7.AP.4.240; 7.AP.4.244; 7.AP.4.243; 7.AP.4.247; 7.AP.5.157; 7.AP.5.158; 7.AP.5.196; 7.AP.5.223; 7.AP.5.240; 7.AP.5.244; 7.AP.5.243; 7.AP.5.247; 7.AP.7.157; 7.AP.7.158; 7.AP.7.196; 7.AP.7.223; 7.AP.7.240; 7.AP.7.244; 7.AP.7.243; 7.AP.7.247; 7.AP.15.157; 7.AP.15.158; 7.AP.15.196; 7.AP.15.223; 7.AP.15.240; 7.AP.15.244; 7.AP.15.243; 7.AP.15.247; 7.AP.16.157; 7.AP.16.158; 7.AP.16.196; 7.AP.16.223; 7.AP.16.240; 7.AP.16.244; 7.AP.16.243; 7.AP.16.247; 7.AP.18.157; 7.AP.18.158; 7.AP.18.196; 7.AP.18.223; 7.AP.18.240; 7.AP.18.244; 7.AP.18.243; 7.AP.18.247; 7.AP.26.157; 7.AP.26.158; 7.AP.26.196; 7.AP.26.223; 7.AP.26.240; 7.AP.26.244; 7.AP.26.243; 7.AP.26.247; 7.AP.27.157; 7.AP.27.158; 7.AP.27.196; 7.AP.27.223; 7.AP.27.240; 7.AP.27.244; 7.AP.27.243; 7.AP.27.247; 7.AP.29.157; 7.AP.29.158; 7.AP.29.196; 7.AP.29.223; 7.AP.29.240; 7.AP.29.244; 7.AP.29.243; 7.AP.29.247; 7.AP.54.157; 7.AP.54.158; 7.AP.54.196; 7.AP.54.223; 7.AP.54.240; 7.AP.54.244; 7.AP.54.243; 7.AP.54.247; 7.AP.55.157; 7.AP.55.158; 7.AP.55.196; 7.AP.55.223; 7.AP.55.240; 7.AP.55.244; 7.AP.55.243; 7.AP.55.247; 7.AP.56.157; 7.AP.56.158; 7.AP.56.196; 7.AP.56.223; 7.AP.56.240; 7.AP.56.244; 7.AP.56.243; 7.AP.56.247; 7.AP.157.157; 7.AP.157.158; 7.AP.157.196; 7.AP.157.223; 7.AP.157.240; 7.AP.157.244; 7.AP.157.243; 7.AP.157.247; 7.AP.196.157; 7.AP.196.158; 7.AP.196.196; 7.AP.196.223; 7.AP.196.240; 7.AP.196.244; 7.AP.196.243; 7.AP.196.247; 7.AP.223.157; 7.AP.223.158; 7.AP.223.196; 7.AP.223.223; 7.AP.223.240; 7.AP.223.244; 7.AP.223.243; 7.AP.223.247; 7.AP.240.157; 7.AP.240.158; 7.AP.240.196; 7.AP.240.223; 7.AP.240.240; 7.AP.240.244; 7.AP.240.243; 7.AP.240.247; 7.AP.244.157; 7.AP.244.158; 7.AP.244.196; 7.AP.244.223; 7.AP.244.240; 7.AP.244.244; 7.AP.244.243; 7.AP.244.247; 7.AP.247.157; 7.AP.247.158; 7.AP.247.196; 7.AP.247.223; 7.AP.247.240; 7.AP.247.244; 7.AP.247.243; 7.AP.247.247;

TABLE 100-continued

Prodrugs of 7.AZ

7.AZ.4.157; 7.AZ.4.158; 7.AZ.4.196; 7.AZ.4.223; 7.AZ.4.240; 7.AZ.4.244; 7.AZ.4.243; 7.AZ.4.247; 7.AZ.5.157; 7.AZ.5.158; 7.AZ.5.196; 7.AZ.5.223; 7.AZ.5.240; 7.AZ.5.244; 7.AZ.5.243; 7.AZ.5.247; 7.AZ.7.157; 7.AZ.7.158; 7.AZ.7.196; 7.AZ.7.223; 7.AZ.7.240; 7.AZ.7.244; 7.AZ.7.243; 7.AZ.7.247; 7.AZ.15.157; 7.AZ.15.158; 7.AZ.15.196; 7.AZ.15.223; 7.AZ.15.240; 7.AZ.15.244; 7.AZ.15.243; 7.AZ.15.247; 7.AZ.16.157; 7.AZ.16.158; 7.AZ.16.196; 7.AZ.16.223; 7.AZ.16.240; 7.AZ.16.244; 7.AZ.16.243; 7.AZ.16.247; 7.AZ.18.157; 7.AZ.18.158; 7.AZ.18.196; 7.AZ.18.223; 7.AZ.18.240; 7.AZ.18.244; 7.AZ.18.243; 7.AZ.18.247; 7.AZ.26.157; 7.AZ.26.158; 7.AZ.26.196; 7.AZ.26.223; 7.AZ.26.240; 7.AZ.26.244; 7.AZ.26.243; 7.AZ.26.247; 7.AZ.27.157; 7.AZ.27.158; 7.AZ.27.196; 7.AZ.27.223; 7.AZ.27.240; 7.AZ.27.244; 7.AZ.27.243; 7.AZ.27.247; 7.AZ.29.157; 7.AZ.29.158; 7.AZ.29.196; 7.AZ.29.223; 7.AZ.29.240; 7.AZ.29.244; 7.AZ.29.243; 7.AZ.29.247; 7.AZ.54.157; 7.AZ.54.158; 7.AZ.54.196; 7.AZ.54.223; 7.AZ.54.240; 7.AZ.54.244; 7.AZ.54.243; 7.AZ.54.247; 7.AZ.55.157; 7.AZ.55.158; 7.AZ.55.196; 7.AZ.55.223; 7.AZ.55.240; 7.AZ.55.244; 7.AZ.55.243; 7.AZ.55.247; 7.AZ.56.157; 7.AZ.56.158; 7.AZ.56.196; 7.AZ.56.223; 7.AZ.56.240; 7.AZ.56.244; 7.AZ.56.243; 7.AZ.56.247; 7.AZ.157.157; 7.AZ.157.158; 7.AZ.157.196; 7.AZ.157.223; 7.AZ.157.240; 7.AZ.157.244; 7.AZ.157.243; 7.AZ.157.247; 7.AZ.196.157; 7.AZ.196.158; 7.AZ.196.196; 7.AZ.196.223; 7.AZ.196.240; 7.AZ.196.244; 7.AZ.196.243; 7.AZ.196.247; 7.AZ.223.157; 7.AZ.223.158; 7.AZ.223.196; 7.AZ.223.223; 7.AZ.223.240; 7.AZ.223.244; 7.AZ.223.243; 7.AZ.223.247; 7.AZ.240.157; 7.AZ.240.158; 7.AZ.240.196; 7.AZ.240.223; 7.AZ.240.240; 7.AZ.240.244; 7.AZ.240.243; 7.AZ.240.247; 7.AZ.244.157; 7.AZ.244.158; 7.AZ.244.196; 7.AZ.244.223; 7.AZ.244.240; 7.AZ.244.244; 7.AZ.244.243; 7.AZ.244.247; 7.AZ.247.157; 7.AZ.247.158; 7.AZ.247.196; 7.AZ.247.223; 7.AZ.247.240; 7.AZ.247.244; 7.AZ.247.243; 7.AZ.247.247;

Prodrugs of 7.BF

7.BF.4.157; 7.BF.4.158; 7.BF.4.196; 7.BF.4.223; 7.BF.4.240; 7.BF.4.244; 7.BF.4.243; 7.BF.4.247; 7.BF.5.157; 7.BF.5.158; 7.BF.5.196; 7.BF.5.223; 7.BF.5.240; 7.BF.5.244; 7.BF.5.243; 7.BF.5.247; 7.BF.7.157; 7.BF.7.158; 7.BF.7.196; 7.BF.7.223; 7.BF.7.240; 7.BF.7.244; 7.BF.7.243; 7.BF.7.247; 7.BF.15.157; 7.BF.15.158; 7.BF.15.196; 7.BF.15.223; 7.BF.15.240; 7.BF.15.244; 7.BF.15.243; 7.BF.15.247; 7.BF.16.157; 7.BF.16.158; 7.BF.16.196; 7.BF.16.223; 7.BF.16.240; 7.BF.16.244; 7.BF.16.243; 7.BF.16.247; 7.BF.18.157; 7.BF.18.158; 7.BF.18.196; 7.BF.18.223; 7.BF.18.240; 7.BF.18.244; 7.BF.18.243; 7.BF.18.247; 7.BF.26.157; 7.BF.26.158; 7.BF.26.196; 7.BF.26.223; 7.BF.26.240; 7.BF.26.244; 7.BF.26.243; 7.BF.26.247; 7.BF.27.157; 7.BF.27.158; 7.BF.27.196; 7.BF.27.223; 7.BF.27.240; 7.BF.27.244; 7.BF.27.243; 7.BF.27.247; 7.BF.29.157; 7.BF.29.158; 7.BF.29.196; 7.BF.29.223; 7.BF.29.240; 7.BF.29.244; 7.BF.29.243; 7.BF.29.247; 7.BF.54.157; 7.BF.54.158; 7.BF.54.196; 7.BF.54.223; 7.BF.54.240; 7.BF.54.244; 7.BF.54.243; 7.BF.54.247; 7.BF.55.157; 7.BF.55.158; 7.BF.55.196; 7.BF.55.223; 7.BF.55.240; 7.BF.55.244; 7.BF.55.243; 7.BF.55.247; 7.BF.56.157; 7.BF.56.158; 7.BF.56.196; 7.BF.56.223; 7.BF.56.240; 7.BF.56.244; 7.BF.56.243; 7.BF.56.247; 7.BF.157.157; 7.BF.157.158; 7.BF.157.196; 7.BF.157.223; 7.BF.157.240; 7.BF.157.244; 7.BF.157.243; 7.BF.157.247; 7.BF.196.157; 7.BF.196.158; 7.BF.196.196; 7.BF.196.223; 7.BF.196.240; 7.BF.196.244; 7.BF.196.243; 7.BF.196.247; 7.BF.223.157; 7.BF.223.158; 7.BF.223.196; 7.BF.223.223; 7.BF.223.240; 7.BF.223.244; 7.BF.223.243; 7.BF.223.247; 7.BF.240.157; 7.BF.240.158; 7.BF.240.196; 7.BF.240.223; 7.BF.240.240; 7.BF.240.244; 7.BF.240.243; 7.BF.240.247; 7.BF.244.157; 7.BF.244.158; 7.BF.244.196; 7.BF.244.223; 7.BF.244.240; 7.BF.244.244; 7.BF.244.243; 7.BF.244.247; 7.BF.247.157; 7.BF.247.158; 7.BF.247.196; 7.BF.247.223; 7.BF.247.240; 7.BF.247.244; 7.BF.247.243; 7.BF.247.247;

Prodrugs of 7.CI

7.CI.4.157; 7.CI.4.158; 7.CI.4.196; 7.CI.4.223; 7.CI.4.240; 7.CI.4.244; 7.CI.4.243; 7.CI.4.247; 7.CI.5.157; 7.CI.5.158; 7.CI.5.196; 7.CI.5.223; 7.CI.5.240; 7.CI.5.244; 7.CI.5.243; 7.CI.5.247; 7.CI.7.157; 7.CI.7.158; 7.CI.7.196; 7.CI.7.223; 7.CI.7.240; 7.CI.7.244; 7.CI.7.243; 7.CI.7.247; 7.CI.15.157; 7.CI.15.158; 7.CI.15.196; 7.CI.15.223; 7.CI.15.240; 7.CI.15.244; 7.CI.15.243; 7.CI.15.247; 7.CI.16.157; 7.CI.16.158; 7.CI.16.196; 7.CI.16.223; 7.CI.16.240; 7.CI.16.244; 7.CI.16.243; 7.CI.16.247; 7.CI.18.157; 7.CI.18.158; 7.CI.18.196; 7.CI.18.223; 7.CI.18.240; 7.CI.18.244; 7.CI.18.243; 7.CI.18.247; 7.CI.26.157; 7.CI.26.158; 7.CI.26.196; 7.CI.26.223; 7.CI.26.240; 7.CI.26.244; 7.CI.26.243; 7.CI.26.247; 7.CI.27.157; 7.CI.27.158; 7.CI.27.196; 7.CI.27.223; 7.CI.27.240; 7.CI.27.244; 7.CI.27.243; 7.CI.27.247; 7.CI.29.157; 7.CI.29.158; 7.CI.29.196; 7.CI.29.223; 7.CI.29.240; 7.CI.29.244; 7.CI.29.243; 7.CI.29.247; 7.CI.54.157; 7.CI.54.158; 7.CI.54.196; 7.CI.54.223; 7.CI.54.240; 7.CI.54.244; 7.CI.54.243; 7.CI.54.247; 7.CI.55.157; 7.CI.55.158; 7.CI.55.196; 7.CI.55.223; 7.CI.55.240; 7.CI.55.244; 7.CI.55.243; 7.CI.55.247; 7.CI.56.157; 7.CI.56.158; 7.CI.56.196; 7.CI.56.223; 7.CI.56.240; 7.CI.56.244; 7.CI.56.243; 7.CI.56.247; 7.CI.157.157; 7.CI.157.158; 7.CI.157.196; 7.CI.157.223; 7.CI.157.240;

TABLE 100-continued

7.CI.157.244; 7.CI.157.243; 7.CI.157.247; 7.CI.196.157; 7.CI.196.158; 7.CI.196.196; 7.CI.196.223; 7.CI.196.240; 7.CI.196.244; 7.CI.196.243; 7.CI.196.247; 7.CI.223.157; 7.CI.223.158; 7.CI.223.196; 7.CI.223.223; 7.CI.223.240; 7.CI.223.244; 7.CI.223.243; 7.CI.223.247; 7.CI.240.157; 7.CI.240.158; 7.CI.240.196; 7.CI.240.223; 7.CI.240.240; 7.CI.240.244; 7.CI.240.243; 7.CI.240.247; 7.CI.244.157; 7.CI.244.158; 7.CI.244.196; 7.CI.244.223; 7.CI.244.240; 7.CI.244.244; 7.CI.244.243; 7.CI.244.247; 7.CI.247.157; 7.CI.247.158; 7.CI.247.196; 7.CI.247.223; 7.CI.247.240; 7.CI.247.244; 7.CI.247.243; 7.CI.247.247;

Prodrugs of 7.CO

7.CO.4.157; 7.CO.4.158; 7.CO.4.196; 7.CO.4.223; 7.CO.4.240; 7.CO.4.244; 7.CO.4.243; 7.CO.4.247; 7.CO.5.157; 7.CO.5.158; 7.CO.5.196; 7.CO.5.223; 7.CO.5.240; 7.CO.5.244; 7.CO.5.243; 7.CO.5.247; 7.CO.7.157; 7.CO.7.158; 7.CO.7.196; 7.CO.7.223; 7.CO.7.240; 7.CO.7.244; 7.CO.7.243; 7.CO.7.247; 7.CO.15.157; 7.CO.15.158; 7.CO.15.196; 7.CO.15.223; 7.CO.15.240; 7.CO.15.244; 7.CO.15.243; 7.CO.15.247; 7.CO.16.157; 7.CO.16.158; 7.CO.16.196; 7.CO.16.223; 7.CO.16.240; 7.CO.16.244; 7.CO.16.243; 7.CO.16.247; 7.CO.18.157; 7.CO.18.158; 7.CO.18.196; 7.CO.18.223; 7.CO.18.240; 7.CO.18.244; 7.CO.18.243; 7.CO.18.247; 7.CO.26.157; 7.CO.26.158; 7.CO.26.196; 7.CO.26.223; 7.CO.26.240; 7.CO.26.244; 7.CO.26.243; 7.CO.26.247; 7.CO.27.157; 7.CO.27.158; 7.CO.27.196; 7.CO.27.223; 7.CO.27.240; 7.CO.27.244; 7.CO.27.243; 7.CO.27.247; 7.CO.29.157; 7.CO.29.158; 7.CO.29.196; 7.CO.29.223; 7.CO.29.240; 7.CO.29.244; 7.CO.29.243; 7.CO.29.247; 7.CO.54.157; 7.CO.54.158; 7.CO.54.196; 7.CO.54.223; 7.CO.54.240; 7.CO.54.244; 7.CO.54.243; 7.CO.54.247; 7.CO.55.157; 7.CO.55.158; 7.CO.55.196; 7.CO.55.223; 7.CO.55.240; 7.CO.55.244; 7.CO.55.243; 7.CO.55.247; 7.CO.56.157; 7.CO.56.158; 7.CO.56.196; 7.CO.56.223; 7.CO.56.240; 7.CO.56.244; 7.CO.56.243; 7.CO.56.247; 7.CO.157.157; 7.CO.157.158; 7.CO.157.196; 7.CO.157.223; 7.CO.157.240; 7.CO.157.244; 7.CO.157.243; 7.CO.157.247; 7.CO.196.157; 7.CO.196.158; 7.CO.196.196; 7.CO.196.223; 7.CO.196.240; 7.CO.196.244; 7.CO.196.243; 7.CO.196.247; 7.CO.223.157; 7.CO.223.158; 7.CO.223.196; 7.CO.223.223; 7.CO.223.240; 7.CO.223.244; 7.CO.223.243; 7.CO.223.247; 7.CO.240.157; 7.CO.240.158; 7.CO.240.196; 7.CO.240.223; 7.CO.240.240; 7.CO.240.244; 7.CO.240.243; 7.CO.240.247; 7.CO.244.157; 7.CO.244.158; 7.CO.244.196; 7.CO.244.223; 7.CO.244.240; 7.CO.244.244; 7.CO.244.243; 7.CO.244.247; 7.CO.4.157; 7.CO.4.158; 7.CO.4.196; 7.CO.4.223; 7.CO.4.240; 7.CO.4.244; 7.CO.4.243; 7.CO.4.247;

Prodrugs of 8.AH

8.AH.4.157; 8.AH.4.158; 8.AH.4.196; 8.AH.4.223; 8.AH.4.240; 8.AH.4.244; 8.AH.4.243; 8.AH.4.247; 8.AH.5.157; 8.AH.5.158; 8.AH.5.196; 8.AH.5.223; 8.AH.5.240; 8.AH.5.244; 8.AH.5.243; 8.AH.5.247; 8.AH.7.157; 8.AH.7.158; 8.AH.7.196; 8.AH.7.223; 8.AH.7.240; 8.AH.7.244; 8.AH.7.243; 8.AH.7.247; 8.AH.15.157; 8.AH.15.158; 8.AH.15.196; 8.AH.15.223; 8.AH.15.240; 8.AH.15.244; 8.AH.15.243; 8.AH.15.247; 8.AH.16.157; 8.AH.16.158; 8.AH.16.196; 8.AH.16.223; 8.AH.16.240; 8.AH.16.244; 8.AH.16.243; 8.AH.16.247; 8.AH.18.157; 8.AH.18.158; 8.AH.18.196; 8.AH.18.223; 8.AH.18.240; 8.AH.18.244; 8.AH.18.243; 8.AH.18.247; 8.AH.26.157; 8.AH.26.158; 8.AH.26.196; 8.AH.26.223; 8.AH.26.240; 8.AH.26.244; 8.AH.26.243; 8.AH.26.247; 8.AH.27.157; 8.AH.27.158; 8.AH.27.196; 8.AH.27.223; 8.AH.27.240; 8.AH.27.244; 8.AH.27.243; 8.AH.27.247; 8.AH.29.157; 8.AH.29.158; 8.AH.29.196; 8.AH.29.223; 8.AH.29.240; 8.AH.29.244; 8.AH.29.243; 8.AH.29.247; 8.AH.54.157; 8.AH.54.158; 8.AH.54.196; 8.AH.54.223; 8.AH.54.240; 8.AH.54.244; 8.AH.54.243; 8.AH.54.247; 8.AH.55.157; 8.AH.55.158; 8.AH.55.196; 8.AH.55.223; 8.AH.55.240; 8.AH.55.244; 8.AH.55.243; 8.AH.55.247; 8.AH.56.157; 8.AH.56.158; 8.AH.56.196; 8.AH.56.223; 8.AH.56.240; 8.AH.56.244; 8.AH.56.243; 8.AH.56.247; 8.AH.157.157; 8.AH.157.158; 8.AH.157.196; 8.AH.157.223; 8.AH.157.240; 8.AH.157.244; 8.AH.157.243; 8.AH.157.247; 8.AH.196.157; 8.AH.196.158; 8.AH.196.196; 8.AH.196.223; 8.AH.196.240; 8.AH.196.244; 8.AH.196.243; 8.AH.196.247; 8.AH.223.157; 8.AH.223.158; 8.AH.223.196; 8.AH.223.223; 8.AH.223.240; 8.AH.223.244; 8.AH.223.243; 8.AH.223.247; 8.AH.240.157; 8.AH.240.158; 8.AH.240.196; 8.AH.240.223; 8.AH.240.240; 8.AH.240.244; 8.AH.240.243; 8.AH.240.247; 8.AH.244.157; 8.AH.244.158; 8.AH.244.196; 8.AH.244.223; 8.AH.244.240; 8.AH.244.244; 8.AH.244.243; 8.AH.244.247; 8.AH.247.157; 8.AH.247.158; 8.AH.247.196; 8.AH.247.223; 8.AH.247.240; 8.AH.247.244; 8.AH.247.243; 8.AH.247.247;

Prodrugs of 8.AJ

8.AJ.4.157; 8.AJ.4.158; 8.AJ.4.196; 8.AJ.4.223; 8.AJ.4.240; 8.AJ.4.244; 8.AJ.4.243; 8.AJ.4.247; 8.AJ.5.157; 8.AJ.5.158; 8.AJ.5.196; 8.AJ.5.223; 8.AJ.5.240; 8.AJ.5.244; 8.AJ.5.243; 8.AJ.5.247; 8.AJ.7.157; 8.AJ.7.158; 8.AJ.7.196; 8.AJ.7.223; 8.AJ.7.240; 8.AJ.7.244; 8.AJ.7.243; 8.AJ.7.247; 8.AJ.15.157; 8.AJ.15.158; 8.AJ.15.196; 8.AJ.15.223; 8.AJ.15.240; 8.AJ.15.244; 8.AJ.15.243; 8.AJ.15.247; 8.AJ.16.157; 8.AJ.16.158; 8.AJ.16.196; 8.AJ.16.223; 8.AJ.16.240; 8.AJ.16.244; 8.AJ.16.243; 8.AJ.16.247; 8.AJ.18.157; 8.AJ.18.158; 8.AJ.18.196; 8.AJ.18.223; 8.AJ.18.240; 8.AJ.18.244; 8.AJ.18.243; 8.AJ.18.247;

TABLE 100-continued

8.AJ.26.157; 8.AJ.26.158; 8.AJ.26.196; 8.AJ.26.223; 8.AJ.26.240; 8.AJ.26.244; 8.AJ.26.243; 8.AJ.26.247; 8.AJ.27.157; 8.AJ.27.158; 8.AJ.27.196; 8.AJ.27.223; 8.AJ.27.240; 8.AJ.27.244; 8.AJ.27.243; 8.AJ.27.247; 8.AJ.29.157; 8.AJ.29.158; 8.AJ.29.196; 8.AJ.29.223; 8.AJ.29.240; 8.AJ.29.244; 8.AJ.29.243; 8.AJ.29.247; 8.AJ.54.157; 8.AJ.54.158; 8.AJ.54.196; 8.AJ.54.223; 8.AJ.54.240; 8.AJ.54.244; 8.AJ.54.243; 8.AJ.54.247; 8.AJ.55.157; 8.AJ.55.158; 8.AJ.55.196; 8.AJ.55.223; 8.AJ.55.240; 8.AJ.55.244; 8.AJ.55.243; 8.AJ.55.247; 8.AJ.56.157; 8.AJ.56.158; 8.AJ.56.196; 8.AJ.56.223; 8.AJ.56.240; 8.AJ.56.244; 8.AJ.56.243; 8.AJ.56.247; 8.AJ.157.157; 8.AJ.157.158; 8.AJ.157.196; 8.AJ.157.223; 8.AJ.157.240; 8.AJ.157.244; 8.AJ.157.243; 8.AJ.157.247; 8.AJ.196.157; 8.AJ.196.158; 8.AJ.196.196; 8.AJ.196.223; 8.AJ.196.240; 8.AJ.196.244; 8.AJ.196.243; 8.AJ.196.247; 8.AJ.223.157; 8.AJ.223.158; 8.AJ.223.196; 8.AJ.223.223; 8.AJ.223.240; 8.AJ.223.244; 8.AJ.223.243; 8.AJ.223.247; 8.AJ.240.157; 8.AJ.240.158; 8.AJ.240.196; 8.AJ.240.223; 8.AJ.240.240; 8.AJ.240.244; 8.AJ.240.243; 8.AJ.240.247; 8.AJ.244.157; 8.AJ.244.158; 8.AJ.244.196; 8.AJ.244.223; 8.AJ.244.240; 8.AJ.244.244; 8.AJ.244.243; 8.AJ.244.247; 8.AJ.247.157; 8.AJ.247.158; 8.AJ.247.196; 8.AJ.247.223; 8.AJ.247.240; 8.AJ.247.244; 8.AJ.247.243; 8.AJ.247.247;

Prodrugs of 8.AN

8.AN.4.157; 8.AN.4.158; 8.AN.4.196; 8.AN.4.223; 8.AN.4.240; 8.AN.4.244; 8.AN.4.243; 8.AN.4.247; 8.AN.5.157; 8.AN.5.158; 8.AN.5.196; 8.AN.5.223; 8.AN.5.240; 8.AN.5.244; 8.AN.5.243; 8.AN.5.247; 8.AN.7.157; 8.AN.7.158; 8.AN.7.196; 8.AN.7.223; 8.AN.7.240; 8.AN.7.244; 8.AN.7.243; 8.AN.7.247; 8.AN.15.157; 8.AN.15.158; 8.AN.15.196; 8.AN.15.223; 8.AN.15.240; 8.AN.15.244; 8.AN.15.243; 8.AN.15.247; 8.AN.16.157; 8.AN.16.158; 8.AN.16.196; 8.AN.16.223; 8.AN.16.240; 8.AN.16.244; 8.AN.16.243; 8.AN.16.247; 8.AN.18.157; 8.AN.18.158; 8.AN.18.196; 8.AN.18.223; 8.AN.18.240; 8.AN.18.244; 8.AN.18.243; 8.AN.18.247; 8.AN.26.157; 8.AN.26.158; 8.AN.26.196; 8.AN.26.223; 8.AN.26.240; 8.AN.26.244; 8.AN.26.243; 8.AN.26.247; 8.AN.27.157; 8.AN.27.158; 8.AN.27.196; 8.AN.27.223; 8.AN.27.240; 8.AN.27.244; 8.AN.27.243; 8.AN.27.247; 8.AN.29.157; 8.AN.29.158; 8.AN.29.196; 8.AN.29.223; 8.AN.29.240; 8.AN.29.244; 8.AN.29.243; 8.AN.29.247; 8.AN.54.157; 8.AN.54.158; 8.AN.54.196; 8.AN.54.223; 8.AN.54.240; 8.AN.54.244; 8.AN.54.243; 8.AN.54.247; 8.AN.55.157; 8.AN.55.158; 8.AN.55.196; 8.AN.55.223; 8.AN.55.240; 8.AN.55.244; 8.AN.55.243; 8.AN.55.247; 8.AN.56.157; 8.AN.56.158; 8.AN.56.196; 8.AN.56.223; 8.AN.56.240; 8.AN.56.244; 8.AN.56.243; 8.AN.56.247; 8.AN.157.157; 8.AN.157.158; 8.AN.157.196; 8.AN.157.223; 8.AN.157.240; 8.AN.157.244; 8.AN.157.243; 8.AN.157.247; 8.AN.196.157; 8.AN.196.158; 8.AN.196.196; 8.AN.196.223; 8.AN.196.240; 8.AN.196.244; 8.AN.196.243; 8.AN.196.247; 8.AN.223.157; 8.AN.223.158; 8.AN.223.196; 8.AN.223.223; 8.AN.223.240; 8.AN.223.244; 8.AN.223.243; 8.AN.223.247; 8.AN.240.157; 8.AN.240.158; 8.AN.240.196; 8.AN.240.223; 8.AN.240.240; 8.AN.240.244; 8.AN.240.243; 8.AN.240.247; 8.AN.244.157; 8.AN.244.158; 8.AN.244.196; 8.AN.244.223; 8.AN.244.240; 8.AN.244.244; 8.AN.244.243; 8.AN.244.247; 8.AN.247.157; 8.AN.247.158; 8.AN.247.196; 8.AN.247.223; 8.AN.247.240; 8.AN.247.244; 8.AN.247.243; 8.AN.247.247;

Prodrugs of 8.AP

8.AP.4.157; 8.AP.4.158; 8.AP.4.196; 8.AP.4.223; 8.AP.4.240; 8.AP.4.244; 8.AP.4.243; 8.AP.4.247; 8.AP.5.157; 8.AP.5.158; 8.AP.5.196; 8.AP.5.223; 8.AP.5.240; 8.AP.5.244; 8.AP.5.243; 8.AP.5.247; 8.AP.7.157; 8.AP.7.158; 8.AP.7.196; 8.AP.7.223; 8.AP.7.240; 8.AP.7.244; 8.AP.7.243; 8.AP.7.247; 8.AP.15.157; 8.AP.15.158; 8.AP.15.196; 8.AP.15.223; 8.AP.15.240; 8.AP.15.244; 8.AP.15.243; 8.AP.15.247; 8.AP.16.157; 8.AP.16.158; 8.AP.16.196; 8.AP.16.223; 8.AP.16.240; 8.AP.16.244; 8.AP.16.243; 8.AP.16.247; 8.AP.18.157; 8.AP.18.158; 8.AP.18.196; 8.AP.18.223; 8.AP.18.240; 8.AP.18.244; 8.AP.18.243; 8.AP.18.247; 8.AP.26.157; 8.AP.26.158; 8.AP.26.196; 8.AP.26.223; 8.AP.26.240; 8.AP.26.244; 8.AP.26.243; 8.AP.26.247; 8.AP.27.157; 8.AP.27.158; 8.AP.27.196; 8.AP.27.223; 8.AP.27.240; 8.AP.27.244; 8.AP.27.243; 8.AP.27.247; 8.AP.29.157; 8.AP.29.158; 8.AP.29.196; 8.AP.29.223; 8.AP.29.240; 8.AP.29.244; 8.AP.29.243; 8.AP.29.247; 8.AP.54.157; 8.AP.54.158; 8.AP.54.196; 8.AP.54.223; 8.AP.54.240; 8.AP.54.244; 8.AP.54.243; 8.AP.54.247; 8.AP.55.157; 8.AP.55.158; 8.AP.55.196; 8.AP.55.223; 8.AP.55.240; 8.AP.55.244; 8.AP.55.243; 8.AP.55.247; 8.AP.56.157; 8.AP.56.158; 8.AP.56.196; 8.AP.56.223; 8.AP.56.240; 8.AP.56.244; 8.AP.56.243; 8.AP.56.247; 8.AP.157.157; 8.AP.157.158; 8.AP.157.196; 8.AP.157.223; 8.AP.157.240; 8.AP.157.244; 8.AP.157.243; 8.AP.157.247; 8.AP.196.157; 8.AP.196.158; 8.AP.196.196; 8.AP.196.223; 8.AP.196.240; 8.AP.196.244; 8.AP.196.243; 8.AP.196.247; 8.AP.223.157; 8.AP.223.158; 8.AP.223.196; 8.AP.223.223; 8.AP.223.240; 8.AP.223.244; 8.AP.223.243; 8.AP.223.247; 8.AP.240.157; 8.AP.240.158; 8.AP.240.196; 8.AP.240.223; 8.AP.240.240; 8.AP.240.244; 8.AP.240.243; 8.AP.240.247; 8.AP.244.157; 8.AP.244.158; 8.AP.244.196; 8.AP.244.223; 8.AP.244.240; 8.AP.244.244; 8.AP.244.243; 8.AP.244.247; 8.AP.247.157; 8.AP.247.158; 8.AP.247.196; 8.AP.247.223; 8.AP.247.240; 8.AP.247.244; 8.AP.247.243; 8.AP.247.247;

TABLE 100-continued

Prodrugs of 8.AZ

8.AZ.4.157; 8.AZ.4.158; 8.AZ.4.196; 8.AZ.4.223; 8.AZ.4.240; 8.AZ.4.244;
8.AZ.4.243; 8.AZ.4.247; 8.AZ.5.157; 8.AZ.5.158; 8.AZ.5.196; 8.AZ.5.223;
8.AZ.5.240; 8.AZ.5.244; 8.AZ.5.243; 8.AZ.5.247; 8.AZ.7.157; 8.AZ.7.158;
8.AZ.7.196; 8.AZ.7.223; 8.AZ.7.240; 8.AZ.7.244; 8.AZ.7.243; 8.AZ.7.247;
8.AZ.15.157; 8.AZ.15.158; 8.AZ.15.196; 8.AZ.15.223; 8.AZ.15.240;
8.AZ.15.244; 8.AZ.15.243; 8.AZ.15.247; 8.AZ.16.157; 8.AZ.16.158;
8.AZ.16.196; 8.AZ.16.223; 8.AZ.16.240; 8.AZ.16.244; 8.AZ.16.243;
8.AZ.16.247; 8.AZ.18.157; 8.AZ.18.158; 8.AZ.18.196; 8.AZ.18.223;
8.AZ.18.240; 8.AZ.18.244; 8.AZ.18.243; 8.AZ.18.247; 8.AZ.26.157;
8.AZ.26.158; 8.AZ.26.196; 8.AZ.26.223; 8.AZ.26.240; 8.AZ.26.244;
8.AZ.26.243; 8.AZ.26.247; 8.AZ.27.157; 8.AZ.27.158; 8.AZ.27.196;
8.AZ.27.223; 8.AZ.27.240; 8.AZ.27.244; 8.AZ.27.243; 8.AZ.27.247;
8.AZ.29.157; 8.AZ.29.158; 8.AZ.29.196; 8.AZ.29.223; 8.AZ.29.240;
8.AZ.29.244; 8.AZ.29.243; 8.AZ.29.247; 8.AZ.54.157; 8.AZ.54.158;
8.AZ.54.196; 8.AZ.54.223; 8.AZ.54.240; 8.AZ.54.244; 8.AZ.54.243;
8.AZ.54.247; 8.AZ.55.157; 8.AZ.55.158; 8.AZ.55.196; 8.AZ.55.223;
8.AZ.55.240; 8.AZ.55.244; 8.AZ.55.243; 8.AZ.55.247; 8.AZ.56.157;
8.AZ.56.158; 8.AZ.56.196; 8.AZ.56.223; 8.AZ.56.240; 8.AZ.56.244;
8.AZ.56.243; 8.AZ.56.247; 8.AZ.157.157; 8.AZ.157.158; 8.AZ.157.196;
8.AZ.157.223; 8.AZ.157.240; 8.AZ.157.244; 8.AZ.157.243; 8.AZ.157.247;
8.AZ.196.157; 8.AZ.196.158; 8.AZ.196.196; 8.AZ.196.223; 8.AZ.196.240;
8.AZ.196.244; 8.AZ.196.243; 8.AZ.196.247; 8.AZ.223.157; 8.AZ.223.158;
8.AZ.223.196; 8.AZ.223.223; 8.AZ.223.240; 8.AZ.223.244; 8.AZ.223.243;
8.AZ.223.247; 8.AZ.240.157; 8.AZ.240.158; 8.AZ.240.196; 8.AZ.240.223;
8.AZ.240.240; 8.AZ.240.244; 8.AZ.240.243; 8.AZ.240.247; 8.AZ.244.157;
8.AZ.244.158; 8.AZ.244.196; 8.AZ.244.223; 8.AZ.244.240; 8.AZ.244.244;
8.AZ.244.243; 8.AZ.244.247; 8.AZ.247.157; 8.AZ.247.158; 8.AZ.247.196;
8.AZ.247.223; 8.AZ.247.240; 8.AZ.247.244; 8.AZ.247.243; 8.AZ.247.247;

Prodrugs of 8.BF

8.BF.4.157; 8.BF.4.158; 8.BF.4.196; 8.BF.4.223; 8.BF.4.240; 8.BF.4.244;
8.BF.4.243; 8.BF.4.247; 8.BF.5.157; 8.BF.5.158; 8.BF.5.196; 8.BF.5.223;
8.BF.5.240; 8.BF.5.244; 8.BF.5.243; 8.BF.5.247; 8.BF.7.157; 8.BF.7.158;
8.BF.7.196; 8.BF.7.223; 8.BF.7.240; 8.BF.7.244; 8.BF.7.243; 8.BF.7.247;
8.BF.15.157; 8.BF.15.158; 8.BF.15.196; 8.BF.15.223; 8.BF.15.240;
8.BF.15.244; 8.BF.15.243; 8.BF.15.247; 8.BF.16.157; 8.BF.16.158;
8.BF.16.196; 8.BF.16.223; 8.BF.16.240; 8.BF.16.244; 8.BF.16.243;
8.BF.16.247; 8.BF.18.157; 8.BF.18.158; 8.BF.18.196; 8.BF.18.223;
8.BF.18.240; 8.BF.18.244; 8.BF.18.243; 8.BF.18.247; 8.BF.26.157;
8.BF.26.158; 8.BF.26.196; 8.BF.26.223; 8.BF.26.240; 8.BF.26.244;
8.BF.26.243; 8.BF.26.247; 8.BF.27.157; 8.BF.27.158; 8.BF.27.196;
8.BF.27.223; 8.BF.27.240; 8.BF.27.244; 8.BF.27.243; 8.BF.27.247;
8.BF.29.157; 8.BF.29.158; 8.BF.29.196; 8.BF.29.223; 8.BF.29.240;
8.BF.29.244; 8.BF.29.243; 8.BF.29.247; 8.BF.54.157; 8.BF.54.158;
8.BF.54.196; 8.BF.54.223; 8.BF.54.240; 8.BF.54.244; 8.BF.54.243;
8.BF.54.247; 8.BF.55.157; 8.BF.55.158; 8.BF.55.196; 8.BF.55.223;
8.BF.55.240; 8.BF.55.244; 8.BF.55.243; 8.BF.55.247; 8.BF.56.157;
8.BF.56.158; 8.BF.56.196; 8.BF.56.223; 8.BF.56.240; 8.BF.56.244;
8.BF.56.243; 8.BF.56.247; 8.BF.157.157; 8.BF.157.158; 8.BF.157.196;
8.BF.157.223; 8.BF.157.240; 8.BF.157.244; 8.BF.157.243; 8.BF.157.247;
8.BF.196.157; 8.BF.196.158; 8.BF.196.196; 8.BF.196.223; 8.BF.196.240;
8.BF.196.244; 8.BF.196.243; 8.BF.196.247; 8.BF.223.157; 8.BF.223.158;
8.BF.223.196; 8.BF.223.223; 8.BF.223.240; 8.BF.223.244; 8.BF.223.243;
8.BF.223.247; 8.BF.240.157; 8.BF.240.158; 8.BF.240.196; 8.BF.240.223;
8.BF.240.240; 8.BF.240.244; 8.BF.240.243; 8.BF.240.247; 8.BF.244.157;
8.BF.244.158; 8.BF.244.196; 8.BF.244.223; 8.BF.244.240; 8.BF.244.244;
8.BF.244.243; 8.BF.244.247; 8.BF.247.157; 8.BF.247.158; 8.BF.247.196;
8.BF.247.223; 8.BF.247.240; 8.BF.247.244; 8.BF.247.243; 8.BF.247.247;

Prodrugs of 8.CI

8.CI.4.157; 8.CI.4.158; 8.CI.4.196; 8.CI.4.223; 8.CI.4.240; 8.CI.4.244;
8.CI.4.243; 8.CI.4.247; 8.CI.5.157; 8.CI.5.158; 8.CI.5.196; 8.CI.5.223;
8.CI.5.240; 8.CI.5.244; 8.CI.5.243; 8.CI.5.247; 8.CI.7.157; 8.CI.7.158;
8.CI.7.196; 8.CI.7.223; 8.CI.7.240; 8.CI.7.244; 8.CI.7.243; 8.CI.7.247;
8.CI.15.157; 8.CI.15.158; 8.CI.15.196; 8.CI.15.223; 8.CI.15.240; 8.CI.15.244;
8.CI.15.243; 8.CI.15.247; 8.CI.16.157; 8.CI.16.158; 8.CI.16.196; 8.CI.16.223;
8.CI.16.240; 8.CI.16.244; 8.CI.16.243; 8.CI.16.247; 8.CI.18.157; 8.CI.18.158;
8.CI.18.196; 8.CI.18.223; 8.CI.18.240; 8.CI.18.244; 8.CI.18.243; 8.CI.18.247;
8.CI.26.157; 8.CI.26.158; 8.CI.26.196; 8.CI.26.223; 8.CI.26.240; 8.CI.26.244;
8.CI.26.243; 8.CI.26.247; 8.CI.27.157; 8.CI.27.158; 8.CI.27.196; 8.CI.27.223;
8.CI.27.240; 8.CI.27.244; 8.CI.27.243; 8.CI.27.247; 8.CI.29.157; 8.CI.29.158;
8.CI.29.196; 8.CI.29.223; 8.CI.29.240; 8.CI.29.244; 8.CI.29.243; 8.CI.29.247;
8.CI.54.157; 8.CI.54.158; 8.CI.54.196; 8.CI.54.223; 8.CI.54.240; 8.CI.54.244;
8.CI.54.243; 8.CI.54.247; 8.CI.55.157; 8.CI.55.158; 8.CI.55.196; 8.CI.55.223;
8.CI.55.240; 8.CI.55.244; 8.CI.55.243; 8.CI.55.247; 8.CI.56.157; 8.CI.56.158;
8.CI.56.196; 8.CI.56.223; 8.CI.56.240; 8.CI.56.244; 8.CI.56.243; 8.CI.56.247;
8.CI.157.157; 8.CI.157.158; 8.CI.157.196; 8.CI.157.223; 8.CI.157.240;

TABLE 100-continued

8.CI.157.244; 8.CI.157.243; 8.CI.157.247; 8.CI.196.157; 8.CI.196.158; 8.CI.196.196; 8.CI.196.223; 8.CI.196.240; 8.CI.196.244; 8.CI.196.243; 8.CI.196.247; 8.CI.223.157; 8.CI.223.158; 8.CI.223.196; 8.CI.223.223; 8.CI.223.240; 8.CI.223.244; 8.CI.223.243; 8.CI.223.247; 8.CI.240.157; 8.CI.240.158; 8.CI.240.196; 8.CI.240.223; 8.CI.240.240; 8.CI.240.244; 8.CI.240.243; 8.CI.240.247; 8.CI.244.157; 8.CI.244.158; 8.CI.244.196; 8.CI.244.223; 8.CI.244.240; 8.CI.244.244; 8.CI.244.243; 8.CI.244.247; 8.CI.247.157; 8.CI.247.158; 8.CI.247.196; 8.CI.247.223; 8.CI.247.240; 8.CI.247.244; 8.CI.247.243; 8.CI.247.247;

Prodrugs of 8.CO

8.CO.4.157; 8.CO.4.158; 8.CO.4.196; 8.CO.4.223; 8.CO.4.240; 8.CO.4.244; 8.CO.4.243; 8.CO.4.247; 8.CO.5.157; 8.CO.5.158; 8.CO.5.196; 8.CO.5.223; 8.CO.5.240; 8.CO.5.244; 8.CO.5.243; 8.CO.5.247; 8.CO.7.157; 8.CO.7.158; 8.CO.7.196; 8.CO.7.223; 8.CO.7.240; 8.CO.7.244; 8.CO.7.243; 8.CO.7.247; 8.CO.15.157; 8.CO.15.158; 8.CO.15.196; 8.CO.15.223; 8.CO.15.240; 8.CO.15.244; 8.CO.15.243; 8.CO.15.247; 8.CO.16.157; 8.CO.16.158; 8.CO.16.196; 8.CO.16.223; 8.CO.16.240; 8.CO.16.244; 8.CO.16.243; 8.CO.16.247; 8.CO.18.157; 8.CO.18.158; 8.CO.18.196; 8.CO.18.223; 8.CO.18.240; 8.CO.18.244; 8.CO.18.243; 8.CO.18.247; 8.CO.26.157; 8.CO.26.158; 8.CO.26.196; 8.CO.26.223; 8.CO.26.240; 8.CO.26.244; 8.CO.26.243; 8.CO.26.247; 8.CO.27.157; 8.CO.27.158; 8.CO.27.196; 8.CO.27.223; 8.CO.27.240; 8.CO.27.244; 8.CO.27.243; 8.CO.27.247; 8.CO.29.157; 8.CO.29.158; 8.CO.29.196; 8.CO.29.223; 8.CO.29.240; 8.CO.29.244; 8.CO.29.243; 8.CO.29.247; 8.CO.54.157; 8.CO.54.158; 8.CO.54.196; 8.CO.54.223; 8.CO.54.240; 8.CO.54.244; 8.CO.54.243; 8.CO.54.247; 8.CO.55.157; 8.CO.55.158; 8.CO.55.196; 8.CO.55.223; 8.CO.55.240; 8.CO.55.244; 8.CO.55.243; 8.CO.55.247; 8.CO.56.157; 8.CO.56.158; 8.CO.56.196; 8.CO.56.223; 8.CO.56.240; 8.CO.56.244; 8.CO.56.243; 8.CO.56.247; 8.CO.157.157; 8.CO.157.158; 8.CO.157.196; 8.CO.157.223; 8.CO.157.240; 8.CO.157.244; 8.CO.157.243; 8.CO.157.247; 8.CO.196.157; 8.CO.196.158; 8.CO.196.196; 8.CO.196.223; 8.CO.196.240; 8.CO.196.244; 8.CO.196.243; 8.CO.196.247; 8.CO.223.157; 8.CO.223.158; 8.CO.223.196; 8.CO.223.223; 8.CO.223.240; 8.CO.223.244; 8.CO.223.243; 8.CO.223.247; 8.CO.240.157; 8.CO.240.158; 8.CO.240.196; 8.CO.240.223; 8.CO.240.240; 8.CO.240.244; 8.CO.240.243; 8.CO.240.247; 8.CO.244.157; 8.CO.244.158; 8.CO.244.196; 8.CO.244.223; 8.CO.244.240; 8.CO.244.244; 8.CO.244.243; 8.CO.244.247; 8.CO.247.157; 8.CO.247.158; 8.CO.247.196; 8.CO.247.223; 8.CO.247.240; 8.CO.247.244; 8.CO.247.243; 8.CO.247.247;

Prodrugs of 9.AH

9.AH.4.157; 9.AH.4.158; 9.AH.4.196; 9.AH.4.223; 9.AH.4.240; 9.AH.4.244; 9.AH.4.243; 9.AH.4.247; 9.AH.5.157; 9.AH.5.158; 9.AH.5.196; 9.AH.5.223; 9.AH.5.240; 9.AH.5.244; 9.AH.5.243; 9.AH.5.247; 9.AH.7.157; 9.AH.7.158; 9.AH.7.196; 9.AH.7.223; 9.AH.7.240; 9.AH.7.244; 9.AH.7.243; 9.AH.7.247; 9.AH.15.157; 9.AH.15.158; 9.AH.15.196; 9.AH.15.223; 9.AH.15.240; 9.AH.15.244; 9.AH.15.243; 9.AH.15.247; 9.AH.16.157; 9.AH.16.158; 9.AH.16.196; 9.AH.16.223; 9.AH.16.240; 9.AH.16.244; 9.AH.16.243; 9.AH.16.247; 9.AH.18.157; 9.AH.18.158; 9.AH.18.196; 9.AH.18.223; 9.AH.18.240; 9.AH.18.244; 9.AH.18.243; 9.AH.18.247; 9.AH.26.157; 9.AH.26.158; 9.AH.26.196; 9.AH.26.223; 9.AH.26.240; 9.AH.26.244; 9.AH.26.243; 9.AH.26.247; 9.AH.27.157; 9.AH.27.158; 9.AH.27.196; 9.AH.27.223; 9.AH.27.240; 9.AH.27.244; 9.AH.27.243; 9.AH.27.247; 9.AH.29.157; 9.AH.29.158; 9.AH.29.196; 9.AH.29.223; 9.AH.29.240; 9.AH.29.244; 9.AH.29.243; 9.AH.29.247; 9.AH.54.157; 9.AH.54.158; 9.AH.54.196; 9.AH.54.223; 9.AH.54.240; 9.AH.54.244; 9.AH.54.243; 9.AH.54.247; 9.AH.55.157; 9.AH.55.158; 9.AH.55.196; 9.AH.55.223; 9.AH.55.240; 9.AH.55.244; 9.AH.55.243; 9.AH.55.247; 9.AH.56.157; 9.AH.56.158; 9.AH.56.196; 9.AH.56.223; 9.AH.56.240; 9.AH.56.244; 9.AH.56.243; 9.AH.56.247; 9.AH.157.157; 9.AH.157.158; 9.AH.157.196; 9.AH.157.223; 9.AH.157.240; 9.AH.157.244; 9.AH.157.243; 9.AH.157.247; 9.AH.196.157; 9.AH.196.158; 9.AH.196.196; 9.AH.196.223; 9.AH.196.240; 9.AH.196.244; 9.AH.196.243; 9.AH.196.247; 9.AH.223.157; 9.AH.223.158; 9.AH.223.196; 9.AH.223.223; 9.AH.223.240; 9.AH.223.244; 9.AH.223.243; 9.AH.223.247; 9.AH.240.157; 9.AH.240.158; 9.AH.240.196; 9.AH.240.223; 9.AH.240.240; 9.AH.240.244; 9.AH.240.243; 9.AH.240.247; 9.AH.244.157; 9.AH.244.158; 9.AH.244.196; 9.AH.244.223; 9.AH.244.240; 9.AH.244.244; 9.AH.244.243; 9.AH.244.247; 9.AH.247.157; 9.AH.247.158; 9.AH.247.196; 9.AH.247.223; 9.AH.247.240; 9.AH.247.244; 9.AH.247.243; 9.AH.247.247;

Prodrugs of 9.AJ

9.AJ.4.157; 9.AJ.4.158; 9.AJ.4.196; 9.AJ.4.223; 9.AJ.4.240; 9.AJ.4.244; 9.AJ.4.243; 9.AJ.4.247; 9.AJ.5.157; 9.AJ.5.158; 9.AJ.5.196; 9.AJ.5.223; 9.AJ.5.240; 9.AJ.5.244; 9.AJ.5.243; 9.AJ.5.247; 9.AJ.7.157; 9.AJ.7.158; 9.AJ.7.196; 9.AJ.7.223; 9.AJ.7.240; 9.AJ.7.244; 9.AJ.7.243; 9.AJ.7.247; 9.AJ.15.157; 9.AJ.15.158; 9.AJ.15.196; 9.AJ.15.223; 9.AJ.15.240; 9.AJ.15.244; 9.AJ.15.243; 9.AJ.15.247; 9.AJ.16.157; 9.AJ.16.158; 9.AJ.16.196; 9.AJ.16.223; 9.AJ.16.240; 9.AJ.16.244; 9.AJ.16.243; 9.AJ.16.247; 9.AJ.18.157; 9.AJ.18.158; 9.AJ.18.196; 9.AJ.18.223; 9.AJ.18.240; 9.AJ.18.244; 9.AJ.18.243; 9.AJ.18.247;

TABLE 100-continued

9.AJ.26.157; 9.AJ.26.158; 9.AJ.26.196; 9.AJ.26.223; 9.AJ.26.240; 9.AJ.26.244; 9.AJ.26.243; 9.AJ.26.247; 9.AJ.27.157; 9.AJ.27.158; 9.AJ.27.196; 9.AJ.27.223; 9.AJ.27.240; 9.AJ.27.244; 9.AJ.27.243; 9.AJ.27.247; 9.AJ.29.157; 9.AJ.29.158; 9.AJ.29.196; 9.AJ.29.223; 9.AJ.29.240; 9.AJ.29.244; 9.AJ.29.243; 9.AJ.29.247; 9.AJ.54.157; 9.AJ.54.158; 9.AJ.54.196; 9.AJ.54.223; 9.AJ.54.240; 9.AJ.54.244; 9.AJ.54.243; 9.AJ.54.247; 9.AJ.55.157; 9.AJ.55.158; 9.AJ.55.196; 9.AJ.55.223; 9.AJ.55.240; 9.AJ.55.244; 9.AJ.55.243; 9.AJ.55.247; 9.AJ.56.157; 9.AJ.56.158; 9.AJ.56.196; 9.AJ.56.223; 9.AJ.56.240; 9.AJ.56.244; 9.AJ.56.243; 9.AJ.56.247; 9.AJ.157.157; 9.AJ.157.158; 9.AJ.157.196; 9.AJ.157.223; 9.AJ.157.240; 9.AJ.157.244; 9.AJ.157.243; 9.AJ.157.247; 9.AJ.196.157; 9.AJ.196.158; 9.AJ.196.196; 9.AJ.196.223; 9.AJ.196.240; 9.AJ.196.244; 9.AJ.196.243; 9.AJ.196.247; 9.AJ.223.157; 9.AJ.223.158; 9.AJ.223.196; 9.AJ.223.223; 9.AJ.223.240; 9.AJ.223.244; 9.AJ.223.243; 9.AJ.223.247; 9.AJ.240.157; 9.AJ.240.158; 9.AJ.240.196; 9.AJ.240.223; 9.AJ.240.240; 9.AJ.240.244; 9.AJ.240.243; 9.AJ.240.247; 9.AJ.244.157; 9.AJ.244.158; 9.AJ.244.196; 9.AJ.244.223; 9.AJ.244.240; 9.AJ.244.244; 9.AJ.244.243; 9.AJ.244.247; 9.AJ.247.157; 9.AJ.247.158; 9.AJ.247.196; 9.AJ.247.223; 9.AJ.247.240; 9.AJ.247.244; 9.AJ.247.243; 9.AJ.247.247;

Prodrugs of 9.AN

9.AN.4.157; 9.AN.4.158; 9.AN.4.196; 9.AN.4.223; 9.AN.4.240; 9.AN.4.244; 9.AN.4.243; 9.AN.4.247; 9.AN.5.157; 9.AN.5.158; 9.AN.5.196; 9.AN.5.223; 9.AN.5.240; 9.AN.5.244; 9.AN.5.243; 9.AN.5.247; 9.AN.7.157; 9.AN.7.158; 9.AN.7.196; 9.AN.7.223; 9.AN.7.240; 9.AN.7.244; 9.AN.7.243; 9.AN.7.247; 9.AN.15.157; 9.AN.15.158; 9.AN.15.196; 9.AN.15.223; 9.AN.15.240; 9.AN.15.244; 9.AN.15.243; 9.AN.15.247; 9.AN.16.157; 9.AN.16.158; 9.AN.16.196; 9.AN.16.223; 9.AN.16.240; 9.AN.16.244; 9.AN.16.243; 9.AN.16.247; 9.AN.18.157; 9.AN.18.158; 9.AN.18.196; 9.AN.18.223; 9.AN.18.240; 9.AN.18.244; 9.AN.18.243; 9.AN.18.247; 9.AN.26.157; 9.AN.26.158; 9.AN.26.196; 9.AN.26.223; 9.AN.26.240; 9.AN.26.244; 9.AN.26.243; 9.AN.26.247; 9.AN.27.157; 9.AN.27.158; 9.AN.27.196; 9.AN.27.223; 9.AN.27.240; 9.AN.27.244; 9.AN.27.243; 9.AN.27.247; 9.AN.29.157; 9.AN.29.158; 9.AN.29.196; 9.AN.29.223; 9.AN.29.240; 9.AN.29.244; 9.AN.29.243; 9.AN.29.247; 9.AN.54.157; 9.AN.54.158; 9.AN.54.196; 9.AN.54.223; 9.AN.54.240; 9.AN.54.244; 9.AN.54.243; 9.AN.54.247; 9.AN.55.157; 9.AN.55.158; 9.AN.55.196; 9.AN.55.223; 9.AN.55.240; 9.AN.55.244; 9.AN.55.243; 9.AN.55.247; 9.AN.56.157; 9.AN.56.158; 9.AN.56.196; 9.AN.56.223; 9.AN.56.240; 9.AN.56.244; 9.AN.56.243; 9.AN.56.247; 9.AN.157.157; 9.AN.157.158; 9.AN.157.196; 9.AN.157.223; 9.AN.157.240; 9.AN.157.244; 9.AN.157.243; 9.AN.157.247; 9.AN.196.157; 9.AN.196.158; 9.AN.196.196; 9.AN.196.223; 9.AN.196.240; 9.AN.196.244; 9.AN.196.243; 9.AN.196.247; 9.AN.223.157; 9.AN.223.158; 9.AN.223.196; 9.AN.223.223; 9.AN.223.240; 9.AN.223.244; 9.AN.223.243; 9.AN.223.247; 9.AN.240.157; 9.AN.240.158; 9.AN.240.196; 9.AN.240.223; 9.AN.240.240; 9.AN.240.244; 9.AN.240.243; 9.AN.240.247; 9.AN.244.157; 9.AN.244.158; 9.AN.244.196; 9.AN.244.223; 9.AN.244.240; 9.AN.244.244; 9.AN.244.243; 9.AN.244.247; 9.AN.247.157; 9.AN.247.158; 9.AN.247.196; 9.AN.247.223; 9.AN.247.240; 9.AN.247.244; 9.AN.247.243; 9.AN.247.247;

Prodrugs of 9.AP

9.AP.4.157; 9.AP.4.158; 9.AP.4.196; 9.AP.4.223; 9.AP.4.240; 9.AP.4.244; 9.AP.4.243; 9.AP.4.247; 9.AP.5.157; 9.AP.5.158; 9.AP.5.196; 9.AP.5.223; 9.AP.5.240; 9.AP.5.244; 9.AP.5.243; 9.AP.5.247; 9.AP.7.157; 9.AP.7.158; 9.AP.7.196; 9.AP.7.223; 9.AP.7.240; 9.AP.7.244; 9.AP.7.243; 9.AP.7.247; 9.AP.15.157; 9.AP.15.158; 9.AP.15.196; 9.AP.15.223; 9.AP.15.240; 9.AP.15.244; 9.AP.15.243; 9.AP.15.247; 9.AP.16.157; 9.AP.16.158; 9.AP.16.196; 9.AP.16.223; 9.AP.16.240; 9.AP.16.244; 9.AP.16.243; 9.AP.16.247; 9.AP.18.157; 9.AP.18.158; 9.AP.18.196; 9.AP.18.223; 9.AP.18.240; 9.AP.18.244; 9.AP.18.243; 9.AP.18.247; 9.AP.26.157; 9.AP.26.158; 9.AP.26.196; 9.AP.26.223; 9.AP.26.240; 9.AP.26.244; 9.AP.26.243; 9.AP.26.247; 9.AP.27.157; 9.AP.27.158; 9.AP.27.196; 9.AP.27.223; 9.AP.27.240; 9.AP.27.244; 9.AP.27.243; 9.AP.27.247; 9.AP.29.157; 9.AP.29.158; 9.AP.29.196; 9.AP.29.223; 9.AP.29.240; 9.AP.29.244; 9.AP.29.243; 9.AP.29.247; 9.AP.54.157; 9.AP.54.158; 9.AP.54.196; 9.AP.54.223; 9.AP.54.240; 9.AP.54.244; 9.AP.54.243; 9.AP.54.247; 9.AP.55.157; 9.AP.55.158; 9.AP.55.196; 9.AP.55.223; 9.AP.55.240; 9.AP.55.244; 9.AP.55.243; 9.AP.55.247; 9.AP.56.157; 9.AP.56.158; 9.AP.56.196; 9.AP.56.223; 9.AP.56.240; 9.AP.56.244; 9.AP.56.243; 9.AP.56.247; 9.AP.157.157; 9.AP.157.158; 9.AP.157.196; 9.AP.157.223; 9.AP.157.240; 9.AP.157.244; 9.AP.157.243; 9.AP.157.247; 9.AP.196.157; 9.AP.196.158; 9.AP.196.196; 9.AP.196.223; 9.AP.196.240; 9.AP.196.244; 9.AP.196.243; 9.AP.196.247; 9.AP.223.157; 9.AP.223.158; 9.AP.223.196; 9.AP.223.223; 9.AP.223.240; 9.AP.223.244; 9.AP.223.243; 9.AP.223.247; 9.AP.240.157; 9.AP.240.158; 9.AP.240.196; 9.AP.240.223; 9.AP.240.240; 9.AP.240.244; 9.AP.240.243; 9.AP.240.247; 9.AP.244.157; 9.AP.244.158; 9.AP.244.196; 9.AP.244.223; 9.AP.244.240; 9.AP.244.244; 9.AP.244.243; 9.AP.244.247; 9.AP.247.157; 9.AP.247.158; 9.AP.247.196; 9.AP.247.223; 9.AP.247.240; 9.AP.247.244; 9.AP.247.243; 9.AP.247.247;

TABLE 100-continued

Prodrugs of 9.AZ

9.AZ.4.157; 9.AZ.4.158; 9.AZ.4.196; 9.AZ.4.223; 9.AZ.4.240; 9.AZ.4.244; 9.AZ.4.243; 9.AZ.4.247; 9.AZ.5.157; 9.AZ.5.158; 9.AZ.5.196; 9.AZ.5.223; 9.AZ.5.240; 9.AZ.5.244; 9.AZ.5.243; 9.AZ.5.247; 9.AZ.7.157; 9.AZ.7.158; 9.AZ.7.196; 9.AZ.7.223; 9.AZ.7.240; 9.AZ.7.244; 9.AZ.7.243; 9.AZ.7.247; 9.AZ.15.157; 9.AZ.15.158; 9.AZ.15.196; 9.AZ.15.223; 9.AZ.15.240; 9.AZ.15.244; 9.AZ.15.243; 9.AZ.15.247; 9.AZ.16.157; 9.AZ.16.158; 9.AZ.16.196; 9.AZ.16.223; 9.AZ.16.240; 9.AZ.16.244; 9.AZ.16.243; 9.AZ.16.247; 9.AZ.18.157; 9.AZ.18.158; 9.AZ.18.196; 9.AZ.18.223; 9.AZ.18.240; 9.AZ.18.244; 9.AZ.18.243; 9.AZ.18.247; 9.AZ.26.157; 9.AZ.26.158; 9.AZ.26.196; 9.AZ.26.223; 9.AZ.26.240; 9.AZ.26.244; 9.AZ.26.243; 9.AZ.26.247; 9.AZ.27.157; 9.AZ.27.158; 9.AZ.27.196; 9.AZ.27.223; 9.AZ.27.240; 9.AZ.27.244; 9.AZ.27.243; 9.AZ.27.247; 9.AZ.29.157; 9.AZ.29.158; 9.AZ.29.196; 9.AZ.29.223; 9.AZ.29.240; 9.AZ.29.244; 9.AZ.29.243; 9.AZ.29.247; 9.AZ.54.157; 9.AZ.54.158; 9.AZ.54.196; 9.AZ.54.223; 9.AZ.54.240; 9.AZ.54.244; 9.AZ.54.243; 9.AZ.54.247; 9.AZ.55.157; 9.AZ.55.158; 9.AZ.55.196; 9.AZ.55.223; 9.AZ.55.240; 9.AZ.55.244; 9.AZ.55.243; 9.AZ.55.247; 9.AZ.56.157; 9.AZ.56.158; 9.AZ.56.196; 9.AZ.56.223; 9.AZ.56.240; 9.AZ.56.244; 9.AZ.56.243; 9.AZ.56.247; 9.AZ.157.157; 9.AZ.157.158; 9.AZ.157.196; 9.AZ.157.223; 9.AZ.157.240; 9.AZ.157.244; 9.AZ.157.243; 9.AZ.157.247; 9.AZ.196.157; 9.AZ.196.158; 9.AZ.196.196; 9.AZ.196.223; 9.AZ.196.240; 9.AZ.196.244; 9.AZ.196.243; 9.AZ.196.247; 9.AZ.223.157; 9.AZ.223.158; 9.AZ.223.196; 9.AZ.223.223; 9.AZ.223.240; 9.AZ.223.244; 9.AZ.223.243; 9.AZ.223.247; 9.AZ.240.157; 9.AZ.240.158; 9.AZ.240.196; 9.AZ.240.223; 9.AZ.240.240; 9.AZ.240.244; 9.AZ.240.243; 9.AZ.240.247; 9.AZ.244.157; 9.AZ.244.158; 9.AZ.244.196; 9.AZ.244.223; 9.AZ.244.240; 9.AZ.244.244; 9.AZ.244.243; 9.AZ.244.247; 9.AZ.247.157; 9.AZ.247.158; 9.AZ.247.196; 9.AZ.247.223; 9.AZ.247.240; 9.AZ.247.244; 9.AZ.247.243; 9.AZ.247.247;

Prodrugs of 9.BF

9.BF.4.157; 9.BF.4.158; 9.BF.4.196; 9.BF.4.223; 9.BF.4.240; 9.BF.4.244; 9.BF.4.243; 9.BF.4.247; 9.BF.5.157; 9.BF.5.158; 9.BF.5.196; 9.BF.5.223; 9.BF.5.240; 9.BF.5.244; 9.BF.5.243; 9.BF.5.247; 9.BF.7.157; 9.BF.7.158; 9.BF.7.196; 9.BF.7.223; 9.BF.7.240; 9.BF.7.244; 9.BF.7.243; 9.BF.7.247; 9.BF.15.157; 9.BF.15.158; 9.BF.15.196; 9.BF.15.223; 9.BF.15.240; 9.BF.15.244; 9.BF.15.243; 9.BF.15.247; 9.BF.16.157; 9.BF.16.158; 9.BF.16.196; 9.BF.16.223; 9.BF.16.240; 9.BF.16.244; 9.BF.16.243; 9.BF.16.247; 9.BF.18.157; 9.BF.18.158; 9.BF.18.196; 9.BF.18.223; 9.BF.18.240; 9.BF.18.244; 9.BF.18.243; 9.BF.18.247; 9.BF.26.157; 9.BF.26.158; 9.BF.26.196; 9.BF.26.223; 9.BF.26.240; 9.BF.26.244; 9.BF.26.243; 9.BF.26.247; 9.BF.27.157; 9.BF.27.158; 9.BF.27.196; 9.BF.27.223; 9.BF.27.240; 9.BF.27.244; 9.BF.27.243; 9.BF.27.247; 9.BF.29.157; 9.BF.29.158; 9.BF.29.196; 9.BF.29.223; 9.BF.29.240; 9.BF.29.244; 9.BF.29.243; 9.BF.29.247; 9.BF.54.157; 9.BF.54.158; 9.BF.54.196; 9.BF.54.223; 9.BF.54.240; 9.BF.54.244; 9.BF.54.243; 9.BF.54.247; 9.BF.55.157; 9.BF.55.158; 9.BF.55.196; 9.BF.55.223; 9.BF.55.240; 9.BF.55.244; 9.BF.55.243; 9.BF.55.247; 9.BF.56.157; 9.BF.56.158; 9.BF.56.196; 9.BF.56.223; 9.BF.56.240; 9.BF.56.244; 9.BF.56.243; 9.BF.56.247; 9.BF.157.157; 9.BF.157.158; 9.BF.157.196; 9.BF.157.223; 9.BF.157.240; 9.BF.157.244; 9.BF.157.243; 9.BF.157.247; 9.BF.196.157; 9.BF.196.158; 9.BF.196.196; 9.BF.196.223; 9.BF.196.240; 9.BF.196.244; 9.BF.196.243; 9.BF.196.247; 9.BF.223.157; 9.BF.223.158; 9.BF.223.196; 9.BF.223.223; 9.BF.223.240; 9.BF.223.244; 9.BF.223.243; 9.BF.223.247; 9.BF.240.157; 9.BF.240.158; 9.BF.240.196; 9.BF.240.223; 9.BF.240.240; 9.BF.240.244; 9.BF.240.243; 9.BF.240.247; 9.BF.244.157; 9.BF.244.158; 9.BF.244.196; 9.BF.244.223; 9.BF.244.240; 9.BF.244.244; 9.BF.244.243; 9.BF.244.247; 9.BF.247.157; 9.BF.247.158; 9.BF.247.196; 9.BF.247.223; 9.BF.247.240; 9.BF.247.244; 9.BF.247.243; 9.BF.247.247;

Prodrugs of 9.CI

9.CI.4.157; 9.CI.4.158; 9.CI.4.196; 9.CI.4.223; 9.CI.4.240; 9.CI.4.244; 9.CI.4.243; 9.CI.4.247; 9.CI.5.157; 9.CI.5.158; 9.CI.5.196; 9.CI.5.223; 9.CI.5.240; 9.CI.5.244; 9.CI.5.243; 9.CI.5.247; 9.CI.7.157; 9.CI.7.158; 9.CI.7.196; 9.CI.7.223; 9.CI.7.240; 9.CI.7.244; 9.CI.7.243; 9.CI.7.247; 9.CI.15.157; 9.CI.15.158; 9.CI.15.196; 9.CI.15.223; 9.CI.15.240; 9.CI.15.244; 9.CI.15.243; 9.CI.15.247; 9.CI.16.157; 9.CI.16.158; 9.CI.16.196; 9.CI.16.223; 9.CI.16.240; 9.CI.16.244; 9.CI.16.243; 9.CI.16.247; 9.CI.18.157; 9.CI.18.158; 9.CI.18.196; 9.CI.18.223; 9.CI.18.240; 9.CI.18.244; 9.CI.18.243; 9.CI.18.247; 9.CI.26.157; 9.CI.26.158; 9.CI.26.196; 9.CI.26.223; 9.CI.26.240; 9.CI.26.244; 9.CI.26.243; 9.CI.26.247; 9.CI.27.157; 9.CI.27.158; 9.CI.27.196; 9.CI.27.223; 9.CI.27.240; 9.CI.27.244; 9.CI.27.243; 9.CI.27.247; 9.CI.29.157; 9.CI.29.158; 9.CI.29.196; 9.CI.29.223; 9.CI.29.240; 9.CI.29.244; 9.CI.29.243; 9.CI.29.247; 9.CI.54.157; 9.CI.54.158; 9.CI.54.196; 9.CI.54.223; 9.CI.54.240; 9.CI.54.244; 9.CI.54.243; 9.CI.54.247; 9.CI.55.157; 9.CI.55.158; 9.CI.55.196; 9.CI.55.223; 9.CI.55.240; 9.CI.55.244; 9.CI.55.243; 9.CI.55.247; 9.CI.56.157; 9.CI.56.158; 9.CI.56.196; 9.CI.56.223; 9.CI.56.240; 9.CI.56.244; 9.CI.56.243; 9.CI.56.247; 9.CI.157.157; 9.CI.157.158; 9.CI.157.196; 9.CI.157.223; 9.CI.157.240;

TABLE 100-continued

9.CI.157.244; 9.CI.157.243; 9.CI.157.247; 9.CI.196.157; 9.CI.196.158; 9.CI.196.196; 9.CI.196.223; 9.CI.196.240; 9.CI.196.244; 9.CI.196.243; 9.CI.196.247; 9.CI.223.157; 9.CI.223.158; 9.CI.223.196; 9.CI.223.223; 9.CI.223.240; 9.CI.223.244; 9.CI.223.243; 9.CI.223.247; 9.CI.240.157; 9.CI.240.158; 9.CI.240.196; 9.CI.240.223; 9.CI.240.240; 9.CI.240.244; 9.CI.240.243; 9.CI.240.247; 9.CI.244.157; 9.CI.244.158; 9.CI.244.196; 9.CI.244.223; 9.CI.244.240; 9.CI.244.244; 9.CI.244.243; 9.CI.244.247; 9.CI.247.157; 9.CI.247.158; 9.CI.247.196; 9.CI.247.223; 9.CI.247.240; 9.CI.247.244; 9.CI.247.243; 9.CI.247.247;

Prodrugs of 9.CO

9.CO.4.157; 9.CO.4.158; 9.CO.4.196; 9.CO.4.223; 9.CO.4.240; 9.CO.4.244; 9.CO.4.243; 9.CO.4.247; 9.CO.5.157; 9.CO.5.158; 9.CO.5.196; 9.CO.5.223; 9.CO.5.240; 9.CO.5.244; 9.CO.5.243; 9.CO.5.247; 9.CO.7.157; 9.CO.7.158; 9.CO.7.196; 9.CO.7.223; 9.CO.7.240; 9.CO.7.244; 9.CO.7.243; 9.CO.7.247; 9.CO.15.157; 9.CO.15.158; 9.CO.15.196; 9.CO.15.223; 9.CO.15.240; 9.CO.15.244; 9.CO.15.243; 9.CO.15.247; 9.CO.16.157; 9.CO.16.158; 9.CO.16.196; 9.CO.16.223; 9.CO.16.240; 9.CO.16.244; 9.CO.16.243; 9.CO.16.247; 9.CO.18.157; 9.CO.18.158; 9.CO.18.196; 9.CO.18.223; 9.CO.18.240; 9.CO.18.244; 9.CO.18.243; 9.CO.18.247; 9.CO.26.157; 9.CO.26.158; 9.CO.26.196; 9.CO.26.223; 9.CO.26.240; 9.CO.26.244; 9.CO.26.243; 9.CO.26.247; 9.CO.27.157; 9.CO.27.158; 9.CO.27.196; 9.CO.27.223; 9.CO.27.240; 9.CO.27.244; 9.CO.27.243; 9.CO.27.247; 9.CO.29.157; 9.CO.29.158; 9.CO.29.196; 9.CO.29.223; 9.CO.29.240; 9.CO.29.244; 9.CO.29.243; 9.CO.29.247; 9.CO.54.157; 9.CO.54.158; 9.CO.54.196; 9.CO.54.223; 9.CO.54.240; 9.CO.54.244; 9.CO.54.243; 9.CO.54.247; 9.CO.55.157; 9.CO.55.158; 9.CO.55.196; 9.CO.55.223; 9.CO.55.240; 9.CO.55.244; 9.CO.55.243; 9.CO.55.247; 9.CO.56.157; 9.CO.56.158; 9.CO.56.196; 9.CO.56.223; 9.CO.56.240; 9.CO.56.244; 9.CO.56.243; 9.CO.56.247; 9.CO.157.157; 9.CO.157.158; 9.CO.157.196; 9.CO.157.223; 9.CO.157.240; 9.CO.157.244; 9.CO.157.243; 9.CO.157.247; 9.CO.196.157; 9.CO.196.158; 9.CO.196.196; 9.CO.196.223; 9.CO.196.240; 9.CO.196.244; 9.CO.196.243; 9.CO.196.247; 9.CO.223.157; 9.CO.223.158; 9.CO.223.196; 9.CO.223.223; 9.CO.223.240; 9.CO.223.244; 9.CO.223.243; 9.CO.223.247; 9.CO.240.157; 9.CO.240.158; 9.CO.240.196; 9.CO.240.223; 9.CO.240.240; 9.CO.240.244; 9.CO.240.243; 9.CO.240.247; 9.CO.244.157; 9.CO.244.158; 9.CO.244.196; 9.CO.244.223; 9.CO.244.240; 9.CO.244.244; 9.CO.244.243; 9.CO.244.247; 9.CO.247.157; 9.CO.247.158; 9.CO.247.196; 9.CO.247.223; 9.CO.247.240; 9.CO.247.244; 9.CO.247.243; 9.CO.247.247;

Prodrugs of 10.AH

10.AH.4.157; 10.AH.4.158; 10.AH.4.196; 10.AH.4.223; 10.AH.4.240; 10.AH.4.244; 10.AH.4.243; 10.AH.4.247; 10.AH.5.157; 10.AH.5.158; 10.AH.5.196; 10.AH.5.223; 10.AH.5.240; 10.AH.5.244; 10.AH.5.243; 10.AH.5.247; 10.AH.7.157; 10.AH.7.158; 10.AH.7.196; 10.AH.7.223; 10.AH.7.240; 10.AH.7.244; 10.AH.7.243; 10.AH.7.247; 10.AH.15.157; 10.AH.15.158; 10.AH.15.196; 10.AH.15.223; 10.AH.15.240; 10.AH.15.244; 10.AH.15.243; 10.AH.15.247; 10.AH.16.157; 10.AH.16.158; 10.AH.16.196; 10.AH.16.223; 10.AH.16.240; 10.AH.16.244; 10.AH.16.243; 10.AH.16.247; 10.AH.18.157; 10.AH.18.158; 10.AH.18.196; 10.AH.18.223; 10.AH.18.240; 10.AH.18.244; 10.AH.18.243; 10.AH.18.247; 10.AH.26.157; 10.AH.26.158; 10.AH.26.196; 10.AH.26.223; 10.AH.26.240; 10.AH.26.244; 10.AH.26.243; 10.AH.26.247; 10.AH.27.157; 10.AH.27.158; 10.AH.27.196; 10.AH.27.223; 10.AH.27.240; 10.AH.27.244; 10.AH.27.243; 10.AH.27.247; 10.AH.29.157; 10.AH.29.158; 10.AH.29.196; 10.AH.29.223; 10.AH.29.240; 10.AH.29.244; 10.AH.29.243; 10.AH.29.247; 10.AH.54.157; 10.AH.54.158; 10.AH.54.196; 10.AH.54.223; 10.AH.54.240; 10.AH.54.244; 10.AH.54.243; 10.AH.54.247; 10.AH.55.157; 10.AH.55.158; 10.AH.55.196; 10.AH.55.223; 10.AH.55.240; 10.AH.55.244; 10.AH.55.243; 10.AH.55.247; 10.AH.56.157; 10.AH.56.158; 10.AH.56.196; 10.AH.56.223; 10.AH.56.240; 10.AH.56.244; 10.AH.56.243; 10.AH.56.247; 10.AH.157.157; 10.AH.157.158; 10.AH.157.196; 10.AH.157.223; 10.AH.157.240; 10.AH.157.244; 10.AH.157.243; 10.AH.157.247; 10.AH.196.157; 10.AH.196.158; 10.AH.196.196; 10.AH.196.223; 10.AH.196.240; 10.AH.196.244; 10.AH.196.243; 10.AH.196.247; 10.AH.223.157; 10.AH.223.158; 10.AH.223.196; 10.AH.223.223; 10.AH.223.240; 10.AH.223.244; 10.AH.223.243; 10.AH.223.247; 10.AH.240.157; 10.AH.240.158; 10.AH.240.196; 10.AH.240.223; 10.AH.240.240; 10.AH.240.244; 10.AH.240.243; 10.AH.240.247; 10.AH.244.157; 10.AH.244.158; 10.AH.244.196; 10.AH.244.223; 10.AH.244.240; 10.AH.244.244; 10.AH.244.243; 10.AH.244.247; 10.AH.247.157; 10.AH.247.158; 10.AH.247.196; 10.AH.247.223; 10.AH.247.240; 10.AH.247.244; 10.AH.247.243; 10.AH.247.247;

Prodrugs of 10.AJ

10.AJ.4.157; 10.AJ.4.158; 10.AJ.4.196; 10.AJ.4.223; 10.AJ.4.240; 10.AJ.4.244; 10.AJ.4.243; 10.AJ.4.247; 10.AJ.5.157; 10.AJ.5.158; 10.AJ.5.196; 10.AJ.5.223; 10.AJ.5.240; 10.AJ.5.244; 10.AJ.5.243; 10.AJ.5.247; 10.AJ.7.157; 10.AJ.7.158; 10.AJ.7.196; 10.AJ.7.223; 10.AJ.7.240; 10.AJ.7.244; 10.AJ.7.243;

TABLE 100-continued

10.AJ.7.247; 10.AJ.15.157; 10.AJ.15.158; 10.AJ.15.196; 10.AJ.15.223; 10.AJ.15.240; 10.AJ.15.244; 10.AJ.15.243; 10.AJ.15.247; 10.AJ.16.157; 10.AJ.16.158; 10.AJ.16.196; 10.AJ.16.223; 10.AJ.16.240; 10.AJ.16.244; 10.AJ.16.243; 10.AJ.16.247; 10.AJ.18.157; 10.AJ.18.158; 10.AJ.18.196; 10.AJ.18.223; 10.AJ.18.240; 10.AJ.18.244; 10.AJ.18.243; 10.AJ.18.247; 10.AJ.26.157; 10.AJ.26.158; 10.AJ.26.196; 10.AJ.26.223; 10.AJ.26.240; 10.AJ.26.244; 10.AJ.26.243; 10.AJ.26.247; 10.AJ.27.157; 10.AJ.27.158; 10.AJ.27.196; 10.AJ.27.223; 10.AJ.27.240; 10.AJ.27.244; 10.AJ.27.243; 10.AJ.27.247; 10.AJ.29.157; 10.AJ.29.158; 10.AJ.29.196; 10.AJ.29.223; 10.AJ.29.240; 10.AJ.29.244; 10.AJ.29.243; 10.AJ.29.247; 10.AJ.54.157; 10.AJ.54.158; 10.AJ.54.196; 10.AJ.54.223; 10.AJ.54.240; 10.AJ.54.244; 10.AJ.54.243; 10.AJ.54.247; 10.AJ.55.157; 10.AJ.55.158; 10.AJ.55.196; 10.AJ.55.223; 10.AJ.55.240; 10.AJ.55.244; 10.AJ.55.243; 10.AJ.55.247; 10.AJ.56.157; 10.AJ.56.158; 10.AJ.56.196; 10.AJ.56.223; 10.AJ.56.240; 10.AJ.56.244; 10.AJ.56.243; 10.AJ.56.247; 10.AJ.157.157; 10.AJ.157.158; 10.AJ.157.196; 10.AJ.157.223; 10.AJ.157.240; 10.AJ.157.244; 10.AJ.157.243; 10.AJ.157.247; 10.AJ.196.157; 10.AJ.196.158; 10.AJ.196.196; 10.AJ.196.223; 10.AJ.196.240; 10.AJ.196.244; 10.AJ.196.243; 10.AJ.196.247; 10.AJ.223.157; 10.AJ.223.158; 10.AJ.223.196; 10.AJ.223.223; 10.AJ.223.240; 10.AJ.223.244; 10.AJ.223.243; 10.AJ.223.247; 10.AJ.240.157; 10.AJ.240.158; 10.AJ.240.196; 10.AJ.240.223; 10.AJ.240.240; 10.AJ.240.244; 10.AJ.240.243; 10.AJ.240.247; 10.AJ.244.157; 10.AJ.244.158; 10.AJ.244.196; 10.AJ.244.223; 10.AJ.244.240; 10.AJ.244.244; 10.AJ.244.243; 10.AJ.244.247; 10.AJ.247.157; 10.AJ.247.158; 10.AJ.247.196; 10.AJ.247.223; 10.AJ.247.240; 10.AJ.247.244; 10.AJ.247.243; 10.AJ.247.247;

Prodrugs of 10.AN

10.AN.4.157; 10.AN.4.158; 10.AN.4.196; 10.AN.4.223; 10.AN.4.240; 10.AN.4.244; 10.AN.4.243; 10.AN.4.247; 10.AN.5.157; 10.AN.5.158; 10.AN.5.196; 10.AN.5.223; 10.AN.5.240; 10.AN.5.244; 10.AN.5.243; 10.AN.5.247; 10.AN.7.157; 10.AN.7.158; 10.AN.7.196; 10.AN.7.223; 10.AN.7.240; 10.AN.7.244; 10.AN.7.243; 10.AN.7.247; 10.AN.15.157; 10.AN.15.158; 10.AN.15.196; 10.AN.15.223; 10.AN.15.240; 10.AN.15.244; 10.AN.15.243; 10.AN.15.247; 10.AN.16.157; 10.AN.16.158; 10.AN.16.196; 10.AN.16.223; 10.AN.16.240; 10.AN.16.244; 10.AN.16.243; 10.AN.16.247; 10.AN.18.157; 10.AN.18.158; 10.AN.18.196; 10.AN.18.223; 10.AN.18.240; 10.AN.18.244; 10.AN.18.243; 10.AN.18.247; 10.AN.26.157; 10.AN.26.158; 10.AN.26.196; 10.AN.26.223; 10.AN.26.240; 10.AN.26.244; 10.AN.26.243; 10.AN.26.247; 10.AN.27.157; 10.AN.27.158; 10.AN.27.196; 10.AN.27.223; 10.AN.27.240; 10.AN.27.244; 10.AN.27.243; 10.AN.27.247; 10.AN.29.157; 10.AN.29.158; 10.AN.29.196; 10.AN.29.223; 10.AN.29.240; 10.AN.29.244; 10.AN.29.243; 10.AN.29.247; 10.AN.54.157; 10.AN.54.158; 10.AN.54.196; 10.AN.54.223; 10.AN.54.240; 10.AN.54.244; 10.AN.54.243; 10.AN.54.247; 10.AN.55.157; 10.AN.55.158; 10.AN.55.196; 10.AN.55.223; 10.AN.55.240; 10.AN.55.244; 10.AN.55.243; 10.AN.55.247; 10.AN.56.157; 10.AN.56.158; 10.AN.56.196; 10.AN.56.223; 10.AN.56.240; 10.AN.56.244; 10.AN.56.243; 10.AN.56.247; 10.AN.157.157; 10.AN.157.158; 10.AN.157.196; 10.AN.157.223; 10.AN.157.240; 10.AN.157.244; 10.AN.157.243; 10.AN.157.247; 10.AN.196.157; 10.AN.196.158; 10.AN.196.196; 10.AN.196.223; 10.AN.196.240; 10.AN.196.244; 10.AN.196.243; 10.AN.196.247; 10.AN.223.157; 10.AN.223.158; 10.AN.223.196; 10.AN.223.223; 10.AN.223.240; 10.AN.223.244; 10.AN.223.243; 10.AN.223.247; 10.AN.240.157; 10.AN.240.158; 10.AN.240.196; 10.AN.240.223; 10.AN.240.240; 10.AN.240.244; 10.AN.240.243; 10.AN.240.247; 10.AN.244.157; 10.AN.244.158; 10.AN.244.196; 10.AN.244.223; 10.AN.244.240; 10.AN.244.244; 10.AN.244.243; 10.AN.244.247; 10.AN.247.157; 10.AN.247.158; 10.AN.247.196; 10.AN.247.223; 10.AN.247.240; 10.AN.247.244; 10.AN.247.243; 10.AN.247.247;

Prodrugs of 10.AP

10.AP.4.157; 10.AP.4.158; 10.AP.4.196; 10.AP.4.223; 10.AP.4.240; 10.AP.4.244; 10.AP.4.243; 10.AP.4.247; 10.AP.5.157; 10.AP.5.158; 10.AP.5.196; 10.AP.5.223; 10.AP.5.240; 10.AP.5.244; 10.AP.5.243; 10.AP.5.247; 10.AP.7.157; 10.AP.7.158; 10.AP.7.196; 10.AP.7.223; 10.AP.7.240; 10.AP.7.244; 10.AP.7.243; 10.AP.7.247; 10.AP.15.157; 10.AP.15.158; 10.AP.15.196; 10.AP.15.223; 10.AP.15.240; 10.AP.15.244; 10.AP.15.243; 10.AP.15.247; 10.AP.16.157; 10.AP.16.158; 10.AP.16.196; 10.AP.16.223; 10.AP.16.240; 10.AP.16.244; 10.AP.16.243; 10.AP.16.247; 10.AP.18.157; 10.AP.18.158; 10.AP.18.196; 10.AP.18.223; 10.AP.18.240; 10.AP.18.244; 10.AP.18.243; 10.AP.18.247; 10.AP.26.157; 10.AP.26.158; 10.AP.26.196; 10.AP.26.223; 10.AP.26.240; 10.AP.26.244; 10.AP.26.243; 10.AP.26.247; 10.AP.27.157; 10.AP.27.158; 10.AP.27.196; 10.AP.27.223; 10.AP.27.240; 10.AP.27.244; 10.AP.27.243; 10.AP.27.247; 10.AP.29.157; 10.AP.29.158; 10.AP.29.196; 10.AP.29.223; 10.AP.29.240; 10.AP.29.244; 10.AP.29.243; 10.AP.29.247; 10.AP.54.157; 10.AP.54.158; 10.AP.54.196; 10.AP.54.223; 10.AP.54.240; 10.AP.54.244; 10.AP.54.243; 10.AP.54.247; 10.AP.55.157; 10.AP.55.158; 10.AP.55.196; 10.AP.55.223; 10.AP.55.240; 10.AP.55.244; 10.AP.55.243; 10.AP.55.247; 10.AP.56.157; 10.AP.56.158;

TABLE 100-continued

10.AP.56.196; 10.AP.56.223; 10.AP.56.240; 10.AP.56.244; 10.AP.56.243; 10.AP.56.247; 10.AP.157.157; 10.AP.157.158; 10.AP.157.196; 10.AP.157.223; 10.AP.157.240; 10.AP.157.244; 10.AP.157.243; 10.AP.157.247; 10.AP.196.157; 10.AP.196.158; 10.AP.196.196; 10.AP.196.223; 10.AP.196.240; 10.AP.196.244; 10.AP.196.243; 10.AP.196.247; 10.AP.223.157; 10.AP.223.158; 10.AP.223.196; 10.AP.223.223; 10.AP.223.240; 10.AP.223.244; 10.AP.223.243; 10.AP.223.247; 10.AP.240.157; 10.AP.240.158; 10.AP.240.196; 10.AP.240.223; 10.AP.240.240; 10.AP.240.244; 10.AP.240.243; 10.AP.240.247; 10.AP.244.157; 10.AP.244.158; 10.AP.244.196; 10.AP.244.223; 10.AP.244.240; 10.AP.244.244; 10.AP.244.243; 10.AP.244.247; 10.AP.247.157; 10.AP.247.158; 10.AP.247.196; 10.AP.247.223; 10.AP.247.240; 10.AP.247.244; 10.AP.247.243; 10.AP.247.247;

Prodrugs of 10.AZ

10.AZ.4.157; 10.AZ.4.158; 10.AZ.4.196; 10.AZ.4.223; 10.AZ.4.240; 10.AZ.4.244; 10.AZ.4.243; 10.AZ.4.247; 10.AZ.5.157; 10.AZ.5.158; 10.AZ.5.196; 10.AZ.5.223; 10.AZ.5.240; 10.AZ.5.244; 10.AZ.5.243; 10.AZ.5.247; 10.AZ.7.157; 10.AZ.7.158; 10.AZ.7.196; 10.AZ.7.223; 10.AZ.7.240; 10.AZ.7.244; 10.AZ.7.243; 10.AZ.7.247; 10.AZ.15.157; 10.AZ.15.158; 10.AZ.15.196; 10.AZ.15.223; 10.AZ.15.240; 10.AZ.15.244; 10.AZ.15.243; 10.AZ.15.247; 10.AZ.16.157; 10.AZ.16.158; 10.AZ.16.196; 10.AZ.16.223; 10.AZ.16.240; 10.AZ.16.244; 10.AZ.16.243; 10.AZ.16.247; 10.AZ.18.157; 10.AZ.18.158; 10.AZ.18.196; 10.AZ.18.223; 10.AZ.18.240; 10.AZ.18.244; 10.AZ.18.243; 10.AZ.18.247; 10.AZ.26.157; 10.AZ.26.158; 10.AZ.26.196; 10.AZ.26.223; 10.AZ.26.240; 10.AZ.26.244; 10.AZ.26.243; 10.AZ.26.247; 10.AZ.27.157; 10.AZ.27.158; 10.AZ.27.196; 10.AZ.27.223; 10.AZ.27.240; 10.AZ.27.244; 10.AZ.27.243; 10.AZ.27.247; 10.AZ.29.157; 10.AZ.29.158; 10.AZ.29.196; 10.AZ.29.223; 10.AZ.29.240; 10.AZ.29.244; 10.AZ.29.243; 10.AZ.29.247; 10.AZ.54.157; 10.AZ.54.158; 10.AZ.54.196; 10.AZ.54.223; 10.AZ.54.240; 10.AZ.54.244; 10.AZ.54.243; 10.AZ.54.247; 10.AZ.55.157; 10.AZ.55.158; 10.AZ.55.196; 10.AZ.55.223; 10.AZ.55.240; 10.AZ.55.244; 10.AZ.55.243; 10.AZ.55.247; 10.AZ.56.157; 10.AZ.56.158; 10.AZ.56.196; 10.AZ.56.223; 10.AZ.56.240; 10.AZ.56.244; 10.AZ.56.243; 10.AZ.56.247; 10.AZ.157.157; 10.AZ.157.158; 10.AZ.157.196; 10.AZ.157.223; 10.AZ.157.240; 10.AZ.157.244; 10.AZ.157.243; 10.AZ.157.247; 10.AZ.196.157; 10.AZ.196.158; 10.AZ.196.196; 10.AZ.196.223; 10.AZ.196.240; 10.AZ.196.244; 10.AZ.196.243; 10.AZ.196.247; 10.AZ.223.157; 10.AZ.223.158; 10.AZ.223.196; 10.AZ.223.223; 10.AZ.223.240; 10.AZ.223.244; 10.AZ.223.243; 10.AZ.223.247; 10.AZ.240.157; 10.AZ.240.158; 10.AZ.240.196; 10.AZ.240.223; 10.AZ.240.240; 10.AZ.240.244; 10.AZ.240.243; 10.AZ.240.247; 10.AZ.244.157; 10.AZ.244.158; 10.AZ.244.196; 10.AZ.244.223; 10.AZ.244.240; 10.AZ.244.244; 10.AZ.244.243; 10.AZ.244.247; 10.AZ.247.157; 10.AZ.247.158; 10.AZ.247.196; 10.AZ.247.223; 10.AZ.247.240; 10.AZ.247.244; 10.AZ.247.243; 10.AZ.247.247;

Prodrugs of 10.BF

10.BF.4.157; 10.BF.4.158; 10.BF.4.196; 10.BF.4.223; 10.BF.4.240; 10.BF.4.244; 10.BF.4.243; 10.BF.4.247; 10.BF.5.157; 10.BF.5.158; 10.BF.5.196; 10.BF.5.223; 10.BF.5.240; 10.BF.5.244; 10.BF.5.243; 10.BF.5.247; 10.BF.7.157; 10.BF.7.158; 10.BF.7.196; 10.BF.7.223; 10.BF.7.240; 10.BF.7.244; 10.BF.7.243; 10.BF.7.247; 10.BF.15.157; 10.BF.15.158; 10.BF.15.196; 10.BF.15.223; 10.BF.15.240; 10.BF.15.244; 10.BF.15.243; 10.BF.15.247; 10.BF.16.157; 10.BF.16.158; 10.BF.16.196; 10.BF.16.223; 10.BF.16.240; 10.BF.16.244; 10.BF.16.243; 10.BF.16.247; 10.BF.18.157; 10.BF.18.158; 10.BF.18.196; 10.BF.18.223; 10.BF.18.240; 10.BF.18.244; 10.BF.18.243; 10.BF.18.247; 10.BF.26.157; 10.BF.26.158; 10.BF.26.196; 10.BF.26.223; 10.BF.26.240; 10.BF.26.244; 10.BF.26.243; 10.BF.26.247; 10.BF.27.157; 10.BF.27.158; 10.BF.27.196; 10.BF.27.223; 10.BF.27.240; 10.BF.27.244; 10.BF.27.243; 10.BF.27.247; 10.BF.29.157; 10.BF.29.158; 10.BF.29.196; 10.BF.29.223; 10.BF.29.240; 10.BF.29.244; 10.BF.29.243; 10.BF.29.247; 10.BF.54.157; 10.BF.54.158; 10.BF.54.196; 10.BF.54.223; 10.BF.54.240; 10.BF.54.244; 10.BF.54.243; 10.BF.54.247; 10.BF.55.157; 10.BF.55.158; 10.BF.55.196; 10.BF.55.223; 10.BF.55.240; 10.BF.55.244; 10.BF.55.243; 10.BF.55.247; 10.BF.56.157; 10.BF.56.158; 10.BF.56.196; 10.BF.56.223; 10.BF.56.240; 10.BF.56.244; 10.BF.56.243; 10.BF.56.247; 10.BF.157.157; 10.BF.157.158; 10.BF.157.196; 10.BF.157.223; 10.BF.157.240; 10.BF.157.244; 10.BF.157.243; 10.BF.157.247; 10.BF.196.157; 10.BF.196.158; 10.BF.196.196; 10.BF.196.223; 10.BF.196.240; 10.BF.196.244; 10.BF.196.243; 10.BF.196.247; 10.BF.223.157; 10.BF.223.158; 10.BF.223.196; 10.BF.223.223; 10.BF.223.240; 10.BF.223.244; 10.BF.223.243; 10.BF.223.247; 10.BF.240.157; 10.BF.240.158; 10.BF.240.196; 10.BF.240.223; 10.BF.240.240; 10.BF.240.244; 10.BF.240.243; 10.BF.240.247; 10.BF.244.157; 10.BF.244.158; 10.BF.244.196; 10.BF.244.223; 10.BF.244.240; 10.BF.244.244; 10.BF.244.243; 10.BF.244.247; 10.BF.247.157; 10.BF.247.158; 10.BF.247.196; 10.BF.247.223; 10.BF.247.240; 10.BF.247.244; 10.BF.247.243; 10.BF.247.247;

TABLE 100-continued

Prodrugs of 10.CI

10.CI.4.157; 10.CI.4.158; 10.CI.4.196; 10.CI.4.223; 10.CI.4.240; 10.CI.4.244; 10.CI.4.243; 10.CI.4.247; 10.CI.5.157; 10.CI.5.158; 10.CI.5.196; 10.CI.5.223; 10.CI.5.240; 10.CI.5.244; 10.CI.5.243; 10.CI.5.247; 10.CI.7.157; 10.CI.7.158; 10.CI.7.196; 10.CI.7.223; 10.CI.7.240; 10.CI.7.244; 10.CI.7.243; 10.CI.7.247; 10.CI.15.157; 10.CI.15.158; 10.CI.15.196; 10.CI.15.223; 10.CI.15.240; 10.CI.15.244; 10.CI.15.243; 10.CI.15.247; 10.CI.16.157; 10.CI.16.158; 10.CI.16.196; 10.CI.16.223; 10.CI.16.240; 10.CI.16.244; 10.CI.16.243; 10.CI.16.247; 10.CI.18.157; 10.CI.18.158; 10.CI.18.196; 10.CI.18.223; 10.CI.18.240; 10.CI.18.244; 10.CI.18.243; 10.CI.18.247; 10.CI.26.157; 10.CI.26.158; 10.CI.26.196; 10.CI.26.223; 10.CI.26.240; 10.CI.26.244; 10.CI.26.243; 10.CI.26.247; 10.CI.27.157; 10.CI.27.158; 10.CI.27.196; 10.CI.27.223; 10.CI.27.240; 10.CI.27.244; 10.CI.27.243; 10.CI.27.247; 10.CI.29.157; 10.CI.29.158; 10.CI.29.196; 10.CI.29.223; 10.CI.29.240; 10.CI.29.244; 10.CI.29.243; 10.CI.29.247; 10.CI.54.157; 10.CI.54.158; 10.CI.54.196; 10.CI.54.223; 10.CI.54.240; 10.CI.54.244; 10.CI.54.243; 10.CI.54.247; 10.CI.55.157; 10.CI.55.158; 10.CI.55.196; 10.CI.55.223; 10.CI.55.240; 10.CI.55.244; 10.CI.55.243; 10.CI.55.247; 10.CI.56.157; 10.CI.56.158; 10.CI.56.196; 10.CI.56.223; 10.CI.56.240; 10.CI.56.244; 10.CI.56.243; 10.CI.56.247; 10.CI.157.157; 10.CI.157.158; 10.CI.157.196; 10.CI.157.223; 10.CI.157.240; 10.CI.157.244; 10.CI.157.243; 10.CI.157.247; 10.CI.196.157; 10.CI.196.158; 10.CI.196.196; 10.CI.196.223; 10.CI.196.240; 10.CI.196.244; 10.CI.196.243; 10.CI.196.247; 10.CI.223.157; 10.CI.223.158; 10.CI.223.196; 10.CI.223.223; 10.CI.223.240; 10.CI.223.244; 10.CI.223.243; 10.CI.223.247; 10.CI.240.157; 10.CI.240.158; 10.CI.240.196; 10.CI.240.223; 10.CI.240.240; 10.CI.240.244; 10.CI.240.243; 10.CI.240.247; 10.CI.244.157; 10.CI.244.158; 10.CI.244.196; 10.CI.244.223; 10.CI.244.240; 10.CI.244.244; 10.CI.244.243; 10.CI.244.247; 10.CI.247.157; 10.CI.247.158; 10.CI.247.196; 10.CI.247.223; 10.CI.247.240; 10.CI.247.244; 10.CI.247.243; 10.CI.247.247;

Prodrugs of 10.CO

10.CO.4.157; 10.CO.4.158; 10.CO.4.196; 10.CO.4.223; 10.CO.4.240; 10.CO.4.244; 10.CO.4.243; 10.CO.4.247; 10.CO.5.157; 10.CO.5.158; 10.CO.5.196; 10.CO.5.223; 10.CO.5.240; 10.CO.5.244; 10.CO.5.243; 10.CO.5.247; 10.CO.7.157; 10.CO.7.158; 10.CO.7.196; 10.CO.7.223; 10.CO.7.240; 10.CO.7.244; 10.CO.7.243; 10.CO.7.247; 10.CO.15.157; 10.CO.15.158; 10.CO.15.196; 10.CO.15.223; 10.CO.15.240; 10.CO.15.244; 10.CO.15.243; 10.CO.15.247; 10.CO.16.157; 10.CO.16.158; 10.CO.16.196; 10.CO.16.223; 10.CO.16.240; 10.CO.16.244; 10.CO.16.243; 10.CO.16.247; 10.CO.18.157; 10.CO.18.158; 10.CO.18.196; 10.CO.18.223; 10.CO.18.240; 10.CO.18.244; 10.CO.18.243; 10.CO.18.247; 10.CO.26.157; 10.CO.26.158; 10.CO.26.196; 10.CO.26.223; 10.CO.26.240; 10.CO.26.244; 10.CO.26.243; 10.CO.26.247; 10.CO.27.157; 10.CO.27.158; 10.CO.27.196; 10.CO.27.223; 10.CO.27.240; 10.CO.27.244; 10.CO.27.243; 10.CO.27.247; 10.CO.29.157; 10.CO.29.158; 10.CO.29.196; 10.CO.29.223; 10.CO.29.240; 10.CO.29.244; 10.CO.29.243; 10.CO.29.247; 10.CO.54.157; 10.CO.54.158; 10.CO.54.196; 10.CO.54.223; 10.CO.54.240; 10.CO.54.244; 10.CO.54.243; 10.CO.54.247; 10.CO.55.157; 10.CO.55.158; 10.CO.55.196; 10.CO.55.223; 10.CO.55.240; 10.CO.55.244; 10.CO.55.243; 10.CO.55.247; 10.CO.56.157; 10.CO.56.158; 10.CO.56.196; 10.CO.56.223; 10.CO.56.240; 10.CO.56.244; 10.CO.56.243; 10.CO.56.247; 10.CO.157.157; 10.CO.157.158; 10.CO.157.196; 10.CO.157.223; 10.CO.157.240; 10.CO.157.244; 10.CO.157.243; 10.CO.157.247; 10.CO.196.157; 10.CO.196.158; 10.CO.196.196; 10.CO.196.223; 10.CO.196.240; 10.CO.196.244; 10.CO.196.243; 10.CO.196.247; 10.CO.223.157; 10.CO.223.158; 10.CO.223.196; 10.CO.223.223; 10.CO.223.240; 10.CO.223.244; 10.CO.223.243; 10.CO.223.247; 10.CO.240.157; 10.CO.240.158; 10.CO.240.196; 10.CO.240.223; 10.CO.240.240; 10.CO.240.244; 10.CO.240.243; 10.CO.240.247; 10.CO.244.157; 10.CO.244.158; 10.CO.244.196; 10.CO.244.223; 10.CO.244.240; 10.CO.244.244; 10.CO.244.243; 10.CO.244.247; 10.CO.247.157; 10.CO.247.158; 10.CO.247.196; 10.CO.247.223; 10.CO.247.240; 10.CO.247.244; 10.CO.247.243; 10.CO.247.247;

Prodrugs of 11.AH

11.AH.4.157; 11.AH.4.158; 11.AH.4.196; 11.AH.4.223; 11.AH.4.240; 11.AH.4.244; 11.AH.4.243; 11.AH.4.247; 11.AH.5.157; 11.AH.5.158; 11.AH.5.196; 11.AH.5.223; 11.AH.5.240; 11.AH.5.244; 11.AH.5.243; 11.AH.5.247; 11.AH.7.157; 11.AH.7.158; 11.AH.7.196; 11.AH.7.223; 11.AH.7.240; 11.AH.7.244; 11.AH.7.243; 11.AH.7.247; 11.AH.15.157; 11.AH.15.158; 11.AH.15.196; 11.AH.15.223; 11.AH.15.240; 11.AH.15.244; 11.AH.15.243; 11.AH.15.247; 11.AH.16.157; 11.AH.16.158; 11.AH.16.196; 11.AH.16.223; 11.AH.16.240; 11.AH.16.244; 11.AH.16.243; 11.AH.16.247; 11.AH.18.157; 11.AH.18.158; 11.AH.18.196; 11.AH.18.223; 11.AH.18.240; 11.AH.18.244; 11.AH.18.243; 11.AH.18.247; 11.AH.26.157; 11.AH.26.158; 11.AH.26.196; 11.AH.26.223; 11.AH.26.240; 11.AH.26.244; 11.AH.26.243; 11.AH.26.247; 11.AH.27.157; 11.AH.27.158; 11.AH.27.196; 11.AH.27.223;

TABLE 100-continued

11.AH.27.240; 11.AH.27.244; 11.AH.27.243; 11.AH.27.247; 11.AH.29.157; 11.AH.29.158; 11.AH.29.196; 11.AH.29.223; 11.AH.29.240; 11.AH.29.244; 11.AH.29.243; 11.AH.29.247; 11.AH.54.157; 11.AH.54.158; 11.AH.54.196; 11.AH.54.223; 11.AH.54.240; 11.AH.54.244; 11.AH.54.243; 11.AH.54.247; 11.AH.55.157; 11.AH.55.158; 11.AH.55.196; 11.AH.55.223; 11.AH.55.240; 11.AH.55.244; 11.AH.55.243; 11.AH.55.247; 11.AH.56.157; 11.AH.56.158; 11.AH.56.196; 11.AH.56.223; 11.AH.56.240; 11.AH.56.244; 11.AH.56.243; 11.AH.56.247; 11.AH.157.157; 11.AH.157.158; 11.AH.157.196; 11.AH.157.223; 11.AH.157.240; 11.AH.157.244; 11.AH.157.243; 11.AH.157.247; 11.AH.196.157; 11.AH.196.158; 11.AH.196.196; 11.AH.196.223; 11.AH.196.240; 11.AH.196.244; 11.AH.196.243; 11.AH.196.247; 11.AH.223.157; 11.AH.223.158; 11.AH.223.196; 11.AH.223.223; 11.AH.223.240; 11.AH.223.244; 11.AH.223.243; 11.AH.223.247; 11.AH.240.157; 11.AH.240.158; 11.AH.240.196; 11.AH.240.223; 11.AH.240.240; 11.AH.240.244; 11.AH.240.243; 11.AH.240.247; 11.AH.244.157; 11.AH.244.158; 11.AH.244.196; 11.AH.244.223; 11.AH.244.240; 11.AH.244.244; 11.AH.244.243; 11.AH.244.247; 11.AH.247.157; 11.AH.247.158; 11.AH.247.196; 11.AH.247.223; 11.AH.247.240; 11.AH.247.244; 11.AH.247.243; 11.AH.247.247;

Prodrugs of 11.AJ

11.AJ.4.157; 11.AJ.4.158; 11.AJ.4.196; 11.AJ.4.223; 11.AJ.4.240; 11.AJ.4.244; 11.AJ.4.243; 11.AJ.4.247; 11.AJ.5.157; 11.AJ.5.158; 11.AJ.5.196; 11.AJ.5.223; 11.AJ.5.240; 11.AJ.5.244; 11.AJ.5.243; 11.AJ.5.247; 11.AJ.7.157; 11.AJ.7.158; 11.AJ.7.196; 11.AJ.7.223; 11.AJ.7.240; 11.AJ.7.244; 11.AJ.7.243; 11.AJ.7.247; 11.AJ.15.157; 11.AJ.15.158; 11.AJ.15.196; 11.AJ.15.223; 11.AJ.15.240; 11.AJ.15.244; 11.AJ.15.243; 11.AJ.15.247; 11.AJ.16.157; 11.AJ.16.158; 11.AJ.16.196; 11.AJ.16.223; 11.AJ.16.240; 11.AJ.16.244; 11.AJ.16.243; 11.AJ.16.247; 11.AJ.18.157; 11.AJ.18.158; 11.AJ.18.196; 11.AJ.18.223; 11.AJ.18.240; 11.AJ.18.244; 11.AJ.18.243; 11.AJ.18.247; 11.AJ.26.157; 11.AJ.26.158; 11.AJ.26.196; 11.AJ.26.223; 11.AJ.26.240; 11.AJ.26.244; 11.AJ.26.243; 11.AJ.26.247; 11.AJ.27.157; 11.AJ.27.158; 11.AJ.27.196; 11.AJ.27.223; 11.AJ.27.240; 11.AJ.27.244; 11.AJ.27.243; 11.AJ.27.247; 11.AJ.29.157; 11.AJ.29.158; 11.AJ.29.196; 11.AJ.29.223; 11.AJ.29.240; 11.AJ.29.244; 11.AJ.29.243; 11.AJ.29.247; 11.AJ.54.157; 11.AJ.54.158; 11.AJ.54.196; 11.AJ.54.223; 11.AJ.54.240; 11.AJ.54.244; 11.AJ.54.243; 11.AJ.54.247; 11.AJ.55.157; 11.AJ.55.158; 11.AJ.55.196; 11.AJ.55.223; 11.AJ.55.240; 11.AJ.55.244; 11.AJ.55.243; 11.AJ.55.247; 11.AJ.56.157; 11.AJ.56.158; 11.AJ.56.196; 11.AJ.56.223; 11.AJ.56.240; 11.AJ.56.244; 11.AJ.56.243; 11.AJ.56.247; 11.AJ.157.157; 11.AJ.157.158; 11.AJ.157.196; 11.AJ.157.223; 11.AJ.157.240; 11.AJ.157.244; 11.AJ.157.243; 11.AJ.157.247; 11.AJ.196.157; 11.AJ.196.158; 11.AJ.196.196; 11.AJ.196.223; 11.AJ.196.240; 11.AJ.196.244; 11.AJ.196.243; 11.AJ.196.247; 11.AJ.223.157; 11.AJ.223.158; 11.AJ.223.196; 11.AJ.223.223; 11.AJ.223.240; 11.AJ.223.244; 11.AJ.223.243; 11.AJ.223.247; 11.AJ.240.157; 11.AJ.240.158; 11.AJ.240.196; 11.AJ.240.223; 11.AJ.240.240; 11.AJ.240.244; 11.AJ.240.243; 11.AJ.240.247; 11.AJ.244.157; 11.AJ.244.158; 11.AJ.244.196; 11.AJ.244.223; 11.AJ.244.240; 11.AJ.244.244; 11.AJ.244.243; 11.AJ.244.247; 11.AJ.247.157; 11.AJ.247.158; 11.AJ.247.196; 11.AJ.247.223; 11.AJ.247.240; 11.AJ.247.244; 11.AJ.247.243; 11.AJ.247.247;

Prodrugs of 11.AN

11.AN.4.157; 11.AN.4.158; 11.AN.4.196; 11.AN.4.223; 11.AN.4.240; 11.AN.4.244; 11.AN.4.243; 11.AN.4.247; 11.AN.5.157; 11.AN.5.158; 11.AN.5.196; 11.AN.5.223; 11.AN.5.240; 11.AN.5.244; 11.AN.5.243; 11.AN.5.247; 11.AN.7.157; 11.AN.7.158; 11.AN.7.196; 11.AN.7.223; 11.AN.7.240; 11.AN.7.244; 11.AN.7.243; 11.AN.7.247; 11.AN.15.157; 11.AN.15.158; 11.AN.15.196; 11.AN.15.223; 11.AN.15.240; 11.AN.15.244; 11.AN.15.243; 11.AN.15.247; 11.AN.16.157; 11.AN.16.158; 11.AN.16.196; 11.AN.16.223; 11.AN.16.240; 11.AN.16.244; 11.AN.16.243; 11.AN.16.247; 11.AN.18.157; 11.AN.18.158; 11.AN.18.196; 11.AN.18.223; 11.AN.18.240; 11.AN.18.244; 11.AN.18.243; 11.AN.18.247; 11.AN.26.157; 11.AN.26.158; 11.AN.26.196; 11.AN.26.223; 11.AN.26.240; 11.AN.26.244; 11.AN.26.243; 11.AN.26.247; 11.AN.27.157; 11.AN.27.158; 11.AN.27.196; 11.AN.27.223; 11.AN.27.240; 11.AN.27.244; 11.AN.27.243; 11.AN.27.247; 11.AN.29.157; 11.AN.29.158; 11.AN.29.196; 11.AN.29.223; 11.AN.29.240; 11.AN.29.244; 11.AN.29.243; 11.AN.29.247; 11.AN.54.157; 11.AN.54.158; 11.AN.54.196; 11.AN.54.223; 11.AN.54.240; 11.AN.54.244; 11.AN.54.243; 11.AN.54.247; 11.AN.55.157; 11.AN.55.158; 11.AN.55.196; 11.AN.55.223; 11.AN.55.240; 11.AN.55.244; 11.AN.55.243; 11.AN.55.247; 11.AN.56.157; 11.AN.56.158; 11.AN.56.196; 11.AN.56.223; 11.AN.56.240; 11.AN.56.244; 11.AN.56.243; 11.AN.56.247; 11.AN.157.157; 11.AN.157.158; 11.AN.157.196; 11.AN.157.223; 11.AN.157.240; 11.AN.157.244; 11.AN.157.243; 11.AN.157.247; 11.AN.196.157; 11.AN.196.158; 11.AN.196.196; 11.AN.196.223; 11.AN.196.240; 11.AN.196.244; 11.AN.196.243; 11.AN.196.247; 11.AN.223.157; 11.AN.223.158; 11.AN.223.196; 11.AN.223.223; 11.AN.223.240; 11.AN.223.244; 11.AN.223.243; 11.AN.223.247; 11.AN.240.157; 11.AN.240.158; 11.AN.240.196;

TABLE 100-continued

11.AN.240.223; 11.AN.240.240; 11.AN.240.244; 11.AN.240.243; 11.AN.240.247; 11.AN.244.157; 11.AN.244.158; 11.AN.244.196; 11.AN.244.223; 11.AN.244.240; 11.AN.244.244; 11.AN.244.243; 11.AN.244.247; 11.AN.247.157; 11.AN.247.158; 11.AN.247.196; 11.AN.247.223; 11.AN.247.240; 11.AN.247.244; 11.AN.247.243; 11.AN.247.247;

Prodrugs of 11.AP

11.AP.4.157; 11.AP.4.158; 11.AP.4.196; 11.AP.4.223; 11.AP.4.240; 11.AP.4.244; 11.AP.4.243; 11.AP.4.247; 11.AP.5.157; 11.AP.5.158; 11.AP.5.196; 11.AP.5.223; 11.AP.5.240; 11.AP.5.244; 11.AP.5.243; 11.AP.5.247; 11.AP.7.157; 11.AP.7.158; 11.AP.7.196; 11.AP.7.223; 11.AP.7.240; 11.AP.7.244; 11.AP.7.243; 11.AP.7.247; 11.AP.15.157; 11.AP.15.158; 11.AP.15.196; 11.AP.15.223; 11.AP.15.240; 11.AP.15.244; 11.AP.15.243; 11.AP.15.247; 11.AP.16.157; 11.AP.16.158; 11.AP.16.196; 11.AP.16.223; 11.AP.16.240; 11.AP.16.244; 11.AP.16.243; 11.AP.16.247; 11.AP.18.157; 11.AP.18.158; 11.AP.18.196; 11.AP.18.223; 11.AP.18.240; 11.AP.18.244; 11.AP.18.243; 11.AP.18.247; 11.AP.26.157; 11.AP.26.158; 11.AP.26.196; 11.AP.26.223; 11.AP.26.240; 11.AP.26.244; 11.AP.26.243; 11.AP.26.247; 11.AP.27.157; 11.AP.27.158; 11.AP.27.196; 11.AP.27.223; 11.AP.27.240; 11.AP.27.244; 11.AP.27.243; 11.AP.27.247; 11.AP.29.157; 11.AP.29.158; 11.AP.29.196; 11.AP.29.223; 11.AP.29.240; 11.AP.29.244; 11.AP.29.243; 11.AP.29.247; 11.AP.54.157; 11.AP.54.158; 11.AP.54.196; 11.AP.54.223; 11.AP.54.240; 11.AP.54.244; 11.AP.54.243; 11.AP.54.247; 11.AP.55.157; 11.AP.55.158; 11.AP.55.196; 11.AP.55.223; 11.AP.55.240; 11.AP.55.244; 11.AP.55.243; 11.AP.55.247; 11.AP.56.157; 11.AP.56.158; 11.AP.56.196; 11.AP.56.223; 11.AP.56.240; 11.AP.56.244; 11.AP.56.243; 11.AP.56.247; 11.AP.157.157; 11.AP.157.158; 11.AP.157.196; 11.AP.157.223; 11.AP.157.240; 11.AP.157.244; 11.AP.157.243; 11.AP.157.247; 11.AP.196.157; 11.AP.196.158; 11.AP.196.196; 11.AP.196.223; 11.AP.196.240; 11.AP.196.244; 11.AP.196.243; 11.AP.196.247; 11.AP.223.157; 11.AP.223.158; 11.AP.223.196; 11.AP.223.223; 11.AP.223.240; 11.AP.223.244; 11.AP.223.243; 11.AP.223.247; 11.AP.240.157; 11.AP.240.158; 11.AP.240.196; 11.AP.240.223; 11.AP.240.240; 11.AP.240.244; 11.AP.240.243; 11.AP.240.247; 11.AP.244.157; 11.AP.244.158; 11.AP.244.196; 11.AP.244.223; 11.AP.244.240; 11.AP.244.244; 11.AP.244.243; 11.AP.244.247; 11.AP.247.157; 11.AP.247.158; 11.AP.247.196; 11.AP.247.223; 11.AP.247.240; 11.AP.247.244; 11.AP.247.243; 11.AP.247.247;

Prodrugs of 11.AZ

11.AZ.4.157; 11.AZ.4.158; 11.AZ.4.196; 11.AZ.4.223; 11.AZ.4.240; 11.AZ.4.244; 11.AZ.4.243; 11.AZ.4.247; 11.AZ.5.157; 11.AZ.5.158; 11.AZ.5.196; 11.AZ.5.223; 11.AZ.5.240; 11.AZ.5.244; 11.AZ.5.243; 11.AZ.5.247; 11.AZ.7.157; 11.AZ.7.158; 11.AZ.7.196; 11.AZ.7.223; 11.AZ.7.240; 11.AZ.7.244; 11.AZ.7.243; 11.AZ.7.247; 11.AZ.15.157; 11.AZ.15.158; 11.AZ.15.196; 11.AZ.15.223; 11.AZ.15.240; 11.AZ.15.244; 11.AZ.15.243; 11.AZ.15.247; 11.AZ.16.157; 11.AZ.16.158; 11.AZ.16.196; 11.AZ.16.223; 11.AZ.16.240; 11.AZ.16.244; 11.AZ.16.243; 11.AZ.16.247; 11.AZ.18.157; 11.AZ.18.158; 11.AZ.18.196; 11.AZ.18.223; 11.AZ.18.240; 11.AZ.18.244; 11.AZ.18.243; 11.AZ.18.247; 11.AZ.26.157; 11.AZ.26.158; 11.AZ.26.196; 11.AZ.26.223; 11.AZ.26.240; 11.AZ.26.244; 11.AZ.26.243; 11.AZ.26.247; 11.AZ.27.157; 11.AZ.27.158; 11.AZ.27.196; 11.AZ.27.223; 11.AZ.27.240; 11.AZ.27.244; 11.AZ.27.243; 11.AZ.27.247; 11.AZ.29.157; 11.AZ.29.158; 11.AZ.29.196; 11.AZ.29.223; 11.AZ.29.240; 11.AZ.29.244; 11.AZ.29.243; 11.AZ.29.247; 11.AZ.54.157; 11.AZ.54.158; 11.AZ.54.196; 11.AZ.54.223; 11.AZ.54.240; 11.AZ.54.244; 11.AZ.54.243; 11.AZ.54.247; 11.AZ.55.157; 11.AZ.55.158; 11.AZ.55.196; 11.AZ.55.223; 11.AZ.55.240; 11.AZ.55.244; 11.AZ.55.243; 11.AZ.55.247; 11.AZ.56.157; 11.AZ.56.158; 11.AZ.56.196; 11.AZ.56.223; 11.AZ.56.240; 11.AZ.56.244; 11.AZ.56.243; 11.AZ.56.247; 11.AZ.157.157; 11.AZ.157.158; 11.AZ.157.196; 11.AZ.157.223; 11.AZ.157.240; 11.AZ.157.244; 11.AZ.157.243; 11.AZ.157.247; 11.AZ.196.157; 11.AZ.196.158; 11.AZ.196.196; 11.AZ.196.223; 11.AZ.196.240; 11.AZ.196.244; 11.AZ.196.243; 11.AZ.196.247; 11.AZ.223.157; 11.AZ.223.158; 11.AZ.223.196; 11.AZ.223.223; 11.AZ.223.240; 11.AZ.223.244; 11.AZ.223.243; 11.AZ.223.247; 11.AZ.240.157; 11.AZ.240.158; 11.AZ.240.196; 11.AZ.240.223; 11.AZ.240.240; 11.AZ.240.244; 11.AZ.240.243; 11.AZ.240.247; 11.AZ.244.157; 11.AZ.244.158; 11.AZ.244.196; 11.AZ.244.223; 11.AZ.244.240; 11.AZ.244.244; 11.AZ.244.243; 11.AZ.244.247; 11.AZ.247.157; 11.AZ.247.158; 11.AZ.247.196; 11.AZ.247.223; 11.AZ.247.240; 11.AZ.247.244; 11.AZ.247.243; 11.AZ.247.247;

Prodrugs of 11.BF

11.BF.4.157; 11.BF.4.158; 11.BF.4.196; 11.BF.4.223; 11.BF.4.240; 11.BF.4.244; 11.BF.4.243; 11.BF.4.247; 11.BF.5.157; 11.BF.5.158; 11.BF.5.196; 11.BF.5.223; 11.BF.5.240; 11.BF.5.244; 11.BF.5.243; 11.BF.5.247; 11.BF.7.157; 11.BF.7.158; 11.BF.7.196; 11.BF.7.223; 11.BF.7.240; 11.BF.7.244; 11.BF.7.243; 11.BF.7.247; 11.BF.15.157;

TABLE 100-continued

11.BF.15.158; 11.BF.15.196; 11.BF.15.223; 11.BF.15.240; 11.BF.15.244; 11.BF.15.243; 11.BF.15.247; 11.BF.16.157; 11.BF.16.158; 11.BF.16.196; 11.BF.16.223; 11.BF.16.240; 11.BF.16.244; 11.BF.16.243; 11.BF.16.247; 11.BF.18.157; 11.BF.18.158; 11.BF.18.196; 11.BF.18.223; 11.BF.18.240; 11.BF.18.244; 11.BF.18.243; 11.BF.18.247; 11.BF.26.157; 11.BF.26.158; 11.BF.26.196; 11.BF.26.223; 11.BF.26.240; 11.BF.26.244; 11.BF.26.243; 11.BF.26.247; 11.BF.27.157; 11.BF.27.158; 11.BF.27.196; 11.BF.27.223; 11.BF.27.240; 11.BF.27.244; 11.BF.27.243; 11.BF.27.247; 11.BF.29.157; 11.BF.29.158; 11.BF.29.196; 11.BF.29.223; 11.BF.29.240; 11.BF.29.244; 11.BF.29.243; 11.BF.29.247; 11.BF.54.157; 11.BF.54.158; 11.BF.54.196; 11.BF.54.223; 11.BF.54.240; 11.BF.54.244; 11.BF.54.243; 11.BF.54.247; 11.BF.55.157; 11.BF.55.158; 11.BF.55.196; 11.BF.55.223; 11.BF.55.240; 11.BF.55.244; 11.BF.55.243; 11.BF.55.247; 11.BF.56.157; 11.BF.56.158; 11.BF.56.196; 11.BF.56.223; 11.BF.56.240; 11.BF.56.244; 11.BF.56.243; 11.BF.56.247; 11.BF.157.157; 11.BF.157.158; 11.BF.157.196; 11.BF.157.223; 11.BF.157.240; 11.BF.157.244; 11.BF.157.243; 11.BF.157.247; 11.BF.196.157; 11.BF.196.158; 11.BF.196.196; 11.BF.196.223; 11.BF.196.240; 11.BF.196.244; 11.BF.196.243; 11.BF.196.247; 11.BF.223.157; 11.BF.223.158; 11.BF.223.196; 11.BF.223.223; 11.BF.223.240; 11.BF.223.244; 11.BF.223.243; 11.BF.223.247; 11.BF.240.157; 11.BF.240.158; 11.BF.240.196; 11.BF.240.223; 11.BF.240.240; 11.BF.240.244; 11.BF.240.243; 11.BF.240.247; 11.BF.244.157; 11.BF.244.158; 11.BF.244.196; 11.BF.244.223; 11.BF.244.240; 11.BF.244.244; 11.BF.244.243; 11.BF.244.247; 11.BF.247.157; 11.BF.247.158; 11.BF.247.196; 11.BF.247.223; 11.BF.247.240; 11.BF.247.244; 11.BF.247.243; 11.BF.247.247;

Prodrugs of 11.CI

11.CI.4.157; 11.CI.4.158; 11.CI.4.196; 11.CI.4.223; 11.CI.4.240; 11.CI.4.244; 11.CI.4.243; 11.CI.4.247; 11.CI.5.157; 11.CI.5.158; 11.CI.5.196; 11.CI.5.223; 11.CI.5.240; 11.CI.5.244; 11.CI.5.243; 11.CI.5.247; 11.CI.7.157; 11.CI.7.158; 11.CI.7.196; 11.CI.7.223; 11.CI.7.240; 11.CI.7.244; 11.CI.7.243; 11.CI.7.247; 11.CI.15.157; 11.CI.15.158; 11.CI.15.196; 11.CI.15.223; 11.CI.15.240; 11.CI.15.244; 11.CI.15.243; 11.CI.15.247; 11.CI.16.157; 11.CI.16.158; 11.CI.16.196; 11.CI.16.223; 11.CI.16.240; 11.CI.16.244; 11.CI.16.243; 11.CI.16.247; 11.CI.18.157; 11.CI.18.158; 11.CI.18.196; 11.CI.18.223; 11.CI.18.240; 11.CI.18.244; 11.CI.18.243; 11.CI.18.247; 11.CI.26.157; 11.CI.26.158; 11.CI.26.196; 11.CI.26.223; 11.CI.26.240; 11.CI.26.244; 11.CI.26.243; 11.CI.26.247; 11.CI.27.157; 11.CI.27.158; 11.CI.27.196; 11.CI.27.223; 11.CI.27.240; 11.CI.27.244; 11.CI.27.243; 11.CI.27.247; 11.CI.29.157; 11.CI.29.158; 11.CI.29.196; 11.CI.29.223; 11.CI.29.240; 11.CI.29.244; 11.CI.29.243; 11.CI.29.247; 11.CI.54.157; 11.CI.54.158; 11.CI.54.196; 11.CI.54.223; 11.CI.54.240; 11.CI.54.244; 11.CI.54.243; 11.CI.54.247; 11.CI.55.157; 11.CI.55.158; 11.CI.55.196; 11.CI.55.223; 11.CI.55.240; 11.CI.55.244; 11.CI.55.243; 11.CI.55.247; 11.CI.56.157; 11.CI.56.158; 11.CI.56.196; 11.CI.56.223; 11.CI.56.240; 11.CI.56.244; 11.CI.56.243; 11.CI.56.247; 11.CI.157.157; 11.CI.157.158; 11.CI.157.196; 11.CI.157.223; 11.CI.157.240; 11.CI.157.244; 11.CI.157.243; 11.CI.157.247; 11.CI.196.157; 11.CI.196.158; 11.CI.196.196; 11.CI.196.223; 11.CI.196.240; 11.CI.196.244; 11.CI.196.243; 11.CI.196.247; 11.CI.223.157; 11.CI.223.158; 11.CI.223.196; 11.CI.223.223; 11.CI.223.240; 11.CI.223.244; 11.CI.223.243; 11.CI.223.247; 11.CI.240.157; 11.CI.240.158; 11.CI.240.196; 11.CI.240.223; 11.CI.240.240; 11.CI.240.244; 11.CI.240.243; 11.CI.240.247; 11.CI.244.157; 11.CI.244.158; 11.CI.244.196; 11.CI.244.223; 11.CI.244.240; 11.CI.244.244; 11.CI.244.243; 11.CI.244.247; 11.CI.247.157; 11.CI.247.158; 11.CI.247.196; 11.CI.247.223; 11.CI.247.240; 11.CI.247.244; 11.CI.247.243; 11.CI.247.247;

Prodrugs of 11.CO

11.CO.4.157; 11.CO.4.158; 11.CO.4.196; 11.CO.4.223; 11.CO.4.240; 11.CO.4.244; 11.CO.4.243; 11.CO.4.247; 11.CO.5.157; 11.CO.5.158; 11.CO.5.196; 11.CO.5.223; 11.CO.5.240; 11.CO.5.244; 11.CO.5.243; 11.CO.5.247; 11.CO.7.157; 11.CO.7.158; 11.CO.7.196; 11.CO.7.223; 11.CO.7.240; 11.CO.7.244; 11.CO.7.243; 11.CO.7.247; 11.CO.15.157; 11.CO.15.158; 11.CO.15.196; 11.CO.15.223; 11.CO.15.240; 11.CO.15.244; 11.CO.15.243; 11.CO.15.247; 11.CO.16.157; 11.CO.16.158; 11.CO.16.196; 11.CO.16.223; 11.CO.16.240; 11.CO.16.244; 11.CO.16.243; 11.CO.16.247; 11.CO.18.157; 11.CO.18.158; 11.CO.18.196; 11.CO.18.223; 11.CO.18.240; 11.CO.18.244; 11.CO.18.243; 11.CO.18.247; 11.CO.26.157; 11.CO.26.158; 11.CO.26.196; 11.CO.26.223; 11.CO.26.240; 11.CO.26.244; 11.CO.26.243; 11.CO.26.247; 11.CO.27.157; 11.CO.27.158; 11.CO.27.196; 11.CO.27.223; 11.CO.27.240; 11.CO.27.244; 11.CO.27.243; 11.CO.27.247; 11.CO.29.157; 11.CO.29.158; 11.CO.29.196; 11.CO.29.223; 11.CO.29.240; 11.CO.29.244; 11.CO.29.243; 11.CO.29.247; 11.CO.54.157; 11.CO.54.158; 11.CO.54.196; 11.CO.54.223; 11.CO.54.240; 11.CO.54.244; 11.CO.54.243; 11.CO.54.247; 11.CO.55.157; 11.CO.55.158; 11.CO.55.196; 11.CO.55.223; 11.CO.55.240; 11.CO.55.244; 11.CO.55.243; 11.CO.55.247; 11.CO.56.157; 11.CO.56.158; 11.CO.56.196; 11.CO.56.223; 11.CO.56.240; 11.CO.56.244; 11.CO.56.243; 11.CO.56.247; 11.CO.157.157; 11.CO.157.158; 11.CO.157.196; 11.CO.157.223; 11.CO.157.240; 11.CO.157.244; 11.CO.157.243; 11.CO.157.247; 11.CO.196.157; 11.CO.196.158; 11.CO.196.196;

TABLE 100-continued

11.CO.196.223; 11.CO.196.240; 11.CO.196.244; 11.CO.196.243; 11.CO.196.247; 11.CO.223.157; 11.CO.223.158; 11.CO.223.196; 11.CO.223.223; 11.CO.223.240; 11.CO.223.244; 11.CO.223.243; 11.CO.223.247; 11.CO.240.157; 11.CO.240.158; 11.CO.240.196; 11.CO.240.223; 11.CO.240.240; 11.CO.240.244; 11.CO.240.243; 11.CO.240.247; 11.CO.244.157; 11.CO.244.158; 11.CO.244.196; 11.CO.244.223; 11.CO.244.240; 11.CO.244.244; 11.CO.244.243; 11.CO.244.247; 11.CO.247.157; 11.CO.247.158; 11.CO.247.196; 11.CO.247.223; 11.CO.247.240; 11.CO.247.244; 11.CO.247.243; 11.CO.247.247;

Prodrugs of 12.AH

12.AH.4.157; 12.AH.4.158; 12.AH.4.196; 12.AH.4.223; 12.AH.4.240; 12.AH.4.244; 12.AH.4.243; 12.AH.4.247; 12.AH.5.157; 12.AH.5.158; 12.AH.5.196; 12.AH.5.223; 12.AH.5.240; 12.AH.5.244; 12.AH.5.243; 12.AH.5.247; 12.AH.7.157; 12.AH.7.158; 12.AH.7.196; 12.AH.7.223; 12.AH.7.240; 12.AH.7.244; 12.AH.7.243; 12.AH.7.247; 12.AH.15.157; 12.AH.15.158; 12.AH.15.196; 12.AH.15.223; 12.AH.15.240; 12.AH.15.244; 12.AH.15.243; 12.AH.15.247; 12.AH.16.157; 12.AH.16.158; 12.AH.16.196; 12.AH.16.223; 12.AH.16.240; 12.AH.16.244; 12.AH.16.243; 12.AH.16.247; 12.AH.18.157; 12.AH.18.158; 12.AH.18.196; 12.AH.18.223; 12.AH.18.240; 12.AH.18.244; 12.AH.18.243; 12.AH.18.247; 12.AH.26.157; 12.AH.26.158; 12.AH.26.196; 12.AH.26.223; 12.AH.26.240; 12.AH.26.244; 12.AH.26.243; 12.AH.26.247; 12.AH.27.157; 12.AH.27.158; 12.AH.27.196; 12.AH.27.223; 12.AH.27.240; 12.AH.27.244; 12.AH.27.243; 12.AH.27.247; 12.AH.29.157; 12.AH.29.158; 12.AH.29.196; 12.AH.29.223; 12.AH.29.240; 12.AH.29.244; 12.AH.29.243; 12.AH.29.247; 12.AH.54.157; 12.AH.54.158; 12.AH.54.196; 12.AH.54.223; 12.AH.54.240; 12.AH.54.244; 12.AH.54.243; 12.AH.54.247; 12.AH.55.157; 12.AH.55.158; 12.AH.55.196; 12.AH.55.223; 12.AH.55.240; 12.AH.55.244; 12.AH.55.243; 12.AH.55.247; 12.AH.56.157; 12.AH.56.158; 12.AH.56.196; 12.AH.56.223; 12.AH.56.240; 12.AH.56.244; 12.AH.56.243; 12.AH.56.247; 12.AH.157.157; 12.AH.157.158; 12.AH.157.196; 12.AH.157.223; 12.AH.157.240; 12.AH.157.244; 12.AH.157.243; 12.AH.157.247; 12.AH.196.157; 12.AH.196.158; 12.AH.196.196; 12.AH.196.223; 12.AH.196.240; 12.AH.196.244; 12.AH.196.243; 12.AH.196.247; 12.AH.223.157; 12.AH.223.158; 12.AH.223.196; 12.AH.223.223; 12.AH.223.240; 12.AH.223.244; 12.AH.223.243; 12.AH.223.247; 12.AH.240.157; 12.AH.240.158; 12.AH.240.196; 12.AH.240.223; 12.AH.240.240; 12.AH.240.244; 12.AH.240.243; 12.AH.240.247; 12.AH.244.157; 12.AH.244.158; 12.AH.244.196; 12.AH.244.223; 12.AH.244.240; 12.AH.244.244; 12.AH.244.243; 12.AH.244.247; 12.AH.247.157; 12.AH.247.158; 12.AH.247.196; 12.AH.247.223; 12.AH.247.240; 12.AH.247.244; 12.AH.247.243; 12.AH.247.247;

Prodrugs of 12.AJ

12.AJ.4.157; 12.AJ.4.158; 12.AJ.4.196; 12.AJ.4.223; 12.AJ.4.240; 12.AJ.4.244; 12.AJ.4.243; 12.AJ.4.247; 12.AJ.5.157; 12.AJ.5.158; 12.AJ.5.196; 12.AJ.5.223; 12.AJ.5.240; 12.AJ.5.244; 12.AJ.5.243; 12.AJ.5.247; 12.AJ.7.157; 12.AJ.7.158; 12.AJ.7.196; 12.AJ.7.223; 12.AJ.7.240; 12.AJ.7.244; 12.AJ.7.243; 12.AJ.7.247; 12.AJ.15.157; 12.AJ.15.158; 12.AJ.15.196; 12.AJ.15.223; 12.AJ.15.240; 12.AJ.15.244; 12.AJ.15.243; 12.AJ.15.247; 12.AJ.16.157; 12.AJ.16.158; 12.AJ.16.196; 12.AJ.16.223; 12.AJ.16.240; 12.AJ.16.244; 12.AJ.16.243; 12.AJ.16.247; 12.AJ.18.157; 12.AJ.18.158; 12.AJ.18.196; 12.AJ.18.223; 12.AJ.18.240; 12.AJ.18.244; 12.AJ.18.243; 12.AJ.18.247; 12.AJ.26.157; 12.AJ.26.158; 12.AJ.26.196; 12.AJ.26.223; 12.AJ.26.240; 12.AJ.26.244; 12.AJ.26.243; 12.AJ.26.247; 12.AJ.27.157; 12.AJ.27.158; 12.AJ.27.196; 12.AJ.27.223; 12.AJ.27.240; 12.AJ.27.244; 12.AJ.27.243; 12.AJ.27.247; 12.AJ.29.157; 12.AJ.29.158; 12.AJ.29.196; 12.AJ.29.223; 12.AJ.29.240; 12.AJ.29.244; 12.AJ.29.243; 12.AJ.29.247; 12.AJ.54.157; 12.AJ.54.158; 12.AJ.54.196; 12.AJ.54.223; 12.AJ.54.240; 12.AJ.54.244; 12.AJ.54.243; 12.AJ.54.247; 12.AJ.55.157; 12.AJ.55.158; 12.AJ.55.196; 12.AJ.55.223; 12.AJ.55.240; 12.AJ.55.244; 12.AJ.55.243; 12.AJ.55.247; 12.AJ.56.157; 12.AJ.56.158; 12.AJ.56.196; 12.AJ.56.223; 12.AJ.56.240; 12.AJ.56.244; 12.AJ.56.243; 12.AJ.56.247; 12.AJ.157.157; 12.AJ.157.158; 12.AJ.157.196; 12.AJ.157.223; 12.AJ.157.240; 12.AJ.157.244; 12.AJ.157.243; 12.AJ.157.247; 12.AJ.196.157; 12.AJ.196.158; 12.AJ.196.196; 12.AJ.196.223; 12.AJ.196.240; 12.AJ.196.244; 12.AJ.196.243; 12.AJ.196.247; 12.AJ.223.157; 12.AJ.223.158; 12.AJ.223.196; 12.AJ.223.223; 12.AJ.223.240; 12.AJ.223.244; 12.AJ.223.243; 12.AJ.223.247; 12.AJ.240.157; 12.AJ.240.158; 12.AJ.240.196; 12.AJ.240.223; 12.AJ.240.240; 12.AJ.240.244; 12.AJ.240.243; 12.AJ.240.247; 12.AJ.244.157; 12.AJ.244.158; 12.AJ.244.196; 12.AJ.244.223; 12.AJ.244.240; 12.AJ.244.244; 12.AJ.244.243; 12.AJ.244.247; 12.AJ.247.157; 12.AJ.247.158; 12.AJ.247.196; 12.AJ.247.223; 12.AJ.247.240; 12.AJ.247.244; 12.AJ.247.243; 12.AJ.247.247;

Prodrugs of 12.AN

12.AN.4.157; 12.AN.4.158; 12.AN.4.196; 12.AN.4.223; 12.AN.4.240; 12.AN.4.244; 12.AN.4.243; 12.AN.4.247; 12.AN.5.157; 12.AN.5.158;

TABLE 100-continued

12.AN.5.196; 12.AN.5.223; 12.AN.5.240; 12.AN.5.244; 12.AN.5.243; 12.AN.5.247; 12.AN.7.157; 12.AN.7.158; 12.AN.7.196; 12.AN.7.223; 12.AN.7.240; 12.AN.7.244; 12.AN.7.243; 12.AN.7.247; 12.AN.15.157; 12.AN.15.158; 12.AN.15.196; 12.AN.15.223; 12.AN.15.240; 12.AN.15.244; 12.AN.15.243; 12.AN.15.247; 12.AN.16.157; 12.AN.16.158; 12.AN.16.196; 12.AN.16.223; 12.AN.16.240; 12.AN.16.244; 12.AN.16.243; 12.AN.16.247; 12.AN.18.157; 12.AN.18.158; 12.AN.18.196; 12.AN.18.223; 12.AN.18.240; 12.AN.18.244; 12.AN.18.243; 12.AN.18.247; 12.AN.26.157; 12.AN.26.158; 12.AN.26.196; 12.AN.26.223; 12.AN.26.240; 12.AN.26.244; 12.AN.26.243; 12.AN.26.247; 12.AN.27.157; 12.AN.27.158; 12.AN.27.196; 12.AN.27.223; 12.AN.27.240; 12.AN.27.244; 12.AN.27.243; 12.AN.27.247; 12.AN.29.157; 12.AN.29.158; 12.AN.29.196; 12.AN.29.223; 12.AN.29.240; 12.AN.29.244; 12.AN.29.243; 12.AN.29.247; 12.AN.54.157; 12.AN.54.158; 12.AN.54.196; 12.AN.54.223; 12.AN.54.240; 12.AN.54.244; 12.AN.54.243; 12.AN.54.247; 12.AN.55.157; 12.AN.55.158; 12.AN.55.196; 12.AN.55.223; 12.AN.55.240; 12.AN.55.244; 12.AN.55.243; 12.AN.55.247; 12.AN.56.157; 12.AN.56.158; 12.AN.56.196; 12.AN.56.223; 12.AN.56.240; 12.AN.56.244; 12.AN.56.243; 12.AN.56.247; 12.AN.157.157; 12.AN.157.158; 12.AN.157.196; 12.AN.157.223; 12.AN.157.240; 12.AN.157.244; 12.AN.157.243; 12.AN.157.247; 12.AN.196.157; 12.AN.196.158; 12.AN.196.196; 12.AN.196.223; 12.AN.196.240; 12.AN.196.244; 12.AN.196.243; 12.AN.196.247; 12.AN.223.157; 12.AN.223.158; 12.AN.223.196; 12.AN.223.223; 12.AN.223.240; 12.AN.223.244; 12.AN.223.243; 12.AN.223.247; 12.AN.240.157; 12.AN.240.158; 12.AN.240.196; 12.AN.240.223; 12.AN.240.240; 12.AN.240.244; 12.AN.240.243; 12.AN.240.247; 12.AN.244.157; 12.AN.244.158; 12.AN.244.196; 12.AN.244.223; 12.AN.244.240; 12.AN.244.244; 12.AN.244.243; 12.AN.244.247; 12.AN.247.157; 12.AN.247.158; 12.AN.247.196; 12.AN.247.223; 12.AN.247.240; 12.AN.247.244; 12.AN.247.243; 12.AN.247.247;

Prodrugs of 12.AP

12.AP.4.157; 12.AP.4.158; 12.AP.4.196; 12.AP.4.223; 12.AP.4.240; 12.AP.4.244; 12.AP.4.243; 12.AP.4.247; 12.AP.5.157; 12.AP.5.158; 12.AP.5.196; 12.AP.5.223; 12.AP.5.240; 12.AP.5.244; 12.AP.5.243; 12.AP.5.247; 12.AP.7.157; 12.AP.7.158; 12.AP.7.196; 12.AP.7.223; 12.AP.7.240; 12.AP.7.244; 12.AP.7.243; 12.AP.7.247; 12.AP.15.157; 12.AP.15.158; 12.AP.15.196; 12.AP.15.223; 12.AP.15.240; 12.AP.15.244; 12.AP.15.243; 12.AP.15.247; 12.AP.16.157; 12.AP.16.158; 12.AP.16.196; 12.AP.16.223; 12.AP.16.240; 12.AP.16.244; 12.AP.16.243; 12.AP.16.247; 12.AP.18.157; 12.AP.18.158; 12.AP.18.196; 12.AP.18.223; 12.AP.18.240; 12.AP.18.244; 12.AP.18.243; 12.AP.18.247; 12.AP.26.157; 12.AP.26.158; 12.AP.26.196; 12.AP.26.223; 12.AP.26.240; 12.AP.26.244; 12.AP.26.243; 12.AP.26.247; 12.AP.27.157; 12.AP.27.158; 12.AP.27.196; 12.AP.27.223; 12.AP.27.240; 12.AP.27.244; 12.AP.27.243; 12.AP.27.247; 12.AP.29.157; 12.AP.29.158; 12.AP.29.196; 12.AP.29.223; 12.AP.29.240; 12.AP.29.244; 12.AP.29.243; 12.AP.29.247; 12.AP.54.157; 12.AP.54.158; 12.AP.54.196; 12.AP.54.223; 12.AP.54.240; 12.AP.54.244; 12.AP.54.243; 12.AP.54.247; 12.AP.55.157; 12.AP.55.158; 12.AP.55.196; 12.AP.55.223; 12.AP.55.240; 12.AP.55.244; 12.AP.55.243; 12.AP.55.247; 12.AP.56.157; 12.AP.56.158; 12.AP.56.196; 12.AP.56.223; 12.AP.56.240; 12.AP.56.244; 12.AP.56.243; 12.AP.56.247; 12.AP.157.157; 12.AP.157.158; 12.AP.157.196; 12.AP.157.223; 12.AP.157.240; 12.AP.157.244; 12.AP.157.243; 12.AP.157.247; 12.AP.196.157; 12.AP.196.158; 12.AP.196.196; 12.AP.196.223; 12.AP.196.240; 12.AP.196.244; 12.AP.196.243; 12.AP.196.247; 12.AP.223.157; 12.AP.223.158; 12.AP.223.196; 12.AP.223.223; 12.AP.223.240; 12.AP.223.244; 12.AP.223.243; 12.AP.223.247; 12.AP.240.157; 12.AP.240.158; 12.AP.240.196; 12.AP.240.223; 12.AP.240.240; 12.AP.240.244; 12.AP.240.243; 12.AP.240.247; 12.AP.244.157; 12.AP.244.158; 12.AP.244.196; 12.AP.244.223; 12.AP.244.240; 12.AP.244.244; 12.AP.244.243; 12.AP.244.247; 12.AP.247.157; 12.AP.247.158; 12.AP.247.196; 12.AP.247.223; 12.AP.247.240; 12.AP.247.244; 12.AP.247.243; 12.AP.247.247;

Prodrugs of 12.AZ

12.AZ.4.157; 12.AZ.4.158; 12.AZ.4.196; 12.AZ.4.223; 12.AZ.4.240; 12.AZ.4.244; 12.AZ.4.243; 12.AZ.4.247; 12.AZ.5.157; 12.AZ.5.158; 12.AZ.5.196; 12.AZ.5.223; 12.AZ.5.240; 12.AZ.5.244; 12.AZ.5.243; 12.AZ.5.247; 12.AZ.7.157; 12.AZ.7.158; 12.AZ.7.196; 12.AZ.7.223; 12.AZ.7.240; 12.AZ.7.244; 12.AZ.7.243; 12.AZ.7.247; 12.AZ.15.157; 12.AZ.15.158; 12.AZ.15.196; 12.AZ.15.223; 12.AZ.15.240; 12.AZ.15.244; 12.AZ.15.243; 12.AZ.15.247; 12.AZ.16.157; 12.AZ.16.158; 12.AZ.16.196; 12.AZ.16.223; 12.AZ.16.240; 12.AZ.16.244; 12.AZ.16.243; 12.AZ.16.247; 12.AZ.18.157; 12.AZ.18.158; 12.AZ.18.196; 12.AZ.18.223; 12.AZ.18.240; 12.AZ.18.244; 12.AZ.18.243; 12.AZ.18.247; 12.AZ.26.157; 12.AZ.26.158; 12.AZ.26.196; 12.AZ.26.223; 12.AZ.26.240; 12.AZ.26.244; 12.AZ.26.243; 12.AZ.26.247; 12.AZ.27.157; 12.AZ.27.158; 12.AZ.27.196; 12.AZ.27.223; 12.AZ.27.240; 12.AZ.27.244; 12.AZ.27.243; 12.AZ.27.247; 12.AZ.29.157; 12.AZ.29.158; 12.AZ.29.196; 12.AZ.29.223; 12.AZ.29.240; 12.AZ.29.244;

TABLE 100-continued

12.AZ.29.243; 12.AZ.29.247; 12.AZ.54.157; 12.AZ.54.158; 12.AZ.54.196; 12.AZ.54.223; 12.AZ.54.240; 12.AZ.54.244; 12.AZ.54.243; 12.AZ.54.247; 12.AZ.55.157; 12.AZ.55.158; 12.AZ.55.196; 12.AZ.55.223; 12.AZ.55.240; 12.AZ.55.244; 12.AZ.55.243; 12.AZ.55.247; 12.AZ.56.157; 12.AZ.56.158; 12.AZ.56.196; 12.AZ.56.223; 12.AZ.56.240; 12.AZ.56.244; 12.AZ.56.243; 12.AZ.56.247; 12.AZ.157.157; 12.AZ.157.158; 12.AZ.157.196; 12.AZ.157.223; 12.AZ.157.240; 12.AZ.157.244; 12.AZ.157.243; 12.AZ.157.247; 12.AZ.196.157; 12.AZ.196.158; 12.AZ.196.196; 12.AZ.196.223; 12.AZ.196.240; 12.AZ.196.244; 12.AZ.196.243; 12.AZ.196.247; 12.AZ.223.157; 12.AZ.223.158; 12.AZ.223.196; 12.AZ.223.223; 12.AZ.223.240; 12.AZ.223.244; 12.AZ.223.243; 12.AZ.223.247; 12.AZ.240.157; 12.AZ.240.158; 12.AZ.240.196; 12.AZ.240.223; 12.AZ.240.240; 12.AZ.240.244; 12.AZ.240.243; 12.AZ.240.247; 12.AZ.244.157; 12.AZ.244.158; 12.AZ.244.196; 12.AZ.244.223; 12.AZ.244.240; 12.AZ.244.244; 12.AZ.244.243; 12.AZ.244.247; 12.AZ.247.157; 12.AZ.247.158; 12.AZ.247.196; 12.AZ.247.223; 12.AZ.247.240; 12.AZ.247.244; 12.AZ.247.243; 12.AZ.247.247;

Prodrugs of 12.BF

12.BF.4.157; 12.BF.4.158; 12.BF.4.196; 12.BF.4.223; 12.BF.4.240; 12.BF.4.244; 12.BF.4.243; 12.BF.4.247; 12.BF.5.157; 12.BF.5.158; 12.BF.5.196; 12.BF.5.223; 12.BF.5.240; 12.BF.5.244; 12.BF.5.243; 12.BF.5.247; 12.BF.7.157; 12.BF.7.158; 12.BF.7.196; 12.BF.7.223; 12.BF.7.240; 12.BF.7.244; 12.BF.7.243; 12.BF.7.247; 12.BF.15.157; 12.BF.15.158; 12.BF.15.196; 12.BF.15.223; 12.BF.15.240; 12.BF.15.244; 12.BF.15.243; 12.BF.15.247; 12.BF.16.157; 12.BF.16.158; 12.BF.16.196; 12.BF.16.223; 12.BF.16.240; 12.BF.16.244; 12.BF.16.243; 12.BF.16.247; 12.BF.18.157; 12.BF.18.158; 12.BF.18.196; 12.BF.18.223; 12.BF.18.240; 12.BF.18.244; 12.BF.18.243; 12.BF.18.247; 12.BF.26.157; 12.BF.26.158; 12.BF.26.196; 12.BF.26.223; 12.BF.26.240; 12.BF.26.244; 12.BF.26.243; 12.BF.26.247; 12.BF.27.157; 12.BF.27.158; 12.BF.27.196; 12.BF.27.223; 12.BF.27.240; 12.BF.27.244; 12.BF.27.243; 12.BF.27.247; 12.BF.29.157; 12.BF.29.158; 12.BF.29.196; 12.BF.29.223; 12.BF.29.240; 12.BF.29.244; 12.BF.29.243; 12.BF.29.247; 12.BF.54.157; 12.BF.54.158; 12.BF.54.196; 12.BF.54.223; 12.BF.54.240; 12.BF.54.244; 12.BF.54.243; 12.BF.54.247; 12.BF.55.157; 12.BF.55.158; 12.BF.55.196; 12.BF.55.223; 12.BF.55.240; 12.BF.55.244; 12.BF.55.243; 12.BF.55.247; 12.BF.56.157; 12.BF.56.158; 12.BF.56.196; 12.BF.56.223; 12.BF.56.240; 12.BF.56.244; 12.BF.56.243; 12.BF.56.247; 12.BF.157.157; 12.BF.157.158; 12.BF.157.196; 12.BF.157.223; 12.BF.157.240; 12.BF.157.244; 12.BF.157.243; 12.BF.157.247; 12.BF.196.157; 12.BF.196.158; 12.BF.196.196; 12.BF.196.223; 12.BF.196.240; 12.BF.196.244; 12.BF.196.243; 12.BF.196.247; 12.BF.223.157; 12.BF.223.158; 12.BF.223.196; 12.BF.223.223; 12.BF.223.240; 12.BF.223.244; 12.BF.223.243; 12.BF.223.247; 12.BF.240.157; 12.BF.240.158; 12.BF.240.196; 12.BF.240.223; 12.BF.240.240; 12.BF.240.244; 12.BF.240.243; 12.BF.240.247; 12.BF.244.157; 12.BF.244.158; 12.BF.244.196; 12.BF.244.223; 12.BF.244.240; 12.BF.244.244; 12.BF.244.243; 12.BF.244.247; 12.BF.247.157; 12.BF.247.158; 12.BF.247.196; 12.BF.247.223; 12.BF.247.240; 12.BF.247.244; 12.BF.247.243; 12.BF.247.247;

Prodrugs of 12.CI

12.CI.4.157; 12.CI.4.158; 12.CI.4.196; 12.CI.4.223; 12.CI.4.240; 12.CI.4.244; 12.CI.4.243; 12.CI.4.247; 12.CI.5.157; 12.CI.5.158; 12.CI.5.196; 12.CI.5.223; 12.CI.5.240; 12.CI.5.244; 12.CI.5.243; 12.CI.5.247; 12.CI.7.157; 12.CI.7.158; 12.CI.7.196; 12.CI.7.223; 12.CI.7.240; 12.CI.7.244; 12.CI.7.243; 12.CI.7.247; 12.CI.15.157; 12.CI.15.158; 12.CI.15.196; 12.CI.15.223; 12.CI.15.240; 12.CI.15.244; 12.CI.15.243; 12.CI.15.247; 12.CI.16.157; 12.CI.16.158; 12.CI.16.196; 12.CI.16.223; 12.CI.16.240; 12.CI.16.244; 12.CI.16.243; 12.CI.16.247; 12.CI.18.157; 12.CI.18.158; 12.CI.18.196; 12.CI.18.223; 12.CI.18.240; 12.CI.18.244; 12.CI.18.243; 12.CI.18.247; 12.CI.26.157; 12.CI.26.158; 12.CI.26.196; 12.CI.26.223; 12.CI.26.240; 12.CI.26.244; 12.CI.26.243; 12.CI.26.247; 12.CI.27.157; 12.CI.27.158; 12.CI.27.196; 12.CI.27.223; 12.CI.27.240; 12.CI.27.244; 12.CI.27.243; 12.CI.27.247; 12.CI.29.157; 12.CI.29.158; 12.CI.29.196; 12.CI.29.223; 12.CI.29.240; 12.CI.29.244; 12.CI.29.243; 12.CI.29.247; 12.CI.54.157; 12.CI.54.158; 12.CI.54.196; 12.CI.54.223; 12.CI.54.240; 12.CI.54.244; 12.CI.54.243; 12.CI.54.247; 12.CI.55.157; 12.CI.55.158; 12.CI.55.196; 12.CI.55.223; 12.CI.55.240; 12.CI.55.244; 12.CI.55.243; 12.CI.55.247; 12.CI.56.157; 12.CI.56.158; 12.CI.56.196; 12.CI.56.223; 12.CI.56.240; 12.CI.56.244; 12.CI.56.243; 12.CI.56.247; 12.CI.157.157; 12.CI.157.158; 12.CI.157.196; 12.CI.157.223; 12.CI.157.240; 12.CI.157.244; 12.CI.157.243; 12.CI.157.247; 12.CI.196.157; 12.CI.196.158; 12.CI.196.196; 12.CI.196.223; 12.CI.196.240; 12.CI.196.244; 12.CI.196.243; 12.CI.196.247; 12.CI.223.157; 12.CI.223.158; 12.CI.223.196; 12.CI.223.223; 12.CI.223.240; 12.CI.223.244; 12.CI.223.243; 12.CI.223.247; 12.CI.240.157; 12.CI.240.158; 12.CI.240.196; 12.CI.240.223; 12.CI.240.240; 12.CI.240.244; 12.CI.240.243; 12.CI.240.247; 12.CI.244.157; 12.CI.244.158; 12.CI.244.196; 12.CI.244.223; 12.CI.244.240; 12.CI.244.244; 12.CI.244.243; 12.CI.244.247; 12.CI.247.157; 12.CI.247.158; 12.CI.247.196; 12.CI.247.223; 12.CI.247.240; 12.CI.247.244; 12.CI.247.243; 12.CI.247.247;

TABLE 100-continued

Prodrugs of 12.CO

12.CO.4.157; 12.CO.4.158; 12.CO.4.196; 12.CO.4.223; 12.CO.4.240; 12.CO.4.244; 12.CO.4.243; 12.CO.4.247; 12.CO.5.157; 12.CO.5.158; 12.CO.5.196; 12.CO.5.223; 12.CO.5.240; 12.CO.5.244; 12.CO.5.243; 12.CO.5.247; 12.CO.7.157; 12.CO.7.158; 12.CO.7.196; 12.CO.7.223; 12.CO.7.240; 12.CO.7.244; 12.CO.7.243; 12.CO.7.247; 12.CO.15.157; 12.CO.15.158; 12.CO.15.196; 12.CO.15.223; 12.CO.15.240; 12.CO.15.244; 12.CO.15.243; 12.CO.15.247; 12.CO.16.157; 12.CO.16.158; 12.CO.16.196; 12.CO.16.223; 12.CO.16.240; 12.CO.16.244; 12.CO.16.243; 12.CO.16.247; 12.CO.18.157; 12.CO.18.158; 12.CO.18.196; 12.CO.18.223; 12.CO.18.240; 12.CO.18.244; 12.CO.18.243; 12.CO.18.247; 12.CO.26.157; 12.CO.26.158; 12.CO.26.196; 12.CO.26.223; 12.CO.26.240; 12.CO.26.244; 12.CO.26.243; 12.CO.26.247; 12.CO.27.157; 12.CO.27.158; 12.CO.27.196; 12.CO.27.223; 12.CO.27.240; 12.CO.27.244; 12.CO.27.243; 12.CO.27.247; 12.CO.29.157; 12.CO.29.158; 12.CO.29.196; 12.CO.29.223; 12.CO.29.240; 12.CO.29.244; 12.CO.29.243; 12.CO.29.247; 12.CO.54.157; 12.CO.54.158; 12.CO.54.196; 12.CO.54.223; 12.CO.54.240; 12.CO.54.244; 12.CO.54.243; 12.CO.54.247; 12.CO.55.157; 12.CO.55.158; 12.CO.55.196; 12.CO.55.223; 12.CO.55.240; 12.CO.55.244; 12.CO.55.243; 12.CO.55.247; 12.CO.56.157; 12.CO.56.158; 12.CO.56.196; 12.CO.56.223; 12.CO.56.240; 12.CO.56.244; 12.CO.56.243; 12.CO.56.247; 12.CO.157.157; 12.CO.157.158; 12.CO.157.196; 12.CO.157.223; 12.CO.157.240; 12.CO.157.244; 12.CO.157.243; 12.CO.157.247; 12.CO.196.157; 12.CO.196.158; 12.CO.196.196; 12.CO.196.223; 12.CO.196.240; 12.CO.196.244; 12.CO.196.243; 12.CO.196.247; 12.CO.223.157; 12.CO.223.158; 12.CO.223.196; 12.CO.223.223; 12.CO.223.240; 12.CO.223.244; 12.CO.223.243; 12.CO.223.247; 12.CO.240.157; 12.CO.240.158; 12.CO.240.196; 12.CO.240.223; 12.CO.240.240; 12.CO.240.244; 12.CO.240.243; 12.CO.240.247; 12.CO.244.157; 12.CO.244.158; 12.CO.244.196; 12.CO.244.223; 12.CO.244.240; 12.CO.244.244; 12.CO.244.243; 12.CO.244.247; 12.CO.247.157; 12.CO.247.158; 12.CO.247.196; 12.CO.247.223; 12.CO.247.240; 12.CO.247.244; 12.CO.247.243; 12.CO.247.247.

Prodrugs of 13.B

13.B.228.228; 13.B.228.229; 13.B.228.230; 13.B.228.231; 13.B.228.236; 13.B.228.237; 13.B.228.238; 13.B.228.239; 13.B.228.154; 13.B.228.157; 13.B.228.166; 13.B.228.169; 13.B.228.172; 13.B.228.175; 13.B.228.240; 13.B.228.244; 13.B.229.228; 13.B.229.229; 13.B.229.230; 13.B.229.231; 13.B.229.236; 13.B.229.237; 13.B.229.238; 13.B.229.239; 13.B.229.154; 13.B.229.157; 13.B.229.166; 13.B.229.169; 13.B.229.172; 13.B.229.175; 13.B.229.240; 13.B.229.244; 13.B.230.228; 13.B.230.229; 13.B.230.230; 13.B.230.231; 13.B.230.236; 13.B.230.237; 13.B.230.238; 13.B.230.239; 13.B.230.154; 13.B.230.157; 13.B.230.166; 13.B.230.169; 13.B.230.172; 13.B.230.175; 13.B.230.240; 13.B.230.244; 13.B.231.228; 13.B.231.229; 13.B.231.230; 13.B.231.231; 13.B.231.236; 13.B.231.237; 13.B.231.238; 13.B.231.239; 13.B.231.154; 13.B.231.157; 13.B.231.166; 13.B.231.169; 13.B.231.172; 13.B.231.175; 13.B.231.240; 13.B.231.244; 13.B.236.228; 13.B.236.229; 13.B.236.230; 13.B.236.231; 13.B.236.236; 13.B.236.237; 13.B.236.238; 13.B.236.239; 13.B.236.154; 13.B.236.157; 13.B.236.166; 13.B.236.169; 13.B.236.172; 13.B.236.175; 13.B.236.240; 13.B.236.244; 13.B.237.228; 13.B.237.229; 13.B.237.230; 13.B.237.231; 13.B.237.236; 13.B.237.237; 13.B.237.238; 13.B.237.239; 13.B.237.154; 13.B.237.157; 13.B.237.166; 13.B.237.169; 13.B.237.172; 13.B.237.175; 13.B.237.240; 13.B.237.244; 13.B.238.228; 13.B.238.229; 13.B.238.230; 13.B.238.231; 13.B.238.236; 13.B.238.237; 13.B.238.238; 13.B.238.239; 13.B.238.154; 13.B.238.157; 13.B.238.166; 13.B.238.169; 13.B.238.172; 13.B.238.175; 13.B.238.240; 13.B.238.244; 13.B.239.228; 13.B.239.229; 13.B.239.230; 13.B.239.231; 13.B.239.236; 13.B.239.237; 13.B.239.238; 13.B.239.239; 13.B.239.154; 13.B.239.157; 13.B.239.166; 13.B.239.169; 13.B.239.172; 13.B.239.175; 13.B.239.240; 13.B.239.244; 13.B.154.228; 13.B.154.229; 13.B.154.230; 13.B.154.231; 13.B.154.236; 13.B.154.237; 13.B.154.238; 13.B.154.239; 13.B.154.154; 13.B.154.157; 13.B.154.166; 13.B.154.169; 13.B.154.172; 13.B.154.175; 13.B.154.240; 13.B.154.244; 13.B.157.228; 13.B.157.229; 13.B.157.230; 13.B.157.231; 13.B.157.236; 13.B.157.237; 13.B.157.238; 13.B.157.239; 13.B.157.154; 13.B.157.157; 13.B.157.166; 13.B.157.169; 13.B.157.172; 13.B.157.175; 13.B.157.240; 13.B.157.244; 13.B.166.228; 13.B.166.229; 13.B.166.230; 13.B.166.231; 13.B.166.236; 13.B.166.237; 13.B.166.238; 13.B.166.239; 13.B.166.154; 13.B.166.157; 13.B.166.166; 13.B.166.169; 13.B.166.172; 13.B.166.175; 13.B.166.240; 13.B.166.244; 13.B.169.228; 13.B.169.229; 13.B.169.230; 13.B.169.231; 13.B.169.236; 13.B.169.237; 13.B.169.238; 13.B.169.239; 13.B.169.154; 13.B.169.157; 13.B.169.166; 13.B.169.169; 13.B.169.172; 13.B.169.175; 13.B.169.240; 13.B.169.244; 13.B.172.228; 13.B.172.229; 13.B.172.230; 13.B.172.231; 13.B.172.236; 13.B.172.237; 13.B.172.238; 13.B.172.239; 13.B.172.154; 13.B.172.157; 13.B.172.166; 13.B.172.169; 13.B.172.172; 13.B.172.175; 13.B.172.240; 13.B.172.244; 13.B.175.228; 13.B.175.229; 13.B.175.230; 13.B.175.231; 13.B.175.236; 13.B.175.237; 13.B.175.238;

TABLE 100-continued

13.B.175.239; 13.B.175.154; 13.B.175.157; 13.B.175.166; 13.B.175.169; 13.B.175.172; 13.B.175.175; 13.B.175.240; 13.B.175.244; 13.B.240.228; 13.B.240.229; 13.B.240.230; 13.B.240.231; 13.B.240.236; 13.B.240.237; 13.B.240.238; 13.B.240.239; 13.B.240.154; 13.B.240.157; 13.B.240.166; 13.B.240.169; 13.B.240.172; 13.B.240.175; 13.B.240.240; 13.B.240.244; 13.B.244.228; 13.B.244.229; 13.B.244.230; 13.B.244.231; 13.B.244.236; 13.B.244.237; 13.B.244.238; 13.B.244.239; 13.B.244.154; 13.B.244.157; 13.B.244.166; 13.B.244.169; 13.B.244.172; 13.B.244.175; 13.B.244.240; 13.B.244.244;

Prodrugs of 13.D

13.D.228.228; 13.D.228.229; 13.D.228.230; 13.D.228.231; 13.D.228.236; 13.D.228.237; 13.D.228.238; 13.D.228.239; 13.D.228.154; 13.D.228.157; 13.D.228.166; 13.D.228.169; 13.D.228.172; 13.D.228.175; 13.D.228.240; 13.D.228.244; 13.D.229.228; 13.D.229.229; 13.D.229.230; 13.D.229.231; 13.D.229.236; 13.D.229.237; 13.D.229.238; 13.D.229.239; 13.D.229.154; 13.D.229.157; 13.D.229.166; 13.D.229.169; 13.D.229.172; 13.D.229.175; 13.D.229.240; 13.D.229.244; 13.D.230.228; 13.D.230.229; 13.D.230.230; 13.D.230.231; 13.D.230.236; 13.D.230.237; 13.D.230.238; 13.D.230.239; 13.D.230.154; 13.D.230.157; 13.D.230.166; 13.D.230.169; 13.D.230.172; 13.D.230.175; 13.D.230.240; 13.D.230.244; 13.D.231.228; 13.D.231.229; 13.D.231.230; 13.D.231.231; 13.D.231.236; 13.D.231.237; 13.D.231.238; 13.D.231.239; 13.D.231.154; 13.D.231.157; 13.D.231.166; 13.D.231.169; 13.D.231.172; 13.D.231.175; 13.D.231.240; 13.D.231.244; 13.D.236.228; 13.D.236.229; 13.D.236.230; 13.D.236.231; 13.D.236.236; 13.D.236.237; 13.D.236.238; 13.D.236.239; 13.D.236.154; 13.D.236.157; 13.D.236.166; 13.D.236.169; 13.D.236.172; 13.D.236.175; 13.D.236.240; 13.D.236.244; 13.D.237.228; 13.D.237.229; 13.D.237.230; 13.D.237.231; 13.D.237.236; 13.D.237.237; 13.D.237.238; 13.D.237.239; 13.D.237.154; 13.D.237.157; 13.D.237.166; 13.D.237.169; 13.D.237.172; 13.D.237.175; 13.D.237.240; 13.D.237.244; 13.D.238.228; 13.D.238.229; 13.D.238.230; 13.D.238.231; 13.D.238.236; 13.D.238.237; 13.D.238.238; 13.D.238.239; 13.D.238.154; 13.D.238.157; 13.D.238.166; 13.D.238.169; 13.D.238.172; 13.D.238.175; 13.D.238.240; 13.D.238.244; 13.D.239.228; 13.D.239.229; 13.D.239.230; 13.D.239.231; 13.D.239.236; 13.D.239.237; 13.D.239.238; 13.D.239.239; 13.D.239.154; 13.D.239.157; 13.D.239.166; 13.D.239.169; 13.D.239.172; 13.D.239.175; 13.D.239.240; 13.D.239.244; 13.D.154.228; 13.D.154.229; 13.D.154.230; 13.D.154.231; 13.D.154.236; 13.D.154.237; 13.D.154.238; 13.D.154.239; 13.D.154.154; 13.D.154.157; 13.D.154.166; 13.D.154.169; 13.D.154.172; 13.D.154.175; 13.D.154.240; 13.D.154.244; 13.D.157.228; 13.D.157.229; 13.D.157.230; 13.D.157.231; 13.D.157.236; 13.D.157.237; 13.D.157.238; 13.D.157.239; 13.D.157.154; 13.D.157.157; 13.D.157.166; 13.D.157.169; 13.D.157.172; 13.D.157.175; 13.D.157.240; 13.D.157.244; 13.D.166.228; 13.D.166.229; 13.D.166.230; 13.D.166.231; 13.D.166.236; 13.D.166.237; 13.D.166.238; 13.D.166.239; 13.D.166.154; 13.D.166.157; 13.D.166.166; 13.D.166.169; 13.D.166.172; 13.D.166.175; 13.D.166.240; 13.D.166.244; 13.D.169.228; 13.D.169.229; 13.D.169.230; 13.D.169.231; 13.D.169.236; 13.D.169.237; 13.D.169.238; 13.D.169.239; 13.D.169.154; 13.D.169.157; 13.D.169.166; 13.D.169.169; 13.D.169.172; 13.D.169.175; 13.D.169.240; 13.D.169.244; 13.D.172.228; 13.D.172.229; 13.D.172.230; 13.D.172.231; 13.D.172.236; 13.D.172.237; 13.D.172.238; 13.D.172.239; 13.D.172.154; 13.D.172.157; 13.D.172.166; 13.D.172.169; 13.D.172.172; 13.D.172.175; 13.D.172.240; 13.D.172.244; 13.D.175.228; 13.D.175.229; 13.D.175.230; 13.D.175.231; 13.D.175.236; 13.D.175.237; 13.D.175.238; 13.D.175.239; 13.D.175.154; 13.D.175.157; 13.D.175.166; 13.D.175.169; 13.D.175.172; 13.D.175.175; 13.D.175.240; 13.D.175.244; 13.D.240.228; 13.D.240.229; 13.D.240.230; 13.D.240.231; 13.D.240.236; 13.D.240.237; 13.D.240.238; 13.D.240.239; 13.D.240.154; 13.D.240.157; 13.D.240.166; 13.D.240.169; 13.D.240.172; 13.D.240.175; 13.D.240.240; 13.D.240.244; 13.D.244.228; 13.D.244.229; 13.D.244.230; 13.D.244.231; 13.D.244.236; 13.D.244.237; 13.D.244.238; 13.D.244.239; 13.D.244.154; 13.D.244.157; 13.D.244.166; 13.D.244.169; 13.D.244.172; 13.D.244.175; 13.D.244.240; 13.D.244.244;

Prodrugs of 13.E

13.E.228.228; 13.E.228.229; 13.E.228.230; 13.E.228.231; 13.E.228.236; 13.E.228.237; 13.E.228.238; 13.E.228.239; 13.E.228.154; 13.E.228.157; 13.E.228.166; 13.E.228.169; 13.E.228.172; 13.E.228.175; 13.E.228.240; 13.E.228.244; 13.E.229.228; 13.E.229.229; 13.E.229.230; 13.E.229.231; 13.E.229.236; 13.E.229.237; 13.E.229.238; 13.E.229.239; 13.E.229.154; 13.E.229.157; 13.E.229.166; 13.E.229.169; 13.E.229.172; 13.E.229.175; 13.E.229.240; 13.E.229.244; 13.E.230.228; 13.E.230.229; 13.E.230.230; 13.E.230.231; 13.E.230.236; 13.E.230.237; 13.E.230.238; 13.E.230.239; 13.E.230.154; 13.E.230.157; 13.E.230.166; 13.E.230.169; 13.E.230.172; 13.E.230.175; 13.E.230.240; 13.E.230.244; 13.E.231.228; 13.E.231.229; 13.E.231.230; 13.E.231.231; 13.E.231.236; 13.E.231.237; 13.E.231.238; 13.E.231.239; 13.E.231.154; 13.E.231.157; 13.E.231.166; 13.E.231.169; 13.E.231.172; 13.E.231.175; 13.E.231.240; 13.E.231.244; 13.E.236.228; 13.E.236.229; 13.E.236.230; 13.E.236.231; 13.E.236.236; 13.E.236.237;

TABLE 100-continued

13.E.236.238; 13.E.236.239; 13.E.236.154; 13.E.236.157; 13.E.236.166; 13.E.236.169; 13.E.236.172; 13.E.236.175; 13.E.236.240; 13.E.236.244; 13.E.237.228; 13.E.237.229; 13.E.237.230; 13.E.237.231; 13.E.237.236; 13.E.237.237; 13.E.237.238; 13.E.237.239; 13.E.237.154; 13.E.237.157; 13.E.237.166; 13.E.237.169; 13.E.237.172; 13.E.237.175; 13.E.237.240; 13.E.237.244; 13.E.238.228; 13.E.238.229; 13.E.238.230; 13.E.238.231; 13.E.238.236; 13.E.238.237; 13.E.238.238; 13.E.238.239; 13.E.238.154; 13.E.238.157; 13.E.238.166; 13.E.238.169; 13.E.238.172; 13.E.238.175; 13.E.238.240; 13.E.238.244; 13.E.239.228; 13.E.239.229; 13.E.239.230; 13.E.239.231; 13.E.239.236; 13.E.239.237; 13.E.239.238; 13.E.239.239; 13.E.239.154; 13.E.239.157; 13.E.239.166; 13.E.239.169; 13.E.239.172; 13.E.239.175; 13.E.239.240; 13.E.239.244; 13.E.154.228; 13.E.154.229; 13.E.154.230; 13.E.154.231; 13.E.154.236; 13.E.154.237; 13.E.154.238; 13.E.154.239; 13.E.154.154; 13.E.154.157; 13.E.154.166; 13.E.154.169; 13.E.154.172; 13.E.154.175; 13.E.154.240; 13.E.154.244; 13.E.157.228; 13.E.157.229; 13.E.157.230; 13.E.157.231; 13.E.157.236; 13.E.157.237; 13.E.157.238; 13.E.157.239; 13.E.157.154; 13.E.157.157; 13.E.157.166; 13.E.157.169; 13.E.157.172; 13.E.157.175; 13.E.157.240; 13.E.157.244; 13.E.166.228; 13.E.166.229; 13.E.166.230; 13.E.166.231; 13.E.166.236; 13.E.166.237; 13.E.166.238; 13.E.166.239; 13.E.166.154; 13.E.166.157; 13.E.166.166; 13.E.166.169; 13.E.166.172; 13.E.166.175; 13.E.166.240; 13.E.166.244; 13.E.169.228; 13.E.169.229; 13.E.169.230; 13.E.169.231; 13.E.169.236; 13.E.169.237; 13.E.169.238; 13.E.169.239; 13.E.169.154; 13.E.169.157; 13.E.169.166; 13.E.169.169; 13.E.169.172; 13.E.169.175; 13.E.169.240; 13.E.169.244; 13.E.172.228; 13.E.172.229; 13.E.172.230; 13.E.172.231; 13.E.172.236; 13.E.172.237; 13.E.172.238; 13.E.172.239; 13.E.172.154; 13.E.172.157; 13.E.172.166; 13.E.172.169; 13.E.172.172; 13.E.172.175; 13.E.172.240; 13.E.172.244; 13.E.175.228; 13.E.175.229; 13.E.175.230; 13.E.175.231; 13.E.175.236; 13.E.175.237; 13.E.175.238; 13.E.175.239; 13.E.175.154; 13.E.175.157; 13.E.175.166; 13.E.175.169; 13.E.175.172; 13.E.175.175; 13.E.175.240; 13.E.175.244; 13.E.240.228; 13.E.240.229; 13.E.240.230; 13.E.240.231; 13.E.240.236; 13.E.240.237; 13.E.240.238; 13.E.240.239; 13.E.240.154; 13.E.240.157; 13.E.240.166; 13.E.240.169; 13.E.240.172; 13.E.240.175; 13.E.240.240; 13.E.240.244; 13.E.244.228; 13.E.244.229; 13.E.244.230; 13.E.244.231; 13.E.244.236; 13.E.244.237; 13.E.244.238; 13.E.244.239; 13.E.244.154; 13.E.244.157; 13.E.244.166; 13.E.244.169; 13.E.244.172; 13.E.244.175; 13.E.244.240; 13.E.244.244;

Prodrugs of 13.G

13.G.228.228; 13.G.228.229; 13.G.228.230; 13.G.228.231; 13.G.228.236; 13.G.228.237; 13.G.228.238; 13.G.228.239; 13.G.228.154; 13.G.228.157; 13.G.228.166; 13.G.228.169; 13.G.228.172; 13.G.228.175; 13.G.228.240; 13.G.228.244; 13.G.229.228; 13.G.229.229; 13.G.229.230; 13.G.229.231; 13.G.229.236; 13.G.229.237; 13.G.229.238; 13.G.229.239; 13.G.229.154; 13.G.229.157; 13.G.229.166; 13.G.229.169; 13.G.229.172; 13.G.229.175; 13.G.229.240; 13.G.229.244; 13.G.230.228; 13.G.230.229; 13.G.230.230; 13.G.230.231; 13.G.230.236; 13.G.230.237; 13.G.230.238; 13.G.230.239; 13.G.230.154; 13.G.230.157; 13.G.230.166; 13.G.230.169; 13.G.230.172; 13.G.230.175; 13.G.230.240; 13.G.230.244; 13.G.231.228; 13.G.231.229; 13.G.231.230; 13.G.231.231; 13.G.231.236; 13.G.231.237; 13.G.231.238; 13.G.231.239; 13.G.231.154; 13.G.231.157; 13.G.231.166; 13.G.231.169; 13.G.231.172; 13.G.231.175; 13.G.231.240; 13.G.231.244; 13.G.236.228; 13.G.236.229; 13.G.236.230; 13.G.236.231; 13.G.236.236; 13.G.236.237; 13.G.236.238; 13.G.236.239; 13.G.236.154; 13.G.236.157; 13.G.236.166; 13.G.236.169; 13.G.236.172; 13.G.236.175; 13.G.236.240; 13.G.236.244; 13.G.237.228; 13.G.237.229; 13.G.237.230; 13.G.237.231; 13.G.237.236; 13.G.237.237; 13.G.237.238; 13.G.237.239; 13.G.237.154; 13.G.237.157; 13.G.237.166; 13.G.237.169; 13.G.237.172; 13.G.237.175; 13.G.237.240; 13.G.237.244; 13.G.238.228; 13.G.238.229; 13.G.238.230; 13.G.238.231; 13.G.238.236; 13.G.238.237; 13.G.238.238; 13.G.238.239; 13.G.238.154; 13.G.238.157; 13.G.238.166; 13.G.238.169; 13.G.238.172; 13.G.238.175; 13.G.238.240; 13.G.238.244; 13.G.239.228; 13.G.239.229; 13.G.239.230; 13.G.239.231; 13.G.239.236; 13.G.239.237; 13.G.239.238; 13.G.239.239; 13.G.239.154; 13.G.239.157; 13.G.239.166; 13.G.239.169; 13.G.239.172; 13.G.239.175; 13.G.239.240; 13.G.239.244; 13.G.154.228; 13.G.154.229; 13.G.154.230; 13.G.154.231; 13.G.154.236; 13.G.154.237; 13.G.154.238; 13.G.154.239; 13.G.154.154; 13.G.154.157; 13.G.154.166; 13.G.154.169; 13.G.154.172; 13.G.154.175; 13.G.154.240; 13.G.154.244; 13.G.157.228; 13.G.157.229; 13.G.157.230; 13.G.157.231; 13.G.157.236; 13.G.157.237; 13.G.157.238; 13.G.157.239; 13.G.157.154; 13.G.157.157; 13.G.157.166; 13.G.157.169; 13.G.157.172; 13.G.157.175; 13.G.157.240; 13.G.157.244; 13.G.166.228; 13.G.166.229; 13.G.166.230; 13.G.166.231; 13.G.166.236; 13.G.166.237; 13.G.166.238; 13.G.166.239; 13.G.166.154; 13.G.166.157; 13.G.166.166; 13.G.166.169; 13.G.166.172; 13.G.166.175; 13.G.166.240; 13.G.166.244; 13.G.169.228; 13.G.169.229; 13.G.169.230; 13.G.169.231; 13.G.169.236; 13.G.169.237; 13.G.169.238; 13.G.169.239; 13.G.169.154; 13.G.169.157; 13.G.169.166; 13.G.169.169; 13.G.169.172; 13.G.169.175; 13.G.169.240; 13.G.169.244; 13.G.172.228; 13.G.172.229; 13.G.172.230;

TABLE 100-continued

13.G.172.231; 13.G.172.236; 13.G.172.237; 13.G.172.238; 13.G.172.239; 13.G.172.154; 13.G.172.157; 13.G.172.166; 13.G.172.169; 13.G.172.172; 13.G.172.175; 13.G.172.240; 13.G.172.244; 13.G.175.228; 13.G.175.229; 13.G.175.230; 13.G.175.231; 13.G.175.236; 13.G.175.237; 13.G.175.238; 13.G.175.239; 13.G.175.154; 13.G.175.157; 13.G.175.166; 13.G.175.169; 13.G.175.172; 13.G.175.175; 13.G.175.240; 13.G.175.244; 13.G.240.228; 13.G.240.229; 13.G.240.230; 13.G.240.231; 13.G.240.236; 13.G.240.237; 13.G.240.238; 13.G.240.239; 13.G.240.154; 13.G.240.157; 13.G.240.166; 13.G.240.169; 13.G.240.172; 13.G.240.175; 13.G.240.240; 13.G.240.244; 13.G.244.228; 13.G.244.229; 13.G.244.230; 13.G.244.231; 13.G.244.236; 13.G.244.237; 13.G.244.238; 13.G.244.239; 13.G.244.154; 13.G.244.157; 13.G.244.166; 13.G.244.169; 13.G.244.172; 13.G.244.175; 13.G.244.240; 13.G.244.244;

Prodrugs of 13.I

13.I.228.228; 13.I.228.229; 13.I.228.230; 13.I.228.231; 13.I.228.236; 13.I.228.237; 13.I.228.238; 13.I.228.239; 13.I.228.154; 13.I.228.157; 13.I.228.166; 13.I.228.169; 13.I.228.172; 13.I.228.175; 13.I.228.240; 13.I.228.244; 13.I.229.228; 13.I.229.229; 13.I.229.230; 13.I.229.231; 13.I.229.236; 13.I.229.237; 13.I.229.238; 13.I.229.239; 13.I.229.154; 13.I.229.157; 13.I.229.166; 13.I.229.169; 13.I.229.172; 13.I.229.175; 13.I.229.240; 13.I.229.244; 13.I.230.228; 13.I.230.229; 13.I.230.230; 13.I.230.231; 13.I.230.236; 13.I.230.237; 13.I.230.238; 13.I.230.239; 13.I.230.154; 13.I.230.157; 13.I.230.166; 13.I.230.169; 13.I.230.172; 13.I.230.175; 13.I.230.240; 13.I.230.244; 13.I.231.228; 13.I.231.229; 13.I.231.230; 13.I.231.231; 13.I.231.236; 13.I.231.237; 13.I.231.238; 13.I.231.239; 13.I.231.154; 13.I.231.157; 13.I.231.166; 13.I.231.169; 13.I.231.172; 13.I.231.175; 13.I.231.240; 13.I.231.244; 13.I.236.228; 13.I.236.229; 13.I.236.230; 13.I.236.231; 13.I.236.236; 13.I.236.237; 13.I.236.238; 13.I.236.239; 13.I.236.154; 13.I.236.157; 13.I.236.166; 13.I.236.169; 13.I.236.172; 13.I.236.175; 13.I.236.240; 13.I.236.244; 13.I.237.228; 13.I.237.229; 13.I.237.230; 13.I.237.231; 13.I.237.236; 13.I.237.237; 13.I.237.238; 13.I.237.239; 13.I.237.154; 13.I.237.157; 13.I.237.166; 13.I.237.169; 13.I.237.172; 13.I.237.175; 13.I.237.240; 13.I.237.244; 13.I.238.228; 13.I.238.229; 13.I.238.230; 13.I.238.231; 13.I.238.236; 13.I.238.237; 13.I.238.238; 13.I.238.239; 13.I.238.154; 13.I.238.157; 13.I.238.166; 13.I.238.169; 13.I.238.172; 13.I.238.175; 13.I.238.240; 13.I.238.244; 13.I.239.228; 13.I.239.229; 13.I.239.230; 13.I.239.231; 13.I.239.236; 13.I.239.237; 13.I.239.238; 13.I.239.239; 13.I.239.154; 13.I.239.157; 13.I.239.166; 13.I.239.169; 13.I.239.172; 13.I.239.175; 13.I.239.240; 13.I.239.244; 13.I.154.228; 13.I.154.229; 13.I.154.230; 13.I.154.231; 13.I.154.236; 13.I.154.237; 13.I.154.238; 13.I.154.239; 13.I.154.154; 13.I.154.157; 13.I.154.166; 13.I.154.169; 13.I.154.172; 13.I.154.175; 13.I.154.240; 13.I.154.244; 13.I.157.228; 13.I.157.229; 13.I.157.230; 13.I.157.231; 13.I.157.236; 13.I.157.237; 13.I.157.238; 13.I.157.239; 13.I.157.154; 13.I.157.157; 13.I.157.166; 13.I.157.169; 13.I.157.172; 13.I.157.175; 13.I.157.240; 13.I.157.244; 13.I.166.228; 13.I.166.229; 13.I.166.230; 13.I.166.231; 13.I.166.236; 13.I.166.237; 13.I.166.238; 13.I.166.239; 13.I.166.154; 13.I.166.157; 13.I.166.166; 13.I.166.169; 13.I.166.172; 13.I.166.175; 13.I.166.240; 13.I.166.244; 13.I.169.228; 13.I.169.229; 13.I.169.230; 13.I.169.231; 13.I.169.236; 13.I.169.237; 13.I.169.238; 13.I.169.239; 13.I.169.154; 13.I.169.157; 13.I.169.166; 13.I.169.169; 13.I.169.172; 13.I.169.175; 13.I.169.240; 13.I.169.244; 13.I.172.228; 13.I.172.229; 13.I.172.230; 13.I.172.231; 13.I.172.236; 13.I.172.237; 13.I.172.238; 13.I.172.239; 13.I.172.154; 13.I.172.157; 13.I.172.166; 13.I.172.169; 13.I.172.172; 13.I.172.175; 13.I.172.240; 13.I.172.244; 13.I.175.228; 13.I.175.229; 13.I.175.230; 13.I.175.231; 13.I.175.236; 13.I.175.237; 13.I.175.238; 13.I.175.239; 13.I.175.154; 13.I.175.157; 13.I.175.166; 13.I.175.169; 13.I.175.172; 13.I.175.175; 13.I.175.240; 13.I.175.244; 13.I.240.228; 13.I.240.229; 13.I.240.230; 13.I.240.231; 13.I.240.236; 13.I.240.237; 13.I.240.238; 13.I.240.239; 13.I.240.154; 13.I.240.157; 13.I.240.166; 13.I.240.169; 13.I.240.172; 13.I.240.175; 13.I.240.240; 13.I.240.244; 13.I.244.228; 13.I.244.229; 13.I.244.230; 13.I.244.231; 13.I.244.236; 13.I.244.237; 13.I.244.238; 13.I.244.239; 13.I.244.154; 13.I.244.157; 13.I.244.166; 13.I.244.169; 13.I.244.172; 13.I.244.175; 13.I.244.240; 13.I.244.244;

Prodrugs of 13.J

13.J.228.228; 13.J.228.229; 13.J.228.230; 13.J.228.231; 13.J.228.236; 13.J.228.237; 13.J.228.238; 13.J.228.239; 13.J.228.154; 13.J.228.157; 13.J.228.166; 13.J.228.169; 13.J.228.172; 13.J.228.175; 13.J.228.240; 13.J.228.244; 13.J.229.228; 13.J.229.229; 13.J.229.230; 13.J.229.231; 13.J.229.236; 13.J.229.237; 13.J.229.238; 13.J.229.239; 13.J.229.154; 13.J.229.157; 13.J.229.166; 13.J.229.169; 13.J.229.172; 13.J.229.175; 13.J.229.240; 13.J.229.244; 13.J.230.228; 13.J.230.229; 13.J.230.230; 13.J.230.231; 13.J.230.236; 13.J.230.237; 13.J.230.238; 13.J.230.239; 13.J.230.154; 13.J.230.157; 13.J.230.166; 13.J.230.169; 13.J.230.172; 13.J.230.175; 13.J.230.240; 13.J.230.244; 13.J.231.228; 13.J.231.229;

TABLE 100-continued

13.J.231.230; 13.J.231.231; 13.J.231.236; 13.J.231.237; 13.J.231.238; 13.J.231.239; 13.J.231.154; 13.J.231.157; 13.J.231.166; 13.J.231.169; 13.J.231.172; 13.J.231.175; 13.J.231.240; 13.J.231.244; 13.J.236.228; 13.J.236.229; 13.J.236.230; 13.J.236.231; 13.J.236.236; 13.J.236.237; 13.J.236.238; 13.J.236.239; 13.J.236.154; 13.J.236.157; 13.J.236.166; 13.J.236.169; 13.J.236.172; 13.J.236.175; 13.J.236.240; 13.J.236.244; 13.J.237.228; 13.J.237.229; 13.J.237.230; 13.J.237.231; 13.J.237.236; 13.J.237.237; 13.J.237.238; 13.J.237.239; 13.J.237.154; 13.J.237.157; 13.J.237.166; 13.J.237.169; 13.J.237.172; 13.J.237.175; 13.J.237.240; 13.J.237.244; 13.J.238.228; 13.J.238.229; 13.J.238.230; 13.J.238.231; 13.J.238.236; 13.J.238.237; 13.J.238.238; 13.J.238.239; 13.J.238.154; 13.J.238.157; 13.J.238.166; 13.J.238.169; 13.J.238.172; 13.J.238.175; 13.J.238.240; 13.J.238.244; 13.J.239.228; 13.J.239.229; 13.J.239.230; 13.J.239.231; 13.J.239.236; 13.J.239.237; 13.J.239.238; 13.J.239.239; 13.J.239.154; 13.J.239.157; 13.J.239.166; 13.J.239.169; 13.J.239.172; 13.J.239.175; 13.J.239.240; 13.J.239.244; 13.J.154.228; 13.J.154.229; 13.J.154.230; 13.J.154.231; 13.J.154.236; 13.J.154.237; 13.J.154.238; 13.J.154.239; 13.J.154.154; 13.J.154.157; 13.J.154.166; 13.J.154.169; 13.J.154.172; 13.J.154.175; 13.J.154.240; 13.J.154.244; 13.J.157.228; 13.J.157.229; 13.J.157.230; 13.J.157.231; 13.J.157.236; 13.J.157.237; 13.J.157.238; 13.J.157.239; 13.J.157.154; 13.J.157.157; 13.J.157.166; 13.J.157.169; 13.J.157.172; 13.J.157.175; 13.J.157.240; 13.J.157.244; 13.J.166.228; 13.J.166.229; 13.J.166.230; 13.J.166.231; 13.J.166.236; 13.J.166.237; 13.J.166.238; 13.J.166.239; 13.J.166.154; 13.J.166.157; 13.J.166.166; 13.J.166.169; 13.J.166.172; 13.J.166.175; 13.J.166.240; 13.J.166.244; 13.J.169.228; 13.J.169.229; 13.J.169.230; 13.J.169.231; 13.J.169.236; 13.J.169.237; 13.J.169.238; 13.J.169.239; 13.J.169.154; 13.J.169.157; 13.J.169.166; 13.J.169.169; 13.J.169.172; 13.J.169.175; 13.J.169.240; 13.J.169.244; 13.J.172.228; 13.J.172.229; 13.J.172.230; 13.J.172.231; 13.J.172.236; 13.J.172.237; 13.J.172.238; 13.J.172.239; 13.J.172.154; 13.J.172.157; 13.J.172.166; 13.J.172.169; 13.J.172.172; 13.J.172.175; 13.J.172.240; 13.J.172.244; 13.J.175.228; 13.J.175.229; 13.J.175.230; 13.J.175.231; 13.J.175.236; 13.J.175.237; 13.J.175.238; 13.J.175.239; 13.J.175.154; 13.J.175.157; 13.J.175.166; 13.J.175.169; 13.J.175.172; 13.J.175.175; 13.J.175.240; 13.J.175.244; 13.J.240.228; 13.J.240.229; 13.J.240.230; 13.J.240.231; 13.J.240.236; 13.J.240.237; 13.J.240.238; 13.J.240.239; 13.J.240.154; 13.J.240.157; 13.J.240.166; 13.J.240.169; 13.J.240.172; 13.J.240.175; 13.J.240.240; 13.J.240.244; 13.J.244.228; 13.J.244.229; 13.J.244.230; 13.J.244.231; 13.J.244.236; 13.J.244.237; 13.J.244.238; 13.J.244.239; 13.J.244.154; 13.J.244.157; 13.J.244.166; 13.J.244.169; 13.J.244.172; 13.J.244.175; 13.J.244.240; 13.J.244.244;

Prodrugs of 13.L

13.L.228.228; 13.L.228.229; 13.L.228.230; 13.L.228.231; 13.L.228.236; 13.L.228.237; 13.L.228.238; 13.L.228.239; 13.L.228.154; 13.L.228.157; 13.L.228.166; 13.L.228.169; 13.L.228.172; 13.L.228.175; 13.L.228.240; 13.L.228.244; 13.L.229.228; 13.L.229.229; 13.L.229.230; 13.L.229.231; 13.L.229.236; 13.L.229.237; 13.L.229.238; 13.L.229.239; 13.L.229.154; 13.L.229.157; 13.L.229.166; 13.L.229.169; 13.L.229.172; 13.L.229.175; 13.L.229.240; 13.L.229.244; 13.L.230.228; 13.L.230.229; 13.L.230.230; 13.L.230.231; 13.L.230.236; 13.L.230.237; 13.L.230.238; 13.L.230.239; 13.L.230.154; 13.L.230.157; 13.L.230.166; 13.L.230.169; 13.L.230.172; 13.L.230.175; 13.L.230.240; 13.L.230.244; 13.L.231.228; 13.L.231.229; 13.L.231.230; 13.L.231.231; 13.L.231.236; 13.L.231.237; 13.L.231.238; 13.L.231.239; 13.L.231.154; 13.L.231.157; 13.L.231.166; 13.L.231.169; 13.L.231.172; 13.L.231.175; 13.L.231.240; 13.L.231.244; 13.L.236.228; 13.L.236.229; 13.L.236.230; 13.L.236.231; 13.L.236.236; 13.L.236.237; 13.L.236.238; 13.L.236.239; 13.L.236.154; 13.L.236.157; 13.L.236.166; 13.L.236.169; 13.L.236.172; 13.L.236.175; 13.L.236.240; 13.L.236.244; 13.L.237.228; 13.L.237.229; 13.L.237.230; 13.L.237.231; 13.L.237.236; 13.L.237.237; 13.L.237.238; 13.L.237.239; 13.L.237.154; 13.L.237.157; 13.L.237.166; 13.L.237.169; 13.L.237.172; 13.L.237.175; 13.L.237.240; 13.L.237.244; 13.L.238.228; 13.L.238.229; 13.L.238.230; 13.L.238.231; 13.L.238.236; 13.L.238.237; 13.L.238.238; 13.L.238.239; 13.L.238.154; 13.L.238.157; 13.L.238.166; 13.L.238.169; 13.L.238.172; 13.L.238.175; 13.L.238.240; 13.L.238.244; 13.L.239.228; 13.L.239.229; 13.L.239.230; 13.L.239.231; 13.L.239.236; 13.L.239.237; 13.L.239.238; 13.L.239.239; 13.L.239.154; 13.L.239.157; 13.L.239.166; 13.L.239.169; 13.L.239.172; 13.L.239.175; 13.L.239.240; 13.L.239.244; 13.L.154.228; 13.L.154.229; 13.L.154.230; 13.L.154.231; 13.L.154.236; 13.L.154.237; 13.L.154.238; 13.L.154.239; 13.L.154.154; 13.L.154.157; 13.L.154.166; 13.L.154.169; 13.L.154.172; 13.L.154.175; 13.L.154.240; 13.L.154.244; 13.L.157.228; 13.L.157.229; 13.L.157.230; 13.L.157.231; 13.L.157.236; 13.L.157.237; 13.L.157.238; 13.L.157.239; 13.L.157.154; 13.L.157.157; 13.L.157.166; 13.L.157.169; 13.L.157.172; 13.L.157.175; 13.L.157.240; 13.L.157.244; 13.L.166.228; 13.L.166.229; 13.L.166.230; 13.L.166.231; 13.L.166.236; 13.L.166.237; 13.L.166.238; 13.L.166.239; 13.L.166.154; 13.L.166.157; 13.L.166.166; 13.L.166.169; 13.L.166.172; 13.L.166.175; 13.L.166.240;

TABLE 100-continued

13.L.166.244; 13.L.169.228; 13.L.169.229; 13.L.169.230; 13.L.169.231; 13.L.169.236; 13.L.169.237; 13.L.169.238; 13.L.169.239; 13.L.169.154; 13.L.169.157; 13.L.169.166; 13.L.169.169; 13.L.169.172; 13.L.169.175; 13.L.169.240; 13.L.169.244; 13.L.172.228; 13.L.172.229; 13.L.172.230; 13.L.172.231; 13.L.172.236; 13.L.172.237; 13.L.172.238; 13.L.172.239; 13.L.172.154; 13.L.172.157; 13.L.172.166; 13.L.172.169; 13.L.172.172; 13.L.172.175; 13.L.172.240; 13.L.172.244; 13.L.175.228; 13.L.175.229; 13.L.175.230; 13.L.175.231; 13.L.175.236; 13.L.175.237; 13.L.175.238; 13.L.175.239; 13.L.175.154; 13.L.175.157; 13.L.175.166; 13.L.175.169; 13.L.175.172; 13.L.175.175; 13.L.175.240; 13.L.175.244; 13.L.240.228; 13.L.240.229; 13.L.240.230; 13.L.240.231; 13.L.240.236; 13.L.240.237; 13.L.240.238; 13.L.240.239; 13.L.240.154; 13.L.240.157; 13.L.240.166; 13.L.240.169; 13.L.240.172; 13.L.240.175; 13.L.240.240; 13.L.240.244; 13.L.244.228; 13.L.244.229; 13.L.244.230; 13.L.244.231; 13.L.244.236; 13.L.244.237; 13.L.244.238; 13.L.244.239; 13.L.244.154; 13.L.244.157; 13.L.244.166; 13.L.244.169; 13.L.244.172; 13.L.244.175; 13.L.244.240; 13.L.244.244;

Prodrugs of 13.O

13.O.228.228; 13.O.228.229; 13.O.228.230; 13.O.228.231; 13.O.228.236; 13.O.228.237; 13.O.228.238; 13.O.228.239; 13.O.228.154; 13.O.228.157; 13.O.228.166; 13.O.228.169; 13.O.228.172; 13.O.228.175; 13.O.228.240; 13.O.228.244; 13.O.229.228; 13.O.229.229; 13.O.229.230; 13.O.229.231; 13.O.229.236; 13.O.229.237; 13.O.229.238; 13.O.229.239; 13.O.229.154; 13.O.229.157; 13.O.229.166; 13.O.229.169; 13.O.229.172; 13.O.229.175; 13.O.229.240; 13.O.229.244; 13.O.230.228; 13.O.230.229; 13.O.230.230; 13.O.230.231; 13.O.230.236; 13.O.230.237; 13.O.230.238; 13.O.230.239; 13.O.230.154; 13.O.230.157; 13.O.230.166; 13.O.230.169; 13.O.230.172; 13.O.230.175; 13.O.230.240; 13.O.230.244; 13.O.231.228; 13.O.231.229; 13.O.231.230; 13.O.231.231; 13.O.231.236; 13.O.231.237; 13.O.231.238; 13.O.231.239; 13.O.231.154; 13.O.231.157; 13.O.231.166; 13.O.231.169; 13.O.231.172; 13.O.231.175; 13.O.231.240; 13.O.231.244; 13.O.236.228; 13.O.236.229; 13.O.236.230; 13.O.236.231; 13.O.236.236; 13.O.236.237; 13.O.236.238; 13.O.236.239; 13.O.236.154; 13.O.236.157; 13.O.236.166; 13.O.236.169; 13.O.236.172; 13.O.236.175; 13.O.236.240; 13.O.236.244; 13.O.237.228; 13.O.237.229; 13.O.237.230; 13.O.237.231; 13.O.237.236; 13.O.237.237; 13.O.237.238; 13.O.237.239; 13.O.237.154; 13.O.237.157; 13.O.237.166; 13.O.237.169; 13.O.237.172; 13.O.237.175; 13.O.237.240; 13.O.237.244; 13.O.238.228; 13.O.238.229; 13.O.238.230; 13.O.238.231; 13.O.238.236; 13.O.238.237; 13.O.238.238; 13.O.238.239; 13.O.238.154; 13.O.238.157; 13.O.238.166; 13.O.238.169; 13.O.238.172; 13.O.238.175; 13.O.238.240; 13.O.238.244; 13.O.239.228; 13.O.239.229; 13.O.239.230; 13.O.239.231; 13.O.239.236; 13.O.239.237; 13.O.239.238; 13.O.239.239; 13.O.239.154; 13.O.239.157; 13.O.239.166; 13.O.239.169; 13.O.239.172; 13.O.239.175; 13.O.239.240; 13.O.239.244; 13.O.154.228; 13.O.154.229; 13.O.154.230; 13.O.154.231; 13.O.154.236; 13.O.154.237; 13.O.154.238; 13.O.154.239; 13.O.154.154; 13.O.154.157; 13.O.154.166; 13.O.154.169; 13.O.154.172; 13.O.154.175; 13.O.154.240; 13.O.154.244; 13.O.157.228; 13.O.157.229; 13.O.157.230; 13.O.157.231; 13.O.157.236; 13.O.157.237; 13.O.157.238; 13.O.157.239; 13.O.157.154; 13.O.157.157; 13.O.157.166; 13.O.157.169; 13.O.157.172; 13.O.157.175; 13.O.157.240; 13.O.157.244; 13.O.166.228; 13.O.166.229; 13.O.166.230; 13.O.166.231; 13.O.166.236; 13.O.166.237; 13.O.166.238; 13.O.166.239; 13.O.166.154; 13.O.166.157; 13.O.166.166; 13.O.166.169; 13.O.166.172; 13.O.166.175; 13.O.166.240; 13.O.166.244; 13.O.169.228; 13.O.169.229; 13.O.169.230; 13.O.169.231; 13.O.169.236; 13.O.169.237; 13.O.169.238; 13.O.169.239; 13.O.169.154; 13.O.169.157; 13.O.169.166; 13.O.169.169; 13.O.169.172; 13.O.169.175; 13.O.169.240; 13.O.169.244; 13.O.172.228; 13.O.172.229; 13.O.172.230; 13.O.172.231; 13.O.172.236; 13.O.172.237; 13.O.172.238; 13.O.172.239; 13.O.172.154; 13.O.172.157; 13.O.172.166; 13.O.172.169; 13.O.172.172; 13.O.172.175; 13.O.172.240; 13.O.172.244; 13.O.175.228; 13.O.175.229; 13.O.175.230; 13.O.175.231; 13.O.175.236; 13.O.175.237; 13.O.175.238; 13.O.175.239; 13.O.175.154; 13.O.175.157; 13.O.175.166; 13.O.175.169; 13.O.175.172; 13.O.175.175; 13.O.175.240; 13.O.175.244; 13.O.240.228; 13.O.240.229; 13.O.240.230; 13.O.240.231; 13.O.240.236; 13.O.240.237; 13.O.240.238; 13.O.240.239; 13.O.240.154; 13.O.240.157; 13.O.240.166; 13.O.240.169; 13.O.240.172; 13.O.240.175; 13.O.240.240; 13.O.240.244; 13.O.244.228; 13.O.244.229; 13.O.244.230; 13.O.244.231; 13.O.244.236; 13.O.244.237; 13.O.244.238; 13.O.244.239; 13.O.244.154; 13.O.244.157; 13.O.244.166; 13.O.244.169; 13.O.244.172; 13.O.244.175; 13.O.244.240; 13.O.244.244;

Prodrugs of 13.P

13.P.228.228; 13.P.228.229; 13.P.228.230; 13.P.228.231; 13.P.228.236; 13.P.228.237; 13.P.228.238; 13.P.228.239; 13.P.228.154; 13.P.228.157; 13.P.228.166; 13.P.228.169; 13.P.228.172; 13.P.228.175; 13.P.228.240; 13.P.228.244; 13.P.229.228; 13.P.229.229; 13.P.229.230; 13.P.229.231; 13.P.229.236; 13.P.229.237; 13.P.229.238; 13.P.229.239; 13.P.229.154; 13.P.229.157; 13.P.229.166; 13.P.229.169; 13.P.229.172; 13.P.229.175;

TABLE 100-continued

13.P.229.240; 13.P.229.244; 13.P.230.228; 13.P.230.229; 13.P.230.230; 13.P.230.231; 13.P.230.236; 13.P.230.237; 13.P.230.238; 13.P.230.239; 13.P.230.154; 13.P.230.157; 13.P.230.166; 13.P.230.169; 13.P.230.172; 13.P.230.175; 13.P.230.240; 13.P.230.244; 13.P.231.228; 13.P.231.229; 13.P.231.230; 13.P.231.231; 13.P.231.236; 13.P.231.237; 13.P.231.238; 13.P.231.239; 13.P.231.154; 13.P.231.157; 13.P.231.166; 13.P.231.169; 13.P.231.172; 13.P.231.175; 13.P.231.240; 13.P.231.244; 13.P.236.228; 13.P.236.229; 13.P.236.230; 13.P.236.231; 13.P.236.236; 13.P.236.237; 13.P.236.238; 13.P.236.239; 13.P.236.154; 13.P.236.157; 13.P.236.166; 13.P.236.169; 13.P.236.172; 13.P.236.175; 13.P.236.240; 13.P.236.244; 13.P.237.228; 13.P.237.229; 13.P.237.230; 13.P.237.231; 13.P.237.236; 13.P.237.237; 13.P.237.238; 13.P.237.239; 13.P.237.154; 13.P.237.157; 13.P.237.166; 13.P.237.169; 13.P.237.172; 13.P.237.175; 13.P.237.240; 13.P.237.244; 13.P.238.228; 13.P.238.229; 13.P.238.230; 13.P.238.231; 13.P.238.236; 13.P.238.237; 13.P.238.238; 13.P.238.239; 13.P.238.154; 13.P.238.157; 13.P.238.166; 13.P.238.169; 13.P.238.172; 13.P.238.175; 13.P.238.240; 13.P.238.244; 13.P.239.228; 13.P.239.229; 13.P.239.230; 13.P.239.231; 13.P.239.236; 13.P.239.237; 13.P.239.238; 13.P.239.239; 13.P.239.154; 13.P.239.157; 13.P.239.166; 13.P.239.169; 13.P.239.172; 13.P.239.175; 13.P.239.240; 13.P.239.244; 13.P.154.228; 13.P.154.229; 13.P.154.230; 13.P.154.231; 13.P.154.236; 13.P.154.237; 13.P.154.238; 13.P.154.239; 13.P.154.154; 13.P.154.157; 13.P.154.166; 13.P.154.169; 13.P.154.172; 13.P.154.175; 13.P.154.240; 13.P.154.244; 13.P.157.228; 13.P.157.229; 13.P.157.230; 13.P.157.231; 13.P.157.236; 13.P.157.237; 13.P.157.238; 13.P.157.239; 13.P.157.154; 13.P.157.157; 13.P.157.166; 13.P.157.169; 13.P.157.172; 13.P.157.175; 13.P.157.240; 13.P.157.244; 13.P.166.228; 13.P.166.229; 13.P.166.230; 13.P.166.231; 13.P.166.236; 13.P.166.237; 13.P.166.238; 13.P.166.239; 13.P.166.154; 13.P.166.157; 13.P.166.166; 13.P.166.169; 13.P.166.172; 13.P.166.175; 13.P.166.240; 13.P.166.244; 13.P.169.228; 13.P.169.229; 13.P.169.230; 13.P.169.231; 13.P.169.236; 13.P.169.237; 13.P.169.238; 13.P.169.239; 13.P.169.154; 13.P.169.157; 13.P.169.166; 13.P.169.169; 13.P.169.172; 13.P.169.175; 13.P.169.240; 13.P.169.244; 13.P.172.228; 13.P.172.229; 13.P.172.230; 13.P.172.231; 13.P.172.236; 13.P.172.237; 13.P.172.238; 13.P.172.239; 13.P.172.154; 13.P.172.157; 13.P.172.166; 13.P.172.169; 13.P.172.172; 13.P.172.175; 13.P.172.240; 13.P.172.244; 13.P.175.228; 13.P.175.229; 13.P.175.230; 13.P.175.231; 13.P.175.236; 13.P.175.237; 13.P.175.238; 13.P.175.239; 13.P.175.154; 13.P.175.157; 13.P.175.166; 13.P.175.169; 13.P.175.172; 13.P.175.175; 13.P.175.240; 13.P.175.244; 13.P.240.228; 13.P.240.229; 13.P.240.230; 13.P.240.231; 13.P.240.236; 13.P.240.237; 13.P.240.238; 13.P.240.239; 13.P.240.154; 13.P.240.157; 13.P.240.166; 13.P.240.169; 13.P.240.172; 13.P.240.175; 13.P.240.240; 13.P.240.244; 13.P.244.228; 13.P.244.229; 13.P.244.230; 13.P.244.231; 13.P.244.236; 13.P.244.237; 13.P.244.238; 13.P.244.239; 13.P.244.154; 13.P.244.157; 13.P.244.166; 13.P.244.169; 13.P.244.172; 13.P.244.175; 13.P.244.240; 13.P.244.244;

Prodrugs of 13.U

13.U.228.228; 13.U.228.229; 13.U.228.230; 13.U.228.231; 13.U.228.236; 13.U.228.237; 13.U.228.238; 13.U.228.239; 13.U.228.154; 13.U.228.157; 13.U.228.166; 13.U.228.169; 13.U.228.172; 13.U.228.175; 13.U.228.240; 13.U.228.244; 13.U.229.228; 13.U.229.229; 13.U.229.230; 13.U.229.231; 13.U.229.236; 13.U.229.237; 13.U.229.238; 13.U.229.239; 13.U.229.154; 13.U.229.157; 13.U.229.166; 13.U.229.169; 13.U.229.172; 13.U.229.175; 13.U.229.240; 13.U.229.244; 13.U.230.228; 13.U.230.229; 13.U.230.230; 13.U.230.231; 13.U.230.236; 13.U.230.237; 13.U.230.238; 13.U.230.239; 13.U.230.154; 13.U.230.157; 13.U.230.166; 13.U.230.169; 13.U.230.172; 13.U.230.175; 13.U.230.240; 13.U.230.244; 13.U.231.228; 13.U.231.229; 13.U.231.230; 13.U.231.231; 13.U.231.236; 13.U.231.237; 13.U.231.238; 13.U.231.239; 13.U.231.154; 13.U.231.157; 13.U.231.166; 13.U.231.169; 13.U.231.172; 13.U.231.175; 13.U.231.240; 13.U.231.244; 13.U.236.228; 13.U.236.229; 13.U.236.230; 13.U.236.231; 13.U.236.236; 13.U.236.237; 13.U.236.238; 13.U.236.239; 13.U.236.154; 13.U.236.157; 13.U.236.166; 13.U.236.169; 13.U.236.172; 13.U.236.175; 13.U.236.240; 13.U.236.244; 13.U.237.228; 13.U.237.229; 13.U.237.230; 13.U.237.231; 13.U.237.236; 13.U.237.237; 13.U.237.238; 13.U.237.239; 13.U.237.154; 13.U.237.157; 13.U.237.166; 13.U.237.169; 13.U.237.172; 13.U.237.175; 13.U.237.240; 13.U.237.244; 13.U.238.228; 13.U.238.229; 13.U.238.230; 13.U.238.231; 13.U.238.236; 13.U.238.237; 13.U.238.238; 13.U.238.239; 13.U.238.154; 13.U.238.157; 13.U.238.166; 13.U.238.169; 13.U.238.172; 13.U.238.175; 13.U.238.240; 13.U.238.244; 13.U.239.228; 13.U.239.229; 13.U.239.230; 13.U.239.231; 13.U.239.236; 13.U.239.237; 13.U.239.238; 13.U.239.239; 13.U.239.154; 13.U.239.157; 13.U.239.166; 13.U.239.169; 13.U.239.172; 13.U.239.175; 13.U.239.240; 13.U.239.244; 13.U.154.228; 13.U.154.229; 13.U.154.230; 13.U.154.231; 13.U.154.236; 13.U.154.237; 13.U.154.238; 13.U.154.239; 13.U.154.154; 13.U.154.157; 13.U.154.166; 13.U.154.169; 13.U.154.172; 13.U.154.175; 13.U.154.240; 13.U.154.244; 13.U.157.228; 13.U.157.229; 13.U.157.230; 13.U.157.231; 13.U.157.236; 13.U.157.237; 13.U.157.238; 13.U.157.239; 13.U.157.154; 13.U.157.157; 13.U.157.166;

TABLE 100-continued

13.U.157.169; 13.U.157.172; 13.U.157.175; 13.U.157.240; 13.U.157.244;
13.U.166.228; 13.U.166.229; 13.U.166.230; 13.U.166.231; 13.U.166.236;
13.U.166.237; 13.U.166.238; 13.U.166.239; 13.U.166.154; 13.U.166.157;
13.U.166.166; 13.U.166.169; 13.U.166.172; 13.U.166.175; 13.U.166.240;
13.U.166.244; 13.U.169.228; 13.U.169.229; 13.U.169.230; 13.U.169.231;
13.U.169.236; 13.U.169.237; 13.U.169.238; 13.U.169.239; 13.U.169.154;
13.U.169.157; 13.U.169.166; 13.U.169.169; 13.U.169.172; 13.U.169.175;
13.U.169.240; 13.U.169.244; 13.U.172.228; 13.U.172.229; 13.U.172.230;
13.U.172.231; 13.U.172.236; 13.U.172.237; 13.U.172.238; 13.U.172.239;
13.U.172.154; 13.U.172.157; 13.U.172.166; 13.U.172.169; 13.U.172.172;
13.U.172.175; 13.U.172.240; 13.U.172.244; 13.U.175.228; 13.U.175.229;
13.U.175.230; 13.U.175.231; 13.U.175.236; 13.U.175.237; 13.U.175.238;
13.U.175.239; 13.U.175.154; 13.U.175.157; 13.U.175.166; 13.U.175.169;
13.U.175.172; 13.U.175.175; 13.U.175.240; 13.U.175.244; 13.U.240.228;
13.U.240.229; 13.U.240.230; 13.U.240.231; 13.U.240.236; 13.U.240.237;
13.U.240.238; 13.U.240.239; 13.U.240.154; 13.U.240.157; 13.U.240.166;
13.U.240.169; 13.U.240.172; 13.U.240.175; 13.U.240.240; 13.U.240.244;
13.U.244.228; 13.U.244.229; 13.U.244.230; 13.U.244.231; 13.U.244.236;
13.U.244.237; 13.U.244.238; 13.U.244.239; 13.U.244.154; 13.U.244.157;
13.U.244.166; 13.U.244.169; 13.U.244.172; 13.U.244.175; 13.U.244.240;
13.U.244.244;

Prodrugs of 13.W

13.W.228.228; 13.W.228.229; 13.W.228.230; 13.W.228.231; 13.W.228.236;
13.W.228.237; 13.W.228.238; 13.W.228.239; 13.W.228.154; 13.W.228.157;
13.W.228.166; 13.W.228.169; 13.W.228.172; 13.W.228.175; 13.W.228.240;
13.W.228.244; 13.W.229.228; 13.W.229.229; 13.W.229.230; 13.W.229.231;
13.W.229.236; 13.W.229.237; 13.W.229.238; 13.W.229.239; 13.W.229.154;
13.W.229.157; 13.W.229.166; 13.W.229.169; 13.W.229.172; 13.W.229.175;
13.W.229.240; 13.W.229.244; 13.W.230.228; 13.W.230.229; 13.W.230.230;
13.W.230.231; 13.W.230.236; 13.W.230.237; 13.W.230.238; 13.W.230.239;
13.W.230.154; 13.W.230.157; 13.W.230.166; 13.W.230.169; 13.W.230.172;
13.W.230.175; 13.W.230.240; 13.W.230.244; 13.W.231.228; 13.W.231.229;
13.W.231.230; 13.W.231.231; 13.W.231.236; 13.W.231.237; 13.W.231.238;
13.W.231.239; 13.W.231.154; 13.W.231.157; 13.W.231.166; 13.W.231.169;
13.W.231.172; 13.W.231.175; 13.W.231.240; 13.W.231.244; 13.W.236.228;
13.W.236.229; 13.W.236.230; 13.W.236.231; 13.W.236.236; 13.W.236.237;
13.W.236.238; 13.W.236.239; 13.W.236.154; 13.W.236.157; 13.W.236.166;
13.W.236.169; 13.W.236.172; 13.W.236.175; 13.W.236.240; 13.W.236.244;
13.W.237.228; 13.W.237.229; 13.W.237.230; 13.W.237.231; 13.W.237.236;
13.W.237.237; 13.W.237.238; 13.W.237.239; 13.W.237.154; 13.W.237.157;
13.W.237.166; 13.W.237.169; 13.W.237.172; 13.W.237.175; 13.W.237.240;
13.W.237.244; 13.W.238.228; 13.W.238.229; 13.W.238.230; 13.W.238.231;
13.W.238.236; 13.W.238.237; 13.W.238.238; 13.W.238.239; 13.W.238.154;
13.W.238.157; 13.W.238.166; 13.W.238.169; 13.W.238.172; 13.W.238.175;
13.W.238.240; 13.W.238.244; 13.W.239.228; 13.W.239.229; 13.W.239.230;
13.W.239.231; 13.W.239.236; 13.W.239.237; 13.W.239.238; 13.W.239.239;
13.W.239.154; 13.W.239.157; 13.W.239.166; 13.W.239.169; 13.W.239.172;
13.W.239.175; 13.W.239.240; 13.W.239.244; 13.W.154.228; 13.W.154.229;
13.W.154.230; 13.W.154.231; 13.W.154.236; 13.W.154.237; 13.W.154.238;
13.W.154.239; 13.W.154.154; 13.W.154.157; 13.W.154.166; 13.W.154.169;
13.W.154.172; 13.W.154.175; 13.W.154.240; 13.W.154.244; 13.W.157.228;
13.W.157.229; 13.W.157.230; 13.W.157.231; 13.W.157.236; 13.W.157.237;
13.W.157.238; 13.W.157.239; 13.W.157.154; 13.W.157.157; 13.W.157.166;
13.W.157.169; 13.W.157.172; 13.W.157.175; 13.W.157.240; 13.W.157.244;
13.W.166.228; 13.W.166.229; 13.W.166.230; 13.W.166.231; 13.W.166.236;
13.W.166.237; 13.W.166.238; 13.W.166.239; 13.W.166.154; 13.W.166.157;
13.W.166.166; 13.W.166.169; 13.W.166.172; 13.W.166.175; 13.W.166.240;
13.W.166.244; 13.W.169.228; 13.W.169.229; 13.W.169.230; 13.W.169.231;
13.W.169.236; 13.W.169.237; 13.W.169.238; 13.W.169.239; 13.W.169.154;
13.W.169.157; 13.W.169.166; 13.W.169.169; 13.W.169.172; 13.W.169.175;
13.W.169.240; 13.W.169.244; 13.W.172.228; 13.W.172.229; 13.W.172.230;
13.W.172.231; 13.W.172.236; 13.W.172.237; 13.W.172.238; 13.W.172.239;
13.W.172.154; 13.W.172.157; 13.W.172.166; 13.W.172.169; 13.W.172.172;
13.W.172.175; 13.W.172.240; 13.W.172.244; 13.W.175.228; 13.W.175.229;
13.W.175.230; 13.W.175.231; 13.W.175.236; 13.W.175.237; 13.W.175.238;
13.W.175.239; 13.W.175.154; 13.W.175.157; 13.W.175.166; 13.W.175.169;
13.W.175.172; 13.W.175.175; 13.W.175.240; 13.W.175.244; 13.W.240.228;
13.W.240.229; 13.W.240.230; 13.W.240.231; 13.W.240.236; 13.W.240.237;
13.W.240.238; 13.W.240.239; 13.W.240.154; 13.W.240.157; 13.W.240.166;
13.W.240.169; 13.W.240.172; 13.W.240.175; 13.W.240.240; 13.W.240.244;
13.W.244.228; 13.W.244.229; 13.W.244.230; 13.W.244.231; 13.W.244.236;
13.W.244.237; 13.W.244.238; 13.W.244.239; 13.W.244.154; 13.W.244.157;
13.W.244.166; 13.W.244.169; 13.W.244.172; 13.W.244.175; 13.W.244.240;
13.W.244.244;

Prodrugs of 13.Y

13.Y.228.228; 13.Y.228.229; 13.Y.228.230; 13.Y.228.231; 13.Y.228.236;
13.Y.228.237; 13.Y.228.238; 13.Y.228.239; 13.Y.228.154; 13.Y.228.157;

TABLE 100-continued

13.Y.228.166; 13.Y.228.169; 13.Y.228.172; 13.Y.228.175; 13.Y.228.240;
13.Y.228.244; 13.Y.229.228; 13.Y.229.229; 13.Y.229.230; 13.Y.229.231;
13.Y.229.236; 13.Y.229.237; 13.Y.229.238; 13.Y.229.239; 13.Y.229.154;
13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230;
13.Y.230.231; 13.Y.230.236; 13.Y.230.237; 13.Y.230.238; 13.Y.230.239;
13.Y.230.154; 13.Y.230.157; 13.Y.230.166; 13.Y.230.169; 13.Y.230.172;
13.Y.230.175; 13.Y.230.240; 13.Y.230.244; 13.Y.231.228; 13.Y.231.229;
13.Y.231.230; 13.Y.231.231; 13.Y.231.236; 13.Y.231.237; 13.Y.231.238;
13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228;
13.Y.236.229; 13.Y.236.230; 13.Y.236.231; 13.Y.236.236; 13.Y.236.237;
13.Y.236.238; 13.Y.236.239; 13.Y.236.154; 13.Y.236.157; 13.Y.236.166;
13.Y.236.169; 13.Y.236.172; 13.Y.236.175; 13.Y.236.240; 13.Y.236.244;
13.Y.237.228; 13.Y.237.229; 13.Y.237.230; 13.Y.237.231; 13.Y.237.236;
13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240;
13.Y.237.244; 13.Y.238.228; 13.Y.238.229; 13.Y.238.230; 13.Y.238.231;
13.Y.238.236; 13.Y.238.237; 13.Y.238.238; 13.Y.238.239; 13.Y.238.154;
13.Y.238.157; 13.Y.238.166; 13.Y.238.169; 13.Y.238.172; 13.Y.238.175;
13.Y.238.240; 13.Y.238.244; 13.Y.239.228; 13.Y.239.229; 13.Y.239.230;
13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172;
13.Y.239.175; 13.Y.239.240; 13.Y.239.244; 13.Y.154.228; 13.Y.154.229;
13.Y.154.230; 13.Y.154.231; 13.Y.154.236; 13.Y.154.237; 13.Y.154.238;
13.Y.154.239; 13.Y.154.154; 13.Y.154.157; 13.Y.154.166; 13.Y.154.169;
13.Y.154.172; 13.Y.154.175; 13.Y.154.240; 13.Y.154.244; 13.Y.157.228;
13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166;
13.Y.157.169; 13.Y.157.172; 13.Y.157.175; 13.Y.157.240; 13.Y.157.244;
13.Y.166.228; 13.Y.166.229; 13.Y.166.230; 13.Y.166.231; 13.Y.166.236;
13.Y.166.237; 13.Y.166.238; 13.Y.166.239; 13.Y.166.154; 13.Y.166.157;
13.Y.166.166; 13.Y.166.169; 13.Y.166.172; 13.Y.166.175; 13.Y.166.240;
13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154;
13.Y.169.157; 13.Y.169.166; 13.Y.169.169; 13.Y.169.172; 13.Y.169.175;
13.Y.169.240; 13.Y.169.244; 13.Y.172.228; 13.Y.172.229; 13.Y.172.230;
13.Y.172.231; 13.Y.172.236; 13.Y.172.237; 13.Y.172.238; 13.Y.172.239;
13.Y.172.154; 13.Y.172.157; 13.Y.172.166; 13.Y.172.169; 13.Y.172.172;
13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238;
13.Y.175.239; 13.Y.175.154; 13.Y.175.157; 13.Y.175.166; 13.Y.175.169;
13.Y.175.172; 13.Y.175.175; 13.Y.175.240; 13.Y.175.244; 13.Y.240.228;
13.Y.240.229; 13.Y.240.230; 13.Y.240.231; 13.Y.240.236; 13.Y.240.237;
13.Y.240.238; 13.Y.240.239; 13.Y.240.154; 13.Y.240.157; 13.Y.240.166;
13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236;
13.Y.244.237; 13.Y.244.238; 13.Y.244.239; 13.Y.244.154; 13.Y.244.157;
13.Y.244.166; 13.Y.244.169; 13.Y.244.172; 13.Y.244.175; 13.Y.244.240;
13.Y.244.244;

Prodrugs of 14.AH

14.AH.4.157; 14.AH.4.158; 14.AH.4.196; 14.AH.4.223; 14.AH.4.240;
14.AH.4.244; 14.AH.4.243; 14.AH.4.247; 14.AH.5.157; 14.AH.5.158;
14.AH.5.196; 14.AH.5.223; 14.AH.5.240; 14.AH.5.244; 14.AH.5.243;
14.AH.5.247; 14.AH.7.157; 14.AH.7.158; 14.AH.7.196; 14.AH.7.223;
14.AH.7.240; 14.AH.7.244; 14.AH.7.243; 14.AH.7.247; 14.AH.15.157;
14.AH.15.158; 14.AH.15.196; 14.AH.15.223; 14.AH.15.240; 14.AH.15.244;
14.AH.15.243; 14.AH.15.247; 14.AH.16.157; 14.AH.16.158; 14.AH.16.196;
14.AH.16.223; 14.AH.16.240; 14.AH.16.244; 14.AH.16.243; 14.AH.16.247;
14.AH.18.157; 14.AH.18.158; 14.AH.18.196; 14.AH.18.223; 14.AH.18.240;
14.AH.18.244; 14.AH.18.243; 14.AH.18.247; 14.AH.26.157; 14.AH.26.158;
14.AH.26.196; 14.AH.26.223; 14.AH.26.240; 14.AH.26.244; 14.AH.26.243;
14.AH.26.247; 14.AH.27.157; 14.AH.27.158; 14.AH.27.196; 14.AH.27.223;
14.AH.27.240; 14.AH.27.244; 14.AH.27.243; 14.AH.27.247; 14.AH.29.157;
14.AH.29.158; 14.AH.29.196; 14.AH.29.223; 14.AH.29.240; 14.AH.29.244;
14.AH.29.243; 14.AH.29.247; 14.AH.54.157; 14.AH.54.158; 14.AH.54.196;
14.AH.54.223; 14.AH.54.240; 14.AH.54.244; 14.AH.54.243; 14.AH.54.247;
14.AH.55.157; 14.AH.55.158; 14.AH.55.196; 14.AH.55.223; 14.AH.55.240;
14.AH.55.244; 14.AH.55.243; 14.AH.55.247; 14.AH.56.157; 14.AH.56.158;
14.AH.56.196; 14.AH.56.223; 14.AH.56.240; 14.AH.56.244; 14.AH.56.243;
14.AH.56.247; 14.AH.157.157; 14.AH.157.158; 14.AH.157.196;
14.AH.157.223; 14.AH.157.240; 14.AH.157.244; 14.AH.157.243;
14.AH.157.247; 14.AH.196.157; 14.AH.196.158; 14.AH.196.196;
14.AH.196.223; 14.AH.196.240; 14.AH.196.244; 14.AH.196.243;
14.AH.196.247; 14.AH.223.157; 14.AH.223.158; 14.AH.223.196;
14.AH.223.223; 14.AH.223.240; 14.AH.223.244; 14.AH.223.243;
14.AH.223.247; 14.AH.240.157; 14.AH.240.158; 14.AH.240.196;
14.AH.240.223; 14.AH.240.240; 14.AH.240.244; 14.AH.240.243;

TABLE 100-continued

14.AH.240.247; 14.AH.244.157; 14.AH.244.158; 14.AH.244.196; 14.AH.244.223; 14.AH.244.240; 14.AH.244.244; 14.AH.244.243; 14.AH.244.247; 14.AH.247.157; 14.AH.247.158; 14.AH.247.196; 14.AH.247.223; 14.AH.247.240; 14.AH.247.244; 14.AH.247.243; 14.AH.247.247;

Prodrugs of 14.AJ

14.AJ.4.157; 14.AJ.4.158; 14.AJ.4.196; 14.AJ.4.223; 14.AJ.4.240; 14.AJ.4.244; 14.AJ.4.243; 14.AJ.4.247; 14.AJ.5.157; 14.AJ.5.158; 14.AJ.5.196; 14.AJ.5.223; 14.AJ.5.240; 14.AJ.5.244; 14.AJ.5.243; 14.AJ.5.247; 14.AJ.7.157; 14.AJ.7.158; 14.AJ.7.196; 14.AJ.7.223; 14.AJ.7.240; 14.AJ.7.244; 14.AJ.7.243; 14.AJ.7.247; 14.AJ.15.157; 14.AJ.15.158; 14.AJ.15.196; 14.AJ.15.223; 14.AJ.15.240; 14.AJ.15.244; 14.AJ.15.243; 14.AJ.15.247; 14.AJ.16.157; 14.AJ.16.158; 14.AJ.16.196; 14.AJ.16.223; 14.AJ.16.240; 14.AJ.16.244; 14.AJ.16.243; 14.AJ.16.247; 14.AJ.18.157; 14.AJ.18.158; 14.AJ.18.196; 14.AJ.18.223; 14.AJ.18.240; 14.AJ.18.244; 14.AJ.18.243; 14.AJ.18.247; 14.AJ.26.157; 14.AJ.26.158; 14.AJ.26.196; 14.AJ.26.223; 14.AJ.26.240; 14.AJ.26.244; 14.AJ.26.243; 14.AJ.26.247; 14.AJ.27.157; 14.AJ.27.158; 14.AJ.27.196; 14.AJ.27.223; 14.AJ.27.240; 14.AJ.27.244; 14.AJ.27.243; 14.AJ.27.247; 14.AJ.29.157; 14.AJ.29.158; 14.AJ.29.196; 14.AJ.29.223; 14.AJ.29.240; 14.AJ.29.244; 14.AJ.29.243; 14.AJ.29.247; 14.AJ.54.157; 14.AJ.54.158; 14.AJ.54.196; 14.AJ.54.223; 14.AJ.54.240; 14.AJ.54.244; 14.AJ.54.243; 14.AJ.54.247; 14.AJ.55.157; 14.AJ.55.158; 14.AJ.55.196; 14.AJ.55.223; 14.AJ.55.240; 14.AJ.55.244; 14.AJ.55.243; 14.AJ.55.247; 14.AJ.56.157; 14.AJ.56.158; 14.AJ.56.196; 14.AJ.56.223; 14.AJ.56.240; 14.AJ.56.244; 14.AJ.56.243; 14.AJ.56.247; 14.AJ.157.157; 14.AJ.157.158; 14.AJ.157.196; 14.AJ.157.223; 14.AJ.157.240; 14.AJ.157.244; 14.AJ.157.243; 14.AJ.157.247; 14.AJ.196.157; 14.AJ.196.158; 14.AJ.196.196; 14.AJ.196.223; 14.AJ.196.240; 14.AJ.196.244; 14.AJ.196.243; 14.AJ.196.247; 14.AJ.223.157; 14.AJ.223.158; 14.AJ.223.196; 14.AJ.223.223; 14.AJ.223.240; 14.AJ.223.244; 14.AJ.223.243; 14.AJ.223.247; 14.AJ.240.157; 14.AJ.240.158; 14.AJ.240.196; 14.AJ.240.223; 14.AJ.240.240; 14.AJ.240.244; 14.AJ.240.243; 14.AJ.240.247; 14.AJ.244.157; 14.AJ.244.158; 14.AJ.244.196; 14.AJ.244.223; 14.AJ.244.240; 14.AJ.244.244; 14.AJ.244.243; 14.AJ.244.247; 14.AJ.247.157; 14.AJ.247.158; 14.AJ.247.196; 14.AJ.247.223; 14.AJ.247.240; 14.AJ.247.244; 14.AJ.247.243; 14.AJ.247.247;

Prodrugs of 14.AN

14.AN.4.157; 14.AN.4.158; 14.AN.4.196; 14.AN.4.223; 14.AN.4.240; 14.AN.4.244; 14.AN.4.243; 14.AN.4.247; 14.AN.5.157; 14.AN.5.158; 14.AN.5.196; 14.AN.5.223; 14.AN.5.240; 14.AN.5.244; 14.AN.5.243; 14.AN.5.247; 14.AN.7.157; 14.AN.7.158; 14.AN.7.196; 14.AN.7.223; 14.AN.7.240; 14.AN.7.244; 14.AN.7.243; 14.AN.7.247; 14.AN.15.157; 14.AN.15.158; 14.AN.15.196; 14.AN.15.223; 14.AN.15.240; 14.AN.15.244; 14.AN.15.243; 14.AN.15.247; 14.AN.16.157; 14.AN.16.158; 14.AN.16.196; 14.AN.16.223; 14.AN.16.240; 14.AN.16.244; 14.AN.16.243; 14.AN.16.247; 14.AN.18.157; 14.AN.18.158; 14.AN.18.196; 14.AN.18.223; 14.AN.18.240; 14.AN.18.244; 14.AN.18.243; 14.AN.18.247; 14.AN.26.157; 14.AN.26.158; 14.AN.26.196; 14.AN.26.223; 14.AN.26.240; 14.AN.26.244; 14.AN.26.243; 14.AN.26.247; 14.AN.27.157; 14.AN.27.158; 14.AN.27.196; 14.AN.27.223; 14.AN.27.240; 14.AN.27.244; 14.AN.27.243; 14.AN.27.247; 14.AN.29.157; 14.AN.29.158; 14.AN.29.196; 14.AN.29.223; 14.AN.29.240; 14.AN.29.244; 14.AN.29.243; 14.AN.29.247; 14.AN.54.157; 14.AN.54.158; 14.AN.54.196; 14.AN.54.223; 14.AN.54.240; 14.AN.54.244; 14.AN.54.243; 14.AN.54.247; 14.AN.55.157; 14.AN.55.158; 14.AN.55.196; 14.AN.55.223; 14.AN.55.240; 14.AN.55.244; 14.AN.55.243; 14.AN.55.247; 14.AN.56.157; 14.AN.56.158; 14.AN.56.196; 14.AN.56.223; 14.AN.56.240; 14.AN.56.244; 14.AN.56.243; 14.AN.56.247; 14.AN.157.157; 14.AN.157.158; 14.AN.157.196; 14.AN.157.223; 14.AN.157.240; 14.AN.157.244; 14.AN.157.243; 14.AN.157.247; 14.AN.196.157; 14.AN.196.158; 14.AN.196.196; 14.AN.196.223; 14.AN.196.240; 14.AN.196.244; 14.AN.196.243; 14.AN.196.247; 14.AN.223.157; 14.AN.223.158; 14.AN.223.196; 14.AN.223.223; 14.AN.223.240; 14.AN.223.244; 14.AN.223.243; 14.AN.223.247; 14.AN.240.157; 14.AN.240.158; 14.AN.240.196; 14.AN.240.223; 14.AN.240.240; 14.AN.240.244; 14.AN.240.243; 14.AN.240.247; 14.AN.244.157; 14.AN.244.158; 14.AN.244.196; 14.AN.244.223; 14.AN.244.240; 14.AN.244.244; 14.AN.244.243; 14.AN.244.247; 14.AN.247.157; 14.AN.247.158; 14.AN.247.196; 14.AN.247.223; 14.AN.247.240; 14.AN.247.244; 14.AN.247.243; 14.AN.247.247;

Prodrugs of 14.AP

14.AP.4.157; 14.AP.4.158; 14.AP.4.196; 14.AP.4.223; 14.AP.4.240; 14.AP.4.244; 14.AP.4.243; 14.AP.4.247; 14.AP.5.157; 14.AP.5.158; 14.AP.5.196; 14.AP.5.223; 14.AP.5.240; 14.AP.5.244; 14.AP.5.243; 14.AP.5.247; 14.AP.7.157; 14.AP.7.158; 14.AP.7.196; 14.AP.7.223; 14.AP.7.240; 14.AP.7.244; 14.AP.7.243; 14.AP.7.247; 14.AP.15.157; 14.AP.15.158; 14.AP.15.196; 14.AP.15.223; 14.AP.15.240; 14.AP.15.244; 14.AP.15.243; 14.AP.15.247; 14.AP.16.157; 14.AP.16.158; 14.AP.16.196;

TABLE 100-continued

14.AP.16.223; 14.AP.16.240; 14.AP.16.244; 14.AP.16.243; 14.AP.16.247; 14.AP.18.157; 14.AP.18.158; 14.AP.18.196; 14.AP.18.223; 14.AP.18.240; 14.AP.18.244; 14.AP.18.243; 14.AP.18.247; 14.AP.26.157; 14.AP.26.158; 14.AP.26.196; 14.AP.26.223; 14.AP.26.240; 14.AP.26.244; 14.AP.26.243; 14.AP.26.247; 14.AP.27.157; 14.AP.27.158; 14.AP.27.196; 14.AP.27.223; 14.AP.27.240; 14.AP.27.244; 14.AP.27.243; 14.AP.27.247; 14.AP.29.157; 14.AP.29.158; 14.AP.29.196; 14.AP.29.223; 14.AP.29.240; 14.AP.29.244; 14.AP.29.243; 14.AP.29.247; 14.AP.54.157; 14.AP.54.158; 14.AP.54.196; 14.AP.54.223; 14.AP.54.240; 14.AP.54.244; 14.AP.54.243; 14.AP.54.247; 14.AP.55.157; 14.AP.55.158; 14.AP.55.196; 14.AP.55.223; 14.AP.55.240; 14.AP.55.244; 14.AP.55.243; 14.AP.55.247; 14.AP.56.157; 14.AP.56.158; 14.AP.56.196; 14.AP.56.223; 14.AP.56.240; 14.AP.56.244; 14.AP.56.243; 14.AP.56.247; 14.AP.157.157; 14.AP.157.158; 14.AP.157.196; 14.AP.157.223; 14.AP.157.240; 14.AP.157.244; 14.AP.157.243; 14.AP.157.247; 14.AP.196.157; 14.AP.196.158; 14.AP.196.196; 14.AP.196.223; 14.AP.196.240; 14.AP.196.244; 14.AP.196.243; 14.AP.196.247; 14.AP.223.157; 14.AP.223.158; 14.AP.223.196; 14.AP.223.223; 14.AP.223.240; 14.AP.223.244; 14.AP.223.243; 14.AP.223.247; 14.AP.240.157; 14.AP.240.158; 14.AP.240.196; 14.AP.240.223; 14.AP.240.240; 14.AP.240.244; 14.AP.240.243; 14.AP.240.247; 14.AP.244.157; 14.AP.244.158; 14.AP.244.196; 14.AP.244.223; 14.AP.244.240; 14.AP.244.244; 14.AP.244.243; 14.AP.244.247; 14.AP.247.157; 14.AP.247.158; 14.AP.247.196; 14.AP.247.223; 14.AP.247.240; 14.AP.247.244; 14.AP.247.243; 14.AP.247.247;

Prodrugs of 14.AZ

14.AZ.4.157; 14.AZ.4.158; 14.AZ.4.196; 14.AZ.4.223; 14.AZ.4.240; 14.AZ.4.244; 14.AZ.4.243; 14.AZ.4.247; 14.AZ.5.157; 14.AZ.5.158; 14.AZ.5.196; 14.AZ.5.223; 14.AZ.5.240; 14.AZ.5.244; 14.AZ.5.243; 14.AZ.5.247; 14.AZ.7.157; 14.AZ.7.158; 14.AZ.7.196; 14.AZ.7.223; 14.AZ.7.240; 14.AZ.7.244; 14.AZ.7.243; 14.AZ.7.247; 14.AZ.15.157; 14.AZ.15.158; 14.AZ.15.196; 14.AZ.15.223; 14.AZ.15.240; 14.AZ.15.244; 14.AZ.15.243; 14.AZ.15.247; 14.AZ.16.157; 14.AZ.16.158; 14.AZ.16.196; 14.AZ.16.223; 14.AZ.16.240; 14.AZ.16.244; 14.AZ.16.243; 14.AZ.16.247; 14.AZ.18.157; 14.AZ.18.158; 14.AZ.18.196; 14.AZ.18.223; 14.AZ.18.240; 14.AZ.18.244; 14.AZ.18.243; 14.AZ.18.247; 14.AZ.26.157; 14.AZ.26.158; 14.AZ.26.196; 14.AZ.26.223; 14.AZ.26.240; 14.AZ.26.244; 14.AZ.26.243; 14.AZ.26.247; 14.AZ.27.157; 14.AZ.27.158; 14.AZ.27.196; 14.AZ.27.223; 14.AZ.27.240; 14.AZ.27.244; 14.AZ.27.243; 14.AZ.27.247; 14.AZ.29.157; 14.AZ.29.158; 14.AZ.29.196; 14.AZ.29.223; 14.AZ.29.240; 14.AZ.29.244; 14.AZ.29.243; 14.AZ.29.247; 14.AZ.54.157; 14.AZ.54.158; 14.AZ.54.196; 14.AZ.54.223; 14.AZ.54.240; 14.AZ.54.244; 14.AZ.54.243; 14.AZ.54.247; 14.AZ.55.157; 14.AZ.55.158; 14.AZ.55.196; 14.AZ.55.223; 14.AZ.55.240; 14.AZ.55.244; 14.AZ.55.243; 14.AZ.55.247; 14.AZ.56.157; 14.AZ.56.158; 14.AZ.56.196; 14.AZ.56.223; 14.AZ.56.240; 14.AZ.56.244; 14.AZ.56.243; 14.AZ.56.247; 14.AZ.157.157; 14.AZ.157.158; 14.AZ.157.196; 14.AZ.157.223; 14.AZ.157.240; 14.AZ.157.244; 14.AZ.157.243; 14.AZ.157.247; 14.AZ.196.157; 14.AZ.196.158; 14.AZ.196.196; 14.AZ.196.223; 14.AZ.196.240; 14.AZ.196.244; 14.AZ.196.243; 14.AZ.196.247; 14.AZ.223.157; 14.AZ.223.158; 14.AZ.223.196; 14.AZ.223.223; 14.AZ.223.240; 14.AZ.223.244; 14.AZ.223.243; 14.AZ.223.247; 14.AZ.240.157; 14.AZ.240.158; 14.AZ.240.196; 14.AZ.240.223; 14.AZ.240.240; 14.AZ.240.244; 14.AZ.240.243; 14.AZ.240.247; 14.AZ.244.157; 14.AZ.244.158; 14.AZ.244.196; 14.AZ.244.223; 14.AZ.244.240; 14.AZ.244.244; 14.AZ.244.243; 14.AZ.244.247; 14.AZ.247.157; 14.AZ.247.158; 14.AZ.247.196; 14.AZ.247.223; 14.AZ.247.240; 14.AZ.247.244; 14.AZ.247.243; 14.AZ.247.247;

Prodrugs of 14.BF

14.BF.4.157; 14.BF.4.158; 14.BF.4.196; 14.BF.4.223; 14.BF.4.240; 14.BF.4.244; 14.BF.4.243; 14.BF.4.247; 14.BF.5.157; 14.BF.5.158; 14.BF.5.196; 14.BF.5.223; 14.BF.5.240; 14.BF.5.244; 14.BF.5.243; 14.BF.5.247; 14.BF.7.157; 14.BF.7.158; 14.BF.7.196; 14.BF.7.223; 14.BF.7.240; 14.BF.7.244; 14.BF.7.243; 14.BF.7.247; 14.BF.15.157; 14.BF.15.158; 14.BF.15.196; 14.BF.15.223; 14.BF.15.240; 14.BF.15.244; 14.BF.15.243; 14.BF.15.247; 14.BF.16.157; 14.BF.16.158; 14.BF.16.196; 14.BF.16.223; 14.BF.16.240; 14.BF.16.244; 14.BF.16.243; 14.BF.16.247; 14.BF.18.157; 14.BF.18.158; 14.BF.18.196; 14.BF.18.223; 14.BF.18.240; 14.BF.18.244; 14.BF.18.243; 14.BF.18.247; 14.BF.26.157; 14.BF.26.158; 14.BF.26.196; 14.BF.26.223; 14.BF.26.240; 14.BF.26.244; 14.BF.26.243; 14.BF.26.247; 14.BF.27.157; 14.BF.27.158; 14.BF.27.196; 14.BF.27.223; 14.BF.27.240; 14.BF.27.244; 14.BF.27.243; 14.BF.27.247; 14.BF.29.157; 14.BF.29.158; 14.BF.29.196; 14.BF.29.223; 14.BF.29.240; 14.BF.29.244; 14.BF.29.243; 14.BF.29.247; 14.BF.54.157; 14.BF.54.158; 14.BF.54.196; 14.BF.54.223; 14.BF.54.240; 14.BF.54.244; 14.BF.54.243; 14.BF.54.247; 14.BF.55.157; 14.BF.55.158; 14.BF.55.196; 14.BF.55.223; 14.BF.55.240; 14.BF.55.244; 14.BF.55.243; 14.BF.55.247; 14.BF.56.157; 14.BF.56.158; 14.BF.56.196; 14.BF.56.223; 14.BF.56.240; 14.BF.56.244; 14.BF.56.243; 14.BF.56.247; 14.BF.157.157; 14.BF.157.158; 14.BF.157.196; 14.BF.157.223;

TABLE 100-continued

14.BF.157.240; 14.BF.157.244; 14.BF.157.243; 14.BF.157.247; 14.BF.196.157; 14.BF.196.158; 14.BF.196.196; 14.BF.196.223; 14.BF.196.240; 14.BF.196.244; 14.BF.196.243; 14.BF.196.247; 14.BF.223.157; 14.BF.223.158; 14.BF.223.196; 14.BF.223.223; 14.BF.223.240; 14.BF.223.244; 14.BF.223.243; 14.BF.223.247; 14.BF.240.157; 14.BF.240.158; 14.BF.240.196; 14.BF.240.223; 14.BF.240.240; 14.BF.240.244; 14.BF.240.243; 14.BF.240.247; 14.BF.244.157; 14.BF.244.158; 14.BF.244.196; 14.BF.244.223; 14.BF.244.240; 14.BF.244.244; 14.BF.244.243; 14.BF.244.247; 14.BF.247.157; 14.BF.247.158; 14.BF.247.196; 14.BF.247.223; 14.BF.247.240; 14.BF.247.244; 14.BF.247.243; 14.BF.247.247;

Prodrugs of 14.CI

14.CI.4.157; 14.CI.4.158; 14.CI.4.196; 14.CI.4.223; 14.CI.4.240; 14.CI.4.244; 14.CI.4.243; 14.CI.4.247; 14.CI.5.157; 14.CI.5.158; 14.CI.5.196; 14.CI.5.223; 14.CI.5.240; 14.CI.5.244; 14.CI.5.243; 14.CI.5.247; 14.CI.7.157; 14.CI.7.158; 14.CI.7.196; 14.CI.7.223; 14.CI.7.240; 14.CI.7.244; 14.CI.7.243; 14.CI.7.247; 14.CI.15.157; 14.CI.15.158; 14.CI.15.196; 14.CI.15.223; 14.CI.15.240; 14.CI.15.244; 14.CI.15.243; 14.CI.15.247; 14.CI.16.157; 14.CI.16.158; 14.CI.16.196; 14.CI.16.223; 14.CI.16.240; 14.CI.16.244; 14.CI.16.243; 14.CI.16.247; 14.CI.18.157; 14.CI.18.158; 14.CI.18.196; 14.CI.18.223; 14.CI.18.240; 14.CI.18.244; 14.CI.18.243; 14.CI.18.247; 14.CI.26.157; 14.CI.26.158; 14.CI.26.196; 14.CI.26.223; 14.CI.26.240; 14.CI.26.244; 14.CI.26.243; 14.CI.26.247; 14.CI.27.157; 14.CI.27.158; 14.CI.27.196; 14.CI.27.223; 14.CI.27.240; 14.CI.27.244; 14.CI.27.243; 14.CI.27.247; 14.CI.29.157; 14.CI.29.158; 14.CI.29.196; 14.CI.29.223; 14.CI.29.240; 14.CI.29.244; 14.CI.29.243; 14.CI.29.247; 14.CI.54.157; 14.CI.54.158; 14.CI.54.196; 14.CI.54.223; 14.CI.54.240; 14.CI.54.244; 14.CI.54.243; 14.CI.54.247; 14.CI.55.157; 14.CI.55.158; 14.CI.55.196; 14.CI.55.223; 14.CI.55.240; 14.CI.55.244; 14.CI.55.243; 14.CI.55.247; 14.CI.56.157; 14.CI.56.158; 14.CI.56.196; 14.CI.56.223; 14.CI.56.240; 14.CI.56.244; 14.CI.56.243; 14.CI.56.247; 14.CI.157.157; 14.CI.157.158; 14.CI.157.196; 14.CI.157.223; 14.CI.157.240; 14.CI.157.244; 14.CI.157.243; 14.CI.157.247; 14.CI.196.157; 14.CI.196.158; 14.CI.196.196; 14.CI.196.223; 14.CI.196.240; 14.CI.196.244; 14.CI.196.243; 14.CI.196.247; 14.CI.223.157; 14.CI.223.158; 14.CI.223.196; 14.CI.223.223; 14.CI.223.240; 14.CI.223.244; 14.CI.223.243; 14.CI.223.247; 14.CI.240.157; 14.CI.240.158; 14.CI.240.196; 14.CI.240.223; 14.CI.240.240; 14.CI.240.244; 14.CI.240.243; 14.CI.240.247; 14.CI.244.157; 14.CI.244.158; 14.CI.244.196; 14.CI.244.223; 14.CI.244.240; 14.CI.244.244; 14.CI.244.243; 14.CI.244.247; 14.CI.247.157; 14.CI.247.158; 14.CI.247.196; 14.CI.247.223; 14.CI.247.240; 14.CI.247.244; 14.CI.247.243; 14.CI.247.247;

Prodrugs of 14.CO

14.CO.4.157; 14.CO.4.158; 14.CO.4.196; 14.CO.4.223; 14.CO.4.240; 14.CO.4.244; 14.CO.4.243; 14.CO.4.247; 14.CO.5.157; 14.CO.5.158; 14.CO.5.196; 14.CO.5.223; 14.CO.5.240; 14.CO.5.244; 14.CO.5.243; 14.CO.5.247; 14.CO.7.157; 14.CO.7.158; 14.CO.7.196; 14.CO.7.223; 14.CO.7.240; 14.CO.7.244; 14.CO.7.243; 14.CO.7.247; 14.CO.15.157; 14.CO.15.158; 14.CO.15.196; 14.CO.15.223; 14.CO.15.240; 14.CO.15.244; 14.CO.15.243; 14.CO.15.247; 14.CO.16.157; 14.CO.16.158; 14.CO.16.196; 14.CO.16.223; 14.CO.16.240; 14.CO.16.244; 14.CO.16.243; 14.CO.16.247; 14.CO.18.157; 14.CO.18.158; 14.CO.18.196; 14.CO.18.223; 14.CO.18.240; 14.CO.18.244; 14.CO.18.243; 14.CO.18.247; 14.CO.26.157; 14.CO.26.158; 14.CO.26.196; 14.CO.26.223; 14.CO.26.240; 14.CO.26.244; 14.CO.26.243; 14.CO.26.247; 14.CO.27.157; 14.CO.27.158; 14.CO.27.196; 14.CO.27.223; 14.CO.27.240; 14.CO.27.244; 14.CO.27.243; 14.CO.27.247; 14.CO.29.157; 14.CO.29.158; 14.CO.29.196; 14.CO.29.223; 14.CO.29.240; 14.CO.29.244; 14.CO.29.243; 14.CO.29.247; 14.CO.54.157; 14.CO.54.158; 14.CO.54.196; 14.CO.54.223; 14.CO.54.240; 14.CO.54.244; 14.CO.54.243; 14.CO.54.247; 14.CO.55.157; 14.CO.55.158; 14.CO.55.196; 14.CO.55.223; 14.CO.55.240; 14.CO.55.244; 14.CO.55.243; 14.CO.55.247; 14.CO.56.157; 14.CO.56.158; 14.CO.56.196; 14.CO.56.223; 14.CO.56.240; 14.CO.56.244; 14.CO.56.243; 14.CO.56.247; 14.CO.157.157; 14.CO.157.158; 14.CO.157.196; 14.CO.157.223; 14.CO.157.240; 14.CO.157.244; 14.CO.157.243; 14.CO.157.247; 14.CO.196.157; 14.CO.196.158; 14.CO.196.196; 14.CO.196.223; 14.CO.196.240; 14.CO.196.244; 14.CO.196.243; 14.CO.196.247; 14.CO.223.157; 14.CO.223.158; 14.CO.223.196; 14.CO.223.223; 14.CO.223.240; 14.CO.223.244; 14.CO.223.243; 14.CO.223.247; 14.CO.240.157; 14.CO.240.158; 14.CO.240.196; 14.CO.240.223; 14.CO.240.240; 14.CO.240.244; 14.CO.240.243; 14.CO.240.247; 14.CO.244.157; 14.CO.244.158; 14.CO.244.196; 14.CO.244.223; 14.CO.244.240; 14.CO.244.244; 14.CO.244.243; 14.CO.244.247; 14.CO.4.157; 14.CO.4.158; 14.CO.4.196; 14.CO.4.223; 14.CO.4.240; 14.CO.4.244; 14.CO.4.243; 14.CO.4.247;

All literature and patent citations herein are hereby expressly incorporated by reference at the locations of the citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

In the claims hereinbelow, the subscript and superscripts of a given variable are distinct. For example, $R_1$ is distinct from $R^1$.

We claim:

1. A method of treating hypercholesterolemia, hyperlipoproteinemia, dyslipidemia or atherosclerosis in a mammal comprising administering a conjugate or a pharmaceutically acceptable salt or solvate thereof to the mammal wherein the conjugate is a compound of formula:

$[DRUG]\text{-}(A^0)_{nn}$;

wherein:

DRUG is a compound of formula 518:

518

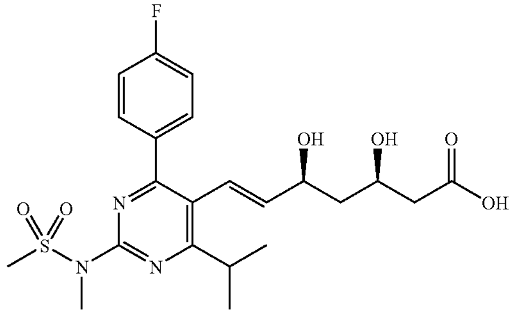

wherein:

nn is 1, 2, or 3:

$A^0$ is $A^1$, $A^2$ or $W^3$ with the proviso that the conjugate includes at least one $A^1$:

$A^1$ is:

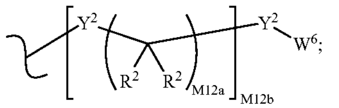

$A^2$ is:

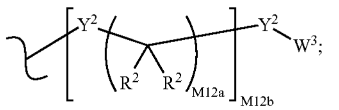

$A^3$ is:

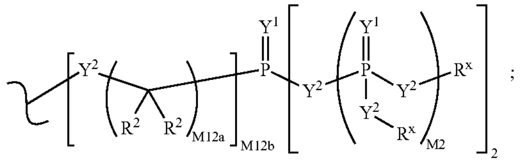

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—; and when $Y^2$ joins two phosphorous atoms $Y^2$ can also be $C(R^2)(R^2)$;

$R^x$ is independently H, $R^1$, $R^2$, $W^3$, a protecting group, or the formula:

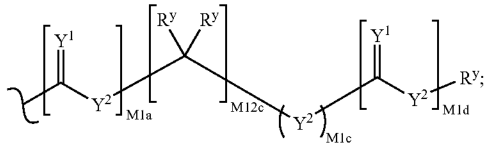

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is —$R^x$, —$N(R^x)(R^x)$—$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$ or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —$C(Y^1)R^5$, —$C(Y^1)W^5$, —$SO_{M2}R^5$, or —$SO_{M2}W^5$;

$W^5$ is carbocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

2. The method of claim 1 wherein the conjugate is a compound of formula 42, 43, or 44:

42

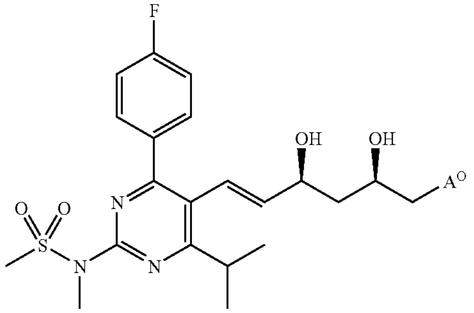

-continued

43

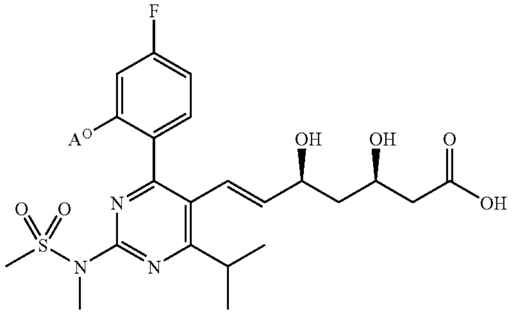

44

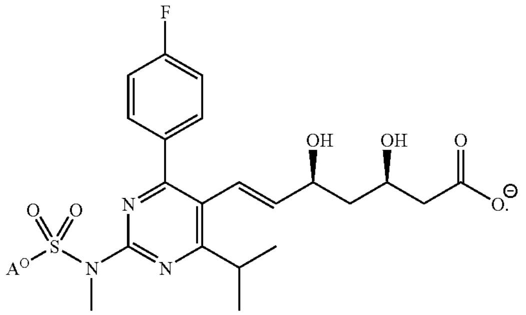

3. The method of claim 1 wherein each $A^3$ is of the formula:

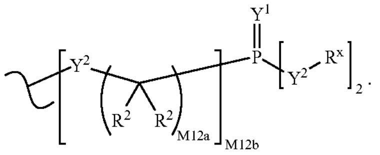

4. The method of claim 1 wherein each $A^3$ is of the formula:

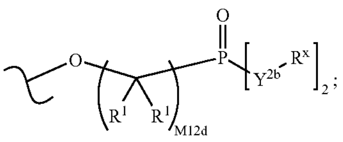

wherein $Y^{2b}$ is O or $N(R^x)$.

5. The method of claim 1 wherein each $A^3$ is of the formula:

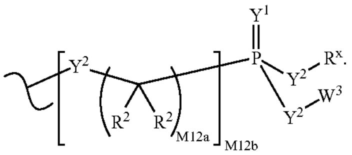

6. The method of claim 1 wherein each $A^3$ is of the formula:

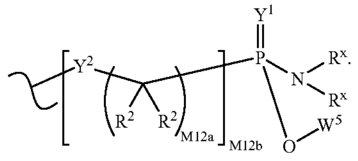

7. The method of claim 1 wherein each $A^3$ is of the formula:

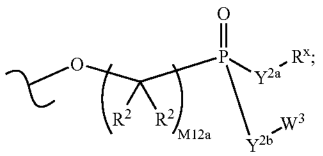

wherein $Y^{2b}$ is O or $N(R^x)$.

8. The method of claim 1 wherein each $A^3$ is of the formula:

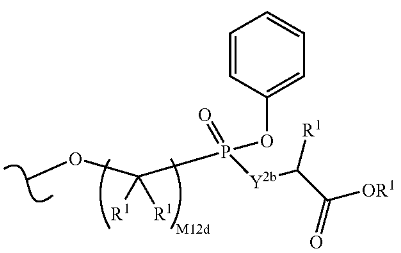

wherein the phenyl carbocycle is substituted with 0, 1, 2, or 3 $R^2$ groups.

9. The method of claim 1 wherein each $A^3$ is of the formula:

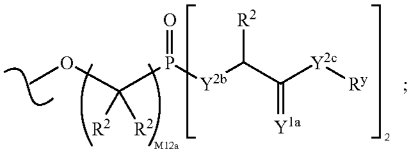

wherein:

$Y^{1a}$ is O or S;

$Y^{2b}$ is O or $N(R^2)$; and $Y^{2c}$ is O, $N(R^y)$ or S.

10. The method of claim 1 wherein $A^0$ is of the formula:

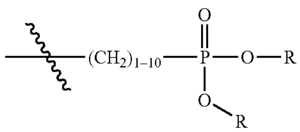

wherein each R is independently alkyl.

11. The method of claim 1 wherein hypercholesterolemia or dyslipidemia is treated.

12. The method of claim 1 wherein dyslipidemia is treated.

* * * * *